US010350285B2

(12) United States Patent
Reyes-Sandoval et al.

(10) Patent No.: US 10,350,285 B2

(45) Date of Patent: Jul. 16, 2019

(54) DENGUE VACCINES

(71) Applicant: Oxford University Innovation Limited, Botley, Oxford (GB)

(72) Inventors: Arturo Reyes-Sandoval, Oxford (GB); Cesar Lopez-Camacho, Oxford (GB); Joshua Blight, Oxford (GB)

(73) Assignee: Oxford University Innovation Limited, Botley, Oxford (GB)

( * ) Notice: Subject to any disclaimer, the term of this patent is extended or adjusted under 35 U.S.C. 154(b) by 0 days.

(21) Appl. No.: 15/573,337

(22) PCT Filed: May 11, 2016

(86) PCT No.: PCT/GB2016/051358

§ 371 (c)(1),
(2) Date: Nov. 10, 2017

(87) PCT Pub. No.: WO2016/181147

PCT Pub. Date: Nov. 17, 2016

(65) Prior Publication Data

US 2018/0193446 A1 Jul. 12, 2018

(30) Foreign Application Priority Data

May 12, 2015 (GB) .................................. 1508099.7

(51) Int. Cl.
*A61K 39/00* (2006.01)
*A61K 39/12* (2006.01)

(52) U.S. Cl.
CPC .......... *A61K 39/12* (2013.01); *A61K 2039/51* (2013.01); *A61K 2039/5258* (2013.01); *A61K 2039/545* (2013.01); *C12N 2710/10023* (2013.01); *C12N 2770/24134* (2013.01); *Y02A 50/386* (2018.01)

(58) Field of Classification Search
CPC .. A61K 39/12; A61K 2039/53; A61K 9/0019; A61K 39/42; A61K 2039/525; A61K 2039/6075; A61K 38/162; C12N 7/00; C12N 2770/24134; C12N 2770/24122; C12N 2770/24171; C12N 2770/24034; C12N 2770/24022; C07K 14/005; C07K 14/1825
See application file for complete search history.

(56) References Cited

FOREIGN PATENT DOCUMENTS

| | | |
|---|---|---|
| WO | 2003048184 | 6/2003 |
| WO | 2011163628 | 12/2011 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10.*

Konishi E. Issues related to recent dengue vaccine development. Trop Med Health. Dec. 2011;39(4 Suppl):63-71. Epub Aug. 6, 2011.*

Halstead SB. Dengvaxia sensitizes seronegatives to vaccine enhanced disease regardless of age. Vaccine. Nov. 7, 2017;35(47): 6355-6358. Epub Oct. 10, 2017.*

Flasche S, et. al. The Long-Term Safety, Public Health Impact, and Cost-Effectiveness of Routine Vaccination with a Recombinant, Live-Attenuated Dengue Vaccine (Dengvaxia): A Model Comparison Study. PLoS Med. Nov. 29, 2016;13(11):e1002181. eCollection Nov. 2016.*

Nascimento EJ, Mailliard RB, Khan AM, Sidney J, Sette A, Guzman N, Paulaitis M, de Melo AB, Cordeiro MT, Gil LV, Lemonnier F, Rinaldo C, August JT, Marques ET Jr. Identification of conserved and HLA promiscuous DENV3 T-cell epitopes. PLoS Negl Trop Dis. Oct. 10, 2013;7(10):e2497.*

Kim MY, Reljic R, Kilbourne J, Ceballos-Olvera I, Yang MS, Reyes-del Valle J, Mason HS. Novel vaccination approach for dengue infection based on recombinant immune complex universal platform. Vaccine. Apr. 8, 2015 8;33(15):1830-8. Epub Feb. 26, 2015.*

Assenberg R, Mastrangelo E, Walter TS, Verma A, Milani M, Owens RJ, Stuart DI, Grimes JM, Mancini EJ. Crystal structure of a novel conformational state of the flavivirus NS3 protein: implications for polyprotein processing and viral replication. J Virol. Dec. 2009;83(24):12895-906. Epub Sep. 30, 2009.*

"Plurality". Merriam-Webster.com. Accessed Jul. 16, 2018. https://www.merriam-webster.com/dictionary/plurality.*

International Preliminary Report on Patentability (IPRP) dated Nov. 23, 2017 for international application PCT/GB2016/051358.

Shi, et al.,Inferring Protective CD8+ T Cell Epitopes for NS5 Protein of Four Serotypes of Dengue Virus Chinese Isolates Based on HLA-A, -B and -C Allelic Distribution: Implications for Epitope-Based Universal Vaccine Design, Plos One, vol. 10, No. 9, Sep. 18, 2015 (Sep. 18, 2015), p. e0138729, DOI: 10.1371/journal.pone.0138729.

Weiskopf, et al., Comprehensive Analysis of Dengue Virus-Specific Responses Supports an HLA-Linked Protective Role for CD8+ T Cells, Proceedings of the National Academy of Sciences, vol. 110, No. 22, May 28, 2013 (May 28, 2013 ), pp. D2046-E2053, XP055155265, ISSN: 0027-8424, DOI: 10.1073/pnas.1305227110.

* cited by examiner

*Primary Examiner* — Rachel B Gill

(74) *Attorney, Agent, or Firm* — Stoel Rives LLP; Zhi-Xiang Oh

(57) ABSTRACT

The invention relates to a protein comprising a plurality of conserved peptide sequences, or variants thereof, wherein at least one of the conserved sequences is conserved across all four dengue virus serotypes DENV-1, DENV-2, DENV-3 and DENV-4, and wherein the conserved sequences comprise at least part of a sequence of one or more non-structural proteins of the dengue virus serotypes. The invention further relates to associated peptides, compositions, nucleic acids, viral vectors, virus-like particles, use, prime boost vaccination kits, agents and methods.

7 Claims, 15 Drawing Sheets

Figure 1:
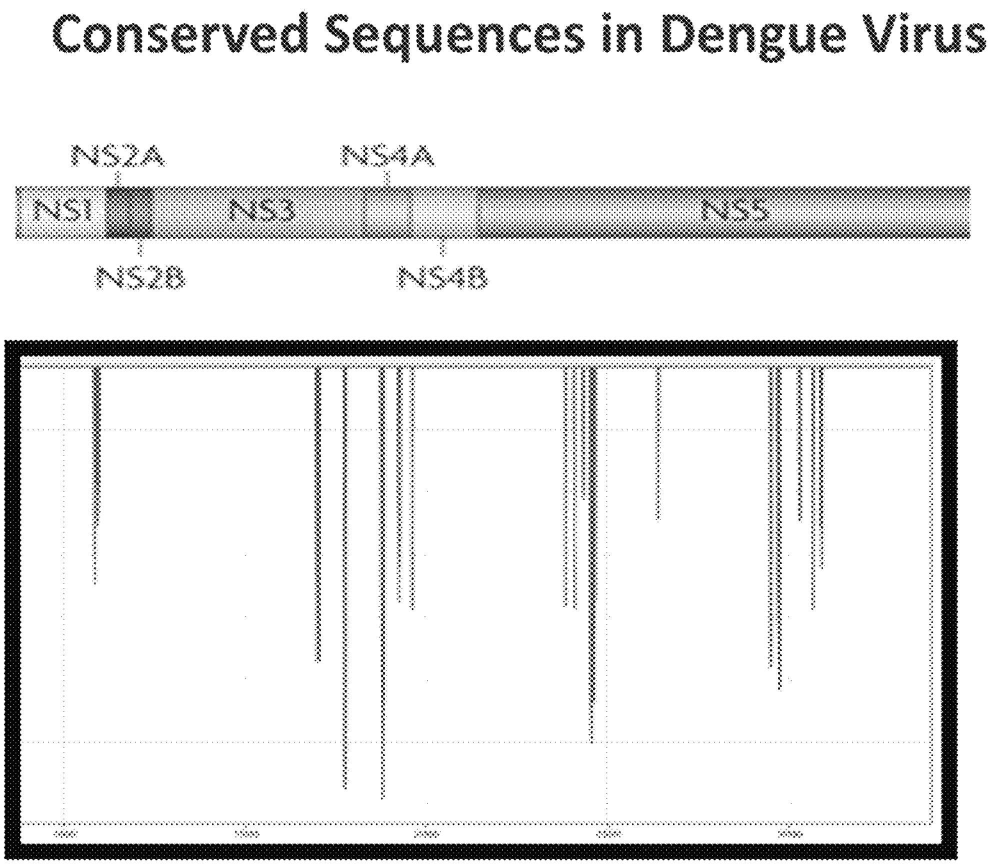

Specification includes a Sequence Listing.

4 different sequences

1_NSALL (1152 bp)

2_NSALL (4671 bp)

3_NSALL (5277 bp)

4_NSALL (5595 bp)

Preclinical assessment of Dengue Virus Vaccines

T-cell Responses generated by 1NSALL vaccines (ELISPOT)

A

B

Antibody Production

DENGUE VACCINES

RELATED APPLICATIONS

This application is a 371 National Phase Application of International Application No. PCT/GB2016/051358 filed May 11, 2016, which claims the benefit of and priority to United Kingdom Application No. GB 1508099.7 filed May 12, 2015; the entire contents of each of the foregoing applications are hereby incorporated by reference herein.

This invention relates to proteins, particularly immunogenic proteins, and associated viral vectors for use in a vaccine against dengue viral infection.

The work leading to this invention has received funding from the European Union Seventh Framework Programme (FP7/2007-2013) under grant agreement n° 281803.

Dengue is the most rapidly spreading mosquito-borne viral disease in the world. Incidence has increased 30-fold in the last 50 years and current WHO estimates indicate that 50 million clinical cases occur each year and approximately 2.5 billion people live in endemic countries (1) More recent estimates, however, have calculated the burden to be more than three times the current published data, reaching astonishing numbers of 390 million infections every year, of which 96 million have clinical manifestations (2) Currently, treatment remains supportive and is based on fluid management and no effective antiviral agents to treat dengue infection are available (3) Moreover, despite various vaccines are being developed, there are no licensed vaccines to prevent dengue infection.

Most DENV (dengue virus) vaccines in clinical development attempt to induce protective antibodies against the four serotypes of dengue. The most advanced is a mixture of four recombinant vectors based on the yellow-fever vaccine Y17. This induces antibodies against the pre-membrane and envelope antigen of all four dengue serotypes and is in late phase III development. However, it is unclear whether in the absence of complete protection, these antibodies will give rise to a risk of enhanced disease through immunological enhancement and this will remain unclear until very large long term follow-up trials are undertaken.

An aim of the present invention is to provide an improved vaccine for dengue viral infection.

According to a first aspect of the invention, there is provided a protein comprising a plurality of conserved peptide sequences, or variants thereof, wherein at least one of the conserved sequences is conserved across all four dengue virus serotypes DENV-1, DENV-2, DENV-3 and DENV-4, and wherein the conserved sequences comprise at least part of a sequence of one or more non-structural proteins of the dengue virus serotypes.

The invention advantageously provides a novel alternative and safer approach to vaccination whereby T cells can be induced to the internal (non-structural) antigens of the dengue virion. This poses no risk of antibody-mediated enhancement and the use of encoded conserved viral segments from the non-structural proteins can provide protection against all serotypes.

The "protein" of the invention may otherwise be termed a "polypeptide". In one embodiment, the protein is a fusion protein. The protein may not be a wild-type protein. The protein may be synthetic/artificial, for example, the protein may not exist in nature. In one embodiment, the protein may not comprise a complete translation from a complete gene sequence. The protein may consist essentially of conserved peptide sequences. In one embodiment, the protein is a recombinant protein, such as a recombinant fusion protein.

The term "fusion protein" used herein is understood to mean a protein comprising a combination of sequences from different gene products (for example different dengue non-structural proteins) or combinations of sequences from the same gene product (for example a single dengue non-structural protein), wherein the sequences are from distinct/separate regions of the wild-type gene product. For example the fusion protein may comprise combinations of sequences which are normally separated by other sequence segments in wild-type, and the separating sequence(s) have been removed.

The term "conserved peptide sequence" used herein is defined as a sequence that is found in more than one serotype or within variant populations of the same serotype, whereby the sequence is identical or highly similar between the serotypes or variants within a serotype. The required similarity for conserved sequences may be at least 60% identity between serotypes and/or within serotype variants. In another embodiment, the required similarity for conserved sequences may be at least 70%, 80% or 90% identity between serotypes and/or within serotype variants. Conserved peptide sequences may be identified using an algorithm which uses a sliding window-based method. Conserved windows within serotypes (intra-serotype) at the same position across different numbers of serotypes (inter-serotype) are identified if the percentage identity between them is greater than 60% and used to create a normalised consensus sequence. These conserved fragments are referred to as conserved sequences. A window size of greater than 9 amino acids and less than 25 amino acids is used.

At least one of the plurality of conserved peptide sequences may comprise a known epitope or a variant of a known epitope. At least one of the plurality of conserved peptide sequences may comprise a known epitope and a known epitope variant. A known epitope variant may be inserted into at least one of the plurality of conserved peptide sequences. A known epitope and/or known epitope variant may be provided in addition to the plurality of conserved peptide sequences. The protein may not consist essentially of known epitopes and/or known epitope variants (e.g. other conserved sequences are required in the protein that are not published known epitopes or variants thereof). The conserved peptide sequences may not consist of a majority (i.e. over 50%) of known epitopes or known epitope variants (e.g. 50% or more conserved sequences are required in the protein that are not published known epitopes or variants thereof). The plurality of conserved peptide sequences may not consist of more than 5%, 10%, 20%, 30%, 40%, 50%, 60%, 70%, 80%, or 90% of known epitopes or known epitope variants. The protein may not consist of more than 1, 2, 3, 4, 5, 6, 7, or 8 known epitopes or known epitope variants. In an embodiment where the protein comprises a known epitope and/or known epitope variant, the protein may comprise a plurality of conserved peptide sequences that do not comprise a known epitope and/or known epitope variant. In an embodiment where the protein comprises a known epitope and/or known epitope variant, at least 90% of the protein sequence comprises conserved peptide sequences that do not comprise a known epitope and/or known epitope variant. In an embodiment where the protein comprises a known epitope and/or known epitope variant, at least 80% of the protein sequence comprises conserved peptide sequences that do not comprise a known epitope and/or known epitope variant. In an embodiment where the protein comprises a known epitope and/or known epitope variant, at least 70% of the protein sequence comprises conserved peptide sequences that do not comprise a known epitope and/or known epitope variant. In an embodiment where the protein comprises a known epitope and/or known epitope variant, at least 60% of the protein sequence comprises conserved peptide sequences that do not comprise a known epitope and/or known epitope variant. In an embodiment where the protein comprises a known epitope and/or known epitope variant, at least 50% of the protein sequence comprises conserved peptide sequences that do not comprise a known epitope and/or known epitope variant.

In one embodiment at least two of the conserved peptide sequences are conserved across all four dengue virus serotypes DENV-1, DENV-2, DENV-3 and DENV-4. In another embodiment at least three of the conserved peptide sequences are conserved across all four dengue virus serotypes DENV-1, DENV-2, DENV-3 and DENV-4. At least 4 of the conserved peptide sequences may be conserved across all four dengue virus serotypes DENV-1, DENV-2, DENV-3 and DENV-4. At least 5 of the conserved sequences may be conserved across all four dengue virus serotypes DENV-1, DENV-2, DENV-3 and DENV-4. At least 8 of the conserved peptide sequences may be conserved across all four dengue virus serotypes DENV-1, DENV-2, DENV-3 and DENV-4. At least 10 of the conserved peptide sequences may be conserved across all four dengue virus serotypes DENV-1, DENV-2, DENV-3 and DENV-4. At least 12 of the conserved peptide sequences may be conserved across all four dengue virus serotypes DENV-1, DENV-2, DENV-3 and DENV-4. At least 15 of the conserved peptide sequences may be conserved across all four dengue virus serotypes DENV-1, DENV-2, DENV-3 and DENV-4.

In another embodiment, 100% of the conserved peptide sequences may be conserved across all four dengue virus serotypes DENV-1, DENV-2, DENV-3 and DENV-4. Alternatively, at least 90% of the conserved peptide sequences may be conserved across all four dengue virus serotypes DENV-1, DENV-2, DENV-3 and DENV-4. Further alternatively, at least 80% of the conserved peptide sequences may be conserved across all four dengue virus serotypes DENV-1, DENV-2, DENV-3 and DENV-4. Further alternatively, at least 60% of the conserved peptide sequences may be conserved across all four dengue virus serotypes DENV-1, DENV-2, DENV-3 and DENV-4. Further alternatively, at least 50% of the conserved peptide sequences may be conserved across all four dengue virus serotypes DENV-1, DENV-2, DENV-3 and DENV-4.

The plurality of conserved peptide sequences may be from distinct regions of the non-structural protein sequence relative to each other (i.e. not-naturally concurrent). For example, in the wild-type genotype the conserved sequences may be separated in the wild-type genotypes by variable/non-conserved sequences. The plurality of conserved peptide sequences may not, or may not significantly, overlap with each other. Two or more, or all, of the plurality of conserved peptide sequences may be directly joined together in the protein, for example not comprising any non-conserved residues there between. The protein sequence may not be found in nature. The protein may not comprise non-conserved sequences or residues. The conserved peptide sequences may not be distanced apart by more than 1, 2, 3, 4, or 5 residues in the protein sequence.

The protein may further comprise at least one conserved peptide sequence conserved across 2 or 3 dengue virus serotypes selected from DENV-1, DENV2, DENV-3 and DENV-4, and wherein the conserved peptide sequence comprises at least part of a sequence of a non-structural protein of the Dengue virus serotypes. The protein may further comprise at least one conserved peptide sequence conserved across 2 dengue virus serotypes selected from DENV-1, DENV2, DENV-3 and DENV-4, and wherein the conserved peptide sequence comprises at least part of a sequence of a non-structural protein of the Dengue virus serotypes. The protein may further comprise at least one conserved peptide sequence conserved across 3 dengue virus serotypes selected from DENV-1, DENV2, DENV-3 and DENV-4, and wherein the conserved peptide sequence comprises at least part of a sequence of a non-structural protein of the Dengue virus serotypes. The protein may further comprise a plurality of conserved peptide sequences conserved across 2 and/or 3 dengue virus serotypes selected from DENV-1, DENV2, DENV-3 and DENV-4, and wherein the conserved peptide sequence comprises at least part of a sequence of a non-structural protein of the Dengue virus serotypes.

The protein may comprise:

a plurality of conserved peptide sequences conserved across all 4 dengue virus serotypes of DENV-1, DENV2, DENV-3 and DENV-4; and a conserved peptide sequence conserved across 2 or 3 dengue virus serotypes selected from DENV-1, DENV2, DENV-3 and DENV-4, wherein the conserved peptide sequences comprise at least part of a sequence of a non-structural protein of the Dengue virus serotypes.

In one embodiment at least two of the conserved peptide sequences are conserved across 2 or 3 dengue virus serotypes selected from DENV-1, DENV-2, DENV-3 and DENV-4. In another embodiment at least three of the conserved peptide sequences are conserved across 2 or 3 dengue virus serotypes selected from DENV-1, DENV-2, DENV-3 and DENV-4. At least 4 of the conserved peptide sequences may be conserved across 2 or 3 dengue virus serotypes selected from DENV-1, DENV-2, DENV-3 and DENV-4. At least 5 of the conserved sequences may be conserved across 2 or 3 dengue virus serotypes selected from DENV-1, DENV-2, DENV-3 and DENV-4. At least 8 of the conserved peptide sequences may be conserved across 2 or 3 dengue virus serotypes selected from DENV-1, DENV-2, DENV-3 and DENV-4. At least 10 of the conserved peptide sequences may be conserved across 2 or 3 dengue virus serotypes selected from DENV-1, DENV-2, DENV-3 and DENV-4.

The protein may further comprise at least one intra-serotype conserved peptide sequence (i.e. a conserved peptide sequence conserved within a single dengue virus serotype) of DENV-1, DENV2, DENV-3 or DENV-4, and wherein the intra-serotype conserved peptide sequence comprises at least part of a sequence of a non-structural protein of the Dengue virus serotype. The protein may further comprise a plurality of conserved peptide sequences conserved within a single dengue virus serotype selected from DENV-1, DENV2, DENV-3 and DENV-4, and wherein the conserved peptide sequence comprises at least part of a sequence of a non-structural protein of the Dengue virus serotype.

In another embodiment, the protein may comprise:

a plurality of conserved peptide sequences conserved across all 4 dengue virus serotypes of DENV-1, DENV2, DENV-3 and DENV-4;

one or more conserved peptide sequence conserved across 2 or 3 dengue virus serotypes selected from DENV-1, DENV2, DENV-3 and DENV-4; and at least one intra-serotype conserved peptide sequence of DENV-1, DENV2, DENV-3 or DENV-4, wherein the intra-serotype conserved peptide sequences and conserved peptide sequences comprise at least part of a sequence of a non-structural protein of the Dengue virus serotypes.

In one embodiment the protein comprises at least two intra-serotype conserved peptide sequences from DENV-1, DENV2, DENV-3 and/or DENV-4. In another embodiment the protein comprises at least three intra-serotype conserved peptide sequences from DENV-1, DENV2, DENV-3 and/or DENV-4. In another embodiment the protein comprises at least 4, 5, 6, 7 or 8 intra-serotype conserved peptide sequences from DENV-1, DENV2, DENV-3 and/or DENV-4.

The conserved peptide sequences may be selected from the group comprising SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; and SEQ ID NO: 90; or combinations thereof.

The conserved peptide sequences conserved across all 4 dengue virus serotypes of DENV-1, DENV2, DENV-3 and DENV-4, may be selected from the group comprising SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; and SEQ ID NO: 22; or combinations thereof.

The conserved peptide sequences conserved across 2 or 3 dengue virus serotypes selected from DENV-1, DENV2, DENV-3 and DENV-4, may be selected from the group comprising SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; and SEQ ID NO: 52; or combinations thereof.

The conserved peptide sequences conserved within a single dengue virus serotype (i.e. intra-serotype) of DENV-1, DENV2, DENV-3 or DENV-4, may be selected from the group comprising SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; and SEQ ID NO: 71; or combinations thereof.

The protein may further comprise at least one sequence providing an epitope of a known immunogenic epitope of Dengue virus. Additionally or alternatively, the protein may comprise variants of known epitopes (also referred to as a "known epitope variant"). A known epitope variant may differ from the known epitope by one amino acid residue. Alternatively, a variant of a known epitope may differ from the known epitope by two amino acid residues. Epitope variants are identified as being present in the same residue location with one or more amino acid change from the epitope sources (4-6). The known epitope or epitope variant may comprise at least part of a conserved peptide sequence between two or more of DENV-1, DENV2, DENV-3 and DENV-4. In an embodiment where a conserved peptide sequence comprises a known epitope or a known epitope variant, the known epitope or known epitope variant may be substituted with any other known epitope variant, for example known epitope variants described herein.

The known immunogenic epitope, or variant thereof, of Dengue virus may comprise or consist of a sequence selected from any of the group comprising SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 111; SEQ ID NO: 112; SEQ ID NO: 113; and SEQ ID NO: 114; or combinations thereof.

Known epitopes or known epitope variants may comprise epitopes experimentally proven by Weiskopf et al[4] or from the IEDB Database[5,6]. A known epitope or known epitope variant may comprise a sequence that is conserved across all four serotypes of DENV-1, DENV-2, DENV-3, and DENV-4. Alternatively, known epitopes may comprise a sequence that is conserved across 2 or 3 serotypes of DENV-1, DENV-2, DENV-3, and DENV-4. The known epitope variant may comprise a sequence that is conserved across all, 2 or 3 serotypes of DENV-1, DENV-2, DENV-3, and DENV-4, with one or two residue changes to the known epitope.

In another embodiment, the protein may comprise:

a plurality of conserved peptide sequences conserved across all 4 dengue virus serotypes of DENV-1, DENV2, DENV-3 and DENV-4;

a conserved peptide sequence conserved across 2 or 3 dengue virus serotypes selected from DENV-1, DENV2, DENV-3 and DENV-4;

at least one intra-serotype conserved peptide sequence from DENV-1, DENV2, DENV-3 or DENV-4; and at least one known epitope variant, wherein the conserved peptide sequences comprise at least part of a sequence of a non-structural protein of the Dengue virus serotypes.

In an embodiment comprising a protein with at least one known epitope variant or a plurality of known epitope variants, the conserved peptide sequences may be selected from the group comprising SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; and SEQ ID NO: 90; or combinations thereof.

The known epitope(s) may be part of the above conserved peptide sequences. The known epitope variant(s) may be insertions into the conserved peptide sequences.

The protein may comprise or consist of the sequence of SEQ ID NO: 1, SEQ ID NO: 2, SEQ ID NO: 3, SEQ ID NO: 23, SEQ ID NO: 53, or SEQ ID NO: 72; or variants thereof. In one embodiment, the protein may comprise or consist of the sequence of SEQ ID NO: 1. In another embodiment, the protein may comprise or consist of the sequence of SEQ ID NO: 2. In one embodiment, the protein may comprise or consist of the sequence of SEQ ID NO: 3. In one embodiment, the protein may comprise or consist of the sequence of SEQ ID NO: 23. In one embodiment, the protein may comprise or consist of the sequence of SEQ ID NO: 53. In one embodiment, the protein may comprise or consist of the sequence of SEQ ID NO: 72.

Variants of the protein may comprise or consist of a sequence having at least 80% identity with the protein of the invention, for example any one of SEQ ID NO: 1, SEQ ID NO: 2, SEQ ID NO: 3, SEQ ID NO: 23, SEQ ID NO: 53, or SEQ ID NO: 72. Alternatively, variants of the protein may comprise or consist of a sequence having at least 85% identity with the protein of the invention. Variants of the protein may comprise or consist of a sequence having at least 90% identity with the conserved sequence. Variants of the protein may comprise or consist of a sequence having at least 95% identity with the protein of the invention. Variants of the protein may comprise or consist of a sequence having at least 98% identity with the protein of the invention. Variants of the protein may comprise or consist of a sequence having at least 99% identity with the protein of the invention.

Variants of conserved peptide sequences may comprise or consist of a sequence having at least 80% identity with the conserved peptide sequence. Alternatively, variants of conserved peptide sequences may comprise or consist of a sequence having at least 85% identity with the conserved peptide sequence. Variants of conserved peptide sequences may comprise or consist of a sequence having at least 90% identity with the conserved peptide sequence. Variants of conserved peptide sequences may comprise or consist of a sequence having at least 95% identity with the conserved peptide sequence. Variants of conserved peptide sequences may comprise or consist of a sequence having at least 98% identity with the conserved peptide sequence. Variants of conserved peptide sequences may comprise or consist of a sequence having at least 99% identity with the conserved peptide sequence. Variants of conserved peptide sequences may comprise or consist of a truncated sequence of the conserved peptide sequences. For example the sequences of SEQ ID NOs 4 to 22, 24 to 52, 54 to 71, or 73 to 90 herein may be truncated and still provide immunogenicity in the protein. The truncated sequence may comprise at least five amino acids of the sequences of SEQ ID NOs 4 to 22, 24 to 52, 58 to 71, or 73 to 90. Alternatively, the truncated sequence may comprise at least six amino acids of the sequences of SEQ ID NOs 4 to 22, 24 to 52, 54 to 71, or 73 to 90. Alternatively, the truncated sequence may comprise at least seven amino acids of the sequences of SEQ ID NOs 4 to 22, 24 to 52, 54 to 71, or 73 to 90. Alternatively, the truncated sequence may comprise at least eight amino acids of the sequences of SEQ ID NOs 4 to 22, 24 to 52, 54 to 71, or 73 to 90.

Reference to sequence "identity" used herein may refer to the percentage identity between two aligned sequences using standard NCBI BLASTp parameters (http://blast.ncbi.nlm-.nih.gov).

The plurality of conserved peptide sequences may comprise 5 or more conserved sequences. The plurality of conserved peptide sequences may comprise 8 or more conserved peptide sequences. The plurality of conserved sequences may comprise 10 or more conserved peptide sequences. The plurality of conserved peptide sequences may comprise 15 or more conserved peptide sequences. In one embodiment, the plurality of conserved peptide sequences consists of about 15 conserved peptide sequences.

At least one conserved peptide sequence may be at least about 15 amino acids in length. At least one conserved peptide sequence may be at least about 20 amino acids in length. At least one conserved peptide sequence may be no more than about 23 amino acids in length. At least one conserved peptide sequence may be no more than about 30 amino acids in length. The conserved peptide sequences may be an average length of about 18 amino acids in a population of conserved peptide sequences. The conserved peptide sequences may be an average length of between about 16 and about 20 amino acids in a population of conserved peptide sequences. The conserved peptide sequences may be an average length of between about 15 and about 23 amino acids in a population of conserved peptide sequences. The conserved peptide sequences may be an average length of between about 10 and about 30 amino acids in a population of conserved peptide sequences. The conserved peptide sequences may be an average length of between about 10 and about 40 amino acids in a population of conserved peptide sequences.

The non-structural (NS) protein may comprise NS1. The non-structural (NS) protein may comprise NS2. The non-structural (NS) protein may comprise NS3. The non-structural (NS) protein may comprise NS4. The non-structural (NS) protein may comprise NS5. The non-structural (NS) protein may be selected from NS1, NS2, NS3, NS4, or NS5. In one embodiment, the non-structural protein is selected from NS1, NS3, NS4, or NS5. In another embodiment, the non-structural protein is selected from NS3, NS4, or NS5. The peptide may comprise conserved sequences from non-structural proteins NS3, NS4, and NS5. The peptide may comprise conserved sequences from non-structural proteins NS1, NS3, NS4, and NS5. The conserved sequences may comprise sequences from non-structural proteins NS1, NS2, NS3, NS4, or NS5; or combinations thereof. The conserved sequences may comprise sequences from non-structural proteins NS1, NS3, NS4, or NS5; or combinations thereof. The conserved sequences may comprise sequences from non-structural proteins NS3, NS4, or NS5; or combinations thereof. The conserved sequence of NS1 may comprise SEQ ID NO: 117.

In one embodiment the protein is an isolated protein. In another embodiment, the protein may be encoded in nucleic acid or in a viral vector.

The protein may be immunogenic. The protein may be immunogenic in a mammal. The mammal may be human. The immune response may be a protective immune response. The protein may be capable of activating T-cell and antibody mediated immunity in a subject. The protein may be capable of activating T-cell mediated immunity in a subject. The protein may be capable of activating antibody-mediated immunity in a subject. In one embodiment the protein may comprise an NS1 sequence for inducing an antibody response in a subject. In one embodiment the protein may comprise an NS1, NS3, NS4 and NS5 sequence for inducing an antibody and T-cell response in a subject.

Combinations of proteins of the invention may be provided as a vaccine. For example, a prime and/or boost vaccine formulation may comprise nucleic acid or viral vector encoding two or more proteins of the invention.

The protein may be used in a vaccine in combination with another therapeutically or prophylactically active ingredient. The protein may be used in a vaccine in combination with an adjuvant.

According to another aspect of the invention there is provided a protein comprising the sequence of SEQ ID NO: 1; SEQ ID NO: 2; or SEQ ID NO: 3.

According to another aspect of the invention there is provided a protein comprising the sequence of SEQ ID NO: 23.

According to another aspect of the invention there is provided a protein comprising the sequence of SEQ ID NO: 53.

According to another aspect of the invention there is provided a protein comprising the sequence of SEQ ID NO: 72.

The protein may be provided in a pharmaceutically acceptable carrier.

According to another aspect of the invention there is provided a nucleic acid comprising a sequence encoding a protein according to the invention herein.

The nucleic acid may be a plasmid vector for vaccination. The nucleic acid may comprise viral vector sequences.

According to another aspect of the invention there is provided a viral vector comprising the nucleic acid according to the invention herein.

The viral vector may comprise a virus. The viral vector may comprise an adenovirus, such as a simian adenovirus. The viral vector may comprise an adenovirus when used in a prime vaccine of a prime boost regime. The viral vector may comprise ChAdOx 1 (a group E simian adenovirus, like the AdCh63 vector used safely in malaria trials). The viral vector may comprise AdCh63. The viral vector may comprise AdC3 or AdH6. The viral vector may be a human serotype. The viral vector may comprise Modified Vaccinia Ankara (MVA). The viral vector may comprise MVA when used as a vaccine boost in a prime boost regime. The viral vector may comprise Adeno-associated virus (AAV) or lentivirus. The viral vector may be an attenuated viral vector. The protein sequence of the invention may be cloned into any suitable viral vector that is known to elicit good immune response. Suitable viral vectors have been described in Dicks et al (Vaccine. 2015 Feb. 25; 33(9):1121-8. doi: 10.1016/j.vaccine.2015.01.042. Epub 2015 Jan. 25), Antrobus et al (Mol Ther. 2014 March; 22(3):668-74. doi: 10.1038/mt.2013.284. Epub 2013 Dec. 30), and (Warimwe et al. (Virol J. 2013 Dec. 5; 10:349. doi: 10.1186/1743-422X-10-349), which are incorporated herein by reference.

The viral vector may comprise or consist of a nucleic acid sequence selected from the group comprising SEQ ID NO: 118; SEQ ID NO: 119; SEQ ID NO: 120; SEQ ID NO: 121; SEQ ID NO: 122; SEQ ID NO: 123 SEQ ID NO: 124; and SEQ ID NO: 125.

According to another aspect of the invention there is provided a virus-like particle comprising the protein in accordance with the invention herein.

It is understood that a virus-like particle may provide viral structural proteins, such as envelope or capsid, but does not contain virus genetic material.

According to another aspect of the invention there is provided a composition comprising one or more of:

the protein according to the invention;
the nucleic acid according to the invention;
the virus-like particle according to the invention; and
the viral vector according to the invention.

The composition may be immunogenic, for example in a mammal, such as a human. The composition may comprise a pharmaceutically acceptable carrier. The composition may be a pharmaceutical composition comprising a pharmaceutically acceptable carrier. The composition may be for use in the prophylaxis or treatment of dengue viral infection.

According to another aspect of the invention there is provided a method of treatment or prophylaxis of dengue viral infection comprising the administration of:

the protein according to the invention;
the nucleic acid according to the invention;
the virus-like particle according to the invention;
the composition according to the invention or
the viral vector according to the invention.

The method of treatment or prophylaxis of dengue viral infection may be a method of vaccination.

According to another aspect of the invention there is provided an agent for use in the prophylaxis or treatment of dengue viral infection, the agent comprising or consisting of:

the protein according to the invention;
the composition according to the invention;
the nucleic acid according to the invention;
the viral vector according to the invention; or
the virus-like particle according to the invention.

According to another aspect of the invention there is provided the protein according to the invention; the composition according to the invention; the nucleic acid according to the invention; the virus-like particle according to the invention; or the viral vector according to the invention; for use in, or as, a vaccine.

According to another aspect of the invention there is provided a vaccine comprising the protein of the invention comprising or consisting of:

the protein according to the invention;
the composition according to the invention;
the nucleic acid according to the invention;
the viral vector according to the invention; or
the virus-like particle according to the invention.

The vaccine may be a prime vaccine. The vaccine may be a boost vaccine. Where a boost vaccine is provided following a prime vaccine, the protein may be different. For example, the protein may comprise a re-ordered sequence of conserved peptide sequences. The conserved peptide sequences may be identical, but the order in which they are provided in the protein may be changed.

Advantageously, the re-ordering of the conserved peptide sequences of the protein between prime and boost vaccines can avoid the provision of "false" epitopes formed across junctions of one conserved peptide sequence with another conserved peptide sequence. i.e. the same junction may not occur in the re-ordered protein.

According to another aspect of the invention, there is provided a protein according to the invention for use in, or as, a vaccine.

According to another aspect of the invention, there is provided a prime boost vaccination kit comprising a prime vaccination according to the invention;
a boost vaccination according to the invention.

The prime and boost vaccinations may be different. The prime and boost vaccination may differ in the protein sequence. The prime and boost vaccination may comprise different viral vectors.

The term "immunogenic", when applied to the protein or composition of the present invention means capable of eliciting an immune response in a human or animal body. The immune response may be protective.

The term "isolated", when applied to the protein of the present invention means a protein: (i) encoded by nucleic acids using recombinant DNA methods; or (ii); synthesized by, for example, chemical synthetic methods; or (iii) separated from naturally-occurring biological materials, and then purified using protein analytical procedures; or (iv) associated with chemical moieties (e.g. peptides, carbohydrates, fatty acids, and the like) other than those associated with the antigenic peptide in its naturally-occurring state; or (v) that do not occur in nature. An isolated protein of the invention includes a protein expressed from a nucleotide sequence encoding the protein, or from a recombinant vector containing a nucleotide sequence encoding the protein. An isolated protein of the invention may include a protein expressed from a virus-like particle.

The term "protective" means prevention of a disease, a reduced risk of disease infection, transmission and/or progression, reduced severity of disease, a cure of a condition or disease, an alleviation of symptoms, or a reduction in severity of a disease or disease symptoms.

The term "prophylaxis" means prevention of or protective treatment for a disease. The prophylaxis may include a reduced risk of disease infection, transmission and/or progression, or reduced severity of disease.

The term "treatment", means a cure of a condition or disease, an alleviation of symptoms, or a reduction in severity of a disease or disease symptoms.

According to another aspect of the invention, there is provided a composition comprising a peptide comprising at least part of an NS1 sequence which is conserved across all four dengue virus serotypes DENV-1, DENV-2, DENV-3 and DENV-4, and a pharmaceutically acceptable carrier.

The peptide comprising at least part of an NS1 sequence may comprise SEQ ID NO: 116. The peptide comprising at least part of an NS1 sequence may comprise or consist of SEQ ID NO: 117. The peptide comprising at least part of an NS1 sequence may comprise or consist of the NS1 (3-ladder.

The composition may not comprise sequences from NS2, NS3, NS4 and/or NS5 of dengue virus. The composition may not comprise wild-type dengue virus. The composition may not comprise structural dengue virus protein sequence.

According to another aspect of the invention, there is provided a peptide comprising at least part of an NS1 sequence which is conserved across all four dengue virus serotypes DENV-1, DENV-2, DENV-3 and DENV-4, for use as a vaccine.

The use may be with a pharmaceutically acceptable carrier. Additionally or alternatively, the use may be with an adjuvant.

According to another aspect of the invention, there is provided a virus-like particle comprising a peptide comprising at least part of an NS1 sequence which is conserved across all four dengue virus serotypes DENV-1, DENV-2, DENV-3 and DENV-4, and a pharmaceutically acceptable carrier.

The virus-like particle may not comprise sequences from NS2, NS3, NS4 and/or NS5 of dengue virus. The virus-like particle may not comprise wild-type dengue virus. The virus-like particle may not comprise non-conserved dengue virus peptide sequences. The virus-like particle may not comprise structural protein sequence of dengue virus.

According to another aspect of the invention, there is provided a nucleic acid encoding essentially or at least a peptide comprising at least part of an NS1 sequence which is conserved across all four dengue virus serotypes DENV-1, DENV-2, DENV-3 and DENV-4.

The nucleic acid encoding a peptide comprising at least part of an NS1 sequence may further encode non-dengue viral structural proteins.

According to another aspect of the invention, there is provided a viral vector encoding a peptide comprising at least part of an NS1 sequence which is conserved across all four dengue virus serotypes DENV-1, DENV-2, DENV-3 and DENV-4.

The viral vector or nucleic acid may be provided in a composition, wherein composition may comprise a pharmaceutically acceptable carrier. The viral vector or nucleic acid may not encode NS2, NS3, NS4 and/or NS5 of dengue virus. The viral vector or nucleic acid may not encode wild-type dengue virus. The viral vector or nucleic acid may not encode structural protein sequence of dengue virus. The viral vector or nucleic acid may not encode non-conserved protein/peptide sequence of dengue virus. The viral vector or nucleic acid may encode a peptide sequence comprising or consisting of SEQ ID NO: 116. The viral vector may encode a peptide sequence comprising or consisting of SEQ ID NO: 117. The viral vector or nucleic acid may comprise at least part of SEQ ID NO: 115. The viral vector or nucleic acid may encode the NS1 (3-ladder.

According to another aspect of the invention, there is provided a composition comprising or consisting of a peptide comprising at least part of an NS1 sequence which is conserved across all four dengue virus serotypes DENV-1, DENV-2, DENV-3 and DENV-4, for use as a vaccine.

The peptide comprising at least part of an NS1 sequence may comprise or consist of SEQ ID NO: 116. The peptide comprising at least part of an NS1 sequence may comprise or consist of SEQ ID NO: 117. The peptide comprising at least part of an NS1 sequence may comprise or consist of the NS1 (3-ladder.

According to another aspect of the invention, there is provided an isolated NS1 peptide sequence or a non-dengue viral vector encoding an NS1 sequence, for use as a vaccine. The NS1 sequence may consist of SEQ ID NO: 116 or SEQ ID NO: 117. The NS1 sequence may comprise or consist of the NS1 (3-ladder.

The above mentioned peptide or compositions of the peptide comprising at least part of an NS1 sequence (or nucleic acid or viral vectors encoding such as peptide) may also be applicable for use in the methods of treatment for the prevention or treatment of dengue virus infection.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

FIG. 1—Analysis of all 4 dengue virus serotypes showed that there is high degree of conservation in sequences that belong to the NS3, NS4 and NS5 proteins. Given the high degree of conservation 4 different array of sequences were proposed. Epitope data from previous studies, protein structure data, hydrophobicity and junctions between epitopes were taken into account. NSALL1 contains regions conserved in all serotypes NS3-NS5. NSALL2 provides regions conserved in all 4, only 3 and only 2 serotypes (e.g. a mosaic). NSALL3 is the same as NSALL2, but also contains regions conserved in only 1 serotype. NSALL4 is the same as NSALL3, but also containing variants of highly immunogenic epitopes from the literature.

Figure 2:
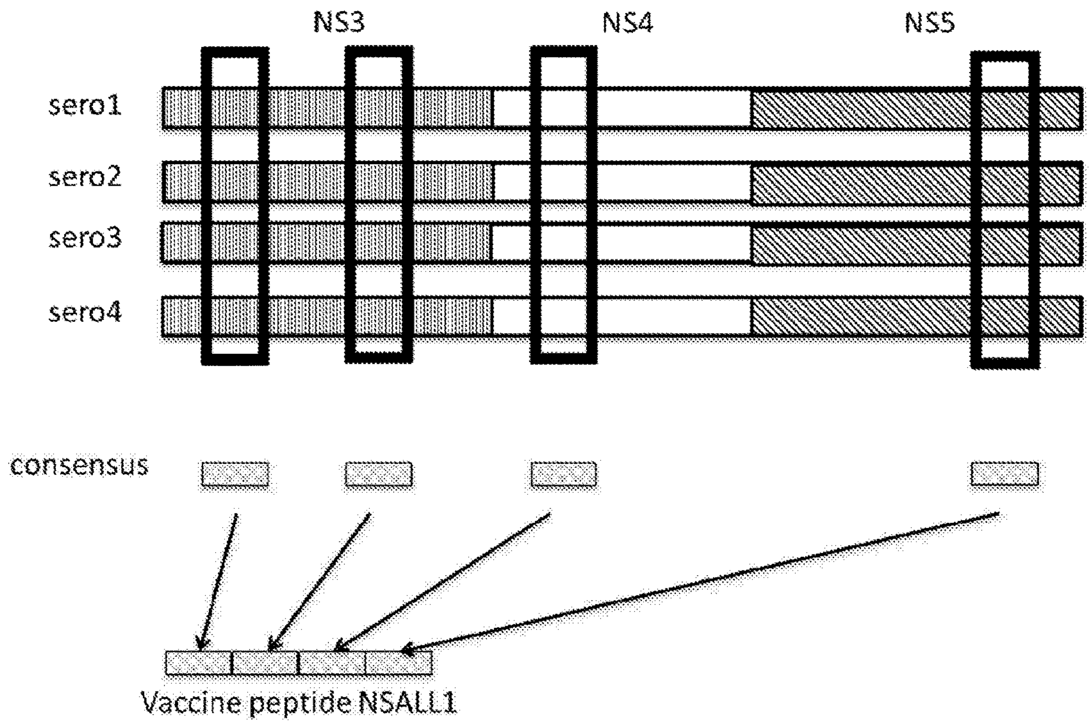

FIG. 2—is a schematic diagram illustrating the composition of a plurality of conserved sequences in NSALL1.

Figure 3:
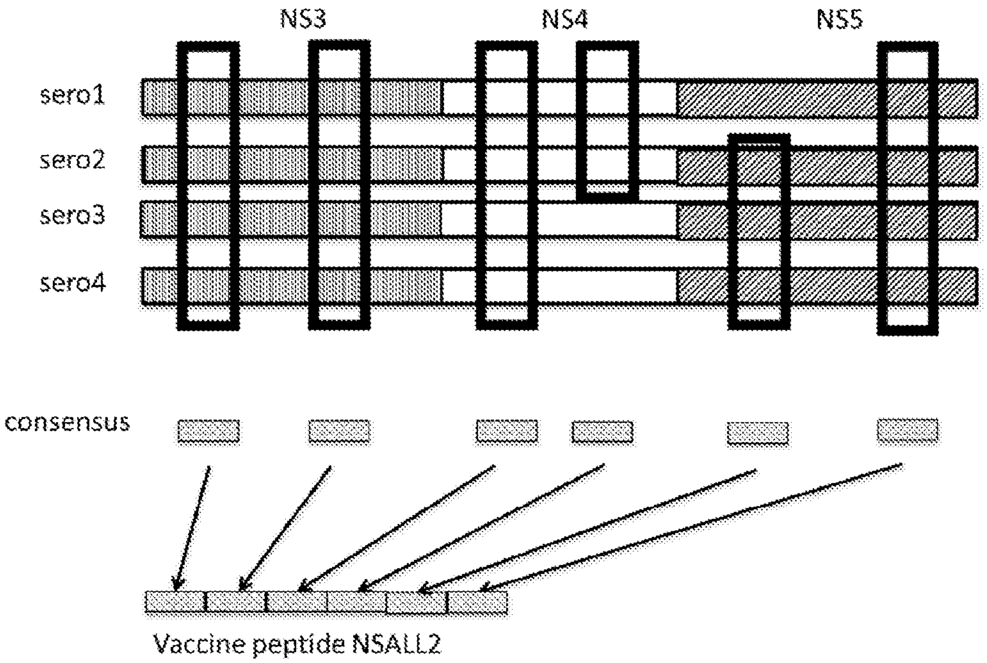

FIG. 3—is a schematic diagram illustrating the composition of a plurality of conserved sequences in NSALL2.

Figure 4:
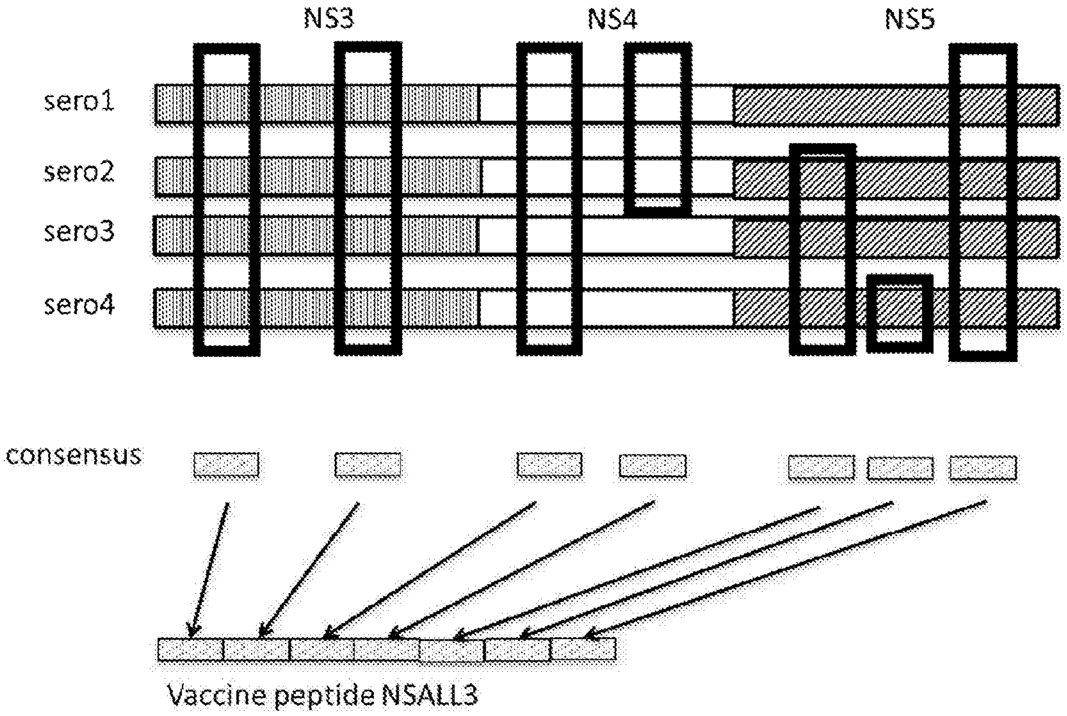

FIG. 4—is a schematic diagram illustrating the composition of a plurality of conserved sequences in NSALL3.

Figure 5:
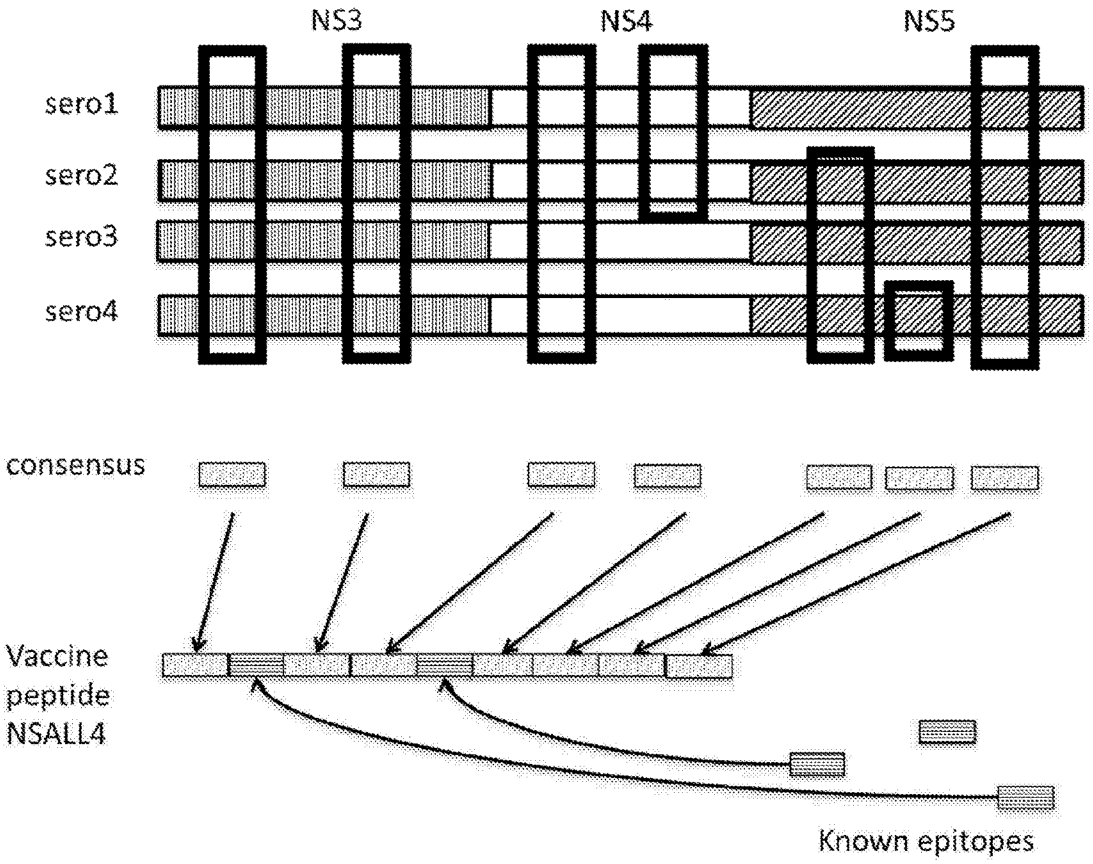

FIG. 5—is a schematic diagram illustrating the composition of a plurality of conserved sequences in NSALL4 plus additional known epitope variants.

Figure 6:
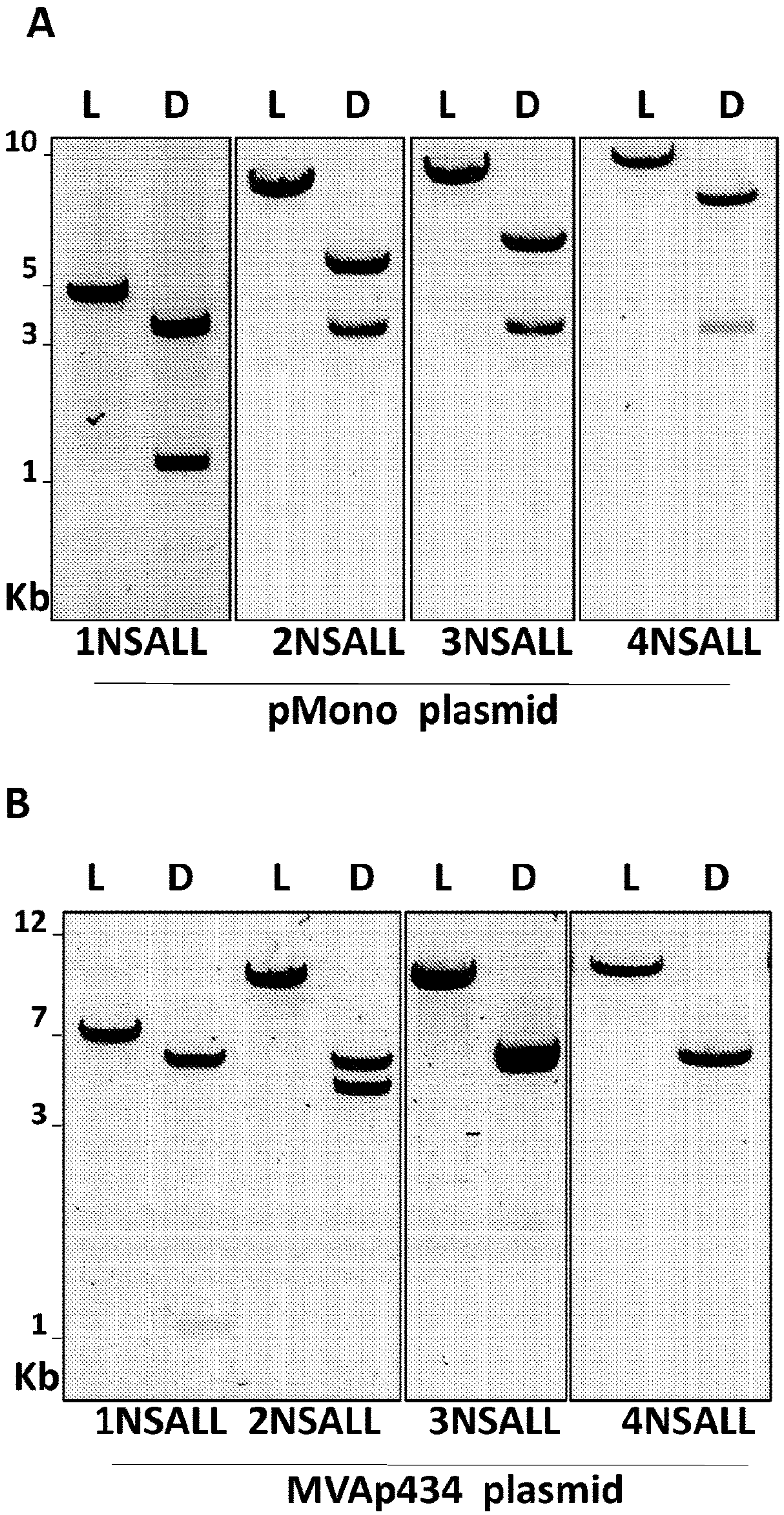

FIG. 6—Restriction patterns for both pMono (A) and MVAp434 (B) plasmids that contain the 4 arrays of highly conserved dengue virus sequences. L, linearised plasmid; D, double digestion. Molecular weight shows at left for each panel.

Figure 7:
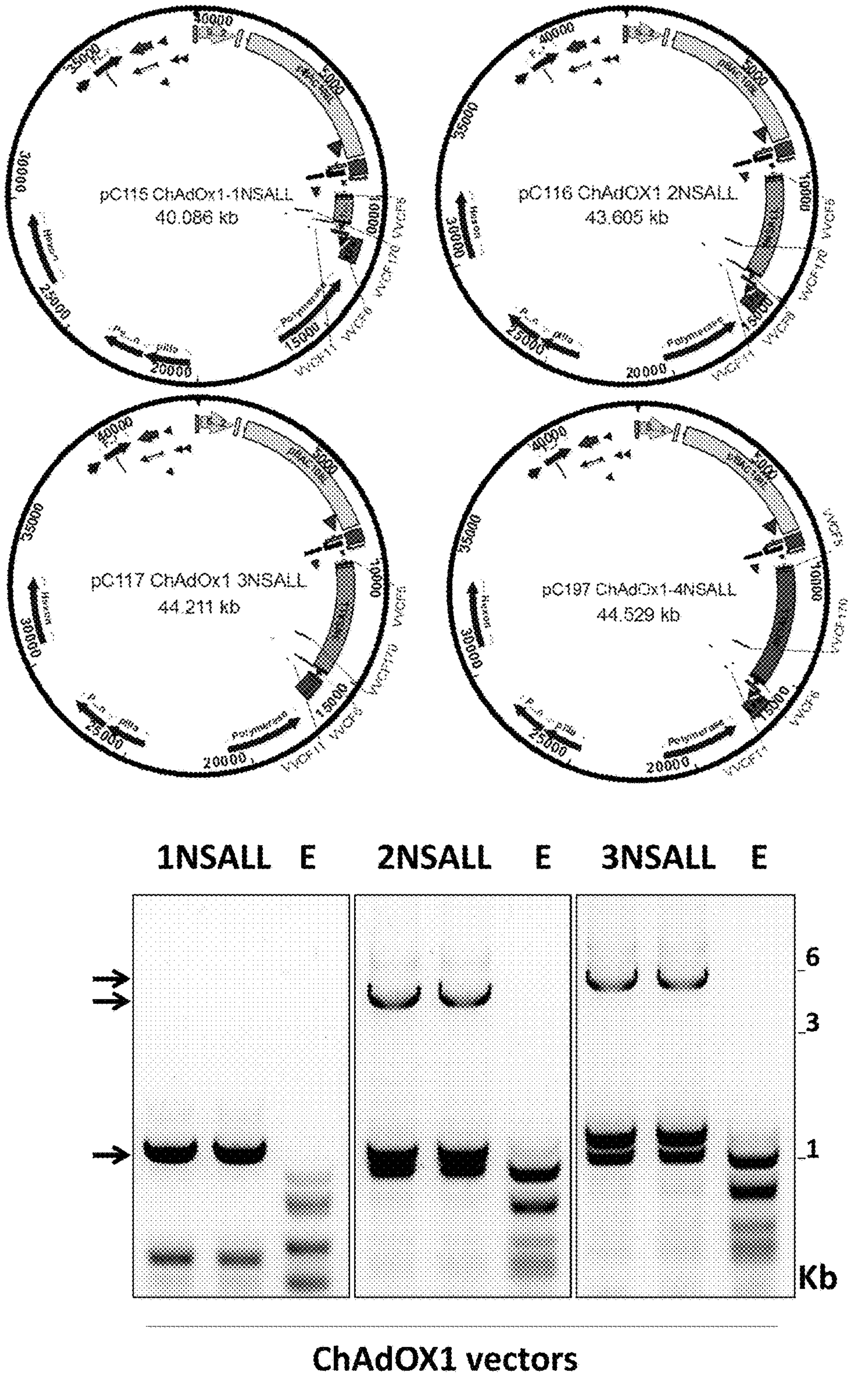

FIG. 7—Design of ChAdOX1 vectors and QC verification by PCR. Upper panel shows the DNA vector map of the four ChAdOX1 vectors containing the dengue virus sequences. Sizes of those vectors vary depending on the size of the sequences recombined from pMono-dengue vectors. Lower panel shows PCR amplification of ChAdOX1 vectors. Flanking primers were designed to amplify size-specific dengue sequences. PCR was performed in duplicate for each construct. Arrows show specific amplification fragments corresponding to the expected sizes (Table 1). As a negative control, ChAdOX1 empty vector (E) was used.

Figure 8:
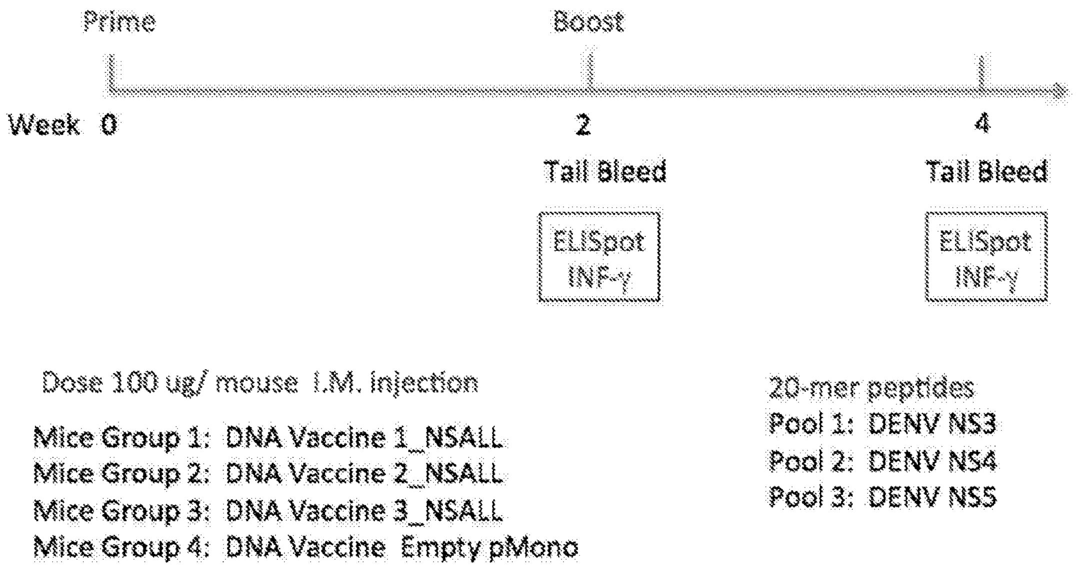

FIG. 8—Experimental plan for DNA vaccine prime-boost regimen in mice.

Figure 9:
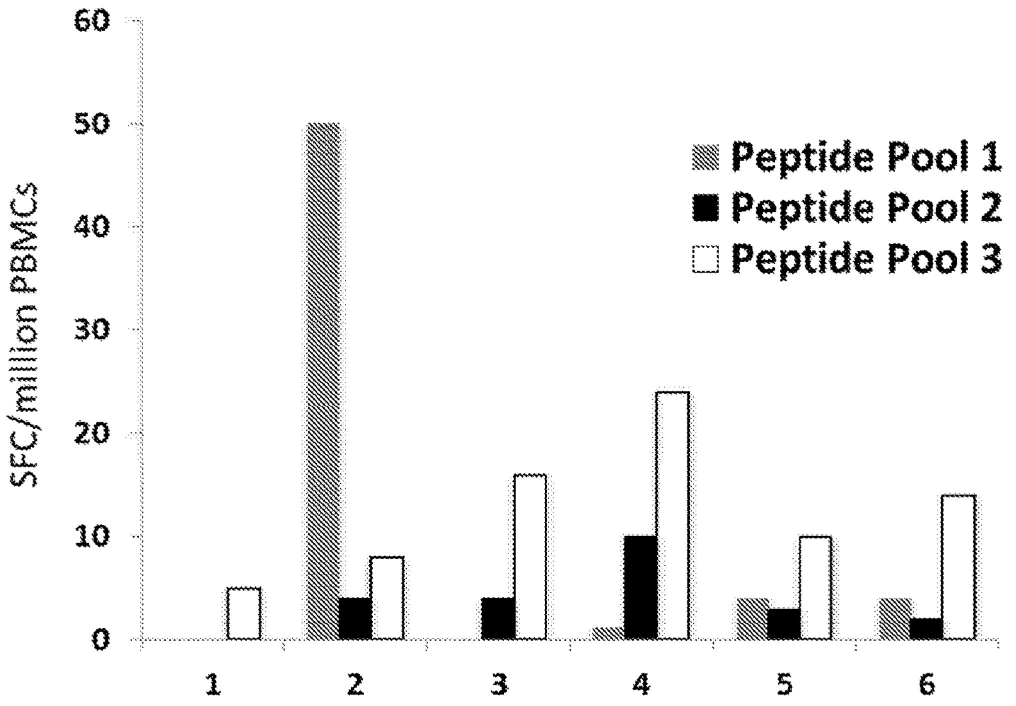
Figure 9:
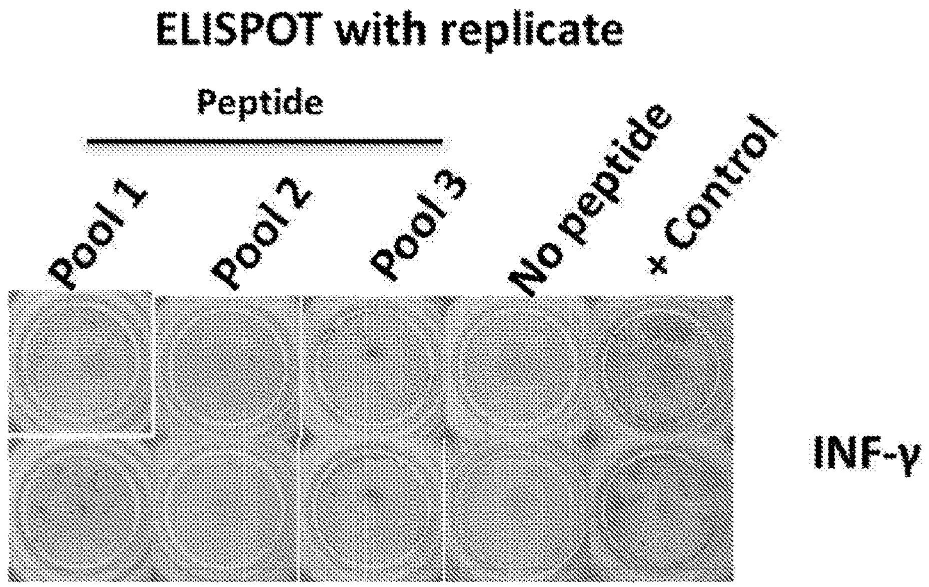

FIG. 9—Quantitative ex vivo IFN-γ ELISPOT analysis in mice vaccinated with a single dose of a DNA vaccine (prime) containing conserved sequences from Dengue Virus. Analysis shows responses two weeks after priming. Spot Forming Cells (SFC) (Right panel) is represented in Y-axis and mouse number in the X-axis (Left graph). Pool 1, 2 and 3 contained peptides from the Non-Structural proteins NS3, NS4 and NS5, respectively.

Figure 10:
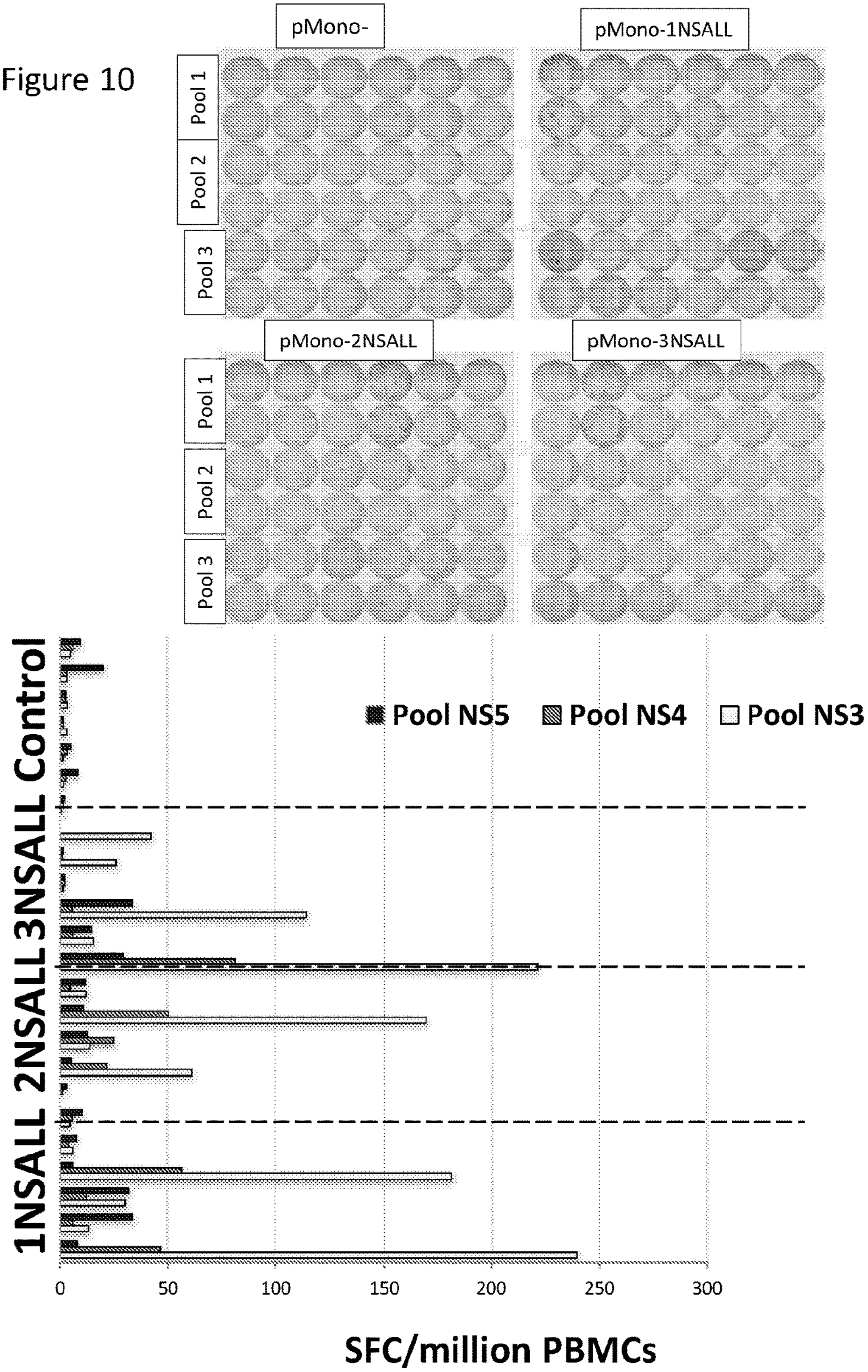

FIG. 10—Quantitative ex vivo IFN-γ ELISPOT analysis in mice vaccinated with prime-boost regime of DNA vaccines containing conserved sequences from Dengue Virus. All vaccines elicited specific responses when PBMCS were incubated with peptide pool 1, 2 and 3 containing non-Structural proteins NS3, NS4 and NS5, respectively. As a control, pMono-Empty vector was utilised (Upper Panel). Quantitate analysis showed responses two weeks after boost (Bottom Graph). Spot Forming Cells (SFC) are represented in Y-axis and mouse number in the X-axis (Lower Graph).

Figure 11:
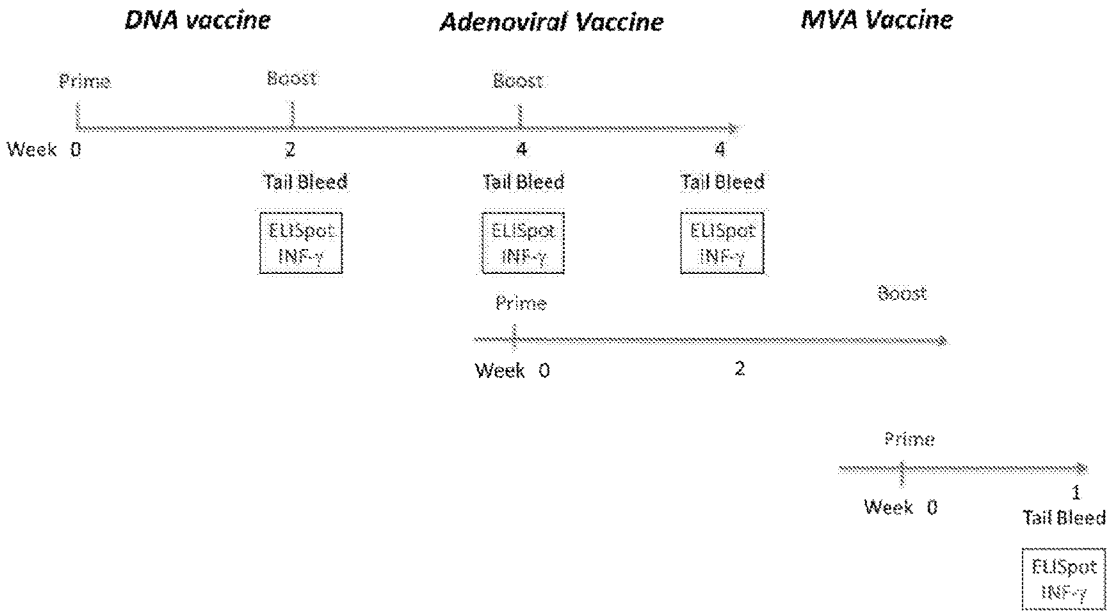

FIG. 11—shows a preclinical assessment plan for different DENV vaccine regimes.

Figure 12:
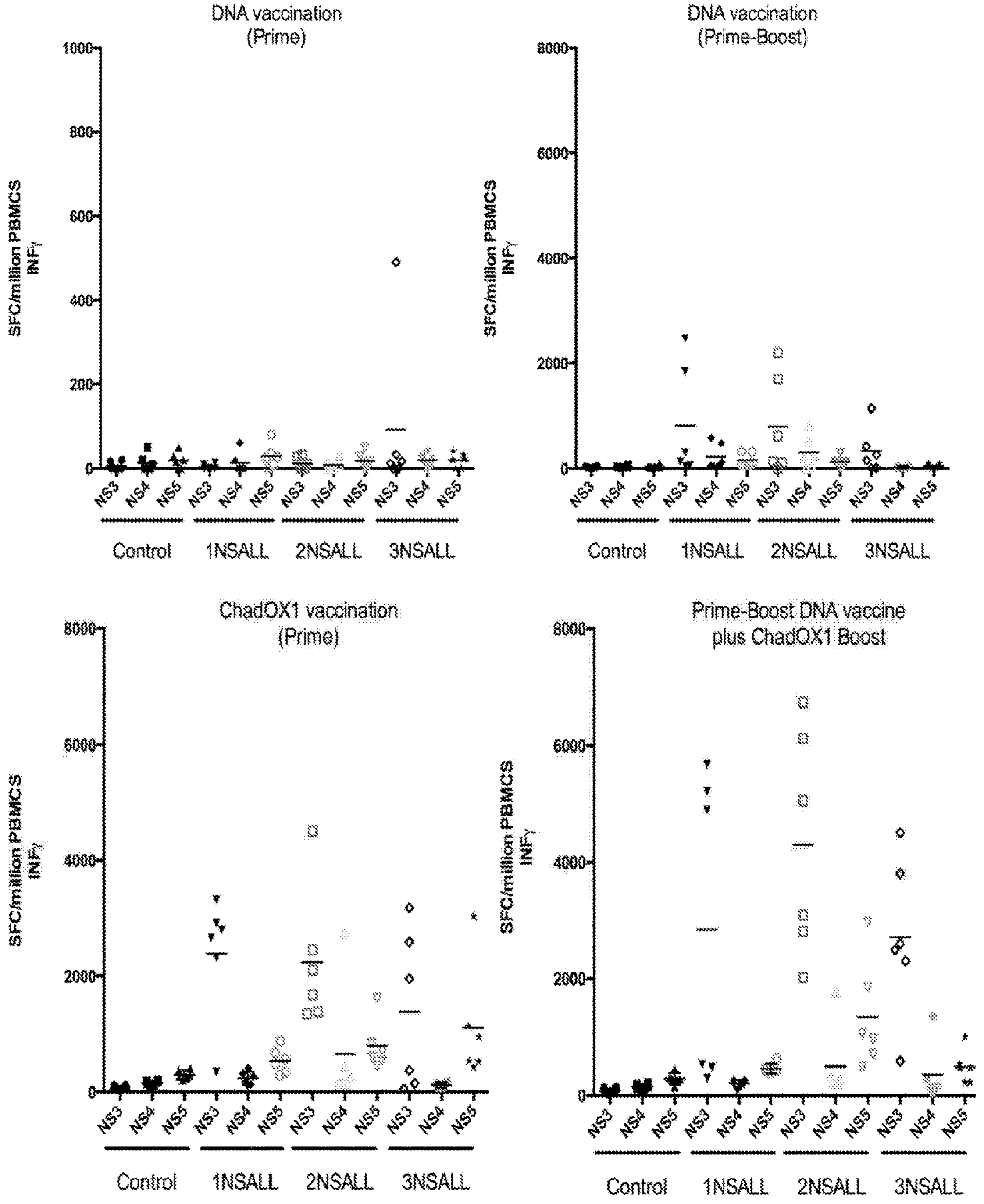

FIG. 12—ELISpot assay shows specific DENV-INF-γ production after vaccination of mice using different Prime-Boost Regimes (Left). Right graph shows IFN-γ spot forming cells (SFC) per million of PBMCs (Y axis) in different groups (X axis). Prime-Boost Regime of ChAd-DENV with MVA-DENV elicited a 10-fold increase of IFN-γ responses when compared to prime vaccination of DNA vaccine or ChAd-DENV only.

Figure 13:
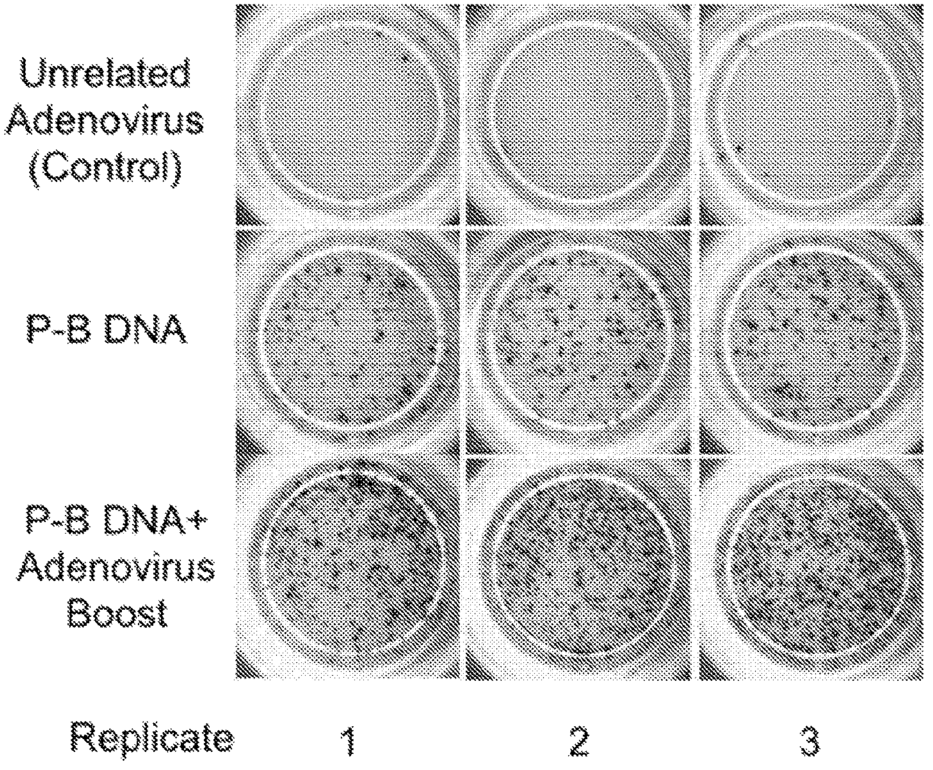

FIG. 13—IFN-γ production after 1NSALL-vaccination regime. Vaccinated mice PBMC's were incubated with a specific peptide pool. After 16 hours, indirect visualisation of cell producing IFN-γ was performed (blue spots). Top panel (Control); middle panel (Prime-Boost with DNA 1NSALL vaccine); Bottom panel (P-B DNA plus Prime ChadOX1-1NSALL followed by Boost with MVA-1NSALL. Figure shows 3 replicates.

Figure 14:
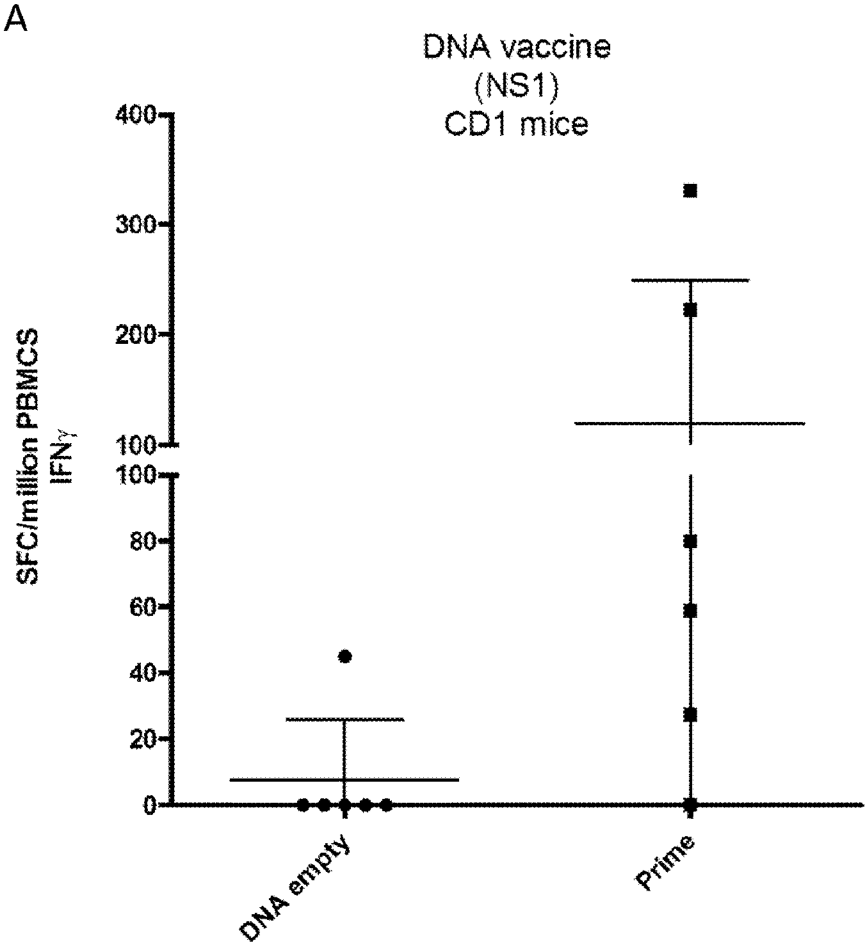
Figure 14:
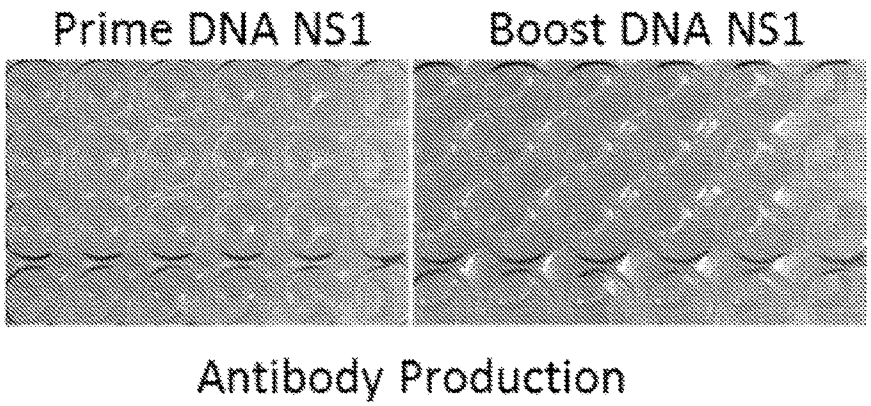
Figure 14C:
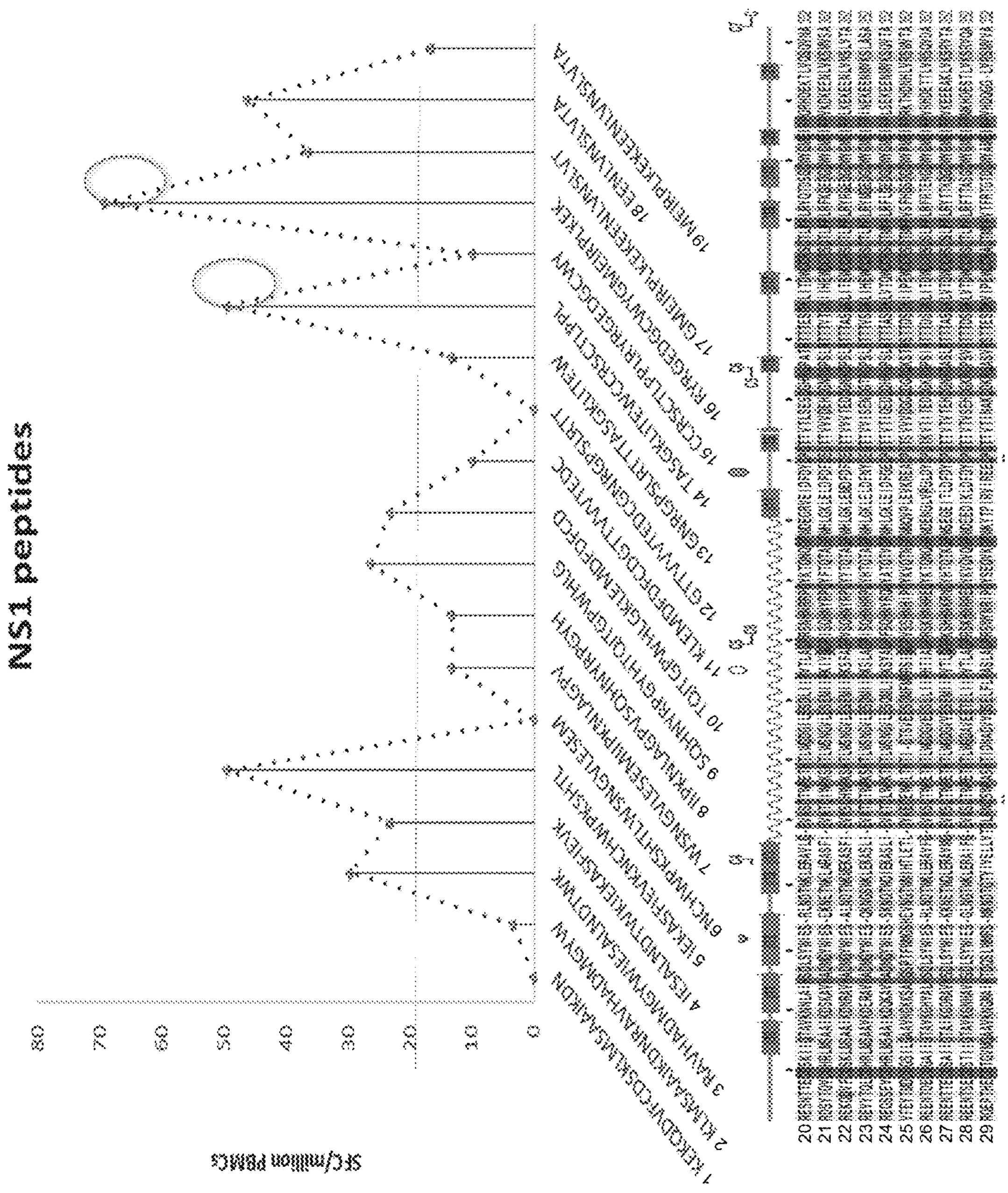

FIG. 14—Immune Responses Elicited by a DNA vaccine encoding NS1. (A) Mice were primed with DNA NS1 vaccine. After two weeks, PBMC's were incubated with a specific peptide pool for NS1 and indirect visualisation of cell producing IFN-γ was performed. DNA empty vector was used as a control. (B) ELISA was performed to detect specific antibodies (Ab) against NS1; yellow color represents relative production of NS1 Ab's. Left and right panel shows Ab production 2 weeks after prime and 2 weeks after boost (respectively). (C) ELISPOT experiments with single-well peptides demonstrate specific immunodominant epitopes (circles) that are contained in the highly conserved region of NS1 beta ladder. Bottom panel shows a diagrammatic representation of NS1 sequence in relation to the peptides shown in the graph. The amino acid sequences 1-29, as identified in (C), correspond to the following SEQ ID NOs as listed in the sequence listing: 1=SEQ ID NO: 305, 2=SEQ ID NO: 306, 3=SEQ ID NO: 307, 4=SEQ ID NO: 308, 5=SEQ ID NO: 309, 6=SEQ ID NO: 310, 7=SEQ ID NO: 311, 8=SEQ ID NO: 312, 9=SEQ ID NO:313, 10=SEQ ID NO:314, 11=SEQ ID NO: 315, 12=SEQ ID NO: 316, 13=SEQ ID NO: 317, 14=SEQ ID NO: 318, 15=SEQ ID NO: 319, 16=SEQ ID NO: 320, 17=SEQ ID NO: 321, 18=SEQ ID NO: 322, 19=SEQ ID NO: 323, 20=SEQ ID NO: 324, 21=SEQ ID NO: 325, 22=SEQ ID NO: 326, 23=SEQ ID NO: 327, 24=SEQ ID NO: 328, 25=SEQ ID NO: 329, 26=SEQ ID NO: 330, 27=SEQ ID NO: 331, 28=SEQ ID NO: 332, and 29=SEQ ID NO: 333.

The invention herein uses a novel alternative and safer approach to vaccination using non-replicating vectors to induce T cells to the internal (non-structural) antigens of the dengue virus. The T cell-based vaccine against dengue should protect against all dengue serotypes and avoid the risk of deleterious antibody-mediated enhancement. A novel insert has been developed, which comprises the most conserved segments of the internal NS3-NS5 genes and this is expressed in the simian adenoviral vector ChAdOxl (a group E simian adenovirus, like the AdCh63 vector used safely in malaria trials) and in the established boosting vector MVA. Results of Immunogenicity trials in mice indicate induction of good frequencies of T cells against the dengue conserved antigen.

For the vaccine design, a bioinformatics tool was developed to assess variability and conservation of DNA or protein sequences of variable pathogens in order to identify the most conserved sequences of DENV and thus design a universal dengue vaccine. Using this data functional and immunological data such as known epitopes was incorporated to create 4 vaccine candidates. One based purely on regions conserved in all 4 serotypes (NSALL1); a second which consists of a mosaic using consensus sequences from the structural proteins that are conserved in different numbers of serotypes providing a greater coverage (NSALL2); a third consists of a mosaic using consensus sequences from the structural proteins that are conserved in different numbers of serotypes and intra-serotype conserved sequences (NSALL3). Finally to try and further promote a protective CD8 response epitopes strings containing all know epitope variants were added to NSALL3 to form NSALL4.

An in house developed engine (Rev1.0) was used to identify conserved sequences using a specific criteria. A sliding window based approach with a sequence normalisation method was used to identify windows conserved within each serotype (intra-serotype). A conserved window was classed as having a window conservation value within one quartile of the overall conservation of the whole sequence. Subsequently conservation between serotypes (inter-serotype) was assessed by, identifying windows between serotypes at the same position and conserved (i.e. within their respective serotype first quartiles) and sharing a consensus identity of greater than 60%.

The invention involved the creation of four arrays of Dengue-conserved sequences retrieved by the bioinformatics analysis. Those sequences were synthesised (Geneart™) and cloned into destination plasmid vectors: pMono 2489 and MVAp434.

To produce the pMono2489-dengue vectors, both Geneart and Empty-pMono2489 plasmids were expanded and digested with Kpnl and Notl restriction enzymes. To produce MVAp434-dengue vectors, both pMono-Dengue and Empty-MVA-p434 plasmids were expanded and digested with Kpnl and Xhol restriction enzymes. Size-specific DNA inserts and DNA backbone plasmids were purified and ligated using T7 DNA Ligase (New England Biolabs). Restriction assays (FIG. 6) and DNA sequencing were performed to verify the correct construction of vectors. See Table 1 for specific size of inserts and vectors.

TABLE 1

Four arrays of highly conserved sequences from all Dengue Virus serotypes were synthesised and cloned into the respective vectors. Insert and vector sizes, as well as restriction sites used for cloning are depicted.

| Name | Insert Size (bp) | Pmono/Insert (bp) | MVA/Insert (bp) | CHADOX1/Insert (bp) |
|---|---|---|---|---|
| 1NSALL | 1152 | 4437 | 6865 | 40086 |
| 2NSALL | 4671 | 7956 | 10384 | 43605 |
| 3NSALL | 5277 | 8562 | 10990 | 44211 |
| 4NSALL | 5595 | 8880 | 11308 | 44529 |
| Restriction | MCS | KpnI/NotI | KpnI/XhoI | Recombination with Pmono |

Development of Adenoviral Vectors.

To generate the adenoviral vectored vaccine, Attl sites in pMono-containing dengue sequences and AttR sites in the adenoviral plasmid were recombined by using the Gateway LR Clonase (Life Technologies) and verified by Polymerase Chain Reaction (PCR) assay (FIG. 7) and DNA sequencing.

The resulting plasmids were further processed by the Jenner Institute Vector Core Facility to generate, expand and purify the adenoviral and MVA vaccines. In total, 4 adenoviral and 4 MVA vaccines were developed.

Prime-Boost Regimen of DNA Vaccines Containing Highly Conserved Sequences from Dengue Virus and Assessing Immunogenicity of the Vaccines by Ex Vivo IFN-γ ELISPOT Assay.

To confirm immunogenicity and to obtain preliminary results in mouse models, DNA vaccines containing highly conserved sequences from dengue virus were generated. Plasmids pMono-expressing dengue antigens were expanded and DNA purified by using the Endo-free DNA isolation Mega prep kit (Qiagen). Four groups of 6 mice were primed and boost (day 0 and day 16, respectively) with either pMono-1NSALL, pMono-2NSALL, pmono 3NSALL or pmono-Empty vaccines (FIG. 8).

Ex vivo IFN-gamma Enzyme-Linked ImmunoSpot (ELISPOT) was utilised in order to assess cellular responses in blood drawn from previously vaccinated mice. ELISPOTs were performed two weeks after prime and two weeks after boost.

Based on the sequences retrieved by the software, a set of 180 individual 20-mer peptides overlapping by 10 were designed for T-cell stimulation and sent for synthesis (Pepscan). Lyophilised peptides were solubilised in DMSO to a stock concentration of 100 mg/ml. Peptide pools were prepared to encompass NS3 (Pool 1), NS4A-B (Pool 2) and NS5 (Pool 3) proteins, respectively. Pool peptides sequences are provided at Appendix 1 below together with an indication of which NS protein the pool peptide matches.

Immunisation and tissue collection were performed following licensed procedures for animal handling. Groups of 6 outbred CD1 mice were immunised intramuscularly with 100 ug/mouse of the DNA vaccines diluted in sterile PBS. A control, mock-vaccinated group received an empty pMono plasmid vector at a similar dose of 100 ug/mouse. At 15 days after prime immunisation and at 15 days after boost immunisation, blood was taken by tail puncture. Peripheral Blood Mononuclear Cells (PBMCs) were isolated and cultured in the presence of peptide pools in ELISPOT plates previously incubated with an anti-IFN-gamma antibody (MAbTech). Splenocytes, prepared from naïve mice, were co-cultured at 2.5×10ˆ5 cells/well.

Peptide pool stimulation (10 ug/ml of each peptide) was performed by duplicate for each mouse. Positive controls for stimulation were included (Ionomycin, PMA or both). Upon development, plates were scanned and number of spots forming cells (SFC) per million of PBMCs were calculated. Background of wells without peptides was subtracted.

Preliminary results indicate that the construct is immunogenic in CD1 mice upon a single vaccination with the DNA vaccine expressing the conserved Dengue antigen sequences. For example, FIG. 9 shows responses elicited after prime vaccination with DNA-pmono 3NSALL. In this cohort of mice it can be appreciated that peptides pools corresponding to NS3 and NS5 elicited moderate immune responses in terms of INF-γ production. However, specific responses were enhanced when those mice were boosted with the same DNA vaccine. Two weeks after boost ELISPOT assay was conducted to search for specific INF-γ elicited by a 16 hour incubation period with peptide pools containing peptides from NS3, NS4 and NS5 dengue (FIG. 10).

Having demonstrated the ability of the DNA vaccines to elicit specific immune responses against the conserved regions; novel vaccine vectors based on Adenovirus (ChadOX1) and Modified Virus Ankara were made to express the sets of highly conserved dengue regions. A preclinical assessment was done in CD1 mice with Prime and Boost Regimes with different DNA and/or viral vector combinations (FIG. 11). ELISPOT assay showed that, after a prime vaccination with ChadOX1 Dengue Vaccine, s the number of PBMCs/million cells substantially increased when compared with prime-boost DNA mice groups. The regime in which mice were previously primed-boosted with DNA vaccines and later boosted with a ChadOX1 dengue vaccines showed further increase in comparison to ChadOX1 Dengue vaccines prime only (FIG. 12).

Alternatively, an embodiment of only a beta-ladder domain of the NS1 that contains a highly conserved region between all 4 dengue serotypes has been synthesized and tested as a DNA vaccine. DNA vaccine coding the NS1 (3-ladder, either in a prime or a prime boost regime, elicited specific immune responses (FIG. 13) against the conserved region identified in the sliding window-based method algorithm. Those responses included both cellular (T-Cell) and humoral antibody (B cell) responses.

Peptides used in the ELISPOT assay are shown in Appendix 2.

In summary, the results provide preliminary evidence that the Dengue sequences contained in DNA vaccines are capable to enter cells, transcribe and translate into proteins. Importantly, the ELISPOT analysis demonstrates the viability of the DNA vaccines to induce specific immune responses. Those responses were greatly increased by the use of adenoviral and/or MVA vectors containing the same dengue sequences either as priming or boosting agents.

Vaccine Peptide Sequences

The sequences below are annotated with ^ and/or *. ^ represents a junction between two conserved sequences. * represents a known epitope insert.

NSALL1 Sequence.

Contains fragments that are conserved in all 4 serotypes, *Sequence* underlined=epitope identified from the EIDB[5,6] or Weiskopf[4] sets (See table 1 and 2) and their variant which was manually added. ^=start/end of fragment.

>1. NSALL 1

(SEQ ID NO: 1)

LIL*APTRVVASEM*APTRVVAAEM*EE^RVVAAEMEEALKGLP^
SIAARGYISTRVEMGEAAAI^LNDWDFVVTTDISEMGANFK^PMPV
TAASAAQRRGRIGRN^DHAHWTEAKMLLDNI^KRTAAGIMKNPTVDG^YD
PKFEKQLGQVMLL^MRTTWALCEALTLATGP^LWEGNPGKFWNTTIAVS
M^PGKFWNTTIAVSMANIFRGSYLA^LCDIGESSPNPTIEE^YNMMGKR
EKKLGEFGKAK^SRAIWYMWLGARFLEFEALGF^MYADDTAGWDTRITE
DDL^FKLTYQNKVVKVQRP^VMDIISRKDQRGSGQVGTY

>1. NSALL 1 alternative A (SEQ ID NO: 2)

LIL*APTRVVASEM*EE^RVVAAEMEEALKGLP^SIAARGYISTRVEMGE
AAAI^LNDWDFVVTTDISEMGANFK^PMPVTAASAAQRRGRIGRN^DHAH
WTEAKMLLDNI^KRTAAGIMKNPTVDG^YDPKFEKQLGQVMLL^MRTTWA
LCEALTLATGP^LWEGNPGKFWNTTIAVSM^PGKFWNTTIAVSMANIFRG
SYLA^LCDIGESSPNPTIEE^YNMMGKREKKLGEFGKAK^SRAIWYMWLG
ARFLEFEALGF^MYADDTAGWDTRITEDDL^FKLTYQNKVVKVQRP^VMD
IISRKDQRGSGQVGTY

>1. NSALL 1 alternative B (SEQ ID NO: 3)

LIL*APTRVVAAEM*EE^RVVAAEMEEALKGLP^SIAARGYISTRVEMGE
AAAI^LNDWDFVVTTDISEMGANFK^PMPVTAASAAQRRGRIGRN^DHAH
WTEAKMLLDNI^KRTAAGIMKNPTVDG^YDPKFEKQLGQVMLL^MRTTWA
LCEALTLATGP^LWEGNPGKFWNTTIAVSM^PGKFWNTTIAVSMANIFRG
SYLA^LCDIGESSPNPTIEE^YNMMGKREKKLGEFGKAK^SRAIWYMWLG
ARFLEFEALGF^MYADDTAGWDTRITEDDL^FKLTYQNKVVKVQRP^VMD
IISRKDQRGSGQVGTY

Conserved Peptide Sequences of NSALL1

SEQ ID NO: 4
LIL*APTRVVASEM*APTRVVASEM*EE

SEQ ID NO: 5
RVVAAEMEEALKGLP

SEQ ID NO: 6
SIAARGYISTRVEMGEAAAI

SEQ ID NO: 7
LNDWDFVVTTDISEMGANFK

SEQ ID NO: 8
PMPVTAASAAQRRGRIGRN

SEQ ID NO: 9
DHAHWTEAKMLLDNI

-continued

SEQ ID NO: 10
KRTAAGIMKNPTVDG

SEQ ID NO: 11
YDPKFEKQLGQVMLL

SEQ ID NO: 12
MRTTWALCEALTLATGP

SEQ ID NO: 13
LWEGNPGKFWNTTIAVSM

SEQ ID NO: 14
PGKFVVNTTIAVSMANIFRGSYLA

SEQ ID NO: 15
LCDIGESSPNPTIEE

SEQ ID NO: 16
YNMMGKREKKLGEFGKAK

SEQ ID NO: 17
SRAIWYMWLGARFLEFEALGF

SEQ ID NO: 18
MYADDTAGWDTRITEDDL

SEQ ID NO: 19
FKLTYQNKVVKVQRP

SEQ ID NO: 20
VMDIISRKDQRGSGQVGTY

Optional Conserved Sequence of NSALL1 in Addition to, or Alternatively to SEQ ID NO: 4

LILAPTRVVASEMEE or (SEQ ID NO: 21)
LILAPTRVVAAEMEE. (SEQ ID NO: 22)

NSALL2 Fragments.

Contains Fragments Conserved in 2, 3 or 4 Serotypes. ^=Start/End of Fragment.

>2. NSALL2

(SEQ ID NO: 23)

SQIGAGVFKEGVFHTMWHVTRGAVLMHQGKRIEPSWADVKKDLISYGGGW
RLEGEWDEGEEVQVIAVEPGKNPKAVQT^GEIGAIALDFKPGTSGSPIVN
REG^VGLYGNGVVTKSGAYVSAIAQT^FRKRNLTIMDLHPGAGKTKRYLP
AIVREAIKRRLRTLILAPTRVVAAEMEEALKGLPIRYQTTAIKAEHTGKE
IVDLMCHATFTMRLLSPVRVPNYNLIIMDEAHFTDPASIAARGYISTRVE
MGEAAAIFMTATPPGSADAFPQSNAPIEDEEREIPERSWNSGFDWITDFA
GKTVWFVPSIKAGNDIANCLRKNGKKVIQLSRKTFDTEYPKTKLNDWDFV
VTTDISEMGANFKADRVIDPRRCLKPVILTDGPERVILAGPMPVTAASAA
QRRGRIGRNHKKENDQYIYMGQPLNNDEDHAHWTEAKMLLDNINTPEGII
PALFEPEREKSAAIDGEYRLRGEARKTFVELMRRGDLPVWLSYKVASAGF
QYKDREWCFDGERNNQILEENMDVEIWT^EGE^KKKLRPRWLDARTYADP
^HALEELPETLETLLLLALLG^FLFFLSGKGIGKMSIGLCCIIAAS^LLW
MAEIQPHWIAASIILEFFLMVLLIPEPEKQRTPQDNQLAYVVIGILTLAA
AIAANEMGLLETTKKDLGIG^AILDVDLHPASAWTLYAVATTIITPMLRH
TIENSTANVSLTAIANQAAVLMGLDKGWPISKMDLGVPLLALGCYSQVNP
LTLT^HYAIIGPGLQAKATREAQKRTAAGIMKNPTVDGIMAIDLDPIPYD

-continued

PKFEKQLGQVMLLILC^SQILLMRTTWALCEALTLATGPITTLWEGNPGK
FWNTTIAVSMANIFRGSYLAGAGLAFSLIKN^GETLGEKWKRQLNQLDKS
^FEEYKKSGILEVDRTEAKEAI^MV^VIDLGCGRGGWSYYCAGLKKVR^G
YTKGGPGHEEPIPMATYGWNLVKLHSGVDVFF^EKCDTLLCDIGESSPNP
TIEEGRTLRVLKMVEPWLKG^NQFCIKILNPYMPSVIE^LEKLQRKHGGM
LVRNPLSRNSTHEMYWVSNGTGNIVSAVNMISRMLINRFTMAHK^DEDNP
YKTWAYHGSYEVKATGSASSMVNGVVKLLTKPWDVVPMVTQMAMTDTTPF
GQQRVFKEKVDTRTPEA^QDENGWKSA^LHLEGKCESCVYNMMGKREKKL
GEFGKAKGSRAIWYMWLGARFLEFEALGFLNEDHWFSRENSLSGVEGEGL
^LGYILRDISKIPGGAMYADDTAGWDTRITEDDLHNEEK^LAKAIFKLTY
QNKVVKVQRPTPRGAVMDIISRKDQRGSGQVGTYGLNTF^TNMEAQLIRQ
MEAE^QWEPSKGWHDWQQVPFCSHHFH^IFMKDGRKLVVPCRNQDELIGR
ARISQGAGWSLRETACLGKSYAQMWQLMYFHRRDLRLASNAICSAVPSHW
VP^SRTTWS^HEWMTTEDMLAVWNRVW^HSWEDVPYLGKREDQWCGSLIG
LTSRATWAKNI

Conserved Peptide Sequences of NSALL2

SEQ ID NO: 24
SQIGAGVFKEGVFHTMWHVTRGAVLMHQGKRIEPSWADVKKDLISYGGG
WRLEGEWDEGEEVQVIAVEPGKNPKAVQT

SEQ ID NO: 25
GEIGAIALDFKPGTSGSPIVNREG

SEQ ID NO: 26
VGLYGNGVVTKSGAYVSAIAQT

SEQ ID NO: 27
FRKRNLTIMDLHPGAGKTKRYLPAIVREAIKRRLRTLILAPTRVVAAEME
EALKGLPIRYQTTAIKAEHTGKEIVDLMCHATFTMRLLSPVRVPNYNLII
MDEAHFTDPASIAARGYISTRVEMGEAAAIFMTATPPGSADAFPQSNAPI
EDEEREIPERSWNSGFDWITDFAGKTVWFVPSIKAGNDIANCLRKNGKKV
IQLSRKTFDTEYPKTKLNDWDFVVTTDISEMGANFKADRVIDPRRCLKPV
ILTDGPERVILAGPMPVTAASAAQRRGRIGRNHKKENDQYIYMGQPLNND
EDHAHWTEAKMLLDNINTPEGIIPALFEPEREKSAAIDGEYRLRGEARKT
FVELMRRGDLPVWLSYKVASAGFQYKDREWCFDGERNNQILEENMDVEIW
TEGE

SEQ ID NO: 28
KKKLRPRWLDARTYADP

SEQ ID NO: 29
HALEELPETLETLLLLALLG

SEQ ID NO: 30
FLFFLSGKGIGKMSIGLCCIIAAS

SEQ ID NO: 31
LLWMAEIQPHWIAASIILEFFLMVLLIPEPEKQRTPQDNQLAYVVIGILT
LAAAIAANEMGLLETTKKDLGIG

SEQ ID NO: 32
AILDVDLHPASAWTLYAVATTIITPMLRHTIENSTANVSLTAIANQAAVL
MGLDKGWPISKMDLGVPLLALGCYSQVNPLTLT

SEQ ID NO: 33
HYAIIGPGLQAKATREAQKRTAAGIMKNPTVDGIMAIDLDPIPYDPKFEK
QLGQVMLLILC

SEQ ID NO: 34
SQILLMRTTWALCEALTLATGPITTLWEGNPGKFWNTTIAVSMANIFRGS
YLAGAGLAFSLIKN

SEQ ID NO: 35
GETLGEKWKRQLNQLDKS

SEQ ID NO: 36
FEEYKKSGILEVDRTEAKEAIMV

SEQ ID NO: 37
VIDLGCGRGGWSYYCAGLKKVR

SEQ ID NO: 38
GYTKGGPGHEEPIPMATYGWNLVKLHSGVDVFF

SEQ ID NO: 39
EKCDTLLCDIGESSPNPTIEEGRTLRVLKMVEPWLKG

SEQ ID NO: 40
NQFCIKILNPYMPSVIE

SEQ ID NO: 41
LEKLQRKHGGMLVRNPLSRNSTHEMYWVSNGTGNIVSAVNMISRMLINR
FTMAHK

SEQ ID NO: 42
DEDNPYKTWAYHGSYEVKATGSASSMVNGVVKLLTKPWDVVPMVTQMAM
TDTTPFGQQRVFKEKVDTRTPEA

SEQ ID NO: 43
QDENGWKSA

SEQ ID NO: 44
LHLEGKCESCVYNMMGKREKKLGEFGKAKGSRAIWYMWLGARFLEFEALG
FLNEDHWFSRENSLSGVEGEGL

SEQ ID NO: 45
LGYILRDISKIPGGAMYADDTAGWDTRITEDDLHNEEK

SEQ ID NO: 46
LAKAIFKLTYQNKVVKVQRPTPRGAVMDIISRKDQRGSGQVGTYGLNTF

SEQ ID NO: 47
TNMEAQLIRQMEAE

SEQ ID NO: 48
QWEPSKGWHDWQQVPFCSHHFH

SEQ ID NO: 49
IFMKDGRKLVVPCRNQDELIGRARISQGAGWSLRETACLGKSYAQMWQLM
YFHRRDLRLASNAICSAVPS
HWVP

SEQ ID NO: 50
SRTTWS

SEQ ID NO: 51
HEWMTTEDMLAVWNRVW

SEQ ID NO: 52
HSWEDVPYLGKREDQWCGSLIGLTSRATWAKNI

NSALL3 Fragments.

Contains fragments conserved in 1, 2, 3 or all 4 serotypes. ^=start/end of fragment. Epitopes identified (all marked with "*" in table 3) are underlined.

>3. NSALL3

(SEQ ID NO: 53)

SQIGAGVFKEGVFHTMWHVTRGAVLMHQGKRIEPSWADVKKDLISYGGGW
RLEGEWDEGEEVQVIAVEPGKNPKAVQTKPGLFKTPEGEIGAIALDFKPG
TSGSPIVNREGKVVGLYGNGVVTKSGAYVSAIAQTNAE^PLPEIEDEVFR
KRNLTIMDLHPGAGKTKRYLPAIVREAIKRRLRTLILAPTRVVAAEMEEA
LKGLPIRYQTTAIKAEHTGKEIVDLMCHATFTMRLLSPVRVPNYNLIIMD
EAHFTDPASIAARGYISTRVEMGEAAAIFMTATPPGSADAFPQSNAPIED
EEREIPERSWNSGFDWITDFAGKTVWFVPSIKAGNDIANCLRKNGKKVIQ
LSRKTFDTEYPKTKLNDWDFVVTTDISEMGANFKADRVIDPRRCLKPVIL
TDGPERVILAGPMPVTAASAAQRRGRIGRNHKKENDQYIYMGQPLNNDED
HAHWTEAKMLLDNINTPEGIIPALFEPEREKSAAIDGEYRLRGEARKTFV
ELMRRGDLPVWLSYKVASAGFQYKDREWCFDGERNNQILEENMDVEIWTK
EGE^KKKLRPRWLDARTYADPLALKEFKDFAAGRKSIA^TEIGRVPSHLA
HRTR^AYQHALEELPETLETLLLLALLGA^FLFFLSGKGIGKMSIGLCCI
IAAS^LLWMAEIQPHWIAASIILEFFLMVLLIPEPEKQRTPQDNQLAYVV
IGILTLAAAIAANEMGLLETTKKDLGIGHVA^PTAILDVDLHPASAWTLY
AVATTIITPMLRHTIENSTANVSLTAIANQAAVLMGLDKGWPISKMDLGV
PLLALGCYSQVNPLTLTAAVLLLITHYAIIGPGLQAKATREAQKRTAAGI
MKNPTVDGIMAIDLDPIPYDPKFEKQLGQVMLLILCVSQILLMRTTWALC
EALTLATGPITTLWEGNPGKFWNTTIAVSMANIFRGSYLAGAGLAFSLIK
N^RRGTGAQGETLGEKWKRQLNQLDKSEFEEYKKSGILEVDRTEAKEAIK
RGETDHHAVSRGSAKLRWFVERNMVIPEGRVIDLGCGRGGWSYYCAGLKK
VREVRGYTKGGPGHEEPIPMATYGWNLVKLHSGVDVFF^PEKCDTLLCDI
GESSPNPTIEEGRTLRVLKMVEPWLKG^NQFCIKILNPYMPSVIEELEKL
QRKHGGMLVRNPLSRNSTHEMYWVSNGTGNIVSAVNMISRMLINRFTMAH
KKPTYERDVDLGAG^STWHYDEDNPYKTWAYHGSYEVKATGSASSMVNGV
VKLLTKPWDVVPMVTQMAMTDTTPFGQQRVFKEKVDTRTPEAKE^NAAIG
AVFQDENGWKSAREAVEDS^ERALHLEGKCESCVYNMMGKREKKLGEFGK
AKGSRAIWYMWLGARFLEFEALGFLNEDHWFSRENSLSGVEGEGLHKLGY
ILRDISKIPGGAMYADDTAGWDTRITEDDLHNEEKI^LAKAIFKLTYQNK
VVKVQRPTPRGAVMDIISRKDQRGSGQVGTYGLNTF^TNMEAQLIRQMEA
EGVIT^ECGVDRLKRMAISGDDCVVKP^PQWEPSKGWHDWQQVPFCSHHF
HEIFMKDGRKLVVPCRNQDELIGRARISQGAGWSLRETACLGKSYAQMWQ
LMYFHRRDLRLASNAICSAVPSHWVPTSRTTWSIHAHHEWMTTEDMLAVW
NRVWIEENPWMEDKTHIHSWEDVPYLGKREDQWCGSLIGLTSRATWAKNI

Conserved Peptide Sequences of NSALL3

SEQ ID NO: 54

SQIGAGVFKEGVFHTMWHVTRGAVLMHQGKRIEPSWADVKKDLISYGGGW
RLEGEWDEGEEVQVIAVEPGKNPKAVQTKPGLFKTPEGEIGAIALDFKPG
TSGSPIVNREGKVVGLYGNGVVTKSGAYVSAIAQTNAE

-continued

SEQ ID NO: 55

PLPEIEDEVFRKRNLTIMDLHPGAGKTKRYLPAIVREAIKRRLRTLILAP
TRVVAAEMEEALKGLPIRYQTTAIKAEHTGKEIVDLMCHATFTMRLLSPV
RVPNYNLIIMDEAHFTDPASIAARGYISTRVEMGEAAAIFMTATPPGSAD
AFPQSNAPIEDEEREIPERSWNSGFDWITDFAGKTVWFVPSIKAGNDIAN
CLRKNGKKVIQLSRKTFDTEYPKTKLNDWDFVVTTDISEMGANFKADRVI
DPRRCLKPVILTDGPERVILAGPMPVTAASAAQRRGRIGRNHKKENDQYI
YMGQPLNNDEDHAHWTEAKMLLDNINTPEGIIPALFEPEREKSAAIDGEY
RLRGEARKTFVELMRRGDLPVWLSYKVASAGFQYKDREWCFDGERNNQIL
EENMDVEIWTKEGE

SEQ ID NO: 56

KKKLRPRWLDARTYADPLALKEFKDFAAGRKSIA

SEQ ID NO: 57

TEIGRVPSHLAHRTR

SEQ ID NO: 58

AYQHALEELPETLETLLLLALLGA

SEQ ID NO: 59

FLFFLSGKGIGKMSIGLCCIIAAS

SEQ ID NO: 60

LLWMAEIQPHWIAASIILEFFLMVLLIPEPEKQRTPQDNQLAYVVIGILT
LAAAIAANEMGLLETTKKDLGIGHVA

SEQ ID NO: 61

PTAILDVDLHPASAWTLYAVATTIITPMLRHTIENSTANVSLTAIANQAA
VLMGLDKGWPISKMDLGVPLLALGCYSQVNPLTLTAAVLLLITHYAIIGP
GLQAKATREAQKRTAAGIMKNPTVDGIMAIDLDPIPYDPKFEKQLGQVML
LILCVSQILLMRTTWALCEALTLATGPITTLWEGNPGKFWNTTIAVSMAN
IFRGSYLAGAGLAFSLIKN

SEQ ID NO: 62

RRGTGAQGETLGEKWKRQLNQLDKSEFEEYKKSGILEVDRTEAKEAIKRG
ETDHHAVSRGSAKLRWFVERNMVIPEGRVIDLGCGRGGWSYYCAGLKKVR
EVRGYTKGGPGHEEPIPMATYGWNLVKLHSGVDVFF

SEQ ID NO: 63

PEKCDTLLCDIGESSPNPTIEEGRTLRVLKMVEPWLKG

SEQ ID NO: 64

NQFCIKILNPYMPSVIEELEKLQRKHGGMLVRNPLSRNSTHEMYWVS
NGTGNIVSAVNMISRMLINRFTMAHKKPTYERDVDLGAG

SEQ ID NO: 65

STWHYDEDNPYKTWAYHGSYEVKATGSASSMVNGVVKLLTKPWDVVPMV
TQMAMTDTTPFGQQRVFKEKVDTRTPEAKE

SEQ ID NO: 66

NAAIGAVFQDENGWKSAREAVEDS

SEQ ID NO: 67

ERALHLEGKCESCVYNMMGKREKKLGEFGKAKGSRAIWYMWLGARFL
EFEALGFLNEDHWFSRENSLSGVEGEGLHKLGYILRDISKIPGGAMY
ADDTAGWDTRITEDDLHNEEKI

SEQ ID NO: 68

LAKAIFKLTYQNKVVKVQRPTPRGAVMDIISRKDQRGSGQVGTYGLNTF

-continued

SEQ ID NO: 69

TNMEAQLIRQMEAEGVIT

SEQ ID NO: 70

ECGVDRLKRMAISGDDCVVKP

SEQ ID NO: 71

PQWEPSKGWHDWQQVPFCSHHFHEIFMKDGRKLVVPCRNQDELIGRARIS
QGAGWSLRETACLGKSYAQMWQLMYFHRRDLRLASNAICSAVPSHWVPTS
RTTWSIHAHHEWMTTEDMLAVWNRVWIEENPWMEDKTHIHSWED
VPYLGKREDQWCGSLIGLTSRATWAKN

NSALL4 Fragments:

Contained all of NSALL3, but where epitopes were matched from Weiskopf[4] et al and IEDB databases[5,6] all variants were also includes. Epitopes and their variants are highlighted in bold type. Underlined epitopes are epitopes which were not in Weiskopf et al or EIDB databases but variants for them which were present in the sequences.

>4. NSALL4

(SEQ ID NO: 72)

SQIGAGVFKEGVFHTMWHVTRGAVLMHQGKRIEPSWAD*VKKDLISY*SV
KKDLISY*GGGWRLEGEWDEGEEVQVIAVEPGKNPKAVQTKPGLFKTPEG
EIGAIALDFKP*GTSGSPIVNRE*GTSGSPIINRE*GKVVGLYGNGVVTK
SGAYVSAIAQTNAEPLPEIEDEVFRKRNLTIMDLHPGAGKTKRYLPAIVR
EAIKRRLRTLIL*APTRVVAAEM*APTRVVASEM*EE*ALKGLPIRY*AL
RGLPIRY*QTTAIKAEHTGKEIVDLMCHATFTMRLLSPVRVPNYNLIIMD
EAHFT*DPASIAARGY*ISTRVEMGEAAAIFMTATPPGSADAFPQSNAPI
EDEEREIPERSWNSGFDWITDFAGKTVWFVPSIKAGNDIANCLRKNGKKV
IQLSRKTFDTEYPKTKLNDWDFVVTTDISEMGANFKADRVIDPRRCLKPV
ILTDGPERVILAGPMPVTAASAAQRRGRIGRNHKKENDQYIYMGQPLNND
EDHAHWTEAKMLLDNIN*TPEGIIPALF*TPEGIIPSMF*TPEGIIPTLF
*TPEGIIPSL*EPEREKSAAIDGEYRLR*GEARKTFVEL*GEARKTFVDL
*GEQRKTFVEL*MRRGD*LPVWLSYKV*ASAGFQYKDREWCFDGERNNQI
LEENMDVEIWTKEGEKKKLRPRWLDARTYADPLALKEFKDFAAGRKSIAT
EIGRVPSHLAHRTRAYQHALEELPETLETLLLLALLGAFLFFLSGKGIGK
MSIGLCCIIAASLLWMAEIQPHWIAASIILEFFLMVLLIPEPEKQRTPQD
NQLAYVVIGILTLAAAIAANEMGLLETTKKDLGIGHVAPTAILDVDLHPA
SAWTLYAVATTII*TPMLRHTIEN*STANVSLTA*IANQAAVLM*IANQA
TVLM*GLDKGWPISKMDLGVPLLALGCYSQVNPLTLTAAVLLLITHYAII
GPGLQAKATREAQKRTAAGIMKNPTVDGIMAIDLDPIPYDPKFEKQLGQV
MLLILCVSQ*ILLMRTTWA*VLLMRTTWA*LCEALTL*ATGPITTLW*EG
NPGKFWNTTIAVSMANIFRGSYLAGAGLAFSLIKNRRGTGAQGETLGEKW
KRQLNQLDKSEFEEYKKSGILEVDRTEAKEAIKRGETDHHAVSRGSAKLR
WFVERNMVIPEGRVIDLGCGRGGWSYYCAGLKKVREVRGYTKGGPGHEEP
IPMATYGWNLVKLHSGVDVFFPEKCDTLLCDIGESSPNPTIEEGRTLRVL
KMVEPWLKGNQFCIKILNPYMPSVIEELEKLQRKHGGMLVRNPLSRNSTH
EMYWVSNGTGNIVSAVNMISRMLINRFTMAHKKPTYERDVDLGAGSTWHY

-continued

DEDNPYKTWAYHGSYEVKATGSASSMVNGVVKLLTKPWDVVPMVTQMAMT
*DTTPFGQQR*VFKEKVDTRTPEAKENAAIGAVFQDENGWKSAREAVEDS
ERALHLEGKCESCVYNMMGKREKKLGEFGKAKGSRAIWYMWLGARFLEFE
ALGFLNEDHWFSRENSLSGVEGEGLHKLGYILRDISKIPGGAMYADDTAG
WDTRITEDDLHNEEKILAKAIFKLTYQNKVVKVQRPTPRGAVMDIISRKD
QRGSGQVGTYGLNTFTNMEAQLIRQMEAEGVITECGVDRLKRMAISGDDC
VVKPPQWEPSKGWHDWQQVPFCSHHFHEIFMKDGRKLVVPCRNQDELIGR
ARISQGAGWSLRETACLGKSYAQMWQLMYFHRRDLRLASNAICSAVPSHW
VPTSRTTWSIHAHHEWMTTEDMLAVWNRVWIEENPWMEDKTHIHSWEDVP
YLGKREDQWCGSLIGLTSRATWAKNI

Conserved Peptide Sequences of NSALL4

SEQ ID NO: 73

SQIGAGVFKEGVFHTMWHVTRGAVLMHQGKRIEPSWAD*VKKDLISY*SV
KKDLISY*GGGWRLEGEWDEGEEVQVIAVEPGKNPKAVQTKPGLFKTPEG
EIGAIALDFKP*GTSGSPIVNRE*GTSGSPIINRE*GKVVGLYGNGVVTK
SGAYVSAIAQTNAE

SEQ ID NO: 74

PLPEIEDEVFRKRNLTIMDLHPGAGKTKRYLPAIVREAIKRRLRTLIL*A
PTRVVAAEM*APTRVVASEM*EE*ALKGLPIRY*ALRGLPIRY*QTTAIK
AEHTGKEIVDLMCHATFTMRLLSPVRVPNYNLIIMDEAHFT*DPASIAAR
GY*ISTRVEMGEAAAIFMTATPPGSADAFPQSNAPIEDEEREIPERSWNS
GFDWITDFAGKTVWFVPSIKAGNDIANCLRKNGKKVIQLSRKTFDTEYPK
TKLNDWDFVVTTDISEMGANFKADRVIDPRRCLKPVILTDGPERVILAGP
MPVTAASAAQRRGRIGRNHKKENDQYIYMGQPLNNDEDHAHWTEAKMLLD
NIN*TPEGIIPALF*TPEGIIPSMF*TPEGIIPTLF*TPEGIIPSL*EPE
REKSAAIDGEYRLR*GEARKTFVEL*GEARKTFVDL*GEQRKTFVEL*MR
RGD*LPVWLSYKV*ASAGFQYKDREWCFDGERNNQILEENMDVEIWTKEG
E

SEQ ID NO: 75

KKKLRPRWLDARTYADPLALKEFKDFAAGRKSIA

SEQ ID NO: 76

TEIGRVPSHLAHRTR

SEQ ID NO: 77

AYQHALEELPETLETLLLLALLGA

SEQ ID NO: 78

FLFFLSGKGIGKMSIGLCCIIAAS

SEQ ID NO: 79

LLWMAEIQPHWIAASIILEFFLMVLLIPEPEKQRTPQDNQLAYVVIGILT
LAAAIAANEMGLLETTKKDLGIGHVA

SEQ ID NO: 80

PTAILDVDLHPASAWTLYAVATTII*TPMLRHTIEN*STANVSLTA*IAN
QAAVLM*IANQATVLM*GLDKGWPISKMDLGVPLLALGCYSQVNPLTLTA
AVLLLITHYAIIGPGLQAKATREAQKRTAAGIMKNPTVDGIMAIDLDPIP

-continued

YDPKFEKQLGQVMLLILCVSQ*ILLMRTTWA*VLLMRTTWA*LCEALTL*

ATGPITTLW*EGNPGKFWNTTIAVSMANIFRGSYLAGAGLAFSLIKN

SEQ ID NO: 81
RRGTGAQGETLGEKWKRQLNQLDKSEFEEYKKSGILEVDRTEAKEAIKRG

ETDHHAVSRGSAKLRWFVERNMVIPEGRVIDLGCGRGGWSYYCAGLKKVR

EVRGYTKGGPGHEEPIPMATYGWNLVKLHSGVDVFF

SEQ ID NO: 82
PEKCDTLLCDIGESSPNPTIEEGRTLRVLKMVEPWLKG

SEQ ID NO: 83
NQFCIKILNPYMPSVIEELEKLQRKHGGMLVRNPLSRNSTHEMYWVSNGT

GNIVSAVNMISRMLINRFTMAHKKPTYERDVDLGAG

SEQ ID NO: 84
STWHYDEDNPYKTWAYHGSYEVKATGSASSMVNGVVKLLTKPWDVVPMVT

QMAMT*DTTPFGQQR*VFKEKVDTRTPEAKE

SEQ ID NO: 85
NAAIGAVFQDENGWKSAREAVEDS

SEQ ID NO: 86
ERALHLEGKCESCVYNMMGKREKKLGEFGKAKGSRAIWYMWLGARFLEFE

ALGFLNEDHWFSRENSLSGVEGEGLHKLGYILRDISKIPGGAMYADDTAG

WDTRITEDDLHNEEKI

SEQ ID NO: 87
LAKAIFKLTYQNKVVKVQRPTPRGAVMDIISRKDQRGSGQVGTYGLNTF

SEQ ID NO: 88
TNMEAQLIRQMEAEGVIT

SEQ ID NO: 89
ECGVDRLKRMAISGDDCVVKP

SEQ ID NO: 90
PQWEPSKGWHDWQQVPFCSHHFHEIFMKDGRKLVVPCRNQDELIGRARIS

QGAGWSLRETACLGKSYAQMWQLMYFHRRDLRLASNAICSAVPSHWVPTS

RTTWSIHAHHEWMTTEDMLAVWNRVWIEENPWMEDKTHIHSWEDVPYLGK

REDQWCGSLIGLTSRATWAKNI

Known Epitopes and Known Epitope Variants (SEQ ID NO: 91)
VKKDLISY
(Present in NSALL2, 3, 4)

(SEQ ID NO: 92)
SVKKDLISY
(Present in NSALL4)

(SEQ ID NO: 93)
GTSGSPIVNRE
(Present in NSALL2, 3, 4)

(SEQ ID NO: 94)
GTSGSPIINRE
(Present in NSALL4)

(SEQ ID NO: 95)
APTRVVAAEM
(Present in NSALL1, 2, 3, 4)

(SEQ ID NO: 96)
APTRVVASEM
(Present in NSALL1, 4)

-continued (SEQ ID NO: 97)
ALKGLPIRY
(Present in NSALL2, 3, 4)

(SEQ ID NO: 98)
ALRGLPIRY
(Present in NSALL4)

(SEQ ID NO: 99)
DPASIAARGY
(Present in NSALL2, 3, 4)

(SEQ ID NO: 100)
TPEGIIPALF
(Present in NSALL2, 3, 4)

(SEQ ID NO: 101)
TPEGIIPSMF
(Present in NSALL4)

(SEQ ID NO: 102)
TPEGIIPTLF
(Present in NSALL4)

(SEQ ID NO: 103)
TPEGIIPSL
(Present in NSALL4)

(SEQ ID NO: 104)
GEARKTFVEL
(Present in NSALL2, 3, 4)

(SEQ ID NO: 105)
GEARKTFVDL
(Present in NSALL4)

(SEQ ID NO: 106)
GEQRKTFVEL
(Present in NSALL4)

(SEQ ID NO: 107)
LPVWLSYKV
(Present in NSALL2, 3, 4)

(SEQ ID NO: 108)
TPMLRHTIEN
(Present in NSALL2, 3, 4)

(SEQ ID NO: 109)
IANQAAVLM
(Present in NSALL2, 3, 4)

(SEQ ID NO: 110)
IANQATVLM
(Present in NSALL4)

(SEQ ID NO: 111)
ILLMRTTWA
(Present in NSALL2, 3, 4)

(SEQ ID NO: 112)
VLLMRTTWA
(Present in NSALL4)

(SEQ ID NO: 113)
ATGPITTLW
(Present in NSALL2, 3, 4)

(SEQ ID NO: 114)
DTTPFGQQR
(Present in NSALL2, 3, 4)

Epitope Data

Tables 2 and 3 shows which epitopes from Wesikopf et al and IEDB are present in the invention sequences and which serotypes they are present in. Table 4 shows the process by which the above epitopes (tables 2-3) are assessed to determine whether they fall within a conserved sequence. Epitopes which did not are excluded.

TABLE 2

Serotypes and percentage appearance of experimentally proven epitopes from Weiskopf et al, identified in the datasets that are below the serotype specific 1st quartile conservation cut off.

| Epitope | Start | End | Serotype found in 1 | 2 | 3 | 4 | Total % |
|---|---|---|---|---|---|---|---|
| LPVWLSYKV | 2013 | 2019 | ✓ | | | ✓ | 99.75 |
| APTRVVASEM | 1694 | 1699 | ✓ | | | | 99.9 |
| TPEGIIPAL | 1971 | 1977 | ✓ | | | | 99.9 |
| TPEGIIPALF | 1972 | 1977 | ✓ | | | | 99.9 |
| GEARKTFVEL | 1999 | 2004 | | ✓ | | | 0.3 |
| DPASIAARGY | 1762 | 1767 | | ✓ | ✓ | | 99.8 |
| DTTPFGQQR | 2834 | 2840 | | ✓ | ✓ | ✓ | 99.9 |
| TPEGIIPSM | 1971 | 1977 | | ✓ | | | 99.4 |
| TPEGIIPSMF | 1972 | 1977 | | ✓ | | | 99.4 |
| GEARKTFVDL | 1999 | 2004 | | ✓ | | | 99.5 |
| IANQATVLM | 2309 | 2315 | | ✓ | | | 99.6 |
| APTRVVAAEM | 1694 | 1699 | | ✓ | ✓ | ✓ | 99.9 |
| ATGPITTLW | 2438 | 2444 | | | ✓ | | 99.8 |
| TPMLRHTIEN | 2291 | 2296 | | | ✓ | ✓ | 100 |
| TPEGIIPTLF | 1972 | 1977 | | | | ✓ | 100 |
| GEQRKTFVEL | 1999 | 2004 | | | | ✓ | 100 |
| GEFRLRGEQR | 1993 | 1998 | | | | ✓ | 100 |

TABLE 3

Serotypes and percentage appearance of experimentally proven epitopes from IEDB Database, identified in the datasets that are below the serotype specific 1st quartile conservation cut off.

| IEDB Epitope | Start | End | Serotype found in (Below Threshold) 1 | 2 | 3 | 4 | % of Seqs |
|---|---|---|---|---|---|---|---|
| SVKKDLISY | 1541 | 1547 | ✓ | | | | 99.4 |
| ILLMRTTWA | 2422 | 2428 | ✓ | | | | 99.8 |
| VLLMRTTWA | 2422 | 2428 | ✓ | | | | 0.16 |
| FLDLPLPWT | 486 | 492 | ✓ | | | | 99.9 |
| TPEGIIPAL | 1971 | 1977 | ✓ | | | | 99.9 |
| ALRGLPIRY | 1705 | 1711 | | ✓ | | | 99.9 |
| TPEGIIPSM | 1971 | 1977 | | ✓ | | | 99.4 |
| TPEGIIPSL | 1971 | 1977 | | ✓ | | | 0.4 |
| GTSGSPIINRE | 1605 | 1609 | | | ✓ | | 99.7 |
| TPEGIIPTL | 1971 | 1977 | | | | ✓ | 100.0 |

TABLE 4

| Epitopes | In NSALL3 | Serotype found in (Below Threshold) 1 | 2 | 3 | 4 | % of Seqs Below Threshold | Total % of Seqs | Individual T-cell Response/ Response Freq | HLA Types |
|---|---|---|---|---|---|---|---|---|---|
| Wesikopf et al Epitopes | | | | | | | | | |
| * LPVWLSYKV | ✓□ | ✓ | x | x | ✓ | 49.9 | | 313 | B*5101 |
| APTRVVASEM | x | ✓ | x | x | x | 25.0 | | 607 | B*0702 |
| * APTRVVAAEM | ✓□ | x | ✓ | ✓ | ✓ | 75.0 | | 1623 | B*0702/3501 |
| * TPEGIIPAL | ✓□ | ✓ | x | ↑ | x | 25.0 | 74.8 | 2396 | B*0702 |
| * TPEGIIPALF | ✓□ | ✓ | x | ↑ | x | | | | B*3501 |
| TPEGIIPSM | x | x | ✓ | x | x | 24.9 | | 4686 | B*3501/5301 |
| TPEGIIPSMF | x | x | ✓ | x | x | | | | B*0702/3501 |
| TPEGIIPTLF | x | x | x | x | ✓ | 25 | | 2914 | B*3501/0702/5301 |
| * GEARKTFVEL | ✓□ | ↑ | ✓ | x | x | 0.1 | 25 | 1330 | B*4001 |
| GEARKTFVDL | x | x | ✓ | x | x | 24.9 | | 1405 | B*4001 |
| GEQRKTFVEL | x | x | x | x | ✓ | 25.0 | | 1050 | B*4001 |
| GEFRLRGEQR | x | x | x | x | ✓ | 25 | | 1373 | B*4001 |
| * DPASIAARGY | ✓□ | ↑ | ✓ | ✓ | x | 49.9 | 55.4 | 2383 | B*3501 |
| * DTTPFGQQR | ✓□ | ↑ | ✓ | ✓ | ✓ | 74.9 | 99.9 | 3260 | A*6801/3301 |
| IANQATVLM | x | x | ✓ | x | x | 24.9 | | 1518 | B*3501 |
| * ATGPITTLW | ✓□ | ↑ | x | ✓ | x | 25.0 | 50.0 | 505 | B*5801 |
| * TPMLRHTIEN | ✓□ | x | x | ✓ | ✓ | 50 | | 388 | B*0702 |
| IEDB Epitopes | | | | | | | | | |
| SVKKDLISY | x | ✓ | x | ↑ | x | 25.0 | 48.8 | 0 | B62 |
| * ILLMRTTWA | ✓□ | ✓ | x | x | x | 25.0 | | 0 | A2 |
| VLLMRTTWA | x | ✓ | x | x | x | 0.1 | | 0 | A2 |
| FLDLPLPWT | x | ✓ | x | ↑ | ↑ | 25 | 48.7 | 0 | A2 |
| * TPEGIIPAL | ✓□ | ✓ | x | ↑ | x | 25 | 49.9 | 0.29 | B35/*0702 |
| TPEGIIPSM | x | x | ✓ | x | x | 24.9 | | 0 | B*3501/5301/0702 |
| TPEGIIPSL | x | x | ✓ | x | x | 0.1 | | 0 | B35 |
| TPEGIIPTL | x | x | x | x | ✓ | 25 | | 0.29 | B*3501 |
| ALRGLPIRY | x | x | ✓ | x | ↑ | 25 | 49.7 | 0 | B62/*0301 |
| GTSGSPIINRE | x | x | x | ✓ | x | 29.9 | | 0.04 | A11 |

Epitopes (and their variants) found to be below the conservation threshold (ie. Are present within a conserved sequence) in at least one serotype. For Serotypes found in, Tick = found, x = not found, downward arrow = found but above respective threshold. Epitopes are from IEDB and Weiskopf et al. These variants are included in NSALL4, additionally there are 4 variants that were not in Weiskopf et at or EIDB databases but were in the sequences, these are: VKKDLISY/GTSGSPIVNRE/ALKGLPIRY/IANQAAVLM NS1 nucleotide sequence

[SEQ ID NO: 115]

AAAGAAAAGCAGGACGTGTTCTGCGACAGCAAGCTGATGAGCGCCGCCAT

CAAGGACAACCGGGCCGTGCACGCCGACATGGGCTACTGGATCGAGAGCG

CCCTGAACGACACCTGGAAGATCGAGAAGGCCAGCTTCATCGAAGTGAAG

AACTGCCACTGGCCCAAGAGCCACACCCTGTGGTCCAACGGCGTGCTGGA

AAGCGAGATGATCATCCCCAAGAACCTGGCCGGACCCGTGTCCCAGCACA

ACTACAGACCCGGCTACCACACCCAGATCACCGGCCCCTGGCACCTGGGC

AAGCTGGAAATGGACTTCGACTTCTGCGACGGCACCACCGTGGTGGTGAC

AGAGGACTGCGGCAACAGAGGCCCCAGCCTGAGAACCACCACCGCCAGCG

GCAAGCTGATCACCGAGTGGTGCTGCAGAAGCTGCACCCTGCCCCCCCTG

CGGTACAGAGGCGAGGATGGCTGTTGGTACGGCATGGAAATCCGGCCCCT

GAAAGAGAAAGAAGAGAACCTGGTCAACTCCCTGGTGACAGCC

-continued

NS1 amino acid sequence

[SEQ ID NO: 116]

KEKQDVFCDSKLMSAAIKDNRAVHADMGYWIESALNDTWKIEKASFIEVK

NCHWPKSHTLWSNGVLESEMIIPKNLAGPVSQHNYRPGYHTQITGPWHLG

KLEMDFDFCDGTTVVVTEDCGNRGPSLRTTTASGKLITEWCCRSCTLPPL

RYRGEDGCWYGMEIRPLKEKEENLVNSLVTA

There is a highly conserved region that is contained in the beta ladder domain of NS1. The protein/vaccine of the invention may provide the full beta ladder domain to preserve tridimensionality. The underlined sequence is the highly conserved region.

NS1 conserved sequence

[SEQ ID NO: 117]

EWCCRSCTLPPLRYRGEDGCWYGMEIRP

Viral Vector Sequences

1NSALL Chadox1

[SEQ ID NO: 118]

GTTTAAACGCGGCCGCCAGGCCTACCCACTAGTCAATTCGGGAGGATCGAAACGGCAGATCG

CAAAAAACAGTACATACAGAAGGAGACATGAACATGAACATCAAAAAAATTGTAAAACAAGCC

ACAGTTCTGACTTTTACGACTGCACTTCTGGCAGGAGGAGCGACTCAAGCCTTCGCGAAAGA

AAATAACCAAAAAGCATACAAAGAAACGTACGGCGTCTCTCATATTACACGCCATGATATGCT

GCAGATCCCTAAACAGCAGCAAAACGAAAAATACCAAGTGCCTCAATTCGATCAATCAACGAT

TAAAAATATTGAGTCTGCAAAAGGACTTGATGTGTGGGACAGCTGGCCGCTGCAAAACGCTG

ACGGAACAGTAGCTGAATACAACGGCTATCACGTTGTGTTTGCTCTTGCGGGAAGCCCGAAA

GACGCTGATGACACATCAATCTACATGTTTTATCAAAAGGTCGGCGACAACTCAATCGACAGC

TGGAAAAACGCGGGCCGTGTCTTTAAAGACAGCGATAAGTTCGACGCCAACGATCCGATCCT

GAAAGATCAGACGCAAGAATGGTCCGGTTCTGCAACCTTTACATCTGACGGAAAAATCCGTTT

ATTCTACACTGACTATTCCGGTAAACATTACGGCAAACAAAGCCTGACAACAGCGCAGGTAAA

TGTGTCAAAATCTGATGACACACTCAAAATCAACGGAGTGGAAGATCACAAAACGATTTTTGA

CGGAGACGGAAAAACATATCAGAACGTTCAGCAGTTTATCGATGAAGGCAATTATACATCCGG

CGACAACCATACGCTGAGAGACCCTCACTACGTTGAAGACAAAGGCCATAAATACCTTGTATT

CGAAGCCAACACGGGAACAGAAAACGGATACCAAGGCGAAGAATCTTTATTTAACAAAGCGT

ACTACGGCGGCGGCACGAACTTCTTCCGTAAAGAAAGCCAGAAGCTTCAGCAGAGCGCTAAA

AAACGCGATGCTGAGTTAGCGAACGGCGCCCTCGGTATCATAGAGTTAAATAATGATTACACA

TTGAAAAAAGTAATGAAGCCGCTGATCACTTCAAACACGGTAACTGATGAAATCGAGCGCGCG

AATGTTTTCAAAATGAACGGCAAATGGTACTTGTTCACTGATTCACGCGGTTCAAAAATGACG

ATCGATGGTATTAACTCAAACGATATTTACATGCTTGGTTATGTATCAAACTCTTTAACCGGCC

CTTACAAGCCGCTGAACAAAACAGGGCTTGTGCTGCAAATGGGTCTTGATCCAAACGATGTG

ACATTCACTTACTCTCACTTCGCAGTGCCGCAAGCCAAAGGCAACAATGTGGTTATCACAAGC

TACATGACAAACAGAGGCTTCTTCGAGGATAAAAAGGCAACATTTGCGCCAAGCTTCTTAATG

AACATCAAAGGCAATAAAACATCCGTTGTCAAAAACAGCATCCTGGAGCAAGGACAGCTGACA

GTCAACTAATAACAGCAAAAAGAAAATGCCGATACTTCATTGGCATTTTCTTTTATTTCTCAAC

AAGATGGTGAATTGACTAGTGGGTAGATCCACAGGACGGGTGTGGTCGCCATGATCGCGTAG

-continued

TCGATAGTGGCTCCAAGTAGCGAAGCGAGCAGGACTGGGCGGCGGCCAAAGCGGTCGGACA

GTGCTCCGAGAACGGGTGCGCATAGAAATTGCATCAACGCATATAGCGCTAGCAGCACGCCA

TAGTGACTGGCGATGCTGTCGGAATGGACGATATCCCGCAAGAGGCCCGGCAGTACCGGCA

TAACCAAGCCTATGCCTACAGCATCCAGGGTGACGGTGCCGAGGATGACGATGAGCGCATTG

TTAGATTTCATACACGGTGCCTGACTGCGTTAGCAATTTAACTGTGATAAACTACCGCATTAAA

GCTTATCGATGATAAGCTGTCAAACATGAGAATTGATCCGGAACCCTTAATATAACTTCGTATA

ATGTATGCTATACGAAGTTATTAGGTCCCTCGACTATAGGGTCACCGTCGACAGCGACACACT

TGCATCGGATGCAGCCCGGTTAACGTGCCGGCACGGCCTGGGTAACCAGGTATTTTGTCCAC

ATAACCGTGCGCAAAATGTTGTGGATAAGCAGGACACAGCAGCAATCCACAGCAGGCATACA

ACCGCACACCGAGGTTACTCCGTTCTACAGGTTACGACGACATGTCAATACTTGCCCTTGACA

GGCATTGATGGAATCGTAGTCTCACGCTGATAGTCTGATCGACAATACAAGTGGGACCGTGG

TCCCAGACCGATAATCAGACCGACRAYACGAGTGGGAYCGTGGTCCCAGACTAATAATCAGA

CCGACGATACGAGTGGGACCGTGGTCCCAGACTAATAATCAGACCGACGATACGAGTGGGA

CCGTGGTYCCAGWCTRATWATCAGACCGACGATACRAGTGGRACMGTGGKCCCAGASAKAA

TAWTCAGRCCGAGWTAYGCWKTCKGGCCTGTAACAAAGGACATTAAGTAAAGACAGATAMR

MGTGRGACTAAAACGTGGTCCCAGTCTGATTATCAGACCGACGATACGAGTGGGACCGTGGT

CCCAGACTAATAATCAGACCGACGATACGAGTGGGACCGTGGTCCCAGACTAATAATCAGAC

CGACGATACGAGTGGGACCGTGGTCCCAGTCTGATTATCAGACCGACGATACAAGTGGAACA

GTGGGCCCAGAGAGAATATTCAGGCCAGTTATGCTTTCTGGCCTGTAACAAAGGACATTAAGT

AAAGACAGATAAACGTAGACTAAAACGTGGTCGCATCAGGGTGCTGGCTTTTCAAGTTCCTTA

AGAATGGCCTCAATTTTCTCTATACACTCAGTTGGAACACGAGACCTGTCCAGGTTAAGCACC

ATTTTATCGCCCTTATACAATACTGTCGCTCCAGGAGCAAACTGATGTCGTGAGCTTAAACTA

GTTCTTGATGCAGATGACGTTTTAAGCACAGAAGTTAAAAGAGTGATAACTTCTTCAGCTTCAA

ATATCACCCCAGCTTTTTTCTGCTCATGAAGGTTAGATGCCTGCTGCTTAAGTAATTCCTCTTT

ATCTGTAAAGGCTTTTTGAAGTGCATCACCTGACCGGGCAGATAGTTCACCGGGGTGAGAAA

AAAGAGCAACAACTGATTTAGGCAATTTGGCGGTGTTGATACAGCGGGTAATAATCTTACGTG

AAATATTTTCCGCATCAGCCAGCGCAGAAATATTTCCAGCAAATTCATTCTGCAATCGGCTTG

CATAACGCTGACCACGTTCATAAGCACTTGTTGGGCGATAATCGTTACCCAATCTGGATAATG

CAGCCATCTGCTCATCATCCAGCTCGCCAACCAGAACACGATAATCACTTTCGGTAAGTGCAG

CAGCTTTACGACGGCGACTCCCATCGGCAATTTCTATGACACCAGATACTCTTCGACCGAACG

CCGGTGTCTGTTGACCAGTCAGTAGAAAAGAAGGGATGAGATCATCCAGTGCGTCCTCAGTA

AGCAGCTCCTGGTCACGTTCATTACCTGACCATACCCGAGAGGTCTTCTCAACACTATCACCC

CGGAGCACTTCAAGAGTAAACTTCACATCCCGACCACATACAGGCAAAGTAATGGCATTACCG

CGAGCCATTACTCCTACGCGCGCAATTAACGAATCCACCATCGGGGCAGCTGGTGTCGATAA

CGAAGTATCTTCAACCGGTTGAGTATTGAGCGTATGTTTTGGAATAACAGGCGCACGCTTCAT

TATCTAATCTCCCAGCGTGGTTTAATCAGACGATCGAAAATTTCATTGCAGACAGGTTCCCAA

ATAGAAAGAGCATTTCTCCAGGCACCAGTTGAAGAGCGTTGATCAATGGCCTGTTCAAAAACA

GTTCTCATCCGGATCTGACCTTTACCAACTTCATCCGTTTCACGTACAACATTTTTTAGAACCA

TGCTTCCCCAGGCATCCCGAATTTGCTCCTCCATCCACGGGGACTGAGAGCCATTACTATTG

CTGTATTTGGTAAGCAAAATACGTACATCAGGCTCGAACCCTTTAAGATCAACGTTCTTGAGC

AGATCACGAAGCATATCGAAAAACTGCAGTGCGGAGGTGTAGTCAAACAACTCAGCAGGCGT

-continued

GGGAACAATCAGCACATCAGCAGCACATACGACATTAATCGTGCCGATACCCAGGTTAGGCG

CGCTGTCAATAACTATGACATCATAGTCATGAGCAACAGTTTCAATGGCCAGTCGGAGCATCA

GGTGTGGATCGGTGGGCAGTTTACCTTCATCAAATTTGCCCATTAACTCAGTTTCAATACGGT

GCAGAGCCAGACAGGAAGGAATAATGTCAAGCCCCGGCCAGCAAGTGGGCTTTATTGCATAA

GTGACATCGTCCTTTTCCCCAAGATAGAAAGGCAGGAGAGTGTCTTCTGCATGAATATGAAGA

TCTGGTACCCATCCGTGATACATTGAGGCTGTTCCCTGGGGGTCGTTACCTTCCACGAGCAA

AACACGTAGCCCCTTCAGAGCCAGATCCTGAGCAAGATGAACAGAAACTGAGGTTTTGTAAAC

GCCACCTTTATGGGCAGCAACCCCGATCACCGGTGGAAATACGTCTTCAGCACGTCGCAATC

GCGTACCAAACACATCACGCATATGATTAATTTGTTCAATTGTATAACCAACACGTTGCTCAAC

CCGTCCTCGAATTTCCATATCCGGGTGCGGTAGTCGCCCTGCTTTCTCGGCATCTCTGATAG

CCTGAGAAGAAACCCCAACTAAATCCGCTGCTTCACCTATTCTCCAGCGCCGGGTTATTTTCC

TCGCTTCCGGGCTGTCATCATTAAACTGTGCAATGGCGATAGCCTTCGTCATTTCATGACCAG

CGTTTATGCACTGGTTAAGTGTTTCCATGAGTTTCATTCTGAACATCCTTTAATCATTGCTTTG

CGTTTTTTTATTAAATCTTGCAATTTACTGCAAAGCAACAACAAAATCGCAAAGTCATCAAAAAA

CCGCAAAGTTGTTTAAAATAAGAGCAACACTACAAAAGGAGATAAGAAGAGCACATACCTCAG

TCACTTATTATCACTAGCGCTCGCCGCAGCCGTGTAACCGAGCATAGCGAGCGAACTGGCGA

GGAAGCAAAGAAGAACTGTTCTGTCAGATAGCTCTTACGCTCAGCGCAAGAAGAAATATCCAC

CGTGGGAAAAACTCCAGGTAGAGGTACACACGCGGATAGCCAATTCAGAGTAATAAACTGTG

ATAATCAACCCTCATCAATGATGACGAACTAACCCCCGATATCAGGTCACATGACGAAGGGAA

AGAGAAGGAAATCAACTGTGACAAACTGCCCTCAAATTTGGCTTCCTTAAAAATTACAGTTCAA

AAAGTATGAGAAAATCCATGCAGGCTGAAGGAAACAGCAAAACTGTGACAAATTACCCTCAGT

AGGTCAGAACAAATGTGACGAACCACCCTCAAATCTGTGACAGATAACCCTCAGACTATCCTG

TCGTCATGGAAGTGATATCGCGGAAGGAAAATACGATATGAGTCGTCTGGCGGCCTTTCTTTT

TCTCAATGTATGAGAGGCGCATTGGAGTTCTGCTGTTGATCTCATTAACACAGACCTGCAGGA

AGCGGCGGCGGAAGTCAGGCATACGCTGGTAACTTTGAGGCAGCTGGTAACGCTCTATGATC

CAGTCGATTTTCAGAGAGACGATGCCTGAGCCATCCGGCTTACGATACTGACACAGGGATTC

GTATAAACGCATGGCATACGGATTGGTGATTTCTTTTGTTTCACTAAGCCGAAACTGCGTAAA

CCGGTTCTGTAACCCGATAAAGAAGGGAATGAGATATGGGTTGATATGTACACTGTAAAGCCC

TCTGGATGGACTGTGCGCACGTTTGATAAACCAAGGAAAAGATTCATAGCCTTTTTCATCGCC

GGCATCCTCTTCAGGGCGATAAAAAACCACTTCCTTCCCCGCGAAACTCTTCAATGCCTGCCG

TATATCCTTACTGGCTTCCGCAGAGGTCAATCCGAATATTTCAGCATATTTAGCAACATGGATC

TCGCAGATACCGTCATGTTCCTGTAGGGTGCCATCAGATTTTCTGATCTGGTCAACGAACAGA

TACAGCATACGTTTTTGATCCCGGGAGAGACTATATGCCGCCTCAGTGAGGTCGTTTGACTG

GACGATTCGCGGGCTATTTTTACGTTTCTTGTGATTGATAACCGCTGTTTCCGCCATGACAGA

TCCATGTGAAGTGTGACAAGTTTTTAGATTGTCACACTAAATAAAAAAGAGTCAATAAGCAGG

GATAACTTTGTGAAAAAACAGCTTCTTCTGAGGGCAATTTGTCACAGGGTTAAGGGCAATTTG

TCACAGACAGGACTGTCATTTGAGGGTGATTTGTCACACTGAAAGGGCAATTTGTCACAACAC

CTTCTCTAGAACCAGCATGGATAAAGGCCTACAAGGCGCTCTAAAAAAGAAGATCTAAAAACT

ATAAAAAAAATAATTATAAAAATATCCCCGTGGATAAGTGGATAACCCCAAGGGAAGTTTTTTC

AGGCATCGTGTGTAAGCAGAATATATAAGTGCTGTTCCCTGGTGCTTCCTCGCTCACTCGAGG

-continued

GCTTCGCCCTGTCGCTCAACTGCGGCGAGCACTACTGGCTGTAAAAGGACAGACCACATCAT

GGTTCTGTGTTCATTAGGTTGTTCTGTCCATTGCTGACATAATCCGCTCCACTTCAACGTAACA

CCGCACGAAGATTTCTATTGTTCCTGAAGGCATATTCAAATCGTTTTCGTTACCGCTTGCAGG

CATCATGACAGAACACTACTTCCTATAAACGCTACACAGGCTCCTGAGATTAATAATGCGGAT

CTCTACGATAATGGGAGATTTTCCCGACTGTTTCGTTCGCTTCTCAGTGGATAACAGCCAGCT

TCTCTGTTTAACAGACAAAAACAGCATATCCACTCAGTTCCACATTTCCATATAAAGGCCAAGG

CATTTATTCTCAGGATAATTGTTTCAGCATCGCAACCGCATCAGACTCCGGCATCGCAAACTG

CACCCGGTGCCGGGCAGCCACATCCAGCGCAAAAACCTTCGTGTAGACTTCCGTTGAACTGA

TGGACTTATGTCCCATCAGGCTTTGCAGAACTTTCAGCGGTATACCGGCATACAGCATGTGCA

TCGCATAGGAATGGCGGAACGTATGTGGTGTGACCGGAACAGAGAACGTCACACCGTCAGCA

GCAGCGGCGGCAACCGCCTCCCCAATCCAGGTCCTGACCGTTCTGTCCGTCACTTCCCAGAT

CCGCGCTTTCTCTGTCCTTCCTGTGCGACGGTTACGCCGCTCCATGAGCTTATCGCGAATAAA

TACCTGTGACGGAAGATCACTTCGCAGAATAAATAAATCCTGGTGTCCCTGTTGATACCGGGA

AGCCCTGGGCCAACTTTTGGCGAAAATGAGACGTTGATCGGCACGTAAGAGGTTCCAACTTT

CACCATAATGAAATAAGATCACTACCGGGCGTATTTTTTGAGTTATCGAGATTTTCAGGAGCTA

AGGAAGCTAAAATGGAGAAAAAAATCACTGGATATACCACCGTTGATATATCCCAATGGCATC

GTAAAGAACATTTTGAGGCATTTCAGTCAGTTGCTCAATGTACCTATAACCAGACCGTTCAGC

TGGATATTACGGCCTTTTTAAAGACCGTAAAGAAAAATAAGCACAAGTTTTATCCGGCCTTTAT

TCACATTCTTGCCCGCCTGATGAATGCTCATCCGGAGTTCCGTATGGCAATGAAAGACGGTG

AGCTGGTGATATGGGATAGTGTTCACCCTTGTTACACCGTTTTCCATGAGCAAACTGAAACGT

TTTCATCGCTCTGGAGTGAATACCACGACGATTTCCGGCAGTTTCTACACATATATTCGCAAG

ATGTGGCGTGTTACGGTGAAAACCTGGCCTATTTCCCTAAAGGGTTTATTGAGAATATGTTTTT

CGTCTCAGCCAATCCCTGGGTGAGTTTCACCAGTTTTGATTTAAACGTGGCCAATATGGACAA

CTTCTTCGCCCCCGTTTTCACCATGGGCAAATATTATACGCAAGGCGACAAGGTGCTGATGCC

GCTGGCGATTCAGGTTCATCATGCCGTTTGTGATGGCTTCCATGTCGGCAGAATGCTTAATGA

ATTACAACAGTACTGCGATGAGTGGCAGGGCGGGGCGTAATTTTTTTAAGGCAGTTATTGGTG

CCCTTAAACGCCTGGTTGCTACGCCTGAATAAGTGATAATAAGCGGATGAATGGCAGAAATTC

GATGATAAGCTGTCAAACATGAGAATTGGTCGACGGCGCGCCAAAGCTTGCATGCCTGCAGC

CGCGTAACCTGGCAAAATCGGTTACGGTTGAGTAATAAATGGATGCCCTGCGTAAGCGGGGC

ACATTTCATTACCTCTTTCTCCGCACCCGACATAGATAATAACTTCGTATAGTATACATTATAC

GAAGTTATCTAGTAGACTTAATCGCGTTTAAACCCATCATCAATAATATACCTCAAACTTTTTGT

GCGCGTTAATATGCAAATGAGGCGTTTGAATTTGGGAAGGGAGGAAGGTGATTGGCCGAGAG

AAGGGCGACCGTTAGGGGCGGGGCGAGTGACGTTTTGATGACGTGACCGCGAGGAGGAGC

CAGTTTGCAAGTTCTCGTGGGAAAAGTGACGTCAAACGAGGTGTGGTTTGAACACGGAAATA

CTCAATTTTCCCGCGCTCTCTGACAGGAAATGAGGTGTTTCTAGGCGGATGCAAGTGAAAAC

GGGCCATTTTCGCGCGAAAACTGAATGAGGAAGTGAAAATCTGAGTAATTTCGCGTTTATGAC

AGGGAGGAGTATTTGCCGAGGGCCGAGTAGACTTTGACCGATTACGTGGGGGTTTCGATTAC

CGTGTTTTTCACCTAAATTTCCGCGTACGGTGTCAAAGTCCGGTGTTTTTACGTAGGTGTCAG

CTGATCGCCAGGGTATTTAAACCTGCGCTCTCCAGTCAAGAGGCCACTCTTGAGTGCCAGCG

AGAAGAGTTTTCTCCTCCGCGCGCGAGTCAGATCTACACTTTGAAAGGCGATCGCTAGCGAC

ATCGATCCAAATAATGATTTTATTTTGACTGATAGTGACCTGTTCGTTGCAACAAATTGATAAG

-continued

CAATGCTTTTTTATAATGCCAACTTTGTACAAAAAAGCAGGCTCCACCATGGGAACCAATTCAG

TCGAGCCTTTCACTCATTAGATGCATGTCGTTACATAACTTACGGTAAATGGCCCGCCTGGCT

GACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAATGGCCCGCC

TGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTT

GACTCACGGGGATTTCCAAGTCTCCACCCCATTGACGTCAATGGGAGTTTGTTTTGGCACCAA

AATCAACGGGACTTTCCAAAATGTCGTAACAACTCCGCCCCATTGACGCAAATGGGCGGTAG

GCGTGTACGGTGGGAGGTCTATATAAGCAGAGCTCTCCCTATCAGTGATAGAGATCTCCCTAT

CAGTGATAGAGATCGTCGACGAGCTCGTTTAGTGAACCGTCAGATCGCCTGGAGACGCCATC

CACGCTGTTTTGACCTCCATAGAAGACACCGGGACCGATCCAGCCTCCGGTTAAGCTCGGTA

CCGCTAGCCGCGCCGCCACCATGGATGCAATGAAGAGAGGGCTCTGCTGTGTGCTGCTGCT

GTGTGGAGCAGTCTTCGTTTCGCCCAGCCAGGAAATCCATGCCCGATTCAGAAGAGGATCGA

AGCTTGCCCTGATCCTGGCCCCCACCAGGGTGGTGGCCAGCGAGATGGCCCCCACCAGGGT

GGTGGCCGCCGAGATGGAGGAGAGGGTGGTGGCCGCCGAGATGGAGGAGGCCCTGAAGGG

CCTGCCCAGCATCGCCGCCAGGGGCTACATCAGCACCAGGGTGGAGATGGGCGAGGCCGC

CGCCATCCTGAACGACTGGGACTTCGTGGTGACCACCGACATCAGCGAGATGGGCGCCAAC

TTCAAGCCCATGCCCGTGACCGCCGCCAGCGCCGCCCAGAGGAGGGGCAGGATCGGCAGG

AACGACCACGCCCACTGGACCGAGGCCAAGATGCTGCTGGACAACATCAAGAGGACCGCCG

CCGGCATCATGAAGAACCCCACCGTGGACGGCTACGACCCCAAGTTCGAGAAGCAGCTGGG

CCAGGTGATGCTGCTGATGAGGACCACCTGGGCCCTGTGCGAGGCCCTGACCCTGGCCACC

GGCCCCCTGTGGGAGGGCAACCCCGGCAAGTTCTGGAACACCACCATCGCCGTGAGCATGC

CCGGCAAGTTCTGGAACACCACCATCGCCGTGAGCATGGCCAACATCTTCAGGGGCAGCTAC

CTGGCCCTGTGCGACATCGGCGAGAGCAGCCCCAACCCCACCATCGAGGAGTACAACATGA

TGGGCAAGAGGGAGAAGAAGCTGGGCGAGTTCGGCAAGGCCAAGAGCAGGGCCATCTGGTA

CATGTGGCTGGGCGCCAGGTTCCTGGAGTTCGAGGCCCTGGGCTTCATGTACGCCGACGAC

ACCGCCGGCTGGGACACCAGGATCACCGAGGACGACCTGTTCAAGCTGACCTACCAGAACA

AGGTGGTGAAGGTGCAGAGGCCCGTGATGGACATCATCAGCAGGAAGGACCAGAGGGGCAG

CGGCCAGGTGGGCACCTACGCTGGATCCGGGCCCGGGGCTTCAGGTAAGCCTATCCCTAAC

CCTCTCCTCGGTCTCGATTCTACGCGGACCTGATGAGCGGCCGCTCGAGCATGCATCTAGAG

GGCCCTATTCTATAGTGTCACCTAAATGCTAGAGCTCGCTGATCAGCCTCGACTGTGCCTTCT

AGTTGCCAGCCATCTGTTGTTTGCCCCTCCCCCGTGCCTTCCTTGACCCTGGAAGGTGCCAC

TCCCACTGTCCTTTCCTAATAAAATGAGGAAATTGCATCGCATTGTCTGAGTAGGTGTCATTCT

ATTCTGGGGGGTGGGGTGGGGCAGGACAGCAAGGGGGAGGATTGGGAAGACAATAGCAGG

CATGCTGGGGATGCGGTGGGCTCTATGGCTTCTGAGGCGGAAAGAACCAGCTGGGGCTCGA

GGGGGGATCGATCCCGTCGAGATATCTAGACCCAGCTTTCTTGTACAAAGTTGGCATTATAAG

AAAGCATTGCTTATCAATTTGTTGCAACGAACAGGTCACTATCAGTCAAAATAAAATCATTATT

TGGATCGATTCGACAGATCGCGATCGCAGTGAGTAGTGTTCTGGGGCGGGGGAGGACCTGC

ATGAGGGCCAGAATGACTGAAATCTGTGCTTTTCTGTGTGTTGCAGCATCATGAGCGGAAGC

-continued

GGCTCCTTTGAGGGAGGGGTATTCAGCCCTTATCTGACGGGGCGTCTCCCCTCCTGGGCGG

GAGTGCGTCAGAATGTGATGGGATCCACGGTGGACGGCCGGCCCGTGCAGCCCGCGAACTC

TTCAACCCTGACCTATGCAACCCTGAGCTCTTCGTCGGTGGACGCAGCTGCCGCCGCAGCTG

CTGCATCCGCCGCCAGCGCCGTGCGCGGAATGGCCATGGGCGCCGGCTACTACGGCACTCT

GGTGGCCAACTCGAGTTCCACCAATAATCCCGCCAGCCTGAACGAGGAGAAGCTGCTGCTGC

TGATGGCCCAGCTTGAGGCCTTGACCCAGCGCCTGGGCGAGCTGACCCAGCAGGTGGCTCA

GCTGCAGGAGCAGACGCGGGCCGCGGTTGCCACGGTGAAATCCAAATAAAAAATGAATCAAT

AAATAAACGGAGACGGTTGTTGATTTTAACACAGAGTCTGAATCTTTATTTGATTTTTCGCGCG

CGGTAGGCCCTGGACCACCGGTCTCGATCATTGAGCACCCGGTGGATCTTTTCCAGGACCCG

GTAGAGGTGGGCTTGGATGTTGAGGTACATGGGCATGAGCCCGTCCCGGGGGTGGAGGTAG

CTCCATTGCAGGGCCTCGTGCTCGGGGGTGGTGTTGTAAATCACCCAGTCATAGCAGGGGC

GCAGGGCGTGGTGTTGCACAATATCTTTGAGGAGGAGACTGATGGCCACGGGCAGCCCTTT

GGTGTAGGTGTTTACAAATCTGTTGAGCTGGGAGGGATGCATGCGGGGGGAGATGAGGTGC

ATCTTGGCCTGGATCTTGAGATTGGCGATGTTACCGCCCAGATCCCGCCTGGGGTTCATGTT

GTGCAGGACCACCAGCACGGTGTATCCGGTGCACTTGGGGAATTTATCATGCAACTTGGAAG

GGAAGGCGTGAAAGAATTTGGCGACGCCCTTGTGTCCGCCCAGGTTTTCCATGCACTCATCC

ATGATGATGGCAATGGGCCCGTGGGCGGCGGCCTGGGCAAAGACGTTTCGGGGGTCGGACA

CATCATAGTTGTGGTCCTGGGTGAGGTCATCATAGGCCATTTTAATGAATTTGGGGCGGAGG

GTGCCGGACTGGGGGACAAAGGTACCCTCGATCCCGGGGGCGTAGTTCCCCTCACAGATCT

GCATCTCCCAGGCTTTGAGCTCAGAGGGGGGGATCATGTCCACCTGCGGGGCGATAAAGAA

CACGGTTTCCGGGGCGGGGGAGATGAGCTGGGCCGAAAGCAAGTTCCGGAGCAGCTGGGA

CTTGCCGCAGCCGGTGGGGCCGTAAATGACCCCGATGACCGGCTGCAGGTGGTAGTTGAGG

GAGAGACAGCTGCCGTCCTCCCGGAGGAGGGGGGCCACCTCGTTCATCATCTCGCGCACGT

GCATGTTCTCGCGCACCAGTTCCGCCAGGAGGCGCTCTCCCCCCAGAGATAGGAGCTCCTG

GAGCGAGGCGAAGTTTTTCAGCGGCTTGAGTCCGTCGGCCATGGGCATTTTGGAGAGGGTCT

GTTGCAAGAGTTCCAAGCGGTCCCAGAGCTCGGTGATGTGCTCTACGGCATCTCGATCCAGC

AGACCTCCTCGTTTCGCGGGTTGGGACGACTGCGGGAGTAGGGCACCAGACGATGGGCGTC

CAGCGCAGCCAGGGTCCGGTCCTTCCAGGGCCGCAGCGTCCGCGTCAGGGTGGTCTCCGTC

ACGGTGAAGGGGTGCGCGCCGGGCTGGGCGCTTGCGAGGGTGCGCTTCAGGCTCATCCGG

CTGGTCGAAAACCGCTCCCGATCGGCGCCCTGCGCGTCGGCCAGGTAGCAATTGACCATGA

GTTCGTAGTTGAGCGCCTCGGCCGCGTGGCCTTTGGCGCGGAGCTTACCTTTGGAAGTCTGC

CCGCAGGCGGGACAGAGGAGGGACTTGAGGGCGTAGAGCTTGGGGGCGAGGAAGACGGAA

TCGGGGGCGTAGGCGTCCGCGCCGCAGTGGGCGCAGACGGTCTCGCACTCCACGAGCCAG

GTGAGGTCGGGCTGGTCGGGGTCAAAAACCAGTTTCCCGCCGTTCTTTTTGATGCGTTTCTTA

CCTTTGGTCTCCATGAGCTCGTGTCCCCGCTGGGTGACAAAGAGGCTGTCCGTGTCCCCGTA

GACCGACTTTATGGGCCGGTCCTCGAGCGGTGTGCCGCGGTCCTCCTCGTAGAGGAACCCC

GCCCACTCCGAGACGAAAGCCCGGGTCCAGGCCAGCACGAAGGAGGCCACGTGGGACGGG

TAGCGGTCGTTGTCCACCAGCGGGTCCACTTTTTCCAGGGTATGCAAACACATGTCCCCCTC

GTCCACATCCAGGAAGGTGATTGGCTTGTAAGTGTAGGCCACGTGACCGGGGGTCCCGGCC

GGGGGGGTATAAAAGGGGGCGGGCCCCTGCTCGTCCTCACTGTCTTCCGGATCGCTGTCCA

GGAGCGCCAGCTGTTGGGGTAGGTATTCCCTCTCGAAGGCGGGCATGACCTCGGCACTCAG

-continued

GTTGTCAGTTTCTAGAAACGAGGAGGATTTGATATTGACGGTGCCAGCGGAGATGCCTTTCAA

GAGCCCCTCGTCCATCTGGTCAGAAAAGACGATTTTTTTGTTGTCGAGCTTGGTGGCGAAGG

AGCCGTAGAGGGCGTTGGAAAGGAGCTTGGCGATGGAGCGCATGGTCTGGTTTTTTTCCTTG

TCGGCGCGCTCCTTGGCCGCGATGTTGAGCTGCACGTACTCGCGCGCCACGCACTTCCATTC

GGGGAAGACGGTGGTCATCTCGTCGGGCACGATTCTGACCTGCCAACCTCGATTATGCAGG

GTGATGAGGTCCACACTGGTGGCCACCTCGCCGCGCAGGGGCTCGTTGGTCCAGCAGAGGC

GGCCGCCCTTGCGCGAGCAGAAGGGGGGCAGAGGGTCCAGCATGACCTCGTCGGGGGGGT

CGGCATCGATGGTGAAGATGCCGGGCAGGAGATCGGGGTCGAAGTAGCTGATGGAAGTGGC

CAGATCGTCCAGGGAAGCTTGCCATTCGCGCACGGCCAGCGCGCGCTCGTAGGGACTGAGG

GGCGTGCCCCAGGGCATGGGGTGGGTGAGCGCGGAGGCGTACATGCCGCAGATGTCGTAG

ACGTAGAGGGGCTCCTCGAGGATGCCGATGTAGGTGGGGTAGCAGCGCCCCCCGCGGATG

CTGGCGCGCACGTAGTCATACAGCTCGTGCGAGGGCGCGAGGAGCCCCGGGCCCAGGTTG

GTGCGACTGGGCTTTTCGGCGCGGTAGACGATCTGGCGAAAGATGGCATGCGAGTTGGAGG

AGATGGTGGGCCTTTGGAAGATGTTGAAGTGGGCGTGGGGGAGGCCGACCGAGTCGCGGAT

GAAGTGGGCGTAGGAGTCTTGCAGTTTGGCGACGAGCTCGGCGGTGACGAGGACGTCCAGA

GCGCAGTAGTCGAGGGTCTCCTGGATGATGTCATACTTGAGCTGGCCCTTTTGTTTCCACAG

CTCGCGGTTGAGAAGGAACTCTTCGCGGTCCTTCCAGTACTCTTCGAGGGGGAACCCGTCCT

GATCTGCACGGTAAGAGCCTAGCATGTAGAACTGGTTGACGGCCTTGTAGGCGCAGCAGCCC

TTCTCCACGGGGAGGGCGTAGGCCTGGGCGGCCTTGCGCAGGGAGGTGTGCGTGAGGGCG

AAGGTGTCCCTGACCATGACCTTGAGGAACTGGTGCTTGAAATCGATATCGTCGCAGCCCCC

CTGCTCCCAGAGCTGGAAGTCCGTGCGCTTCTTGTAGGCGGGGTTGGGCAAAGCGAAAGTA

ACATCGTTGAAAAGGATCTTGCCCGCGCGGGGCATAAAGTTGCGAGTGATGCGGAAAGGCTG

GGGCACCTCGGCCCGGTTGTTGATGACCTGGGCGGCGAGCACGATCTCGTCGAAACCGTTG

ATGTTGTGGCCCACGATGTAGAGTTCCACGAATCGCGGGCGGCCCTTGACGTGGGGCAGCT

TCTTGAGCTCCTCGTAGGTGAGCTCGTCGGGGTCGCTGAGACCGTGCTGCTCGAGCGCCCA

GTCGGCGAGATGGGGGTTGGCGCGGAGGAAGGAAGTCCAGAGATCCACGGCCAGGGCGGT

TTGCAGACGGTCCCGGTACTGACGGAACTGCTGCCCGACGGCCATTTTTTCGGGGGTGACG

CAGTAGAAGGTGCGGGGGTCCCCGTGCCAGCGGTCCCATTTGAGCTGGAGGGCGAGATCGA

GGGCGAGCTCGACGAGGCGGTCGTCCCCTGAGAGTTTCATGACCAGCATGAAGGGGACGAG

CTGCTTGCCGAAGGACCCCATCCAGGTGTAGGTTTCCACATCGTAGGTGAGGAAGAGCCTTT

CGGTGCGAGGATGCGAGCCGATGGGGAAGAACTGGATCTCCTGCCACCAATTGGAGGAATG

GCTGTTGATGTGATGGAAGTAGAAATGCCGACGGCGCGCCGAACACTCGTGCTTGTGTTTAT

ACAAGCGGCCACAGTGCTCGCAACGCTGCACGGGATGCACGTGCTGCACGAGCTGTACCTG

AGTTCCTTTGACGAGGAATTTCAGTGGGAAGTGGAGTCGTGGCGCCTGCATCTCGTGCTGTA

CTACGTCGTGGTGGTCGGCCTGGCCCTCTTCTGCCTCGATGGTGGTCATGCTGACGAGCCC

GCGCGGGAGGCAGGTCCAGACCTCGGCGCGAGCGGGTCGGAGAGCGAGGACGAGGGCGC

GCAGGCCGGAGCTGTCCAGGGTCCTGAGACGCTGCGGAGTCAGGTCAGTGGGCAGCGGCG

GCGCGCGGTTGACTTGCAGGAGTTTTTCCAGGGCGCGCGGGAGGTCCAGATGGTACTTGAT

CTCCACCGCGCCGTTGGTGGCGACGTCGATGGCTTGCAGGGTCCCGTGCCCCTGGGGTGTG

ACCACCGTCCCCCGTTTCTTCTTGGGCGGCTGGGGCGACGGGGGCGGTGCCTCTTCCATGG

-continued

TTAGAAGCGGCGGCGAGGACGCGCGCCGGGCGGCAGAGGCGGCTCGGGGCCCGGAGGCA

GGGGCGGCAGGGGCACGTCGGCGCCGCGCGCGGGTAGGTTCTGGTACTGCGCCCGGAGAA

GACTGGCGTGAGCGACGACGCGACGGTTGACGTCCTGGATCTGACGCCTCTGGGTGAAGGC

CACGGGACCCGTGAGTTTGAACCTGAAAGAGAGTTCGACAGAATCAATCTCGGTATCGTTGA

CGGCGGCCTGCCGCAGGATCTCTTGCACGTCGCCCGAGTTGTCCTGGTAGGCGATCTCGGT

CATGAACTGCTCGATCTCCTCCTCCTGAAGGTCTCCGCGACCGGCGCGCTCCACGGTGGCC

GCGAGGTCGTTGGAGATGCGGCCCATGAGCTGCGAGAAGGCGTTCATGCCCGCCTCGTTCC

AGACGCGGCTGTAGACCACGACGCCCTCGGGATCGCGGGCGCGCATGACCACCTGGGCGA

GGTTGAGCTCCACGTGGCGCGTGAAGACCGCGTAGTTGCAGAGGCGCTGGTAGAGGTAGTT

GAGCGTGGTGGCGATGTGCTCGGTGACGAAGAAATACATGATCCAGCGGCGGAGCGGCATC

TCGCTGACGTCGCCCAGCGCCTCCAAGCGTTCCATGGCCTCGTAAAAGTCCACGGCGAAGTT

GAAAAACTGGGAGTTGCGCGCCGAGACGGTCAACTCCTCCTCCAGAAGACGGATGAGCTCG

GCGATGGTGGCGCGCACCTCGCGCTCGAAGGCCCCCGGGAGTTCCTCCACTTCCTCCTCTT

CTTCCTCCTCCACTAACATCTCTTCTACTTCCTCCTCAGGCGGTGGTGGTGGCGGGGGAGGG

GGCCTGCGTCGCCGGCGGCGCACGGGCAGACGGTCGATGAAGCGCTCGATGGTCTCGCCG

CGCCGGCGTCGCATGGTCTCGGTGACGGCGCGCCCGTCCTCGCGGGGCCGCAGCGTGAAG

ACGCCGCCGCGCATCTCCAGGTGGCCGGGGGGGTCCCCGTTGGGCAGGGAGAGGGCGCTG

ACGATGCATCTTATCAATTGCCCCGTAGGGACTCCGCGCAAGGACCTGAGCGTCTCGAGATC

CACGGGATCTGAAAACCGTTGAACGAAGGCTTCGAGCCAGTCGCAGTCGCAAGGTAGGCTG

AGCACGGTTTCTTCTGCCGGGTCATGTTGGGGAGCGGGGCGGGCGATGCTGCTGGTGATGA

AGTTGAAATAGGCGGTTCTGAGACGGCGGATGGTGGCGAGGAGCACCAGGTCTTTGGGCCC

GGCTTGCTGGATGCGCAGACGGTCGGCCATGCCCCAGGCGTGGTCCTGACACCTGGCCAGG

TCCTTGTAGTAGTCCTGCATGAGCCGCTCCACGGGCACCTCCTCCTCGCCCGCGCGGCCGT

GCATGCGCGTGAGCCCGAAGCCGCGCTGGGGCTGGACGAGCGCCAGGTCGGCGACGACGC

GCTCGGCGAGGATGGCCTGCTGGATCTGGGTGAGGGTGGTCTGGAAGTCGTCAAAGTCGAC

GAAGCGGTGGTAGGCTCCGGTGTTGATGGTGTAGGAGCAGTTGGCCATGACGGACCAGTTG

ACGGTCTGGTGGCCCGGACGCACGAGCTCGTGGTACTTGAGGCGCGAGTAGGCGCGCGTGT

CGAAGATGTAGTCGTTGCAGGTGCGCACCAGGTACTGGTAGCCGATGAGGAAGTGCGGCGG

CGGCTGGCGGTAGAGCGGCCATCGCTCGGTGGCGGGGGCGCCGGGCGCGAGGTCCTCGA

GCATGGTGCGGTGGTAGCCGTAGATGTACCTGGACATCCAGGTGATGCCGGCGGCGGTGGT

GGAGGCGCGCGGGAACTCGCGGACGCGGTTCCAGATGTTGCGCAGCGGCAGGAAGTAGTT

CATGGTGGGCACGGTCTGGCCCGTGAGGCGCGCGCAGTCGTGGATGCTCTATACGGGCAAA

AACGAAAGCGGTCAGCGGCTCGACTCCGTGGCCTGGAGGCTAAGCGAACGGGTTGGGCTGC

GCGTGTACCCCGGTTCGAATCTCGAATCAGGCTGGAGCCGCAGCTAACGTGGTACTGGCACT

CCCGTCTCGACCCAAGCCTGCACCAACCCTCCAGGATACGGAGGCGGGTCGTTTTGCAACTT

TTTTTGGAGGCCGGAAATGAAACTAGTAAGCGCGGAAAGCGGCCGACCGCGATGGCTCGCT

GCCGTAGTCTGGAGAAGAATCGCCAGGGTTGCGTTGCGGTGTGCCCCGGTTCGAGGCCGGC

CGGATTCCGCGGCTAACGAGGGCGTGGCTGCCCCGTCGTTTCCAAGACCCCATAGCCAGCC

GACTTCTCCAGTTACGGAGCGAGCCCCTCTTTTGTTTTGTTTGTTTTTGCCAGATGCATCCCG

TACTGCGGCAGATGCGCCCCCACCACCCTCCACCGCAACAACAGCCCCCTCCTCCACAGCC

GGCGCTTCTGCCCCCGCCCCAGCAGCAGCAGCAACTTCCAGCCACGACCGCCGCGGCCGC

-continued

CGTGAGCGGGGCTGGACAGACTTCTCAGTATGATCACCTGGCCTTGGAAGAGGGCGAGGGG

CTGGCGCGCCTGGGGGCGTCGTCGCCGGAGCGGCACCCGCGCGTGCAGATGAAAAGGGAC

GCTCGCGAGGCCTACGTGCCCAAGCAGAACCTGTTCAGAGACAGGAGCGGCGAGGAGCCCG

AGGAGATGCGCGCGGCCCGGTTCCACGCGGGGCGGGAGCTGCGGCGCGGCCTGGACCGAA

AGAGGGTGCTGAGGGACGAGGATTTCGAGGCGGACGAGCTGACGGGGATCAGCCCCGCGC

GCGCGCACGTGGCCGCGGCCAACCTGGTCACGGCGTACGAGCAGACCGTGAAGGAGGAGA

GCAACTTCCAAAAATCCTTCAACAACCACGTGCGCACCCTGATCGCGCGCGAGGAGGTGACC

CTGGGCCTGATGCACCTGTGGGACCTGCTGGAGGCCATCGTGCAGAACCCCACCAGCAAGC

CGCTGACGGCGCAGCTGTTCCTGGTGGTGCAGCATAGTCGGGACAACGAGGCGTTCAGGGA

GGCGCTGCTGAATATCACCGAGCCCGAGGGCCGCTGGCTCCTGGACCTGGTGAACATTCTG

CAGAGCATCGTGGTGCAGGAGCGCGGGCTGCCGCTGTCCGAGAAGCTGGCGGCCATCAACT

TCTCGGTGCTGAGTCTGGGCAAGTACTACGCTAGGAAGATCTACAAGACCCCGTACGTGCCC

ATAGACAAGGAGGTGAAGATCGACGGGTTTTACATGCGCATGACCCTGAAAGTGCTGACCCT

GAGCGACGATCTGGGGGTGTACCGCAACGACAGGATGCACCGCGCGGTGAGCGCCAGCAG

GCGGCGCGAGCTGAGCGACCAGGAGCTGATGCACAGCCTGCAGCGGGCCCTGACCGGGGC

CGGGACCGAGGGGGAGAGCTACTTTGACATGGGCGCGGACCTGCACTGGCAGCCCAGCCG

CCGGGCCTTGGAGGCGGCAGGCGGTCCCCCCTACATAGAAGAGGTGGACGATGAGGTGGA

CGAGGAGGGCGAGTACCTGGAAGACTGATGGCGCGACCGTATTTTTGCTAGATGCAACAACA

GCCACCTCCTGATCCCGCGATGCGGGCGGCGCTGCAGAGCCAGCCGTCCGGCATTAACTCC

TCGGACGATTGGACCCAGGCCATGCAACGCATCATGGCGCTGACGACCCGCAACCCCGAAG

CCTTTAGACAGCAGCCCCAGGCCAACCGGCTCTCGGCCATCCTGGAGGCCGTGGTGCCCTC

GCGCTCCAACCCCACGCACGAGAAGGTCCTGGCCATCGTGAACGCGCTGGTGGAGAACAAG

GCCATCCGCGGCGACGAGGCCGGCCTGGTGTACAACGCGCTGCTGGAGCGCGTGGCCCGC

TACAACAGCACCAACGTGCAGACCAACCTGGACCGCATGGTGACCGACGTGCGCGAGGCCG

TGGCCCAGCGCGAGCGGTTCCACCGCGAGTCCAACCTGGGATCCATGGTGGCGCTGAACGC

CTTCCTCAGCACCCAGCCCGCCAACGTGCCCCGGGGCCAGGAGGACTACACCAACTTCATC

AGCGCCCTGCGCCTGATGGTGACCGAGGTGCCCCAGAGCGAGGTGTACCAGTCCGGGCCG

GACTACTTCTTCCAGACCAGTCGCCAGGGCTTGCAGACCGTGAACCTGAGCCAGGCGTTCAA

GAACTTGCAGGGCCTGTGGGGCGTGCAGGCCCCGGTCGGGGACCGCGCGACGGTGTCGAG

CCTGCTGACGCCGAACTCGCGCCTGCTGCTGCTGCTGGTGGCCCCCTTCACGGACAGCGGC

AGCATCAACCGCAACTCGTACCTGGGCTACCTGATTAACCTGTACCGCGAGGCCATCGGCCA

GGCGCACGTGGACGAGCAGACCTACCAGGAGATCACCCACGTGAGCCGCGCCCTGGGCCA

GGACGACCCGGGCAATCTGGAAGCCACCCTGAACTTTTTGCTGACCAACCGGTCGCAGAAGA

TCCCGCCCCAGTACACGCTCAGCGCCGAGGAGGAGCGCATCCTGCGATACGTGCAGCAGAG

CGTGGGCCTGTTCCTGATGCAGGAGGGGGCCACCCCCAGCGCCGCGCTCGACATGACCGC

GCGCAACATGGAGCCCAGCATGTACGCCAGCAACCGCCCGTTCATCAATAAACTGATGGACT

ACTTGCATCGGGCGGCCGCCATGAACTCTGACTATTTCACCAACGCCATCCTGAATCCCCAC

TGGCTCCCGCCGCCGGGGTTCTACACGGGCGAGTACGACATGCCCGACCCCAATGACGGGT

TCCTGTGGGACGATGTGGACAGCAGCGTGTTCTCCCCCCGACCGGGTGCTAACGAGCGCCC

CTTGTGGAAGAAGGAAGGCAGCGACCGACGCCCGTCCTCGGCGCTGTCCGGCCGCGAGGG

-continued

TGCTGCCGCGGCGGTGCCCGAGGCCGCCAGTCCTTTCCCGAGCTTGCCCTTCTCGCTGAAC

AGTATTCGCAGCAGCGAGCTGGGCAGGATCACGCGCCCGCGCTTGCTGGGCGAGGAGGAGT

ACTTGAATGACTCGCTGTTGAGACCCGAGCGGGAGAAGAACTTCCCCAATAACGGGATAGAG

AGCCTGGTGGACAAGATGAGCCGCTGGAAGACGTATGCGCAGGAGCACAGGGACGATCCGT

CGCAGGGGGCCACGAGCCGGGGCAGCGCCGCCCGTAAACGCCGGTGGCACGACAGGCAGC

GGGGACTGATGTGGGACGATGAGGATTCCGCCGACGACAGCAGCGTGTTGGACTTGGGTGG

GAGTGGTAACCCGTTCGCTCACCTGCGCCCCCGCATCGGGCGCATGATGTAAGAGAAACCG

AAAATAAATGATACTCACCAAGGCCATGGCGACCAGCGTGCGTTCGTTTCTTCTCTGTTGTTG

TATCTAGTATGATGAGGCGTGCGTACCCGGAGGGTCCTCCTCCCTCGTACGAGAGCGTGATG

CAGCAGGCGATGGCGGCGGCGGCGGCGATGCAGCCCCCGCTGGAGGCTCCTTACGTGCCC

CCGCGGTACCTGGCGCCTACGGAGGGGCGGAACAGCATTCGTTACTCGGAGCTGGCACCCT

TGTACGATACCACCCGGTTGTACCTGGTGGACAACAAGTCGGCGGACATCGCCTCGCTGAAC

TACCAGAACGACCACAGCAACTTCCTGACCACCGTGGTGCAGAACAATGACTTCACCCCCAC

GGAGGCCAGCACCCAGACCATCAACTTTGACGAGCGCTCGCGGTGGGGCGGTCAGCTGAAA

ACCATCATGCACACCAACATGCCCAACGTGAACGAGTTCATGTACAGCAACAAGTTCAAGGC

GCGGGTGATGGTCTCCCGCAAGACCCCCAACGGGGTGACAGTGACAGATGGTAGTCAGGAT

ATCTTGGAGTATGAATGGGTGGAGTTTGAGCTGCCCGAAGGCAACTTCTCGGTGACCATGAC

CATCGACCTGATGAACAACGCCATCATCGACAATTACTTGGCGGTGGGGCGGCAGAACGGG

GTCCTGGAGAGCGATATCGGCGTGAAGTTCGACACTAGGAACTTCAGGCTGGGCTGGGACC

CCGTGACCGAGCTGGTCATGCCCGGGGTGTACACCAACGAGGCCTTCCACCCCGATATTGTC

TTGCTGCCCGGCTGCGGGGTGGACTTCACCGAGAGCCGCCTCAGCAACCTGCTGGGCATTC

GCAAGAGGCAGCCCTTCCAGGAGGGCTTCCAGATCATGTACGAGGATCTGGAGGGGGGCAA

CATCCCCGCGCTCCTGGATGTCGACGCCTATGAGAAAAGCAAGGAGGAGAGCGCCGCCGCG

GCGACTGCAGCTGTAGCCACCGCCTCTACCGAGGTCAGGGGCGATAATTTTGCCAGCCCTG

CAGCAGTGGCAGCGGCCGAGGCGGCTGAAACCGAAAGTAAGATAGTCATTCAGCCGGTGGA

GAAGGATAGCAAGGACAGGAGCTACAACGTGCTGCCGGACAAGATAAACACCGCCTACCGC

AGCTGGTACCTGGCCTACAACTATGGCGACCCCGAGAAGGGCGTGCGCTCCTGGACGCTGC

TCACCACCTCGGACGTCACCTGCGGCGTGGAGCAAGTCTACTGGTCGCTGCCCGACATGAT

GCAAGACCCGGTCACCTTCCGCTCCACGCGTCAAGTTAGCAACTACCCGGTGGTGGGCGCC

GAGCTCCTGCCCGTCTACTCCAAGAGCTTCTTCAACGAGCAGGCCGTCTACTCGCAGCAGCT

GCGCGCCTTCACCTCGCTCACGCACGTCTTCAACCGCTTCCCCGAGAACCAGATCCTCGTCC

GCCCGCCCGCGCCCACCATTACCACCGTCAGTGAAAACGTTCCTGCTCTCACAGATCACGGG

ACCCTGCCGCTGCGCAGCAGTATCCGGGGAGTCCAGCGCGTGACCGTTACTGACGCCAGAC

GCCGCACCTGCCCCTACGTCTACAAGGCCCTGGGCATAGTCGCGCCGCGCGTCCTCTCGAG

CCGCACCTTCTAAAAAATGTCCATTCTCATCTCGCCCAGTAATAACACCGGTTGGGGCCTGCG

CGCGCCCAGCAAGATGTACGGAGGCGCTCGCCAACGCTCCACGCAACACCCCGTGCGCGTG

CGCGGGCACTTCCGCGCTCCCTGGGGCGCCCTCAAGGGCCGCGTGCGGTCGCGCACCACC

GTCGACGACGTGATCGACCAGGTGGTGGCCGACGCGCGCAACTACACCCCCGCCGCCGCG

CCCGTCTCCACCGTGGACGCCGTCATCGACAGCGTGGTGGCCGACGCGCGCCGGTACGCC

CGCGCCAAGAGCCGGCGGCGGCGCATCGCCCGGCGGCACCGGAGCACCCCCGCCATGCGC

GCGGCGCGAGCCTTGCTGCGCAGGGCCAGGCGCACGGGACGCAGGGCCATGCTCAGGGCG

-continued

```
GCCAGACGCGCGGCTTCAGGCGCCAGCGCCGGCAGGACCCGGAGACGCGCGGCCACGGC

GGCGGCAGCGGCCATCGCCAGCATGTCCCGCCCGCGGCGAGGGAACGTGTACTGGGTGCG

CGACGCCGCCACCGGTGTGCGCGTGCCCGTGCGCACCCGCCCCCCTCGCACTTGAAGATGT

TCACTTCGCGATGTTGATGTGTCCCAGCGGCGAGGAGGATGTCCAAGCGCAAATTCAAGGAA

GAGATGCTCCAGGTCATCGCGCCTGAGATCTACGGCCCCGCGGTGGTGAAGGAGGAAAGAA

AGCCCCGCAAAATCAAGCGGGTCAAAAAGGACAAAAAGGAAGAAGATGACGATCTGGTGGAG

TTTGTGCGCGAGTTCGCCCCCCGGCGGCGCGTGCAGTGGCGCGGGCGGAAAGTGCACCCG

GTGCTGAGACCCGGCACCACCGTGGTCTTCACGCCCGGCGAGCGCTCCGGCAGCGCTTCCA

AGCGCTCCTACGACGAGGTGTACGGGGACGAGGACATCCTCGAGCAGGCGGCCGAGCGCC

TGGGCGAGTTTGCTTACGGCAAGCGCAGCCGCCCCGCCCTGAAGGAAGAGGCGGTGTCCAT

CCCGCTGGACCACGGCAACCCCACGCCGAGCCTCAAGCCCGTGACCCTGCAGCAGGTGCTG

CCGAGCGCAGCGCCGCGCCGGGGGTTCAAGCGCGAGGGCGAGGATCTGTACCCCACCATG

CAGCTGATGGTGCCCAAGCGCCAGAAGCTGGAAGACGTGCTGGAGACCATGAAGGTGGACC

CGGACGTGCAGCCCGAGGTCAAGGTGCGGCCCATCAAGCAGGTGGCCCCGGGCCTGGGCG

TGCAGACCGTGGACATCAAGATCCCCACGGAGCCCATGGAAACGCAGACCGAGCCCATGAT

CAAGCCCAGCACCAGCACCATGGAGGTGCAGACGGATCCCTGGATGCCATCGGCTCCTAGC

CGAAGACCCCGGCGCAAGTACGGCGCGGCCAGCCTGCTGATGCCCAACTACGCGCTGCATC

CTTCCATCATCCCCACGCCGGGCTACCGCGGCACGCGCTTCTACCGCGGTCATACAACCAGC

CGCCGCCGCAAGACCACCACCCGCCGCCGCCGTCGCCGCACAGCCGCTGCATCTACCCCTG

CCGCCCTGGTGCGGAGAGTGTACCGCCGCGGCCGCGCGCCTCTGACCCTACCGCGCGCGC

GCTACCACCCGAGCATCGCCATTTAAACTTTCGCCTGCTTTGCAGATGGCCCTCACATGCCG

CCTCCGCGTTCCCATTACGGGCTACCGAGGAAGAAAACCGCGCCGTAGAAGGCTGGCGGGG

AACGGGATGCGTCGCCACCACCATCGGCGGCGGCGCGCCATCAGCAAGCGGTTGGGGGGA

GGCTTCCTGCCCGCGCTGATCCCCATCATCGCCGCGGCGATCGGGGCGATCCCCGGCATTG

CTTCCGTGGCGGTGCAGGCCTCTCAGCGCCACTGAGACACTTGGAAAACATCTTGTAATAAA

CCAATGGACTCTGACGCTCCTGGTCCTGTGATGTGTTTTCGTAGACAGATGGAAGACATCAAT

TTTTCGTCCCTGGCTCCGCGACACGGCACGCGGCCGTTCATGGGCACCTGGAGCGACATCG

GCACCAGCCAACTGAACGGGGGCGCCTTCAATTGGAGCAGTCTCTGGAGCGGGCTTAAGAA

TTTCGGGTCCACGCTTAAAACCTATGGCAGCAAGGCGTGGAACAGCACCACAGGGCAGGCG

CTGAGGGATAAGCTGAAAGAGCAGAACTTCCAGCAGAAGGTGGTCGATGGGCTCGCCTCGG

GCATCAACGGGGTGGTGGACCTGGCCAACCAGGCCGTGCAGCGGCAGATCAACAGCCGCCT

GGACCCGGTGCCGCCCGCCGGCTCCGTGGAGATGCCGCAGGTGGAGGAGGAGCTGCCTCC

CCTGGACAAGCGGGGCGAGAAGCGACCCCGCCCCGACGCGGAGGAGACGCTGCTGACGCA

CACGGACGAGCCGCCCCCGTACGAGGAGGCGGTGAAACTGGGTCTGCCCACCACGCGGCC

CATCGCGCCCCTGGCCACCGGGGTGCTGAAACCCGAAAGTAATAAGCCCGCGACCCTGGAC

TTGCCTCCTCCCGCTTCCCGCCCCTCTACAGTGGCTAAGCCCCTGCCGCCGGTGGCCGTGG

CCCGCGCGCGACCCGGGGGCTCCGCCCGCCCTCATGCGAACTGGCAGAGCACTCTGAACA

GCATCGTGGGTCTGGGAGTGCAGAGTGTGAAGCGCCGCCGCTGCTATTAAACCTACCGTAG

CGCTTAACTTGCTTGTCTGTGTGTGTATGTATTATGTCGCCGCTGTCCGCCAGAAGGAGGAGT

GAAGAGGCGCGTCGCCGAGTTGCAAGATGGCCACCCCATCGATGCTGCCCCAGTGGGCGTA
```

-continued

CATGCACATCGCCGGACAGGACGCTTCGGAGTACCTGAGTCCGGGTCTGGTGCAGTTCGCC

CGCGCCACAGACACCTACTTCAGTCTGGGGAACAAGTTTAGGAACCCCACGGTGGCGCCCA

CGCACGATGTGACCACCGACCGCAGCCAGCGGCTGACGCTGCGCTTCGTGCCCGTGGACCG

CGAGGACAACACCTACTCGTACAAAGTGCGCTACACGCTGGCCGTGGGCGACAACCGCGTG

CTGGACATGGCCAGCACCTACTTTGACATCCGCGGCGTGCTGGATCGGGGCCCTAGCTTCAA

ACCCTACTCCGGCACCGCCTACAACAGCCTGGCTCCCAAGGGAGCGCCCAATTCCAGCCAG

TGGGAGCAAAAAAAGGCAGGCAATGGTGACACTATGGAAACACACACATTTGGTGTGGCCCC

AATGGGCGGTGAGAATATTACAATCGACGGATTACAAATTGGAACTGACGCTACAGCTGATCA

GGATAAACCAATTTATGCTGACAAAACATTCCAGCCTGAACCTCAAGTAGGAGAAGAAAATTG

GCAAGAAACTGAAAGCTTTTATGGCGGTAGGGCTCTTAAAAAAGACACAAGCATGAAACCTTG

CTATGGCTCCTATGCTAGACCCACCAATGTAAAGGGAGGTCAAGCTAAACTTAAAGTTGGAGC

TGATGGAGTTCCTACCAAAGAATTTGACATAGACCTGGCTTTCTTTGATACTCCCGGTGGCAC

AGTGAATGGACAAGATGAGTATAAAGCAGACATTGTCATGTATACCGAAAACACGTATCTGGA

AACTCCAGACACGCATGTGGTATACAAACCAGGCAAGGATGATGCAAGTTCTGAAATTAACCT

GGTTCAGCAGTCCATGCCCAATAGACCCAACTATATTGGGTTCAGAGACAACTTTATTGGGCT

CATGTATTACAACAGTACTGGCAATATGGGGGTGCTGGCTGGTCAGGCCTCACAGCTGAATG

CTGTGGTCGACTTGCAAGACAGAAACACCGAGCTGTCATACCAGCTCTTGCTTGACTCTTTGG

GTGACAGAACCCGGTATTTCAGTATGTGGAATCAGGCGGTGGACAGTTATGATCCTGATGTG

CGCATTATTGAAAACCATGGTGTGGAAGACGAACTTCCCAACTATTGCTTCCCCCTGGATGGG

TCTGGCACTAATGCCGCTTACCAAGGTGTGAAAGTAAAAAATGGTAACGATGGTGATGTTGAG

AGCGAATGGGAAAATGATGATACTGTCGCAGCTCGAAATCAATTATGCAAGGGCAACATTTTT

GCCATGGAAATTAACCTCCAAGCCAACCTGTGGAGAAGTTTCCTCTACTCGAACGTGGCCCT

GTACCTGCCCGACTCTTACAAGTACACGCCAGCCAACATCACCCTGCCCACCAACACCAACA

CTTATGATTACATGAACGGGAGAGTGGTGCCTCCCTCGCTGGTGGACGCCTACATCAACATC

GGGGCGCGCTGGTCGCTGGACCCCATGGACAACGTCAATCCCTTCAACCACCACCGCAACG

CGGGCCTGCGCTACCGCTCCATGCTCCTGGGCAACGGGCGCTACGTGCCCTTCCACATCCA

GGTGCCCCAGAAATTTTTCGCCATCAAGAGCCTCCTGCTCCTGCCCGGGTCCTACACCTACG

AGTGGAACTTCCGCAAGGACGTCAACATGATCCTGCAGAGCTCCCTCGGCAACGACCTGCGC

ACGGACGGGGCCTCCATCTCCTTCACCAGCATCAACCTCTACGCCACCTTCTTCCCCATGGC

GCACAACACGGCCTCCACGCTCGAGGCCATGCTGCGCAACGACACCAACGACCAGTCCTTC

AACGACTACCTCTCGGCGGCCAACATGCTCTACCCCATCCCGGCCAACGCCACCAACGTGCC

CATCTCCATCCCCTCGCGCAACTGGGCCGCCTTCCGCGGCTGGTCCTTCACGCGCCTCAAGA

CCAAGGAGACGCCCTCGCTGGGCTCCGGGTTCGACCCCTACTTCGTCTACTCGGGCTCCATC

CCCTACCTCGACGGCACCTTCTACCTCAACCACACCTTCAAGAAGGTCTCCATCACCTTCGAC

TCCTCCGTCAGCTGGCCCGGCAACGACCGGCTCCTGACGCCCAACGAGTTCGAAATCAAGC

GCACCGTCGACGGCGAGGGATACAACGTGGCCCAGTGCAACATGACCAAGGACTGGTTCCT

GGTCCAGATGCTGGCCCACTACAACATCGGCTACCAGGGCTTCTACGTGCCCGAGGGCTACA

AGGACCGCATGTACTCCTTCTTCCGCAACTTCCAGCCCATGAGCCGCCAGGTGGTGGACGAG

GTCAACTACAAGGACTACCAGGCCGTCACCCTGGCCTACCAGCACAACAACTCGGGCTTCGT

CGGCTACCTCGCGCCCACCATGCGCCAGGGCCAGCCCTACCCCGCCAACTACCCGTACCCG

CTCATCGGCAAGAGCGCCGTCACCAGCGTCACCCAGAAAAAGTTCCTCTGCGACAGGGTCAT

-continued

GTGGCGCATCCCCTTCTCCAGCAACTTCATGTCCATGGGCGCGCTCACCGACCTCGGCCAGA

ACATGCTCTATGCCAACTCCGCCCACGCGCTAGACATGAATTTCGAAGTCGACCCCATGGAT

GAGTCCACCCTTCTCTATGTTGTCTTCGAAGTCTTCGACGTCGTCCGAGTGCACCAGCCCCA

CCGCGGCGTCATCGAGGCCGTCTACCTGCGCACCCCCTTCTCGGCCGGTAACGCCACCACC

TAAATTGCTACTTGCATGATGGCTGAGCCCACAGGCTCCGGCGAGCAGGAGCTCAGGGCCAT

CATCCGCGACCTGGGCTGCGGGCCCTACTTCCTGGGCACCTTCGATAAGCGCTTCCCGGGA

TTCATGGCCCCGCACAAGCTGGCCTGCGCCATCGTCAACACGGCCGGCCGCGAGACCGGGG

GCGAGCACTGGCTGGCCTTCGCCTGGAACCCGCGCTCGAACACCTGCTACCTCTTCGACCC

CTTCGGGTTCTCGGACGAGCGCCTCAAGCAGATCTACCAGTTCGAGTACGAGGGCCTGCTGC

GCCGTAGCGCCCTGGCCACCGAGGACCGCTGCGTCACCCTGGAAAAGTCCACCCAGACCGT

GCAGGGTCCGCGCTCGGCCGCCTGCGGGCTCTTCTGCTGCATGTTCCTGCACGCCTTCGTG

CACTGGCCCGACCGCCCCATGGACAAGAACCCCACCATGAACTTGCTGACGGGGGTGCCCA

ACGGCATGCTCCAGTCGCCCCAGGTGGAACCCACCCTGCGCCGCAACCAGGAGGCGCTCTA

CCGCTTCCTCAACTCCCACTCCGCCTACTTTCGCTCCCACCGCGCGCGCATCGAGAAGGCCA

CCGCCTTCGACCGCATGAACAATCAAGACATGTAAACCGTGTGTGTATGTTTAAAATATCTTTT

AATAAACAGCACTTTAATGTTACACATGCATCTGAGATGATTTTATTTTAGAAATCGAAAGGGT

TCTGCCGGGTCTCGGCATGGCCCGCGGGCAGGGACACGTTGCGGAACTGGTACTTGGCCAG

CCACTTGAACTCGGGGATCAGCAGTTTGGGCAGCGGGGTGTCGGGGAAGGAGTCGGTCCAC

AGCTTCCGCGTCAGCTGCAGGGCGCCCAGCAGGTCGGGCGCGGAGATCTTGAAATCGCAGT

TGGGACCCGCGTTCTGCGCGCGAGAGTTGCGGTACACGGGGTTGCAGCACTGGAACACCAT

CAGGGCCGGGTGCTTCACGCTCGCCAGCACCGCCGCGTCGGTGATGCTCTCCACGTCGAGG

TCCTCGGCGTTGGCCATCCCGAAGGGGGTCATCTTGCAGGTCTGCCTTCCCATGGTGGGCA

CGCACCCGGGCTTGTGGTTGCAATCGCAGTGCAGGGGGATCAGCATCATCTGGGCCTGGTC

GGCGTTCATCCCCGGGTACATGGCCTTCATGAAAGCCTCCAATTGCCTGAACGCCTGCTGGG

CCTTGGCTCCCTCGGTGAAGAAGACCCCGCAGGACTTGCTAGAGAACTGGTTGGTGGCACA

GCCGGCATCGTGCACGCAGCAGCGCGCGTCGTTGTTGGCCAGCTGCACCACGCTGCGCCCC

CAGCGGTTCTGGGTGATCTTGGCCCGGTCGGGGTTCTCCTTCAGCGCGCGCTGCCCGTTCT

CGCTCGCCACATCCATCTCGATCATGTGCTCCTTCTGGATCATGGTGGTCCCGTGCAGGCAC

CGCAGTTTGCCCTCGGCCTCGGTGCACCCGTGCAGCCACAGCGCGCACCCGGTGCACTCCC

AGTTCTTGTGGGCGATCTGGGAATGCGCGTGCACGAACCCTTGCAGGAAGCGGCCCATCAT

GGTCGTCAGGGTCTTGTTGCTAGTGAAGGTCAACGGGATGCCGCGGTGCTCCTCGTTGATGT

ACAGGTGGCAGATGCGGCGGTACACCTCGCCCTGCTCGGGCATCAGTTGGAAGTTGGCTTT

CAGGTCGGTCTCCACGCGGTAGCGGTCCATCAGCATAGTCATGATTTCCATGCCCTTCTCCC

AGGCCGAGACGATGGGCAGGCTCATAGGGTTCTTCACCATCATCTTAGCACTAGCAGCCGCG

GCCAGGGGGTCGCTCTCATCCAGGGTCTCAAAGCTCCGCTTGCCGTCCTTCTCGGTGATCCG

CACCGGGGGGTAGCTGAAGCCCACGGCCGCCAGCTCCTCCTCGGCCTGTCTTTCGTCCTCG

CTGTCCTGGCTGACGTCCTGCATGACCACATGCTTGGTCTTGCGGGGTTTCTTCTTGGGCGG

CAGTGGCGGCGGAGATGCTTGTGGCGAGGGGGAGCGCGAGTTCTCGCTCACCACTACTATC

TCTTCCTCTTCTTGGTCCGAGGCCACGCGGCGGTAGGTATGTCTCTTCGGGGGCAGAGGCG

GAGGCGACGGGCTCTCGCCGCCGCGACTTGGCGGATGGCTGGCAGAGCCCCTTCCGCGTT

-continued

CGGGGGTGCGCTCCCGGCGGCGCTCTGACTGACTTCCTCCGCGGCCGGCCATTGTGTTCTC

CTAGGGAGGAACAACAAGCATGGAGACTCAGCCATCGCCAACCTCGCCATCTGCCCCCACC

GCCGGCGACGAGAAGCAGCAGCAGCAGAATGAAAGCTTAACCGCCCCGCCGCCCAGCCCCG

CCTCCGACGCAGCCGCGGTCCCAGACATGCAAGAGATGGAGGAATCCATCGAGATTGACCT

GGGCTATGTGACGCCCGCGGAGCATGAGGAGGAGCTGGCAGTGCGCTTTCAATCGTCAAGC

CAGGAAGATAAAGAACAGCCAGAGCAGGAAGCAGAGAACGAGCAGAGTCAGGCTGGGCTCG

AGCATGGCGACTACCTCCACCTGAGCGGGGAGGAGGACGCGCTCATCAAGCATCTGGCCCG

GCAGGCCACCATCGTCAAGGACGCGCTGCTCGACCGCACCGAGGTGCCCCTCAGCGTGGAG

GAGCTCAGCCGCGCCTACGAGCTCAACCTCTTCTCGCCGCGCGTGCCCCCCAAGCGCCAGC

CCAACGGCACCTGCGAGCCCAACCCCCGCCTCAACTTCTACCCGGTCTTCGCGGTGCCCGA

GGCCCTGGCCACCTACCACATCTTTTTCAAGAACCAAAAGATCCCCGTCTCCTGCCGCGCCA

ACCGCACCCGCGCCGACGCCCTCTTCAACCTGGGTCCCGGCGCCCGCCTACCTGATATCGC

CTCCTTGGAAGAGGTTCCCAAGATCTTCGAGGGTCTGGGCAGCGACGAGACTCGGGCCGCG

AACGCTCTGCAAGGAGAAGGAGGAGGAGAGCATGAGCACCACAGCGCCCTGGTCGAGTTGG

AAGGCGACAACGCGCGGCTGGCGGTGCTCAAACGCACGGTCGAGCTGACCCATTTCGCCTA

CCCGGCTCTGAACCTGCCCCCGAAAGTCATGAGCGCGGTCATGGACCAGGTGCTCATCAAG

CGCGCGTCGCCCATCTCCGAGGACGAGGGCATGCAAGACTCCGAGGAGGGCAAGCCCGTG

GTCAGCGACGAGCAGCTGGCCCGGTGGCTGGGTCCTAATGCTACCCCTCAAAGTTTGGAAG

AGCGGCGCAAGCTCATGATGGCCGTGGTCCTGGTGACCGTGGAGCTGGAGTGCCTGCGCCG

CTTCTTCGCCGACGCGGAGACCCTGCGCAAGGTCGAGGAGAACCTGCACTACCTCTTCAGG

CACGGGTTCGTGCGCCAGGCCTGCAAGATCTCCAACGTGGAGCTGACCAACCTGGTCTCCTA

CATGGGCATCTTGCACGAGAACCGCCTGGGGCAGAACGTGCTGCACACCACCCTGCGCGGG

GAGGCCCGCCGCGACTACATCCGCGACTGCGTCTACCTCTACCTCTGCCACACCTGGCAGA

CGGGCATGGGCGTGTGGCAGCAGTGTCTGGAGGAGCAGAACCTGAAAGAGCTCTGCAAGCT

CCTGCAAAAGAACCTCAAGGGTCTGTGGACCGGGTTCGACGAGCGGACCACCGCCTCGGAC

CTGGCCGACCTCATCTTCCCCGAGCGCCTCAGGCTGACGCTGCGCAACGGCCTGCCCGACT

TTATGAGCCAAAGCATGTTGCAAAACTTTCGCTCTTTCATCCTCGAACGCTCCGGAATCCTGC

CCGCCACCTGCTCCGCGCTGCCCTCGGACTTCGTGCCGCTGACCTTCCGCGAGTGCCCCCC

GCCGCTGTGGAGCCACTGCTACCTGCTGCGCCTGGCCAACTACCTGGCCTACCACTCGGAC

GTGATCGAGGACGTCAGCGGCGAGGGCCTGCTCGAGTGCCACTGCCGCTGCAACCTCTGCA

CGCCGCACCGCTCCCTGGCCTGCAACCCCCAGCTGCTGAGCGAGACCCAGATCATCGGCAC

CTTCGAGTTGCAAGGGCCCAGCGAGGGCGAGGGAGCCAAGGGGGGTCTGAAACTCACCCC

GGGGCTGTGGACCTCGGCCTACTTGCGCAAGTTCGTGCCCGAGGATTACCATCCCTTCGAGA

TCAGGTTCTACGAGGACCAATCCCAGCCGCCCAAGGCCGAGCTGTCGGCCTGCGTCATCAC

CCAGGGGGCGATCCTGGCCCAATTGCAAGCCATCCAGAAATCCCGCCAAGAATTCTTGCTGA

AAAAGGGCCGCGGGGTCTACCTCGACCCCCAGACCGGTGAGGAGCTCAACCCCGGCTTCCC

CCAGGATGCCCCGAGGAAACAAGAAGCTGAAAGTGGAGCTGCCGCCCGTGGAGGATTTGGA

GGAAGACTGGGAGAACAGCAGTCAGGCAGAGGAGATGGAGGAAGACTGGGACAGCACTCAG

GCAGAGGAGGACAGCCTGCAAGACAGTCTGGAGGAAGACGAGGAGGAGGCAGAGGAGGAG

GTGGAAGAAGCAGCCGCCGCCAGACCGTCGTCCTCGGCGGGGGAGAAAGCAAGCAGCACG

GATACCATCTCCGCTCCGGGTCGGGGTCCCGCTCGGCCCCACAGTAGATGGGACGAGACCG

-continued

GGCGATTCCCGAACCCCACCACCCAGACCGGTAAGAAGGAGCGGCAGGGATACAAGTCCTG

GCGGGGGCACAAAAACGCCATCGTCTCCTGCTTGCAGGCCTGCGGGGGCAACATCTCCTTC

ACCCGGCGCTACCTGCTCTTCCACCGCGGGGTGAACTTCCCCCGCAACATCTTGCATTACTA

CCGTCACCTCCACAGCCCCTACTACTTCCAAGAAGAGGCAGCAGCAGCAGAAAAAGACCAGA

AAACCAGCTAGAAAATCCACAGCGGCGGCAGCGGCAGGTGGACTGAGGATCGCGGCGAACG

AGCCGGCGCAGACCCGGGAGCTGAGGAACCGGATCTTTCCCACCCTCTATGCCATCTTCCAG

CAGAGTCGGGGGCAGGAGCAGGAACTGAAAGTCAAGAACCGTTCTCTGCGCTCGCTCACCC

GCAGTTGTCTGTATCACAAGAGCGAAGACCAACTTCAGCGCACTCTCGAGGACGCCGAGGCT

CTCTTCAACAAGTACTGCGCGCTCACTCTTAAAGAGTAGCCCGCGCCCGCCCAGTCGCAGAA

AAAGGCGGGAATTACGTCACCTGTGCCCTTCGCCCTAGCCGCCTCCACCCAGCACCGCCATG

AGCAAAGAGATTCCCACGCCTTACATGTGGAGCTACCAGCCCCAGATGGGCCTGGCCGCCG

GCGCCGCCCAGGACTACTCCACCCGCATGAATTGGCTCAGCGCCGGGCCCGCGATGATCTC

ACGGGTGAATGACATCCGCGCCCACCGAAACCAGATACTCCTAGAACAGTCAGCGCTCACCG

CCACGCCCCGCAATCACCTCAATCCGCGTAATTGGCCCGCCGCCCTGGTGTACCAGGAAATT

CCCCAGCCCACGACCGTACTACTTCCGCGAGACGCCCAGGCCGAAGTCCAGCTGACTAACT

CAGGTGTCCAGCTGGCGGGCGGCGCCACCCTGTGTCGTCACCGCCCCGCTCAGGGTATAAA

GCGGCTGGTGATCCGGGGCAGAGGCACACAGCTCAACGACGAGGTGGTGAGCTCTTCGCTG

GGTCTGCGACCTGACGGAGTCTTCCAACTCGCCGGATCGGGGAGATCTTCCTTCACGCCTCG

TCAGGCGGTCCTGACTTTGGAGAGTTCGTCCTCGCAGCCCCGCTCGGGCGGCATCGGCACT

CTCCAGTTCGTGGAGGAGTTCACTCCCTCGGTCTACTTCAACCCCTTCTCCGGCTCCCCCGG

CCACTACCCGGACGAGTTCATCCCGAACTTTGACGCCATCAGCGAGTCGGTGGACGGCTACG

ATTGATTAATTAATCAACTAACCCCTTACCCCTTTACCCTCCAGTAAAAATAAAGATTAAAAATG

ATTGAATTGATCAATAAAGAATCACTTACTTGAAATCTGAAACCAGGTCTCTGTCCATGTTTTC

TGTCAGCAGCACTTCACTCCCCTCTTCCCAACTCTGGTACTGCAGGCCCCGGCGGGCTGCAA

ACTTCCTCCACACTCTGAAGGGGATGTCAAATTCCTCCTGTCCCTCAATCTTCATTTTTATCTT

CTATCAGATGTCCAAAAAGCGCGCGCGGGTGGATGATGGCTTCGACCCCGTGTACCCCTACG

ATGCAGACAACGCACCGACTGTGCCCTTCATCAACCCTCCCTTCGTCTCTTCAGATGGATTCC

AAGAAAAGCCCCTGGGGGTGTTGTCCCTGCGACTGGCCGACCCCGTCACCACCAAGAATGG

GGCTGTCACCCTCAAGCTGGGGGAGGGGGTGGACCTCGACGACTCGGGAAAACTCATCTCC

AAAAATGCCACCAAGGCCACTGCCCCTCTCAGTATTTCCAACGGCACCATTTCCCTTAACATG

GCTGCCCCTTTTTACAACAACAATGGAACGTTAAGTCTCAATGTTTCTACACCATTAGCAGTAT

TTCCCACTTTTAACACTTTAGGTATCAGTCTTGGAAACGGTCTTCAAACTTCTAATAAGTTGCT

GACTGTACAGTTAACTCATCCTCTTACATTCAGCTCAAATAGCATCACAGTAAAAACAGACAAA

GGACTCTATATTAATTCTAGTGGAAACAGAGGGCTTGAGGCTAACATAAGCCTAAAAAGAGGA

CTGATTTTTGATGGTAATGCTATTGCAACATACCTTGGAAGTGGTTTAGACTATGGATCCTATG

ATAGCGATGGGAAAACAAGACCCATCATCACCAAAATTGGAGCAGGTTTGAATTTTGATGCTA

ATAATGCCATGGCTGTGAAGCTAGGCACAGGTTTAAGTTTTGACTCTGCCGGTGCCTTAACAG

CTGGAAACAAAGAGGATGACAAGCTAACACTTTGGACTACACCTGACCCAAGCCCTAATTGTC

AATTACTTTCAGACAGAGATGCCAAATTTACCCTATGTCTTACAAAATGCGGTAGTCAAATACT

AGGCACTGTTGCAGTAGCTGCTGTTACTGTAGGTTCAGCACTAAATCCAATTAATGACACAGT

-continued

AAAAAGCGCCATAGTATTCCTTAGATTTGACTCTGACGGTGTGCTCATGTCAAACTCATCAAT

GGTAGGTGATTACTGGAACTTTAGGGAAGGACAGACCACCCAAAGTGTGGCCTATACAAATG

CTGTGGGATTCATGCCCAATCTAGGTGCATATCCTAAAACCCAAAGCAAAACACCAAAAAATA

GTATAGTAAGTCAGGTATATTTAAATGGAGAAACTACTATGCCAATGACACTGACAATAACTTT

CAATGGCACTGATGAAAAAGACACAACACCTGTGAGCACTTACTCCATGACTTTTACATGGCA

GTGGACTGGAGACTATAAGGACAAGAATATTACCTTTGCTACCAACTCCTTTACTTTCTCCTAC

ATGGCCCAAGAATAAACCCTGCATGCCAACCCCATTGTTCCCACCACTATGGAAAACTCTGAA

GCAGAAAAAAATAAAGTTCAAGTGTTTTATTGATTCAACAGTTTTCTCACAGAACCCTAGTATT

CAACCTGCCACCTCCCTCCCAACACACAGAGTACACAGTCCTTTCTCCCCGGCTGGCCTTAA

AAAGCATCATATCATGGGTAACAGACATATTCTTAGGTGTTATATTCCACACGGTTTCCTGTCG

AGCCAAACGCTCATCAGTGATATTAATAAACTCCCCGGGCAGCTCACTTAAGTTCATGTCGCT

GTCCAGCTGCTGAGCCACAGGCTGCTGTCCAACTTGCGGTTGCTTAACGGGCGGCGAAGGA

GAAGTCCACGCCTACATGGGGGTAGAGTCATAATCGTGCATCAGGATAGGGCGGTGGTGCT

GCAGCAGCGCGCGAATAAACTGCTGCCGCCGCCGCTCCGTCCTGCAGGAATACAACATGGC

AGTGGTCTCCTCAGCGATGATTCGCACCGCCCGCAGCATAAGGCGCCTTGTCCTCCGGGCA

CAGCAGCGCACCCTGATCTCACTTAAATCAGCACAGTAACTGCAGCACAGCACCACAATATTG

TTCAAAATCCCACAGTGCAAGGCGCTGTATCCAAAGCTCATGGCGGGGACCACAGAACCCAC

GTGGCCATCATACCACAAGCGCAGGTAGATTAAGTGGCGACCCCTCATAAACACGCTGGACA

TAAACATTACCTCTTTTGGCATGTTGTAATTCACCACCTCCCGGTACCATATAAACCTCTGATT

AAACATGGCGCCATCCACCACCATCCTAAACCAGCTGGCCAAAACCTGCCCGCCGGCTATAC

ACTGCAGGGAACCGGGACTGGAACAATGACAGTGGAGAGCCCAGGACTCGTAACCATGGAT

CATCATGCTCGTCATGATATCAATGTTGGCACAACACAGGCACACGTGCATACACTTCCTCAG

GATTACAAGCTCCTCCCGCGTTAGAACCATATCCCAGGGAACAACCCATTCCTGAATCAGCGT

AAATCCCACACTGCAGGGAAGACCTCGCACGTAACTCACGTTGTGCATTGTCAAAGTGTTACA

TTCGGGCAGCAGCGGATGATCCTCCAGTATGGTAGCGCGGGTTTCTGTCTCAAAAGGAGGTA

GACGATCCCTACTGTACGGAGTGCGCCGAGACAACCGAGATCGTGTTGGTCGTAGTGTCATG

CCAAATGGAACGCCGGACGTAGTCATATTTCCTGAAGCAAAACCAGGTGCGGGCGTGACAAA

CAGATCTGCGTCTCCGGTCTCGCCGCTTAGATCGCTCTGTGTAGTAGTTGTAGTATATCCACT

CTCTCAAAGCATCCAGGCGCCCCCTGGCTTCGGGTTCTATGTAAACTCCTTCATGCGCCGCT

GCCCTGATAACATCCACCACCGCAGAATAAGCCACACCCAGCCAACCTACACATTCGTTCTG

CGAGTCACACACGGGAGGAGCGGGAAGAGCTGGAAGAACCATGATTAACTTTATTCCAAACG

GTCTCGGAGCACTTCAAAATGCAGGTCCCGGAGGTGGCACCTCTCGCCCCCACTGTGTTGGT

GGAAAATAACAGCCAGGTCAAAGGTGACACGGTTCTCGAGATGTTCCACGGTGGCTTCCAGC

AAAGCCTCCACGCGCACATCCAGAAACAAGAGGACAGCGAAAGCGGGAGCGTTTTCTAATTC

CTCAATCATCATATTACACTCCTGCACCATCCCCAGATAATTTTCATTTTTCCAGCCTTGAATG

ATTCGTATTAGTTCCTGAGGTAAATCCAAGCCAGCCATGATAAAAAGCTCGCGCAGAGCGCC

CTCCACCGGCATTCTTAAGCACACCCTCATAATTCCAAGAGATTCTGCTCCTGGTTCACCTGC

AGCAGATTAACAATGGGAATATCAAAATCTCTGCCGCGATCCCTAAGCTCCTCCCTCAACAAT

AACTGTATGTAATCTTTCATATCATCTCCGAAATTTTTAGCCATAGGGCCGCCAGGAATAAGAG

CAGGGCAAGCCACATTACAGATAAAGCGAAGTCCTCCCCAGTGWGCATTGCCAAATGTAAGA

TTGAAATAAGCATGCTGGCTAGACCCTGTGATATCTTCCAGATAACTGGACAGAAAATCAGGC

-continued

AAGCAATTTTTAAGAAAATCAACAAAAGAAAAGTCGTCCAGGTGCAGGTTTAGAGCCTCAGGA

ACAACGATGGAATAAGTGCAAGGAGTGCGTTCCAGCATGGTTAGTGTTTTTTTGGTGATCTGT

AGAACAAAAAATAAACATGCAATATTAAACCATGCTAGCCTGGCGAACAGGTGGGTAAATCAC

TCTTTCCAGCACCAGGCAGGCTACGGGGTCTCCGGCGCGACCCTCGTAGAAGCTGTCGCCA

TGATTGAAAAGCATCACCGAGAGACCTTCCCGGTGGCCGGCATGGATGATTCGAGAAGAAGC

ATACACTCCGGGAACATTGGCATCCGTGAGTGAAAAAAAGCGACCTATAAAGCCTCGGGGCA

CTACAATGCTCAATCTCAATTCCAGCAAAGCCACCCCATGCGGATGGAGCACAAAATTGGCA

GGTGCGTAAAAAATGTAATTACTCCCCTCCTGCACAGGCAGCAAAGCCCCCGCTCCCTCCAG

AAACACATACAAAGCCTCAGCGTCCATAGCTTACCGAGCACGGCAGGCGCAAGAGTCAGAGA

AAAGGCTGAGCTCTAACCTGACTGCCCGCTCCTGTGCTCAATATATAGCCCTAACCTACACTG

ACGTAAAGGCCAAAGTCTAAAAATACCCGCCAAAATGACACACACGCCCAGCACACGCCCAG

AAACCGGTGACACACTCAAAAAAATACGTGCGCTTCCTCAAACGCCCAAACCGGCGTCATTTC

CGGGTTCCCACGCTACGTCACCGCTCAGCGACTTTCAAATTCCGTCGACCGTTAAAAACGTC

ACTCGCCCCGCCCCTAACGGTCGCCCTTCTCTCGGCCAATCACCTTCCTCCCTTCCCAAATTC

AAACGCCTCATTTGCATATTAACGCGCACAAAAAGTTTGAGGTATATATTTGAATGATG

2NSALL Chadox1

[SEQ ID NO: 119]

GTTTAAACGCGGCCGCCAGGCCTACCCACTAGTCAATTCGGGAGGATCGAAACGGCAGATCG

CAAAAAACAGTACATACAGAAGGAGACATGAACATGAACATCAAAAAAATTGTAAAACAAGCC

ACAGTTCTGACTTTTACGACTGCACTTCTGGCAGGAGGAGCGACTCAAGCCTTCGCGAAAGA

AAATAACCAAAAAGCATACAAAGAAACGTACGGCGTCTCTCATATTACACGCCATGATATGCT

GCAGATCCCTAAACAGCAGCAAAACGAAAAATACCAAGTGCCTCAATTCGATCAATCAACGAT

TAAAAATATTGAGTCTGCAAAAGGACTTGATGTGTGGGACAGCTGGCCGCTGCAAAACGCTG

ACGGAACAGTAGCTGAATACAACGGCTATCACGTTGTGTTTGCTCTTGCGGGAAGCCCGAAA

GACGCTGATGACACATCAATCTACATGTTTTATCAAAAGGTCGGCGACAACTCAATCGACAGC

TGGAAAAACGCGGGCCGTGTCTTTAAAGACAGCGATAAGTTCGACGCCAACGATCCGATCCT

GAAAGATCAGACGCAAGAATGGTCCGGTTCTGCAACCTTTACATCTGACGGAAAAATCCGTTT

ATTCTACACTGACTATTCCGGTAAACATTACGGCAAACAAAGCCTGACAACAGCGCAGGTAAA

TGTGTCAAAATCTGATGACACACTCAAAATCAACGGAGTGGAAGATCACAAAACGATTTTTGA

CGGAGACGGAAAAACATATCAGAACGTTCAGCAGTTTATCGATGAAGGCAATTATACATCCGG

CGACAACCATACGCTGAGAGACCCTCACTACGTTGAAGACAAAGGCCATAAATACCTTGTATT

CGAAGCCAACACGGGAACAGAAAACGGATACCAAGGCGAAGAATCTTTATTTAACAAAGCGT

ACTACGGCGGCGGCACGAACTTCTTCCGTAAAGAAAGCCAGAAGCTTCAGCAGAGCGCTAAA

AAACGCGATGCTGAGTTAGCGAACGGCGCCCTCGGTATCATAGAGTTAAATAATGATTACACA

TTGAAAAAAGTAATGAAGCCGCTGATCACTTCAAACACGGTAACTGATGAAATCGAGCGCGCG

AATGTTTTCAAAATGAACGGCAAATGGTACTTGTTCACTGATTCACGCGGTTCAAAAATGACG

ATCGATGGTATTAACTCAAACGATATTTACATGCTTGGTTATGTATCAAACTCTTTAACCGGCC

CTTACAAGCCGCTGAACAAAACAGGGCTTGTGCTGCAAATGGGTCTTGATCCAAACGATGTG

ACATTCACTTACTCTCACTTCGCAGTGCCGCAAGCCAAAGGCAACAATGTGGTTATCACAAGC

TACATGACAAACAGAGGCTTCTTCGAGGATAAAAAGGCAACATTTGCGCCAAGCTTCTTAATG

AACATCAAAGGCAATAAAACATCCGTTGTCAAAAACAGCATCCTGGAGCAAGGACAGCTGACA

-continued

GTCAACTAATAACAGCAAAAAGAAAATGCCGATACTTCATTGGCATTTTCTTTTATTTCTCAAC

AAGATGGTGAATTGACTAGTGGGTAGATCCACAGGACGGGTGTGGTCGCCATGATCGCGTAG

TCGATAGTGGCTCCAAGTAGCGAAGCGAGCAGGACTGGGCGGCGGCCAAAGCGGTCGGACA

GTGCTCCGAGAACGGGTGCGCATAGAAATTGCATCAACGCATATAGCGCTAGCAGCACGCCA

TAGTGACTGGCGATGCTGTCGGAATGGACGATATCCCGCAAGAGGCCCGGCAGTACCGGCA

TAACCAAGCCTATGCCTACAGCATCCAGGGTGACGGTGCCGAGGATGACGATGAGCGCATTG

TTAGATTTCATACACGGTGCCTGACTGCGTTAGCAATTTAACTGTGATAAACTACCGCATTAAA

GCTTATCGATGATAAGCTGTCAAACATGAGAATTGATCCGGAACCCTTAATATAACTTCGTATA

ATGTATGCTATACGAAGTTATTAGGTCCCTCGACTATAGGGTCACCGTCGACAGCGACACACT

TGCATCGGATGCAGCCCGGTTAACGTGCCGGCACGGCCTGGGTAACCAGGTATTTTGTCCAC

ATAACCGTGCGCAAAATGTTGTGGATAAGCAGGACACAGCAGCAATCCACAGCAGGCATACA

ACCGCACACCGAGGTTACTCCGTTCTACAGGTTACGACGACATGTCAATACTTGCCCTTGACA

GGCATTGATGGAATCGTAGTCTCACGCTGATAGTCTGATCGACAATACAAGTGGGACCGTGG

TCCCAGACCGATAATCAGACCGACRAYACGAGTGGGAYCGTGGTCCCAGACTAATAATCAGA

CCGACGATACGAGTGGGACCGTGGTCCCAGACTAATAATCAGACCGACGATACGAGTGGGA

CCGTGGTYCCAGWCTRATWATCAGACCGACGATACRAGTGGRACMGTGGKCCCAGASAKAA

TAWTCAGRCCGAGWTAYGCWKTCKGGCCTGTAACAAAGGACATTAAGTAAAGACAGATAMR

MGTGRGACTAAAACGTGGTCCCAGTCTGATTATCAGACCGACGATACGAGTGGGACCGTGGT

CCCAGACTAATAATCAGACCGACGATACGAGTGGGACCGTGGTCCCAGACTAATAATCAGAC

CGACGATACGAGTGGGACCGTGGTCCCAGTCTGATTATCAGACCGACGATACAAGTGGAACA

GTGGGCCCAGAGAGAATATTCAGGCCAGTTATGCTTTCTGGCCTGTAACAAAGGACATTAAGT

AAAGACAGATAAACGTAGACTAAAACGTGGTCGCATCAGGGTGCTGGCTTTTCAAGTTCCTTA

AGAATGGCCTCAATTTTCTCTATACACTCAGTTGGAACACGAGACCTGTCCAGGTTAAGCACC

ATTTTATCGCCCTTATACAATACTGTCGCTCCAGGAGCAAACTGATGTCGTGAGCTTAAACTA

GTTCTTGATGCAGATGACGTTTTAAGCACAGAAGTTAAAAGAGTGATAACTTCTTCAGCTTCAA

ATATCACCCCAGCTTTTTTCTGCTCATGAAGGTTAGATGCCTGCTGCTTAAGTAATTCCTCTTT

ATCTGTAAAGGCTTTTTGAAGTGCATCACCTGACCGGGCAGATAGTTCACCGGGGTGAGAAA

AAAGAGCAACAACTGATTTAGGCAATTTGGCGGTGTTGATACAGCGGGTAATAATCTTACGTG

AAATATTTTCCGCATCAGCCAGCGCAGAAATATTTCCAGCAAATTCATTCTGCAATCGGCTTG

CATAACGCTGACCACGTTCATAAGCACTTGTTGGGCGATAATCGTTACCCAATCTGGATAATG

CAGCCATCTGCTCATCATCCAGCTCGCCAACCAGAACACGATAATCACTTTCGGTAAGTGCAG

CAGCTTTACGACGGCGACTCCCATCGGCAATTTCTATGACACCAGATACTCTTCGACCGAACG

CCGGTGTCTGTTGACCAGTCAGTAGAAAAGAAGGGATGAGATCATCCAGTGCGTCCTCAGTA

AGCAGCTCCTGGTCACGTTCATTACCTGACCATACCCGAGAGGTCTTCTCAACACTATCACCC

CGGAGCACTTCAAGAGTAAACTTCACATCCCGACCACATACAGGCAAAGTAATGGCATTACCG

CGAGCCATTACTCCTACGCGCGCAATTAACGAATCCACCATCGGGGCAGCTGGTGTCGATAA

CGAAGTATCTTCAACCGGTTGAGTATTGAGCGTATGTTTTGGAATAACAGGCGCACGCTTCAT

TATCTAATCTCCCAGCGTGGTTTAATCAGACGATCGAAAATTTCATTGCAGACAGGTTCCCAA

ATAGAAAGAGCATTTCTCCAGGCACCAGTTGAAGAGCGTTGATCAATGGCCTGTTCAAAAACA

GTTCTCATCCGGATCTGACCTTTACCAACTTCATCCGTTTCACGTACAACATTTTTAGAACCA

TGCTTCCCCAGGCATCCCGAATTTGCTCCTCCATCCACGGGGACTGAGAGCCATTACTATTG

-continued

CTGTATTTGGTAAGCAAAATACGTACATCAGGCTCGAACCCTTTAAGATCAACGTTCTTGAGC

AGATCACGAAGCATATCGAAAAACTGCAGTGCGGAGGTGTAGTCAAACAACTCAGCAGGCGT

GGGAACAATCAGCACATCAGCAGCACATACGACATTAATCGTGCCGATACCCAGGTTAGGCG

CGCTGTCAATAACTATGACATCATAGTCATGAGCAACAGTTTCAATGGCCAGTCGGAGCATCA

GGTGTGGATCGGTGGGCAGTTTACCTTCATCAAATTTGCCCATTAACTCAGTTTCAATACGGT

GCAGAGCCAGACAGGAAGGAATAATGTCAAGCCCCGGCCAGCAAGTGGGCTTTATTGCATAA

GTGACATCGTCCTTTTCCCCAAGATAGAAAGGCAGGAGAGTGTCTTCTGCATGAATATGAAGA

TCTGGTACCCATCCGTGATACATTGAGGCTGTTCCCTGGGGGTCGTTACCTTCCACGAGCAA

AACACGTAGCCCCTTCAGAGCCAGATCCTGAGCAAGATGAACAGAAACTGAGGTTTTGTAAAC

GCCACCTTTATGGGCAGCAACCCCGATCACCGGTGGAAATACGTCTTCAGCACGTCGCAATC

GCGTACCAAACACATCACGCATATGATTAATTTGTTCAATTGTATAACCAACACGTTGCTCAAC

CCGTCCTCGAATTTCCATATCCGGGTGCGGTAGTCGCCCTGCTTTCTCGGCATCTCTGATAG

CCTGAGAAGAAACCCCAACTAAATCCGCTGCTTCACCTATTCTCCAGCGCCGGGTTATTTTCC

TCGCTTCCGGGCTGTCATCATTAAACTGTGCAATGGCGATAGCCTTCGTCATTTCATGACCAG

CGTTTATGCACTGGTTAAGTGTTTCCATGAGTTTCATTCTGAACATCCTTTAATCATTGCTTTG

CGTTTTTTTATTAAATCTTGCAATTTACTGCAAAGCAACAACAAAATCGCAAAGTCATCAAAAAA

CCGCAAAGTTGTTTAAAATAAGAGCAACACTACAAAAGGAGATAAGAAGAGCACATACCTCAG

TCACTTATTATCACTAGCGCTCGCCGCAGCCGTGTAACCGAGCATAGCGAGCGAACTGGCGA

GGAAGCAAAGAAGAACTGTTCTGTCAGATAGCTCTTACGCTCAGCGCAAGAAGAAATATCCAC

CGTGGGAAAAACTCCAGGTAGAGGTACACACGCGGATAGCCAATTCAGAGTAATAAACTGTG

ATAATCAACCCTCATCAATGATGACGAACTAACCCCCGATATCAGGTCACATGACGAAGGGAA

AGAGAAGGAAATCAACTGTGACAAACTGCCCTCAAATTTGGCTTCCTTAAAAATTACAGTTCAA

AAAGTATGAGAAAATCCATGCAGGCTGAAGGAAACAGCAAAACTGTGACAAATTACCCTCAGT

AGGTCAGAACAAATGTGACGAACCACCCTCAAATCTGTGACAGATAACCCTCAGACTATCCTG

TCGTCATGGAAGTGATATCGCGGAAGGAAAATACGATATGAGTCGTCTGGCGGCCTTTCTTTT

TCTCAATGTATGAGAGGCGCATTGGAGTTCTGCTGTTGATCTCATTAACACAGACCTGCAGGA

AGCGGCGGCGGAAGTCAGGCATACGCTGGTAACTTTGAGGCAGCTGGTAACGCTCTATGATC

CAGTCGATTTTCAGAGAGACGATGCCTGAGCCATCCGGCTTACGATACTGACACAGGGATTC

GTATAAACGCATGGCATACGGATTGGTGATTTCTTTTGTTTCACTAAGCCGAAACTGCGTAAA

CCGGTTCTGTAACCCGATAAAGAAGGGAATGAGATATGGGTTGATATGTACACTGTAAAGCCC

TCTGGATGGACTGTGCGCACGTTTGATAAACCAAGGAAAAGATTCATAGCCTTTTTCATCGCC

GGCATCCTCTTCAGGGCGATAAAAAACCACTTCCTTCCCCGCGAAACTCTTCAATGCCTGCCG

TATATCCTTACTGGCTTCCGCAGAGGTCAATCCGAATATTTCAGCATATTTAGCAACATGGATC

TCGCAGATACCGTCATGTTCCTGTAGGGTGCCATCAGATTTTCTGATCTGGTCAACGAACAGA

TACAGCATACGTTTTTGATCCCGGGAGAGACTATATGCCGCCTCAGTGAGGTCGTTTGACTG

GACGATTCGCGGGCTATTTTTACGTTTCTTGTGATTGATAACCGCTGTTTCCGCCATGACAGA

TCCATGTGAAGTGTGACAAGTTTTTAGATTGTCACACTAAATAAAAAAGAGTCAATAAGCAGG

GATAACTTTGTGAAAAAACAGCTTCTTCTGAGGGCAATTTGTCACAGGGTTAAGGGCAATTTG

TCACAGACAGGACTGTCATTTGAGGGTGATTTGTCACACTGAAAGGGCAATTTGTCACAACAC

CTTCTCTAGAACCAGCATGGATAAAGGCCTACAAGGCGCTCTAAAAAAGAAGATCTAAAAACT

-continued

ATAAAAAAAATAATTATAAAAATATCCCCGTGGATAAGTGGATAACCCCAAGGGAAGTTTTTTC

AGGCATCGTGTGTAAGCAGAATATATAAGTGCTGTTCCCTGGTGCTTCCTCGCTCACTCGAGG

GCTTCGCCCTGTCGCTCAACTGCGGCGAGCACTACTGGCTGTAAAAGGACAGACCACATCAT

GGTTCTGTGTTCATTAGGTTGTTCTGTCCATTGCTGACATAATCCGCTCCACTTCAACGTAACA

CCGCACGAAGATTTCTATTGTTCCTGAAGGCATATTCAAATCGTTTTCGTTACCGCTTGCAGG

CATCATGACAGAACACTACTTCCTATAAACGCTACACAGGCTCCTGAGATTAATAATGCGGAT

CTCTACGATAATGGGAGATTTTCCCGACTGTTTCGTTCGCTTCTCAGTGGATAACAGCCAGCT

TCTCTGTTTAACAGACAAAAACAGCATATCCACTCAGTTCCACATTTCCATATAAAGGCCAAGG

CATTTATTCTCAGGATAATTGTTTCAGCATCGCAACCGCATCAGACTCCGGCATCGCAAACTG

CACCCGGTGCCGGGCAGCCACATCCAGCGCAAAAACCTTCGTGTAGACTTCCGTTGAACTGA

TGGACTTATGTCCCATCAGGCTTTGCAGAACTTTCAGCGGTATACCGGCATACAGCATGTGCA

TCGCATAGGAATGGCGGAACGTATGTGGTGTGACCGGAACAGAGAACGTCACACCGTCAGCA

GCAGCGGCGGCAACCGCCTCCCCAATCCAGGTCCTGACCGTTCTGTCCGTCACTTCCCAGAT

CCGCGCTTTCTCTGTCCTTCCTGTGCGACGGTTACGCCGCTCCATGAGCTTATCGCGAATAAA

TACCTGTGACGGAAGATCACTTCGCAGAATAAATAAATCCTGGTGTCCCTGTTGATACCGGGA

AGCCCTGGGCCAACTTTTGGCGAAAATGAGACGTTGATCGGCACGTAAGAGGTTCCAACTTT

CACCATAATGAAATAAGATCACTACCGGGCGTATTTTTTGAGTTATCGAGATTTTCAGGAGCTA

AGGAAGCTAAAATGGAGAAAAAAATCACTGGATATACCACCGTTGATATATCCCAATGGCATC

GTAAAGAACATTTTGAGGCATTTCAGTCAGTTGCTCAATGTACCTATAACCAGACCGTTCAGC

TGGATATTACGGCCTTTTTAAAGACCGTAAAGAAAAATAAGCACAAGTTTTATCCGGCCTTTAT

TCACATTCTTGCCCGCCTGATGAATGCTCATCCGGAGTTCCGTATGGCAATGAAAGACGGTG

AGCTGGTGATATGGGATAGTGTTCACCCTTGTTACACCGTTTTCCATGAGCAAACTGAAACGT

TTTCATCGCTCTGGAGTGAATACCACGACGATTTCCGGCAGTTTCTACACATATATTCGCAAG

ATGTGGCGTGTTACGGTGAAAACCTGGCCTATTTCCCTAAAGGGTTTATTGAGAATATGTTTTT

CGTCTCAGCCAATCCCTGGGTGAGTTTCACCAGTTTTGATTTAAACGTGGCCAATATGGACAA

CTTCTTCGCCCCCGTTTTCACCATGGGCAAATATTATACGCAAGGCGACAAGGTGCTGATGCC

GCTGGCGATTCAGGTTCATCATGCCGTTTGTGATGGCTTCCATGTCGGCAGAATGCTTAATGA

ATTACAACAGTACTGCGATGAGTGGCAGGGCGGGGCGTAATTTTTTTAAGGCAGTTATTGGTG

CCCTTAAACGCCTGGTTGCTACGCCTGAATAAGTGATAATAAGCGGATGAATGGCAGAAATTC

GATGATAAGCTGTCAAACATGAGAATTGGTCGACGGCGCGCCAAAGCTTGCATGCCTGCAGC

CGCGTAACCTGGCAAAATCGGTTACGGTTGAGTAATAAATGGATGCCCTGCGTAAGCGGGGC

ACATTTCATTACCTCTTTCTCCGCACCCGACATAGATAATAACTTCGTATAGTATACATTATAC

GAAGTTATCTAGTAGACTTAATCGCGTTTAAACCCATCATCAATAATATACCTCAAACTTTTTGT

GCGCGTTAATATGCAAATGAGGCGTTTGAATTTGGGAAGGGAGGAAGGTGATTGGCCGAGAG

AAGGGCGACCGTTAGGGGCGGGGCGAGTGACGTTTTGATGACGTGACCGCGAGGAGGAGC

CAGTTTGCAAGTTCTCGTGGGAAAAGTGACGTCAAACGAGGTGTGGTTTGAACACGGAAATA

CTCAATTTTCCCGCGCTCTCTGACAGGAAATGAGGTGTTTCTAGGCGGATGCAAGTGAAAAC

GGGCCATTTTCGCGCGAAAACTGAATGAGGAAGTGAAAATCTGAGTAATTTCGCGTTTATGAC

AGGGAGGAGTATTTGCCGAGGGCCGAGTAGACTTTGACCGATTACGTGGGGGTTTCGATTAC

CGTGTTTTTCACCTAAATTTCCGCGTACGGTGTCAAAGTCCGGTGTTTTTACGTAGGTGTCAG

CTGATCGCCAGGGTATTTAAACCTGCGCTCTCCAGTCAAGAGGCCACTCTTGAGTGCCAGCG

-continued

```
AGAAGAGTTTTCTCCTCCGCGCGCGAGTCAGATCTACACTTTGAAAGGCGATCGCTAGCGAC
ATCGATCCAAATAATGATTTTATTTTGACTGATAGTGACCTGTTCGTTGCAACAAATTGATAAG
CAATGCTTTTTTATAATGCCAACTTTGTACAAAAAAGCAGGCTCCACCATGGGAACCAATTCAG
TCGAGCCTTTCACTCATTAGATGCATGTCGTTACATAACTTACGGTAAATGGCCCGCCTGGCT
GACCGCCCAACGACCCCCGCCCATTGACGTCAATAATGACGTATGTTCCCATAGTAACGCCA
ATAGGGACTTTCCATTGACGTCAATGGGTGGAGTATTTACGGTAAACTGCCCACTTGGCAGTA
CATCAAGTGTATCATATGCCAAGTACGCCCCCTATTGACGTCAATGACGGTAAATGGCCCGCC
TGGCATTATGCCCAGTACATGACCTTATGGGACTTTCCTACTTGGCAGTACATCTACGTATTA
GTCATCGCTATTACCATGGTGATGCGGTTTTGGCAGTACATCAATGGGCGTGGATAGCGGTTT
GACTCACGGGGATTTCCAAGTCTCCACCCCATTGACGTCAATGGGAGTTTGTTTTGGCACCAA
AATCAACGGGACTTTCCAAAATGTCGTAACAACTCCGCCCCATTGACGCAAATGGGCGGTAG
GCGTGTACGGTGGGAGGTCTATATAAGCAGAGCTCTCCCTATCAGTGATAGAGATCTCCCTAT
CAGTGATAGAGATCGTCGACGAGCTCGTTTAGTGAACCGTCAGATCGCCTGGAGACGCCATC
CACGCTGTTTTGACCTCCATAGAAGACACCGGGACCGATCCAGCCTCCGGTTAAGCTCGGTA
CCGCTAGCCGCGCCGCCACCATGGATGCAATGAAGAGAGGGCTCTGCTGTGTGCTGCTGCT
GTGTGGAGCAGTCTTCGTTTCGCCCAGCCAGGAAATCCATGCCCGATTCAGAAGAGGATCGA
AGCTTGCCAGCCAGATCGGCGCCGGCGTGTTCAAGGAGGGCGTGTTCCACACCATGTGGCA
CGTGACCAGGGGCGCCGTGCTGATGCACCAGGGCAAGAGGATCGAGCCCAGCTGGGCCGA
CGTGAAGAAGGACCTGATCAGCTACGGCGGCGGCTGGAGGCTGGAGGGCGAGTGGGACGA
GGGCGAGGAGGTGCAGGTGATCGCCGTGGAGCCCGGCAAGAACCCCAAGGCCGTGCAGAC
CGGCGAGATCGGCGCCATCGCCCTGGACTTCAAGCCCGGCACCAGCGGCAGCCCCATCGTG
AACAGGGAGGGCGTGGGCCTGTACGGCAACGGCGTGGTGACCAAGAGCGGCGCCTACGTG
AGCGCCATCGCCCAGACCTTCAGGAAGAGGAACCTGACCATCATGGACCTGCACCCCGGCG
CCGGCAAGACCAAGAGGTATCTGCCCGCCATCGTGAGGGAGGCCATCAAGAGGAGGCTGAG
GACCCTGATCCTGGCCCCCACCAGGGTGGTGGCCGCCGAGATGGAGGAGGCCCTGAAGGG
CCTGCCCATCAGGTATCAGACCACCGCCATCAAGGCCGAGCACACCGGCAAGGAGATCGTG
GACCTGATGTGCCACGCCACCTTCACCATGAGGCTGCTGAGCCCCGTGAGGGTGCCCAACT
ACAACCTGATCATCATGGACGAGGCCCACTTCACCGACCCCGCCAGCATCGCCGCCAGGGG
CTACATCAGCACCAGGGTGGAGATGGGCGAGGCCGCCGCCATCTTCATGACCGCCACCCCC
CCCGGCAGCGCCGACGCCTTCCCCCAGAGCAACGCCCCCATCGAGGACGAGGAGAGGGAG
ATCCCCGAGAGGAGCTGGAACAGCGGCTTCGACTGGATCACCGACTTCGCCGGCAAGACCG
TGTGGTTCGTGCCCAGCATCAAGGCCGGCAACGACATCGCCAACTGCCTGAGGAAGAACGG
CAAGAAGGTGATCCAGCTGAGCAGGAAGACCTTCGACACCGAGTACCCCAAGACCAAGCTGA
ACGACTGGGACTTCGTGGTGACCACCGACATCAGCGAGATGGGCGCCAACTTCAAGGCCGA
CAGGGTGATCGACCCCAGGAGGTGCCTGAAGCCCGTGATCCTGACCGACGGCCCCGAGAGG
GTGATCCTGGCCGGCCCCATGCCCGTGACCGCCGCCAGCGCCGCCCAGAGGAGGGGCAGG
ATCGGCAGGAACCACAAGAAGGAGAACGACCAGTACATCTACATGGGCCAGCCCCTGAACAA
CGACGAGGACCACGCCCACTGGACCGAGGCCAAGATGCTGCTGGACAACATCAACACCCCC
GAGGGCATCATCCCCGCCCTGTTCGAGCCCGAGAGGGAGAAGAGCGCCGCCATCGACGGC
GAGTACAGGCTGAGGGGCGAGGCCAGGAAGACCTTCGTGGAGCTGATGAGGAGGGGCGAC
```

-continued

CTGCCCGTGTGGCTGAGCTACAAGGTGGCCAGCGCCGGCTTCCAGTACAAGGACAGGGAGT

GGTGCTTCGACGGCGAGAGGAACAACCAGATCCTGGAGGAGAACATGGACGTGGAGATCTG

GACCGAGGGCGAGAAGAAGAAGCTGAGGCCCAGGTGGCTGGACGCCAGGACCTACGCCGA

CCCCCACGCCCTGGAGGAGCTGCCCGAGACCCTGGAGACCCTGCTGCTGCTGGCCCTGCTG

GGCTTCCTGTTCTTCCTGAGCGGCAAGGGCATCGGCAAGATGAGCATCGGCCTGTGCTGCAT

CATCGCCGCCAGCCTGCTGTGGATGGCCGAGATCCAGCCCCACTGGATCGCCGCCAGCATC

ATCCTGGAGTTCTTCCTGATGGTGCTGCTGATCCCCGAGCCCGAGAAGCAGAGGACCCCCCA

GGACAACCAGCTGGCCTACGTGGTGATCGGCATCCTGACCCTGGCCGCCGCCATCGCCGCC

AACGAGATGGGCCTGCTGGAGACCACCAAGAAGGACCTGGGCATCGGCGCCATCCTGGACG

TGGACCTGCACCCCGCCAGCGCCTGGACCCTGTACGCCGTGGCCACCACCATCATCACCCC

CATGCTGAGGCACACCATCGAGAACAGCACCGCCAACGTGAGCCTGACCGCCATCGCCAAC

CAGGCCGCCGTGCTGATGGGCCTGGACAAGGGCTGGCCCATCAGCAAGATGGACCTGGGC

GTGCCCCTGCTGGCCCTGGGCTGCTACAGCCAGGTGAACCCCCTGACCCTGACCCACTACG

CCATCATCGGCCCCGGCCTGCAGGCCAAGGCCACCAGGGAGGCCCAGAAGAGGACCGCCG

CCGGCATCATGAAGAACCCCACCGTGGACGGCATCATGGCCATCGACCTGGACCCCATCCC

CTACGACCCCAAGTTCGAGAAGCAGCTGGGCCAGGTGATGCTGCTGATCCTGTGCAGCCAG

ATCCTGCTGATGAGGACCACCTGGGCCCTGTGCGAGGCCCTGACCCTGGCCACCGGCCCCA

TCACCACCCTGTGGGAGGGCAACCCCGGCAAGTTCTGGAACACCACCATCGCCGTGAGCAT

GGCCAACATCTTCAGGGGCAGCTACCTGGCCGGCGCCGGCCTGGCCTTCAGCCTGATCAAG

AACGGCGAGACCCTGGGCGAGAAGTGGAAGAGGCAGCTGAACCAGCTGGACAAGAGCTTCG

AGGAGTACAAGAAGAGCGGCATCCTGGAGGTGGACAGGACCGAGGCCAAGGAGGCCATCAT

GGTGGTGATCGACCTGGGCTGCGGCAGGGGCGGCTGGAGCTACTACTGCGCCGGCCTGAA

GAAGGTGAGGGGCTACACCAAGGGCGGCCCCGGCCACGAGGAGCCCATCCCCATGGCCAC

CTACGGCTGGAACCTGGTGAAGCTGCACAGCGGCGTGGACGTGTTCTTCGAGAAGTGCGAC

ACCCTGCTGTGCGACATCGGCGAGAGCAGCCCCAACCCCACCATCGAGGAGGGCAGGACCC

TGAGGGTGCTGAAGATGGTGGAGCCCTGGCTGAAGGGCAACCAGTTCTGCATCAAGATCCTG

AACCCCTACATGCCCAGCGTGATCGAGCTGGAGAAGCTGCAGAGGAAGCACGGCGGCATGC

TGGTGAGGAACCCCCTGAGCAGGAACAGCACCCACGAGATGTACTGGGTGAGCAACGGCAC

CGGCAACATCGTGAGCGCCGTGAACATGATCAGCAGGATGCTGATCAACAGGTTCACCATGG

CCCACAAGGACGAGGACAACCCCTACAAGACCTGGGCCTACCACGGCAGCTACGAGGTGAA

GGCCACCGGCAGCGCCAGCAGCATGGTGAACGGCGTGGTGAAGCTGCTGACCAAGCCCTG

GGACGTGGTGCCCATGGTGACCCAGATGGCCATGACCGACACCACCCCCTTCGGCCAGCAG

AGGGTGTTCAAGGAGAAGGTGGACACCAGGACCCCCGAGGCCCAGGACGAGAACGGCTGG

AAGAGCGCCCTGCACCTGGAGGGCAAGTGCGAGAGCTGCGTGTACAACATGATGGGCAAGA

GGGAGAAGAAGCTGGGCGAGTTCGGCAAGGCCAAGGGCAGCAGGGCCATCTGGTACATGTG

GCTGGGCGCCAGGTTCCTGGAGTTCGAGGCCCTGGGCTTCCTGAACGAGGACCACTGGTTC

AGCAGGGAGAACAGCCTGAGCGGCGTGGAGGGCGAGGGCCTGCTGGGCTACATCCTGAGG

GACATCAGCAAGATCCCCGGCGGCGCCATGTACGCCGACGACACCGCCGGCTGGGACACCA

GGATCACCGAGGACGACCTGCACAACGAGGAGAAGCTGGCCAAGGCCATCTTCAAGCTGAC

CTACCAGAACAAGGTGGTGAAGGTGCAGAGGCCCACCCCCAGGGGCGCCGTGATGGACATC

ATCAGCAGGAAGGACCAGAGGGGCAGCGGCCAGGTGGGCACCTACGGCCTGAACACCTTCA

-continued

CCAACATGGAGGCCCAGCTGATCAGGCAGATGGAGGCCGAGCAGTGGGAGCCCAGCAAGG

GCTGGCACGACTGGCAGCAGGTGCCCTTCTGCAGCCACCACTTCCACATCTTCATGAAGGAC

GGCAGGAAGCTGGTGGTGCCCTGCAGGAACCAGGACGAGCTGATCGGCAGGGCCAGGATC

AGCCAGGGCGCCGGCTGGAGCCTGAGGGAGACCGCCTGCCTGGGCAAGAGCTACGCCCAG

ATGTGGCAGCTGATGTACTTCCACAGGAGGGACCTGAGGCTGGCCAGCAACGCCATCTGCA

GCGCCGTGCCCAGCCACTGGGTGCCCAGCAGGACCACCTGGAGCCACGAGTGGATGACCAC

CGAGGACATGCTGGCCGTGTGGAACAGGGTGTGGCACAGCTGGGAGGACGTGCCCTACCTG

GGCAAGAGGGAGGACCAGTGGTGCGGCAGCCTGATCGGCCTGACCAGCAGGGCCACCTGG

GCCAAGAACATCGCTGGATCCGGGCCCGGGGCTTCAGGTAAGCCTATCCCTAACCCTCTCCT

CGGTCTCGATTCTACGCGGACCTGATGAGCGGCCGCTCGAGCATGCATCTAGAGGGCCCTAT

TCTATAGTGTCACCTAAATGCTAGAGCTCGCTGATCAGCCTCGACTGTGCCTTCTAGTTGCCA

GCCATCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTATTCTGGG

GGGTGGGGTGGGGCAGGACAGCAAGGGGGAGGATTGGGAAGACAATAGCAGGCATGCTGG

GGATGCGGTGGGCTCTATGGCTTCTGAGGCGGAAAGAACCAGCTGGGGCTCGAGGGGGGAT

CGATCCCGTCGAGATATCTAGACCCAGCTTTCTTGTACAAAGTTGGCATTATAAGAAAGCATT

GCTTATCAATTTGTTGCAACGAACAGGTCACTATCAGTCAAAATAAAATCATTATTTGGATCGA

TTCGACAGATCGCGATCGCAGTGAGTAGTGTTCTGGGGCGGGGGAGGACCTGCATGAGGGC

CAGAATGACTGAAATCTGTGCTTTTCTGTGTGTTGCAGCATCATGAGCGGAAGCGGCTCCTTT

GAGGGAGGGGTATTCAGCCCTTATCTGACGGGGCGTCTCCCCTCCTGGGCGGGAGTGCGTC

AGAATGTGATGGGATCCACGGTGGACGGCCGGCCCGTGCAGCCCGCGAACTCTTCAACCCT

GACCTATGCAACCCTGAGCTCTTCGTCGGTGGACGCAGCTGCCGCCGCAGCTGCTGCATCC

GCCGCCAGCGCCGTGCGCGGAATGGCCATGGGCGCCGGCTACTACGGCACTCTGGTGGCC

AACTCGAGTTCCACCAATAATCCCGCCAGCCTGAACGAGGAGAAGCTGCTGCTGCTGATGGC

CCAGCTTGAGGCCTTGACCCAGCGCCTGGGCGAGCTGACCCAGCAGGTGGCTCAGCTGCAG

GAGCAGACGCGGGCCGCGGTTGCCACGGTGAAATCCAAATAAAAAATGAATCAATAAATAAA

CGGAGACGGTTGTTGATTTTAACACAGAGTCTGAATCTTTATTTGATTTTTCGCGCGCGGTAG

GCCCTGGACCACCGGTCTCGATCATTGAGCACCCGGTGGATCTTTTCCAGGACCCGGTAGAG

GTGGGCTTGGATGTTGAGGTACATGGGCATGAGCCCGTCCCGGGGGTGGAGGTAGCTCCAT

TGCAGGGCCTCGTGCTCGGGGGTGGTGTTGTAAATCACCCAGTCATAGCAGGGGCGCAGGG

CGTGGTGTTGCACAATATCTTTGAGGAGGAGACTGATGGCCACGGGCAGCCCTTTGGTGTAG

GTGTTTACAAATCTGTTGAGCTGGGAGGGATGCATGCGGGGGGAGATGAGGTGCATCTTGGC

CTGGATCTTGAGATTGGCGATGTTACCGCCCAGATCCCGCCTGGGGTTCATGTTGTGCAGGA

CCACCAGCACGGTGTATCCGGTGCACTTGGGGAATTTATCATGCAACTTGGAAGGGAAGGCG

TGAAAGAATTTGGCGACGCCCTTGTGTCCGCCCAGGTTTTCCATGCACTCATCCATGATGATG

GCAATGGGCCCGTGGGCGGCGGCCTGGGCAAAGACGTTTCGGGGGTCGGACACATCATAGT

TGTGGTCCTGGGTGAGGTCATCATAGGCCATTTTAATGAATTTGGGGCGGAGGGTGCCGGAC

TGGGGGACAAAGGTACCCTCGATCCCGGGGGCGTAGTTCCCCTCACAGATCTGCATCTCCCA

GGCTTTGAGCTCAGAGGGGGGGATCATGTCCACCTGCGGGGCGATAAAGAACACGGTTTCC

GGGGCGGGGGAGATGAGCTGGGCCGAAAGCAAGTTCCGGAGCAGCTGGGACTTGCCGCAG

-continued

CCGGTGGGGCCGTAAATGACCCCGATGACCGGCTGCAGGTGGTAGTTGAGGGAGAGACAGC

TGCCGTCCTCCCGGAGGAGGGGGGCCACCTCGTTCATCATCTCGCGCACGTGCATGTTCTC

GCGCACCAGTTCCGCCAGGAGGCGCTCTCCCCCCAGAGATAGGAGCTCCTGGAGCGAGGCG

AAGTTTTTCAGCGGCTTGAGTCCGTCGGCCATGGGCATTTTGGAGAGGGTCTGTTGCAAGAG

TTCCAAGCGGTCCCAGAGCTCGGTGATGTGCTCTACGGCATCTCGATCCAGCAGACCTCCTC

GTTTCGCGGGTTGGGACGACTGCGGGAGTAGGGCACCAGACGATGGGCGTCCAGCGCAGC

CAGGGTCCGGTCCTTCCAGGGCCGCAGCGTCCGCGTCAGGGTGGTCTCCGTCACGGTGAAG

GGGTGCGCGCCGGGCTGGGCGCTTGCGAGGGTGCGCTTCAGGCTCATCCGGCTGGTCGAA

AACCGCTCCCGATCGGCGCCCTGCGCGTCGGCCAGGTAGCAATTGACCATGAGTTCGTAGTT

GAGCGCCTCGGCCGCGTGGCCTTTGGCGCGGAGCTTACCTTTGGAAGTCTGCCCGCAGGCG

GGACAGAGGAGGGACTTGAGGGCGTAGAGCTTGGGGGCGAGGAAGACGGAATCGGGGGCG

TAGGCGTCCGCGCCGCAGTGGGCGCAGACGGTCTCGCACTCCACGAGCCAGGTGAGGTCG

GGCTGGTCGGGGTCAAAAACCAGTTTCCCGCCGTTCTTTTTGATGCGTTTCTTACCTTTGGTC

TCCATGAGCTCGTGTCCCCGCTGGGTGACAAAGAGGCTGTCCGTGTCCCCGTAGACCGACTT

TATGGGCCGGTCCTCGAGCGGTGTGCCGCGGTCCTCCTCGTAGAGGAACCCCGCCCACTCC

GAGACGAAAGCCCGGGTCCAGGCCAGCACGAAGGAGGCCACGTGGGACGGGTAGCGGTCG

TTGTCCACCAGCGGGTCCACTTTTTCCAGGGTATGCAAACACATGTCCCCCTCGTCCACATCC

AGGAAGGTGATTGGCTTGTAAGTGTAGGCCACGTGACCGGGGGTCCCGGCCGGGGGGGTAT

AAAAGGGGGCGGGCCCCTGCTCGTCCTCACTGTCTTCCGGATCGCTGTCCAGGAGCGCCAG

CTGTTGGGGTAGGTATTCCCTCTCGAAGGCGGGCATGACCTCGGCACTCAGGTTGTCAGTTT

CTAGAAACGAGGAGGATTTGATATTGACGGTGCCAGCGGAGATGCCTTTCAAGAGCCCCTCG

TCCATCTGGTCAGAAAAGACGATTTTTTTGTTGTCGAGCTTGGTGGCGAAGGAGCCGTAGAG

GGCGTTGGAAAGGAGCTTGGCGATGGAGCGCATGGTCTGGTTTTTTTCCTTGTCGGCGCGCT

CCTTGGCCGCGATGTTGAGCTGCACGTACTCGCGCGCCACGCACTTCCATTCGGGGAAGAC

GGTGGTCATCTCGTCGGGCACGATTCTGACCTGCCAACCTCGATTATGCAGGGTGATGAGGT

CCACACTGGTGGCCACCTCGCCGCGCAGGGGCTCGTTGGTCCAGCAGAGGCGGCCGCCCTT

GCGCGAGCAGAAGGGGGGCAGAGGGTCCAGCATGACCTCGTCGGGGGGGTCGGCATCGAT

GGTGAAGATGCCGGGCAGGAGATCGGGGTCGAAGTAGCTGATGGAAGTGGCCAGATCGTCC

AGGGAAGCTTGCCATTCGCGCACGGCCAGCGCGCGCTCGTAGGGACTGAGGGGCGTGCCC

CAGGGCATGGGGTGGGTGAGCGCGGAGGCGTACATGCCGCAGATGTCGTAGACGTAGAGG

GGCTCCTCGAGGATGCCGATGTAGGTGGGGTAGCAGCGCCCCCCGCGGATGCTGGCGCGC

ACGTAGTCATACAGCTCGTGCGAGGGCGCGAGGAGCCCCGGGCCCAGGTTGGTGCGACTG

GGCTTTTCGGCGCGGTAGACGATCTGGCGAAAGATGGCATGCGAGTTGGAGGAGATGGTGG

GCCTTTGGAAGATGTTGAAGTGGGCGTGGGGGAGGCCGACCGAGTCGCGGATGAAGTGGGC

GTAGGAGTCTTGCAGTTTGGCGACGAGCTCGGCGGTGACGAGGACGTCCAGAGCGCAGTAG

TCGAGGGTCTCCTGGATGATGTCATACTTGAGCTGGCCCTTTTGTTTCCACAGCTCGCGGTTG

AGAAGGAACTCTTCGCGGTCCTTCCAGTACTCTTCGAGGGGGAACCCGTCCTGATCTGCACG

GTAAGAGCCTAGCATGTAGAACTGGTTGACGGCCTTGTAGGCGCAGCAGCCCTTCTCCACGG

GGAGGGCGTAGGCCTGGGCGGCCTTGCGCAGGGAGGTGTGCGTGAGGGCGAAGGTGTCCC

TGACCATGACCTTGAGGAACTGGTGCTTGAAATCGATATCGTCGCAGCCCCCCTGCTCCCAG

AGCTGGAAGTCCGTGCGCTTCTTGTAGGCGGGGTTGGGCAAAGCGAAAGTAACATCGTTGAA

-continued

AAGGATCTTGCCCGCGCGGGGCATAAAGTTGCGAGTGATGCGGAAAGGCTGGGGCACCTCG

GCCCGGTTGTTGATGACCTGGGCGGCGAGCACGATCTCGTCGAAACCGTTGATGTTGTGGC

CCACGATGTAGAGTTCCACGAATCGCGGGCGGCCCTTGACGTGGGGCAGCTTCTTGAGCTC

CTCGTAGGTGAGCTCGTCGGGGTCGCTGAGACCGTGCTGCTCGAGCGCCCAGTCGGCGAGA

TGGGGGTTGGCGCGGAGGAAGGAAGTCCAGAGATCCACGGCCAGGGCGGTTTGCAGACGG

TCCCGGTACTGACGGAACTGCTGCCCGACGGCCATTTTTTCGGGGGTGACGCAGTAGAAGGT

GCGGGGGTCCCCGTGCCAGCGGTCCCATTTGAGCTGGAGGGCGAGATCGAGGGCGAGCTC

GACGAGGCGGTCGTCCCCTGAGAGTTTCATGACCAGCATGAAGGGGACGAGCTGCTTGCCG

AAGGACCCCATCCAGGTGTAGGTTTCCACATCGTAGGTGAGGAAGAGCCTTTCGGTGCGAGG

ATGCGAGCCGATGGGGAAGAACTGGATCTCCTGCCACCAATTGGAGGAATGGCTGTTGATGT

GATGGAAGTAGAAATGCCGACGGCGCGCCGAACACTCGTGCTTGTGTTTATACAAGCGGCCA

CAGTGCTCGCAACGCTGCACGGGATGCACGTGCTGCACGAGCTGTACCTGAGTTCCTTTGAC

GAGGAATTTCAGTGGGAAGTGGAGTCGTGGCGCCTGCATCTCGTGCTGTACTACGTCGTGGT

GGTCGGCCTGGCCCTCTTCTGCCTCGATGGTGGTCATGCTGACGAGCCCGCGCGGGAGGCA

GGTCCAGACCTCGGCGCGAGCGGGTCGGAGAGCGAGGACGAGGGCGCGCAGGCCGGAGC

TGTCCAGGGTCCTGAGACGCTGCGGAGTCAGGTCAGTGGGCAGCGGCGGCGCGCGGTTGA

CTTGCAGGAGTTTTTCCAGGGCGCGCGGGAGGTCCAGATGGTACTTGATCTCCACCGCGCC

GTTGGTGGCGACGTCGATGGCTTGCAGGGTCCCGTGCCCCTGGGGTGTGACCACCGTCCCC

CGTTTCTTCTTGGGCGGCTGGGGCGACGGGGGCGGTGCCTCTTCCATGGTTAGAAGCGGCG

GCGAGGACGCGCGCCGGGCGGCAGAGGCGGCTCGGGGCCCGGAGGCAGGGGCGGCAGG

GGCACGTCGGCGCCGCGCGCGGGTAGGTTCTGGTACTGCGCCCGGAGAAGACTGGCGTGA

GCGACGACGCGACGGTTGACGTCCTGGATCTGACGCCTCTGGGTGAAGGCCACGGGACCCG

TGAGTTTGAACCTGAAAGAGAGTTCGACAGAATCAATCTCGGTATCGTTGACGGCGGCCTGC

CGCAGGATCTCTTGCACGTCGCCCGAGTTGTCCTGGTAGGCGATCTCGGTCATGAACTGCTC

GATCTCCTCCTCCTGAAGGTCTCCGCGACCGGCGCGCTCCACGGTGGCCGCGAGGTCGTTG

GAGATGCGGCCCATGAGCTGCGAGAAGGCGTTCATGCCCGCCTCGTTCCAGACGCGGCTGT

AGACCACGACGCCCTCGGGATCGCGGGCGCGCATGACCACCTGGGCGAGGTTGAGCTCCAC

GTGGCGCGTGAAGACCGCGTAGTTGCAGAGGCGCTGGTAGAGGTAGTTGAGCGTGGTGGCG

ATGTGCTCGGTGACGAAGAAATACATGATCCAGCGGCGGAGCGGCATCTCGCTGACGTCGC

CCAGCGCCTCCAAGCGTTCCATGGCCTCGTAAAAGTCCACGGCGAAGTTGAAAAACTGGGAG

TTGCGCGCCGAGACGGTCAACTCCTCCTCCAGAAGACGGATGAGCTCGGCGATGGTGGCGC

GCACCTCGCGCTCGAAGGCCCCCGGGAGTTCCTCCACTTCCTCCTCTTCTTCCTCCTCCACT

AACATCTCTTCTACTTCCTCCTCAGGCGGTGGTGGTGGCGGGGGAGGGGGCCTGCGTCGCC

GGCGGCGCACGGGCAGACGGTCGATGAAGCGCTCGATGGTCTCGCCGCGCCGGCGTCGCA

TGGTCTCGGTGACGGCGCGCCCGTCCTCGCGGGGCCGCAGCGTGAAGACGCCGCCGCGCA

TCTCCAGGTGGCCGGGGGGGTCCCCGTTGGGCAGGGAGAGGGCGCTGACGATGCATCTTAT

CAATTGCCCCGTAGGGACTCCGCGCAAGGACCTGAGCGTCTCGAGATCCACGGGATCTGAA

AACCGTTGAACGAAGGCTTCGAGCCAGTCGCAGTCGCAAGGTAGGCTGAGCACGGTTTCTTC

TGCCGGGTCATGTTGGGGAGCGGGGCGGGCGATGCTGCTGGTGATGAAGTTGAAATAGGCG

GTTCTGAGACGGCGGATGGTGGCGAGGAGCACCAGGTCTTTGGGCCCGGCTTGCTGGATGC

-continued

GCAGACGGTCGGCCATGCCCCAGGCGTGGTCCTGACACCTGGCCAGGTCCTTGTAGTAGTC

CTGCATGAGCCGCTCCACGGGCACCTCCTCCTCGCCCGCGCGGCCGTGCATGCGCGTGAGC

CCGAAGCCGCGCTGGGGCTGGACGAGCGCCAGGTCGGCGACGACGCGCTCGGCGAGGATG

GCCTGCTGGATCTGGGTGAGGGTGGTCTGGAAGTCGTCAAAGTCGACGAAGCGGTGGTAGG

CTCCGGTGTTGATGGTGTAGGAGCAGTTGGCCATGACGGACCAGTTGACGGTCTGGTGGCC

CGGACGCACGAGCTCGTGGTACTTGAGGCGCGAGTAGGCGCGCGTGTCGAAGATGTAGTCG

TTGCAGGTGCGCACCAGGTACTGGTAGCCGATGAGGAAGTGCGGCGGCGGCTGGCGGTAGA

GCGGCCATCGCTCGGTGGCGGGGGCGCCGGGCGCGAGGTCCTCGAGCATGGTGCGGTGGT

AGCCGTAGATGTACCTGGACATCCAGGTGATGCCGGCGGCGGTGGTGGAGGCGCGCGGGA

ACTCGCGGACGCGGTTCCAGATGTTGCGCAGCGGCAGGAAGTAGTTCATGGTGGGCACGGT

CTGGCCCGTGAGGCGCGCGCAGTCGTGGATGCTCTATACGGGCAAAAACGAAAGCGGTCAG

CGGCTCGACTCCGTGGCCTGGAGGCTAAGCGAACGGGTTGGGCTGCGCGTGTACCCCGGTT

CGAATCTCGAATCAGGCTGGAGCCGCAGCTAACGTGGTACTGGCACTCCCGTCTCGACCCAA

GCCTGCACCAACCCTCCAGGATACGGAGGCGGGTCGTTTTGCAACTTTTTTTGGAGGCCGGA

AATGAAACTAGTAAGCGCGGAAAGCGGCCGACCGCGATGGCTCGCTGCCGTAGTCTGGAGA

AGAATCGCCAGGGTTGCGTTGCGGTGTGCCCCGGTTCGAGGCCGGCCGGATTCCGCGGCTA

ACGAGGGCGTGGCTGCCCCGTCGTTTCCAAGACCCCATAGCCAGCCGACTTCTCCAGTTACG

GAGCGAGCCCCTCTTTTGTTTTGTTTGTTTTTGCCAGATGCATCCCGTACTGCGGCAGATGCG

CCCCCACCACCCTCCACCGCAACAACAGCCCCCTCCTCCACAGCCGGCGCTTCTGCCCCCG

CCCCAGCAGCAGCAGCAACTTCCAGCCACGACCGCCGCGGCCGCCGTGAGCGGGGCTGGA

CAGACTTCTCAGTATGATCACCTGGCCTTGGAAGAGGGCGAGGGGCTGGCGCGCCTGGGGG

CGTCGTCGCCGGAGCGGCACCCGCGCGTGCAGATGAAAAGGGACGCTCGCGAGGCCTACG

TGCCCAAGCAGAACCTGTTCAGAGACAGGAGCGGCGAGGAGCCCGAGGAGATGCGCGCGG

CCCGGTTCCACGCGGGGCGGGAGCTGCGGCGCGGCCTGGACCGAAAGAGGGTGCTGAGGG

ACGAGGATTTCGAGGCGGACGAGCTGACGGGGATCAGCCCCGCGCGCGCGCACGTGGCCG

CGGCCAACCTGGTCACGGCGTACGAGCAGACCGTGAAGGAGGAGAGCAACTTCCAAAAATC

CTTCAACAACCACGTGCGCACCCTGATCGCGCGCGAGGAGGTGACCCTGGGCCTGATGCAC

CTGTGGGACCTGCTGGAGGCCATCGTGCAGAACCCCACCAGCAAGCCGCTGACGGCGCAGC

TGTTCCTGGTGGTGCAGCATAGTCGGGACAACGAGGCGTTCAGGGAGGCGCTGCTGAATAT

CACCGAGCCCGAGGGCCGCTGGCTCCTGGACCTGGTGAACATTCTGCAGAGCATCGTGGTG

CAGGAGCGCGGGCTGCCGCTGTCCGAGAAGCTGGCGGCCATCAACTTCTCGGTGCTGAGTC

TGGGCAAGTACTACGCTAGGAAGATCTACAAGACCCCGTACGTGCCCATAGACAAGGAGGTG

AAGATCGACGGGTTTTACATGCGCATGACCCTGAAAGTGCTGACCCTGAGCGACGATCTGGG

GGTGTACCGCAACGACAGGATGCACCGCGCGGTGAGCGCCAGCAGGCGGCGCGAGCTGAG

CGACCAGGAGCTGATGCACAGCCTGCAGCGGGCCCTGACCGGGGCCGGGACCGAGGGGGA

GAGCTACTTTGACATGGGCGCGGACCTGCACTGGCAGCCCAGCCGCCGGGCCTTGGAGGCG

GCAGGCGGTCCCCCCTACATAGAAGAGGTGGACGATGAGGTGGACGAGGAGGGCGAGTACC

TGGAAGACTGATGGCGCGACCGTATTTTTGCTAGATGCAACAACAGCCACCTCCTGATCCCG

CGATGCGGGCGGCGCTGCAGAGCCAGCCGTCCGGCATTAACTCCTCGGACGATTGGACCCA

GGCCATGCAACGCATCATGGCGCTGACGACCCGCAACCCCGAAGCCTTTAGACAGCAGCCC

CAGGCCAACCGGCTCTCGGCCATCCTGGAGGCCGTGGTGCCCTCGCGCTCCAACCCCACGC

-continued

ACGAGAAGGTCCTGGCCATCGTGAACGCGCTGGTGGAGAACAAGGCCATCCGCGGCGACGA

GGCCGGCCTGGTGTACAACGCGCTGCTGGAGCGCGTGGCCCGCTACAACAGCACCAACGTG

CAGACCAACCTGGACCGCATGGTGACCGACGTGCGCGAGGCCGTGGCCCAGCGCGAGCGG

TTCCACCGCGAGTCCAACCTGGGATCCATGGTGGCGCTGAACGCCTTCCTCAGCACCCAGCC

CGCCAACGTGCCCCGGGGCCAGGAGGACTACACCAACTTCATCAGCGCCCTGCGCCTGATG

GTGACCGAGGTGCCCCAGAGCGAGGTGTACCAGTCCGGGCCGGACTACTTCTTCCAGACCA

GTCGCCAGGGCTTGCAGACCGTGAACCTGAGCCAGGCGTTCAAGAACTTGCAGGGCCTGTG

GGGCGTGCAGGCCCCGGTCGGGGACCGCGCGACGGTGTCGAGCCTGCTGACGCCGAACTC

GCGCCTGCTGCTGCTGCTGGTGGCCCCCTTCACGGACAGCGGCAGCATCAACCGCAACTCG

TACCTGGGCTACCTGATTAACCTGTACCGCGAGGCCATCGGCCAGGCGCACGTGGACGAGC

AGACCTACCAGGAGATCACCCACGTGAGCCGCGCCCTGGGCCAGGACGACCCGGGCAATCT

GGAAGCCACCCTGAACTTTTTGCTGACCAACCGGTCGCAGAAGATCCCGCCCCAGTACACGC

TCAGCGCCGAGGAGGAGCGCATCCTGCGATACGTGCAGCAGAGCGTGGGCCTGTTCCTGAT

GCAGGAGGGGGCCACCCCCAGCGCCGCGCTCGACATGACCGCGCGCAACATGGAGCCCAG

CATGTACGCCAGCAACCGCCCGTTCATCAATAAACTGATGGACTACTTGCATCGGGCGGCCG

CCATGAACTCTGACTATTTCACCAACGCCATCCTGAATCCCCACTGGCTCCCGCCGCCGGGG

TTCTACACGGGCGAGTACGACATGCCCGACCCCAATGACGGGTTCCTGTGGGACGATGTGG

ACAGCAGCGTGTTCTCCCCCCGACCGGGTGCTAACGAGCGCCCCTTGTGGAAGAAGGAAGG

CAGCGACCGACGCCCGTCCTCGGCGCTGTCCGGCCGCGAGGGTGCTGCCGCGGCGGTGCC

CGAGGCCGCCAGTCCTTTCCCGAGCTTGCCCTTCTCGCTGAACAGTATTCGCAGCAGCGAGC

TGGGCAGGATCACGCGCCCGCGCTTGCTGGGCGAGGAGGAGTACTTGAATGACTCGCTGTT

GAGACCCGAGCGGGAGAAGAACTTCCCCAATAACGGGATAGAGAGCCTGGTGGACAAGATG

AGCCGCTGGAAGACGTATGCGCAGGAGCACAGGGACGATCCGTCGCAGGGGGCCACGAGC

CGGGGCAGCGCCGCCCGTAAACGCCGGTGGCACGACAGGCAGCGGGGACTGATGTGGGAC

GATGAGGATTCCGCCGACGACAGCAGCGTGTTGGACTTGGGTGGGAGTGGTAACCCGTTCG

CTCACCTGCGCCCCCGCATCGGGCGCATGATGTAAGAGAAACCGAAAATAAATGATACTCAC

CAAGGCCATGGCGACCAGCGTGCGTTCGTTTCTTCTCTGTTGTTGTATCTAGTATGATGAGGC

GTGCGTACCCGGAGGGTCCTCCTCCCTCGTACGAGAGCGTGATGCAGCAGGCGATGGCGGC

GGCGGCGGCGATGCAGCCCCCGCTGGAGGCTCCTTACGTGCCCCCGCGGTACCTGGCGCC

TACGGAGGGGCGGAACAGCATTCGTTACTCGGAGCTGGCACCCTTGTACGATACCACCCGGT

TGTACCTGGTGGACAACAAGTCGGCGGACATCGCCTCGCTGAACTACCAGAACGACCACAGC

AACTTCCTGACCACCGTGGTGCAGAACAATGACTTCACCCCCACGGAGGCCAGCACCCAGAC

CATCAACTTTGACGAGCGCTCGCGGTGGGGCGGTCAGCTGAAAACCATCATGCACACCAACA

TGCCCAACGTGAACGAGTTCATGTACAGCAACAAGTTCAAGGCGCGGGTGATGGTCTCCCGC

AAGACCCCCAACGGGGTGACAGTGACAGATGGTAGTCAGGATATCTTGGAGTATGAATGGGT

GGAGTTTGAGCTGCCCGAAGGCAACTTCTCGGTGACCATGACCATCGACCTGATGAACAACG

CCATCATCGACAATTACTTGGCGGTGGGGCGGCAGAACGGGGTCCTGGAGAGCGATATCGG

CGTGAAGTTCGACACTAGGAACTTCAGGCTGGGCTGGGACCCCGTGACCGAGCTGGTCATG

CCCGGGGTGTACACCAACGAGGCCTTCCACCCCGATATTGTCTTGCTGCCCGGCTGCGGGG

TGGACTTCACCGAGAGCCGCCTCAGCAACCTGCTGGGCATTCGCAAGAGGCAGCCCTTCCA

-continued

GGAGGGCTTCCAGATCATGTACGAGGATCTGGAGGGGGGCAACATCCCCGCGCTCCTGGAT

GTCGACGCCTATGAGAAAAGCAAGGAGGAGAGCGCCGCCGCGGCGACTGCAGCTGTAGCCA

CCGCCTCTACCGAGGTCAGGGGCGATAATTTTGCCAGCCCTGCAGCAGTGGCAGCGGCCGA

GGCGGCTGAAACCGAAAGTAAGATAGTCATTCAGCCGGTGGAGAAGGATAGCAAGGACAGG

AGCTACAACGTGCTGCCGGACAAGATAAACACCGCCTACCGCAGCTGGTACCTGGCCTACAA

CTATGGCGACCCCGAGAAGGGCGTGCGCTCCTGGACGCTGCTCACCACCTCGGACGTCACC

TGCGGCGTGGAGCAAGTCTACTGGTCGCTGCCCGACATGATGCAAGACCCGGTCACCTTCC

GCTCCACGCGTCAAGTTAGCAACTACCCGGTGGTGGGCGCCGAGCTCCTGCCCGTCTACTC

CAAGAGCTTCTTCAACGAGCAGGCCGTCTACTCGCAGCAGCTGCGCGCCTTCACCTCGCTCA

CGCACGTCTTCAACCGCTTCCCCGAGAACCAGATCCTCGTCCGCCCGCCCGCGCCCACCATT

ACCACCGTCAGTGAAAACGTTCCTGCTCTCACAGATCACGGGACCCTGCCGCTGCGCAGCAG

TATCCGGGGAGTCCAGCGCGTGACCGTTACTGACGCCAGACGCCGCACCTGCCCCTACGTC

TACAAGGCCCTGGGCATAGTCGCGCCGCGCGTCCTCTCGAGCCGCACCTTCTAAAAAATGTC

CATTCTCATCTCGCCCAGTAATAACACCGGTTGGGGCCTGCGCGCGCCCAGCAAGATGTACG

GAGGCGCTCGCCAACGCTCCACGCAACACCCCGTGCGCGTGCGCGGGCACTTCCGCGCTCC

CTGGGGCGCCCTCAAGGGCCGCGTGCGGTCGCGCACCACCGTCGACGACGTGATCGACCA

GGTGGTGGCCGACGCGCGCAACTACACCCCCGCCGCCGCGCCCGTCTCCACCGTGGACGC

CGTCATCGACAGCGTGGTGGCCGACGCGCGCCGGTACGCCCGCGCCAAGAGCCGGCGGCG

GCGCATCGCCCGGCGGCACCGGAGCACCCCCGCCATGCGCGCGGCGCGAGCCTTGCTGCG

CAGGGCCAGGCGCACGGGACGCAGGGCCATGCTCAGGGCGGCCAGACGCGCGGCTTCAGG

CGCCAGCGCCGGCAGGACCCGGAGACGCGCGGCCACGGCGGCGGCAGCGGCCATCGCCA

GCATGTCCCGCCCGCGGCGAGGGAACGTGTACTGGGTGCGCGACGCCGCCACCGGTGTGC

GCGTGCCCGTGCGCACCCGCCCCCCTCGCACTTGAAGATGTTCACTTCGCGATGTTGATGTG

TCCCAGCGGCGAGGAGGATGTCCAAGCGCAAATTCAAGGAAGAGATGCTCCAGGTCATCGC

GCCTGAGATCTACGGCCCCGCGGTGGTGAAGGAGGAAAGAAAGCCCCGCAAAATCAAGCGG

GTCAAAAAGGACAAAAAGGAAGAAGATGACGATCTGGTGGAGTTTGTGCGCGAGTTCGCCCC

CCGGCGGCGCGTGCAGTGGCGCGGGCGGAAAGTGCACCCGGTGCTGAGACCCGGCACCAC

CGTGGTCTTCACGCCCGGCGAGCGCTCCGGCAGCGCTTCCAAGCGCTCCTACGACGAGGTG

TACGGGGACGAGGACATCCTCGAGCAGGCGGCCGAGCGCCTGGGCGAGTTTGCTTACGGCA

AGCGCAGCCGCCCCGCCCTGAAGGAAGAGGCGGTGTCCATCCCGCTGGACCACGGCAACC

CCACGCCGAGCCTCAAGCCCGTGACCCTGCAGCAGGTGCTGCCGAGCGCAGCGCCGCGCC

GGGGGTTCAAGCGCGAGGGCGAGGATCTGTACCCCACCATGCAGCTGATGGTGCCCAAGCG

CCAGAAGCTGGAAGACGTGCTGGAGACCATGAAGGTGGACCCGGACGTGCAGCCCGAGGTC

AAGGTGCGGCCCATCAAGCAGGTGGCCCCGGGCCTGGGCGTGCAGACCGTGGACATCAAGA

TCCCCACGGAGCCCATGGAAACGCAGACCGAGCCCATGATCAAGCCCAGCACCAGCACCAT

GGAGGTGCAGACGGATCCCTGGATGCCATCGGCTCCTAGCCGAAGACCCCGGCGCAAGTAC

GGCGCGGCCAGCCTGCTGATGCCCAACTACGCGCTGCATCCTTCCATCATCCCCACGCCGG

GCTACCGCGGCACGCGCTTCTACCGCGGTCATACAACCAGCCGCCGCCGCAAGACCACCAC

CCGCCGCCGCCGTCGCCGCACAGCCGCTGCATCTACCCCTGCCGCCCTGGTGCGGAGAGT

GTACCGCCGCGGCCGCGCGCCTCTGACCCTACCGCGCGCGCGCTACCACCCGAGCATCGC

CATTTAAACTTTCGCCTGCTTTGCAGATGGCCCTCACATGCCGCCTCCGCGTTCCCATTACGG

-continued

GCTACCGAGGAAGAAAACCGCGCCGTAGAAGGCTGGCGGGGAACGGGATGCGTCGCCACC

ACCATCGGCGGCGGCGCGCCATCAGCAAGCGGTTGGGGGGAGGCTTCCTGCCCGCGCTGA

TCCCCATCATCGCCGCGGCGATCGGGGCGATCCCCGGCATTGCTTCCGTGGCGGTGCAGGC

CTCTCAGCGCCACTGAGACACTTGGAAAACATCTTGTAATAAACCAATGGACTCTGACGCTCC

TGGTCCTGTGATGTGTTTTCGTAGACAGATGGAAGACATCAATTTTTCGTCCCTGGCTCCGCG

ACACGGCACGCGGCCGTTCATGGGCACCTGGAGCGACATCGGCACCAGCCAACTGAACGGG

GGCGCCTTCAATTGGAGCAGTCTCTGGAGCGGGCTTAAGAATTTCGGGTCCACGCTTAAAAC

CTATGGCAGCAAGGCGTGGAACAGCACCACAGGGCAGGCGCTGAGGGATAAGCTGAAAGAG

CAGAACTTCCAGCAGAAGGTGGTCGATGGGCTCGCCTCGGGCATCAACGGGGTGGTGGACC

TGGCCAACCAGGCCGTGCAGCGGCAGATCAACAGCCGCCTGGACCCGGTGCCGCCCGCCG

GCTCCGTGGAGATGCCGCAGGTGGAGGAGGAGCTGCCTCCCCTGGACAAGCGGGGCGAGA

AGCGACCCCGCCCCGACGCGGAGGAGACGCTGCTGACGCACACGGACGAGCCGCCCCCGT

ACGAGGAGGCGGTGAAACTGGGTCTGCCCACCACGCGGCCCATCGCGCCCCTGGCCACCG

GGGTGCTGAAACCCGAAAGTAATAAGCCCGCGACCCTGGACTTGCCTCCTCCCGCTTCCCGC

CCCTCTACAGTGGCTAAGCCCCTGCCGCCGGTGGCCGTGGCCCGCGCGCGACCCGGGGGC

TCCGCCCGCCCTCATGCGAACTGGCAGAGCACTCTGAACAGCATCGTGGGTCTGGGAGTGC

AGAGTGTGAAGCGCCGCCGCTGCTATTAAACCTACCGTAGCGCTTAACTTGCTTGTCTGTGT

GTGTATGTATTATGTCGCCGCTGTCCGCCAGAAGGAGGAGTGAAGAGGCGCGTCGCCGAGT

TGCAAGATGGCCACCCCATCGATGCTGCCCCAGTGGGCGTACATGCACATCGCCGGACAGG

ACGCTTCGGAGTACCTGAGTCCGGGTCTGGTGCAGTTCGCCCGCGCCACAGACACCTACTTC

AGTCTGGGGAACAAGTTTAGGAACCCCACGGTGGCGCCCACGCACGATGTGACCACCGACC

GCAGCCAGCGGCTGACGCTGCGCTTCGTGCCCGTGGACCGCGAGGACAACACCTACTCGTA

CAAAGTGCGCTACACGCTGGCCGTGGGCGACAACCGCGTGCTGGACATGGCCAGCACCTAC

TTTGACATCCGCGGCGTGCTGGATCGGGGCCCTAGCTTCAAACCCTACTCCGGCACCGCCTA

CAACAGCCTGGCTCCCAAGGGAGCGCCCAATTCCAGCCAGTGGGAGCAAAAAAAGGCAGGC

AATGGTGACACTATGGAAACACACACATTTGGTGTGGCCCCAATGGGCGGTGAGAATATTAC

AATCGACGGATTACAAATTGGAACTGACGCTACAGCTGATCAGGATAAACCAATTTATGCTGA

CAAAACATTCCAGCCTGAACCTCAAGTAGGAGAAGAAAATTGGCAAGAAACTGAAAGCTTTTA

TGGCGGTAGGGCTCTTAAAAAAGACACAAGCATGAAACCTTGCTATGGCTCCTATGCTAGACC

CACCAATGTAAAGGGAGGTCAAGCTAAACTTAAAGTTGGAGCTGATGGAGTTCCTACCAAAGA

ATTTGACATAGACCTGGCTTTCTTTGATACTCCCGGTGGCACAGTGAATGGACAAGATGAGTA

TAAAGCAGACATTGTCATGTATACCGAAAACACGTATCTGGAAACTCCAGACACGCATGTGGT

ATACAAACCAGGCAAGGATGATGCAAGTTCTGAAATTAACCTGGTTCAGCAGTCCATGCCCAA

TAGACCCAACTATATTGGGTTCAGAGACAACTTTATTGGGCTCATGTATTACAACAGTACTGG

CAATATGGGGGTGCTGGCTGGTCAGGCCTCACAGCTGAATGCTGTGGTCGACTTGCAAGACA

GAAACACCGAGCTGTCATACCAGCTCTTGCTTGACTCTTTGGGTGACAGAACCCGGTATTTCA

GTATGTGGAATCAGGCGGTGGACAGTTATGATCCTGATGTGCGCATTATTGAAAACCATGGTG

TGGAAGACGAACTTCCCAACTATTGCTTCCCCCTGGATGGGTCTGGCACTAATGCCGCTTAC

CAAGGTGTGAAAGTAAAAAATGGTAACGATGGTGATGTTGAGAGCGAATGGGAAAATGATGAT

ACTGTCGCAGCTCGAAATCAATTATGCAAGGGCAACATTTTTGCCATGGAAATTAACCTCCAA

-continued

GCCAACCTGTGGAGAAGTTTCCTCTACTCGAACGTGGCCCTGTACCTGCCCGACTCTTACAA

GTACACGCCAGCCAACATCACCCTGCCCACCAACACCAACACTTATGATTACATGAACGGGA

GAGTGGTGCCTCCCTCGCTGGTGGACGCCTACATCAACATCGGGGCGCGCTGGTCGCTGGA

CCCCATGGACAACGTCAATCCCTTCAACCACCACCGCAACGCGGGCCTGCGCTACCGCTCCA

TGCTCCTGGGCAACGGGCGCTACGTGCCCTTCCACATCCAGGTGCCCCAGAAATTTTTCGCC

ATCAAGAGCCTCCTGCTCCTGCCCGGGTCCTACACCTACGAGTGGAACTTCCGCAAGGACGT

CAACATGATCCTGCAGAGCTCCCTCGGCAACGACCTGCGCACGGACGGGGCCTCCATCTCC

TTCACCAGCATCAACCTCTACGCCACCTTCTTCCCCATGGCGCACAACACGGCCTCCACGCT

CGAGGCCATGCTGCGCAACGACACCAACGACCAGTCCTTCAACGACTACCTCTCGGCGGCC

AACATGCTCTACCCCATCCCGGCCAACGCCACCAACGTGCCCATCTCCATCCCCTCGCGCAA

CTGGGCCGCCTTCCGCGGCTGGTCCTTCACGCGCCTCAAGACCAAGGAGACGCCCTCGCTG

GGCTCCGGGTTCGACCCCTACTTCGTCTACTCGGGCTCCATCCCCTACCTCGACGGCACCTT

CTACCTCAACCACACCTTCAAGAAGGTCTCCATCACCTTCGACTCCTCCGTCAGCTGGCCCG

GCAACGACCGGCTCCTGACGCCCAACGAGTTCGAAATCAAGCGCACCGTCGACGGCGAGGG

ATACAACGTGGCCCAGTGCAACATGACCAAGGACTGGTTCCTGGTCCAGATGCTGGCCCACT

ACAACATCGGCTACCAGGGCTTCTACGTGCCCGAGGGCTACAAGGACCGCATGTACTCCTTC

TTCCGCAACTTCCAGCCCATGAGCCGCCAGGTGGTGGACGAGGTCAACTACAAGGACTACCA

GGCCGTCACCCTGGCCTACCAGCACAACAACTCGGGCTTCGTCGGCTACCTCGCGCCCACC

ATGCGCCAGGGCCAGCCCTACCCCGCCAACTACCCGTACCCGCTCATCGGCAAGAGCGCCG

TCACCAGCGTCACCCAGAAAAAGTTCCTCTGCGACAGGGTCATGTGGCGCATCCCCTTCTCC

AGCAACTTCATGTCCATGGGCGCGCTCACCGACCTCGGCCAGAACATGCTCTATGCCAACTC

CGCCCACGCGCTAGACATGAATTTCGAAGTCGACCCCATGGATGAGTCCACCCTTCTCTATG

TTGTCTTCGAAGTCTTCGACGTCGTCCGAGTGCACCAGCCCCACCGCGGCGTCATCGAGGCC

GTCTACCTGCGCACCCCCTTCTCGGCCGGTAACGCCACCACCTAAATTGCTACTTGCATGAT

GGCTGAGCCCACAGGCTCCGGCGAGCAGGAGCTCAGGGCCATCATCCGCGACCTGGGCTG

CGGGCCCTACTTCCTGGGCACCTTCGATAAGCGCTTCCCGGGATTCATGGCCCCGCACAAGC

TGGCCTGCGCCATCGTCAACACGGCCGGCCGCGAGACCGGGGGCGAGCACTGGCTGGCCT

TCGCCTGGAACCCGCGCTCGAACACCTGCTACCTCTTCGACCCCTTCGGGTTCTCGGACGAG

CGCCTCAAGCAGATCTACCAGTTCGAGTACGAGGGCCTGCTGCGCCGTAGCGCCCTGGCCA

CCGAGGACCGCTGCGTCACCCTGGAAAAGTCCACCCAGACCGTGCAGGGTCCGCGCTCGGC

CGCCTGCGGGCTCTTCTGCTGCATGTTCCTGCACGCCTTCGTGCACTGGCCCGACCGCCCC

ATGGACAAGAACCCCACCATGAACTTGCTGACGGGGGTGCCCAACGGCATGCTCCAGTCGC

CCCAGGTGGAACCCACCCTGCGCCGCAACCAGGAGGCGCTCTACCGCTTCCTCAACTCCCA

CTCCGCCTACTTTCGCTCCCACCGCGCGCGCATCGAGAAGGCCACCGCCTTCGACCGCATG

AACAATCAAGACATGTAAACCGTGTGTGTATGTTTAAAATATCTTTTAATAAACAGCACTTTAAT

GTTACACATGCATCTGAGATGATTTTATTTTAGAAATCGAAAGGGTTCTGCCGGGTCTCGGCA

TGGCCCGCGGGCAGGGACACGTTGCGGAACTGGTACTTGGCCAGCCACTTGAACTCGGGGA

TCAGCAGTTTGGGCAGCGGGGTGTCGGGGAAGGAGTCGGTCCACAGCTTCCGCGTCAGCTG

CAGGGCGCCCAGCAGGTCGGGCGCGGAGATCTTGAAATCGCAGTTGGGACCCGCGTTCTGC

GCGCGAGAGTTGCGGTACACGGGGTTGCAGCACTGGAACACCATCAGGGCCGGGTGCTTCA

CGCTCGCCAGCACCGCCGCGTCGGTGATGCTCTCCACGTCGAGGTCCTCGGCGTTGGCCAT

-continued

CCCGAAGGGGGTCATCTTGCAGGTCTGCCTTCCCATGGTGGGCACGCACCCGGGCTTGTGG

TTGCAATCGCAGTGCAGGGGGATCAGCATCATCTGGGCCTGGTCGGCGTTCATCCCCGGGT

ACATGGCCTTCATGAAAGCCTCCAATTGCCTGAACGCCTGCTGGGCCTTGGCTCCCTCGGTG

AAGAAGACCCCGCAGGACTTGCTAGAGAACTGGTTGGTGGCACAGCCGGCATCGTGCACGC

AGCAGCGCGCGTCGTTGTTGGCCAGCTGCACCACGCTGCGCCCCCAGCGGTTCTGGGTGAT

CTTGGCCCGGTCGGGGTTCTCCTTCAGCGCGCGCTGCCCGTTCTCGCTCGCCACATCCATCT

CGATCATGTGCTCCTTCTGGATCATGGTGGTCCCGTGCAGGCACCGCAGTTTGCCCTCGGCC

TCGGTGCACCCGTGCAGCCACAGCGCGCACCCGGTGCACTCCCAGTTCTTGTGGGCGATCT

GGGAATGCGCGTGCACGAACCCTTGCAGGAAGCGGCCCATCATGGTCGTCAGGGTCTTGTT

GCTAGTGAAGGTCAACGGGATGCCGCGGTGCTCCTCGTTGATGTACAGGTGGCAGATGCGG

CGGTACACCTCGCCCTGCTCGGGCATCAGTTGGAAGTTGGCTTTCAGGTCGGTCTCCACGCG

GTAGCGGTCCATCAGCATAGTCATGATTTCCATGCCCTTCTCCCAGGCCGAGACGATGGGCA

GGCTCATAGGGTTCTTCACCATCATCTTAGCACTAGCAGCCGCGGCCAGGGGGTCGCTCTCA

TCCAGGGTCTCAAAGCTCCGCTTGCCGTCCTTCTCGGTGATCCGCACCGGGGGGTAGCTGAA

GCCCACGGCCGCCAGCTCCTCCTCGGCCTGTCTTTCGTCCTCGCTGTCCTGGCTGACGTCCT

GCATGACCACATGCTTGGTCTTGCGGGGTTTCTTCTTGGGCGGCAGTGGCGGCGGAGATGC

TTGTGGCGAGGGGGAGCGCGAGTTCTCGCTCACCACTACTATCTCTTCCTCTTCTTGGTCCG

AGGCCACGCGGCGGTAGGTATGTCTCTTCGGGGGCAGAGGCGGAGGCGACGGGCTCTCGC

CGCCGCGACTTGGCGGATGGCTGGCAGAGCCCCTTCCGCGTTCGGGGGTGCGCTCCCGGC

GGCGCTCTGACTGACTTCCTCCGCGGCCGGCCATTGTGTTCTCCTAGGGAGGAACAACAAGC

ATGGAGACTCAGCCATCGCCAACCTCGCCATCTGCCCCCACCGCCGGCGACGAGAAGCAGC

AGCAGCAGAATGAAAGCTTAACCGCCCCGCCGCCCAGCCCCGCCTCCGACGCAGCCGCGGT

CCCAGACATGCAAGAGATGGAGGAATCCATCGAGATTGACCTGGGCTATGTGACGCCCGCG

GAGCATGAGGAGGAGCTGGCAGTGCGCTTTCAATCGTCAAGCCAGGAAGATAAAGAACAGCC

AGAGCAGGAAGCAGAGAACGAGCAGAGTCAGGCTGGGCTCGAGCATGGCGACTACCTCCAC

CTGAGCGGGGAGGAGGACGCGCTCATCAAGCATCTGGCCCGGCAGGCCACCATCGTCAAGG

ACGCGCTGCTCGACCGCACCGAGGTGCCCCTCAGCGTGGAGGAGCTCAGCCGCGCCTACGA

GCTCAACCTCTTCTCGCCGCGCGTGCCCCCCAAGCGCCAGCCCAACGGCACCTGCGAGCCC

AACCCCCGCCTCAACTTCTACCCGGTCTTCGCGGTGCCCGAGGCCCTGGCCACCTACCACAT

CTTTTTCAAGAACCAAAAGATCCCCGTCTCCTGCCGCGCCAACCGCACCCGCGCCGACGCCC

TCTTCAACCTGGGTCCCGGCGCCCGCCTACCTGATATCGCCTCCTTGGAAGAGGTTCCCAAG

ATCTTCGAGGGTCTGGGCAGCGACGAGACTCGGGCCGCGAACGCTCTGCAAGGAGAAGGAG

GAGGAGAGCATGAGCACCACAGCGCCCTGGTCGAGTTGGAAGGCGACAACGCGCGGCTGG

CGGTGCTCAAACGCACGGTCGAGCTGACCCATTTCGCCTACCCGGCTCTGAACCTGCCCCC

GAAAGTCATGAGCGCGGTCATGGACCAGGTGCTCATCAAGCGCGCGTCGCCCATCTCCGAG

GACGAGGGCATGCAAGACTCCGAGGAGGGCAAGCCCGTGGTCAGCGACGAGCAGCTGGCC

CGGTGGCTGGGTCCTAATGCTACCCCTCAAAGTTTGGAAGAGCGGCGCAAGCTCATGATGGC

CGTGGTCCTGGTGACCGTGGAGCTGGAGTGCCTGCGCCGCTTCTTCGCCGACGCGGAGACC

CTGCGCAAGGTCGAGGAGAACCTGCACTACCTCTTCAGGCACGGGTTCGTGCGCCAGGCCT

GCAAGATCTCCAACGTGGAGCTGACCAACCTGGTCTCCTACATGGGCATCTTGCACGAGAAC

-continued

CGCCTGGGGCAGAACGTGCTGCACACCACCCTGCGCGGGGAGGCCCGCCGCGACTACATC

CGCGACTGCGTCTACCTCTACCTCTGCCACACCTGGCAGACGGGCATGGGCGTGTGGCAGC

AGTGTCTGGAGGAGCAGAACCTGAAAGAGCTCTGCAAGCTCCTGCAAAAGAACCTCAAGGGT

CTGTGGACCGGGTTCGACGAGCGGACCACCGCCTCGGACCTGGCCGACCTCATCTTCCCCG

AGCGCCTCAGGCTGACGCTGCGCAACGGCCTGCCCGACTTTATGAGCCAAAGCATGTTGCAA

AACTTTCGCTCTTTCATCCTCGAACGCTCCGGAATCCTGCCCGCCACCTGCTCCGCGCTGCC

CTCGGACTTCGTGCCGCTGACCTTCCGCGAGTGCCCCCCGCCGCTGTGGAGCCACTGCTAC

CTGCTGCGCCTGGCCAACTACCTGGCCTACCACTCGGACGTGATCGAGGACGTCAGCGGCG

AGGGCCTGCTCGAGTGCCACTGCCGCTGCAACCTCTGCACGCCGCACCGCTCCCTGGCCTG

CAACCCCCAGCTGCTGAGCGAGACCCAGATCATCGGCACCTTCGAGTTGCAAGGGCCCAGC

GAGGGCGAGGGAGCCAAGGGGGGTCTGAAACTCACCCCGGGGCTGTGGACCTCGGCCTAC

TTGCGCAAGTTCGTGCCCGAGGATTACCATCCCTTCGAGATCAGGTTCTACGAGGACCAATC

CCAGCCGCCCAAGGCCGAGCTGTCGGCCTGCGTCATCACCCAGGGGGCGATCCTGGCCCAA

TTGCAAGCCATCCAGAAATCCCGCCAAGAATTCTTGCTGAAAAAGGGCCGCGGGGTCTACCT

CGACCCCCAGACCGGTGAGGAGCTCAACCCCGGCTTCCCCCAGGATGCCCCGAGGAAACAA

GAAGCTGAAAGTGGAGCTGCCGCCCGTGGAGGATTTGGAGGAAGACTGGGAGAACAGCAGT

CAGGCAGAGGAGATGGAGGAAGACTGGGACAGCACTCAGGCAGAGGAGGACAGCCTGCAA

GACAGTCTGGAGGAAGACGAGGAGGAGGCAGAGGAGGAGGTGGAAGAAGCAGCCGCCGCC

AGACCGTCGTCCTCGGCGGGGGAGAAAGCAAGCAGCACGGATACCATCTCCGCTCCGGGTC

GGGGTCCCGCTCGGCCCCACAGTAGATGGGACGAGACCGGGCGATTCCCGAACCCCACCAC

CCAGACCGGTAAGAAGGAGCGGCAGGGATACAAGTCCTGGCGGGGGCACAAAAACGCCATC

GTCTCCTGCTTGCAGGCCTGCGGGGGCAACATCTCCTTCACCCGGCGCTACCTGCTCTTCCA

CCGCGGGGTGAACTTCCCCCGCAACATCTTGCATTACTACCGTCACCTCCACAGCCCCTACT

ACTTCCAAGAAGAGGCAGCAGCAGCAGAAAAAGACCAGAAAACCAGCTAGAAAATCCACAGC

GGCGGCAGCGGCAGGTGGACTGAGGATCGCGGCGAACGAGCCGGCGCAGACCCGGGAGCT

GAGGAACCGGATCTTTCCCACCCTCTATGCCATCTTCCAGCAGAGTCGGGGGCAGGAGCAG

GAACTGAAAGTCAAGAACCGTTCTCTGCGCTCGCTCACCCGCAGTTGTCTGTATCACAAGAG

CGAAGACCAACTTCAGCGCACTCTCGAGGACGCCGAGGCTCTCTTCAACAAGTACTGCGCGC

TCACTCTTAAAGAGTAGCCCGCGCCCGCCCAGTCGCAGAAAAAGGCGGGAATTACGTCACCT

GTGCCCTTCGCCCTAGCCGCCTCCACCCAGCACCGCCATGAGCAAAGAGATTCCCACGCCTT

ACATGTGGAGCTACCAGCCCCAGATGGGCCTGGCCGCCGGCGCCGCCCAGGACTACTCCAC

CCGCATGAATTGGCTCAGCGCCGGGCCCGCGATGATCTCACGGGTGAATGACATCCGCGCC

CACCGAAACCAGATACTCCTAGAACAGTCAGCGCTCACCGCCACGCCCCGCAATCACCTCAA

TCCGCGTAATTGGCCCGCCGCCCTGGTGTACCAGGAAATTCCCCAGCCCACGACCGTACTAC

TTCCGCGAGACGCCCAGGCCGAAGTCCAGCTGACTAACTCAGGTGTCCAGCTGGCGGGCGG

CGCCACCCTGTGTCGTCACCGCCCCGCTCAGGGTATAAAGCGGCTGGTGATCCGGGGCAGA

GGCACACAGCTCAACGACGAGGTGGTGAGCTCTTCGCTGGGTCTGCGACCTGACGGAGTCT

TCCAACTCGCCGGATCGGGGAGATCTTCCTTCACGCCTCGTCAGGCGGTCCTGACTTTGGAG

AGTTCGTCCTCGCAGCCCCGCTCGGGCGGCATCGGCACTCTCCAGTTCGTGGAGGAGTTCA

CTCCCTCGGTCTACTTCAACCCCTTCTCCGGCTCCCCCGGCCACTACCCGGACGAGTTCATC

CCGAACTTTGACGCCATCAGCGAGTCGGTGGACGGCTACGATTGATTAATTAATCAACTAACC

-continued

CCTTACCCCTTTACCCTCCAGTAAAAATAAAGATTAAAAATGATTGAATTGATCAATAAAGAAT

CACTTACTTGAAATCTGAAACCAGGTCTCTGTCCATGTTTTCTGTCAGCAGCACTTCACTCCC

CTCTTCCCAACTCTGGTACTGCAGGCCCCGGCGGGCTGCAAACTTCCTCCACACTCTGAAGG

GGATGTCAAATTCCTCCTGTCCCTCAATCTTCATTTTTATCTTCTATCAGATGTCCAAAAAGCG

CGCGCGGGTGGATGATGGCTTCGACCCCGTGTACCCCTACGATGCAGACAACGCACCGACT

GTGCCCTTCATCAACCCTCCCTTCGTCTCTTCAGATGGATTCCAAGAAAAGCCCCTGGGGGT

GTTGTCCCTGCGACTGGCCGACCCCGTCACCACCAAGAATGGGGCTGTCACCCTCAAGCTG

GGGGAGGGGGTGGACCTCGACGACTCGGGAAAACTCATCTCCAAAAATGCCACCAAGGCCA

CTGCCCCTCTCAGTATTTCCAACGGCACCATTTCCCTTAACATGGCTGCCCCTTTTTACAACA

ACAATGGAACGTTAAGTCTCAATGTTTCTACACCATTAGCAGTATTTCCCACTTTTAACACTTT

AGGTATCAGTCTTGGAAACGGTCTTCAAACTTCTAATAAGTTGCTGACTGTACAGTTAACTCAT

CCTCTTACATTCAGCTCAAATAGCATCACAGTAAAAACAGACAAAGGACTCTATATTAATTCTA

GTGGAAACAGAGGGCTTGAGGCTAACATAAGCCTAAAAAGAGGACTGATTTTTGATGGTAATG

CTATTGCAACATACCTTGGAAGTGGTTTAGACTATGGATCCTATGATAGCGATGGGAAAACAA

GACCCATCATCACCAAAATTGGAGCAGGTTTGAATTTTGATGCTAATAATGCCATGGCTGTGA

AGCTAGGCACAGGTTTAAGTTTTGACTCTGCCGGTGCCTTAACAGCTGGAAACAAAGAGGAT

GACAAGCTAACACTTTGGACTACACCTGACCCAAGCCCTAATTGTCAATTACTTTCAGACAGA

GATGCCAAATTTACCCTATGTCTTACAAAATGCGGTAGTCAAATACTAGGCACTGTTGCAGTA

GCTGCTGTTACTGTAGGTTCAGCACTAAATCCAATTAATGACACAGTAAAAAGCGCCATAGTA

TTCCTTAGATTTGACTCTGACGGTGTGCTCATGTCAAACTCATCAATGGTAGGTGATTACTGG

AACTTTAGGGAAGGACAGACCACCCAAAGTGTGGCCTATACAAATGCTGTGGGATTCATGCC

CAATCTAGGTGCATATCCTAAAACCCAAAGCAAAACACCAAAAAATAGTATAGTAAGTCAGGT

ATATTTAAATGGAGAAACTACTATGCCAATGACACTGACAATAACTTTCAATGGCACTGATGAA

AAAGACACAACACCTGTGAGCACTTACTCCATGACTTTTACATGGCAGTGGACTGGAGACTAT

AAGGACAAGAATATTACCTTTGCTACCAACTCCTTTACTTTCTCCTACATGGCCCAAGAATAAA

CCCTGCATGCCAACCCCATTGTTCCCACCACTATGGAAAACTCTGAAGCAGAAAAAAATAAAG

TTCAAGTGTTTTATTGATTCAACAGTTTTCTCACAGAACCCTAGTATTCAACCTGCCACCTCCC

TCCCAACACACAGAGTACACAGTCCTTTCTCCCCGGCTGGCCTTAAAAAGCATCATATCATGG

GTAACAGACATATTCTTAGGTGTTATATTCCACACGGTTTCCTGTCGAGCCAAACGCTCATCA

GTGATATTAATAAACTCCCCGGGCAGCTCACTTAAGTTCATGTCGCTGTCCAGCTGCTGAGCC

ACAGGCTGCTGTCCAACTTGCGGTTGCTTAACGGGCGGCGAAGGAGAAGTCCACGCCTACAT

GGGGGTAGAGTCATAATCGTGCATCAGGATAGGGCGGTGGTGCTGCAGCAGCGCGCGAATA

AACTGCTGCCGCCGCCGCTCCGTCCTGCAGGAATACAACATGGCAGTGGTCTCCTCAGCGAT

GATTCGCACCGCCCGCAGCATAAGGCGCCTTGTCCTCCGGGCACAGCAGCGCACCCTGATC

TCACTTAAATCAGCACAGTAACTGCAGCACAGCACCACAATATTGTTCAAAATCCCACAGTGC

AAGGCGCTGTATCCAAAGCTCATGGCGGGGACCACAGAACCCACGTGGCCATCATACCACAA

GCGCAGGTAGATTAAGTGGCGACCCCTCATAAACACGCTGGACATAAACATTACCTCTTTTGG

CATGTTGTAATTCACCACCTCCCGGTACCATATAAACCTCTGATTAAACATGGCGCCATCCAC

CACCATCCTAAACCAGCTGGCCAAAACCTGCCCGCCGGCTATACACTGCAGGGAACCGGGA

CTGGAACAATGACAGTGGAGAGCCCAGGACTCGTAACCATGGATCATCATGCTCGTCATGAT

-continued

ATCAATGTTGGCACAACACAGGCACACGTGCATACACTTCCTCAGGATTACAAGCTCCTCCCG

CGTTAGAACCATATCCCAGGGAACAACCCATTCCTGAATCAGCGTAAATCCCACACTGCAGG

GAAGACCTCGCACGTAACTCACGTTGTGCATTGTCAAAGTGTTACATTCGGGCAGCAGCGGA

TGATCCTCCAGTATGGTAGCGCGGGTTTCTGTCTCAAAAGGAGGTAGACGATCCCTACTGTA

CGGAGTGCGCCGAGACAACCGAGATCGTGTTGGTCGTAGTGTCATGCCAAATGGAACGCCG

GACGTAGTCATATTTCCTGAAGCAAAACCAGGTGCGGGCGTGACAAACAGATCTGCGTCTCC

GGTCTCGCCGCTTAGATCGCTCTGTGTAGTAGTTGTAGTATATCCACTCTCTCAAAGCATCCA

GGCGCCCCCTGGCTTCGGGTTCTATGTAAACTCCTTCATGCGCCGCTGCCCTGATAACATCC

ACCACCGCAGAATAAGCCACACCCAGCCAACCTACACATTCGTTCTGCGAGTCACACACGGG

AGGAGCGGGAAGAGCTGGAAGAACCATGATTAACTTTATTCCAAACGGTCTCGGAGCACTTC

AAAATGCAGGTCCCGGAGGTGGCACCTCTCGCCCCCACTGTGTTGGTGGAAAATAACAGCCA

GGTCAAAGGTGACACGGTTCTCGAGATGTTCCACGGTGGCTTCCAGCAAAGCCTCCACGCGC

ACATCCAGAAACAAGAGGACAGCGAAAGCGGGAGCGTTTTCTAATTCCTCAATCATCATATTA

CACTCCTGCACCATCCCCAGATAATTTTCATTTTTCCAGCCTTGAATGATTCGTATTAGTTCCT

GAGGTAAATCCAAGCCAGCCATGATAAAAAGCTCGCGCAGAGCGCCCTCCACCGGCATTCTT

AAGCACACCCTCATAATTCCAAGAGATTCTGCTCCTGGTTCACCTGCAGCAGATTAACAATGG

GAATATCAAAATCTCTGCCGCGATCCCTAAGCTCCTCCCTCAACAATAACTGTATGTAATCTTT

CATATCATCTCCGAAATTTTTAGCCATAGGGCCGCCAGGAATAAGAGCAGGGCAAGCCACATT

ACAGATAAAGCGAAGTCCTCCCCAGTGWGCATTGCCAAATGTAAGATTGAAATAAGCATGCT

GGCTAGACCCTGTGATATCTTCCAGATAACTGGACAGAAAATCAGGCAAGCAATTTTTAAGAA

AATCAACAAAAGAAAAGTCGTCCAGGTGCAGGTTTAGAGCCTCAGGAACAACGATGGAATAA

GTGCAAGGAGTGCGTTCCAGCATGGTTAGTGTTTTTTTGGTGATCTGTAGAACAAAAAATAAA

CATGCAATATTAAACCATGCTAGCCTGGCGAACAGGTGGGTAAATCACTCTTTCCAGCACCAG

GCAGGCTACGGGGTCTCCGGCGCGACCCTCGTAGAAGCTGTCGCCATGATTGAAAAGCATC

ACCGAGAGACCTTCCCGGTGGCCGGCATGGATGATTCGAGAAGAAGCATACACTCCGGGAA

CATTGGCATCCGTGAGTGAAAAAAAGCGACCTATAAAGCCTCGGGGCACTACAATGCTCAAT

CTCAATTCCAGCAAAGCCACCCCATGCGGATGGAGCACAAAATTGGCAGGTGCGTAAAAAAT

GTAATTACTCCCCTCCTGCACAGGCAGCAAAGCCCCCGCTCCCTCCAGAAACACATACAAAG

CCTCAGCGTCCATAGCTTACCGAGCACGGCAGGCGCAAGAGTCAGAGAAAAGGCTGAGCTC

TAACCTGACTGCCCGCTCCTGTGCTCAATATATAGCCCTAACCTACACTGACGTAAAGGCCAA

AGTCTAAAAATACCCGCCAAAATGACACACACGCCCAGCACACGCCCAGAAACCGGTGACAC

ACTCAAAAAAATACGTGCGCTTCCTCAAACGCCCAAACCGGCGTCATTTCCGGGTTCCCACG

CTACGTCACCGCTCAGCGACTTTCAAATTCCGTCGACCGTTAAAAACGTCACTCGCCCCGCC

CCTAACGGTCGCCCTTCTCTCGGCCAATCACCTTCCTCCCTTCCCAAATTCAAACGCCTCATT

TGCATATTAACGCGCACAAAAAGTTTGAGGTATATATTTGAATGATG

3NSALL Chadox1

[SEQ ID NO: 120]

GTTTAAACGCGGCCGCCAGGCCTACCCACTAGTCAATTCGGGAGGATCGAAACGGCAGATCG

CAAAAAACAGTACATACAGAAGGAGACATGAACATGAACATCAAAAAAATTGTAAAACAAGCC

ACAGTTCTGACTTTTACGACTGCACTTCTGGCAGGAGGAGCGACTCAAGCCTTCGCGAAAGA

AAATAACCAAAAAGCATACAAAGAAACGTACGGCGTCTCTCATATTACACGCCATGATATGCT

GCAGATCCCTAAACAGCAGCAAAACGAAAAATACCAAGTGCCTCAATTCGATCAATCAACGAT

-continued

TAAAAATATTGAGTCTGCAAAAGGACTTGATGTGTGGGACAGCTGGCCGCTGCAAAACGCTG

ACGGAACAGTAGCTGAATACAACGGCTATCACGTTGTGTTTGCTCTTGCGGGAAGCCCGAAA

GACGCTGATGACACATCAATCTACATGTTTTATCAAAAGGTCGGCGACAACTCAATCGACAGC

TGGAAAAACGCGGGCCGTGTCTTTAAAGACAGCGATAAGTTCGACGCCAACGATCCGATCCT

GAAAGATCAGACGCAAGAATGGTCCGGTTCTGCAACCTTTACATCTGACGGAAAAATCCGTTT

ATTCTACACTGACTATTCCGGTAAACATTACGGCAAACAAAGCCTGACAACAGCGCAGGTAAA

TGTGTCAAAATCTGATGACACACTCAAAATCAACGGAGTGGAAGATCACAAAACGATTTTTGA

CGGAGACGGAAAAACATATCAGAACGTTCAGCAGTTTATCGATGAAGGCAATTATACATCCGG

CGACAACCATACGCTGAGAGACCCTCACTACGTTGAAGACAAAGGCCATAAATACCTTGTATT

CGAAGCCAACACGGGAACAGAAAACGGATACCAAGGCGAAGAATCTTTATTTAACAAAGCGT

ACTACGGCGGCGGCACGAACTTCTTCCGTAAAGAAAGCCAGAAGCTTCAGCAGAGCGCTAAA

AAACGCGATGCTGAGTTAGCGAACGGCGCCCTCGGTATCATAGAGTTAAATAATGATTACACA

TTGAAAAAAGTAATGAAGCCGCTGATCACTTCAAACACGGTAACTGATGAAATCGAGCGCGCG

AATGTTTTCAAAATGAACGGCAAATGGTACTTGTTCACTGATTCACGCGGTTCAAAAATGACG

ATCGATGGTATTAACTCAAACGATATTTACATGCTTGGTTATGTATCAAACTCTTTAACCGGCC

CTTACAAGCCGCTGAACAAAACAGGGCTTGTGCTGCAAATGGGTCTTGATCCAAACGATGTG

ACATTCACTTACTCTCACTTCGCAGTGCCGCAAGCCAAAGGCAACAATGTGGTTATCACAAGC

TACATGACAAACAGAGGCTTCTTCGAGGATAAAAAGGCAACATTTGCGCCAAGCTTCTTAATG

AACATCAAAGGCAATAAAACATCCGTTGTCAAAAACAGCATCCTGGAGCAAGGACAGCTGACA

GTCAACTAATAACAGCAAAAAGAAAATGCCGATACTTCATTGGCATTTTCTTTTATTTCTCAAC

AAGATGGTGAATTGACTAGTGGGTAGATCCACAGGACGGGTGTGGTCGCCATGATCGCGTAG

TCGATAGTGGCTCCAAGTAGCGAAGCGAGCAGGACTGGGCGGCGGCCAAAGCGGTCGGACA

GTGCTCCGAGAACGGGTGCGCATAGAAATTGCATCAACGCATATAGCGCTAGCAGCACGCCA

TAGTGACTGGCGATGCTGTCGGAATGGACGATATCCCGCAAGAGGCCCGGCAGTACCGGCA

TAACCAAGCCTATGCCTACAGCATCCAGGGTGACGGTGCCGAGGATGACGATGAGCGCATTG

TTAGATTTCATACACGGTGCCTGACTGCGTTAGCAATTTAACTGTGATAAACTACCGCATTAAA

GCTTATCGATGATAAGCTGTCAAACATGAGAATTGATCCGGAACCCTTAATATAACTTCGTATA

ATGTATGCTATACGAAGTTATTAGGTCCCTCGACTATAGGGTCACCGTCGACAGCGACACACT

TGCATCGGATGCAGCCCGGTTAACGTGCCGGCACGGCCTGGGTAACCAGGTATTTTGTCCAC

ATAACCGTGCGCAAAATGTTGTGGATAAGCAGGACACAGCAGCAATCCACAGCAGGCATACA

ACCGCACACCGAGGTTACTCCGTTCTACAGGTTACGACGACATGTCAATACTTGCCCTTGACA

GGCATTGATGGAATCGTAGTCTCACGCTGATAGTCTGATCGACAATACAAGTGGGACCGTGG

TCCCAGACCGATAATCAGACCGACRAYACGAGTGGGAYCGTGGTCCCAGACTAATAATCAGA

CCGACGATACGAGTGGGACCGTGGTCCCAGACTAATAATCAGACCGACGATACGAGTGGGA

CCGTGGTYCCAGWCTRATWATCAGACCGACGATACRAGTGGRACMGTGGKCCCAGASAKAA

TAWTCAGRCCGAGWTAYGCWKTCKGGCCTGTAACAAAGGACATTAAGTAAAGACAGATAMR

MGTGRGACTAAAACGTGGTCCCAGTCTGATTATCAGACCGACGATACGAGTGGGACCGTGGT

CCCAGACTAATAATCAGACCGACGATACGAGTGGGACCGTGGTCCCAGACTAATAATCAGAC

CGACGATACGAGTGGGACCGTGGTCCCAGTCTGATTATCAGACCGACGATACAAGTGGAACA

GTGGGCCCAGAGAGAATATTCAGGCCAGTTATGCTTTCTGGCCTGTAACAAAGGACATTAAGT

-continued

```
AAAGACAGATAAACGTAGACTAAAACGTGGTCGCATCAGGGTGCTGGCTTTTCAAGTTCCTTA
AGAATGGCCTCAATTTTCTCTATACACTCAGTTGGAACACGAGACCTGTCCAGGTTAAGCACC
ATTTTATCGCCCTTATACAATACTGTCGCTCCAGGAGCAAACTGATGTCGTGAGCTTAAACTA
GTTCTTGATGCAGATGACGTTTTAAGCACAGAAGTTAAAAGAGTGATAACTTCTTCAGCTTCAA
ATATCACCCCAGCTTTTTTCTGCTCATGAAGGTTAGATGCCTGCTGCTTAAGTAATTCCTCTTT
ATCTGTAAAGGCTTTTTGAAGTGCATCACCTGACCGGGCAGATAGTTCACCGGGGTGAGAAA
AAAGAGCAACAACTGATTTAGGCAATTTGGCGGTGTTGATACAGCGGGTAATAATCTTACGTG
AAATATTTTCCGCATCAGCCAGCGCAGAAATATTTCCAGCAAATTCATTCTGCAATCGGCTTG
CATAACGCTGACCACGTTCATAAGCACTTGTTGGGCGATAATCGTTACCCAATCTGGATAATG
CAGCCATCTGCTCATCATCCAGCTCGCCAACCAGAACACGATAATCACTTTCGGTAAGTGCAG
CAGCTTTACGACGGCGACTCCCATCGGCAATTTCTATGACACCAGATACTCTTCGACCGAACG
CCGGTGTCTGTTGACCAGTCAGTAGAAAAGAAGGGATGAGATCATCCAGTGCGTCCTCAGTA
AGCAGCTCCTGGTCACGTTCATTACCTGACCATACCCGAGAGGTCTTCTCAACACTATCACCC
CGGAGCACTTCAAGAGTAAACTTCACATCCCGACCACATACAGGCAAAGTAATGGCATTACCG
CGAGCCATTACTCCTACGCGCGCAATTAACGAATCCACCATCGGGGCAGCTGGTGTCGATAA
CGAAGTATCTTCAACCGGTTGAGTATTGAGCGTATGTTTTGGAATAACAGGCGCACGCTTCAT
TATCTAATCTCCCAGCGTGGTTTAATCAGACGATCGAAAATTTCATTGCAGACAGGTTCCCAA
ATAGAAAGAGCATTTCTCCAGGCACCAGTTGAAGAGCGTTGATCAATGGCCTGTTCAAAAACA
GTTCTCATCCGGATCTGACCTTTACCAACTTCATCCGTTTCACGTACAACATTTTTTAGAACCA
TGCTTCCCCAGGCATCCCGAATTTGCTCCTCCATCCACGGGGACTGAGAGCCATTACTATTG
CTGTATTTGGTAAGCAAAATACGTACATCAGGCTCGAACCCTTTAAGATCAACGTTCTTGAGC
AGATCACGAAGCATATCGAAAAACTGCAGTGCGGAGGTGTAGTCAAACAACTCAGCAGGCGT
GGGAACAATCAGCACATCAGCAGCACATACGACATTAATCGTGCCGATACCCAGGTTAGGCG
CGCTGTCAATAACTATGACATCATAGTCATGAGCAACAGTTTCAATGGCCAGTCGGAGCATCA
GGTGTGGATCGGTGGGCAGTTTACCTTCATCAAATTTGCCCATTAACTCAGTTTCAATACGGT
GCAGAGCCAGACAGGAAGGAATAATGTCAAGCCCCGGCCAGCAAGTGGGCTTTATTGCATAA
GTGACATCGTCCTTTTCCCCAAGATAGAAAGGCAGGAGAGTGTCTTCTGCATGAATATGAAGA
TCTGGTACCCATCCGTGATACATTGAGGCTGTTCCCTGGGGGTCGTTACCTTCCACGAGCAA
AACACGTAGCCCCTTCAGAGCCAGATCCTGAGCAAGATGAACAGAAACTGAGGTTTTGTAAAC
GCCACCTTTATGGGCAGCAACCCCGATCACCGGTGGAAATACGTCTTCAGCACGTCGCAATC
GCGTACCAAACACATCACGCATATGATTAATTTGTTCAATTGTATAACCAACACGTTGCTCAAC
CCGTCCTCGAATTTCCATATCCGGGTGCGGTAGTCGCCCTGCTTTCTCGGCATCTCTGATAG
CCTGAGAAGAAACCCCAACTAAATCCGCTGCTTCACCTATTCTCCAGCGCCGGGTTATTTTCC
TCGCTTCCGGGCTGTCATCATTAAACTGTGCAATGGCGATAGCCTTCGTCATTTCATGACCAG
CGTTTATGCACTGGTTAAGTGTTTCCATGAGTTTCATTCTGAACATCCTTTAATCATTGCTTTG
CGTTTTTTTATTAAATCTTGCAATTTACTGCAAAGCAACAACAAAATCGCAAAGTCATCAAAAAA
CCGCAAAGTTGTTTAAAATAAGAGCAACACTACAAAAGGAGATAAGAAGAGCACATACCTCAG
TCACTTATTATCACTAGCGCTCGCCGCAGCCGTGTAACCGAGCATAGCGAGCGAACTGGCGA
GGAAGCAAAGAAGAACTGTTCTGTCAGATAGCTCTTACGCTCAGCGCAAGAAGAAATATCCAC
CGTGGGAAAAACTCCAGGTAGAGGTACACACGCGGATAGCCAATTCAGAGTAATAAACTGTG
ATAATCAACCCTCATCAATGATGACGAACTAACCCCCGATATCAGGTCACATGACGAAGGGAA
```

-continued

AGAGAAGGAAATCAACTGTGACAAACTGCCCTCAAATTTGGCTTCCTTAAAAATTACAGTTCAA

AAAGTATGAGAAAATCCATGCAGGCTGAAGGAAACAGCAAAACTGTGACAAATTACCCTCAGT

AGGTCAGAACAAATGTGACGAACCACCCTCAAATCTGTGACAGATAACCCTCAGACTATCCTG

TCGTCATGGAAGTGATATCGCGGAAGGAAAATACGATATGAGTCGTCTGGCGGCCTTTCTTTT

TCTCAATGTATGAGAGGCGCATTGGAGTTCTGCTGTTGATCTCATTAACACAGACCTGCAGGA

AGCGGCGGCGGAAGTCAGGCATACGCTGGTAACTTTGAGGCAGCTGGTAACGCTCTATGATC

CAGTCGATTTTCAGAGAGACGATGCCTGAGCCATCCGGCTTACGATACTGACACAGGGATTC

GTATAAACGCATGGCATACGGATTGGTGATTTCTTTTGTTTCACTAAGCCGAAACTGCGTAAA

CCGGTTCTGTAACCCGATAAAGAAGGGAATGAGATATGGGTTGATATGTACACTGTAAAGCCC

TCTGGATGGACTGTGCGCACGTTTGATAAACCAAGGAAAAGATTCATAGCCTTTTTCATCGCC

GGCATCCTCTTCAGGGCGATAAAAAACCACTTCCTTCCCCGCGAAACTCTTCAATGCCTGCCG

TATATCCTTACTGGCTTCCGCAGAGGTCAATCCGAATATTTCAGCATATTTAGCAACATGGATC

TCGCAGATACCGTCATGTTCCTGTAGGGTGCCATCAGATTTTCTGATCTGGTCAACGAACAGA

TACAGCATACGTTTTTGATCCCGGGAGAGACTATATGCCGCCTCAGTGAGGTCGTTTGACTG

GACGATTCGCGGGCTATTTTTACGTTTCTTGTGATTGATAACCGCTGTTTCCGCCATGACAGA

TCCATGTGAAGTGTGACAAGTTTTTAGATTGTCACACTAAATAAAAAAGAGTCAATAAGCAGG

GATAACTTTGTGAAAAAACAGCTTCTTCTGAGGGCAATTTGTCACAGGGTTAAGGGCAATTTG

TCACAGACAGGACTGTCATTTGAGGGTGATTTGTCACACTGAAAGGGCAATTTGTCACAACAC

CTTCTCTAGAACCAGCATGGATAAAGGCCTACAAGGCGCTCTAAAAAAGAAGATCTAAAAACT

ATAAAAAAAATAATTATAAAAATATCCCCGTGGATAAGTGGATAACCCCAAGGGAAGTTTTTTC

AGGCATCGTGTGTAAGCAGAATATATAAGTGCTGTTCCCTGGTGCTTCCTCGCTCACTCGAGG

GCTTCGCCCTGTCGCTCAACTGCGGCGAGCACTACTGGCTGTAAAAGGACAGACCACATCAT

GGTTCTGTGTTCATTAGGTTGTTCTGTCCATTGCTGACATAATCCGCTCCACTTCAACGTAACA

CCGCACGAAGATTTCTATTGTTCCTGAAGGCATATTCAAATCGTTTTCGTTACCGCTTGCAGG

CATCATGACAGAACACTACTTCCTATAAACGCTACACAGGCTCCTGAGATTAATAATGCGGAT

CTCTACGATAATGGGAGATTTTCCCGACTGTTTCGTTCGCTTCTCAGTGGATAACAGCCAGCT

TCTCTGTTTAACAGACAAAAACAGCATATCCACTCAGTTCCACATTTCCATATAAAGGCCAAGG

CATTTATTCTCAGGATAATTGTTTCAGCATCGCAACCGCATCAGACTCCGGCATCGCAAACTG

CACCCGGTGCCGGGCAGCCACATCCAGCGCAAAAACCTTCGTGTAGACTTCCGTTGAACTGA

TGGACTTATGTCCCATCAGGCTTTGCAGAACTTTCAGCGGTATACCGGCATACAGCATGTGCA

TCGCATAGGAATGGCGGAACGTATGTGGTGTGACCGGAACAGAGAACGTCACACCGTCAGCA

GCAGCGGCGGCAACCGCCTCCCCAATCCAGGTCCTGACCGTTCTGTCCGTCACTTCCCAGAT

CCGCGCTTTCTCTGTCCTTCCTGTGCGACGGTTACGCCGCTCCATGAGCTTATCGCGAATAAA

TACCTGTGACGGAAGATCACTTCGCAGAATAAATAAATCCTGGTGTCCCTGTTGATACCGGGA

AGCCCTGGGCCAACTTTTGGCGAAAATGAGACGTTGATCGGCACGTAAGAGGTTCCAACTTT

CACCATAATGAAATAAGATCACTACCGGGCGTATTTTTTGAGTTATCGAGATTTTCAGGAGCTA

AGGAAGCTAAAATGGAGAAAAAAATCACTGGATATACCACCGTTGATATATCCCAATGGCATC

GTAAAGAACATTTTGAGGCATTTCAGTCAGTTGCTCAATGTACCTATAACCAGACCGTTCAGC

TGGATATTACGGCCTTTTTAAAGACCGTAAAGAAAAATAAGCACAAGTTTTATCCGGCCTTTAT

TCACATTCTTGCCCGCCTGATGAATGCTCATCCGGAGTTCCGTATGGCAATGAAAGACGGTG

-continued

AGCTGGTGATATGGGATAGTGTTCACCCTTGTTACACCGTTTTCCATGAGCAAACTGAAACGT

TTTCATCGCTCTGGAGTGAATACCACGACGATTTCCGGCAGTTTCTACACATATATTCGCAAG

ATGTGGCGTGTTACGGTGAAAACCTGGCCTATTTCCCTAAAGGGTTTATTGAGAATATGTTTTT

CGTCTCAGCCAATCCCTGGGTGAGTTTCACCAGTTTTGATTTAAACGTGGCCAATATGGACAA

CTTCTTCGCCCCCGTTTTCACCATGGGCAAATATTATACGCAAGGCGACAAGGTGCTGATGCC

GCTGGCGATTCAGGTTCATCATGCCGTTTGTGATGGCTTCCATGTCGGCAGAATGCTTAATGA

ATTACAACAGTACTGCGATGAGTGGCAGGGCGGGGCGTAATTTTTTTAAGGCAGTTATTGGTG

CCCTTAAACGCCTGGTTGCTACGCCTGAATAAGTGATAATAAGCGGATGAATGGCAGAAATTC

GATGATAAGCTGTCAAACATGAGAATTGGTCGACGGCGCGCCAAAGCTTGCATGCCTGCAGC

CGCGTAACCTGGCAAAATCGGTTACGGTTGAGTAATAAATGGATGCCCTGCGTAAGCGGGGC

ACATTTCATTACCTCTTTCTCCGCACCCGACATAGATAATAACTTCGTATAGTATACATTATAC

GAAGTTATCTAGTAGACTTAATCGCGTTTAAACCCATCATCAATAATATACCTCAAACTTTTTGT

GCGCGTTAATATGCAAATGAGGCGTTTGAATTTGGGAAGGGAGGAAGGTGATTGGCCGAGAG

AAGGGCGACCGTTAGGGGCGGGGCGAGTGACGTTTTGATGACGTGACCGCGAGGAGGAGC

CAGTTTGCAAGTTCTCGTGGGAAAAGTGACGTCAAACGAGGTGTGGTTTGAACACGGAAATA

CTCAATTTTCCCGCGCTCTCTGACAGGAAATGAGGTGTTTCTAGGCGGATGCAAGTGAAAAC

GGGCCATTTTCGCGCGAAAACTGAATGAGGAAGTGAAAATCTGAGTAATTTCGCGTTTATGAC

AGGGAGGAGTATTTGCCGAGGGCCGAGTAGACTTTGACCGATTACGTGGGGGTTTCGATTAC

CGTGTTTTTCACCTAAATTTCCGCGTACGGTGTCAAAGTCCGGTGTTTTTACGTAGGTGTCAG

CTGATCGCCAGGGTATTTAAACCTGCGCTCTCCAGTCAAGAGGCCACTCTTGAGTGCCAGCG

AGAAGAGTTTTCTCCTCCGCGCGCGAGTCAGATCTACACTTTGAAAGGCGATCGCTAGCGAC

ATCGATCCAAATAATGATTTTATTTTGACTGATAGTGACCTGTTCGTTGCAACAAATTGATAAG

CAATGCTTTTTTATAATGCCAACTTTGTACAAAAAAGCAGGCTCCACCATGGGAACCAATTCAG

TCGAGCCTTTCACTCATTAGATGCATGTCGTTACATAACTTACGGTAAATGGCCCGCCTGGCT

GACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAATGGCCCGCC

TGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTT

GACTCACGGGGATTTCCAAGTCTCCACCCCATTGACGTCAATGGGAGTTTGTTTTGGCACCAA

AATCAACGGGACTTTCCAAAATGTCGTAACAACTCCGCCCCATTGACGCAAATGGGCGGTAG

GCGTGTACGGTGGGAGGTCTATATAAGCAGAGCTCTCCCTATCAGTGATAGAGATCTCCCTAT

CAGTGATAGAGATCGTCGACGAGCTCGTTTAGTGAACCGTCAGATCGCCTGGAGACGCCATC

CACGCTGTTTTGACCTCCATAGAAGACACCGGGACCGATCCAGCCTCCGGTTAAGCTCGGTA

CCGCTAGCCGCGCCGCCACCATGGATGCAATGAAGAGAGGGCTCTGCTGTGTGCTGCTGCT

GTGTGGAGCAGTCTTCGTTTCGCCCAGCCAGGAAATCCATGCCCGATTCAGAAGAGGATCGA

AGCTTGCCAGCCAGATCGGCGCCGGCGTGTTCAAGGAGGGCGTGTTCCACACCATGTGGCA

CGTGACCAGGGGCGCCGTGCTGATGCACCAGGGCAAGAGGATCGAGCCCAGCTGGGCCGA

CGTGAAGAAGGACCTGATCAGCTACGGCGGCGGCTGGAGGCTGGAGGGCGAGTGGGACGA

GGGCGAGGAGGTGCAGGTGATCGCCGTGGAGCCCGGCAAGAACCCCAAGGCCGTGCAGAC

CAAGCCCGGCCTGTTCAAGACCCCCGAGGGCGAGATCGGCGCCATCGCCCTGGACTTCAAG

-continued

CCCGGCACCAGCGGCAGCCCCATCGTGAACAGGGAGGGCAAGGTGGTGGGCCTGTACGGC

AACGGCGTGGTGACCAAGAGCGGCGCCTACGTGAGCGCCATCGCCCAGACCAACGCCGAGC

CCCTGCCCGAGATCGAGGACGAGGTGTTCAGGAAGAGGAACCTGACCATCATGGACCTGCA

CCCCGGCGCCGGCAAGACCAAGAGGTATCTGCCCGCCATCGTGAGGGAGGCCATCAAGAGG

AGGCTGAGGACCCTGATCCTGGCCCCCACCAGGGTGGTGGCCGCCGAGATGGAGGAGGCC

CTGAAGGGCCTGCCCATCAGGTATCAGACCACCGCCATCAAGGCCGAGCACACCGGCAAGG

AGATCGTGGACCTGATGTGCCACGCCACCTTCACCATGAGGCTGCTGAGCCCCGTGAGGGT

GCCCAACTACAACCTGATCATCATGGACGAGGCCCACTTCACCGACCCCGCCAGCATCGCCG

CCAGGGGCTACATCAGCACCAGGGTGGAGATGGGCGAGGCCGCCGCCATCTTCATGACCGC

CACCCCCCCCGGCAGCGCCGACGCCTTCCCCCAGAGCAACGCCCCCATCGAGGACGAGGA

GAGGGAGATCCCCGAGAGGAGCTGGAACAGCGGCTTCGACTGGATCACCGACTTCGCCGGC

AAGACCGTGTGGTTCGTGCCCAGCATCAAGGCCGGCAACGACATCGCCAACTGCCTGAGGA

AGAACGGCAAGAAGGTGATCCAGCTGAGCAGGAAGACCTTCGACACCGAGTACCCCAAGAC

CAAGCTGAACGACTGGGACTTCGTGGTGACCACCGACATCAGCGAGATGGGCGCCAACTTCA

AGGCCGACAGGGTGATCGACCCCAGGAGGTGCCTGAAGCCCGTGATCCTGACCGACGGCCC

CGAGAGGGTGATCCTGGCCGGCCCCATGCCCGTGACCGCCGCCAGCGCCGCCCAGAGGAG

GGGCAGGATCGGCAGGAACCACAAGAAGGAGAACGACCAGTACATCTACATGGGCCAGCCC

CTGAACAACGACGAGGACCACGCCCACTGGACCGAGGCCAAGATGCTGCTGGACAACATCA

ACACCCCCGAGGGCATCATCCCCGCCCTGTTCGAGCCCGAGAGGGAGAAGAGCGCCGCCAT

CGACGGCGAGTACAGGCTGAGGGGCGAGGCCAGGAAGACCTTCGTGGAGCTGATGAGGAG

GGGCGACCTGCCCGTGTGGCTGAGCTACAAGGTGGCCAGCGCCGGCTTCCAGTACAAGGAC

AGGGAGTGGTGCTTCGACGGCGAGAGGAACAACCAGATCCTGGAGGAGAACATGGACGTGG

AGATCTGGACCAAGGAGGGCGAGAAGAAGAAGCTGAGGCCCAGGTGGCTGGACGCCAGGA

CCTACGCCGACCCCCTGGCCCTGAAGGAGTTCAAGGACTTCGCCGCCGGCAGGAAGAGCAT

CGCCACCGAGATCGGCAGGGTGCCCAGCCACCTGGCCCACAGGACCAGGGCCTACCAGCA

CGCCCTGGAGGAGCTGCCCGAGACCCTGGAGACCCTGCTGCTGCTGGCCCTGCTGGGCGC

CTTCCTGTTCTTCCTGAGCGGCAAGGGCATCGGCAAGATGAGCATCGGCCTGTGCTGCATCA

TCGCCGCCAGCCTGCTGTGGATGGCCGAGATCCAGCCCCACTGGATCGCCGCCAGCATCAT

CCTGGAGTTCTTCCTGATGGTGCTGCTGATCCCCGAGCCCGAGAAGCAGAGGACCCCCCAG

GACAACCAGCTGGCCTACGTGGTGATCGGCATCCTGACCCTGGCCGCCGCCATCGCCGCCA

ACGAGATGGGCCTGCTGGAGACCACCAAGAAGGACCTGGGCATCGGCCACGTGGCCCCCAC

CGCCATCCTGGACGTGGACCTGCACCCCGCCAGCGCCTGGACCCTGTACGCCGTGGCCACC

ACCATCATCACCCCCATGCTGAGGCACACCATCGAGAACAGCACCGCCAACGTGAGCCTGAC

CGCCATCGCCAACCAGGCCGCCGTGCTGATGGGCCTGGACAAGGGCTGGCCCATCAGCAAG

ATGGACCTGGGCGTGCCCCTGCTGGCCCTGGGCTGCTACAGCCAGGTGAACCCCCTGACCC

TGACCGCCGCCGTGCTGCTGCTGATCACCCACTACGCCATCATCGGCCCCGGCCTGCAGGC

CAAGGCCACCAGGGAGGCCCAGAAGAGGACCGCCGCCGGCATCATGAAGAACCCCACCGTG

GACGGCATCATGGCCATCGACCTGGACCCCATCCCCTACGACCCCAAGTTCGAGAAGCAGCT

GGGCCAGGTGATGCTGCTGATCCTGTGCGTGAGCCAGATCCTGCTGATGAGGACCACCTGG

GCCCTGTGCGAGGCCCTGACCCTGGCCACCGGCCCCATCACCACCCTGTGGGAGGGCAACC

-continued

CCGGCAAGTTCTGGAACACCACCATCGCCGTGAGCATGGCCAACATCTTCAGGGGCAGCTAC

CTGGCCGGCGCCGGCCTGGCCTTCAGCCTGATCAAGAACAGGAGGGGCACCGGCGCCCAG

GGCGAGACCCTGGGCGAGAAGTGGAAGAGGCAGCTGAACCAGCTGGACAAGAGCGAGTTCG

AGGAGTACAAGAAGAGCGGCATCCTGGAGGTGGACAGGACCGAGGCCAAGGAGGCCATCAA

GAGGGGCGAGACCGACCACCACGCCGTGAGCAGGGGCAGCGCCAAGCTGAGGTGGTTCGT

GGAGAGGAACATGGTGATCCCCGAGGGCAGGGTGATCGACCTGGGCTGCGGCAGGGGCGG

CTGGAGCTACTACTGCGCCGGCCTGAAGAAGGTGAGGGAGGTGAGGGGCTACACCAAGGGC

GGCCCCGGCCACGAGGAGCCCATCCCCATGGCCACCTACGGCTGGAACCTGGTGAAGCTGC

ACAGCGGCGTGGACGTGTTCTTCCCCGAGAAGTGCGACACCCTGCTGTGCGACATCGGCGA

GAGCAGCCCCAACCCCACCATCGAGGAGGGCAGGACCCTGAGGGTGCTGAAGATGGTGGAG

CCCTGGCTGAAGGGCAACCAGTTCTGCATCAAGATCCTGAACCCCTACATGCCCAGCGTGAT

CGAGGAGCTGGAGAAGCTGCAGAGGAAGCACGGCGGCATGCTGGTGAGGAACCCCCTGAG

CAGGAACAGCACCCACGAGATGTACTGGGTGAGCAACGGCACCGGCAACATCGTGAGCGCC

GTGAACATGATCAGCAGGATGCTGATCAACAGGTTCACCATGGCCCACAAGAAGCCCACCTA

CGAGAGGGACGTGGACCTGGGCGCCGGCAGCACCTGGCACTACGACGAGGACAACCCCTA

CAAGACCTGGGCCTACCACGGCAGCTACGAGGTGAAGGCCACCGGCAGCGCCAGCAGCATG

GTGAACGGCGTGGTGAAGCTGCTGACCAAGCCCTGGGACGTGGTGCCCATGGTGACCCAGA

TGGCCATGACCGACACCACCCCCTTCGGCCAGCAGAGGGTGTTCAAGGAGAAGGTGGACAC

CAGGACCCCCGAGGCCAAGGAGAACGCCGCCATCGGCGCCGTGTTCCAGGACGAGAACGG

CTGGAAGAGCGCCAGGGAGGCCGTGGAGGACAGCGAGAGGGCCCTGCACCTGGAGGGCAA

GTGCGAGAGCTGCGTGTACAACATGATGGGCAAGAGGGAGAAGAAGCTGGGCGAGTTCGGC

AAGGCCAAGGGCAGCAGGGCCATCTGGTACATGTGGCTGGGCGCCAGGTTCCTGGAGTTCG

AGGCCCTGGGCTTCCTGAACGAGGACCACTGGTTCAGCAGGGAGAACAGCCTGAGCGGCGT

GGAGGGCGAGGGCCTGCACAAGCTGGGCTACATCCTGAGGGACATCAGCAAGATCCCCGGC

GGCGCCATGTACGCCGACGACACCGCCGGCTGGGACACCAGGATCACCGAGGACGACCTG

CACAACGAGGAGAAGATCCTGGCCAAGGCCATCTTCAAGCTGACCTACCAGAACAAGGTGGT

GAAGGTGCAGAGGCCCACCCCCAGGGGCGCCGTGATGGACATCATCAGCAGGAAGGACCAG

AGGGGCAGCGGCCAGGTGGGCACCTACGGCCTGAACACCTTCACCAACATGGAGGCCCAGC

TGATCAGGCAGATGGAGGCCGAGGGCGTGATCACCGAGTGCGGCGTGGACAGGCTGAAGA

GGATGGCCATCAGCGGCGACGACTGCGTGGTGAAGCCCCCCCAGTGGGAGCCCAGCAAGG

GCTGGCACGACTGGCAGCAGGTGCCCTTCTGCAGCCACCACTTCCACGAGATCTTCATGAAG

GACGGCAGGAAGCTGGTGGTGCCCTGCAGGAACCAGGACGAGCTGATCGGCAGGGCCAGG

ATCAGCCAGGGCGCCGGCTGGAGCCTGAGGGAGACCGCCTGCCTGGGCAAGAGCTACGCC

CAGATGTGGCAGCTGATGTACTTCCACAGGAGGGACCTGAGGCTGGCCAGCAACGCCATCT

GCAGCGCCGTGCCCAGCCACTGGGTGCCCACCAGCAGGACCACCTGGAGCATCCACGCCCA

CCACGAGTGGATGACCACCGAGGACATGCTGGCCGTGTGGAACAGGGTGTGGATCGAGGAG

AACCCCTGGATGGAGGACAAGACCCACATCCACAGCTGGGAGGACGTGCCCTACCTGGGCA

AGAGGGAGGACCAGTGGTGCGGCAGCCTGATCGGCCTGACCAGCAGGGCCACCTGGGCCA

AGAACATCGCTGGATCCGGGCCCGGGGCTTCAGGTAAGCCTATCCCTAACCCTCTCCTCGGT

CTCGATTCTACGCGGACCTGATGAGCGGCCGCTCGAGCATGCATCTAGAGGGCCCTATTCTA

TAGTGTCACCTAAATGCTAGAGCTCGCTGATCAGCCTCGACTGTGCCTTCTAGTTGCCAGCCA

-continued

TCTGTTGTTTGCCCCTCCCCCGTGCCTTCCTTGACCCTGGAAGGTGCCACTCCCACTGTCCTT

TCCTAATAAAATGAGGAAATTGCATCGCATTGTCTGAGTAGGTGTCATTCTATTCTGGGGGGT

GGGGTGGGGCAGGACAGCAAGGGGGAGGATTGGGAAGACAATAGCAGGCATGCTGGGGAT

GCGGTGGGCTCTATGGCTTCTGAGGCGGAAAGAACCAGCTGGGGCTCGAGGGGGGATCGAT

CCCGTCGAGATATCTAGACCCAGCTTTCTTGTACAAAGTTGGCATTATAAGAAAGCATTGCTT

ATCAATTTGTTGCAACGAACAGGTCACTATCAGTCAAAATAAAATCATTATTTGGATCGATTCG

ACAGATCGCGATCGCAGTGAGTAGTGTTCTGGGGCGGGGGAGGACCTGCATGAGGGCCAGA

ATGACTGAAATCTGTGCTTTTCTGTGTGTTGCAGCATCATGAGCGGAAGCGGCTCCTTTGAGG

GAGGGGTATTCAGCCCTTATCTGACGGGGCGTCTCCCCTCCTGGGCGGGAGTGCGTCAGAA

TGTGATGGGATCCACGGTGGACGGCCGGCCCGTGCAGCCCGCGAACTCTTCAACCCTGACC

TATGCAACCCTGAGCTCTTCGTCGGTGGACGCAGCTGCCGCCGCAGCTGCTGCATCCGCCG

CCAGCGCCGTGCGCGGAATGGCCATGGGCGCCGGCTACTACGGCACTCTGGTGGCCAACTC

GAGTTCCACCAATAATCCCGCCAGCCTGAACGAGGAGAAGCTGCTGCTGCTGATGGCCCAGC

TTGAGGCCTTGACCCAGCGCCTGGGCGAGCTGACCCAGCAGGTGGCTCAGCTGCAGGAGCA

GACGCGGGCCGCGGTTGCCACGGTGAAATCCAAATAAAAAATGAATCAATAAATAAACGGAG

ACGGTTGTTGATTTTAACACAGAGTCTGAATCTTTATTTGATTTTTCGCGCGCGGTAGGCCCT

GGACCACCGGTCTCGATCATTGAGCACCCGGTGGATCTTTTCCAGGACCCGGTAGAGGTGG

GCTTGGATGTTGAGGTACATGGGCATGAGCCCGTCCCGGGGGTGGAGGTAGCTCCATTGCA

GGGCCTCGTGCTCGGGGGTGGTGTTGTAAATCACCCAGTCATAGCAGGGGCGCAGGGCGTG

GTGTTGCACAATATCTTTGAGGAGGAGACTGATGGCCACGGGCAGCCCTTTGGTGTAGGTGT

TTACAAATCTGTTGAGCTGGGAGGGATGCATGCGGGGGGAGATGAGGTGCATCTTGGCCTG

GATCTTGAGATTGGCGATGTTACCGCCCAGATCCCGCCTGGGGTTCATGTTGTGCAGGACCA

CCAGCACGGTGTATCCGGTGCACTTGGGGAATTTATCATGCAACTTGGAAGGGAAGGCGTGA

AAGAATTTGGCGACGCCCTTGTGTCCGCCCAGGTTTTCCATGCACTCATCCATGATGATGGCA

ATGGGCCCGTGGGCGGCGGCCTGGGCAAAGACGTTTCGGGGGTCGGACACATCATAGTTGT

GGTCCTGGGTGAGGTCATCATAGGCCATTTTAATGAATTTGGGGCGGAGGGTGCCGGACTGG

GGGACAAAGGTACCCTCGATCCCGGGGGCGTAGTTCCCCTCACAGATCTGCATCTCCCAGG

CTTTGAGCTCAGAGGGGGGGATCATGTCCACCTGCGGGGCGATAAAGAACACGGTTTCCGG

GGCGGGGGAGATGAGCTGGGCCGAAAGCAAGTTCCGGAGCAGCTGGGACTTGCCGCAGCC

GGTGGGGCCGTAAATGACCCCGATGACCGGCTGCAGGTGGTAGTTGAGGGAGAGACAGCTG

CCGTCCTCCCGGAGGAGGGGGGCCACCTCGTTCATCATCTCGCGCACGTGCATGTTCTCGC

GCACCAGTTCCGCCAGGAGGCGCTCTCCCCCCAGAGATAGGAGCTCCTGGAGCGAGGCGAA

GTTTTTCAGCGGCTTGAGTCCGTCGGCCATGGGCATTTTGGAGAGGGTCTGTTGCAAGAGTT

CCAAGCGGTCCCAGAGCTCGGTGATGTGCTCTACGGCATCTCGATCCAGCAGACCTCCTCGT

TTCGCGGGTTGGGACGACTGCGGGAGTAGGGCACCAGACGATGGGCGTCCAGCGCAGCCA

GGGTCCGGTCCTTCCAGGGCCGCAGCGTCCGCGTCAGGGTGGTCTCCGTCACGGTGAAGG

GGTGCGCGCCGGGCTGGGCGCTTGCGAGGGTGCGCTTCAGGCTCATCCGGCTGGTCGAAA

ACCGCTCCCGATCGGCGCCCTGCGCGTCGGCCAGGTAGCAATTGACCATGAGTTCGTAGTT

GAGCGCCTCGGCCGCGTGGCCTTTGGCGCGGAGCTTACCTTTGGAAGTCTGCCCGCAGGCG

GGACAGAGGAGGGACTTGAGGGCGTAGAGCTTGGGGGCGAGGAAGACGGAATCGGGGGCG

-continued
TAGGCGTCCGCGCCGCAGTGGGCGCAGACGGTCTCGCACTCCACGAGCCAGGTGAGGTCG

GGCTGGTCGGGGTCAAAAACCAGTTTCCCGCCGTTCTTTTTGATGCGTTTCTTACCTTTGGTC

TCCATGAGCTCGTGTCCCCGCTGGGTGACAAAGAGGCTGTCCGTGTCCCCGTAGACCGACTT

TATGGGCCGGTCCTCGAGCGGTGTGCCGCGGTCCTCCTCGTAGAGGAACCCCGCCCACTCC

GAGACGAAAGCCCGGGTCCAGGCCAGCACGAAGGAGGCCACGTGGGACGGGTAGCGGTCG

TTGTCCACCAGCGGGTCCACTTTTTCCAGGGTATGCAAACACATGTCCCCCTCGTCCACATCC

AGGAAGGTGATTGGCTTGTAAGTGTAGGCCACGTGACCGGGGGTCCCGGCCGGGGGGGTAT

AAAAGGGGGCGGGCCCCTGCTCGTCCTCACTGTCTTCCGGATCGCTGTCCAGGAGCGCCAG

CTGTTGGGGTAGGTATTCCCTCTCGAAGGCGGGCATGACCTCGGCACTCAGGTTGTCAGTTT

CTAGAAACGAGGAGGATTTGATATTGACGGTGCCAGCGGAGATGCCTTTCAAGAGCCCCTCG

TCCATCTGGTCAGAAAAGACGATTTTTTTGTTGTCGAGCTTGGTGGCGAAGGAGCCGTAGAG

GGCGTTGGAAAGGAGCTTGGCGATGGAGCGCATGGTCTGGTTTTTTTCCTTGTCGGCGCGCT

CCTTGGCCGCGATGTTGAGCTGCACGTACTCGCGCGCCACGCACTTCCATTCGGGGAAGAC

GGTGGTCATCTCGTCGGGCACGATTCTGACCTGCCAACCTCGATTATGCAGGGTGATGAGGT

CCACACTGGTGGCCACCTCGCCGCGCAGGGGCTCGTTGGTCCAGCAGAGGCGGCCGCCCTT

GCGCGAGCAGAAGGGGGGCAGAGGGTCCAGCATGACCTCGTCGGGGGGGTCGGCATCGAT

GGTGAAGATGCCGGGCAGGAGATCGGGGTCGAAGTAGCTGATGGAAGTGGCCAGATCGTCC

AGGGAAGCTTGCCATTCGCGCACGGCCAGCGCGCGCTCGTAGGGACTGAGGGGCGTGCCC

CAGGGCATGGGGTGGGTGAGCGCGGAGGCGTACATGCCGCAGATGTCGTAGACGTAGAGG

GGCTCCTCGAGGATGCCGATGTAGGTGGGGTAGCAGCGCCCCCCGCGGATGCTGGCGCGC

ACGTAGTCATACAGCTCGTGCGAGGGCGCGAGGAGCCCCGGGCCCAGGTTGGTGCGACTG

GGCTTTTCGGCGCGGTAGACGATCTGGCGAAAGATGGCATGCGAGTTGGAGGAGATGGTGG

GCCTTTGGAAGATGTTGAAGTGGGCGTGGGGGAGGCCGACCGAGTCGCGGATGAAGTGGGC

GTAGGAGTCTTGCAGTTTGGCGACGAGCTCGGCGGTGACGAGGACGTCCAGAGCGCAGTAG

TCGAGGGTCTCCTGGATGATGTCATACTTGAGCTGGCCCTTTTGTTTCCACAGCTCGCGGTTG

AGAAGGAACTCTTCGCGGTCCTTCCAGTACTCTTCGAGGGGGAACCCGTCCTGATCTGCACG

GTAAGAGCCTAGCATGTAGAACTGGTTGACGGCCTTGTAGGCGCAGCAGCCCTTCTCCACGG

GGAGGGCGTAGGCCTGGGCGGCCTTGCGCAGGGAGGTGTGCGTGAGGGCGAAGGTGTCCC

TGACCATGACCTTGAGGAACTGGTGCTTGAAATCGATATCGTCGCAGCCCCCCTGCTCCCAG

AGCTGGAAGTCCGTGCGCTTCTTGTAGGCGGGGTTGGGCAAAGCGAAAGTAACATCGTTGAA

AAGGATCTTGCCCGCGCGGGGCATAAAGTTGCGAGTGATGCGGAAAGGCTGGGGCACCTCG

GCCCGGTTGTTGATGACCTGGGCGGCGAGCACGATCTCGTCGAAACCGTTGATGTTGTGGC

CCACGATGTAGAGTTCCACGAATCGCGGGCGGCCCTTGACGTGGGGCAGCTTCTTGAGCTC

CTCGTAGGTGAGCTCGTCGGGGTCGCTGAGACCGTGCTGCTCGAGCGCCCAGTCGGCGAGA

TGGGGGTTGGCGCGGAGGAAGGAAGTCCAGAGATCCACGGCCAGGGCGGTTTGCAGACGG

TCCCGGTACTGACGGAACTGCTGCCCGACGGCCATTTTTTCGGGGGTGACGCAGTAGAAGGT

GCGGGGGTCCCCGTGCCAGCGGTCCCATTTGAGCTGGAGGGCGAGATCGAGGGCGAGCTC

GACGAGGCGGTCGTCCCCTGAGAGTTTCATGACCAGCATGAAGGGGACGAGCTGCTTGCCG

AAGGACCCCATCCAGGTGTAGGTTTCCACATCGTAGGTGAGGAAGAGCCTTTCGGTGCGAGG

ATGCGAGCCGATGGGGAAGAACTGGATCTCCTGCCACCAATTGGAGGAATGGCTGTTGATGT

GATGGAAGTAGAAATGCCGACGGCGCGCCGAACACTCGTGCTTGTGTTTATACAAGCGGCCA

-continued

CAGTGCTCGCAACGCTGCACGGGATGCACGTGCTGCACGAGCTGTACCTGAGTTCCTTTGAC

GAGGAATTTCAGTGGGAAGTGGAGTCGTGGCGCCTGCATCTCGTGCTGTACTACGTCGTGGT

GGTCGGCCTGGCCCTCTTCTGCCTCGATGGTGGTCATGCTGACGAGCCCGCGCGGGAGGCA

GGTCCAGACCTCGGCGCGAGCGGGTCGGAGAGCGAGGACGAGGGCGCGCAGGCCGGAGC

TGTCCAGGGTCCTGAGACGCTGCGGAGTCAGGTCAGTGGGCAGCGGCGGCGCGCGGTTGA

CTTGCAGGAGTTTTTCCAGGGCGCGCGGGAGGTCCAGATGGTACTTGATCTCCACCGCGCC

GTTGGTGGCGACGTCGATGGCTTGCAGGGTCCCGTGCCCCTGGGGTGTGACCACCGTCCCC

CGTTTCTTCTTGGGCGGCTGGGGCGACGGGGGCGGTGCCTCTTCCATGGTTAGAAGCGGCG

GCGAGGACGCGCGCCGGGCGGCAGAGGCGGCTCGGGGCCCGGAGGCAGGGGCGGCAGG

GGCACGTCGGCGCCGCGCGCGGGTAGGTTCTGGTACTGCGCCCGGAGAAGACTGGCGTGA

GCGACGACGCGACGGTTGACGTCCTGGATCTGACGCCTCTGGGTGAAGGCCACGGGACCCG

TGAGTTTGAACCTGAAAGAGAGTTCGACAGAATCAATCTCGGTATCGTTGACGGCGGCCTGC

CGCAGGATCTCTTGCACGTCGCCCGAGTTGTCCTGGTAGGCGATCTCGGTCATGAACTGCTC

GATCTCCTCCTCCTGAAGGTCTCCGCGACCGGCGCGCTCCACGGTGGCCGCGAGGTCGTTG

GAGATGCGGCCCATGAGCTGCGAGAAGGCGTTCATGCCCGCCTCGTTCCAGACGCGGCTGT

AGACCACGACGCCCTCGGGATCGCGGGCGCGCATGACCACCTGGGCGAGGTTGAGCTCCAC

GTGGCGCGTGAAGACCGCGTAGTTGCAGAGGCGCTGGTAGAGGTAGTTGAGCGTGGTGGCG

ATGTGCTCGGTGACGAAGAAATACATGATCCAGCGGCGGAGCGGCATCTCGCTGACGTCGC

CCAGCGCCTCCAAGCGTTCCATGGCCTCGTAAAAGTCCACGGCGAAGTTGAAAAACTGGGAG

TTGCGCGCCGAGACGGTCAACTCCTCCTCCAGAAGACGGATGAGCTCGGCGATGGTGGCGC

GCACCTCGCGCTCGAAGGCCCCCGGGAGTTCCTCCACTTCCTCCTCTTCTTCCTCCTCCACT

AACATCTCTTCTACTTCCTCCTCAGGCGGTGGTGGTGGCGGGGGAGGGGGCCTGCGTCGCC

GGCGGCGCACGGGCAGACGGTCGATGAAGCGCTCGATGGTCTCGCCGCGCCGGCGTCGCA

TGGTCTCGGTGACGGCGCGCCCGTCCTCGCGGGGCCGCAGCGTGAAGACGCCGCCGCGCA

TCTCCAGGTGGCCGGGGGGGTCCCCGTTGGGCAGGGAGAGGGCGCTGACGATGCATCTTAT

CAATTGCCCCGTAGGGACTCCGCGCAAGGACCTGAGCGTCTCGAGATCCACGGGATCTGAA

AACCGTTGAACGAAGGCTTCGAGCCAGTCGCAGTCGCAAGGTAGGCTGAGCACGGTTTCTTC

TGCCGGGTCATGTTGGGGAGCGGGGCGGGCGATGCTGCTGGTGATGAAGTTGAAATAGGCG

GTTCTGAGACGGCGGATGGTGGCGAGGAGCACCAGGTCTTTGGGCCCGGCTTGCTGGATGC

GCAGACGGTCGGCCATGCCCCAGGCGTGGTCCTGACACCTGGCCAGGTCCTTGTAGTAGTC

CTGCATGAGCCGCTCCACGGGCACCTCCTCCTCGCCCGCGCGGCCGTGCATGCGCGTGAGC

CCGAAGCCGCGCTGGGGCTGGACGAGCGCCAGGTCGGCGACGACGCGCTCGGCGAGGATG

GCCTGCTGGATCTGGGTGAGGGTGGTCTGGAAGTCGTCAAAGTCGACGAAGCGGTGGTAGG

CTCCGGTGTTGATGGTGTAGGAGCAGTTGGCCATGACGGACCAGTTGACGGTCTGGTGGCC

CGGACGCACGAGCTCGTGGTACTTGAGGCGCGAGTAGGCGCGCGTGTCGAAGATGTAGTCG

TTGCAGGTGCGCACCAGGTACTGGTAGCCGATGAGGAAGTGCGGCGGCGGCTGGCGGTAGA

GCGGCCATCGCTCGGTGGCGGGGGCGCCGGGCGCGAGGTCCTCGAGCATGGTGCGGTGGT

AGCCGTAGATGTACCTGGACATCCAGGTGATGCCGGCGGCGGTGGTGGAGGCGCGCGGGA

ACTCGCGGACGCGGTTCCAGATGTTGCGCAGCGGCAGGAAGTAGTTCATGGTGGGCACGGT

CTGGCCCGTGAGGCGCGCGCAGTCGTGGATGCTCTATACGGGCAAAAACGAAAGCGGTCAG

-continued

CGGCTCGACTCCGTGGCCTGGAGGCTAAGCGAACGGGTTGGGCTGCGCGTGTACCCCGGTT

CGAATCTCGAATCAGGCTGGAGCCGCAGCTAACGTGGTACTGGCACTCCCGTCTCGACCCAA

GCCTGCACCAACCCTCCAGGATACGGAGGCGGGTCGTTTTGCAACTTTTTTTGGAGGCCGGA

AATGAAACTAGTAAGCGCGGAAAGCGGCCGACCGCGATGGCTCGCTGCCGTAGTCTGGAGA

AGAATCGCCAGGGTTGCGTTGCGGTGTGCCCCGGTTCGAGGCCGGCCGGATTCCGCGGCTA

ACGAGGGCGTGGCTGCCCCGTCGTTTCCAAGACCCCATAGCCAGCCGACTTCTCCAGTTACG

GAGCGAGCCCCTCTTTTGTTTTGTTTGTTTTTGCCAGATGCATCCCGTACTGCGGCAGATGCG

CCCCCACCACCCTCCACCGCAACAACAGCCCCCTCCTCCACAGCCGGCGCTTCTGCCCCCG

CCCCAGCAGCAGCAGCAACTTCCAGCCACGACCGCCGCGGCCGCCGTGAGCGGGGCTGGA

CAGACTTCTCAGTATGATCACCTGGCCTTGGAAGAGGGCGAGGGGCTGGCGCGCCTGGGGG

CGTCGTCGCCGGAGCGGCACCCGCGCGTGCAGATGAAAAGGGACGCTCGCGAGGCCTACG

TGCCCAAGCAGAACCTGTTCAGAGACAGGAGCGGCGAGGAGCCCGAGGAGATGCGCGCGG

CCCGGTTCCACGCGGGGCGGGAGCTGCGGCGCGGCCTGGACCGAAAGAGGGTGCTGAGGG

ACGAGGATTTCGAGGCGGACGAGCTGACGGGGATCAGCCCCGCGCGCGCGCACGTGGCCG

CGGCCAACCTGGTCACGGCGTACGAGCAGACCGTGAAGGAGGAGAGCAACTTCCAAAAATC

CTTCAACAACCACGTGCGCACCCTGATCGCGCGCGAGGAGGTGACCCTGGGCCTGATGCAC

CTGTGGGACCTGCTGGAGGCCATCGTGCAGAACCCCACCAGCAAGCCGCTGACGGCGCAGC

TGTTCCTGGTGGTGCAGCATAGTCGGGACAACGAGGCGTTCAGGGAGGCGCTGCTGAATAT

CACCGAGCCCGAGGGCCGCTGGCTCCTGGACCTGGTGAACATTCTGCAGAGCATCGTGGTG

CAGGAGCGCGGGCTGCCGCTGTCCGAGAAGCTGGCGGCCATCAACTTCTCGGTGCTGAGTC

TGGGCAAGTACTACGCTAGGAAGATCTACAAGACCCCGTACGTGCCCATAGACAAGGAGGTG

AAGATCGACGGGTTTTACATGCGCATGACCCTGAAAGTGCTGACCCTGAGCGACGATCTGGG

GGTGTACCGCAACGACAGGATGCACCGCGCGGTGAGCGCCAGCAGGCGGCGCGAGCTGAG

CGACCAGGAGCTGATGCACAGCCTGCAGCGGGCCCTGACCGGGGCCGGGACCGAGGGGGA

GAGCTACTTTGACATGGGCGCGGACCTGCACTGGCAGCCCAGCCGCCGGGCCTTGGAGGCG

GCAGGCGGTCCCCCCTACATAGAAGAGGTGGACGATGAGGTGGACGAGGAGGGCGAGTACC

TGGAAGACTGATGGCGCGACCGTATTTTTGCTAGATGCAACAACAGCCACCTCCTGATCCCG

CGATGCGGGCGGCGCTGCAGAGCCAGCCGTCCGGCATTAACTCCTCGGACGATTGGACCCA

GGCCATGCAACGCATCATGGCGCTGACGACCCGCAACCCCGAAGCCTTTAGACAGCAGCCC

CAGGCCAACCGGCTCTCGGCCATCCTGGAGGCCGTGGTGCCCTCGCGCTCCAACCCCACGC

ACGAGAAGGTCCTGGCCATCGTGAACGCGCTGGTGGAGAACAAGGCCATCCGCGGCGACGA

GGCCGGCCTGGTGTACAACGCGCTGCTGGAGCGCGTGGCCCGCTACAACAGCACCAACGTG

CAGACCAACCTGGACCGCATGGTGACCGACGTGCGCGAGGCCGTGGCCCAGCGCGAGCGG

TTCCACCGCGAGTCCAACCTGGGATCCATGGTGGCGCTGAACGCCTTCCTCAGCACCCAGCC

CGCCAACGTGCCCCGGGGCCAGGAGGACTACACCAACTTCATCAGCGCCCTGCGCCTGATG

GTGACCGAGGTGCCCCAGAGCGAGGTGTACCAGTCCGGGCCGGACTACTTCTTCCAGACCA

GTCGCCAGGGCTTGCAGACCGTGAACCTGAGCCAGGCGTTCAAGAACTTGCAGGGCCTGTG

GGGCGTGCAGGCCCCGGTCGGGGACCGCGCGACGGTGTCGAGCCTGCTGACGCCGAACTC

GCGCCTGCTGCTGCTGCTGGTGGCCCCCTTCACGGACAGCGGCAGCATCAACCGCAACTCG

TACCTGGGCTACCTGATTAACCTGTACCGCGAGGCCATCGGCCAGGCGCACGTGGACGAGC

AGACCTACCAGGAGATCACCCACGTGAGCCGCGCCCTGGGCCAGGACGACCCGGGCAATCT

-continued

```
GGAAGCCACCCTGAACTTTTTGCTGACCAACCGGTCGCAGAAGATCCCGCCCCAGTACACGC
TCAGCGCCGAGGAGGAGCGCATCCTGCGATACGTGCAGCAGAGCGTGGGCCTGTTCCTGAT
GCAGGAGGGGGCCACCCCCAGCGCCGCGCTCGACATGACCGCGCGCAACATGGAGCCCAG
CATGTACGCCAGCAACCGCCCGTTCATCAATAAACTGATGGACTACTTGCATCGGGCGGCCG
CCATGAACTCTGACTATTTCACCAACGCCATCCTGAATCCCCACTGGCTCCCGCCGCCGGGG
TTCTACACGGGCGAGTACGACATGCCCGACCCCAATGACGGGTTCCTGTGGGACGATGTGG
ACAGCAGCGTGTTCTCCCCCCGACCGGGTGCTAACGAGCGCCCCTTGTGGAAGAAGGAAGG
CAGCGACCGACGCCCGTCCTCGGCGCTGTCCGGCCGCGAGGGTGCTGCCGCGGCGGTGCC
CGAGGCCGCCAGTCCTTTCCCGAGCTTGCCCTTCTCGCTGAACAGTATTCGCAGCAGCGAGC
TGGGCAGGATCACGCGCCCGCGCTTGCTGGGCGAGGAGGAGTACTTGAATGACTCGCTGTT
GAGACCCGAGCGGGAGAAGAACTTCCCCAATAACGGGATAGAGAGCCTGGTGGACAAGATG
AGCCGCTGGAAGACGTATGCGCAGGAGCACAGGGACGATCCGTCGCAGGGGGCCACGAGC
CGGGGCAGCGCCGCCCGTAAACGCCGGTGGCACGACAGGCAGCGGGGACTGATGTGGGAC
GATGAGGATTCCGCCGACGACAGCAGCGTGTTGGACTTGGGTGGGAGTGGTAACCCGTTCG
CTCACCTGCGCCCCCGCATCGGGCGCATGATGTAAGAGAAACCGAAAATAAATGATACTCAC
CAAGGCCATGGCGACCAGCGTGCGTTCGTTTCTTCTCTGTTGTTGTATCTAGTATGATGAGGC
GTGCGTACCCGGAGGGTCCTCCTCCCTCGTACGAGAGCGTGATGCAGCAGGCGATGGCGGC
GGCGGCGGCGATGCAGCCCCCGCTGGAGGCTCCTTACGTGCCCCCGCGGTACCTGGCGCC
TACGGAGGGGCGGAACAGCATTCGTTACTCGGAGCTGGCACCCTTGTACGATACCACCCGGT
TGTACCTGGTGGACAACAAGTCGGCGGACATCGCCTCGCTGAACTACCAGAACGACCACAGC
AACTTCCTGACCACCGTGGTGCAGAACAATGACTTCACCCCCACGGAGGCCAGCACCCAGAC
CATCAACTTTGACGAGCGCTCGCGGTGGGGCGGTCAGCTGAAAACCATCATGCACACCAACA
TGCCCAACGTGAACGAGTTCATGTACAGCAACAAGTTCAAGGCGCGGGTGATGGTCTCCCGC
AAGACCCCCAACGGGGTGACAGTGACAGATGGTAGTCAGGATATCTTGGAGTATGAATGGGT
GGAGTTTGAGCTGCCCGAAGGCAACTTCTCGGTGACCATGACCATCGACCTGATGAACAACG
CCATCATCGACAATTACTTGGCGGTGGGGCGGCAGAACGGGGTCCTGGAGAGCGATATCGG
CGTGAAGTTCGACACTAGGAACTTCAGGCTGGGCTGGGACCCCGTGACCGAGCTGGTCATG
CCCGGGGTGTACACCAACGAGGCCTTCCACCCCGATATTGTCTTGCTGCCCGGCTGCGGGG
TGGACTTCACCGAGAGCCGCCTCAGCAACCTGCTGGGCATTCGCAAGAGGCAGCCCTTCCA
GGAGGGCTTCCAGATCATGTACGAGGATCTGGAGGGGGGCAACATCCCCGCGCTCCTGGAT
GTCGACGCCTATGAGAAAAGCAAGGAGGAGAGCGCCGCCGCGGCGACTGCAGCTGTAGCCA
CCGCCTCTACCGAGGTCAGGGGCGATAATTTTGCCAGCCCTGCAGCAGTGGCAGCGGCCGA
GGCGGCTGAAACCGAAAGTAAGATAGTCATTCAGCCGGTGGAGAAGGATAGCAAGGACAGG
AGCTACAACGTGCTGCCGGACAAGATAAACACCGCCTACCGCAGCTGGTACCTGGCCTACAA
CTATGGCGACCCCGAGAAGGGCGTGCGCTCCTGGACGCTGCTCACCACCTCGGACGTCACC
TGCGGCGTGGAGCAAGTCTACTGGTCGCTGCCCGACATGATGCAAGACCCGGTCACCTTCC
GCTCCACGCGTCAAGTTAGCAACTACCCGGTGGTGGGCGCCGAGCTCCTGCCCGTCTACTC
CAAGAGCTTCTTCAACGAGCAGGCCGTCTACTCGCAGCAGCTGCGCGCCTTCACCTCGCTCA
CGCACGTCTTCAACCGCTTCCCCGAGAACCAGATCCTCGTCCGCCCGCCCGCGCCCACCATT
ACCACCGTCAGTGAAAACGTTCCTGCTCTCACAGATCACGGGACCCTGCCGCTGCGCAGCAG
```

-continued

TATCCGGGGAGTCCAGCGCGTGACCGTTACTGACGCCAGACGCCGCACCTGCCCCTACGTC

TACAAGGCCCTGGGCATAGTCGCGCCGCGCGTCCTCTCGAGCCGCACCTTCTAAAAAATGTC

CATTCTCATCTCGCCCAGTAATAACACCGGTTGGGGCCTGCGCGCGCCCAGCAAGATGTACG

GAGGCGCTCGCCAACGCTCCACGCAACACCCCGTGCGCGTGCGCGGGCACTTCCGCGCTCC

CTGGGGCGCCCTCAAGGGCCGCGTGCGGTCGCGCACCACCGTCGACGACGTGATCGACCA

GGTGGTGGCCGACGCGCGCAACTACACCCCCGCCGCCGCGCCCGTCTCCACCGTGGACGC

CGTCATCGACAGCGTGGTGGCCGACGCGCGCCGGTACGCCCGCGCCAAGAGCCGGCGGCG

GCGCATCGCCCGGCGGCACCGGAGCACCCCCGCCATGCGCGCGGCGCGAGCCTTGCTGCG

CAGGGCCAGGCGCACGGGACGCAGGGCCATGCTCAGGGCGGCCAGACGCGCGGCTTCAGG

CGCCAGCGCCGGCAGGACCCGGAGACGCGCGGCCACGGCGGCGGCAGCGGCCATCGCCA

GCATGTCCCGCCCGCGGCGAGGGAACGTGTACTGGGTGCGCGACGCCGCCACCGGTGTGC

GCGTGCCCGTGCGCACCCGCCCCCCTCGCACTTGAAGATGTTCACTTCGCGATGTTGATGTG

TCCCAGCGGCGAGGAGGATGTCCAAGCGCAAATTCAAGGAAGAGATGCTCCAGGTCATCGC

GCCTGAGATCTACGGCCCCGCGGTGGTGAAGGAGGAAAGAAAGCCCCGCAAAATCAAGCGG

GTCAAAAAGGACAAAAAGGAAGAAGATGACGATCTGGTGGAGTTTGTGCGCGAGTTCGCCCC

CCGGCGGCGCGTGCAGTGGCGCGGGCGGAAAGTGCACCCGGTGCTGAGACCCGGCACCAC

CGTGGTCTTCACGCCCGGCGAGCGCTCCGGCAGCGCTTCCAAGCGCTCCTACGACGAGGTG

TACGGGGACGAGGACATCCTCGAGCAGGCGGCCGAGCGCCTGGGCGAGTTTGCTTACGGCA

AGCGCAGCCGCCCCGCCCTGAAGGAAGAGGCGGTGTCCATCCCGCTGGACCACGGCAACC

CCACGCCGAGCCTCAAGCCCGTGACCCTGCAGCAGGTGCTGCCGAGCGCAGCGCCGCGCC

GGGGGTTCAAGCGCGAGGGCGAGGATCTGTACCCCACCATGCAGCTGATGGTGCCCAAGCG

CCAGAAGCTGGAAGACGTGCTGGAGACCATGAAGGTGGACCCGGACGTGCAGCCCGAGGTC

AAGGTGCGGCCCATCAAGCAGGTGGCCCCGGGCCTGGGCGTGCAGACCGTGGACATCAAGA

TCCCCACGGAGCCCATGGAAACGCAGACCGAGCCCATGATCAAGCCCAGCACCAGCACCAT

GGAGGTGCAGACGGATCCCTGGATGCCATCGGCTCCTAGCCGAAGACCCCGGCGCAAGTAC

GGCGCGGCCAGCCTGCTGATGCCCAACTACGCGCTGCATCCTTCCATCATCCCCACGCCGG

GCTACCGCGGCACGCGCTTCTACCGCGGTCATACAACCAGCCGCCGCCGCAAGACCACCAC

CCGCCGCCGCCGTCGCCGCACAGCCGCTGCATCTACCCCTGCCGCCCTGGTGCGGAGAGT

GTACCGCCGCGGCCGCGCGCCTCTGACCCTACCGCGCGCGCGCTACCACCCGAGCATCGC

CATTTAAACTTTCGCCTGCTTTGCAGATGGCCCTCACATGCCGCCTCCGCGTTCCCATTACGG

GCTACCGAGGAAGAAAACCGCGCCGTAGAAGGCTGGCGGGGAACGGGATGCGTCGCCACC

ACCATCGGCGGCGGCGCGCCATCAGCAAGCGGTTGGGGGGAGGCTTCCTGCCCGCGCTGA

TCCCCATCATCGCCGCGGCGATCGGGGCGATCCCCGGCATTGCTTCCGTGGCGGTGCAGGC

CTCTCAGCGCCACTGAGACACTTGGAAAACATCTTGTAATAAACCAATGGACTCTGACGCTCC

TGGTCCTGTGATGTGTTTTCGTAGACAGATGGAAGACATCAATTTTTCGTCCCTGGCTCCGCG

ACACGGCACGCGGCCGTTCATGGGCACCTGGAGCGACATCGGCACCAGCCAACTGAACGGG

GGCGCCTTCAATTGGAGCAGTCTCTGGAGCGGGCTTAAGAATTTCGGGTCCACGCTTAAAAC

CTATGGCAGCAAGGCGTGGAACAGCACCACAGGGCAGGCGCTGAGGGATAAGCTGAAAGAG

CAGAACTTCCAGCAGAAGGTGGTCGATGGGCTCGCCTCGGGCATCAACGGGGTGGTGGACC

TGGCCAACCAGGCCGTGCAGCGGCAGATCAACAGCCGCCTGGACCCGGTGCCGCCCGCCG

GCTCCGTGGAGATGCCGCAGGTGGAGGAGGAGCTGCCTCCCCTGGACAAGCGGGGCGAGA

-continued

AGCGACCCCGCCCCGACGCGGAGGAGACGCTGCTGACGCACACGGACGAGCCGCCCCCGT

ACGAGGAGGCGGTGAAACTGGGTCTGCCCACCACGCGGCCCATCGCGCCCCTGGCCACCG

GGGTGCTGAAACCCGAAAGTAATAAGCCCGCGACCCTGGACTTGCCTCCTCCCGCTTCCCGC

CCCTCTACAGTGGCTAAGCCCCTGCCGCCGGTGGCCGTGGCCCGCGCGCGACCCGGGGGC

TCCGCCCGCCCTCATGCGAACTGGCAGAGCACTCTGAACAGCATCGTGGGTCTGGGAGTGC

AGAGTGTGAAGCGCCGCCGCTGCTATTAAACCTACCGTAGCGCTTAACTTGCTTGTCTGTGT

GTGTATGTATTATGTCGCCGCTGTCCGCCAGAAGGAGGAGTGAAGAGGCGCGTCGCCGAGT

TGCAAGATGGCCACCCCATCGATGCTGCCCCAGTGGGCGTACATGCACATCGCCGGACAGG

ACGCTTCGGAGTACCTGAGTCCGGGTCTGGTGCAGTTCGCCCGCGCCACAGACACCTACTTC

AGTCTGGGGAACAAGTTTAGGAACCCCACGGTGGCGCCCACGCACGATGTGACCACCGACC

GCAGCCAGCGGCTGACGCTGCGCTTCGTGCCCGTGGACCGCGAGGACAACACCTACTCGTA

CAAAGTGCGCTACACGCTGGCCGTGGGCGACAACCGCGTGCTGGACATGGCCAGCACCTAC

TTTGACATCCGCGGCGTGCTGGATCGGGGCCCTAGCTTCAAACCCTACTCCGGCACCGCCTA

CAACAGCCTGGCTCCCAAGGGAGCGCCCAATTCCAGCCAGTGGGAGCAAAAAAAGGCAGGC

AATGGTGACACTATGGAAACACACACATTTGGTGTGGCCCCAATGGGCGGTGAGAATATTAC

AATCGACGGATTACAAATTGGAACTGACGCTACAGCTGATCAGGATAAACCAATTTATGCTGA

CAAAACATTCCAGCCTGAACCTCAAGTAGGAGAAGAAAATTGGCAAGAAACTGAAAGCTTTTA

TGGCGGTAGGGCTCTTAAAAAAGACACAAGCATGAAACCTTGCTATGGCTCCTATGCTAGACC

CACCAATGTAAAGGGAGGTCAAGCTAAACTTAAAGTTGGAGCTGATGGAGTTCCTACCAAAGA

ATTTGACATAGACCTGGCTTTCTTTGATACTCCCGGTGGCACAGTGAATGGACAAGATGAGTA

TAAAGCAGACATTGTCATGTATACCGAAAACACGTATCTGGAAACTCCAGACACGCATGTGGT

ATACAAACCAGGCAAGGATGATGCAAGTTCTGAAATTAACCTGGTTCAGCAGTCCATGCCCAA

TAGACCCAACTATATTGGGTTCAGAGACAACTTTATTGGGCTCATGTATTACAACAGTACTGG

CAATATGGGGGTGCTGGCTGGTCAGGCCTCACAGCTGAATGCTGTGGTCGACTTGCAAGACA

GAAACACCGAGCTGTCATACCAGCTCTTGCTTGACTCTTTGGGTGACAGAACCCGGTATTTCA

GTATGTGGAATCAGGCGGTGGACAGTTATGATCCTGATGTGCGCATTATTGAAAACCATGGTG

TGGAAGACGAACTTCCCAACTATTGCTTCCCCCTGGATGGGTCTGGCACTAATGCCGCTTAC

CAAGGTGTGAAAGTAAAAAATGGTAACGATGGTGATGTTGAGAGCGAATGGGAAAATGATGAT

ACTGTCGCAGCTCGAAATCAATTATGCAAGGGCAACATTTTTGCCATGGAAATTAACCTCCAA

GCCAACCTGTGGAGAAGTTTCCTCTACTCGAACGTGGCCCTGTACCTGCCCGACTCTTACAA

GTACACGCCAGCCAACATCACCCTGCCCACCAACACCAACACTTATGATTACATGAACGGGA

GAGTGGTGCCTCCCTCGCTGGTGGACGCCTACATCAACATCGGGGCGCGCTGGTCGCTGGA

CCCCATGGACAACGTCAATCCCTTCAACCACCACCGCAACGCGGGCCTGCGCTACCGCTCCA

TGCTCCTGGGCAACGGGCGCTACGTGCCCTTCCACATCCAGGTGCCCCAGAAATTTTTCGCC

ATCAAGAGCCTCCTGCTCCTGCCCGGGTCCTACACCTACGAGTGGAACTTCCGCAAGGACGT

CAACATGATCCTGCAGAGCTCCCTCGGCAACGACCTGCGCACGGACGGGGCCTCCATCTCC

TTCACCAGCATCAACCTCTACGCCACCTTCTTCCCCATGGCGCACAACACGGCCTCCACGCT

CGAGGCCATGCTGCGCAACGACACCAACGACCAGTCCTTCAACGACTACCTCTCGGCGGCC

AACATGCTCTACCCCATCCCGGCCAACGCCACCAACGTGCCCATCTCCATCCCCTCGCGCAA

CTGGGCCGCCTTCCGCGGCTGGTCCTTCACGCGCCTCAAGACCAAGGAGACGCCCTCGCTG

-continued

GGCTCCGGGTTCGACCCCTACTTCGTCTACTCGGGCTCCATCCCCTACCTCGACGGCACCTT

CTACCTCAACCACACCTTCAAGAAGGTCTCCATCACCTTCGACTCCTCCGTCAGCTGGCCCG

GCAACGACCGGCTCCTGACGCCCAACGAGTTCGAAATCAAGCGCACCGTCGACGGCGAGGG

ATACAACGTGGCCCAGTGCAACATGACCAAGGACTGGTTCCTGGTCCAGATGCTGGCCCACT

ACAACATCGGCTACCAGGGCTTCTACGTGCCCGAGGGCTACAAGGACCGCATGTACTCCTTC

TTCCGCAACTTCCAGCCCATGAGCCGCCAGGTGGTGGACGAGGTCAACTACAAGGACTACCA

GGCCGTCACCCTGGCCTACCAGCACAACAACTCGGGCTTCGTCGGCTACCTCGCGCCCACC

ATGCGCCAGGGCCAGCCCTACCCCGCCAACTACCCGTACCCGCTCATCGGCAAGAGCGCCG

TCACCAGCGTCACCCAGAAAAAGTTCCTCTGCGACAGGGTCATGTGGCGCATCCCCTTCTCC

AGCAACTTCATGTCCATGGGCGCGCTCACCGACCTCGGCCAGAACATGCTCTATGCCAACTC

CGCCCACGCGCTAGACATGAATTTCGAAGTCGACCCCATGGATGAGTCCACCCTTCTCTATG

TTGTCTTCGAAGTCTTCGACGTCGTCCGAGTGCACCAGCCCCACCGCGGCGTCATCGAGGCC

GTCTACCTGCGCACCCCCTTCTCGGCCGGTAACGCCACCACCTAAATTGCTACTTGCATGAT

GGCTGAGCCCACAGGCTCCGGCGAGCAGGAGCTCAGGGCCATCATCCGCGACCTGGGCTG

CGGGCCCTACTTCCTGGGCACCTTCGATAAGCGCTTCCCGGGATTCATGGCCCCGCACAAGC

TGGCCTGCGCCATCGTCAACACGGCCGGCCGCGAGACCGGGGGCGAGCACTGGCTGGCCT

TCGCCTGGAACCCGCGCTCGAACACCTGCTACCTCTTCGACCCCTTCGGGTTCTCGGACGAG

CGCCTCAAGCAGATCTACCAGTTCGAGTACGAGGGCCTGCTGCGCCGTAGCGCCCTGGCCA

CCGAGGACCGCTGCGTCACCCTGGAAAAGTCCACCCAGACCGTGCAGGGTCCGCGCTCGGC

CGCCTGCGGGCTCTTCTGCTGCATGTTCCTGCACGCCTTCGTGCACTGGCCCGACCGCCCC

ATGGACAAGAACCCCACCATGAACTTGCTGACGGGGGTGCCCAACGGCATGCTCCAGTCGC

CCCAGGTGGAACCCACCCTGCGCCGCAACCAGGAGGCGCTCTACCGCTTCCTCAACTCCCA

CTCCGCCTACTTTCGCTCCCACCGCGCGCGCATCGAGAAGGCCACCGCCTTCGACCGCATG

AACAATCAAGACATGTAAACCGTGTGTGTATGTTTAAAATATCTTTTAATAAACAGCACTTTAAT

GTTACACATGCATCTGAGATGATTTTATTTTAGAAATCGAAAGGGTTCTGCCGGGTCTCGGCA

TGGCCCGCGGGCAGGGACACGTTGCGGAACTGGTACTTGGCCAGCCACTTGAACTCGGGGA

TCAGCAGTTTGGGCAGCGGGGTGTCGGGGAAGGAGTCGGTCCACAGCTTCCGCGTCAGCTG

CAGGGCGCCCAGCAGGTCGGGCGCGGAGATCTTGAAATCGCAGTTGGGACCCGCGTTCTGC

GCGCGAGAGTTGCGGTACACGGGGTTGCAGCACTGGAACACCATCAGGGCCGGGTGCTTCA

CGCTCGCCAGCACCGCCGCGTCGGTGATGCTCTCCACGTCGAGGTCCTCGGCGTTGGCCAT

CCCGAAGGGGGTCATCTTGCAGGTCTGCCTTCCCATGGTGGGCACGCACCCGGGCTTGTGG

TTGCAATCGCAGTGCAGGGGGATCAGCATCATCTGGGCCTGGTCGGCGTTCATCCCCGGGT

ACATGGCCTTCATGAAAGCCTCCAATTGCCTGAACGCCTGCTGGGCCTTGGCTCCCTCGGTG

AAGAAGACCCCGCAGGACTTGCTAGAGAACTGGTTGGTGGCACAGCCGGCATCGTGCACGC

AGCAGCGCGCGTCGTTGTTGGCCAGCTGCACCACGCTGCGCCCCCAGCGGTTCTGGGTGAT

CTTGGCCCGGTCGGGGTTCTCCTTCAGCGCGCGCTGCCCGTTCTCGCTCGCCACATCCATCT

CGATCATGTGCTCCTTCTGGATCATGGTGGTCCCGTGCAGGCACCGCAGTTTGCCCTCGGCC

TCGGTGCACCCGTGCAGCCACAGCGCGCACCCGGTGCACTCCCAGTTCTTGTGGGCGATCT

GGGAATGCGCGTGCACGAACCCTTGCAGGAAGCGGCCCATCATGGTCGTCAGGGTCTTGTT

GCTAGTGAAGGTCAACGGGATGCCGCGGTGCTCCTCGTTGATGTACAGGTGGCAGATGCGG

CGGTACACCTCGCCCTGCTCGGGCATCAGTTGGAAGTTGGCTTTCAGGTCGGTCTCCACGCG

-continued

GTAGCGGTCCATCAGCATAGTCATGATTTCCATGCCCTTCTCCCAGGCCGAGACGATGGGCA

GGCTCATAGGGTTCTTCACCATCATCTTAGCACTAGCAGCCGCGGCCAGGGGGTCGCTCTCA

TCCAGGGTCTCAAAGCTCCGCTTGCCGTCCTTCTCGGTGATCCGCACCGGGGGGTAGCTGAA

GCCCACGGCCGCCAGCTCCTCCTCGGCCTGTCTTTCGTCCTCGCTGTCCTGGCTGACGTCCT

GCATGACCACATGCTTGGTCTTGCGGGGTTTCTTCTTGGGCGGCAGTGGCGGCGGAGATGC

TTGTGGCGAGGGGGAGCGCGAGTTCTCGCTCACCACTACTATCTCTTCCTCTTCTTGGTCCG

AGGCCACGCGGCGGTAGGTATGTCTCTTCGGGGGCAGAGGCGGAGGCGACGGGCTCTCGC

CGCCGCGACTTGGCGGATGGCTGGCAGAGCCCCTTCCGCGTTCGGGGGTGCGCTCCCGGC

GGCGCTCTGACTGACTTCCTCCGCGGCCGGCCATTGTGTTCTCCTAGGGAGGAACAACAAGC

ATGGAGACTCAGCCATCGCCAACCTCGCCATCTGCCCCCACCGCCGGCGACGAGAAGCAGC

AGCAGCAGAATGAAAGCTTAACCGCCCCGCCGCCCAGCCCCGCCTCCGACGCAGCCGCGGT

CCCAGACATGCAAGAGATGGAGGAATCCATCGAGATTGACCTGGGCTATGTGACGCCCGCG

GAGCATGAGGAGGAGCTGGCAGTGCGCTTTCAATCGTCAAGCCAGGAAGATAAAGAACAGCC

AGAGCAGGAAGCAGAGAACGAGCAGAGTCAGGCTGGGCTCGAGCATGGCGACTACCTCCAC

CTGAGCGGGGAGGAGGACGCGCTCATCAAGCATCTGGCCCGGCAGGCCACCATCGTCAAGG

ACGCGCTGCTCGACCGCACCGAGGTGCCCCTCAGCGTGGAGGAGCTCAGCCGCGCCTACGA

GCTCAACCTCTTCTCGCCGCGCGTGCCCCCCAAGCGCCAGCCCAACGGCACCTGCGAGCCC

AACCCCCGCCTCAACTTCTACCCGGTCTTCGCGGTGCCCGAGGCCCTGGCCACCTACCACAT

CTTTTTCAAGAACCAAAAGATCCCCGTCTCCTGCCGCGCCAACCGCACCCGCGCCGACGCCC

TCTTCAACCTGGGTCCCGGCGCCCGCCTACCTGATATCGCCTCCTTGGAAGAGGTTCCCAAG

ATCTTCGAGGGTCTGGGCAGCGACGAGACTCGGGCCGCGAACGCTCTGCAAGGAGAAGGAG

GAGGAGAGCATGAGCACCACAGCGCCCTGGTCGAGTTGGAAGGCGACAACGCGCGGCTGG

CGGTGCTCAAACGCACGGTCGAGCTGACCCATTTCGCCTACCCGGCTCTGAACCTGCCCCC

GAAAGTCATGAGCGCGGTCATGGACCAGGTGCTCATCAAGCGCGCGTCGCCCATCTCCGAG

GACGAGGGCATGCAAGACTCCGAGGAGGGCAAGCCCGTGGTCAGCGACGAGCAGCTGGCC

CGGTGGCTGGGTCCTAATGCTACCCCTCAAAGTTTGGAAGAGCGGCGCAAGCTCATGATGGC

CGTGGTCCTGGTGACCGTGGAGCTGGAGTGCCTGCGCCGCTTCTTCGCCGACGCGGAGACC

CTGCGCAAGGTCGAGGAGAACCTGCACTACCTCTTCAGGCACGGGTTCGTGCGCCAGGCCT

GCAAGATCTCCAACGTGGAGCTGACCAACCTGGTCTCCTACATGGGCATCTTGCACGAGAAC

CGCCTGGGGCAGAACGTGCTGCACACCACCCTGCGCGGGGAGGCCCGCCGCGACTACATC

CGCGACTGCGTCTACCTCTACCTCTGCCACACCTGGCAGACGGGCATGGGCGTGTGGCAGC

AGTGTCTGGAGGAGCAGAACCTGAAAGAGCTCTGCAAGCTCCTGCAAAAGAACCTCAAGGGT

CTGTGGACCGGGTTCGACGAGCGGACCACCGCCTCGGACCTGGCCGACCTCATCTTCCCCG

AGCGCCTCAGGCTGACGCTGCGCAACGGCCTGCCCGACTTTATGAGCCAAAGCATGTTGCAA

AACTTTCGCTCTTTCATCCTCGAACGCTCCGGAATCCTGCCCGCCACCTGCTCCGCGCTGCC

CTCGGACTTCGTGCCGCTGACCTTCCGCGAGTGCCCCCCGCCGCTGTGGAGCCACTGCTAC

CTGCTGCGCCTGGCCAACTACCTGGCCTACCACTCGGACGTGATCGAGGACGTCAGCGGCG

AGGGCCTGCTCGAGTGCCACTGCCGCTGCAACCTCTGCACGCCGCACCGCTCCCTGGCCTG

CAACCCCCAGCTGCTGAGCGAGACCCAGATCATCGGCACCTTCGAGTTGCAAGGGCCCAGC

GAGGGCGAGGGAGCCAAGGGGGGTCTGAAACTCACCCCGGGGCTGTGGACCTCGGCCTAC

-continued

TTGCGCAAGTTCGTGCCCGAGGATTACCATCCCTTCGAGATCAGGTTCTACGAGGACCAATC

CCAGCCGCCCAAGGCCGAGCTGTCGGCCTGCGTCATCACCCAGGGGGCGATCCTGGCCCAA

TTGCAAGCCATCCAGAAATCCCGCCAAGAATTCTTGCTGAAAAAGGGCCGCGGGGTCTACCT

CGACCCCCAGACCGGTGAGGAGCTCAACCCCGGCTTCCCCCAGGATGCCCCGAGGAAACAA

GAAGCTGAAAGTGGAGCTGCCGCCCGTGGAGGATTTGGAGGAAGACTGGGAGAACAGCAGT

CAGGCAGAGGAGATGGAGGAAGACTGGGACAGCACTCAGGCAGAGGAGGACAGCCTGCAA

GACAGTCTGGAGGAAGACGAGGAGGAGGCAGAGGAGGAGGTGGAAGAAGCAGCCGCCGCC

AGACCGTCGTCCTCGGCGGGGGAGAAAGCAAGCAGCACGGATACCATCTCCGCTCCGGGTC

GGGGTCCCGCTCGGCCCCACAGTAGATGGGACGAGACCGGGCGATTCCCGAACCCCACCAC

CCAGACCGGTAAGAAGGAGCGGCAGGGATACAAGTCCTGGCGGGGGCACAAAAACGCCATC

GTCTCCTGCTTGCAGGCCTGCGGGGGCAACATCTCCTTCACCCGGCGCTACCTGCTCTTCCA

CCGCGGGGTGAACTTCCCCCGCAACATCTTGCATTACTACCGTCACCTCCACAGCCCCTACT

ACTTCCAAGAAGAGGCAGCAGCAGCAGAAAAAGACCAGAAAACCAGCTAGAAAATCCACAGC

GGCGGCAGCGGCAGGTGGACTGAGGATCGCGGCGAACGAGCCGGCGCAGACCCGGGAGCT

GAGGAACCGGATCTTTCCCACCCTCTATGCCATCTTCCAGCAGAGTCGGGGGCAGGAGCAG

GAACTGAAAGTCAAGAACCGTTCTCTGCGCTCGCTCACCCGCAGTTGTCTGTATCACAAGAG

CGAAGACCAACTTCAGCGCACTCTCGAGGACGCCGAGGCTCTCTTCAACAAGTACTGCGCGC

TCACTCTTAAAGAGTAGCCCGCGCCCGCCCAGTCGCAGAAAAAGGCGGGAATTACGTCACCT

GTGCCCTTCGCCCTAGCCGCCTCCACCCAGCACCGCCATGAGCAAAGAGATTCCCACGCCTT

ACATGTGGAGCTACCAGCCCCAGATGGGCCTGGCCGCCGGCGCCGCCCAGGACTACTCCAC

CCGCATGAATTGGCTCAGCGCCGGGCCCGCGATGATCTCACGGGTGAATGACATCCGCGCC

CACCGAAACCAGATACTCCTAGAACAGTCAGCGCTCACCGCCACGCCCCGCAATCACCTCAA

TCCGCGTAATTGGCCCGCCGCCCTGGTGTACCAGGAAATTCCCCAGCCCACGACCGTACTAC

TTCCGCGAGACGCCCAGGCCGAAGTCCAGCTGACTAACTCAGGTGTCCAGCTGGCGGGCGG

CGCCACCCTGTGTCGTCACCGCCCCGCTCAGGGTATAAAGCGGCTGGTGATCCGGGGCAGA

GGCACACAGCTCAACGACGAGGTGGTGAGCTCTTCGCTGGGTCTGCGACCTGACGGAGTCT

TCCAACTCGCCGGATCGGGGAGATCTTCCTTCACGCCTCGTCAGGCGGTCCTGACTTTGGAG

AGTTCGTCCTCGCAGCCCCGCTCGGGCGGCATCGGCACTCTCCAGTTCGTGGAGGAGTTCA

CTCCCTCGGTCTACTTCAACCCCTTCTCCGGCTCCCCCGGCCACTACCCGGACGAGTTCATC

CCGAACTTTGACGCCATCAGCGAGTCGGTGGACGGCTACGATTGATTAATTAATCAACTAACC

CCTTACCCCTTTACCCTCCAGTAAAAATAAAGATTAAAAATGATTGAATTGATCAATAAAGAAT

CACTTACTTGAAATCTGAAACCAGGTCTCTGTCCATGTTTTCTGTCAGCAGCACTTCACTCCC

CTCTTCCCAACTCTGGTACTGCAGGCCCCGGCGGGCTGCAAACTTCCTCCACACTCTGAAGG

GGATGTCAAATTCCTCCTGTCCCTCAATCTTCATTTTTATCTTCTATCAGATGTCCAAAAAGCG

CGCGCGGGTGGATGATGGCTTCGACCCCGTGTACCCCTACGATGCAGACAACGCACCGACT

GTGCCCTTCATCAACCCTCCCTTCGTCTCTTCAGATGGATTCCAAGAAAAGCCCCTGGGGGT

GTTGTCCCTGCGACTGGCCGACCCCGTCACCACCAAGAATGGGGCTGTCACCCTCAAGCTG

GGGGAGGGGGTGGACCTCGACGACTCGGGAAAACTCATCTCCAAAAATGCCACCAAGGCCA

CTGCCCCTCTCAGTATTTCCAACGGCACCATTTCCCTTAACATGGCTGCCCCTTTTTACAACA

ACAATGGAACGTTAAGTCTCAATGTTTCTACACCATTAGCAGTATTTCCCACTTTTAACACTTT

AGGTATCAGTCTTGGAAACGGTCTTCAAACTTCTAATAAGTTGCTGACTGTACAGTTAACTCAT

-continued

CCTCTTACATTCAGCTCAAATAGCATCACAGTAAAAACAGACAAAGGACTCTATATTAATTCTA

GTGGAAACAGAGGGCTTGAGGCTAACATAAGCCTAAAAAGAGGACTGATTTTTGATGGTAATG

CTATTGCAACATACCTTGGAAGTGGTTTAGACTATGGATCCTATGATAGCGATGGGAAAACAA

GACCCATCATCACCAAAATTGGAGCAGGTTTGAATTTTGATGCTAATAATGCCATGGCTGTGA

AGCTAGGCACAGGTTTAAGTTTTGACTCTGCCGGTGCCTTAACAGCTGGAAACAAAGAGGAT

GACAAGCTAACACTTTGGACTACACCTGACCCAAGCCCTAATTGTCAATTACTTTCAGACAGA

GATGCCAAATTTACCCTATGTCTTACAAAATGCGGTAGTCAAATACTAGGCACTGTTGCAGTA

GCTGCTGTTACTGTAGGTTCAGCACTAAATCCAATTAATGACACAGTAAAAAGCGCCATAGTA

TTCCTTAGATTTGACTCTGACGGTGTGCTCATGTCAAACTCATCAATGGTAGGTGATTACTGG

AACTTTAGGGAAGGACAGACCACCCAAAGTGTGGCCTATACAAATGCTGTGGGATTCATGCC

CAATCTAGGTGCATATCCTAAAACCCAAAGCAAAACACCAAAAAATAGTATAGTAAGTCAGGT

ATATTTAAATGGAGAAACTACTATGCCAATGACACTGACAATAACTTTCAATGGCACTGATGAA

AAAGACACAACACCTGTGAGCACTTACTCCATGACTTTTACATGGCAGTGGACTGGAGACTAT

AAGGACAAGAATATTACCTTTGCTACCAACTCCTTTACTTTCTCCTACATGGCCCAAGAATAAA

CCCTGCATGCCAACCCCATTGTTCCCACCACTATGGAAAACTCTGAAGCAGAAAAAAATAAAG

TTCAAGTGTTTTATTGATTCAACAGTTTTCTCACAGAACCCTAGTATTCAACCTGCCACCTCCC

TCCCAACACACAGAGTACACAGTCCTTTCTCCCCGGCTGGCCTTAAAAAGCATCATATCATGG

GTAACAGACATATTCTTAGGTGTTATATTCCACACGGTTTCCTGTCGAGCCAAACGCTCATCA

GTGATATTAATAAACTCCCCGGGCAGCTCACTTAAGTTCATGTCGCTGTCCAGCTGCTGAGCC

ACAGGCTGCTGTCCAACTTGCGGTTGCTTAACGGGCGGCGAAGGAGAAGTCCACGCCTACAT

GGGGGTAGAGTCATAATCGTGCATCAGGATAGGGCGGTGGTGCTGCAGCAGCGCGCGAATA

AACTGCTGCCGCCGCCGCTCCGTCCTGCAGGAATACAACATGGCAGTGGTCTCCTCAGCGAT

GATTCGCACCGCCCGCAGCATAAGGCGCCTTGTCCTCCGGGCACAGCAGCGCACCCTGATC

TCACTTAAATCAGCACAGTAACTGCAGCACAGCACCACAATATTGTTCAAAATCCCACAGTGC

AAGGCGCTGTATCCAAAGCTCATGGCGGGGACCACAGAACCCACGTGGCCATCATACCACAA

GCGCAGGTAGATTAAGTGGCGACCCCTCATAAACACGCTGGACATAAACATTACCTCTTTTGG

CATGTTGTAATTCACCACCTCCCGGTACCATATAAACCTCTGATTAAACATGGCGCCATCCAC

CACCATCCTAAACCAGCTGGCCAAAACCTGCCCGCCGGCTATACACTGCAGGGAACCGGGA

CTGGAACAATGACAGTGGAGAGCCCAGGACTCGTAACCATGGATCATCATGCTCGTCATGAT

ATCAATGTTGGCACAACACAGGCACACGTGCATACACTTCCTCAGGATTACAAGCTCCTCCCG

CGTTAGAACCATATCCCAGGGAACAACCCATTCCTGAATCAGCGTAAATCCCACACTGCAGG

GAAGACCTCGCACGTAACTCACGTTGTGCATTGTCAAAGTGTTACATTCGGGCAGCAGCGGA

TGATCCTCCAGTATGGTAGCGCGGGTTTCTGTCTCAAAAGGAGGTAGACGATCCCTACTGTA

CGGAGTGCGCCGAGACAACCGAGATCGTGTTGGTCGTAGTGTCATGCCAAATGGAACGCCG

GACGTAGTCATATTTCCTGAAGCAAAACCAGGTGCGGGCGTGACAAACAGATCTGCGTCTCC

GGTCTCGCCGCTTAGATCGCTCTGTGTAGTAGTTGTAGTATATCCACTCTCTCAAAGCATCCA

GGCGCCCCCTGGCTTCGGGTTCTATGTAAACTCCTTCATGCGCCGCTGCCCTGATAACATCC

ACCACCGCAGAATAAGCCACACCCAGCCAACCTACACATTCGTTCTGCGAGTCACACACGGG

AGGAGCGGGAAGAGCTGGAAGAACCATGATTAACTTTATTCCAAACGGTCTCGGAGCACTTC

AAAATGCAGGTCCCGGAGGTGGCACCTCTCGCCCCCACTGTGTTGGTGGAAAATAACAGCCA

-continued

GGTCAAAGGTGACACGGTTCTCGAGATGTTCCACGGTGGCTTCCAGCAAAGCCTCCACGCGC

ACATCCAGAAACAAGAGGACAGCGAAAGCGGGAGCGTTTTCTAATTCCTCAATCATCATATTA

CACTCCTGCACCATCCCCAGATAATTTTCATTTTTCCAGCCTTGAATGATTCGTATTAGTTCCT

GAGGTAAATCCAAGCCAGCCATGATAAAAAGCTCGCGCAGAGCGCCCTCCACCGGCATTCTT

AAGCACACCCTCATAATTCCAAGAGATTCTGCTCCTGGTTCACCTGCAGCAGATTAACAATGG

GAATATCAAAATCTCTGCCGCGATCCCTAAGCTCCTCCCTCAACAATAACTGTATGTAATCTTT

CATATCATCTCCGAAATTTTTAGCCATAGGGCCGCCAGGAATAAGAGCAGGGCAAGCCACATT

ACAGATAAAGCGAAGTCCTCCCCAGTGWGCATTGCCAAATGTAAGATTGAAATAAGCATGCT

GGCTAGACCCTGTGATATCTTCCAGATAACTGGACAGAAAATCAGGCAAGCAATTTTTAAGAA

AATCAACAAAAGAAAAGTCGTCCAGGTGCAGGTTTAGAGCCTCAGGAACAACGATGGAATAA

GTGCAAGGAGTGCGTTCCAGCATGGTTAGTGTTTTTTTGGTGATCTGTAGAACAAAAAATAAA

CATGCAATATTAAACCATGCTAGCCTGGCGAACAGGTGGGTAAATCACTCTTTCCAGCACCAG

GCAGGCTACGGGGTCTCCGGCGCGACCCTCGTAGAAGCTGTCGCCATGATTGAAAAGCATC

ACCGAGAGACCTTCCCGGTGGCCGGCATGGATGATTCGAGAAGAAGCATACACTCCGGGAA

CATTGGCATCCGTGAGTGAAAAAAAGCGACCTATAAAGCCTCGGGGCACTACAATGCTCAAT

CTCAATTCCAGCAAAGCCACCCCATGCGGATGGAGCACAAAATTGGCAGGTGCGTAAAAAAT

GTAATTACTCCCCTCCTGCACAGGCAGCAAAGCCCCCGCTCCCTCCAGAAACACATACAAAG

CCTCAGCGTCCATAGCTTACCGAGCACGGCAGGCGCAAGAGTCAGAGAAAAGGCTGAGCTC

TAACCTGACTGCCCGCTCCTGTGCTCAATATATAGCCCTAACCTACACTGACGTAAAGGCCAA

AGTCTAAAAATACCCGCCAAAATGACACACACGCCCAGCACACGCCCAGAAACCGGTGACAC

ACTCAAAAAAATACGTGCGCTTCCTCAAACGCCCAAACCGGCGTCATTTCCGGGTTCCCACG

CTACGTCACCGCTCAGCGACTTTCAAATTCCGTCGACCGTTAAAAACGTCACTCGCCCCGCC

CCTAACGGTCGCCCTTCTCTCGGCCAATCACCTTCCTCCCTTCCCAAATTCAAACGCCTCATT

TGCATATTAACGCGCACAAAAAGTTTGAGGTATATATTTGAATGATG

4NSALL Chadox1

[SEQ ID NO: 121]

GTTTAAACGCGGCCGCCAGGCCTACCCACTAGTCAATTCGGGAGGATCGAAACGGCAGATCG

CAAAAAACAGTACATACAGAAGGAGACATGAACATGAACATCAAAAAAATTGTAAAACAAGCC

ACAGTTCTGACTTTTACGACTGCACTTCTGGCAGGAGGAGCGACTCAAGCCTTCGCGAAAGA

AAATAACCAAAAAGCATACAAAGAAACGTACGGCGTCTCTCATATTACACGCCATGATATGCT

GCAGATCCCTAAACAGCAGCAAAACGAAAAATACCAAGTGCCTCAATTCGATCAATCAACGAT

TAAAAATATTGAGTCTGCAAAAGGACTTGATGTGTGGGACAGCTGGCCGCTGCAAAACGCTG

ACGGAACAGTAGCTGAATACAACGGCTATCACGTTGTGTTTGCTCTTGCGGGAAGCCCGAAA

GACGCTGATGACACATCAATCTACATGTTTTATCAAAAGGTCGGCGACAACTCAATCGACAGC

TGGAAAAACGCGGGCCGTGTCTTTAAAGACAGCGATAAGTTCGACGCCAACGATCCGATCCT

GAAAGATCAGACGCAAGAATGGTCCGGTTCTGCAACCTTTACATCTGACGGAAAAATCCGTTT

ATTCTACACTGACTATTCCGGTAAACATTACGGCAAACAAAGCCTGACAACAGCGCAGGTAAA

TGTGTCAAAATCTGATGACACACTCAAAATCAACGGAGTGGAAGATCACAAAACGATTTTTGA

CGGAGACGGAAAAACATATCAGAACGTTCAGCAGTTTATCGATGAAGGCAATTATACATCCGG

CGACAACCATACGCTGAGAGACCCTCACTACGTTGAAGACAAAGGCCATAAATACCTTGTATT

CGAAGCCAACACGGGAACAGAAAACGGATACCAAGGCGAAGAATCTTTATTTAACAAAGCGT

ACTACGGCGGCGGCACGAACTTCTTCCGTAAAGAAAGCCAGAAGCTTCAGCAGAGCGCTAAA

-continued

AAACGCGATGCTGAGTTAGCGAACGGCGCCCTCGGTATCATAGAGTTAAATAATGATTACACA

TTGAAAAAAGTAATGAAGCCGCTGATCACTTCAAACACGGTAACTGATGAAATCGAGCGCGCG

AATGTTTTCAAAATGAACGGCAAATGGTACTTGTTCACTGATTCACGCGGTTCAAAAATGACG

ATCGATGGTATTAACTCAAACGATATTTACATGCTTGGTTATGTATCAAACTCTTTAACCGGCC

CTTACAAGCCGCTGAACAAAACAGGGCTTGTGCTGCAAATGGGTCTTGATCCAAACGATGTG

ACATTCACTTACTCTCACTTCGCAGTGCCGCAAGCCAAAGGCAACAATGTGGTTATCACAAGC

TACATGACAAACAGAGGCTTCTTCGAGGATAAAAAGGCAACATTTGCGCCAAGCTTCTTAATG

AACATCAAAGGCAATAAAACATCCGTTGTCAAAAACAGCATCCTGGAGCAAGGACAGCTGACA

GTCAACTAATAACAGCAAAAAGAAAATGCCGATACTTCATTGGCATTTTCTTTTATTTCTCAAC

AAGATGGTGAATTGACTAGTGGGTAGATCCACAGGACGGGTGTGGTCGCCATGATCGCGTAG

TCGATAGTGGCTCCAAGTAGCGAAGCGAGCAGGACTGGGCGGCGGCCAAAGCGGTCGGACA

GTGCTCCGAGAACGGGTGCGCATAGAAATTGCATCAACGCATATAGCGCTAGCAGCACGCCA

TAGTGACTGGCGATGCTGTCGGAATGGACGATATCCCGCAAGAGGCCCGGCAGTACCGGCA

TAACCAAGCCTATGCCTACAGCATCCAGGGTGACGGTGCCGAGGATGACGATGAGCGCATTG

TTAGATTTCATACACGGTGCCTGACTGCGTTAGCAATTTAACTGTGATAAACTACCGCATTAAA

GCTTATCGATGATAAGCTGTCAAACATGAGAATTGATCCGGAACCCTTAATATAACTTCGTATA

ATGTATGCTATACGAAGTTATTAGGTCCCTCGACTATAGGGTCACCGTCGACAGCGACACACT

TGCATCGGATGCAGCCCGGTTAACGTGCCGGCACGGCCTGGGTAACCAGGTATTTTGTCCAC

ATAACCGTGCGCAAAATGTTGTGGATAAGCAGGACACAGCAGCAATCCACAGCAGGCATACA

ACCGCACACCGAGGTTACTCCGTTCTACAGGTTACGACGACATGTCAATACTTGCCCTTGACA

GGCATTGATGGAATCGTAGTCTCACGCTGATAGTCTGATCGACAATACAAGTGGGACCGTGG

TCCCAGACCGATAATCAGACCGACRAYACGAGTGGGAYCGTGGTCCCAGACTAATAATCAGA

CCGACGATACGAGTGGGACCGTGGTCCCAGACTAATAATCAGACCGACGATACGAGTGGGA

CCGTGGTYCCAGWCTRATWATCAGACCGACGATACRAGTGGRACMGTGGKCCCAGASAKAA

TAWTCAGRCCGAGWTAYGCWKTCKGGCCTGTAACAAAGGACATTAAGTAAAGACAGATAMR

MGTGRGACTAAAACGTGGTCCCAGTCTGATTATCAGACCGACGATACGAGTGGGACCGTGGT

CCCAGACTAATAATCAGACCGACGATACGAGTGGGACCGTGGTCCCAGACTAATAATCAGAC

CGACGATACGAGTGGGACCGTGGTCCCAGTCTGATTATCAGACCGACGATACAAGTGGAACA

GTGGGCCCAGAGAGAATATTCAGGCCAGTTATGCTTTCTGGCCTGTAACAAAGGACATTAAGT

AAAGACAGATAAACGTAGACTAAAACGTGGTCGCATCAGGGTGCTGGCTTTTCAAGTTCCTTA

AGAATGGCCTCAATTTTCTCTATACACTCAGTTGGAACACGAGACCTGTCCAGGTTAAGCACC

ATTTTATCGCCCTTATACAATACTGTCGCTCCAGGAGCAAACTGATGTCGTGAGCTTAAACTA

GTTCTTGATGCAGATGACGTTTTAAGCACAGAAGTTAAAAGAGTGATAACTTCTTCAGCTTCAA

ATATCACCCCAGCTTTTTTCTGCTCATGAAGGTTAGATGCCTGCTGCTTAAGTAATTCCTCTTT

ATCTGTAAAGGCTTTTTGAAGTGCATCACCTGACCGGGCAGATAGTTCACCGGGGTGAGAAA

AAAGAGCAACAACTGATTTAGGCAATTTGGCGGTGTTGATACAGCGGGTAATAATCTTACGTG

AAATATTTTCCGCATCAGCCAGCGCAGAAATATTTCCAGCAAATTCATTCTGCAATCGGCTTG

CATAACGCTGACCACGTTCATAAGCACTTGTTGGGCGATAATCGTTACCCAATCTGGATAATG

CAGCCATCTGCTCATCATCCAGCTCGCCAACCAGAACACGATAATCACTTTCGGTAAGTGCAG

CAGCTTTACGACGGCGACTCCCATCGGCAATTTCTATGACACCAGATACTCTTCGACCGAACG

-continued

CCGGTGTCTGTTGACCAGTCAGTAGAAAAGAAGGGATGAGATCATCCAGTGCGTCCTCAGTA

AGCAGCTCCTGGTCACGTTCATTACCTGACCATACCCGAGAGGTCTTCTCAACACTATCACCC

CGGAGCACTTCAAGAGTAAACTTCACATCCCGACCACATACAGGCAAAGTAATGGCATTACCG

CGAGCCATTACTCCTACGCGCGCAATTAACGAATCCACCATCGGGGCAGCTGGTGTCGATAA

CGAAGTATCTTCAACCGGTTGAGTATTGAGCGTATGTTTTGGAATAACAGGCGCACGCTTCAT

TATCTAATCTCCCAGCGTGGTTTAATCAGACGATCGAAAATTTCATTGCAGACAGGTTCCCAA

ATAGAAAGAGCATTTCTCCAGGCACCAGTTGAAGAGCGTTGATCAATGGCCTGTTCAAAAACA

GTTCTCATCCGGATCTGACCTTTACCAACTTCATCCGTTTCACGTACAACATTTTTTAGAACCA

TGCTTCCCCAGGCATCCCGAATTTGCTCCTCCATCCACGGGGACTGAGAGCCATTACTATTG

CTGTATTTGGTAAGCAAAATACGTACATCAGGCTCGAACCCTTTAAGATCAACGTTCTTGAGC

AGATCACGAAGCATATCGAAAAACTGCAGTGCGGAGGTGTAGTCAAACAACTCAGCAGGCGT

GGGAACAATCAGCACATCAGCAGCACATACGACATTAATCGTGCCGATACCCAGGTTAGGCG

CGCTGTCAATAACTATGACATCATAGTCATGAGCAACAGTTTCAATGGCCAGTCGGAGCATCA

GGTGTGGATCGGTGGGCAGTTTACCTTCATCAAATTTGCCCATTAACTCAGTTTCAATACGGT

GCAGAGCCAGACAGGAAGGAATAATGTCAAGCCCCGGCCAGCAAGTGGGCTTTATTGCATAA

GTGACATCGTCCTTTTCCCCAAGATAGAAAGGCAGGAGAGTGTCTTCTGCATGAATATGAAGA

TCTGGTACCCATCCGTGATACATTGAGGCTGTTCCCTGGGGGTCGTTACCTTCCACGAGCAA

AACACGTAGCCCCTTCAGAGCCAGATCCTGAGCAAGATGAACAGAAACTGAGGTTTTGTAAAC

GCCACCTTTATGGGCAGCAACCCCGATCACCGGTGGAAATACGTCTTCAGCACGTCGCAATC

GCGTACCAAACACATCACGCATATGATTAATTTGTTCAATTGTATAACCAACACGTTGCTCAAC

CCGTCCTCGAATTTCCATATCCGGGTGCGGTAGTCGCCCTGCTTTCTCGGCATCTCTGATAG

CCTGAGAAGAAACCCCAACTAAATCCGCTGCTTCACCTATTCTCCAGCGCCGGGTTATTTTCC

TCGCTTCCGGGCTGTCATCATTAAACTGTGCAATGGCGATAGCCTTCGTCATTTCATGACCAG

CGTTTATGCACTGGTTAAGTGTTTCCATGAGTTTCATTCTGAACATCCTTTAATCATTGCTTTG

CGTTTTTTTATTAAATCTTGCAATTTACTGCAAAGCAACAACAAAATCGCAAAGTCATCAAAAAA

CCGCAAAGTTGTTTAAAATAAGAGCAACACTACAAAAGGAGATAAGAAGAGCACATACCTCAG

TCACTTATTATCACTAGCGCTCGCCGCAGCCGTGTAACCGAGCATAGCGAGCGAACTGGCGA

GGAAGCAAAGAAGAACTGTTCTGTCAGATAGCTCTTACGCTCAGCGCAAGAAGAAATATCCAC

CGTGGGAAAAACTCCAGGTAGAGGTACACACGCGGATAGCCAATTCAGAGTAATAAACTGTG

ATAATCAACCCTCATCAATGATGACGAACTAACCCCCGATATCAGGTCACATGACGAAGGGAA

AGAGAAGGAAATCAACTGTGACAAACTGCCCTCAAATTTGGCTTCCTTAAAAATTACAGTTCAA

AAAGTATGAGAAAATCCATGCAGGCTGAAGGAAACAGCAAAACTGTGACAAATTACCCTCAGT

AGGTCAGAACAAATGTGACGAACCACCCTCAAATCTGTGACAGATAACCCTCAGACTATCCTG

TCGTCATGGAAGTGATATCGCGGAAGGAAAATACGATATGAGTCGTCTGGCGGCCTTTCTTTT

TCTCAATGTATGAGAGGCGCATTGGAGTTCTGCTGTTGATCTCATTAACACAGACCTGCAGGA

AGCGGCGGCGGAAGTCAGGCATACGCTGGTAACTTTGAGGCAGCTGGTAACGCTCTATGATC

CAGTCGATTTTCAGAGAGACGATGCCTGAGCCATCCGGCTTACGATACTGACACAGGGATTC

GTATAAACGCATGGCATACGGATTGGTGATTTCTTTTGTTTCACTAAGCCGAAACTGCGTAAA

CCGGTTCTGTAACCCGATAAAGAAGGGAATGAGATATGGGTTGATATGTACACTGTAAAGCCC

TCTGGATGGACTGTGCGCACGTTTGATAAACCAAGGAAAAGATTCATAGCCTTTTTCATCGCC

GGCATCCTCTTCAGGGCGATAAAAAACCACTTCCTTCCCCGCGAAACTCTTCAATGCCTGCCG

-continued

TATATCCTTACTGGCTTCCGCAGAGGTCAATCCGAATATTTCAGCATATTTAGCAACATGGATC

TCGCAGATACCGTCATGTTCCTGTAGGGTGCCATCAGATTTTCTGATCTGGTCAACGAACAGA

TACAGCATACGTTTTTGATCCCGGGAGAGACTATATGCCGCCTCAGTGAGGTCGTTTGACTG

GACGATTCGCGGGCTATTTTTACGTTTCTTGTGATTGATAACCGCTGTTTCCGCCATGACAGA

TCCATGTGAAGTGTGACAAGTTTTTAGATTGTCACACTAAATAAAAAAGAGTCAATAAGCAGG

GATAACTTTGTGAAAAAACAGCTTCTTCTGAGGGCAATTTGTCACAGGGTTAAGGGCAATTTG

TCACAGACAGGACTGTCATTTGAGGGTGATTTGTCACACTGAAAGGGCAATTTGTCACAACAC

CTTCTCTAGAACCAGCATGGATAAAGGCCTACAAGGCGCTCTAAAAAAGAAGATCTAAAAACT

ATAAAAAAAATAATTATAAAAATATCCCCGTGGATAAGTGGATAACCCCAAGGGAAGTTTTTC

AGGCATCGTGTGTAAGCAGAATATATAAGTGCTGTTCCCTGGTGCTTCCTCGCTCACTCGAGG

GCTTCGCCCTGTCGCTCAACTGCGGCGAGCACTACTGGCTGTAAAAGGACAGACCACATCAT

GGTTCTGTGTTCATTAGGTTGTTCTGTCCATTGCTGACATAATCCGCTCCACTTCAACGTAACA

CCGCACGAAGATTTCTATTGTTCCTGAAGGCATATTCAAATCGTTTTCGTTACCGCTTGCAGG

CATCATGACAGAACACTACTTCCTATAAACGCTACACAGGCTCCTGAGATTAATAATGCGGAT

CTCTACGATAATGGGAGATTTTCCCGACTGTTTCGTTCGCTTCTCAGTGGATAACAGCCAGCT

TCTCTGTTTAACAGACAAAAACAGCATATCCACTCAGTTCCACATTTCCATATAAAGGCCAAGG

CATTTATTCTCAGGATAATTGTTTCAGCATCGCAACCGCATCAGACTCCGGCATCGCAAACTG

CACCCGGTGCCGGGCAGCCACATCCAGCGCAAAAACCTTCGTGTAGACTTCCGTTGAACTGA

TGGACTTATGTCCCATCAGGCTTTGCAGAACTTTCAGCGGTATACCGGCATACAGCATGTGCA

TCGCATAGGAATGGCGGAACGTATGTGGTGTGACCGGAACAGAGAACGTCACACCGTCAGCA

GCAGCGGCGGCAACCGCCTCCCCAATCCAGGTCCTGACCGTTCTGTCCGTCACTTCCCAGAT

CCGCGCTTTCTCTGTCCTTCCTGTGCGACGGTTACGCCGCTCCATGAGCTTATCGCGAATAAA

TACCTGTGACGGAAGATCACTTCGCAGAATAAATAAATCCTGGTGTCCCTGTTGATACCGGGA

AGCCCTGGGCCAACTTTTGGCGAAAATGAGACGTTGATCGGCACGTAAGAGGTTCCAACTTT

CACCATAATGAAATAAGATCACTACCGGGCGTATTTTTTGAGTTATCGAGATTTTCAGGAGCTA

AGGAAGCTAAAATGGAGAAAAAAATCACTGGATATACCACCGTTGATATATCCCAATGGCATC

GTAAAGAACATTTTGAGGCATTTCAGTCAGTTGCTCAATGTACCTATAACCAGACCGTTCAGC

TGGATATTACGGCCTTTTTAAAGACCGTAAAGAAAAATAAGCACAAGTTTTATCCGGCCTTTAT

TCACATTCTTGCCCGCCTGATGAATGCTCATCCGGAGTTCCGTATGGCAATGAAAGACGGTG

AGCTGGTGATATGGGATAGTGTTCACCCTTGTTACACCGTTTTCCATGAGCAAACTGAAACGT

TTTCATCGCTCTGGAGTGAATACCACGACGATTTCCGGCAGTTTCTACACATATATTCGCAAG

ATGTGGCGTGTTACGGTGAAAACCTGGCCTATTTCCCTAAAGGGTTTATTGAGAATATGTTTTT

CGTCTCAGCCAATCCCTGGGTGAGTTTCACCAGTTTTGATTTAAACGTGGCCAATATGGACAA

CTTCTTCGCCCCCGTTTTCACCATGGGCAAATATTATACGCAAGGCGACAAGGTGCTGATGCC

GCTGGCGATTCAGGTTCATCATGCCGTTTGTGATGGCTTCCATGTCGGCAGAATGCTTAATGA

ATTACAACAGTACTGCGATGAGTGGCAGGGCGGGGCGTAATTTTTTTAAGGCAGTTATTGGTG

CCCTTAAACGCCTGGTTGCTACGCCTGAATAAGTGATAATAAGCGGATGAATGGCAGAAATTC

GATGATAAGCTGTCAAACATGAGAATTGGTCGACGGCGCGCCAAAGCTTGCATGCCTGCAGC

CGCGTAACCTGGCAAAATCGGTTACGGTTGAGTAATAAATGGATGCCCTGCGTAAGCGGGGC

ACATTTCATTACCTCTTTCTCCGCACCCGACATAGATAATAACTTCGTATAGTATACATTATAC

-continued

GAAGTTATCTAGTAGACTTAATCGCGTTTAAACCCATCATCAATAATATACCTCAAACTTTTTGT

GCGCGTTAATATGCAAATGAGGCGTTTGAATTTGGGAAGGGAGGAAGGTGATTGGCCGAGAG

AAGGGCGACCGTTAGGGGCGGGGCGAGTGACGTTTTGATGACGTGACCGCGAGGAGGAGC

CAGTTTGCAAGTTCTCGTGGGAAAAGTGACGTCAAACGAGGTGTGGTTTGAACACGGAAATA

CTCAATTTTCCCGCGCTCTCTGACAGGAAATGAGGTGTTTCTAGGCGGATGCAAGTGAAAAC

GGGCCATTTTCGCGCGAAAACTGAATGAGGAAGTGAAAATCTGAGTAATTTCGCGTTTATGAC

AGGGAGGAGTATTTGCCGAGGGCCGAGTAGACTTTGACCGATTACGTGGGGGTTTCGATTAC

CGTGTTTTTCACCTAAATTTCCGCGTACGGTGTCAAAGTCCGGTGTTTTTACGTAGGTGTCAG

CTGATCGCCAGGGTATTTAAACCTGCGCTCTCCAGTCAAGAGGCCACTCTTGAGTGCCAGCG

AGAAGAGTTTTCTCCTCCGCGCGCGAGTCAGATCTACACTTTGAAAGGCGATCGCTAGCGAC

ATCGATCCAAATAATGATTTTATTTTGACTGATAGTGACCTGTTCGTTGCAACAAATTGATAAG

CAATGCTTTTTTATAATGCCAACTTTGTACAAAAAAGCAGGCTCCACCATGGGAACCAATTCAG

TCGAGCCTTTCACTCATTAGATGCATGTCGTTACATAACTTACGGTAAATGGCCCGCCTGGCT

GACCGCCCAACGACCCCCGCCCATTGACGTCAATAATGACGTATGTTCCCATAGTAACGCCA

ATAGGGACTTTCCATTGACGTCAATGGGTGGAGTATTTACGGTAAACTGCCCACTTGGCAGTA

CATCAAGTGTATCATATGCCAAGTACGCCCCCTATTGACGTCAATGACGGTAAATGGCCCGCC

TGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTT

GACTCACGGGGATTTCCAAGTCTCCACCCCATTGACGTCAATGGGAGTTTGTTTTGGCACCAA

AATCAACGGGACTTTCCAAAATGTCGTAACAACTCCGCCCCATTGACGCAAATGGGCGGTAG

GCGTGTACGGTGGGAGGTCTATATAAGCAGAGCTCTCCCTATCAGTGATAGAGATCTCCCTAT

CAGTGATAGAGATCGTCGACGAGCTCGTTTAGTGAACCGTCAGATCGCCTGGAGACGCCATC

CACGCTGTTTTGACCTCCATAGAAGACACCGGGACCGATCCAGCCTCCGGTTAAGCTCGGTA

CCGCTAGCCGCGCCGCCACCATGGATGCAATGAAGAGAGGGCTCTGCTGTGTGCTGCTGCT

GTGTGGAGCAGTCTTCGTTTCGCCCAGCCAGGAAATCCATGCCCGATTCAGAAGAGGATCGA

AGCTTGCCAGCCAGATCGGCGCCGGCGTGTTCAAGGAGGGCGTGTTCCACACCATGTGGCA

CGTGACCAGGGGCGCCGTGCTGATGCACCAGGGCAAGAGGATCGAGCCCAGCTGGGCCGA

CGTGAAGAAGGACCTGATCAGCTACAGCGTGAAGAAGGACCTGATCAGCTACGGCGGCGGC

TGGAGGCTGGAGGGCGAGTGGGACGAGGGCGAGGAGGTGCAGGTGATCGCCGTGGAGCCC

GGCAAGAACCCCAAGGCCGTGCAGACCAAGCCCGGCCTGTTCAAGACCCCCGAGGGCGAGA

TCGGCGCCATCGCCCTGGACTTCAAGCCCGGCACCAGCGGCAGCCCCATCGTGAACAGGGA

GGGCACCAGCGGCAGCCCCATCATCAACAGGGAGGGCAAGGTGGTGGGCCTGTACGGCAA

CGGCGTGGTGACCAAGAGCGGCGCCTACGTGAGCGCCATCGCCCAGACCAACGCCGAGCC

CCTGCCCGAGATCGAGGACGAGGTGTTCAGGAAGAGGAACCTGACCATCATGGACCTGCAC

CCCGGCGCCGGCAAGACCAAGAGGTACCTGCCCGCCATCGTGAGGGAGGCCATCAAGAGGA

GGCTGAGGACCCTGATCCTGGCCCCCACCAGGGTGGTGGCCGCCGAGATGGCCCCCACCA

GGGTGGTGGCCAGCGAGATGGAGGAGGCCCTGAAGGGCCTGCCCATCAGGTACGCCCTGA

GGGGCCTGCCCATCAGGTACCAGACCACCGCCATCAAGGCCGAGCACACCGGCAAGGAGAT

CGTGGACCTGATGTGCCACGCCACCTTCACCATGAGGCTGCTGAGCCCCGTGAGGGTGCCC

AACTACAACCTGATCATCATGGACGAGGCCCACTTCACCGACCCCGCCAGCATCGCCGCCAG

GGGCTACATCAGCACCAGGGTGGAGATGGGCGAGGCCGCCGCCATCTTCATGACCGCCACC

-continued

```
CCCCCCGGCAGCGCCGACGCCTTCCCCCAGAGCAACGCCCCCATCGAGGACGAGGAGAGG

GAGATCCCCGAGAGGAGCTGGAACAGCGGCTTCGACTGGATCACCGACTTCGCCGGCAAGA

CCGTGTGGTTCGTGCCCAGCATCAAGGCCGGCAACGACATCGCCAACTGCCTGAGGAAGAA

CGGCAAGAAGGTGATCCAGCTGAGCAGGAAGACCTTCGACACCGAGTACCCCAAGACCAAG

CTGAACGACTGGGACTTCGTGGTGACCACCGACATCAGCGAGATGGGCGCCAACTTCAAGG

CCGACAGGGTGATCGACCCCAGGAGGTGCCTGAAGCCCGTGATCCTGACCGACGGCCCCGA

GAGGGTGATCCTGGCCGGCCCCATGCCCGTGACCGCCGCCAGCGCCGCCCAGAGGAGGGG

CAGGATCGGCAGGAACCACAAGAAGGAGAACGACCAGTACATCTACATGGGCCAGCCCCTG

AACAACGACGAGGACCACGCCCACTGGACCGAGGCCAAGATGCTGCTGGACAACATCAACA

CCCCCGAGGGCATCATCCCCGCCCTGTTCACCCCCGAGGGCATCATCCCCAGCATGTTCACC

CCCGAGGGCATCATCCCCACCCTGTTCACCCCCGAGGGCATCATCCCCAGCCTGGAGCCCG

AGAGGGAGAAGAGCGCCGCCATCGACGGCGAGTACAGGCTGAGGGGCGAGGCCAGGAAGA

CCTTCGTGGAGCTGGGCGAGGCCAGGAAGACCTTCGTGGACCTGGGCGAGCAGAGGAAGAC

CTTCGTGGAGCTGATGAGGAGGGGCGACCTGCCCGTGTGGCTGAGCTACAAGGTGGCCAGC

GCCGGCTTCCAGTACAAGGACAGGGAGTGGTGCTTCGACGGCGAGAGGAACAACCAGATCC

TGGAGGAGAACATGGACGTGGAGATCTGGACCAAGGAGGGCGAGAAGAAGAAGCTGAGGCC

CAGGTGGCTGGACGCCAGGACCTACGCCGACCCCCTGGCCCTGAAGGAGTTCAAGGACTTC

GCCGCCGGCAGGAAGAGCATCGCCACCGAGATCGGCAGGGTGCCCAGCCACCTGGCCCAC

AGGACCAGGGCCTACCAGCACGCCCTGGAGGAGCTGCCCGAGACCCTGGAGACCCTGCTGC

TGCTGGCCCTGCTGGGCGCCTTCCTGTTCTTCCTGAGCGGCAAGGGCATCGGCAAGATGAG

CATCGGCCTGTGCTGCATCATCGCCGCCAGCCTGCTGTGGATGGCCGAGATCCAGCCCCAC

TGGATCGCCGCCAGCATCATCCTGGAGTTCTTCCTGATGGTGCTGCTGATCCCCGAGCCCGA

GAAGCAGAGGACCCCCCAGGACAACCAGCTGGCCTACGTGGTGATCGGCATCCTGACCCTG

GCCGCCGCCATCGCCGCCAACGAGATGGGCCTGCTGGAGACCACCAAGAAGGACCTGGGCA

TCGGCCACGTGGCCCCCACCGCCATCCTGGACGTGGACCTGCACCCCGCCAGCGCCTGGAC

CCTGTACGCCGTGGCCACCACCATCATCACCCCCATGCTGAGGCACACCATCGAGAACAGCA

CCGCCAACGTGAGCCTGACCGCCATCGCCAACCAGGCCGCCGTGCTGATGATCGCCAACCA

GGCCACCGTGCTGATGGGCCTGGACAAGGGCTGGCCCATCAGCAAGATGGACCTGGGCGTG

CCCCTGCTGGCCCTGGGCTGCTACAGCCAGGTGAACCCCCTGACCCTGACCGCCGCCGTGC

TGCTGCTGATCACCCACTACGCCATCATCGGCCCCGGCCTGCAGGCCAAGGCCACCAGGGA

GGCCCAGAAGAGGACCGCCGCCGGCATCATGAAGAACCCCACCGTGGACGGCATCATGGCC

ATCGACCTGGACCCCATCCCCTACGACCCCAAGTTCGAGAAGCAGCTGGGCCAGGTGATGCT

GCTGATCCTGTGCGTGAGCCAGATCCTGCTGATGAGGACCACCTGGGCCGTGCTGCTGATG

AGGACCACCTGGGCCCTGTGCGAGGCCCTGACCCTGGCCACCGGCCCCATCACCACCCTGT

GGGAGGGCAACCCCGGCAAGTTCTGGAACACCACCATCGCCGTGAGCATGGCCAACATCTT

CAGGGGCAGCTACCTGGCCGGCGCCGGCCTGGCCTTCAGCCTGATCAAGAACAGGAGGGG

CACCGGCGCCCAGGGCGAGACCCTGGGCGAGAAGTGGAAGAGGCAGCTGAACCAGCTGGA

CAAGAGCGAGTTCGAGGAGTACAAGAAGAGCGGCATCCTGGAGGTGGACAGGACCGAGGCC

AAGGAGGCCATCAAGAGGGGCGAGACCGACCACCACGCCGTGAGCAGGGGCAGCGCCAAG

CTGAGGTGGTTCGTGGAGAGGAACATGGTGATCCCCGAGGGCAGGGTGATCGACCTGGGCT
```

-continued

GCGGCAGGGGCGGCTGGAGCTACTACTGCGCCGGCCTGAAGAAGGTGAGGGAGGTGAGGG

GCTACACCAAGGGCGGCCCCGGCCACGAGGAGCCCATCCCCATGGCCACCTACGGCTGGAA

CCTGGTGAAGCTGCACAGCGGCGTGGACGTGTTCTTCCCCGAGAAGTGCGACACCCTGCTG

TGCGACATCGGCGAGAGCAGCCCCAACCCCACCATCGAGGAGGGCAGGACCCTGAGGGTG

CTGAAGATGGTGGAGCCCTGGCTGAAGGGCAACCAGTTCTGCATCAAGATCCTGAACCCCTA

CATGCCCAGCGTGATCGAGGAGCTGGAGAAGCTGCAGAGGAAGCACGGCGGCATGCTGGTG

AGGAACCCCCTGAGCAGGAACAGCACCCACGAGATGTACTGGGTGAGCAACGGCACCGGCA

ACATCGTGAGCGCCGTGAACATGATCAGCAGGATGCTGATCAACAGGTTCACCATGGCCCAC

AAGAAGCCCACCTACGAGAGGGACGTGGACCTGGGCGCCGGCAGCACCTGGCACTACGACG

AGGACAACCCCTACAAGACCTGGGCCTACCACGGCAGCTACGAGGTGAAGGCCACCGGCAG

CGCCAGCAGCATGGTGAACGGCGTGGTGAAGCTGCTGACCAAGCCCTGGGACGTGGTGCCC

ATGGTGACCCAGATGGCCATGACCGACACCACCCCCTTCGGCCAGCAGAGGGTGTTCAAGG

AGAAGGTGGACACCAGGACCCCCGAGGCCAAGGAGAACGCCGCCATCGGCGCCGTGTTCCA

GGACGAGAACGGCTGGAAGAGCGCCAGGGAGGCCGTGGAGGACAGCGAGAGGGCCCTGCA

CCTGGAGGGCAAGTGCGAGAGCTGCGTGTACAACATGATGGGCAAGAGGGAGAAGAAGCTG

GGCGAGTTCGGCAAGGCCAAGGGCAGCAGGGCCATCTGGTACATGTGGCTGGGCGCCAGG

TTCCTGGAGTTCGAGGCCCTGGGCTTCCTGAACGAGGACCACTGGTTCAGCAGGGAGAACA

GCCTGAGCGGCGTGGAGGGCGAGGGCCTGCACAAGCTGGGCTACATCCTGAGGGACATCA

GCAAGATCCCCGGCGGCGCCATGTACGCCGACGACACCGCCGGCTGGGACACCAGGATCAC

CGAGGACGACCTGCACAACGAGGAGAAGATCCTGGCCAAGGCCATCTTCAAGCTGACCTACC

AGAACAAGGTGGTGAAGGTGCAGAGGCCCACCCCCAGGGGCGCCGTGATGGACATCATCAG

CAGGAAGGACCAGAGGGGCAGCGGCCAGGTGGGCACCTACGGCCTGAACACCTTCACCAAC

ATGGAGGCCCAGCTGATCAGGCAGATGGAGGCCGAGGGCGTGATCACCGAGTGCGGCGTG

GACAGGCTGAAGAGGATGGCCATCAGCGGCGACGACTGCGTGGTGAAGCCCCCCCAGTGG

GAGCCCAGCAAGGGCTGGCACGACTGGCAGCAGGTGCCCTTCTGCAGCCACCACTTCCACG

AGATCTTCATGAAGGACGGCAGGAAGCTGGTGGTGCCCTGCAGGAACCAGGACGAGCTGAT

CGGCAGGGCCAGGATCAGCCAGGGCGCCGGCTGGAGCCTGAGGGAGACCGCCTGCCTGGG

CAAGAGCTACGCCCAGATGTGGCAGCTGATGTACTTCCACAGGAGGGACCTGAGGCTGGCC

AGCAACGCCATCTGCAGCGCCGTGCCCAGCCACTGGGTGCCCACCAGCAGGACCACCTGGA

GCATCCACGCCCACCACGAGTGGATGACCACCGAGGACATGCTGGCCGTGTGGAACAGGGT

GTGGATCGAGGAGAACCCCTGGATGGAGGACAAGACCCACATCCACAGCTGGGAGGACGTG

CCCTACCTGGGCAAGAGGGAGGACCAGTGGTGCGGCAGCCTGATCGGCCTGACCAGCAGG

GCCACCTGGGCCAAGAACATCGCTGGATCCGGGCCCGGGGCTTCAGGTAAGCCTATCCCTA

ACCCTCTCCTCGGTCTCGATTCTACGCGGACCTGATGAGCGGCCGCTCGAGCATGCATCTAG

AGGGCCCTATTCTATAGTGTCACCTAAATGCTAGAGCTCGCTGATCAGCCTCGACTGTGCCTT

CTAGTTGCCAGCCATCTGTTGTTTGCCCCTCCCCCGTGCCTTCCTTGACCCTGGAAGGTGCC

ACTCCCACTGTCCTTTCCTAATAAAATGAGGAAATTGCATCGCATTGTCTGAGTAGGTGTCATT

CTATTCTGGGGGGTGGGGTGGGGCAGGACAGCAAGGGGGAGGATTGGGAAGACAATAGCA

GGCATGCTGGGGATGCGGTGGGCTCTATGGCTTCTGAGGCGGAAAGAACCAGCTGGGGCTC

GAGGGGGGATCGATCCCGTCGAGATATCTAGACCCAGCTTTCTTGTACAAAGTTGGCATTATA

AGAAAGCATTGCTTATCAATTTGTTGCAACGAACAGGTCACTATCAGTCAAAATAAAATCATTA

-continued

TTTGGATCGATTCGACAGATCGCGATCGCAGTGAGTAGTGTTCTGGGGCGGGGGAGGACCT

GCATGAGGGCCAGAATGACTGAAATCTGTGCTTTTCTGTGTGTTGCAGCATCATGAGCGGAA

GCGGCTCCTTTGAGGGAGGGGTATTCAGCCCTTATCTGACGGGGCGTCTCCCCTCCTGGGC

GGGAGTGCGTCAGAATGTGATGGGATCCACGGTGGACGGCCGGCCCGTGCAGCCCGCGAA

CTCTTCAACCCTGACCTATGCAACCCTGAGCTCTTCGTCGGTGGACGCAGCTGCCGCCGCAG

CTGCTGCATCCGCCGCCAGCGCCGTGCGCGGAATGGCCATGGGCGCCGGCTACTACGGCA

CTCTGGTGGCCAACTCGAGTTCCACCAATAATCCCGCCAGCCTGAACGAGGAGAAGCTGCTG

CTGCTGATGGCCCAGCTTGAGGCCTTGACCCAGCGCCTGGGCGAGCTGACCCAGCAGGTGG

CTCAGCTGCAGGAGCAGACGCGGGCCGCGGTTGCCACGGTGAAATCCAAATAAAAAATGAAT

CAATAAATAAACGGAGACGGTTGTTGATTTTAACACAGAGTCTGAATCTTTATTTGATTTTTCG

CGCGCGGTAGGCCCTGGACCACCGGTCTCGATCATTGAGCACCCGGTGGATCTTTTCCAGG

ACCCGGTAGAGGTGGGCTTGGATGTTGAGGTACATGGGCATGAGCCCGTCCCGGGGGTGGA

GGTAGCTCCATTGCAGGGCCTCGTGCTCGGGGGTGGTGTTGTAAATCACCCAGTCATAGCAG

GGGCGCAGGGCGTGGTGTTGCACAATATCTTTGAGGAGGAGACTGATGGCCACGGGCAGCC

CTTTGGTGTAGGTGTTTACAAATCTGTTGAGCTGGGAGGGATGCATGCGGGGGGAGATGAGG

TGCATCTTGGCCTGGATCTTGAGATTGGCGATGTTACCGCCCAGATCCCGCCTGGGGTTCAT

GTTGTGCAGGACCACCAGCACGGTGTATCCGGTGCACTTGGGGAATTTATCATGCAACTTGG

AAGGGAAGGCGTGAAAGAATTTGGCGACGCCCTTGTGTCCGCCCAGGTTTTCCATGCACTCA

TCCATGATGATGGCAATGGGCCCGTGGGCGGCGGCCTGGGCAAAGACGTTTCGGGGGTCGG

ACACATCATAGTTGTGGTCCTGGGTGAGGTCATCATAGGCCATTTTAATGAATTTGGGGCGGA

GGGTGCCGGACTGGGGGACAAAGGTACCCTCGATCCCGGGGGCGTAGTTCCCCTCACAGAT

CTGCATCTCCCAGGCTTTGAGCTCAGAGGGGGGGATCATGTCCACCTGCGGGGCGATAAAG

AACACGGTTTCCGGGGCGGGGGAGATGAGCTGGGCCGAAAGCAAGTTCCGGAGCAGCTGG

GACTTGCCGCAGCCGGTGGGGCCGTAAATGACCCCGATGACCGGCTGCAGGTGGTAGTTGA

GGGAGAGACAGCTGCCGTCCTCCCGGAGGAGGGGGGCCACCTCGTTCATCATCTCGCGCAC

GTGCATGTTCTCGCGCACCAGTTCCGCCAGGAGGCGCTCTCCCCCCAGAGATAGGAGCTCC

TGGAGCGAGGCGAAGTTTTTCAGCGGCTTGAGTCCGTCGGCCATGGGCATTTTGGAGAGGG

TCTGTTGCAAGAGTTCCAAGCGGTCCCAGAGCTCGGTGATGTGCTCTACGGCATCTCGATCC

AGCAGACCTCCTCGTTTCGCGGGTTGGGACGACTGCGGGAGTAGGGCACCAGACGATGGGC

GTCCAGCGCAGCCAGGGTCCGGTCCTTCCAGGGCCGCAGCGTCCGCGTCAGGGTGGTCTCC

GTCACGGTGAAGGGGTGCGCGCCGGGCTGGGCGCTTGCGAGGGTGCGCTTCAGGCTCATC

CGGCTGGTCGAAAACCGCTCCCGATCGGCGCCCTGCGCGTCGGCCAGGTAGCAATTGACCA

TGAGTTCGTAGTTGAGCGCCTCGGCCGCGTGGCCTTTGGCGCGGAGCTTACCTTTGGAAGTC

TGCCCGCAGGCGGGACAGAGGAGGGACTTGAGGGCGTAGAGCTTGGGGGCGAGGAAGACG

GAATCGGGGGCGTAGGCGTCCGCGCCGCAGTGGGCGCAGACGGTCTCGCACTCCACGAGC

CAGGTGAGGTCGGGCTGGTCGGGGTCAAAAACCAGTTTCCCGCCGTTCTTTTTGATGCGTTT

CTTACCTTTGGTCTCCATGAGCTCGTGTCCCCGCTGGGTGACAAAGAGGCTGTCCGTGTCCC

CGTAGACCGACTTTATGGGCCGGTCCTCGAGCGGTGTGCCGCGGTCCTCCTCGTAGAGGAA

CCCCGCCCACTCCGAGACGAAAGCCCGGGTCCAGGCCAGCACGAAGGAGGCCACGTGGGA

CGGGTAGCGGTCGTTGTCCACCAGCGGGTCCACTTTTTCCAGGGTATGCAAACACATGTCCC

-continued

CCTCGTCCACATCCAGGAAGGTGATTGGCTTGTAAGTGTAGGCCACGTGACCGGGGGTCCC

GGCCGGGGGGGTATAAAAGGGGGCGGGCCCCTGCTCGTCCTCACTGTCTTCCGGATCGCTG

TCCAGGAGCGCCAGCTGTTGGGGTAGGTATTCCCTCTCGAAGGCGGGCATGACCTCGGCAC

TCAGGTTGTCAGTTTCTAGAAACGAGGAGGATTTGATATTGACGGTGCCAGCGGAGATGCCT

TTCAAGAGCCCCTCGTCCATCTGGTCAGAAAAGACGATTTTTTTGTTGTCGAGCTTGGTGGCG

AAGGAGCCGTAGAGGGCGTTGGAAAGGAGCTTGGCGATGGAGCGCATGGTCTGGTTTTTTTC

CTTGTCGGCGCGCTCCTTGGCCGCGATGTTGAGCTGCACGTACTCGCGCGCCACGCACTTC

CATTCGGGGAAGACGGTGGTCATCTCGTCGGGCACGATTCTGACCTGCCAACCTCGATTATG

CAGGGTGATGAGGTCCACACTGGTGGCCACCTCGCCGCGCAGGGGCTCGTTGGTCCAGCAG

AGGCGGCCGCCCTTGCGCGAGCAGAAGGGGGGCAGAGGGTCCAGCATGACCTCGTCGGGG

GGGTCGGCATCGATGGTGAAGATGCCGGGCAGGAGATCGGGGTCGAAGTAGCTGATGGAAG

TGGCCAGATCGTCCAGGGAAGCTTGCCATTCGCGCACGGCCAGCGCGCGCTCGTAGGGACT

GAGGGGCGTGCCCCAGGGCATGGGGTGGGTGAGCGCGGAGGCGTACATGCCGCAGATGTC

GTAGACGTAGAGGGGCTCCTCGAGGATGCCGATGTAGGTGGGGTAGCAGCGCCCCCCGCG

GATGCTGGCGCGCACGTAGTCATACAGCTCGTGCGAGGGCGCGAGGAGCCCCGGGCCCAG

GTTGGTGCGACTGGGCTTTTCGGCGCGGTAGACGATCTGGCGAAAGATGGCATGCGAGTTG

GAGGAGATGGTGGGCCTTTGGAAGATGTTGAAGTGGGCGTGGGGGAGGCCGACCGAGTCG

CGGATGAAGTGGGCGTAGGAGTCTTGCAGTTTGGCGACGAGCTCGGCGGTGACGAGGACGT

CCAGAGCGCAGTAGTCGAGGGTCTCCTGGATGATGTCATACTTGAGCTGGCCCTTTTGTTTC

CACAGCTCGCGGTTGAGAAGGAACTCTTCGCGGTCCTTCCAGTACTCTTCGAGGGGGAACCC

GTCCTGATCTGCACGGTAAGAGCCTAGCATGTAGAACTGGTTGACGGCCTTGTAGGCGCAGC

AGCCCTTCTCCACGGGGAGGGCGTAGGCCTGGGCGGCCTTGCGCAGGGAGGTGTGCGTGA

GGGCGAAGGTGTCCCTGACCATGACCTTGAGGAACTGGTGCTTGAAATCGATATCGTCGCAG

CCCCCCTGCTCCCAGAGCTGGAAGTCCGTGCGCTTCTTGTAGGCGGGGTTGGGCAAAGCGA

AAGTAACATCGTTGAAAAGGATCTTGCCCGCGCGGGGCATAAAGTTGCGAGTGATGCGGAAA

GGCTGGGGCACCTCGGCCCGGTTGTTGATGACCTGGGCGGCGAGCACGATCTCGTCGAAAC

CGTTGATGTTGTGGCCCACGATGTAGAGTTCCACGAATCGCGGGCGGCCCTTGACGTGGGG

CAGCTTCTTGAGCTCCTCGTAGGTGAGCTCGTCGGGGTCGCTGAGACCGTGCTGCTCGAGC

GCCCAGTCGGCGAGATGGGGGTTGGCGCGGAGGAAGGAAGTCCAGAGATCCACGGCCAGG

GCGGTTTGCAGACGGTCCCGGTACTGACGGAACTGCTGCCCGACGGCCATTTTTTCGGGGG

TGACGCAGTAGAAGGTGCGGGGGTCCCCGTGCCAGCGGTCCCATTTGAGCTGGAGGGCGAG

ATCGAGGGCGAGCTCGACGAGGCGGTCGTCCCCTGAGAGTTTCATGACCAGCATGAAGGGG

ACGAGCTGCTTGCCGAAGGACCCCATCCAGGTGTAGGTTTCCACATCGTAGGTGAGGAAGAG

CCTTTCGGTGCGAGGATGCGAGCCGATGGGGAAGAACTGGATCTCCTGCCACCAATTGGAG

GAATGGCTGTTGATGTGATGGAAGTAGAAATGCCGACGGCGCGCCGAACACTCGTGCTTGTG

TTTATACAAGCGGCCACAGTGCTCGCAACGCTGCACGGGATGCACGTGCTGCACGAGCTGTA

CCTGAGTTCCTTTGACGAGGAATTTCAGTGGGAAGTGGAGTCGTGGCGCCTGCATCTCGTGC

TGTACTACGTCGTGGTGGTCGGCCTGGCCCTCTTCTGCCTCGATGGTGGTCATGCTGACGAG

CCCGCGCGGGAGGCAGGTCCAGACCTCGGCGCGAGCGGGTCGGAGAGCGAGGACGAGGG

CGCGCAGGCCGGAGCTGTCCAGGGTCCTGAGACGCTGCGGAGTCAGGTCAGTGGGCAGCG

GCGGCGCGCGGTTGACTTGCAGGAGTTTTTCCAGGGCGCGCGGGAGGTCCAGATGGTACTT

-continued

GATCTCCACCGCGCCGTTGGTGGCGACGTCGATGGCTTGCAGGGTCCCGTGCCCCTGGGGT

GTGACCACCGTCCCCCGTTTCTTCTTGGGCGGCTGGGGCGACGGGGGCGGTGCCTCTTCCA

TGGTTAGAAGCGGCGGCGAGGACGCGCGCCGGGCGGCAGAGGCGGCTCGGGGCCCGGAG

GCAGGGGCGGCAGGGGCACGTCGGCGCCGCGCGCGGGTAGGTTCTGGTACTGCGCCCGGA

GAAGACTGGCGTGAGCGACGACGCGACGGTTGACGTCCTGGATCTGACGCCTCTGGGTGAA

GGCCACGGGACCCGTGAGTTTGAACCTGAAAGAGAGTTCGACAGAATCAATCTCGGTATCGT

TGACGGCGGCCTGCCGCAGGATCTCTTGCACGTCGCCCGAGTTGTCCTGGTAGGCGATCTC

GGTCATGAACTGCTCGATCTCCTCCTCCTGAAGGTCTCCGCGACCGGCGCGCTCCACGGTG

GCCGCGAGGTCGTTGGAGATGCGGCCCATGAGCTGCGAGAAGGCGTTCATGCCCGCCTCGT

TCCAGACGCGGCTGTAGACCACGACGCCCTCGGGATCGCGGGCGCGCATGACCACCTGGG

CGAGGTTGAGCTCCACGTGGCGCGTGAAGACCGCGTAGTTGCAGAGGCGCTGGTAGAGGTA

GTTGAGCGTGGTGGCGATGTGCTCGGTGACGAAGAAATACATGATCCAGCGGCGGAGCGGC

ATCTCGCTGACGTCGCCCAGCGCCTCCAAGCGTTCCATGGCCTCGTAAAAGTCCACGGCGAA

GTTGAAAAACTGGGAGTTGCGCGCCGAGACGGTCAACTCCTCCTCCAGAAGACGGATGAGCT

CGGCGATGGTGGCGCGCACCTCGCGCTCGAAGGCCCCCGGGAGTTCCTCCACTTCCTCCTC

TTCTTCCTCCTCCACTAACATCTCTTCTACTTCCTCCTCAGGCGGTGGTGGTGGCGGGGGAG

GGGGCCTGCGTCGCCGGCGGCGCACGGGCAGACGGTCGATGAAGCGCTCGATGGTCTCGC

CGCGCCGGCGTCGCATGGTCTCGGTGACGGCGCGCCCGTCCTCGCGGGGCCGCAGCGTGA

AGACGCCGCCGCGCATCTCCAGGTGGCCGGGGGGGTCCCCGTTGGGCAGGGAGAGGGCGC

TGACGATGCATCTTATCAATTGCCCCGTAGGGACTCCGCGCAAGGACCTGAGCGTCTCGAGA

TCCACGGGATCTGAAAACCGTTGAACGAAGGCTTCGAGCCAGTCGCAGTCGCAAGGTAGGCT

GAGCACGGTTTCTTCTGCCGGGTCATGTTGGGGAGCGGGGCGGGCGATGCTGCTGGTGATG

AAGTTGAAATAGGCGGTTCTGAGACGGCGGATGGTGGCGAGGAGCACCAGGTCTTTGGGCC

CGGCTTGCTGGATGCGCAGACGGTCGGCCATGCCCCAGGCGTGGTCCTGACACCTGGCCAG

GTCCTTGTAGTAGTCCTGCATGAGCCGCTCCACGGGCACCTCCTCCTCGCCCGCGCGGCCG

TGCATGCGCGTGAGCCCGAAGCCGCGCTGGGGCTGGACGAGCGCCAGGTCGGCGACGACG

CGCTCGGCGAGGATGGCCTGCTGGATCTGGGTGAGGGTGGTCTGGAAGTCGTCAAAGTCGA

CGAAGCGGTGGTAGGCTCCGGTGTTGATGGTGTAGGAGCAGTTGGCCATGACGGACCAGTT

GACGGTCTGGTGGCCCGGACGCACGAGCTCGTGGTACTTGAGGCGCGAGTAGGCGCGCGT

GTCGAAGATGTAGTCGTTGCAGGTGCGCACCAGGTACTGGTAGCCGATGAGGAAGTGCGGC

GGCGGCTGGCGGTAGAGCGGCCATCGCTCGGTGGCGGGGGCGCCGGGCGCGAGGTCCTC

GAGCATGGTGCGGTGGTAGCCGTAGATGTACCTGGACATCCAGGTGATGCCGGCGGCGGTG

GTGGAGGCGCGCGGGAACTCGCGGACGCGGTTCCAGATGTTGCGCAGCGGCAGGAAGTAG

TTCATGGTGGGCACGGTCTGGCCCGTGAGGCGCGCGCAGTCGTGGATGCTCTATACGGGCA

AAAACGAAAGCGGTCAGCGGCTCGACTCCGTGGCCTGGAGGCTAAGCGAACGGGTTGGGCT

GCGCGTGTACCCCGGTTCGAATCTCGAATCAGGCTGGAGCCGCAGCTAACGTGGTACTGGC

ACTCCCGTCTCGACCCAAGCCTGCACCAACCCTCCAGGATACGGAGGCGGGTCGTTTTGCAA

CTTTTTTTGGAGGCCGGAAATGAAACTAGTAAGCGCGGAAAGCGGCCGACCGCGATGGCTCG

CTGCCGTAGTCTGGAGAAGAATCGCCAGGGTTGCGTTGCGGTGTGCCCCGGTTCGAGGCCG

GCCGGATTCCGCGGCTAACGAGGGCGTGGCTGCCCCGTCGTTTCCAAGACCCCATAGCCAG

-continued

CCGACTTCTCCAGTTACGGAGCGAGCCCCTCTTTTGTTTTGTTTGTTTTTGCCAGATGCATCC

CGTACTGCGGCAGATGCGCCCCCACCACCCTCCACCGCAACAACAGCCCCCTCCTCCACAG

CCGGCGCTTCTGCCCCCGCCCCAGCAGCAGCAGCAACTTCCAGCCACGACCGCCGCGGCC

GCCGTGAGCGGGGCTGGACAGACTTCTCAGTATGATCACCTGGCCTTGGAAGAGGGCGAGG

GGCTGGCGCGCCTGGGGGCGTCGTCGCCGGAGCGGCACCCGCGCGTGCAGATGAAAAGGG

ACGCTCGCGAGGCCTACGTGCCCAAGCAGAACCTGTTCAGAGACAGGAGCGGCGAGGAGCC

CGAGGAGATGCGCGCGGCCCGGTTCCACGCGGGGCGGGAGCTGCGGCGCGGCCTGGACC

GAAAGAGGGTGCTGAGGGACGAGGATTTCGAGGCGGACGAGCTGACGGGGATCAGCCCCG

CGCGCGCGCACGTGGCCGCGGCCAACCTGGTCACGGCGTACGAGCAGACCGTGAAGGAGG

AGAGCAACTTCCAAAAATCCTTCAACAACCACGTGCGCACCCTGATCGCGCGCGAGGAGGTG

ACCCTGGGCCTGATGCACCTGTGGGACCTGCTGGAGGCCATCGTGCAGAACCCCACCAGCA

AGCCGCTGACGGCGCAGCTGTTCCTGGTGGTGCAGCATAGTCGGGACAACGAGGCGTTCAG

GGAGGCGCTGCTGAATATCACCGAGCCCGAGGGCCGCTGGCTCCTGGACCTGGTGAACATT

CTGCAGAGCATCGTGGTGCAGGAGCGCGGGCTGCCGCTGTCCGAGAAGCTGGCGGCCATCA

ACTTCTCGGTGCTGAGTCTGGGCAAGTACTACGCTAGGAAGATCTACAAGACCCCGTACGTG

CCCATAGACAAGGAGGTGAAGATCGACGGGTTTTACATGCGCATGACCCTGAAAGTGCTGAC

CCTGAGCGACGATCTGGGGGTGTACCGCAACGACAGGATGCACCGCGCGGTGAGCGCCAG

CAGGCGGCGCGAGCTGAGCGACCAGGAGCTGATGCACAGCCTGCAGCGGGCCCTGACCGG

GGCCGGGACCGAGGGGGAGAGCTACTTTGACATGGGCGCGGACCTGCACTGGCAGCCCAG

CCGCCGGGCCTTGGAGGCGGCAGGCGGTCCCCCCTACATAGAAGAGGTGGACGATGAGGT

GGACGAGGAGGGCGAGTACCTGGAAGACTGATGGCGCGACCGTATTTTTGCTAGATGCAACA

ACAGCCACCTCCTGATCCCGCGATGCGGGCGGCGCTGCAGAGCCAGCCGTCCGGCATTAAC

TCCTCGGACGATTGGACCCAGGCCATGCAACGCATCATGGCGCTGACGACCCGCAACCCCG

AAGCCTTTAGACAGCAGCCCCAGGCCAACCGGCTCTCGGCCATCCTGGAGGCCGTGGTGCC

CTCGCGCTCCAACCCCACGCACGAGAAGGTCCTGGCCATCGTGAACGCGCTGGTGGAGAAC

AAGGCCATCCGCGGCGACGAGGCCGGCCTGGTGTACAACGCGCTGCTGGAGCGCGTGGCC

CGCTACAACAGCACCAACGTGCAGACCAACCTGGACCGCATGGTGACCGACGTGCGCGAGG

CCGTGGCCCAGCGCGAGCGGTTCCACCGCGAGTCCAACCTGGGATCCATGGTGGCGCTGAA

CGCCTTCCTCAGCACCCAGCCCGCCAACGTGCCCCGGGGCCAGGAGGACTACACCAACTTC

ATCAGCGCCCTGCGCCTGATGGTGACCGAGGTGCCCCAGAGCGAGGTGTACCAGTCCGGGC

CGGACTACTTCTTCCAGACCAGTCGCCAGGGCTTGCAGACCGTGAACCTGAGCCAGGCGTTC

AAGAACTTGCAGGGCCTGTGGGGCGTGCAGGCCCCGGTCGGGGACCGCGCGACGGTGTCG

AGCCTGCTGACGCCGAACTCGCGCCTGCTGCTGCTGCTGGTGGCCCCCTTCACGGACAGCG

GCAGCATCAACCGCAACTCGTACCTGGGCTACCTGATTAACCTGTACCGCGAGGCCATCGGC

CAGGCGCACGTGGACGAGCAGACCTACCAGGAGATCACCCACGTGAGCCGCGCCCTGGGC

CAGGACGACCCGGGCAATCTGGAAGCCACCCTGAACTTTTTGCTGACCAACCGGTCGCAGAA

GATCCCGCCCCAGTACACGCTCAGCGCCGAGGAGGAGCGCATCCTGCGATACGTGCAGCAG

AGCGTGGGCCTGTTCCTGATGCAGGAGGGGGCCACCCCCAGCGCCGCGCTCGACATGACC

GCGCGCAACATGGAGCCCAGCATGTACGCCAGCAACCGCCCGTTCATCAATAAACTGATGGA

CTACTTGCATCGGGCGGCCGCCATGAACTCTGACTATTTCACCAACGCCATCCTGAATCCCC

ACTGGCTCCCGCCGCCGGGGTTCTACACGGGCGAGTACGACATGCCCGACCCCAATGACGG

-continued

GTTCCTGTGGGACGATGTGGACAGCAGCGTGTTCTCCCCCCGACCGGGTGCTAACGAGCGC

CCCTTGTGGAAGAAGGAAGGCAGCGACCGACGCCCGTCCTCGGCGCTGTCCGGCCGCGAG

GGTGCTGCCGCGGCGGTGCCCGAGGCCGCCAGTCCTTTCCCGAGCTTGCCCTTCTCGCTGA

ACAGTATTCGCAGCAGCGAGCTGGGCAGGATCACGCGCCCGCGCTTGCTGGGCGAGGAGGA

GTACTTGAATGACTCGCTGTTGAGACCCGAGCGGGAGAAGAACTTCCCCAATAACGGGATAG

AGAGCCTGGTGGACAAGATGAGCCGCTGGAAGACGTATGCGCAGGAGCACAGGGACGATCC

GTCGCAGGGGGCCACGAGCCGGGGCAGCGCCGCCCGTAAACGCCGGTGGCACGACAGGCA

GCGGGGACTGATGTGGGACGATGAGGATTCCGCCGACGACAGCAGCGTGTTGGACTTGGGT

GGGAGTGGTAACCCGTTCGCTCACCTGCGCCCCCGCATCGGGCGCATGATGTAAGAGAAAC

CGAAAATAAATGATACTCACCAAGGCCATGGCGACCAGCGTGCGTTCGTTTCTTCTCTGTTGT

TGTATCTAGTATGATGAGGCGTGCGTACCCGGAGGGTCCTCCTCCCTCGTACGAGAGCGTGA

TGCAGCAGGCGATGGCGGCGGCGGCGGCGATGCAGCCCCCGCTGGAGGCTCCTTACGTGC

CCCCGCGGTACCTGGCGCCTACGGAGGGGCGGAACAGCATTCGTTACTCGGAGCTGGCACC

CTTGTACGATACCACCCGGTTGTACCTGGTGGACAACAAGTCGGCGGACATCGCCTCGCTGA

ACTACCAGAACGACCACAGCAACTTCCTGACCACCGTGGTGCAGAACAATGACTTCACCCCC

ACGGAGGCCAGCACCCAGACCATCAACTTTGACGAGCGCTCGCGGTGGGGCGGTCAGCTGA

AAACCATCATGCACACCAACATGCCCAACGTGAACGAGTTCATGTACAGCAACAAGTTCAAGG

CGCGGGTGATGGTCTCCCGCAAGACCCCCAACGGGGTGACAGTGACAGATGGTAGTCAGGA

TATCTTGGAGTATGAATGGGTGGAGTTTGAGCTGCCCGAAGGCAACTTCTCGGTGACCATGA

CCATCGACCTGATGAACAACGCCATCATCGACAATTACTTGGCGGTGGGGCGGCAGAACGG

GGTCCTGGAGAGCGATATCGGCGTGAAGTTCGACACTAGGAACTTCAGGCTGGGCTGGGAC

CCCGTGACCGAGCTGGTCATGCCCGGGGTGTACACCAACGAGGCCTTCCACCCCGATATTGT

CTTGCTGCCCGGCTGCGGGGTGGACTTCACCGAGAGCCGCCTCAGCAACCTGCTGGGCATT

CGCAAGAGGCAGCCCTTCCAGGAGGGCTTCCAGATCATGTACGAGGATCTGGAGGGGGGCA

ACATCCCCGCGCTCCTGGATGTCGACGCCTATGAGAAAAGCAAGGAGGAGAGCGCCGCCGC

GGCGACTGCAGCTGTAGCCACCGCCTCTACCGAGGTCAGGGGCGATAATTTTGCCAGCCCT

GCAGCAGTGGCAGCGGCCGAGGCGGCTGAAACCGAAAGTAAGATAGTCATTCAGCCGGTGG

AGAAGGATAGCAAGGACAGGAGCTACAACGTGCTGCCGGACAAGATAAACACCGCCTACCG

CAGCTGGTACCTGGCCTACAACTATGGCGACCCCGAGAAGGGCGTGCGCTCCTGGACGCTG

CTCACCACCTCGGACGTCACCTGCGGCGTGGAGCAAGTCTACTGGTCGCTGCCCGACATGAT

GCAAGACCCGGTCACCTTCCGCTCCACGCGTCAAGTTAGCAACTACCCGGTGGTGGGCGCC

GAGCTCCTGCCCGTCTACTCCAAGAGCTTCTTCAACGAGCAGGCCGTCTACTCGCAGCAGCT

GCGCGCCTTCACCTCGCTCACGCACGTCTTCAACCGCTTCCCCGAGAACCAGATCCTCGTCC

GCCCGCCCGCGCCCACCATTACCACCGTCAGTGAAAACGTTCCTGCTCTCACAGATCACGGG

ACCCTGCCGCTGCGCAGCAGTATCCGGGGAGTCCAGCGCGTGACCGTTACTGACGCCAGAC

GCCGCACCTGCCCCTACGTCTACAAGGCCCTGGGCATAGTCGCGCCGCGCGTCCTCTCGAG

CCGCACCTTCTAAAAAATGTCCATTCTCATCTCGCCCAGTAATAACACCGGTTGGGGCCTGCG

CGCGCCCAGCAAGATGTACGGAGGCGCTCGCCAACGCTCCACGCAACACCCCGTGCGCGTG

CGCGGGCACTTCCGCGCTCCCTGGGGCGCCCTCAAGGGCCGCGTGCGGTCGCGCACCACC

GTCGACGACGTGATCGACCAGGTGGTGGCCGACGCGCGCAACTACACCCCCGCCGCCGCG

-continued

CCCGTCTCCACCGTGGACGCCGTCATCGACAGCGTGGTGGCCGACGCGCGCCGGTACGCC

CGCGCCAAGAGCCGGCGGCGGCGCATCGCCCGGCGGCACCGGAGCACCCCCGCCATGCGC

GCGGCGCGAGCCTTGCTGCGCAGGGCCAGGCGCACGGGACGCAGGGCCATGCTCAGGGCG

GCCAGACGCGCGGCTTCAGGCGCCAGCGCCGGCAGGACCCGGAGACGCGCGGCCACGGC

GGCGGCAGCGGCCATCGCCAGCATGTCCCGCCCGCGGCGAGGGAACGTGTACTGGGTGCG

CGACGCCGCCACCGGTGTGCGCGTGCCCGTGCGCACCCGCCCCCCTCGCACTTGAAGATGT

TCACTTCGCGATGTTGATGTGTCCCAGCGGCGAGGAGGATGTCCAAGCGCAAATTCAAGGAA

GAGATGCTCCAGGTCATCGCGCCTGAGATCTACGGCCCCGCGGTGGTGAAGGAGGAAAGAA

AGCCCCGCAAAATCAAGCGGGTCAAAAAGGACAAAAAGGAAGAAGATGACGATCTGGTGGAG

TTTGTGCGCGAGTTCGCCCCCCGGCGGCGCGTGCAGTGGCGCGGGCGGAAAGTGCACCCG

GTGCTGAGACCCGGCACCACCGTGGTCTTCACGCCCGGCGAGCGCTCCGGCAGCGCTTCCA

AGCGCTCCTACGACGAGGTGTACGGGGACGAGGACATCCTCGAGCAGGCGGCCGAGCGCC

TGGGCGAGTTTGCTTACGGCAAGCGCAGCCGCCCCGCCCTGAAGGAAGAGGCGGTGTCCAT

CCCGCTGGACCACGGCAACCCCACGCCGAGCCTCAAGCCCGTGACCCTGCAGCAGGTGCTG

CCGAGCGCAGCGCCGCGCCGGGGGTTCAAGCGCGAGGGCGAGGATCTGTACCCCACCATG

CAGCTGATGGTGCCCAAGCGCCAGAAGCTGGAAGACGTGCTGGAGACCATGAAGGTGGACC

CGGACGTGCAGCCCGAGGTCAAGGTGCGGCCCATCAAGCAGGTGGCCCCGGGCCTGGGCG

TGCAGACCGTGGACATCAAGATCCCCACGGAGCCCATGGAAACGCAGACCGAGCCCATGAT

CAAGCCCAGCACCAGCACCATGGAGGTGCAGACGGATCCCTGGATGCCATCGGCTCCTAGC

CGAAGACCCCGGCGCAAGTACGGCGCGGCCAGCCTGCTGATGCCCAACTACGCGCTGCATC

CTTCCATCATCCCCACGCCGGGCTACCGCGGCACGCGCTTCTACCGCGGTCATACAACCAGC

CGCCGCCGCAAGACCACCACCCGCCGCCGCCGTCGCCGCACAGCCGCTGCATCTACCCCTG

CCGCCCTGGTGCGGAGAGTGTACCGCCGCGGCCGCGCGCCTCTGACCCTACCGCGCGCGC

GCTACCACCCGAGCATCGCCATTTAAACTTTCGCCTGCTTTGCAGATGGCCCTCACATGCCG

CCTCCGCGTTCCCATTACGGGCTACCGAGGAAGAAAACCGCGCCGTAGAAGGCTGGCGGGG

AACGGGATGCGTCGCCACCACCATCGGCGGCGGCGCGCCATCAGCAAGCGGTTGGGGGGA

GGCTTCCTGCCCGCGCTGATCCCCATCATCGCCGCGGCGATCGGGGCGATCCCCGGCATTG

CTTCCGTGGCGGTGCAGGCCTCTCAGCGCCACTGAGACACTTGGAAAACATCTTGTAATAAA

CCAATGGACTCTGACGCTCCTGGTCCTGTGATGTGTTTTCGTAGACAGATGGAAGACATCAAT

TTTTCGTCCCTGGCTCCGCGACACGGCACGCGGCCGTTCATGGGCACCTGGAGCGACATCG

GCACCAGCCAACTGAACGGGGGCGCCTTCAATTGGAGCAGTCTCTGGAGCGGGCTTAAGAA

TTTCGGGTCCACGCTTAAAACCTATGGCAGCAAGGCGTGGAACAGCACCACAGGGCAGGCG

CTGAGGGATAAGCTGAAAGAGCAGAACTTCCAGCAGAAGGTGGTCGATGGGCTCGCCTCGG

GCATCAACGGGGTGGTGGACCTGGCCAACCAGGCCGTGCAGCGGCAGATCAACAGCCGCCT

GGACCCGGTGCCGCCCGCCGGCTCCGTGGAGATGCCGCAGGTGGAGGAGGAGCTGCCTCC

CCTGGACAAGCGGGGCGAGAAGCGACCCCGCCCCGACGCGGAGGAGACGCTGCTGACGCA

CACGGACGAGCCGCCCCCGTACGAGGAGGCGGTGAAACTGGGTCTGCCCACCACGCGGCC

CATCGCGCCCCTGGCCACCGGGGTGCTGAAACCCGAAAGTAATAAGCCCGCGACCCTGGAC

TTGCCTCCTCCCGCTTCCCGCCCCTCTACAGTGGCTAAGCCCCTGCCGCCGGTGGCCGTGG

CCCGCGCGCGACCCGGGGGCTCCGCCCGCCCTCATGCGAACTGGCAGAGCACTCTGAACA

GCATCGTGGGTCTGGGAGTGCAGAGTGTGAAGCGCCGCCGCTGCTATTAAACCTACCGTAG

-continued

CGCTTAACTTGCTTGTCTGTGTGTGTATGTATTATGTCGCCGCTGTCCGCCAGAAGGAGGAGT

GAAGAGGCGCGTCGCCGAGTTGCAAGATGGCCACCCCATCGATGCTGCCCCAGTGGGCGTA

CATGCACATCGCCGGACAGGACGCTTCGGAGTACCTGAGTCCGGGTCTGGTGCAGTTCGCC

CGCGCCACAGACACCTACTTCAGTCTGGGGAACAAGTTTAGGAACCCCACGGTGGCGCCCA

CGCACGATGTGACCACCGACCGCAGCCAGCGGCTGACGCTGCGCTTCGTGCCCGTGGACCG

CGAGGACAACACCTACTCGTACAAAGTGCGCTACACGCTGGCCGTGGGCGACAACCGCGTG

CTGGACATGGCCAGCACCTACTTTGACATCCGCGGCGTGCTGGATCGGGGCCCTAGCTTCAA

ACCCTACTCCGGCACCGCCTACAACAGCCTGGCTCCCAAGGGAGCGCCCAATTCCAGCCAG

TGGGAGCAAAAAAAGGCAGGCAATGGTGACACTATGGAAACACACACATTTGGTGTGGCCCC

AATGGGCGGTGAGAATATTACAATCGACGGATTACAAATTGGAACTGACGCTACAGCTGATCA

GGATAAACCAATTTATGCTGACAAAACATTCCAGCCTGAACCTCAAGTAGGAGAAGAAAATTG

GCAAGAAACTGAAAGCTTTTATGGCGGTAGGGCTCTTAAAAAAGACACAAGCATGAAACCTTG

CTATGGCTCCTATGCTAGACCCACCAATGTAAAGGGAGGTCAAGCTAAACTTAAAGTTGGAGC

TGATGGAGTTCCTACCAAAGAATTTGACATAGACCTGGCTTTCTTTGATACTCCCGGTGGCAC

AGTGAATGGACAAGATGAGTATAAAGCAGACATTGTCATGTATACCGAAAACACGTATCTGGA

AACTCCAGACACGCATGTGGTATACAAACCAGGCAAGGATGATGCAAGTTCTGAAATTAACCT

GGTTCAGCAGTCCATGCCCAATAGACCCAACTATATTGGGTTCAGAGACAACTTTATTGGGCT

CATGTATTACAACAGTACTGGCAATATGGGGGTGCTGGCTGGTCAGGCCTCACAGCTGAATG

CTGTGGTCGACTTGCAAGACAGAAACACCGAGCTGTCATACCAGCTCTTGCTTGACTCTTTGG

GTGACAGAACCCGGTATTTCAGTATGTGGAATCAGGCGGTGGACAGTTATGATCCTGATGTG

CGCATTATTGAAAACCATGGTGTGGAAGACGAACTTCCCAACTATTGCTTCCCCCTGGATGGG

TCTGGCACTAATGCCGCTTACCAAGGTGTGAAAGTAAAAAATGGTAACGATGGTGATGTTGAG

AGCGAATGGGAAAATGATGATACTGTCGCAGCTCGAAATCAATTATGCAAGGGCAACATTTTT

GCCATGGAAATTAACCTCCAAGCCAACCTGTGGAGAAGTTTCCTCTACTCGAACGTGGCCCT

GTACCTGCCCGACTCTTACAAGTACACGCCAGCCAACATCACCCTGCCCACCAACACCAACA

CTTATGATTACATGAACGGGAGAGTGGTGCCTCCCTCGCTGGTGGACGCCTACATCAACATC

GGGGCGCGCTGGTCGCTGGACCCCATGGACAACGTCAATCCCTTCAACCACCACCGCAACG

CGGGCCTGCGCTACCGCTCCATGCTCCTGGGCAACGGGCGCTACGTGCCCTTCCACATCCA

GGTGCCCCAGAAATTTTTCGCCATCAAGAGCCTCCTGCTCCTGCCCGGGTCCTACACCTACG

AGTGGAACTTCCGCAAGGACGTCAACATGATCCTGCAGAGCTCCCTCGGCAACGACCTGCGC

ACGGACGGGGCCTCCATCTCCTTCACCAGCATCAACCTCTACGCCACCTTCTTCCCCATGGC

GCACAACACGGCCTCCACGCTCGAGGCCATGCTGCGCAACGACACCAACGACCAGTCCTTC

AACGACTACCTCTCGGCGGCCAACATGCTCTACCCCATCCCGGCCAACGCCACCAACGTGCC

CATCTCCATCCCCTCGCGCAACTGGGCCGCCTTCCGCGGCTGGTCCTTCACGCGCCTCAAGA

CCAAGGAGACGCCCTCGCTGGGCTCCGGGTTCGACCCCTACTTCGTCTACTCGGGCTCCATC

CCCTACCTCGACGGCACCTTCTACCTCAACCACACCTTCAAGAAGGTCTCCATCACCTTCGAC

TCCTCCGTCAGCTGGCCCGGCAACGACCGGCTCCTGACGCCCAACGAGTTCGAAATCAAGC

GCACCGTCGACGGCGAGGGATACAACGTGGCCCAGTGCAACATGACCAAGGACTGGTTCCT

GGTCCAGATGCTGGCCCACTACAACATCGGCTACCAGGGCTTCTACGTGCCCGAGGGCTACA

AGGACCGCATGTACTCCTTCTTCCGCAACTTCCAGCCCATGAGCCGCCAGGTGGTGGACGAG

-continued

GTCAACTACAAGGACTACCAGGCCGTCACCCTGGCCTACCAGCACAACAACTCGGGCTTCGT

CGGCTACCTCGCGCCCACCATGCGCCAGGGCCAGCCCTACCCCGCCAACTACCCGTACCCG

CTCATCGGCAAGAGCGCCGTCACCAGCGTCACCCAGAAAAAGTTCCTCTGCGACAGGGTCAT

GTGGCGCATCCCCTTCTCCAGCAACTTCATGTCCATGGGCGCGCTCACCGACCTCGGCCAGA

ACATGCTCTATGCCAACTCCGCCCACGCGCTAGACATGAATTTCGAAGTCGACCCCATGGAT

GAGTCCACCCTTCTCTATGTTGTCTTCGAAGTCTTCGACGTCGTCCGAGTGCACCAGCCCCA

CCGCGGCGTCATCGAGGCCGTCTACCTGCGCACCCCCTTCTCGGCCGGTAACGCCACCACC

TAAATTGCTACTTGCATGATGGCTGAGCCCACAGGCTCCGGCGAGCAGGAGCTCAGGGCCAT

CATCCGCGACCTGGGCTGCGGGCCCTACTTCCTGGGCACCTTCGATAAGCGCTTCCCGGGA

TTCATGGCCCCGCACAAGCTGGCCTGCGCCATCGTCAACACGGCCGGCCGCGAGACCGGGG

GCGAGCACTGGCTGGCCTTCGCCTGGAACCCGCGCTCGAACACCTGCTACCTCTTCGACCC

CTTCGGGTTCTCGGACGAGCGCCTCAAGCAGATCTACCAGTTCGAGTACGAGGGCCTGCTGC

GCCGTAGCGCCCTGGCCACCGAGGACCGCTGCGTCACCCTGGAAAAGTCCACCCAGACCGT

GCAGGGTCCGCGCTCGGCCGCCTGCGGGCTCTTCTGCTGCATGTTCCTGCACGCCTTCGTG

CACTGGCCCGACCGCCCCATGGACAAGAACCCCACCATGAACTTGCTGACGGGGGTGCCCA

ACGGCATGCTCCAGTCGCCCCAGGTGGAACCCACCCTGCGCCGCAACCAGGAGGCGCTCTA

CCGCTTCCTCAACTCCCACTCCGCCTACTTTCGCTCCCACCGCGCGCGCATCGAGAAGGCCA

CCGCCTTCGACCGCATGAACAATCAAGACATGTAAACCGTGTGTGTATGTTTAAAATATCTTTT

AATAAACAGCACTTTAATGTTACACATGCATCTGAGATGATTTTATTTTAGAAATCGAAAGGGT

TCTGCCGGGTCTCGGCATGGCCCGCGGGCAGGGACACGTTGCGGAACTGGTACTTGGCCAG

CCACTTGAACTCGGGGATCAGCAGTTTGGGCAGCGGGGTGTCGGGGAAGGAGTCGGTCCAC

AGCTTCCGCGTCAGCTGCAGGGCGCCCAGCAGGTCGGGCGCGGAGATCTTGAAATCGCAGT

TGGGACCCGCGTTCTGCGCGCGAGAGTTGCGGTACACGGGGTTGCAGCACTGGAACACCAT

CAGGGCCGGGTGCTTCACGCTCGCCAGCACCGCCGCGTCGGTGATGCTCTCCACGTCGAGG

TCCTCGGCGTTGGCCATCCCGAAGGGGGTCATCTTGCAGGTCTGCCTTCCCATGGTGGGCA

CGCACCCGGGCTTGTGGTTGCAATCGCAGTGCAGGGGGATCAGCATCATCTGGGCCTGGTC

GGCGTTCATCCCCGGGTACATGGCCTTCATGAAAGCCTCCAATTGCCTGAACGCCTGCTGGG

CCTTGGCTCCCTCGGTGAAGAAGACCCCGCAGGACTTGCTAGAGAACTGGTTGGTGGCACA

GCCGGCATCGTGCACGCAGCAGCGCGCGTCGTTGTTGGCCAGCTGCACCACGCTGCGCCCC

CAGCGGTTCTGGGTGATCTTGGCCCGGTCGGGGTTCTCCTTCAGCGCGCGCTGCCCGTTCT

CGCTCGCCACATCCATCTCGATCATGTGCTCCTTCTGGATCATGGTGGTCCCGTGCAGGCAC

CGCAGTTTGCCCTCGGCCTCGGTGCACCCGTGCAGCCACAGCGCGCACCCGGTGCACTCCC

AGTTCTTGTGGGCGATCTGGGAATGCGCGTGCACGAACCCTTGCAGGAAGCGGCCCATCAT

GGTCGTCAGGGTCTTGTTGCTAGTGAAGGTCAACGGGATGCCGCGGTGCTCCTCGTTGATGT

ACAGGTGGCAGATGCGGCGGTACACCTCGCCCTGCTCGGGCATCAGTTGGAAGTTGGCTTT

CAGGTCGGTCTCCACGCGGTAGCGGTCCATCAGCATAGTCATGATTTCCATGCCCTTCTCCC

AGGCCGAGACGATGGGCAGGCTCATAGGGTTCTTCACCATCATCTTAGCACTAGCAGCCGCG

GCCAGGGGGTCGCTCTCATCCAGGGTCTCAAAGCTCCGCTTGCCGTCCTTCTCGGTGATCCG

CACCGGGGGGTAGCTGAAGCCCACGGCCGCCAGCTCCTCCTCGGCCTGTCTTTCGTCCTCG

CTGTCCTGGCTGACGTCCTGCATGACCACATGCTTGGTCTTGCGGGGTTTCTTCTTGGGCGG

CAGTGGCGGCGGAGATGCTTGTGGCGAGGGGGAGCGCGAGTTCTCGCTCACCACTACTATC

-continued

TCTTCCTCTTCTTGGTCCGAGGCCACGCGGCGGTAGGTATGTCTCTTCGGGGGCAGAGGCG

GAGGCGACGGGCTCTCGCCGCCGCGACTTGGCGGATGGCTGGCAGAGCCCCTTCCGCGTT

CGGGGGTGCGCTCCCGGCGGCGCTCTGACTGACTTCCTCCGCGGCCGGCCATTGTGTTCTC

CTAGGGAGGAACAACAAGCATGGAGACTCAGCCATCGCCAACCTCGCCATCTGCCCCCACC

GCCGGCGACGAGAAGCAGCAGCAGCAGAATGAAAGCTTAACCGCCCCGCCGCCCAGCCCCG

CCTCCGACGCAGCCGCGGTCCCAGACATGCAAGAGATGGAGGAATCCATCGAGATTGACCT

GGGCTATGTGACGCCCGCGGAGCATGAGGAGGAGCTGGCAGTGCGCTTTCAATCGTCAAGC

CAGGAAGATAAAGAACAGCCAGAGCAGGAAGCAGAGAACGAGCAGAGTCAGGCTGGGCTCG

AGCATGGCGACTACCTCCACCTGAGCGGGGAGGAGGACGCGCTCATCAAGCATCTGGCCCG

GCAGGCCACCATCGTCAAGGACGCGCTGCTCGACCGCACCGAGGTGCCCCTCAGCGTGGAG

GAGCTCAGCCGCGCCTACGAGCTCAACCTCTTCTCGCCGCGCGTGCCCCCCAAGCGCCAGC

CCAACGGCACCTGCGAGCCCAACCCCCGCCTCAACTTCTACCCGGTCTTCGCGGTGCCCGA

GGCCCTGGCCACCTACCACATCTTTTTCAAGAACCAAAAGATCCCCGTCTCCTGCCGCGCCA

ACCGCACCCGCGCCGACGCCCTCTTCAACCTGGGTCCCGGCGCCCGCCTACCTGATATCGC

CTCCTTGGAAGAGGTTCCCAAGATCTTCGAGGGTCTGGGCAGCGACGAGACTCGGGCCGCG

AACGCTCTGCAAGGAGAAGGAGGAGGAGAGCATGAGCACCACAGCGCCCTGGTCGAGTTGG

AAGGCGACAACGCGCGGCTGGCGGTGCTCAAACGCACGGTCGAGCTGACCCATTTCGCCTA

CCCGGCTCTGAACCTGCCCCCGAAAGTCATGAGCGCGGTCATGGACCAGGTGCTCATCAAG

CGCGCGTCGCCCATCTCCGAGGACGAGGGCATGCAAGACTCCGAGGAGGGCAAGCCCGTG

GTCAGCGACGAGCAGCTGGCCCGGTGGCTGGGTCCTAATGCTACCCCTCAAAGTTTGGAAG

AGCGGCGCAAGCTCATGATGGCCGTGGTCCTGGTGACCGTGGAGCTGGAGTGCCTGCGCCG

CTTCTTCGCCGACGCGGAGACCCTGCGCAAGGTCGAGGAGAACCTGCACTACCTCTTCAGG

CACGGGTTCGTGCGCCAGGCCTGCAAGATCTCCAACGTGGAGCTGACCAACCTGGTCTCCTA

CATGGGCATCTTGCACGAGAACCGCCTGGGGCAGAACGTGCTGCACACCACCCTGCGCGGG

GAGGCCCGCCGCGACTACATCCGCGACTGCGTCTACCTCTACCTCTGCCACACCTGGCAGA

CGGGCATGGGCGTGTGGCAGCAGTGTCTGGAGGAGCAGAACCTGAAAGAGCTCTGCAAGCT

CCTGCAAAAGAACCTCAAGGGTCTGTGGACCGGGTTCGACGAGCGGACCACCGCCTCGGAC

CTGGCCGACCTCATCTTCCCCGAGCGCCTCAGGCTGACGCTGCGCAACGGCCTGCCCGACT

TTATGAGCCAAAGCATGTTGCAAAACTTTCGCTCTTTCATCCTCGAACGCTCCGGAATCCTGC

CCGCCACCTGCTCCGCGCTGCCCTCGGACTTCGTGCCGCTGACCTTCCGCGAGTGCCCCCC

GCCGCTGTGGAGCCACTGCTACCTGCTGCGCCTGGCCAACTACCTGGCCTACCACTCGGAC

GTGATCGAGGACGTCAGCGGCGAGGGCCTGCTCGAGTGCCACTGCCGCTGCAACCTCTGCA

CGCCGCACCGCTCCCTGGCCTGCAACCCCCAGCTGCTGAGCGAGACCCAGATCATCGGCAC

CTTCGAGTTGCAAGGGCCCAGCGAGGGCGAGGGAGCCAAGGGGGGTCTGAAACTCACCCC

GGGGCTGTGGACCTCGGCCTACTTGCGCAAGTTCGTGCCCGAGGATTACCATCCCTTCGAGA

TCAGGTTCTACGAGGACCAATCCCAGCCGCCCAAGGCCGAGCTGTCGGCCTGCGTCATCAC

CCAGGGGGCGATCCTGGCCCAATTGCAAGCCATCCAGAAATCCCGCCAAGAATTCTTGCTGA

AAAAGGGCCGCGGGGTCTACCTCGACCCCCAGACCGGTGAGGAGCTCAACCCCGGCTTCCC

CCAGGATGCCCCGAGGAAACAAGAAGCTGAAAGTGGAGCTGCCGCCCGTGGAGGATTTGGA

GGAAGACTGGGAGAACAGCAGTCAGGCAGAGGAGATGGAGGAAGACTGGGACAGCACTCAG

-continued

GCAGAGGAGGACAGCCTGCAAGACAGTCTGGAGGAAGACGAGGAGGAGGCAGAGGAGGAG

GTGGAAGAAGCAGCCGCCGCCAGACCGTCGTCCTCGGCGGGGGAGAAAGCAAGCAGCACG

GATACCATCTCCGCTCCGGGTCGGGGTCCCGCTCGGCCCCACAGTAGATGGGACGAGACCG

GGCGATTCCCGAACCCCACCACCCAGACCGGTAAGAAGGAGCGGCAGGGATACAAGTCCTG

GCGGGGGCACAAAAACGCCATCGTCTCCTGCTTGCAGGCCTGCGGGGGCAACATCTCCTTC

ACCCGGCGCTACCTGCTCTTCCACCGCGGGGTGAACTTCCCCCGCAACATCTTGCATTACTA

CCGTCACCTCCACAGCCCCTACTACTTCCAAGAAGAGGCAGCAGCAGCAGAAAAAGACCAGA

AAACCAGCTAGAAAATCCACAGCGGCGGCAGCGGCAGGTGGACTGAGGATCGCGGCGAACG

AGCCGGCGCAGACCCGGGAGCTGAGGAACCGGATCTTTCCCACCCTCTATGCCATCTTCCAG

CAGAGTCGGGGGCAGGAGCAGGAACTGAAAGTCAAGAACCGTTCTCTGCGCTCGCTCACCC

GCAGTTGTCTGTATCACAAGAGCGAAGACCAACTTCAGCGCACTCTCGAGGACGCCGAGGCT

CTCTTCAACAAGTACTGCGCGCTCACTCTTAAAGAGTAGCCCGCGCCCGCCCAGTCGCAGAA

AAAGGCGGGAATTACGTCACCTGTGCCCTTCGCCCTAGCCGCCTCCACCCAGCACCGCCATG

AGCAAAGAGATTCCCACGCCTTACATGTGGAGCTACCAGCCCCAGATGGGCCTGGCCGCCG

GCGCCGCCCAGGACTACTCCACCCGCATGAATTGGCTCAGCGCCGGGCCCGCGATGATCTC

ACGGGTGAATGACATCCGCGCCCACCGAAACCAGATACTCCTAGAACAGTCAGCGCTCACCG

CCACGCCCCGCAATCACCTCAATCCGCGTAATTGGCCCGCCGCCCTGGTGTACCAGGAAATT

CCCCAGCCCACGACCGTACTACTTCCGCGAGACGCCCAGGCCGAAGTCCAGCTGACTAACT

CAGGTGTCCAGCTGGCGGGCGGCGCCACCCTGTGTCGTCACCGCCCCGCTCAGGGTATAAA

GCGGCTGGTGATCCGGGGCAGAGGCACACAGCTCAACGACGAGGTGGTGAGCTCTTCGCTG

GGTCTGCGACCTGACGGAGTCTTCCAACTCGCCGGATCGGGGAGATCTTCCTTCACGCCTCG

TCAGGCGGTCCTGACTTTGGAGAGTTCGTCCTCGCAGCCCCGCTCGGGCGGCATCGGCACT

CTCCAGTTCGTGGAGGAGTTCACTCCCTCGGTCTACTTCAACCCCTTCTCCGGCTCCCCCGG

CCACTACCCGGACGAGTTCATCCCGAACTTTGACGCCATCAGCGAGTCGGTGGACGGCTACG

ATTGATTAATTAATCAACTAACCCCTTACCCCTTTACCCTCCAGTAAAAATAAAGATTAAAAATG

ATTGAATTGATCAATAAAGAATCACTTACTTGAAATCTGAAACCAGGTCTCTGTCCATGTTTTC

TGTCAGCAGCACTTCACTCCCCTCTTCCCAACTCTGGTACTGCAGGCCCCGGCGGGCTGCAA

ACTTCCTCCACACTCTGAAGGGGATGTCAAATTCCTCCTGTCCCTCAATCTTCATTTTTATCTT

CTATCAGATGTCCAAAAAGCGCGCGCGGGTGGATGATGGCTTCGACCCCGTGTACCCCTACG

ATGCAGACAACGCACCGACTGTGCCCTTCATCAACCCTCCCTTCGTCTCTTCAGATGGATTCC

AAGAAAAGCCCCTGGGGGTGTTGTCCCTGCGACTGGCCGACCCCGTCACCACCAAGAATGG

GGCTGTCACCCTCAAGCTGGGGGAGGGGGTGGACCTCGACGACTCGGGAAAACTCATCTCC

AAAAATGCCACCAAGGCCACTGCCCCTCTCAGTATTTCCAACGGCACCATTTCCCTTAACATG

GCTGCCCCTTTTTACAACAACAATGGAACGTTAAGTCTCAATGTTTCTACACCATTAGCAGTAT

TTCCCACTTTTAACACTTTAGGTATCAGTCTTGGAAACGGTCTTCAAACTTCTAATAAGTTGCT

GACTGTACAGTTAACTCATCCTCTTACATTCAGCTCAAATAGCATCACAGTAAAAACAGACAAA

GGACTCTATATTAATTCTAGTGGAAACAGAGGGCTTGAGGCTAACATAAGCCTAAAAAGAGGA

CTGATTTTTGATGGTAATGCTATTGCAACATACCTTGGAAGTGGTTTAGACTATGGATCCTATG

ATAGCGATGGGAAAACAAGACCCATCATCACCAAAATTGGAGCAGGTTTGAATTTTGATGCTA

ATAATGCCATGGCTGTGAAGCTAGGCACAGGTTTAAGTTTTGACTCTGCCGGTGCCTTAACAG

CTGGAAACAAAGAGGATGACAAGCTAACACTTTGGACTACACCTGACCCAAGCCCTAATTGTC

-continued

AATTACTTTCAGACAGAGATGCCAAATTTACCCTATGTCTTACAAAATGCGGTAGTCAAATACT

AGGCACTGTTGCAGTAGCTGCTGTTACTGTAGGTTCAGCACTAAATCCAATTAATGACACAGT

AAAAAGCGCCATAGTATTCCTTAGATTTGACTCTGACGGTGTGCTCATGTCAAACTCATCAAT

GGTAGGTGATTACTGGAACTTTAGGGAAGGACAGACCACCCAAAGTGTGGCCTATACAAATG

CTGTGGGATTCATGCCCAATCTAGGTGCATATCCTAAAACCCAAAGCAAAACACCAAAAAATA

GTATAGTAAGTCAGGTATATTTAAATGGAGAAACTACTATGCCAATGACACTGACAATAACTTT

CAATGGCACTGATGAAAAAGACACAACACCTGTGAGCACTTACTCCATGACTTTTACATGGCA

GTGGACTGGAGACTATAAGGACAAGAATATTACCTTTGCTACCAACTCCTTTACTTTCTCCTAC

ATGGCCCAAGAATAAACCCTGCATGCCAACCCCATTGTTCCCACCACTATGGAAAACTCTGAA

GCAGAAAAAAATAAAGTTCAAGTGTTTTATTGATTCAACAGTTTTCTCACAGAACCCTAGTATT

CAACCTGCCACCTCCCTCCCAACACACAGAGTACACAGTCCTTTCTCCCCGGCTGGCCTTAA

AAAGCATCATATCATGGGTAACAGACATATTCTTAGGTGTTATATTCCACACGGTTTCCTGTCG

AGCCAAACGCTCATCAGTGATATTAATAAACTCCCCGGGCAGCTCACTTAAGTTCATGTCGCT

GTCCAGCTGCTGAGCCACAGGCTGCTGTCCAACTTGCGGTTGCTTAACGGGCGGCGAAGGA

GAAGTCCACGCCTACATGGGGGTAGAGTCATAATCGTGCATCAGGATAGGGCGGTGGTGCT

GCAGCAGCGCGCGAATAAACTGCTGCCGCCGCCGCTCCGTCCTGCAGGAATACAACATGGC

AGTGGTCTCCTCAGCGATGATTCGCACCGCCCGCAGCATAAGGCGCCTTGTCCTCCGGGCA

CAGCAGCGCACCCTGATCTCACTTAAATCAGCACAGTAACTGCAGCACAGCACCACAATATTG

TTCAAAATCCCACAGTGCAAGGCGCTGTATCCAAAGCTCATGGCGGGGACCACAGAACCCAC

GTGGCCATCATACCACAAGCGCAGGTAGATTAAGTGGCGACCCCTCATAAACACGCTGGACA

TAAACATTACCTCTTTTGGCATGTTGTAATTCACCACCTCCCGGTACCATATAAACCTCTGATT

AAACATGGCGCCATCCACCACCATCCTAAACCAGCTGGCCAAAACCTGCCCGCCGGCTATAC

ACTGCAGGGAACCGGGACTGGAACAATGACAGTGGAGAGCCCAGGACTCGTAACCATGGAT

CATCATGCTCGTCATGATATCAATGTTGGCACAACACAGGCACACGTGCATACACTTCCTCAG

GATTACAAGCTCCTCCCGCGTTAGAACCATATCCCAGGGAACAACCCATTCCTGAATCAGCGT

AAATCCCACACTGCAGGGAAGACCTCGCACGTAACTCACGTTGTGCATTGTCAAAGTGTTACA

TTCGGGCAGCAGCGGATGATCCTCCAGTATGGTAGCGCGGGTTTCTGTCTCAAAAGGAGGTA

GACGATCCCTACTGTACGGAGTGCGCCGAGACAACCGAGATCGTGTTGGTCGTAGTGTCATG

CCAAATGGAACGCCGGACGTAGTCATATTTCCTGAAGCAAAACCAGGTGCGGGCGTGACAAA

CAGATCTGCGTCTCCGGTCTCGCCGCTTAGATCGCTCTGTGTAGTAGTTGTAGTATATCCACT

CTCTCAAAGCATCCAGGCGCCCCCTGGCTTCGGGTTCTATGTAAACTCCTTCATGCGCCGCT

GCCCTGATAACATCCACCACCGCAGAATAAGCCACACCCAGCCAACCTACACATTCGTTCTG

CGAGTCACACACGGGAGGAGCGGGAAGAGCTGGAAGAACCATGATTAACTTTATTCCAAACG

GTCTCGGAGCACTTCAAAATGCAGGTCCCGGAGGTGGCACCTCTCGCCCCCACTGTGTTGGT

GGAAAATAACAGCCAGGTCAAAGGTGACACGGTTCTCGAGATGTTCCACGGTGGCTTCCAGC

AAAGCCTCCACGCGCACATCCAGAAACAAGAGGACAGCGAAAGCGGGAGCGTTTTCTAATTC

CTCAATCATCATATTACACTCCTGCACCATCCCCAGATAATTTTCATTTTTCCAGCCTTGAATG

ATTCGTATTAGTTCCTGAGGTAAATCCAAGCCAGCCATGATAAAAAGCTCGCGCAGAGCGCC

CTCCACCGGCATTCTTAAGCACACCCTCATAATTCCAAGAGATTCTGCTCCTGGTTCACCTGC

AGCAGATTAACAATGGGAATATCAAAATCTCTGCCGCGATCCCTAAGCTCCTCCCTCAACAAT

-continued

AACTGTATGTAATCTTTCATATCATCTCCGAAATTTTTAGCCATAGGGCCGCCAGGAATAAGAG

CAGGGCAAGCCACATTACAGATAAAGCGAAGTCCTCCCCAGTGWGCATTGCCAAATGTAAGA

TTGAAATAAGCATGCTGGCTAGACCCTGTGATATCTTCCAGATAACTGGACAGAAAATCAGGC

AAGCAATTTTTAAGAAAATCAACAAAAGAAAAGTCGTCCAGGTGCAGGTTTAGAGCCTCAGGA

ACAACGATGGAATAAGTGCAAGGAGTGCGTTCCAGCATGGTTAGTGTTTTTTTGGTGATCTGT

AGAACAAAAAATAAACATGCAATATTAAACCATGCTAGCCTGGCGAACAGGTGGGTAAATCAC

TCTTTCCAGCACCAGGCAGGCTACGGGGTCTCCGGCGCGACCCTCGTAGAAGCTGTCGCCA

TGATTGAAAAGCATCACCGAGAGACCTTCCCGGTGGCCGGCATGGATGATTCGAGAAGAAGC

ATACACTCCGGGAACATTGGCATCCGTGAGTGAAAAAAAGCGACCTATAAAGCCTCGGGGCA

CTACAATGCTCAATCTCAATTCCAGCAAAGCCACCCCATGCGGATGGAGCACAAAATTGGCA

GGTGCGTAAAAAATGTAATTACTCCCCTCCTGCACAGGCAGCAAAGCCCCCGCTCCCTCCAG

AAACACATACAAAGCCTCAGCGTCCATAGCTTACCGAGCACGGCAGGCGCAAGAGTCAGAGA

AAAGGCTGAGCTCTAACCTGACTGCCCGCTCCTGTGCTCAATATATAGCCCTAACCTACACTG

ACGTAAAGGCCAAAGTCTAAAAATACCCGCCAAAATGACACACACGCCCAGCACACGCCCAG

AAACCGGTGACACACTCAAAAAAATACGTGCGCTTCCTCAAACGCCCAAACCGGCGTCATTTC

CGGGTTCCCACGCTACGTCACCGCTCAGCGACTTTCAAATTCCGTCGACCGTTAAAAACGTC

ACTCGCCCCGCCCCTAACGGTCGCCCTTCTCTCGGCCAATCACCTTCCTCCCTTCCCAAATTC

AAACGCCTCATTTGCATATTAACGCGCACAAAAAGTTTGAGGTATATATTTGAATGATG

1NSALL MVA

[SEQ ID NO: 122]

GCGCCCAATACGCAAACCGCCTCTCCCCGCGCGTTGGCCGATTCATTAATGCAGCTGGCACG

ACAGGTTTCCCGACTGGAAAGCGGGCAGTGAGCGCAACGCAATTAATGTGAGTTAGCTCACT

CATTAGGCACCCCAGGCTTTACACTTTATGCTTCCGGCTCGTATGTTGTGTGGAATTGTGAGC

GGATAACAATTTCACACAGGAAACAGCTATGACCATGATTACGCCAAGCTTGCATGCATCTGG

AAACGGGCATCTCCATTTAAGACTAGATGCCACGGGGTTTAAAATACTAATCATGACATTTTGT

AGAGCGTAATTACTTAGTAAATCCGCCGTACTAGGTTCATTTCCTCCTCGTTTGGATCTCACAT

CAGAAATTAAAATAATCTTAGAAGGATGCAGTTGTTTTTTGATGGATCGTAGATATTCCTCATC

AACGAACCGAGTCACTAGAGTCACATCACGCAATCCATTTAAAATAGGATCATGATGGCGGCC

GTCAATTAGCATCCATTTGATGATCACTCCTAAATTATAGAAATGATCTCTCAAATAACGTATAT

GTGTACCGGGAGCAGATCCTATATACACTACGGTGGCACCATCTAATATACCGTGTCGCTGTA

ACTTACTAAGAAAAAATAATTCTCCTAGTAATAGTTTTAACTGTCCTTGATACGGTAGTTTTTTT

GCGACCTCATTTGCACTTTCTGGTTCGTAATCTAACTCATTATCAATTTCCTCAAAATACATAAA

CGGTTTATCTAACGACACAACATCCATTTTTAAGTATTATATTAAAATTTAATCAATGTTTATTTT

TAGTTTTTTAGATAAAAAATATAATATTATGAGTCGATGTAACACTTTCTACACACCGATTGATA

CATATCATTACCTCCTATTATCTCTATCTCGGTTTCCTCACCCAATCGTTTAGAAAAGGAAGCC

TCCTTAAAGCATTTCATACACACAGCAGTTAGTTTTACCACCATTTCAGATAATGGAATAAGAT

TCAAAATATTATTAAACGGTTTACGTTGAAATGTCCCATCGAGTGCGGCTACTATAACTATTTT

TCCTTCGTTTGCCATACAGATCCTACGTACTCGAGCGGCCGCTCATCAGGTCCGCGTAGAAT

CGAGACCGAGGAGAGGGTTAGGGATAGGCTTACCTGAAGCCCCGGGCCCGGATCCAGCGTA

GGTGCCCACCTGGCCGCTGCCCCTCTGGTCCTTCCTGCTGATGATGTCCATCACGGGCCTCT

GCACCTTCACCACCTTGTTCTGGTAGGTCAGCTTGAACAGGTCGTCCTCGGTGATCCTGGTG

TCCCAGCCGGCGGTGTCGTCGGCGTACATGAAGCCCAGGGCCTCGAACTCCAGGAACCTGG

-continued

CGCCCAGCCACATGTACCAGATGGCCCTGCTCTTGGCCTTGCCGAACTCGCCCAGCTTCTTC

TCCCTCTTGCCCATCATGTTGTACTCCTCGATGGTGGGGTTGGGGCTGCTCTCGCCGATGTC

GCACAGGGCCAGGTAGCTGCCCCTGAAGATGTTGGCCATGCTCACGGCGATGGTGGTGTTC

CAGAACTTGCCGGGCATGCTCACGGCGATGGTGGTGTTCCAGAACTTGCCGGGGTTGCCCT

CCCACAGGGGGCCGGTGGCCAGGGTCAGGGCCTCGCACAGGGCCCAGGTGGTCCTCATCA

GCAGCATCACCTGGCCCAGCTGCTTCTCGAACTTGGGGTCGTAGCCGTCCACGGTGGGGTT

CTTCATGATGCCGGCGGCGGTCCTCTTGATGTTGTCCAGCAGCATCTTGGCCTCGGTCCAGT

GGGCGTGGTCGTTCCTGCCGATCCTGCCCCTCCTCTGGGCGGCGCTGGCGGCGGTCACGG

GCATGGGCTTGAAGTTGGCGCCCATCTCGCTGATGTCGGTGGTCACCACGAAGTCCCAGTCG

TTCAGGATGGCGGCGGCCTCGCCCATCTCCACCCTGGTGCTGATGTAGCCCCTGGCGGCGA

TGCTGGGCAGGCCCTTCAGGGCCTCCTCCATCTCGGCGGCCACCACCCTCTCCTCCATCTCG

GCGGCCACCACCCTGGTGGGGGCCATCTCGCTGGCCACCACCCTGGTGGGGGCCAGGATC

AGGGCAAGCTTCGATCCTCTTCTGAATCGGGCATGGATTTCCTGGCTGGGCGAAACGAAGAC

TGCTCCACACAGCAGCAGCACACAGCAGAGCCCTCTCTTCATTGCATCCATGGTGGCGGCGC

GGCTAGCGGTACCGGATCTAGATGGGGATCCGTCACTGTTCTTTATGATTCTACTTCCTTACC

GTGCAATAAATTAGAATATATTTTCTACTTTTACGAGAAATTAATTATTGTATTTATTATTTATGG

GTGAAAAACTTACTATAAAAAGCGGGTGGGTTTGGAATTAGTGATCAGTTTATGTATATCGCAA

CTACCGGGCATATGGCTATCGACATCGAGAACATTACCCACATGATAAGAGATTGTATCAGTT

TCGTAGTCTTGAGTATTGGTATTACTATATAGTATATAGATGTCGACCTGCAGGTCGACGAAG

TTCCTATACTTTCTAGAGAATAGGAACTTCGCAGCCAAGCTGGAATTCATCCACTTTGGATAA

GAAATCTGCATGATAAATATATTGATATCCTACCACCTATTAAAGTACCATTATCTAATAGCAAT

AAGATAGATAAACAAATGTTTTTTGATGAAGTTATTACGTGGATAAATATATATCTTCAGGAAAA

GGGTATTATGTTACCAGATGATATAAGAGAACTCAGAGATGCTATTATTCCTTAACTAGTTACG

TCTCTTTAGGTACTTATTTTGATACGTTACAAGTAAAAAACTATCAAATATAAATGGAATCTGAT

TCTAATATAGCGATTGAAGAGGATCCACCGGTCGCCACCATGGTGAGCAAGGGCGAGGAGCT

GTTCACCGGGGTGGTGCCCATCCTGGTCGAGCTGGACGGCGACGTAAACGGCCACAAGTTC

AGCGTGTCCGGCGAGGGCGAGGGCGATGCCACCTACGGCAAGCTGACCCTGAAGTTCATCT

GCACCACCGGCAAGCTGCCCGTGCCCTGGCCCACCCTCGTGACCACCCTGACCTACGGCGT

GCAGTGCTTCAGCCGCTACCCCGACCACATGAAGCAGCACGACTTCTTCAAGTCCGCCATGC

CCGAAGGCTACGTCCAGGAGCGCACCATCTTCTTCAAGGACGACGGCAACTACAAGACCCGC

GCCGAGGTGAAGTTCGAGGGCGACACCCTGGTGAACCGCATCGAGCTGAAGGGCATCGACT

TCAAGGAGGACGGCAACATCCTGGGGCACAAGCTGGAGTACAACTACAACAGCCACAACGTC

TATATCATGGCCGACAAGCAGAAGAACGGCATCAAGGTGAACTTCAAGATCCGCCACAACAT

CGAGGACGGCAGCGTGCAGCTCGCCGACCACTACCAGCAGAACACCCCCATCGGCGACGGC

CCCGTGCTGCTGCCCGACAACCACTACCTGAGCACCCAGTCCGCCCTGAGCAAAGACCCCA

ACGAGAAGCGCGATCACATGGTCCTGCTGGAGTTCGTGACCGCCGCCGGGATCACTCTCGG

CATGGACGAGCTGTACAAGTAAAGCGGCCGCGAAGTTCCTATACTTTCTAGAGAATAGGAACT

TCAACAATGTCTGGAAAGAACTGTCCTTCATCGATACCTATCACGGAGAAATCTGTAATTGATT

CCAAGACATCACATAGTTTAGTTGCTTCCAATGCTTCAAAATTATTCTTATCATGCGTCCATAG

TCCCGTTCCGTATCTATTATCGTTAGAATATTTTATAGTCACGCATTTATATTGAGCTATTTGAT

-continued

AACGTCTAACTCGTCTAATTAATTCTGTACTTTTACCTGAAAACATGGGGCCGATTATCAACTG

AATATGTCCGCCGTTCATGATGACAATAAAGAATTAATTATTGTTCACTTTATTCGACTTTAATA

TATCCATCACGTTAGAAAATGCGATATCGCGACGAGGATCTATGTATCTAACAGGATCTATTG

CGGTGGTAGCTAGAGCTGATTCTTTTTTGAATCGCATCAAACTAATCACAAAGTCGAACAAATA

TCCTTTATTAAGTTTGACCCTTCCATCTGTAACAATAGGGACCTTGTTAAACAGTTTTTTAAAAT

CTTGAGAGTCTGTGAATTTTGTCAATTGTCTGTATTCCTCTGAAAGAGATTCATAACAATGACC

CACGGCTTCTAATTTATTTTTTGATTGGATCAATAATAATAACAGAAAGTCTAGATATTGAGTGA

TTTGCAATATATCAGATAATGAAGATTCATCATCTTGACTAGCCAAATACTTAAAAAATGAATCA

TCATCTGCGAAGAACATCGTTAAGAGATACTGGTTGTGATCCATTTATGAGCTCGCGAAAGCT

TGGCACTGGCCGTCGTTTTACAACGTCGTGACTGGGAAAACCCTGGCGTTACCCAACTTAAT

CGCCTTGCAGCACATCCCCCTTTCGCCAGCTGGCGTAATAGCGAAGAGGCCCGCACCGATC

GCCCTTCCCAACAGTTGCGCAGCCTGAATGGCGAATGGCGCCTGATGCGGTATTTTCTCCTT

ACGCATCTGTGCGGTATTTCACACCGCATATGGTGCACTCTCAGTACAATCTGCTCTGATGCC

GCATAGTTAAGCCAGCCCCGACACCCGCCAACACCCGCTGACGCGCCCTGACGGGCTTGTC

TGCTCCCGGCATCCGCTTACAGACAAGCTGTGACCGTCTCCGGGAGCTGCATGTGTCAGAGG

TTTTCACCGTCATCACCGAAACGCGCGAGACGAAAGGGCCTCGTGATACGCCTATTTTTATAG

GTTAATGTCATGATAATAATGGTTTCTTAGACGTCAGGTGGCACTTTTCGGGGAAATGTGCGC

GGAACCCCTATTTGTTTATTTTTCTAAATACATTCAAATATGTATCCGCTCATGAGACAATAACC

CTGATAAATGCTTCAATAATATTGAAAAAGGAAGAGTATGAGTATTCAACATTTCCGTGTCGCC

CTTATTCCCTTTTTTGCGGCATTTTGCCTTCCTGTTTTTGCTCACCCAGAAACGCTGGTGAAAG

TAAAAGATGCTGAAGATCAGTTGGGTGCACGAGTGGGTTACATCGAACTGGATCTCAACAGC

GGTAAGATCCTTGAGAGTTTTCGCCCCGAAGAACGTTTTCCAATGATGAGCACTTTTAAAGTT

CTGCTATGTGGCGCGGTATTATCCCGTATTGACGCCGGGCAAGAGCAACTCGGTCGCCGCAT

ACACTATTCTCAGAATGACTTGGTTGAGTACTCACCAGTCACAGAAAAGCATCTTACGGATGG

CATGACAGTAAGAGAATTATGCAGTGCTGCCATAACCATGAGTGATAACACTGCGGCCAACTT

ACTTCTGACAACGATCGGAGGACCGAAGGAGCTAACCGCTTTTTTGCACAACATGGGGGATC

ATGTAACTCGCCTTGATCGTTGGGAACCGGAGCTGAATGAAGCCATACCAAACGACGAGCGT

GACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACT

TCTGCGCTCGGCCCTTCCGGCTGGCTGGTTTATTGCTGATAAATCTGGAGCCGGTGAGCGTG

GGTCTCGCGGTATCATTGCAGCACTGGGGCCAGATGGTAAGCCCTCCCGTATCGTAGTTATC

TACACGACGGGGAGTCAGGCAACTATGGATGAACGAAATAGACAGATCGCTGAGATAGGTGC

CTCACTGATTAAGCATTGGTAACTGTCAGACCAAGTTTACTCATATATACTTTAGATTGATTTAA

AACTTCATTTTTAATTTAAAAGGATCTAGGTGAAGATCCTTTTTGATAATCTCATGACCAAAATC

CCTTAACGTGAGTTTTCGTTCCACTGAGCGTCAGACCCCGTAGAAAAGATCAAAGGATCTTCT

TGAGATCCTTTTTTTCTGCGCGTAATCTGCTGCTTGCAAACAAAAAAACCACCGCTACCAGCG

GTGGTTTGTTTGCCGGATCAAGAGCTACCAACTCTTTTTCCGAAGGTAACTGGCTTCAGCAGA

GCGCAGATACCAAATACTGTTCTTCTAGTGTAGCCGTAGTTAGGCCACCACTTCAAGAACTCT

GTAGCACCGCCTACATACCTCGCTCTGCTAATCCTGTTACCAGTGGCTGCTGCCAGTGGCGA

TAAGTCGTGTCTTACCGGGTTGGACTCAAGACGATAGTTACCGGATAAGGCGCAGCGGTCGG

GCTGAACGGGGGGTTCGTGCACACAGCCCAGCTTGGAGCGAACGACCTACACCGAACTGAG

-continued

ATACCTACAGCGTGAGCTATGAGAAAGCGCCACGCTTCCCGAAGGGAGAAAGGCGGACAGG

TATCCGGTAAGCGGCAGGGTCGGAACAGGAGAGCGCACGAGGGAGCTTCCAGGGGGAAAC

GCCTGGTATCTTTATAGTCCTGTCGGGTTTCGCCACCTCTGACTTGAGCGTCGATTTTTGTGA

TGCTCGTCAGGGGGGCGGAGCCTATGGAAAAACGCCAGCAACGCGGCCTTTTTACGGTTCCT

GGCCTTTTGCTGGCCTTTTGCTCACATGTTCTTTCCTGCGTTATCCCCTGATTCTGTGGATAAC

CGTATTACCGCCTTTGAGTGAGCTGATACCGCTCGCCGCAGCCGAACGACCGAGCGCAGCG

AGTCAGTGAGCGAGGAAGCGGAAGA

2NSALL MVA

[SEQ ID NO: 123]

GCGCCCAATACGCAAACCGCCTCTCCCCGCGCGTTGGCCGATTCATTAATGCAGCTGGCACG

ACAGGTTTCCCGACTGGAAAGCGGGCAGTGAGCGCAACGCAATTAATGTGAGTTAGCTCACT

CATTAGGCACCCCAGGCTTTACACTTTATGCTTCCGGCTCGTATGTTGTGTGGAATTGTGAGC

GGATAACAATTTCACACAGGAAACAGCTATGACCATGATTACGCCAAGCTTGCATGCATCTGG

AAACGGGCATCTCCATTTAAGACTAGATGCCACGGGGTTTAAAATACTAATCATGACATTTTGT

AGAGCGTAATTACTTAGTAAATCCGCCGTACTAGGTTCATTTCCTCCTCGTTTGGATCTCACAT

CAGAAATTAAAATAATCTTAGAAGGATGCAGTTGTTTTTTGATGGATCGTAGATATTCCTCATC

AACGAACCGAGTCACTAGAGTCACATCACGCAATCCATTTAAAATAGGATCATGATGGCGGCC

GTCAATTAGCATCCATTTGATGATCACTCCTAAATTATAGAAATGATCTCTCAAATAACGTATAT

GTGTACCGGGAGCAGATCCTATATACACTACGGTGGCACCATCTAATATACCGTGTCGCTGTA

ACTTACTAAGAAAAAATAATTCTCCTAGTAATAGTTTTAACTGTCCTTGATACGGTAGTTTTTTT

GCGACCTCATTTGCACTTTCTGGTTCGTAATCTAACTCATTATCAATTTCCTCAAAATACATAAA

CGGTTTATCTAACGACACAACATCCATTTTTAAGTATTATATTAAAATTTAATCAATGTTTATTTT

TAGTTTTTTAGATAAAAAATATAATATTATGAGTCGATGTAACACTTTCTACACACCGATTGATA

CATATCATTACCTCCTATTATCTCTATCTCGGTTTCCTCACCCAATCGTTTAGAAAAGGAAGCC

TCCTTAAAGCATTTCATACACACAGCAGTTAGTTTTACCACCATTTCAGATAATGGAATAAGAT

TCAAAATATTATTAAACGGTTTACGTTGAAATGTCCCATCGAGTGCGGCTACTATAACTATTTT

TCCTTCGTTTGCCATACAGATCCTACGTACTCGAGCGGCCGCTCATCAGGTCCGCGTAGAAT

CGAGACCGAGGAGAGGGTTAGGGATAGGCTTACCTGAAGCCCCGGGCCCGGATCCAGCGAT

GTTCTTGGCCCAGGTGGCCCTGCTGGTCAGGCCGATCAGGCTGCCGCACCACTGGTCCTCC

CTCTTGCCCAGGTAGGGCACGTCCTCCCAGCTGTGCCACACCCTGTTCCACACGGCCAGCAT

GTCCTCGGTGGTCATCCACTCGTGGCTCCAGGTGGTCCTGCTGGGCACCCAGTGGCTGGGC

ACGGCGCTGCAGATGGCGTTGCTGGCCAGCCTCAGGTCCCTCCTGTGGAAGTACATCAGCT

GCCACATCTGGGCGTAGCTCTTGCCCAGGCAGGCGGTCTCCCTCAGGCTCCAGCCGGCGCC

CTGGCTGATCCTGGCCCTGCCGATCAGCTCGTCCTGGTTCCTGCAGGGCACCACCAGCTTCC

TGCCGTCCTTCATGAAGATGTGGAAGTGGTGGCTGCAGAAGGGCACCTGCTGCCAGTCGTG

CCAGCCCTTGCTGGGCTCCCACTGCTCGGCCTCCATCTGCCTGATCAGCTGGGCCTCCATGT

TGGTGAAGGTGTTCAGGCCGTAGGTGCCCACCTGGCCGCTGCCCCTCTGGTCCTTCCTGCT

GATGATGTCCATCACGGCGCCCCTGGGGGTGGGCCTCTGCACCTTCACCACCTTGTTCTGGT

AGGTCAGCTTGAAGATGGCCTTGGCCAGCTTCTCCTCGTTGTGCAGGTCGTCCTCGGTGATC

CTGGTGTCCCAGCCGGCGGTGTCGTCGGCGTACATGGCGCCGCCGGGGATCTTGCTGATGT

CCCTCAGGATGTAGCCCAGCAGGCCCTCGCCCTCCACGCCGCTCAGGCTGTTCTCCCTGCT

-continued

GAACCAGTGGTCCTCGTTCAGGAAGCCCAGGGCCTCGAACTCCAGGAACCTGGCGCCCAGC

CACATGTACCAGATGGCCCTGCTGCCCTTGGCCTTGCCGAACTCGCCCAGCTTCTTCTCCCT

CTTGCCCATCATGTTGTACACGCAGCTCTCGCACTTGCCCTCCAGGTGCAGGGCGCTCTTCC

AGCCGTTCTCGTCCTGGGCCTCGGGGGTCCTGGTGTCCACCTTCTCCTTGAACACCCTCTGC

TGGCCGAAGGGGGTGGTGTCGGTCATGGCCATCTGGGTCACCATGGGCACCACGTCCCAGG

GCTTGGTCAGCAGCTTCACCACGCCGTTCACCATGCTGCTGGCGCTGCCGGTGGCCTTCACC

TCGTAGCTGCCGTGGTAGGCCCAGGTCTTGTAGGGGTTGTCCTCGTCCTTGTGGGCCATGGT

GAACCTGTTGATCAGCATCCTGCTGATCATGTTCACGGCGCTCACGATGTTGCCGGTGCCGT

TGCTCACCCAGTACATCTCGTGGGTGCTGTTCCTGCTCAGGGGGTTCCTCACCAGCATGCCG

CCGTGCTTCCTCTGCAGCTTCTCCAGCTCGATCACGCTGGGCATGTAGGGGTTCAGGATCTT

GATGCAGAACTGGTTGCCCTTCAGCCAGGGCTCCACCATCTTCAGCACCCTCAGGGTCCTGC

CCTCCTCGATGGTGGGGTTGGGGCTGCTCTCGCCGATGTCGCACAGCAGGGTGTCGCACTT

CTCGAAGAACACGTCCACGCCGCTGTGCAGCTTCACCAGGTTCCAGCCGTAGGTGGCCATG

GGGATGGGCTCCTCGTGGCCGGGGCCGCCCTTGGTGTAGCCCCTCACCTTCTTCAGGCCGG

CGCAGTAGTAGCTCCAGCCGCCCCTGCCGCAGCCCAGGTCGATCACCACCATGATGGCCTC

CTTGGCCTCGGTCCTGTCCACCTCCAGGATGCCGCTCTTCTTGTACTCCTCGAAGCTCTTGTC

CAGCTGGTTCAGCTGCCTCTTCCACTTCTCGCCCAGGGTCTCGCCGTTCTTGATCAGGCTGA

AGGCCAGGCCGGCGCCGGCCAGGTAGCTGCCCCTGAAGATGTTGGCCATGCTCACGGCGAT

GGTGGTGTTCCAGAACTTGCCGGGGTTGCCCTCCCACAGGGTGGTGATGGGGCCGGTGGCC

AGGGTCAGGGCCTCGCACAGGGCCCAGGTGGTCCTCATCAGCAGGATCTGGCTGCACAGGA

TCAGCAGCATCACCTGGCCCAGCTGCTTCTCGAACTTGGGGTCGTAGGGGATGGGGTCCAG

GTCGATGGCCATGATGCCGTCCACGGTGGGGTTCTTCATGATGCCGGCGGCGGTCCTCTTCT

GGGCCTCCCTGGTGGCCTTGGCCTGCAGGCCGGGGCCGATGATGGCGTAGTGGGTCAGGG

TCAGGGGGTTCACCTGGCTGTAGCAGCCCAGGGCCAGCAGGGGGCACGCCCAGGTCCATCTT

GCTGATGGGCCAGCCCTTGTCCAGGCCCATCAGCACGGCGGCCTGGTTGGCGATGGCGGTC

AGGCTCACGTTGGCGGTGCTGTTCTCGATGGTGTGCCTCAGCATGGGGGTGATGATGGTGG

TGGCCACGGCGTACAGGGTCCAGGCGCTGGCGGGGTGCAGGTCCACGTCCAGGATGGCGC

CGATGCCCAGGTCCTTCTTGGTGGTCTCCAGCAGGCCCATCTCGTTGGCGGCGATGGCGGC

GGCCAGGGTCAGGATGCCGATCACCACGTAGGCCAGCTGGTTGTCCTGGGGGGTCCTCTGC

TTCTCGGGCTCGGGGATCAGCAGCACCATCAGGAAGAACTCCAGGATGATGCTGGCGGCGA

TCCAGTGGGGCTGGATCTCGGCCATCCACAGCAGGCTGGCGGCGATGATGCAGCACAGGCC

GATGCTCATCTTGCCGATGCCCTTGCCGCTCAGGAAGAACAGGAAGCCCAGCAGGGCCAGC

AGCAGCAGGGTCTCCAGGGTCTCGGGCAGCTCCTCCAGGGCGTGGGGGTCGGCGTAGGTC

CTGGCGTCCAGCCACCTGGGCCTCAGCTTCTTCTTCTCGCCCTCGGTCCAGATCTCCACGTC

CATGTTCTCCTCCAGGATCTGGTTGTTCCTCTCGCCGTCGAAGCACCACTCCCTGTCCTTGTA

CTGGAAGCCGGCGCTGGCCACCTTGTAGCTCAGCCACACGGGCAGGTCGCCCCTCCTCATC

AGCTCCACGAAGGTCTTCCTGGCCTCGCCCCTCAGCCTGTACTCGCCGTCGATGGCGGCGC

TCTTCTCCCTCTCGGGCTCGAACAGGGCGGGGATGATGCCCTCGGGGGTGTTGATGTTGTCC

AGCAGCATCTTGGCCTCGGTCCAGTGGGCGTGGTCCTCGTCGTTGTTCAGGGGCTGGCCCA

TGTAGATGTACTGGTCGTTCTCCTTCTTGTGGTTCCTGCCGATCCTGCCCCTCCTCTGGGCG

GCGCTGGCGGCGGTCACGGGCATGGGGCCGGCCAGGATCACCCTCTCGGGGCCGTCGGTC

-continued

AGGATCACGGGCTTCAGGCACCTCCTGGGGTCGATCACCCTGTCGGCCTTGAAGTTGGCGC

CCATCTCGCTGATGTCGGTGGTCACCACGAAGTCCCAGTCGTTCAGCTTGGTCTTGGGGTAC

TCGGTGTCGAAGGTCTTCCTGCTCAGCTGGATCACCTTCTTGCCGTTCTTCCTCAGGCAGTTG

GCGATGTCGTTGCCGGCCTTGATGCTGGGCACGAACCACACGGTCTTGCCGGCGAAGTCGG

TGATCCAGTCGAAGCCGCTGTTCCAGCTCCTCTCGGGGATCTCCCTCTCCTCGTCCTCGATG

GGGGCGTTGCTCTGGGGGAAGGCGTCGGCGCTGCCGGGGGGGGTGGCGGTCATGAAGATG

GCGGCGGCCTCGCCCATCTCCACCCTGGTGCTGATGTAGCCCCTGGCGGCGATGCTGGCGG

GGTCGGTGAAGTGGGCCTCGTCCATGATGATCAGGTTGTAGTTGGGCACCCTCACGGGGCT

CAGCAGCCTCATGGTGAAGGTGGCGTGGCACATCAGGTCCACGATCTCCTTGCCGGTGTGCT

CGGCCTTGATGGCGGTGGTCTGATACCTGATGGGCAGGCCCTTCAGGGCCTCCTCCATCTC

GGCGGCCACCACCCTGGTGGGGGCCAGGATCAGGGTCCTCAGCCTCCTCTTGATGGCCTCC

CTCACGATGGCGGGCAGATACCTCTTGGTCTTGCCGGCGCCGGGGTGCAGGTCCATGATGG

TCAGGTTCCTCTTCCTGAAGGTCTGGGCGATGGCGCTCACGTAGGCGCCGCTCTTGGTCACC

ACGCCGTTGCCGTACAGGCCCACGCCCTCCCTGTTCACGATGGGGCTGCCGCTGGTGCCGG

GCTTGAAGTCCAGGGCGATGGCGCCGATCTCGCCGGTCTGCACGGCCTTGGGGTTCTTGCC

GGGCTCCACGGCGATCACCTGCACCTCCTCGCCCTCGTCCCACTCGCCCTCCAGCCTCCAG

CCGCCGCCGTAGCTGATCAGGTCCTTCTTCACGTCGGCCCAGCTGGGCTCGATCCTCTTGCC

CTGGTGCATCAGCACGGCGCCCCTGGTCACGTGCCACATGGTGTGGAACACGCCCTCCTTG

AACACGCCGGCGCCGATCTGGCTGGCAAGCTTCGATCCTCTTCTGAATCGGGCATGGATTTC

CTGGCTGGGCGAAACGAAGACTGCTCCACACAGCAGCAGCACACAGCAGAGCCCTCTCTTCA

TTGCATCCATGGTGGCGGCGCGGCTAGCGGTACCGGATCTAGATGGGGATCCGTCACTGTT

CTTTATGATTCTACTTCCTTACCGTGCAATAAATTAGAATATATTTTCTACTTTTACGAGAAATT

AATTATTGTATTTATTATTTATGGGTGAAAAACTTACTATAAAAAGCGGGTGGGTTTGGAATTA

GTGATCAGTTTATGTATATCGCAACTACCGGGCATATGGCTATCGACATCGAGAACATTACCC

ACATGATAAGAGATTGTATCAGTTTCGTAGTCTTGAGTATTGGTATTACTATATAGTATATAGAT

GTCGACCTGCAGGTCGACGAAGTTCCTATACTTTCTAGAGAATAGGAACTTCGCAGCCAAGCT

GGAATTCATCCACTTTGGATAAGAAATCTGCATGATAAATATATTGATATCCTACCACCTATTA

AAGTACCATTATCTAATAGCAATAAGATAGATAAACAAATGTTTTTTGATGAAGTTATTACGTG

GATAAATATATATCTTCAGGAAAAGGGTATTATGTTACCAGATGATATAAGAGAACTCAGAGAT

GCTATTATTCCTTAACTAGTTACGTCTCTTTAGGTACTTATTTTGATACGTTACAAGTAAAAAAC

TATCAAATATAAATGGAATCTGATTCTAATATAGCGATTGAAGAGGATCCACCGGTCGCCACC

ATGGTGAGCAAGGGCGAGGAGCTGTTCACCGGGGTGGTGCCCATCCTGGTCGAGCTGGACG

GCGACGTAAACGGCCACAAGTTCAGCGTGTCCGGCGAGGGCGAGGGCGATGCCACCTACGG

CAAGCTGACCCTGAAGTTCATCTGCACCACCGGCAAGCTGCCCGTGCCCTGGCCCACCCTC

GTGACCACCCTGACCTACGGCGTGCAGTGCTTCAGCCGCTACCCCGACCACATGAAGCAGC

ACGACTTCTTCAAGTCCGCCATGCCCGAAGGCTACGTCCAGGAGCGCACCATCTTCTTCAAG

GACGACGGCAACTACAAGACCCGCGCCGAGGTGAAGTTCGAGGGCGACACCCTGGTGAACC

GCATCGAGCTGAAGGGCATCGACTTCAAGGAGGACGGCAACATCCTGGGGCACAAGCTGGA

GTACAACTACAACAGCCACAACGTCTATATCATGGCCGACAAGCAGAAGAACGGCATCAAGG

TGAACTTCAAGATCCGCCACAACATCGAGGACGGCAGCGTGCAGCTCGCCGACCACTACCAG

-continued

CAGAACACCCCCATCGGCGACGGCCCCGTGCTGCTGCCCGACAACCACTACCTGAGCACCC

AGTCCGCCCTGAGCAAAGACCCCAACGAGAAGCGCGATCACATGGTCCTGCTGGAGTTCGT

GACCGCCGCCGGGATCACTCTCGGCATGGACGAGCTGTACAAGTAAAGCGGCCGCGAAGTT

CCTATACTTTCTAGAGAATAGGAACTTCAACAATGTCTGGAAAGAACTGTCCTTCATCGATACC

TATCACGGAGAAATCTGTAATTGATTCCAAGACATCACATAGTTTAGTTGCTTCCAATGCTTCA

AAATTATTCTTATCATGCGTCCATAGTCCCGTTCCGTATCTATTATCGTTAGAATATTTTATAGT

CACGCATTTATATTGAGCTATTTGATAACGTCTAACTCGTCTAATTAATTCTGTACTTTTACCTG

AAAACATGGGGCCGATTATCAACTGAATATGTCCGCCGTTCATGATGACAATAAAGAATTAATT

ATTGTTCACTTTATTCGACTTTAATATATCCATCACGTTAGAAAATGCGATATCGCGACGAGGA

TCTATGTATCTAACAGGATCTATTGCGGTGGTAGCTAGAGCTGATTCTTTTTTGAATCGCATCA

AACTAATCACAAAGTCGAACAAATATCCTTTATTAAGTTTGACCCTTCCATCTGTAACAATAGG

GACCTTGTTAAACAGTTTTTTAAAATCTTGAGAGTCTGTGAATTTTGTCAATTGTCTGTATTCCT

CTGAAAGAGATTCATAACAATGACCCACGGCTTCTAATTTATTTTTTGATTGGATCAATAATAAT

AACAGAAAGTCTAGATATTGAGTGATTTGCAATATATCAGATAATGAAGATTCATCATCTTGAC

TAGCCAAATACTTAAAAAATGAATCATCATCTGCGAAGAACATCGTTAAGAGATACTGGTTGTG

ATCCATTTATGAGCTCGCGAAAGCTTGGCACTGGCCGTCGTTTTACAACGTCGTGACTGGGA

AAACCCTGGCGTTACCCAACTTAATCGCCTTGCAGCACATCCCCCTTTCGCCAGCTGGCGTA

ATAGCGAAGAGGCCCGCACCGATCGCCCTTCCCAACAGTTGCGCAGCCTGAATGGCGAATG

GCGCCTGATGCGGTATTTTCTCCTTACGCATCTGTGCGGTATTTCACACCGCATATGGTGCAC

TCTCAGTACAATCTGCTCTGATGCCGCATAGTTAAGCCAGCCCCGACACCCGCCAACACCCG

CTGACGCGCCCTGACGGGCTTGTCTGCTCCCGGCATCCGCTTACAGACAAGCTGTGACCGTC

TCCGGGAGCTGCATGTGTCAGAGGTTTTCACCGTCATCACCGAAACGCGCGAGACGAAAGG

GCCTCGTGATACGCCTATTTTTATAGGTTAATGTCATGATAATAATGGTTTCTTAGACGTCAGG

TGGCACTTTTCGGGGAAATGTGCGCGGAACCCCTATTTGTTTATTTTTCTAAATACATTCAAAT

ATGTATCCGCTCATGAGACAATAACCCTGATAAATGCTTCAATAATATTGAAAAAGGAAGAGTA

TGAGTATTCAACATTTCCGTGTCGCCCTTATTCCCTTTTTTGCGGCATTTTGCCTTCCTGTTTT

TGCTCACCCAGAAACGCTGGTGAAAGTAAAAGATGCTGAAGATCAGTTGGGTGCACGAGTGG

GTTACATCGAACTGGATCTCAACAGCGGTAAGATCCTTGAGAGTTTTCGCCCCGAAGAACGTT

TTCCAATGATGAGCACTTTTAAAGTTCTGCTATGTGGCGCGGTATTATCCCGTATTGACGCCG

GGCAAGAGCAACTCGGTCGCCGCATACACTATTCTCAGAATGACTTGGTTGAGTACTCACCA

GTCACAGAAAAGCATCTTACGGATGGCATGACAGTAAGAGAATTATGCAGTGCTGCCATAACC

ATGAGTGATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGAGCTGA

ATGAAGCCATACCAAACGACGAGCGTGACACCACGATGCCTGTAGCAATGGCAACAACGTTG

CGCAAACTATTAACTGGCGAACTACTTACTCTAGCTTCCCGGCAACAATTAATAGACTGGATG

GAGGCGGATAAAGTTGCAGGACCACTTCTGCGCTCGGCCCTTCCGGCTGGCTGGTTTATTGC

TGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACG

AAATAGACAGATCGCTGAGATAGGTGCCTCACTGATTAAGCATTGGTAACTGTCAGACCAAGT

TTACTCATATATACTTTAGATTGATTTAAAACTTCATTTTTAATTTAAAAGGATCTAGGTGAAGA

TCCTTTTTGATAATCTCATGACCAAAATCCCTTAACGTGAGTTTTCGTTCCACTGAGCGTCAGA

-continued

CCCCGTAGAAAAGATCAAAGGATCTTCTTGAGATCCTTTTTTTCTGCGCGTAATCTGCTGCTT

GCAAACAAAAAAACCACCGCTACCAGCGGTGGTTTGTTTGCCGGATCAAGAGCTACCAACTC

TTTTTCCGAAGGTAACTGGCTTCAGCAGAGCGCAGATACCAAATACTGTTCTTCTAGTGTAGC

CGTAGTTAGGCCACCACTTCAAGAACTCTGTAGCACCGCCTACATACCTCGCTCTGCTAATCC

TGTTACCAGTGGCTGCTGCCAGTGGCGATAAGTCGTGTCTTACCGGGTTGGACTCAAGACGA

TAGTTACCGGATAAGGCGCAGCGGTCGGGCTGAACGGGGGGTTCGTGCACACAGCCCAGCT

TGGAGCGAACGACCTACACCGAACTGAGATACCTACAGCGTGAGCTATGAGAAAGCGCCACG

CTTCCCGAAGGGAGAAAGGCGGACAGGTATCCGGTAAGCGGCAGGGTCGGAACAGGAGAGC

GCACGAGGGAGCTTCCAGGGGGAAACGCCTGGTATCTTTATAGTCCTGTCGGGTTTCGCCAC

CTCTGACTTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATGTTCTTTCC

TGCGTTATCCCCTGATTCTGTGGATAACCGTATTACCGCCTTTGAGTGAGCTGATACCGCTCG

CCGCAGCCGAACGACCGAGCGCAGCGAGTCAGTGAGCGAGGAAGCGGAAGA

3NSALL MVA

[SEQ ID NO: 124]

GCGCCCAATACGCAAACCGCCTCTCCCCGCGCGTTGGCCGATTCATTAATGCAGCTGGCACG

ACAGGTTTCCCGACTGGAAAGCGGGCAGTGAGCGCAACGCAATTAATGTGAGTTAGCTCACT

CATTAGGCACCCCAGGCTTTACACTTTATGCTTCCGGCTCGTATGTTGTGTGGAATTGTGAGC

GGATAACAATTTCACACAGGAAACAGCTATGACCATGATTACGCCAAGCTTGCATGCATCTGG

AAACGGGCATCTCCATTTAAGACTAGATGCCACGGGGTTTAAAATACTAATCATGACATTTTGT

AGAGCGTAATTACTTAGTAAATCCGCCGTACTAGGTTCATTTCCTCCTCGTTTGGATCTCACAT

CAGAAATTAAAATAATCTTAGAAGGATGCAGTTGTTTTTTGATGGATCGTAGATATTCCTCATC

AACGAACCGAGTCACTAGAGTCACATCACGCAATCCATTTAAAATAGGATCATGATGGCGGCC

GTCAATTAGCATCCATTTGATGATCACTCCTAAATTATAGAAATGATCTCTCAAATAACGTATAT

GTGTACCGGGAGCAGATCCTATATACACTACGGTGGCACCATCTAATATACCGTGTCGCTGTA

ACTTACTAAGAAAAAATAATTCTCCTAGTAATAGTTTTAACTGTCCTTGATACGGTAGTTTTTTT

GCGACCTCATTTGCACTTTCTGGTTCGTAATCTAACTCATTATCAATTTCCTCAAAATACATAAA

CGGTTTATCTAACGACACAACATCCATTTTTAAGTATTATATTAAAATTTAATCAATGTTTATTTT

TAGTTTTTTAGATAAAAAATATAATATTATGAGTCGATGTAACACTTTCTACACACCGATTGATA

CATATCATTACCTCCTATTATCTCTATCTCGGTTTCCTCACCCAATCGTTTAGAAAAGGAAGCC

TCCTTAAAGCATTTCATACACACAGCAGTTAGTTTTACCACCATTTCAGATAATGGAATAAGAT

TCAAAATATTATTAAACGGTTTACGTTGAAATGTCCCATCGAGTGCGGCTACTATAACTATTTT

TCCTTCGTTTGCCATACAGATCCTACGTACTCGAGCGGCCGCTCATCAGGTCCGCGTAGAAT

CGAGACCGAGGAGAGGGTTAGGGATAGGCTTACCTGAAGCCCCGGGCCCGGATCCAGCGAT

GTTCTTGGCCCAGGTGGCCCTGCTGGTCAGGCCGATCAGGCTGCCGCACCACTGGTCCTCC

CTCTTGCCCAGGTAGGGCACGTCCTCCCAGCTGTGGATGTGGGTCTTGTCCTCCATCCAGGG

GTTCTCCTCGATCCACACCCTGTTCCACACGGCCAGCATGTCCTCGGTGGTCATCCACTCGT

GGTGGGCGTGGATGCTCCAGGTGGTCCTGCTGGTGGGCACCCAGTGGCTGGGCACGGCGC

TGCAGATGGCGTTGCTGGCCAGCCTCAGGTCCCTCCTGTGGAAGTACATCAGCTGCCACATC

TGGGCGTAGCTCTTGCCCAGGCAGGCGGTCTCCCTCAGGCTCCAGCCGGCGCCCTGGCTGA

TCCTGGCCCTGCCGATCAGCTCGTCCTGGTTCCTGCAGGGCACCACCAGCTTCCTGCCGTCC

-continued

TTCATGAAGATCTCGTGGAAGTGGTGGCTGCAGAAGGGCACCTGCTGCCAGTCGTGCCAGC

CCTTGCTGGGCTCCCACTGGGGGGGCTTCACCACGCAGTCGTCGCCGCTGATGGCCATCCT

CTTCAGCCTGTCCACGCCGCACTCGGTGATCACGCCCTCGGCCTCCATCTGCCTGATCAGCT

GGGCCTCCATGTTGGTGAAGGTGTTCAGGCCGTAGGTGCCCACCTGGCCGCTGCCCCTCTG

GTCCTTCCTGCTGATGATGTCCATCACGGCGCCCCTGGGGGTGGGCCTCTGCACCTTCACCA

CCTTGTTCTGGTAGGTCAGCTTGAAGATGGCCTTGGCCAGGATCTTCTCCTCGTTGTGCAGG

TCGTCCTCGGTGATCCTGGTGTCCCAGCCGGCGGTGTCGTCGGCGTACATGGCGCCGCCGG

GGATCTTGCTGATGTCCCTCAGGATGTAGCCCAGCTTGTGCAGGCCCTCGCCCTCCACGCCG

CTCAGGCTGTTCTCCCTGCTGAACCAGTGGTCCTCGTTCAGGAAGCCCAGGGCCTCGAACTC

CAGGAACCTGGCGCCCAGCCACATGTACCAGATGGCCCTGCTGCCCTTGGCCTTGCCGAAC

TCGCCCAGCTTCTTCTCCCTCTTGCCCATCATGTTGTACACGCAGCTCTCGCACTTGCCCTCC

AGGTGCAGGGCCCTCTCGCTGTCCTCCACGGCCTCCCTGGCGCTCTTCCAGCCGTTCTCGTC

CTGGAACACGGCGCCGATGGCGGCGTTCTCCTTGGCCTCGGGGGTCCTGGTGTCCACCTTC

TCCTTGAACACCCTCTGCTGGCCGAAGGGGGTGGTGTCGGTCATGGCCATCTGGGTCACCAT

GGGCACCACGTCCCAGGGCTTGGTCAGCAGCTTCACCACGCCGTTCACCATGCTGCTGGCG

CTGCCGGTGGCCTTCACCTCGTAGCTGCCGTGGTAGGCCCAGGTCTTGTAGGGGTTGTCCTC

GTCGTAGTGCCAGGTGCTGCCGGCGCCCAGGTCCACGTCCCTCTCGTAGGTGGGCTTCTTG

TGGGCCATGGTGAACCTGTTGATCAGCATCCTGCTGATCATGTTCACGGCGCTCACGATGTT

GCCGGTGCCGTTGCTCACCCAGTACATCTCGTGGGTGCTGTTCCTGCTCAGGGGGTTCCTCA

CCAGCATGCCGCCGTGCTTCCTCTGCAGCTTCTCCAGCTCCTCGATCACGCTGGGCATGTAG

GGGTTCAGGATCTTGATGCAGAACTGGTTGCCCTTCAGCCAGGGCTCCACCATCTTCAGCAC

CCTCAGGGTCCTGCCCTCCTCGATGGTGGGGTTGGGGCTGCTCTCGCCGATGTCGCACAGC

AGGGTGTCGCACTTCTCGGGGAAGAACACGTCCACGCCGCTGTGCAGCTTCACCAGGTTCCA

GCCGTAGGTGGCCATGGGGATGGGCTCCTCGTGGCCGGGGCCGCCCTTGGTGTAGCCCCT

CACCTCCCTCACCTTCTTCAGGCCGGCGCAGTAGTAGCTCCAGCCGCCCCTGCCGCAGCCC

AGGTCGATCACCCTGCCCTCGGGGATCACCATGTTCCTCTCCACGAACCACCTCAGCTTGGC

GCTGCCCCTGCTCACGGCGTGGTGGTCGGTCTCGCCCCTCTTGATGGCCTCCTTGGCCTCG

GTCCTGTCCACCTCCAGGATGCCGCTCTTCTTGTACTCCTCGAACTCGCTCTTGTCCAGCTGG

TTCAGCTGCCTCTTCCACTTCTCGCCCAGGGTCTCGCCCTGGGCGCCGGTGCCCCTCCTGTT

CTTGATCAGGCTGAAGGCCAGGCCGGCGCCGGCCAGGTAGCTGCCCCTGAAGATGTTGGCC

ATGCTCACGGCGATGGTGGTGTTCCAGAACTTGCCGGGGTTGCCCTCCCACAGGGTGGTGA

TGGGGCCGGTGGCCAGGGTCAGGGCCTCGCACAGGGCCCAGGTGGTCCTCATCAGCAGGA

TCTGGCTCACGCACAGGATCAGCAGCATCACCTGGCCCAGCTGCTTCTCGAACTTGGGGTCG

TAGGGGATGGGGTCCAGGTCGATGGCCATGATGCCGTCCACGGTGGGGTTCTTCATGATGC

CGGCGGCGGTCCTCTTCTGGGCCTCCCTGGTGGCCTTGGCCTGCAGGCCGGGGCCGATGAT

GGCGTAGTGGGTGATCAGCAGCAGCACGGCGGCGGTCAGGGTCAGGGGGTTCACCTGGCT

GTAGCAGCCCAGGGCCAGCAGGGGCACGCCCAGGTCCATCTTGCTGATGGGCCAGCCCTTG

TCCAGGCCCATCAGCACGGCGGCCTGGTTGGCGATGGCGGTCAGGCTCACGTTGGCGGTGC

TGTTCTCGATGGTGTGCCTCAGCATGGGGGTGATGATGGTGGTGGCCACGGCGTACAGGGT

CCAGGCGCTGGCGGGGTGCAGGTCCACGTCCAGGATGGCGGTGGGGGCCACGTGGCCGAT

GCCCAGGTCCTTCTTGGTGGTCTCCAGCAGGCCCATCTCGTTGGCGGCGATGGCGGCGGCC

-continued

AGGGTCAGGATGCCGATCACCACGTAGGCCAGCTGGTTGTCCTGGGGGGTCCTCTGCTTCT

CGGGCTCGGGGATCAGCAGCACCATCAGGAAGAACTCCAGGATGATGCTGGCGGCGATCCA

GTGGGGCTGGATCTCGGCCATCCACAGCAGGCTGGCGGCGATGATGCAGCACAGGCCGATG

CTCATCTTGCCGATGCCCTTGCCGCTCAGGAAGAACAGGAAGGCGCCCAGCAGGGCCAGCA

GCAGCAGGGTCTCCAGGGTCTCGGGCAGCTCCTCCAGGGCGTGCTGGTAGGCCCTGGTCCT

GTGGGCCAGGTGGCTGGGCACCCTGCCGATCTCGGTGGCGATGCTCTTCCTGCCGGCGGC

GAAGTCCTTGAACTCCTTCAGGGCCAGGGGGTCGGCGTAGGTCCTGGCGTCCAGCCACCTG

GGCCTCAGCTTCTTCTTCTCGCCCTCCTTGGTCCAGATCTCCACGTCCATGTTCTCCTCCAGG

ATCTGGTTGTTCCTCTCGCCGTCGAAGCACCACTCCCTGTCCTTGTACTGGAAGCCGGCGCT

GGCCACCTTGTAGCTCAGCCACACGGGCAGGTCGCCCCTCCTCATCAGCTCCACGAAGGTCT

TCCTGGCCTCGCCCCTCAGCCTGTACTCGCCGTCGATGGCGGCGCTCTTCTCCCTCTCGGG

CTCGAACAGGGCGGGGATGATGCCCTCGGGGGTGTTGATGTTGTCCAGCAGCATCTTGGCC

TCGGTCCAGTGGGCGTGGTCCTCGTCGTTGTTCAGGGGCTGGCCCATGTAGATGTACTGGTC

GTTCTCCTTCTTGTGGTTCCTGCCGATCCTGCCCCTCCTCTGGGCGGCGCTGGCGGCGGTCA

CGGGCATGGGGCCGGCCAGGATCACCCTCTCGGGGCCGTCGGTCAGGATCACGGGCTTCA

GGCACCTCCTGGGGTCGATCACCCTGTCGGCCTTGAAGTTGGCGCCCATCTCGCTGATGTCG

GTGGTCACCACGAAGTCCCAGTCGTTCAGCTTGGTCTTGGGGTACTCGGTGTCGAAGGTCTT

CCTGCTCAGCTGGATCACCTTCTTGCCGTTCTTCCTCAGGCAGTTGGCGATGTCGTTGCCGG

CCTTGATGCTGGGCACGAACCACACGGTCTTGCCGGCGAAGTCGGTGATCCAGTCGAAGCC

GCTGTTCCAGCTCCTCTCGGGGATCTCCCTCTCCTCGTCCTCGATGGGGGCGTTGCTCTGGG

GGAAGGCGTCGGCGCTGCCGGGGGGGGTGGCGGTCATGAAGATGGCGGCGGCCTCGCCCA

TCTCCACCCTGGTGCTGATGTAGCCCCTGGCGGCGATGCTGGCGGGGTCGGTGAAGTGGGC

CTCGTCCATGATGATCAGGTTGTAGTTGGGCACCCTCACGGGGCTCAGCAGCCTCATGGTGA

AGGTGGCGTGGCACATCAGGTCCACGATCTCCTTGCCGGTGTGCTCGGCCTTGATGGCGGT

GGTCTGATACCTGATGGGCAGGCCCTTCAGGGCCTCCTCCATCTCGGCGGCCACCACCCTG

GTGGGGGCCAGGATCAGGGTCCTCAGCCTCCTCTTGATGGCCTCCCTCACGATGGCGGGCA

GATACCTCTTGGTCTTGCCGGCGCCGGGGTGCAGGTCCATGATGGTCAGGTTCCTCTTCCTG

AACACCTCGTCCTCGATCTCGGGCAGGGGCTCGGCGTTGGTCTGGGCGATGGCGCTCACGT

AGGCGCCGCTCTTGGTCACCACGCCGTTGCCGTACAGGCCCACCACCTTGCCCTCCCTGTTC

ACGATGGGGCTGCCGCTGGTGCCGGGCTTGAAGTCCAGGGCGATGGCGCCGATCTCGCCCT

CGGGGGTCTTGAACAGGCCGGGCTTGGTCTGCACGGCCTTGGGGTTCTTGCCGGGCTCCAC

GGCGATCACCTGCACCTCCTCGCCCTCGTCCCACTCGCCCTCCAGCCTCCAGCCGCCGCCG

TAGCTGATCAGGTCCTTCTTCACGTCGGCCCAGCTGGGCTCGATCCTCTTGCCCTGGTGCAT

CAGCACGGCGCCCCTGGTCACGTGCCACATGGTGTGGAACACGCCCTCCTTGAACACGCCG

GCGCCGATCTGGCTGGCAAGCTTCGATCCTCTTCTGAATCGGGCATGGATTTCCTGGCTGGG

CGAAACGAAGACTGCTCCACACAGCAGCAGCACACAGCAGAGCCCTCTCTTCATTGCATCCA

TGGTGGCGGCGCGGCTAGCGGTACCGGATCTAGATGGGGATCCGTCACTGTTCTTTATGATT

CTACTTCCTTACCGTGCAATAAATTAGAATATATTTTCTACTTTTACGAGAAATTAATTATTGTA

TTTATTATTTATGGGTGAAAAACTTACTATAAAAAGCGGGTGGGTTTGGAATTAGTGATCAGTT

TATGTATATCGCAACTACCGGGCATATGGCTATCGACATCGAGAACATTACCCACATGATAAG

-continued

AGATTGTATCAGTTTCGTAGTCTTGAGTATTGGTATTACTATATAGTATATAGATGTCGACCTG

CAGGTCGACGAAGTTCCTATACTTTCTAGAGAATAGGAACTTCGCAGCCAAGCTGGAATTCAT

CCACTTTGGATAAGAAATCTGCATGATAAATATATTGATATCCTACCACCTATTAAAGTACCAT

TATCTAATAGCAATAAGATAGATAAACAAATGTTTTTTGATGAAGTTATTACGTGGATAAATATA

TATCTTCAGGAAAAGGGTATTATGTTACCAGATGATATAAGAGAACTCAGAGATGCTATTATTC

CTTAACTAGTTACGTCTCTTTAGGTACTTATTTTGATACGTTACAAGTAAAAAACTATCAAATAT

AAATGGAATCTGATTCTAATATAGCGATTGAAGAGGATCCACCGGTCGCCACCATGGTGAGCA

AGGGCGAGGAGCTGTTCACCGGGGTGGTGCCCATCCTGGTCGAGCTGGACGGCGACGTAAA

CGGCCACAAGTTCAGCGTGTCCGGCGAGGGCGAGGGCGATGCCACCTACGGCAAGCTGACC

CTGAAGTTCATCTGCACCACCGGCAAGCTGCCCGTGCCCTGGCCCACCCTCGTGACCACCCT

GACCTACGGCGTGCAGTGCTTCAGCCGCTACCCCGACCACATGAAGCAGCACGACTTCTTCA

AGTCCGCCATGCCCGAAGGCTACGTCCAGGAGCGCACCATCTTCTTCAAGGACGACGGCAA

CTACAAGACCCGCGCCGAGGTGAAGTTCGAGGGCGACACCCTGGTGAACCGCATCGAGCTG

AAGGGCATCGACTTCAAGGAGGACGGCAACATCCTGGGGCACAAGCTGGAGTACAACTACAA

CAGCCACAACGTCTATATCATGGCCGACAAGCAGAAGAACGGCATCAAGGTGAACTTCAAGA

TCCGCCACAACATCGAGGACGGCAGCGTGCAGCTCGCCGACCACTACCAGCAGAACACCCC

CATCGGCGACGGCCCCGTGCTGCTGCCCGACAACCACTACCTGAGCACCCAGTCCGCCCTG

AGCAAAGACCCCAACGAGAAGCGCGATCACATGGTCCTGCTGGAGTTCGTGACCGCCGCCG

GGATCACTCTCGGCATGGACGAGCTGTACAAGTAAAGCGGCCGCGAAGTTCCTATACTTTCT

AGAGAATAGGAACTTCAACAATGTCTGGAAAGAACTGTCCTTCATCGATACCTATCACGGAGA

AATCTGTAATTGATTCCAAGACATCACATAGTTTAGTTGCTTCCAATGCTTCAAAATTATTCTTA

TCATGCGTCCATAGTCCCGTTCCGTATCTATTATCGTTAGAATATTTTATAGTCACGCATTTAT

ATTGAGCTATTTGATAACGTCTAACTCGTCTAATTAATTCTGTACTTTTACCTGAAAACATGGG

GCCGATTATCAACTGAATATGTCCGCCGTTCATGATGACAATAAAGAATTAATTATTGTTCACT

TTATTCGACTTTAATATATCCATCACGTTAGAAAATGCGATATCGCGACGAGGATCTATGTATC

TAACAGGATCTATTGCGGTGGTAGCTAGAGCTGATTCTTTTTTGAATCGCATCAAACTAATCAC

AAAGTCGAACAAATATCCTTTATTAAGTTTGACCCTTCCATCTGTAACAATAGGGACCTTGTTA

AACAGTTTTTTAAAATCTTGAGAGTCTGTGAATTTTGTCAATTGTCTGTATTCCTCTGAAAGAG

ATTCATAACAATGACCCACGGCTTCTAATTTATTTTTTGATTGGATCAATAATAATAACAGAAAG

TCTAGATATTGAGTGATTTGCAATATATCAGATAATGAAGATTCATCATCTTGACTAGCCAAAT

ACTTAAAAAATGAATCATCATCTGCGAAGAACATCGTTAAGAGATACTGGTTGTGATCCATTTA

TGAGCTCGCGAAAGCTTGGCACTGGCCGTCGTTTTACAACGTCGTGACTGGGAAAACCCTGG

CGTTACCCAACTTAATCGCCTTGCAGCACATCCCCCTTTCGCCAGCTGGCGTAATAGCGAAG

AGGCCCGCACCGATCGCCCTTCCCAACAGTTGCGCAGCCTGAATGGCGAATGGCGCCTGAT

GCGGTATTTTCTCCTTACGCATCTGTGCGGTATTTCACACCGCATATGGTGCACTCTCAGTAC

AATCTGCTCTGATGCCGCATAGTTAAGCCAGCCCCGACACCCGCCAACACCCGCTGACGCGC

CCTGACGGGCTTGTCTGCTCCCGGCATCCGCTTACAGACAAGCTGTGACCGTCTCCGGGAG

CTGCATGTGTCAGAGGTTTTCACCGTCATCACCGAAACGCGCGAGACGAAAGGGCCTCGTGA

TACGCCTATTTTTATAGGTTAATGTCATGATAATAATGGTTTCTTAGACGTCAGGTGGCACTTT

TCGGGGAAATGTGCGCGGAACCCCTATTTGTTTATTTTTCTAAATACATTCAAATATGTATCCG

CTCATGAGACAATAACCCTGATAAATGCTTCAATAATATTGAAAAAGGAAGAGTATGAGTATTC

-continued

AACATTTCCGTGTCGCCCTTATTCCCTTTTTTGCGGCATTTTGCCTTCCTGTTTTTGCTCACCC

AGAAACGCTGGTGAAAGTAAAAGATGCTGAAGATCAGTTGGGTGCACGAGTGGGTTACATCG

AACTGGATCTCAACAGCGGTAAGATCCTTGAGAGTTTTCGCCCCGAAGAACGTTTTCCAATGA

TGAGCACTTTTAAAGTTCTGCTATGTGGCGCGGTATTATCCCGTATTGACGCCGGGCAAGAG

CAACTCGGTCGCCGCATACACTATTCTCAGAATGACTTGGTTGAGTACTCACCAGTCACAGAA

AAGCATCTTACGGATGGCATGACAGTAAGAGAATTATGCAGTGCTGCCATAACCATGAGTGAT

AACACTGCGGCCAACTTACTTCTGACAACGATCGGAGGACCGAAGGAGCTAACCGCTTTTTT

GCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTA

TTAACTGGCGAACTACTTACTCTAGCTTCCCGGCAACAATTAATAGACTGGATGGAGGCGGAT

AAAGTTGCAGGACCACTTCTGCGCTCGGCCCTTCCGGCTGGCTGGTTTATTGCTGATAAATCT

GGAGCCGGTGAGCGTGGGTCTCGCGGTATCATTGCAGCACTGGGGCCAGATGGTAAGCCCT

CCCGTATCGTAGTTATCTACACGACGGGGAGTCAGGCAACTATGGATGAACGAAATAGACAG

ATCGCTGAGATAGGTGCCTCACTGATTAAGCATTGGTAACTGTCAGACCAAGTTTACTCATAT

ATACTTTAGATTGATTTAAAACTTCATTTTTAATTTAAAAGGATCTAGGTGAAGATCCTTTTTGA

TAATCTCATGACCAAAATCCCTTAACGTGAGTTTTCGTTCCACTGAGCGTCAGACCCCGTAGA

AAAGATCAAAGGATCTTCTTGAGATCCTTTTTTTCTGCGCGTAATCTGCTGCTTGCAAACAAAA

AAACCACCGCTACCAGCGGTGGTTTGTTTGCCGGATCAAGAGCTACCAACTCTTTTTCCGAAG

GTAACTGGCTTCAGCAGAGCGCAGATACCAAATACTGTTCTTCTAGTGTAGCCGTAGTTAGGC

CACCACTTCAAGAACTCTGTAGCACCGCCTACATACCTCGCTCTGCTAATCCTGTTACCAGTG

GCTGCTGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGCGAAC

GACCTACACCGAACTGAGATACCTACAGCGTGAGCTATGAGAAAGCGCCACGCTTCCCGAAG

GGAGAAAGGCGGACAGGTATCCGGTAAGCGGCAGGGTCGGAACAGGAGAGCGCACGAGGG

AGCTTCCAGGGGGAAACGCCTGGTATCTTTATAGTCCTGTCGGGTTTCGCCACCTCTGACTT

GAGCGTCGATTTTTGTGATGCTCGTCAGGGGGGCGGAGCCTATGGAAAAACGCCAGCAACG

CGGCCTTTTTACGGTTCCTGGCCTTTTGCTGGCCTTTTGCTCACATGTTCTTTCCTGCGTTATC

CCCTGATTCTGTGGATAACCGTATTACCGCCTTTGAGTGAGCTGATACCGCTCGCCGCAGCC

GAACGACCGAGCGCAGCGAGTCAGTGAGCGAGGAAGCGGAAGA

4NSALL MVA

[SEQ ID NO: 125]

GCGCCCAATACGCAAACCGCCTCTCCCCGCGCGTTGGCCGATTCATTAATGCAGCTGGCACG

ACAGGTTTCCCGACTGGAAAGCGGGCAGTGAGCGCAACGCAATTAATGTGAGTTAGCTCACT

CATTAGGCACCCCAGGCTTTACACTTTATGCTTCCGGCTCGTATGTTGTGTGGAATTGTGAGC

GGATAACAATTTCACACAGGAAACAGCTATGACCATGATTACGCCAAGCTTGCATGCATCTGG

AAACGGGCATCTCCATTTAAGACTAGATGCCACGGGGTTTAAAATACTAATCATGACATTTTGT

AGAGCGTAATTACTTAGTAAATCCGCCGTACTAGGTTCATTTCCTCCTCGTTTGGATCTCACAT

CAGAAATTAAAATAATCTTAGAAGGATGCAGTTGTTTTTTGATGGATCGTAGATATTCCTCATC

AACGAACCGAGTCACTAGAGTCACATCACGCAATCCATTTAAAATAGGATCATGATGGCGGCC

GTCAATTAGCATCCATTTGATGATCACTCCTAAATTATAGAAATGATCTCTCAAATAACGTATAT

GTGTACCGGGAGCAGATCCTATATACACTACGGTGGCACCATCTAATATACCGTGTCGCTGTA

-continued

ACTTACTAAGAAAAAATAATTCTCCTAGTAATAGTTTTAACTGTCCTTGATACGGTAGTTTTTTT

GCGACCTCATTTGCACTTTCTGGTTCGTAATCTAACTCATTATCAATTTCCTCAAAATACATAAA

CGGTTTATCTAACGACACAACATCCATTTTTAAGTATTATATTAAAATTTAATCAATGTTTATTTT

TAGTTTTTTAGATAAAAAATATAATATTATGAGTCGATGTAACACTTTCTACACACCGATTGATA

CATATCATTACCTCCTATTATCTCTATCTCGGTTTCCTCACCCAATCGTTTAGAAAAGGAAGCC

TCCTTAAAGCATTTCATACACACAGCAGTTAGTTTTACCACCATTTCAGATAATGGAATAAGAT

TCAAAATATTATTAAACGGTTTACGTTGAAATGTCCCATCGAGTGCGGCTACTATAACTATTTT

TCCTTCGTTTGCCATACAGATCCTACGTACTCGAGCGGCCGCTCATCAGGTCCGCGTAGAAT

CGAGACCGAGGAGAGGGTTAGGGATAGGCTTACCTGAAGCCCCGGGCCCGGATCCAGCGAT

GTTCTTGGCCCAGGTGGCCCTGCTGGTCAGGCCGATCAGGCTGCCGCACCACTGGTCCTCC

CTCTTGCCCAGGTAGGGCACGTCCTCCCAGCTGTGGATGTGGGTCTTGTCCTCCATCCAGGG

GTTCTCCTCGATCCACACCCTGTTCCACACGGCCAGCATGTCCTCGGTGGTCATCCACTCGT

GGTGGGCGTGGATGCTCCAGGTGGTCCTGCTGGTGGGCACCCAGTGGCTGGGCACGGCGC

TGCAGATGGCGTTGCTGGCCAGCCTCAGGTCCCTCCTGTGGAAGTACATCAGCTGCCACATC

TGGGCGTAGCTCTTGCCCAGGCAGGCGGTCTCCCTCAGGCTCCAGCCGGCGCCCTGGCTGA

TCCTGGCCCTGCCGATCAGCTCGTCCTGGTTCCTGCAGGGCACCACCAGCTTCCTGCCGTCC

TTCATGAAGATCTCGTGGAAGTGGTGGCTGCAGAAGGGCACCTGCTGCCAGTCGTGCCAGC

CCTTGCTGGGCTCCCACTGGGGGGGCTTCACCACGCAGTCGTCGCCGCTGATGGCCATCCT

CTTCAGCCTGTCCACGCCGCACTCGGTGATCACGCCCTCGGCCTCCATCTGCCTGATCAGCT

GGGCCTCCATGTTGGTGAAGGTGTTCAGGCCGTAGGTGCCCACCTGGCCGCTGCCCCTCTG

GTCCTTCCTGCTGATGATGTCCATCACGGCGCCCCTGGGGGTGGGCCTCTGCACCTTCACCA

CCTTGTTCTGGTAGGTCAGCTTGAAGATGGCCTTGGCCAGGATCTTCTCCTCGTTGTGCAGG

TCGTCCTCGGTGATCCTGGTGTCCCAGCCGGCGGTGTCGTCGGCGTACATGGCGCCGCCGG

GGATCTTGCTGATGTCCCTCAGGATGTAGCCCAGCTTGTGCAGGCCCTCGCCCTCCACGCCG

CTCAGGCTGTTCTCCCTGCTGAACCAGTGGTCCTCGTTCAGGAAGCCCAGGGCCTCGAACTC

CAGGAACCTGGCGCCCAGCCACATGTACCAGATGGCCCTGCTGCCCTTGGCCTTGCCGAAC

TCGCCCAGCTTCTTCTCCCTCTTGCCCATCATGTTGTACACGCAGCTCTCGCACTTGCCCTCC

AGGTGCAGGGCCCTCTCGCTGTCCTCCACGGCCTCCCTGGCGCTCTTCCAGCCGTTCTCGTC

CTGGAACACGGCGCCGATGGCGGCGTTCTCCTTGGCCTCGGGGGTCCTGGTGTCCACCTTC

TCCTTGAACACCCTCTGCTGGCCGAAGGGGGTGGTGTCGGTCATGGCCATCTGGGTCACCAT

GGGCACCACGTCCCAGGGCTTGGTCAGCAGCTTCACCACGCCGTTCACCATGCTGCTGGCG

CTGCCGGTGGCCTTCACCTCGTAGCTGCCGTGGTAGGCCCAGGTCTTGTAGGGGTTGTCCTC

GTCGTAGTGCCAGGTGCTGCCGGCGCCCAGGTCCACGTCCCTCTCGTAGGTGGGCTTCTTG

TGGGCCATGGTGAACCTGTTGATCAGCATCCTGCTGATCATGTTCACGGCGCTCACGATGTT

GCCGGTGCCGTTGCTCACCCAGTACATCTCGTGGGTGCTGTTCCTGCTCAGGGGGTTCCTCA

CCAGCATGCCGCCGTGCTTCCTCTGCAGCTTCTCCAGCTCCTCGATCACGCTGGGCATGTAG

GGGTTCAGGATCTTGATGCAGAACTGGTTGCCCTTCAGCCAGGGCTCCACCATCTTCAGCAC

CCTCAGGGTCCTGCCCTCCTCGATGGTGGGGTTGGGGCTGCTCTCGCCGATGTCGCACAGC

AGGGTGTCGCACTTCTCGGGGAAGAACACGTCCACGCCGCTGTGCAGCTTCACCAGGTTCCA

GCCGTAGGTGGCCATGGGGATGGGCTCCTCGTGGCCGGGGCCGCCCTTGGTGTAGCCCCT

CACCTCCCTCACCTTCTTCAGGCCGGCGCAGTAGTAGCTCCAGCCGCCCCTGCCGCAGCCC

-continued

AGGTCGATCACCCTGCCCTCGGGGATCACCATGTTCCTCTCCACGAACCACCTCAGCTTGGC

GCTGCCCCTGCTCACGGCGTGGTGGTCGGTCTCGCCCCTCTTGATGGCCTCCTTGGCCTCG

GTCCTGTCCACCTCCAGGATGCCGCTCTTCTTGTACTCCTCGAACTCGCTCTTGTCCAGCTGG

TTCAGCTGCCTCTTCCACTTCTCGCCCAGGGTCTCGCCCTGGGCGCCGGTGCCCCTCCTGTT

CTTGATCAGGCTGAAGGCCAGGCCGGCGCCGGCCAGGTAGCTGCCCCTGAAGATGTTGGCC

ATGCTCACGGCGATGGTGGTGTTCCAGAACTTGCCGGGGTTGCCCTCCCACAGGGTGGTGA

TGGGGCCGGTGGCCAGGGTCAGGGCCTCGCACAGGGCCCAGGTGGTCCTCATCAGCAGCA

CGGCCCAGGTGGTCCTCATCAGCAGGATCTGGCTCACGCACAGGATCAGCAGCATCACCTG

GCCCAGCTGCTTCTCGAACTTGGGGTCGTAGGGGATGGGGTCCAGGTCGATGGCCATGATG

CCGTCCACGGTGGGGTTCTTCATGATGCCGGCGGCGGTCCTCTTCTGGGCCTCCCTGGTGG

CCTTGGCCTGCAGGCCGGGGCCGATGATGGCGTAGTGGGTGATCAGCAGCAGCACGGCGG

CGGTCAGGGTCAGGGGGTTCACCTGGCTGTAGCAGCCCAGGGCCAGCAGGGGCACGCCCA

GGTCCATCTTGCTGATGGGCCAGCCCTTGTCCAGGCCCATCAGCACGGTGGCCTGGTTGGC

GATCATCAGCACGGCGGCCTGGTTGGCGATGGCGGTCAGGCTCACGTTGGCGGTGCTGTTC

TCGATGGTGTGCCTCAGCATGGGGGTGATGATGGTGGTGGCCACGGCGTACAGGGTCCAGG

CGCTGGCGGGGTGCAGGTCCACGTCCAGGATGGCGGTGGGGGCCACGTGGCCGATGCCCA

GGTCCTTCTTGGTGGTCTCCAGCAGGCCCATCTCGTTGGCGGCGATGGCGGCGGCCAGGGT

CAGGATGCCGATCACCACGTAGGCCAGCTGGTTGTCCTGGGGGGTCCTCTGCTTCTCGGGC

TCGGGGATCAGCAGCACCATCAGGAAGAACTCCAGGATGATGCTGGCGGCGATCCAGTGGG

GCTGGATCTCGGCCATCCACAGCAGGCTGGCGGCGATGATGCAGCACAGGCCGATGCTCAT

CTTGCCGATGCCCTTGCCGCTCAGGAAGAACAGGAAGGCGCCCAGCAGGGCCAGCAGCAGC

AGGGTCTCCAGGGTCTCGGGCAGCTCCTCCAGGGCGTGCTGGTAGGCCCTGGTCCTGTGGG

CCAGGTGGCTGGGCACCCTGCCGATCTCGGTGGCGATGCTCTTCCTGCCGGCGGCGAAGTC

CTTGAACTCCTTCAGGGCCAGGGGGTCGGCGTAGGTCCTGGCGTCCAGCCACCTGGGCCTC

AGCTTCTTCTTCTCGCCCTCCTTGGTCCAGATCTCCACGTCCATGTTCTCCTCCAGGATCTGG

TTGTTCCTCTCGCCGTCGAAGCACCACTCCCTGTCCTTGTACTGGAAGCCGGCGCTGGCCAC

CTTGTAGCTCAGCCACACGGGCAGGTCGCCCCTCCTCATCAGCTCCACGAAGGTCTTCCTCT

GCTCGCCCAGGTCCACGAAGGTCTTCCTGGCCTCGCCCAGCTCCACGAAGGTCTTCCTGGC

CTCGCCCCTCAGCCTGTACTCGCCGTCGATGGCGGCGCTCTTCTCCCTCTCGGGCTCCAGG

CTGGGGATGATGCCCTCGGGGGTGAACAGGGTGGGGATGATGCCCTCGGGGGTGAACATGC

TGGGGATGATGCCCTCGGGGGTGAACAGGGCGGGGATGATGCCCTCGGGGGTGTTGATGTT

GTCCAGCAGCATCTTGGCCTCGGTCCAGTGGGCGTGGTCCTCGTCGTTGTTCAGGGGCTGG

CCCATGTAGATGTACTGGTCGTTCTCCTTCTTGTGGTTCCTGCCGATCCTGCCCCTCCTCTGG

GCGGCGCTGGCGGCGGTCACGGGCATGGGGCCGGCCAGGATCACCCTCTCGGGGCCGTCG

GTCAGGATCACGGGCTTCAGGCACCTCCTGGGGTCGATCACCCTGTCGGCCTTGAAGTTGG

CGCCCATCTCGCTGATGTCGGTGGTCACCACGAAGTCCCAGTCGTTCAGCTTGGTCTTGGGG

TACTCGGTGTCGAAGGTCTTCCTGCTCAGCTGGATCACCTTCTTGCCGTTCTTCCTCAGGCAG

TTGGCGATGTCGTTGCCGGCCTTGATGCTGGGCACGAACCACACGGTCTTGCCGGCGAAGT

CGGTGATCCAGTCGAAGCCGCTGTTCCAGCTCCTCTCGGGGATCTCCCTCTCCTCGTCCTCG

ATGGGGGCGTTGCTCTGGGGGAAGGCGTCGGCGCTGCCGGGGGGGGTGGCGGTCATGAAG

-continued

ATGGCGGCGGCCTCGCCCATCTCCACCCTGGTGCTGATGTAGCCCCTGGCGGCGATGCTGG

CGGGGTCGGTGAAGTGGGCCTCGTCCATGATGATCAGGTTGTAGTTGGGCACCCTCACGGG

GCTCAGCAGCCTCATGGTGAAGGTGGCGTGGCACATCAGGTCCACGATCTCCTTGCCGGTGT

GCTCGGCCTTGATGGCGGTGGTCTGATACCTGATGGGCAGGCCCCTCAGGGCGTACCTGAT

GGGCAGGCCCTTCAGGGCCTCCTCCATCTCGCTGGCCACCACCCTGGTGGGGGCCATCTCG

GCGGCCACCACCCTGGTGGGGGCCAGGATCAGGGTCCTCAGCCTCCTCTTGATGGCCTCCC

TCACGATGGCGGGCAGATACCTCTTGGTCTTGCCGGCGCCGGGGTGCAGGTCCATGATGGT

CAGGTTCCTCTTCCTGAACACCTCGTCCTCGATCTCGGGCAGGGGCTCGGCGTTGGTCTGGG

CGATGGCGCTCACGTAGGCGCCGCTCTTGGTCACCACGCCGTTGCCGTACAGGCCCACCAC

CTTGCCCTCCCTGTTGATGATGGGGCTGCCGCTGGTGCCCTCCCTGTTCACGATGGGGCTGC

CGCTGGTGCCGGGCTTGAAGTCCAGGGCGATGGCGCCGATCTCGCCCTCGGGGGTCTTGAA

CAGGCCGGGCTTGGTCTGCACGGCCTTGGGGTTCTTGCCGGGCTCCACGGCGATCACCTGC

ACCTCCTCGCCCTCGTCCCACTCGCCCTCCAGCCTCCAGCCGCCGCCGTAGCTGATCAGGT

CCTTCTTCACGCTGTAGCTGATCAGGTCCTTCTTCACGTCGGCCCAGCTGGGCTCGATCCTC

TTGCCCTGGTGCATCAGCACGGCGCCCCTGGTCACGTGCCACATGGTGTGGAACACGCCCT

CCTTGAACACGCCGGCGCCGATCTGGCTGGCAAGCTTCGATCCTCTTCTGAATCGGGCATGG

ATTTCCTGGCTGGGCGAAACGAAGACTGCTCCACACAGCAGCAGCACACAGCAGAGCCCTCT

CTTCATTGCATCCATGGTGGCGGCGCGGCTAGCGGTACCGGATCTAGATGGGGATCCGTCA

CTGTTCTTTATGATTCTACTTCCTTACCGTGCAATAAATTAGAATATATTTTCTACTTTTACGAG

AAATTAATTATTGTATTTATTATTTATGGGTGAAAAACTTACTATAAAAAGCGGGTGGGTTTGG

AATTAGTGATCAGTTTATGTATATCGCAACTACCGGGCATATGGCTATCGACATCGAGAACAT

TACCCACATGATAAGAGATTGTATCAGTTTCGTAGTCTTGAGTATTGGTATTACTATATAGTAT

ATAGATGTCGACCTGCAGGTCGACGAAGTTCCTATACTTTCTAGAGAATAGGAACTTCGCAGC

CAAGCTGGAATTCATCCACTTTGGATAAGAAATCTGCATGATAAATATATTGATATCCTACCAC

CTATTAAAGTACCATTATCTAATAGCAATAAGATAGATAAACAAATGTTTTTTGATGAAGTTATT

ACGTGGATAAATATATATCTTCAGGAAAAGGGTATTATGTTACCAGATGATATAAGAGAACTCA

GAGATGCTATTATTCCTTAACTAGTTACGTCTCTTTAGGTACTTATTTTGATACGTTACAAGTAA

AAAACTATCAAATATAAATGGAATCTGATTCTAATATAGCGATTGAAGAGGATCCACCGGTCG

CCACCATGGTGAGCAAGGGCGAGGAGCTGTTCACCGGGGTGGTGCCCATCCTGGTCGAGCT

GGACGGCGACGTAAACGGCCACAAGTTCAGCGTGTCCGGCGAGGGCGAGGGCGATGCCAC

CTACGGCAAGCTGACCCTGAAGTTCATCTGCACCACCGGCAAGCTGCCCGTGCCCTGGCCC

ACCCTCGTGACCACCCTGACCTACGGCGTGCAGTGCTTCAGCCGCTACCCCGACCACATGAA

GCAGCACGACTTCTTCAAGTCCGCCATGCCCGAAGGCTACGTCCAGGAGCGCACCATCTTCT

TCAAGGACGACGGCAACTACAAGACCCGCGCCGAGGTGAAGTTCGAGGGCGACACCCTGGT

GAACCGCATCGAGCTGAAGGGCATCGACTTCAAGGAGGACGGCAACATCCTGGGGCACAAG

CTGGAGTACAACTACAACAGCCACAACGTCTATATCATGGCCGACAAGCAGAAGAACGGCAT

CAAGGTGAACTTCAAGATCCGCCACAACATCGAGGACGGCAGCGTGCAGCTCGCCGACCAC

TACCAGCAGAACACCCCCATCGGCGACGGCCCCGTGCTGCTGCCCGACAACCACTACCTGA

GCACCCAGTCCGCCCTGAGCAAAGACCCCAACGAGAAGCGCGATCACATGGTCCTGCTGGA

GTTCGTGACCGCCGCCGGGATCACTCTCGGCATGGACGAGCTGTACAAGTAAAGCGGCCGC

GAAGTTCCTATACTTTCTAGAGAATAGGAACTTCAACAATGTCTGGAAAGAACTGTCCTTCATC

-continued

GATACCTATCACGGAGAAATCTGTAATTGATTCCAAGACATCACATAGTTTAGTTGCTTCCAAT

GCTTCAAAATTATTCTTATCATGCGTCCATAGTCCCGTTCCGTATCTATTATCGTTAGAATATTT

TATAGTCACGCATTTATATTGAGCTATTTGATAACGTCTAACTCGTCTAATTAATTCTGTACTTT

TACCTGAAAACATGGGGCCGATTATCAACTGAATATGTCCGCCGTTCATGATGACAATAAAGA

ATTAATTATTGTTCACTTTATTCGACTTTAATATATCCATCACGTTAGAAAATGCGATATCGCGA

CGAGGATCTATGTATCTAACAGGATCTATTGCGGTGGTAGCTAGAGCTGATTCTTTTTTGAAT

CGCATCAAACTAATCACAAAGTCGAACAAATATCCTTTATTAAGTTTGACCCTTCCATCTGTAA

CAATAGGGACCTTGTTAAACAGTTTTTTAAAATCTTGAGAGTCTGTGAATTTTGTCAATTGTCT

GTATTCCTCTGAAAGAGATTCATAACAATGACCCACGGCTTCTAATTTATTTTTTGATTGGATC

AATAATAATAACAGAAAGTCTAGATATTGAGTGATTTGCAATATATCAGATAATGAAGATTCAT

CATCTTGACTAGCCAAATACTTAAAAAATGAATCATCATCTGCGAAGAACATCGTTAAGAGATA

CTGGTTGTGATCCATTTATGAGCTCGCGAAAGCTTGGCACTGGCCGTCGTTTTACAACGTCGT

GACTGGGAAAACCCTGGCGTTACCCAACTTAATCGCCTTGCAGCACATCCCCCTTTCGCCAG

CTGGCGTAATAGCGAAGAGGCCCGCACCGATCGCCCTTCCCAACAGTTGCGCAGCCTGAAT

GGCGAATGGCGCCTGATGCGGTATTTTCTCCTTACGCATCTGTGCGGTATTTCACACCGCATA

TGGTGCACTCTCAGTACAATCTGCTCTGATGCCGCATAGTTAAGCCAGCCCCGACACCCGCC

AACACCCGCTGACGCGCCCTGACGGGCTTGTCTGCTCCCGGCATCCGCTTACAGACAAGCT

GTGACCGTCTCCGGGAGCTGCATGTGTCAGAGGTTTTCACCGTCATCACCGAAACGCGCGAG

ACGAAAGGGCCTCGTGATACGCCTATTTTTATAGGTTAATGTCATGATAATAATGGTTTCTTAG

ACGTCAGGTGGCACTTTTCGGGGAAATGTGCGCGGAACCCCTATTTGTTTATTTTTCTAAATA

CATTCAAATATGTATCCGCTCATGAGACAATAACCCTGATAAATGCTTCAATAATATTGAAAAA

GGAAGAGTATGAGTATTCAACATTTCCGTGTCGCCCTTATTCCCTTTTTTGCGGCATTTTGCCT

TCCTGTTTTTGCTCACCCAGAAACGCTGGTGAAAGTAAAAGATGCTGAAGATCAGTTGGGTGC

ACGAGTGGGTTACATCGAACTGGATCTCAACAGCGGTAAGATCCTTGAGAGTTTTCGCCCCG

AAGAACGTTTTCCAATGATGAGCACTTTTAAAGTTCTGCTATGTGGCGCGGTATTATCCCGTAT

TGACGCCGGGCAAGAGCAACTCGGTCGCCGCATACACTATTCTCAGAATGACTTGGTTGAGT

ACTCACCAGTCACAGAAAAGCATCTTACGGATGGCATGACAGTAAGAGAATTATGCAGTGCTG

CCATAACCATGAGTGATAACACTGCGGCCAACTTACTTCTGACAACGATCGGAGGACCGAAG

GAGCTAACCGCTTTTTTGCACAACATGGGGGATCATGTAACTCGCCTTGATCGTTGGGAACC

GGAGCTGAATGAAGCCATACCAAACGACGAGCGTGACACCACGATGCCTGTAGCAATGGCAA

CAACGTTGCGCAAACTATTAACTGGCGAACTACTTACTCTAGCTTCCCGGCAACAATTAATAG

ACTGGATGGAGGCGGATAAAGTTGCAGGACCACTTCTGCGCTCGGCCCTTCCGGCTGGCTG

GTTTATTGCTGATAAATCTGGAGCCGGTGAGCGTGGGTCTCGCGGTATCATTGCAGCACTGG

GGCCAGATGGTAAGCCCTCCCGTATCGTAGTTATCTACACGACGGGGAGTCAGGCAACTATG

GATGAACGAAATAGACAGATCGCTGAGATAGGTGCCTCACTGATTAAGCATTGGTAACTGTCA

GACCAAGTTTACTCATATATACTTTAGATTGATTTAAAACTTCATTTTTAATTTAAAAGGATCTA

GGTGAAGATCCTTTTTGATAATCTCATGACCAAAATCCCTTAACGTGAGTTTTCGTTCCACTGA

GCGTCAGACCCCGTAGAAAAGATCAAAGGATCTTCTTGAGATCCTTTTTTTCTGCGCGTAATC

TGCTGCTTGCAAACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAAATACTGTTCTTCT

-continued

AGTGTAGCCGTAGTTAGGCCACCACTTCAAGAACTCTGTAGCACCGCCTACATACCTCGCTCT

GCTAATCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGCACACA

GCCCAGCTTGGAGCGAACGACCTACACCGAACTGAGATACCTACAGCGTGAGCTATGAGAAA

GCGCCACGCTTCCCGAAGGGAGAAAGGCGGACAGGTATCCGGTAAGCGGCAGGGTCGGAA

CAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTAT

GGAAAAACGCCAGCAACGCGGCCTTTTTACGGTTCCTGGCCTTTTGCTGGCCTTTTGCTCACA

TGTTCTTTCCTGCGTTATCCCCTGATTCTGTGGATAACCGTATTACCGCCTTTGAGTGAGCTG

ATACCGCTCGCCGCAGCCGAACGACCGAGCGCAGCGAGTCAGTGAGCGAGGAAGCGGAAGA

APPENDIX 1

| Pool peptides | |
|---|---|
| SQIGAGVFKEGVFHTMWHVT | 3 |
| GVFHTMWHVTRGAVLMHQGK | 3 |
| RGAVLMHQGKRIEPSWADVK | 3 |
| RIEPSWADVKKDLISYSVKK | 3 |
| KDLISYSVKKDLISYGGGWR | 3 |
| DLISYGGGWRLEGEWDEGEE | 3 |
| LEGEWDEGEEVQVIAVEPGK | 3 |
| VQVIAVEPGKNPKAVQTKPG | 3 |
| NPKAVQTKPGLFKTPEGEIG | 3 |
| LFKTPEGEIGAIALDFKPGT | 3 |
| AIALDFKPGTSGSPIVNREG | 3 |
| SGSPIVNREGTSGSPIINRE | 3 |
| TSGSPIINREGKVVGLYGNG | 3 |
| GKVVGLYGNGVVTKSGAYVS | 3 |
| VVTKSGAYVSAIAQTNAEPL | 3 |
| AIAQTNAEPLPEIEDEVFRK | 3 |
| PEIEDEVFRKRNLTIMDLHP | 3 |
| RNLTIMDLHPGAGKTKRYLP | 3 |
| GAGKTKRYLPAIVREAIKRR | 3 |
| AIVREAIKRRLRTLILAPTR | 3 |
| LRTLILAPTRVVAAEMAPTR | 3 |
| VVAAEMAPTRVVASEMEEAL | 3 |
| VVASEMEEALKGLPIRYALR | 3 |
| KGLPIRYALRGLPIRYQTTA | 3 |
| GLPIRYQTTAIKAEHTGKEI | 3 |
| IKAEHTGKEIVDLMCHATFT | 3 |
| VDLMCHATFTMRLLSPVRVP | 3 |
| MRLLSPVRVPNYNLIIMDEA | 3 |

APPENDIX 1-continued

| Pool peptides | |
|---|---|
| NYNLIIMDEAHFTDPASIAA | 3 |
| HFTDPASIAARGYISTRVEM | 3 |
| RGYISTRVEMGEAAAIFMTA | 3 |
| GEAAAIFMTATPPGSADAFP | 3 |
| TPPGSADAFPQSNAPIEDEE | 3 |
| QSNAPIEDEEREIPERSWNS | 3 |
| REIPERSWNSGFDWITDFAG | 3 |
| GFDWITDFAGKTVWFVPSIK | 3 |
| KTVWFVPSIKAGNDIANCLR | 3 |
| AGNDIANCLRKNGKKVIQLS | 3 |
| KNGKKVIQLSRKTFDTEYPK | 3 |
| RKTFDTEYPKTKLNDWDFVV | 3 |
| TKLNDWDFVVTTDISEMGAN | 3 |
| TTDISEMGANFKADRVIDPR | 3 |
| FKADRVIDPRRCLKPVILTD | 3 |
| RCLKPVILTDGPERVILAGP | 3 |
| GPERVILAGPMPVTAASAAQ | 3 |
| MPVTAASAAQRRGRIGRNHK | 3 |
| RRGRIGRNHKKENDQYIYMG | 3 |
| KENDQYIYMGQPLNNDEDHA | 3 |
| QPLNNDEDHAHWTEAKMLLD | 3 |
| HWTEAKMLLDNINTPEGIIP | 3 |
| NINTPEGIIPALFTPEGIIP | 3 |
| ALFTPEGIIPSMFTPEGIIP | 3 |
| SMFTPEGIIPTLFTPEGIIP | 3 |
| TLFTPEGIIPSLEPEREKSA | 3 |
| SLEPEREKSAAIDGEYRLRG | 3 |

APPENDIX 1-continued

| Pool peptides | |
|---|---|
| AIDGEYRLRGEARKTFVELG | 3 |
| EARKTFVELGEARKTFVDLG | 3 |
| EARKTFVDLGEQRKTFVELM | 3 |
| EQRKTFVELMRRGDLPVWLS | 3 |
| RRGDLPVWLSYKVASAGFQY | 3 |
| YKVASAGFQYKDREWCFDGE | 3 |
| KDREWCFDGERNNQILEENM | 3 |
| RNNQILEENMDVEIWTKEGE | 3 |
| DVEIWTKEGEKKKLRPRWLD | 3 |
| KKKLRPRWLDARTYADPLAL | 3 |
| ARTYADPLALKEFKDFAAGR | 3 |
| KEFKDFAAGRKSIATEIGRV | 3 |
| KSIATEIGRVPSHLAHRTRA | 3 |
| PSHLAHRTRAYQHALEELPE | 3 |
| YQHALEELPETLETLLLLAL | 3 |
| TLETLLLLALLGAFLFFLSG | 4A |
| LGAFLFFLSGKGIGKMSIGL | 4A |
| KGIGKMSIGLCCIIAASLLW | 4A |
| CCIIAASLLWMAEIQPHWIA | 4A |
| MAEIQPHWIAASIILEFFLM | 4A |
| ASIILEFFLMVLLIPEPEKQ | 4A |
| VLLIPEPEKQRTPQDNQLAY | 4A |
| RTPQDNQLAYVVIGILTLAA | 4A |
| VVIGILTLAAAIAANEMGLL | 4A |
| AIAANEMGLLETTKKDLGIG | 4B |
| ETTKKDLGIGHVAPTAILDV | 4B |
| HVAPTAILDVDLHPASAWTL | 4B |
| DLHPASAWTLYAVATTIITP | 4B |
| YAVATTIITPMLRHTIENST | 4B |
| MLRHTIENSTANVSLTAIAN | 4B |
| ANVSLTAIANQAAVLMIANQ | 4B |
| QAAVLMIANQATVLMGLDKG | 4B |
| ATVLMGLDKGWPISKMDLGV | 4B |
| WPISKMDLGVPLLALGCYSQ | 4B |
| PLLALGCYSQVNPLTLTAAV | 4B |
| VNPLTLTAAVLLLITHYAII | 4B |
| LLLITHYAIIGPGLQAKATR | 4B |
| GPGLQAKATREAQKRTAAGI | 4B |
| EAQKRTAAGIMKNPTVDGIM | 4B |

APPENDIX 1-continued

| Pool peptides | |
|---|---|
| MKNPTVDGIMAIDLDPIPYD | 4B |
| AIDLDPIPYDPKFEKQLGQV | 4B |
| PKFEKQLGQVMLLILCVSQI | 4B |
| MLLILCVSQILLMRTTWAVL | 4B |
| LLMRTTWAVLLMRTTWALCE | 4B |
| LMRTTWALCEALTLATGPIT | 4B |
| ALTLATGPITTLWEGNPGKF | 4B |
| TLWEGNPGKFWNTTIAVSMA | 4B |
| WNTTIAVSMANIFRGSYLAG | 4B |
| NIFRGSYLAGAGLAFSLIKN | 4B |
| AGLAFSLIKNRRGTGAQGET | 4B |
| RRGTGAQGETLGEKWKRQLN | 4B |
| LGEKWKRQLNQLDKSEFEEY | 4B |
| QLDKSEFEEYKKSGILEVDR | 4B |
| KKSGILEVDRTEAKEAIKRG | 4B |
| TEAKEAIKRGETDHHAVSRG | 4B |
| ETDHHAVSRGSAKLRWFVER | 5 |
| SAKLRWFVERNMVIPEGRVI | 5 |
| NMVIPEGRVIDLGCGRGGWS | 5 |
| DLGCGRGGWSYYCAGLKKVR | 5 |
| YYCAGLKKVREVRGYTKGGP | 5 |
| EVRGYTKGGPGHEEPIPMAT | 5 |
| GHEEPIPMATYGWNLVKLHS | 5 |
| YGWNLVKLHSGVDVFFPEKC | 5 |
| GVDVFFPEKCDTLLCDIGES | 5 |
| DTLLCDIGESSPNPTIEEGR | 5 |
| SPNPTIEEGRTLRVLKMVEP | 5 |
| TLRVLKMVEPWLKGNQFCIK | 5 |
| WLKGNQFCIKILNPYMPSVI | 5 |
| ILNPYMPSVIEELEKLQRKH | 5 |
| EELEKLQRKHGGMLVRNPLS | 5 |
| GGMLVRNPLSRNSTHEMYWV | 5 |
| RNSTHEMYWVSNGTGNIVSA | 5 |
| SNGTGNIVSAVNMISRMLIN | 5 |
| VNMISRMLINRFTMAHKKPT | 5 |
| RFTMAHKKPTYERDVDLGAG | 5 |
| YERDVDLGAGSTWHYDEDNP | 5 |
| STWHYDEDNPYKTWAYHGSY | 5 |
| YKTWAYHGSYEVKATGSASS | 5 |

APPENDIX 1-continued

| Pool peptides | |
|---|---|
| EVKATGSASSMVNGVVKLLT | 5 |
| MVNGVVKLLTKPWDVVPMVT | 5 |
| KPWDVVPMVTQMAMTDTTPF | 5 |
| QMAMTDTTPFGQQRVFKEKV | 5 |
| GQQRVFKEKVDTRTPEAKEN | 5 |
| DTRTPEAKENAAIGAVFQDE | 5 |
| AAIGAVFQDENGWKSAREAV | 5 |
| NGWKSAREAVEDSERALHLE | 5 |
| EDSERALHLEGKCESCVYNM | 5 |
| GKCESCVYNMMGKREKKLGE | 5 |
| MGKREKKLGEFGKAKGSRAI | 5 |
| FGKAKGSRAIWYMWLGARFL | 5 |
| WYMWLGARFLEFEALGFLNE | 5 |
| EFEALGFLNEDHWFSRENSL | 5 |
| DHWFSRENSLSGVEGEGLHK | 5 |
| SGVEGEGLHKLGYILRDISK | 5 |
| LGYILRDISKIPGGAMYADD | 5 |
| IPGGAMYADDTAGWDTRITE | 5 |
| TAGWDTRITEDDLHNEEKIL | 5 |
| DDLHNEEKILAKAIFKLTYQ | 5 |
| AKAIFKLTYQNKVVKVQRPT | 5 |
| NKVVKVQRPTPRGAVMDIIS | 5 |
| PRGAVMDIISRKDQRGSGQV | 5 |
| RKDQRGSGQVGTYGLNTFTN | 5 |
| GTYGLNTFTNMEAQLIRQME | 5 |
| MEAQLIRQMEAEGVITECGV | 5 |
| AEGVITECGVDRLKRMAISG | 5 |
| DRLKRMAISGDDCVVKPPQW | 5 |
| DDCVVKPPQWEPSKGWHDWQ | 5 |
| EPSKGWHDWQQVPFCSHHFH | 5 |
| QVPFCSHHFHEIFMKDGRKL | 5 |
| EIFMKDGRKLVVPCRNQDEL | 5 |
| VVPCRNQDELIGRARISQGA | 5 |
| IGRARISQGAGWSLRETACL | 5 |
| GWSLRETACLGKSYAQMWQL | 5 |
| GKSYAQMWQLMYFHRRDLRL | 5 |
| MYFHRRDLRLASNAICSAVP | 5 |
| ASNAICSAVPSHWVPTSRTT | 5 |
| SHWVPTSRTTWSIHAHHEWM | 5 |

APPENDIX 1-continued

| Pool peptides | |
|---|---|
| WSIHAHHEWMTTEDMLAVWN | 5 |
| TTEDMLAVWNRVWIEENPWM | 5 |
| RVWIEENPWMEDKTHIHSWE | 5 |
| EDKTHIHSWEDVPYLGKRED | 5 |
| DVPYLGKREDQWCGSLIGLT | 5 |
| QWCGSLIGLTSRATWAKNI | 5 |
| DQWCGSLIGLTSRATWAKNI | 5 |

APPENDIX 2

| Peptide pools |
|---|
| KEKQDVFCDSKLMSAAIKDN |
| KLMSAAIKDNRAVHADMGYW |
| RAVHADMGYWIESALNDTWK |
| IESALNDTWKIEKASFIEVK |
| IEKASFIEVKNCHWPKSHTL |
| NCHWPKSHTLWSNGVLESEM |
| WSNGVLESEMIIPKNLAGPV |
| IIPKNLAGPVSQHNYRPGYH |
| SQHNYRPGYHTQITGPWHLG |
| TQITGPWHLGKLEMDFDFCD |
| KLEMDFDFCDGTTVVVTEDC |
| GTTVVVTEDCGNRGPSLRTT |
| GNRGPSLRTTTASGKLITEW |
| TASGKLITEWCCRSCTLPPL |
| CCRSCTLPPLRYRGEDGCWY |
| RYRGEDGCWYGMEIRPLKEK |
| GMEIRPLKEKEENLVNSLVT |
| EENLVNSLVTA |
| MEIRPLKEKEENLVNSLVTA |

REFERENCE

1. WHO (2009) Dengue guidelines for diagnosis, treatment, prevention and control. *Dengue: Guidelines for Diagnosis, Treatment, Prevention and Control: New Edition*, WHO Guidelines Approved by the Guidelines Review Committee, ed ORGANIZATION WH (WORLD HEALTH ORGANIZATION, Geneva).
2. Bhatt S, et al. (2013) The global distribution and burden of dengue. *Nature* 496(7446):504-507.
3. Simmons C P, Farrar J J, Nguyen v V, & Wills B (2012) Dengue. *The New England journal of medicine* 366(15): 1423-1432.

4. Wesikopf et al (2013) *Comprehensive analysis of dengue virus-specific responses supports an HLA-linked protective role for CD8+ T cells*. PNAS. 110(22):E2046-53.
5. Vita R, Zarebski L, Greenbaum J A, Emami H, Hoof I, Salimi N, Damle R, Sette A, Peters B. (2010) *The immune epitope database* 2.0. Nucleic Acids Res. 38(Database issue):D854-62.
6. Immune Epitope Database and Analysis Resource. *IEDB*. [Online] Available from: iedb.org

The invention claimed is:

1. A nucleic acid comprising a sequence encoding a fusion protein, wherein the fusion protein comprises the peptide sequences of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, and SEQ ID NO: 114, or variants thereof, and wherein the variants of the peptide sequences comprise sequences having at least 80% identity with the peptide sequences.

2. The nucleic acid according to claim 1, wherein the fusion protein comprises a sequence of SEQ ID NO: 72 or a variant thereof having at least 80% identity with SEQ ID NO: 72.

3. The nucleic acid according to claim 1, wherein the fusion protein is capable of activating T-cell mediated immunity in a subject.

4. A viral vector comprising the nucleic acid according to claim 1.

5. The viral vector according to claim 4, wherein the viral vector further comprises a virus particle.

6. A method of preventing disease associated with dengue virus infection or treating or inhibiting a dengue viral infection in a subject, the method comprising:

administering the nucleic acid according to claim 1 to the subject.

7. A method of preventing disease associated with dengue virus infection or treating or inhibiting a dengue viral infection in a subject, the method comprising:

administering a prime vaccination to the subject, wherein the vaccine for the prime vaccination comprises the nucleic acid according to claim 1; and administering a boost vaccination to the subject after the prime vaccination has been administered, wherein the vaccine for the boost vaccination comprises the nucleic acid according to claim 1, wherein the order of the encoded peptide sequences in the boost vaccination is different from the order of the encoded peptide sequences in the prime vaccination.

* * * * *

SEQUENCE LISTING

```
<160> NUMBER OF SEQ ID NOS: 333

<210> SEQ ID NO 1
<211> LENGTH: 308
<212> TYPE: PRT
<213> ORGANISM: Artificial Sequence
<220> FEATURE:
<223> OTHER INFORMATION: Fusion protein

<400> SEQUENCE: 1

Leu Ile Leu Ala Pro Thr Arg Val Val Ala Ser Glu Met Ala Pro Thr
1               5                   10                  15

Arg Val Val Ala Ala Glu Met Glu Glu Arg Val Val Ala Ala Glu Met
            20                  25                  30

Glu Glu Ala Leu Lys Gly Leu Pro Ser Ile Ala Ala Arg Gly Tyr Ile
        35                  40                  45

Ser Thr Arg Val Glu Met Gly Glu Ala Ala Ala Ile Leu Asn Asp Trp
    50                  55                  60

Asp Phe Val Val Thr Thr Asp Ile Ser Glu Met Gly Ala Asn Phe Lys
65                  70                  75                  80

Pro Met Pro Val Thr Ala Ala Ser Ala Ala Gln Arg Arg Gly Arg Ile
                85                  90                  95

Gly Arg Asn Asp His Ala His Trp Thr Glu Ala Lys Met Leu Leu Asp
            100                 105                 110

Asn Ile Lys Arg Thr Ala Ala Gly Ile Met Lys Asn Pro Thr Val Asp
        115                 120                 125

Gly Tyr Asp Pro Lys Phe Glu Lys Gln Leu Gly Gln Val Met Leu Leu
    130                 135                 140

Met Arg Thr Thr Trp Ala Leu Cys Glu Ala Leu Thr Leu Ala Thr Gly
145                 150                 155                 160

Pro Leu Trp Glu Gly Asn Pro Gly Lys Phe Trp Asn Thr Thr Ile Ala
                165                 170                 175

Val Ser Met Pro Gly Lys Phe Trp Asn Thr Thr Ile Ala Val Ser Met
            180                 185                 190

Ala Asn Ile Phe Arg Gly Ser Tyr Leu Ala Leu Cys Asp Ile Gly Glu
        195                 200                 205

Ser Ser Pro Asn Pro Thr Ile Glu Glu Tyr Asn Met Met Gly Lys Arg
    210                 215                 220

Glu Lys Lys Leu Gly Glu Phe Gly Lys Ala Lys Ser Arg Ala Ile Trp
225                 230                 235                 240

Tyr Met Trp Leu Gly Ala Arg Phe Leu Glu Phe Glu Ala Leu Gly Phe
                245                 250                 255

Met Tyr Ala Asp Asp Thr Ala Gly Trp Asp Thr Arg Ile Thr Glu Asp
            260                 265                 270

Asp Leu Phe Lys Leu Thr Tyr Gln Asn Lys Val Val Lys Val Gln Arg
        275                 280                 285

Pro Val Met Asp Ile Ile Ser Arg Lys Asp Gln Arg Gly Ser Gly Gln
    290                 295                 300
```

```
Val Gly Thr Tyr
305


<210> SEQ ID NO 2
<211> LENGTH: 298
<212> TYPE: PRT
<213> ORGANISM: Artificial Sequence
<220> FEATURE:
<223> OTHER INFORMATION: Fusion protein

<400> SEQUENCE: 2

Leu Ile Leu Ala Pro Thr Arg Val Val Ala Ser Glu Met Glu Glu Arg
1               5                   10                  15

Val Val Ala Ala Glu Met Glu Glu Ala Leu Lys Gly Leu Pro Ser Ile
            20                  25                  30

Ala Ala Arg Gly Tyr Ile Ser Thr Arg Val Glu Met Gly Glu Ala Ala
        35                  40                  45

Ala Ile Leu Asn Asp Trp Asp Phe Val Val Thr Thr Asp Ile Ser Glu
    50                  55                  60

Met Gly Ala Asn Phe Lys Pro Met Pro Val Thr Ala Ala Ser Ala Ala
65                  70                  75                  80

Gln Arg Arg Gly Arg Ile Gly Arg Asn Asp His Ala His Trp Thr Glu
                85                  90                  95

Ala Lys Met Leu Leu Asp Asn Ile Lys Arg Thr Ala Ala Gly Ile Met
            100                 105                 110

Lys Asn Pro Thr Val Asp Gly Tyr Asp Pro Lys Phe Glu Lys Gln Leu
        115                 120                 125

Gly Gln Val Met Leu Leu Met Arg Thr Thr Trp Ala Leu Cys Glu Ala
    130                 135                 140

Leu Thr Leu Ala Thr Gly Pro Leu Trp Glu Gly Asn Pro Gly Lys Phe
145                 150                 155                 160

Trp Asn Thr Thr Ile Ala Val Ser Met Pro Gly Lys Phe Trp Asn Thr
                165                 170                 175

Thr Ile Ala Val Ser Met Ala Asn Ile Phe Arg Gly Ser Tyr Leu Ala
            180                 185                 190

Leu Cys Asp Ile Gly Glu Ser Ser Pro Asn Pro Thr Ile Glu Glu Tyr
        195                 200                 205

Asn Met Met Gly Lys Arg Glu Lys Lys Leu Gly Glu Phe Gly Lys Ala
    210                 215                 220

Lys Ser Arg Ala Ile Trp Tyr Met Trp Leu Gly Ala Arg Phe Leu Glu
225                 230                 235                 240

Phe Glu Ala Leu Gly Phe Met Tyr Ala Asp Asp Thr Ala Gly Trp Asp
                245                 250                 255

Thr Arg Ile Thr Glu Asp Asp Leu Phe Lys Leu Thr Tyr Gln Asn Lys
            260                 265                 270

Val Val Lys Val Gln Arg Pro Val Met Asp Ile Ile Ser Arg Lys Asp
        275                 280                 285

Gln Arg Gly Ser Gly Gln Val Gly Thr Tyr
    290                 295


<210> SEQ ID NO 3
<211> LENGTH: 298
<212> TYPE: PRT
<213> ORGANISM: Artificial Sequence
<220> FEATURE:
<223> OTHER INFORMATION: Fusion protein

<400> SEQUENCE: 3
```

```
Leu Ile Leu Ala Pro Thr Arg Val Val Ala Ala Glu Met Glu Glu Arg
1               5                   10                  15

Val Val Ala Ala Glu Met Glu Glu Ala Leu Lys Gly Leu Pro Ser Ile
            20                  25                  30

Ala Ala Arg Gly Tyr Ile Ser Thr Arg Val Glu Met Gly Glu Ala Ala
        35                  40                  45

Ala Ile Leu Asn Asp Trp Asp Phe Val Val Thr Thr Asp Ile Ser Glu
    50                  55                  60

Met Gly Ala Asn Phe Lys Pro Met Pro Val Thr Ala Ala Ser Ala Ala
65                  70                  75                  80

Gln Arg Arg Gly Arg Ile Gly Arg Asn Asp His Ala His Trp Thr Glu
                85                  90                  95

Ala Lys Met Leu Leu Asp Asn Ile Lys Arg Thr Ala Ala Gly Ile Met
            100                 105                 110

Lys Asn Pro Thr Val Asp Gly Tyr Asp Pro Lys Phe Glu Lys Gln Leu
        115                 120                 125

Gly Gln Val Met Leu Leu Met Arg Thr Thr Trp Ala Leu Cys Glu Ala
    130                 135                 140

Leu Thr Leu Ala Thr Gly Pro Leu Trp Glu Gly Asn Pro Gly Lys Phe
145                 150                 155                 160

Trp Asn Thr Thr Ile Ala Val Ser Met Pro Gly Lys Phe Trp Asn Thr
                165                 170                 175

Thr Ile Ala Val Ser Met Ala Asn Ile Phe Arg Gly Ser Tyr Leu Ala
            180                 185                 190

Leu Cys Asp Ile Gly Glu Ser Ser Pro Asn Pro Thr Ile Glu Glu Tyr
        195                 200                 205

Asn Met Met Gly Lys Arg Glu Lys Lys Leu Gly Glu Phe Gly Lys Ala
    210                 215                 220

Lys Ser Arg Ala Ile Trp Tyr Met Trp Leu Gly Ala Arg Phe Leu Glu
225                 230                 235                 240

Phe Glu Ala Leu Gly Phe Met Tyr Ala Asp Asp Thr Ala Gly Trp Asp
                245                 250                 255

Thr Arg Ile Thr Glu Asp Asp Leu Phe Lys Leu Thr Tyr Gln Asn Lys
            260                 265                 270

Val Val Lys Val Gln Arg Pro Val Met Asp Ile Ile Ser Arg Lys Asp
        275                 280                 285

Gln Arg Gly Ser Gly Gln Val Gly Thr Tyr
    290                 295
```

<210> SEQ ID NO 4
<211> LENGTH: 25
<212> TYPE: PRT
<213> ORGANISM: Dengue virus

<400> SEQUENCE: 4

```
Leu Ile Leu Ala Pro Thr Arg Val Val Ala Ser Glu Met Ala Pro Thr
1               5                   10                  15

Arg Val Val Ala Ala Glu Met Glu Glu
            20                  25
```

<210> SEQ ID NO 5
<211> LENGTH: 15
<212> TYPE: PRT
<213> ORGANISM: Dengue virus

<400> SEQUENCE: 5

```
Arg Val Val Ala Ala Glu Met Glu Glu Ala Leu Lys Gly Leu Pro
1               5                   10                  15


<210> SEQ ID NO 6
<211> LENGTH: 20
<212> TYPE: PRT
<213> ORGANISM: Dengue virus

<400> SEQUENCE: 6

Ser Ile Ala Ala Arg Gly Tyr Ile Ser Thr Arg Val Glu Met Gly Glu
1               5                   10                  15

Ala Ala Ala Ile
            20


<210> SEQ ID NO 7
<211> LENGTH: 20
<212> TYPE: PRT
<213> ORGANISM: Dengue virus

<400> SEQUENCE: 7

Leu Asn Asp Trp Asp Phe Val Val Thr Thr Asp Ile Ser Glu Met Gly
1               5                   10                  15

Ala Asn Phe Lys
            20


<210> SEQ ID NO 8
<211> LENGTH: 19
<212> TYPE: PRT
<213> ORGANISM: Dengue virus

<400> SEQUENCE: 8

Pro Met Pro Val Thr Ala Ala Ser Ala Ala Gln Arg Arg Gly Arg Ile
1               5                   10                  15

Gly Arg Asn


<210> SEQ ID NO 9
<211> LENGTH: 15
<212> TYPE: PRT
<213> ORGANISM: Dengue virus

<400> SEQUENCE: 9

Asp His Ala His Trp Thr Glu Ala Lys Met Leu Leu Asp Asn Ile
1               5                   10                  15


<210> SEQ ID NO 10
<211> LENGTH: 15
<212> TYPE: PRT
<213> ORGANISM: Dengue virus

<400> SEQUENCE: 10

Lys Arg Thr Ala Ala Gly Ile Met Lys Asn Pro Thr Val Asp Gly
1               5                   10                  15


<210> SEQ ID NO 11
<211> LENGTH: 15
<212> TYPE: PRT
<213> ORGANISM: Dengue virus

<400> SEQUENCE: 11

Tyr Asp Pro Lys Phe Glu Lys Gln Leu Gly Gln Val Met Leu Leu
1               5                   10                  15
```

<210> SEQ ID NO 12
<211> LENGTH: 17
<212> TYPE: PRT
<213> ORGANISM: Dengue virus

<400> SEQUENCE: 12

```
Met Arg Thr Thr Trp Ala Leu Cys Glu Ala Leu Thr Leu Ala Thr Gly
1               5                   10                  15

Pro
```

<210> SEQ ID NO 13
<211> LENGTH: 18
<212> TYPE: PRT
<213> ORGANISM: Dengue virus

<400> SEQUENCE: 13

```
Leu Trp Glu Gly Asn Pro Gly Lys Phe Trp Asn Thr Thr Ile Ala Val
1               5                   10                  15

Ser Met
```

<210> SEQ ID NO 14
<211> LENGTH: 23
<212> TYPE: PRT
<213> ORGANISM: Dengue virus

<400> SEQUENCE: 14

```
Pro Gly Lys Phe Trp Asn Thr Thr Ile Ala Val Ser Met Ala Asn Ile
1               5                   10                  15

Phe Arg Gly Ser Tyr Leu Ala
            20
```

<210> SEQ ID NO 15
<211> LENGTH: 15
<212> TYPE: PRT
<213> ORGANISM: Dengue virus

<400> SEQUENCE: 15

```
Leu Cys Asp Ile Gly Glu Ser Ser Pro Asn Pro Thr Ile Glu Glu
1               5                   10                  15
```

<210> SEQ ID NO 16
<211> LENGTH: 18
<212> TYPE: PRT
<213> ORGANISM: Dengue virus

<400> SEQUENCE: 16

```
Tyr Asn Met Met Gly Lys Arg Glu Lys Lys Leu Gly Glu Phe Gly Lys
1               5                   10                  15

Ala Lys
```

<210> SEQ ID NO 17
<211> LENGTH: 21
<212> TYPE: PRT
<213> ORGANISM: Dengue virus

<400> SEQUENCE: 17

```
Ser Arg Ala Ile Trp Tyr Met Trp Leu Gly Ala Arg Phe Leu Glu Phe
1               5                   10                  15

Glu Ala Leu Gly Phe
            20
```

<210> SEQ ID NO 18

-continued

<211> LENGTH: 18
<212> TYPE: PRT
<213> ORGANISM: Dengue virus

<400> SEQUENCE: 18

Met Tyr Ala Asp Asp Thr Ala Gly Trp Asp Thr Arg Ile Thr Glu Asp
1               5                   10                  15

Asp Leu

<210> SEQ ID NO 19
<211> LENGTH: 15
<212> TYPE: PRT
<213> ORGANISM: Dengue virus

<400> SEQUENCE: 19

Phe Lys Leu Thr Tyr Gln Asn Lys Val Val Lys Val Gln Arg Pro
1               5                   10                  15

<210> SEQ ID NO 20
<211> LENGTH: 19
<212> TYPE: PRT
<213> ORGANISM: Dengue virus

<400> SEQUENCE: 20

Val Met Asp Ile Ile Ser Arg Lys Asp Gln Arg Gly Ser Gly Gln Val
1               5                   10                  15

Gly Thr Tyr

<210> SEQ ID NO 21
<211> LENGTH: 15
<212> TYPE: PRT
<213> ORGANISM: Dengue virus

<400> SEQUENCE: 21

Leu Ile Leu Ala Pro Thr Arg Val Val Ala Ser Glu Met Glu Glu
1               5                   10                  15

<210> SEQ ID NO 22
<211> LENGTH: 15
<212> TYPE: PRT
<213> ORGANISM: Dengue virus

<400> SEQUENCE: 22

Leu Ile Leu Ala Pro Thr Arg Val Val Ala Ala Glu Met Glu Glu
1               5                   10                  15

<210> SEQ ID NO 23
<211> LENGTH: 1481
<212> TYPE: PRT
<213> ORGANISM: Artificial Sequence
<220> FEATURE:
<223> OTHER INFORMATION: Fusion protein

<400> SEQUENCE: 23

Ser Gln Ile Gly Ala Gly Val Phe Lys Glu Gly Val Phe His Thr Met
1               5                   10                  15

Trp His Val Thr Arg Gly Ala Val Leu Met His Gln Gly Lys Arg Ile
            20                  25                  30

Glu Pro Ser Trp Ala Asp Val Lys Lys Asp Leu Ile Ser Tyr Gly Gly
        35                  40                  45

Gly Trp Arg Leu Glu Gly Glu Trp Asp Glu Gly Glu Glu Val Gln Val
    50                  55                  60

-continued

```
Ile Ala Val Glu Pro Gly Lys Asn Pro Lys Ala Val Gln Thr Gly Glu
65                  70                  75                  80

Ile Gly Ala Ile Ala Leu Asp Phe Lys Pro Gly Thr Ser Gly Ser Pro
                85                  90                  95

Ile Val Asn Arg Glu Gly Val Gly Leu Tyr Gly Asn Gly Val Val Thr
            100                 105                 110

Lys Ser Gly Ala Tyr Val Ser Ala Ile Ala Gln Thr Phe Arg Lys Arg
        115                 120                 125

Asn Leu Thr Ile Met Asp Leu His Pro Gly Ala Gly Lys Thr Lys Arg
    130                 135                 140

Tyr Leu Pro Ala Ile Val Arg Glu Ala Ile Lys Arg Arg Leu Arg Thr
145                 150                 155                 160

Leu Ile Leu Ala Pro Thr Arg Val Val Ala Ala Glu Met Glu Glu Ala
                165                 170                 175

Leu Lys Gly Leu Pro Ile Arg Tyr Gln Thr Thr Ala Ile Lys Ala Glu
            180                 185                 190

His Thr Gly Lys Glu Ile Val Asp Leu Met Cys His Ala Thr Phe Thr
        195                 200                 205

Met Arg Leu Leu Ser Pro Val Arg Val Pro Asn Tyr Asn Leu Ile Ile
    210                 215                 220

Met Asp Glu Ala His Phe Thr Asp Pro Ala Ser Ile Ala Ala Arg Gly
225                 230                 235                 240

Tyr Ile Ser Thr Arg Val Glu Met Gly Glu Ala Ala Ala Ile Phe Met
                245                 250                 255

Thr Ala Thr Pro Pro Gly Ser Ala Asp Ala Phe Pro Gln Ser Asn Ala
            260                 265                 270

Pro Ile Glu Asp Glu Glu Arg Glu Ile Pro Glu Arg Ser Trp Asn Ser
        275                 280                 285

Gly Phe Asp Trp Ile Thr Asp Phe Ala Gly Lys Thr Val Trp Phe Val
    290                 295                 300

Pro Ser Ile Lys Ala Gly Asn Asp Ile Ala Asn Cys Leu Arg Lys Asn
305                 310                 315                 320

Gly Lys Lys Val Ile Gln Leu Ser Arg Lys Thr Phe Asp Thr Glu Tyr
                325                 330                 335

Pro Lys Thr Lys Leu Asn Asp Trp Asp Phe Val Val Thr Thr Asp Ile
            340                 345                 350

Ser Glu Met Gly Ala Asn Phe Lys Ala Asp Arg Val Ile Asp Pro Arg
        355                 360                 365

Arg Cys Leu Lys Pro Val Ile Leu Thr Asp Gly Pro Glu Arg Val Ile
    370                 375                 380

Leu Ala Gly Pro Met Pro Val Thr Ala Ala Ser Ala Ala Gln Arg Arg
385                 390                 395                 400

Gly Arg Ile Gly Arg Asn His Lys Lys Glu Asn Asp Gln Tyr Ile Tyr
                405                 410                 415

Met Gly Gln Pro Leu Asn Asn Asp Glu Asp His Ala His Trp Thr Glu
            420                 425                 430

Ala Lys Met Leu Leu Asp Asn Ile Asn Thr Pro Glu Gly Ile Ile Pro
        435                 440                 445

Ala Leu Phe Glu Pro Glu Arg Glu Lys Ser Ala Ala Ile Asp Gly Glu
    450                 455                 460

Tyr Arg Leu Arg Gly Glu Ala Arg Lys Thr Phe Val Glu Leu Met Arg
465                 470                 475                 480

Arg Gly Asp Leu Pro Val Trp Leu Ser Tyr Lys Val Ala Ser Ala Gly
```

```
                485                 490                 495

Phe Gln Tyr Lys Asp Arg Glu Trp Cys Phe Asp Gly Glu Arg Asn Asn
            500                 505                 510

Gln Ile Leu Glu Glu Asn Met Asp Val Glu Ile Trp Thr Glu Gly Glu
        515                 520                 525

Lys Lys Lys Leu Arg Pro Arg Trp Leu Asp Ala Arg Thr Tyr Ala Asp
    530                 535                 540

Pro His Ala Leu Glu Glu Leu Pro Glu Thr Leu Glu Thr Leu Leu Leu
545                 550                 555                 560

Leu Ala Leu Leu Gly Phe Leu Phe Phe Leu Ser Gly Lys Gly Ile Gly
                565                 570                 575

Lys Met Ser Ile Gly Leu Cys Cys Ile Ile Ala Ala Ser Leu Leu Trp
            580                 585                 590

Met Ala Glu Ile Gln Pro His Trp Ile Ala Ala Ser Ile Ile Leu Glu
        595                 600                 605

Phe Phe Leu Met Val Leu Leu Ile Pro Glu Pro Glu Lys Gln Arg Thr
    610                 615                 620

Pro Gln Asp Asn Gln Leu Ala Tyr Val Val Ile Gly Ile Leu Thr Leu
625                 630                 635                 640

Ala Ala Ala Ile Ala Ala Asn Glu Met Gly Leu Leu Glu Thr Thr Lys
                645                 650                 655

Lys Asp Leu Gly Ile Gly Ala Ile Leu Asp Val Asp Leu His Pro Ala
            660                 665                 670

Ser Ala Trp Thr Leu Tyr Ala Val Ala Thr Thr Ile Ile Thr Pro Met
        675                 680                 685

Leu Arg His Thr Ile Glu Asn Ser Thr Ala Asn Val Ser Leu Thr Ala
    690                 695                 700

Ile Ala Asn Gln Ala Ala Val Leu Met Gly Leu Asp Lys Gly Trp Pro
705                 710                 715                 720

Ile Ser Lys Met Asp Leu Gly Val Pro Leu Leu Ala Leu Gly Cys Tyr
                725                 730                 735

Ser Gln Val Asn Pro Leu Thr Leu Thr His Tyr Ala Ile Ile Gly Pro
            740                 745                 750

Gly Leu Gln Ala Lys Ala Thr Arg Glu Ala Gln Lys Arg Thr Ala Ala
        755                 760                 765

Gly Ile Met Lys Asn Pro Thr Val Asp Gly Ile Met Ala Ile Asp Leu
    770                 775                 780

Asp Pro Ile Pro Tyr Asp Pro Lys Phe Glu Lys Gln Leu Gly Gln Val
785                 790                 795                 800

Met Leu Leu Ile Leu Cys Ser Gln Ile Leu Leu Met Arg Thr Thr Trp
                805                 810                 815

Ala Leu Cys Glu Ala Leu Thr Leu Ala Thr Gly Pro Ile Thr Thr Leu
            820                 825                 830

Trp Glu Gly Asn Pro Gly Lys Phe Trp Asn Thr Thr Ile Ala Val Ser
        835                 840                 845

Met Ala Asn Ile Phe Arg Gly Ser Tyr Leu Ala Gly Ala Gly Leu Ala
    850                 855                 860

Phe Ser Leu Ile Lys Asn Gly Glu Thr Leu Gly Glu Lys Trp Lys Arg
865                 870                 875                 880

Gln Leu Asn Gln Leu Asp Lys Ser Phe Glu Glu Tyr Lys Lys Ser Gly
                885                 890                 895

Ile Leu Glu Val Asp Arg Thr Glu Ala Lys Glu Ala Ile Met Val Val
            900                 905                 910
```

-continued

```
Ile Asp Leu Gly Cys Gly Arg Gly Gly Trp Ser Tyr Tyr Cys Ala Gly
        915                 920                 925

Leu Lys Lys Val Arg Gly Tyr Thr Lys Gly Gly Pro Gly His Glu Glu
    930                 935                 940

Pro Ile Pro Met Ala Thr Tyr Gly Trp Asn Leu Val Lys Leu His Ser
945                 950                 955                 960

Gly Val Asp Val Phe Phe Glu Lys Cys Asp Thr Leu Leu Cys Asp Ile
                965                 970                 975

Gly Glu Ser Ser Pro Asn Pro Thr Ile Glu Glu Gly Arg Thr Leu Arg
            980                 985                 990

Val Leu Lys Met Val Glu Pro Trp  Leu Lys Gly Asn Gln  Phe Cys Ile
        995                 1000                1005

Lys Ile  Leu Asn Pro Tyr Met  Pro Ser Val Ile Glu  Leu Glu Lys
    1010                 1015                 1020

Leu Gln  Arg Lys His Gly Gly  Met Leu Val Arg Asn  Pro Leu Ser
    1025                 1030                 1035

Arg Asn  Ser Thr His Glu Met  Tyr Trp Val Ser Asn  Gly Thr Gly
    1040                 1045                 1050

Asn Ile  Val Ser Ala Val Asn  Met Ile Ser Arg Met  Leu Ile Asn
    1055                 1060                 1065

Arg Phe  Thr Met Ala His Lys  Asp Glu Asp Asn Pro  Tyr Lys Thr
    1070                 1075                 1080

Trp Ala  Tyr His Gly Ser Tyr  Glu Val Lys Ala Thr  Gly Ser Ala
    1085                 1090                 1095

Ser Ser  Met Val Asn Gly Val  Val Lys Leu Leu Thr  Lys Pro Trp
    1100                 1105                 1110

Asp Val  Val Pro Met Val Thr  Gln Met Ala Met Thr  Asp Thr Thr
    1115                 1120                 1125

Pro Phe  Gly Gln Gln Arg Val  Phe Lys Glu Lys Val  Asp Thr Arg
    1130                 1135                 1140

Thr Pro  Glu Ala Gln Asp Glu  Asn Gly Trp Lys Ser  Ala Leu His
    1145                 1150                 1155

Leu Glu  Gly Lys Cys Glu Ser  Cys Val Tyr Asn Met  Met Gly Lys
    1160                 1165                 1170

Arg Glu  Lys Lys Leu Gly Glu  Phe Gly Lys Ala Lys  Gly Ser Arg
    1175                 1180                 1185

Ala Ile  Trp Tyr Met Trp Leu  Gly Ala Arg Phe Leu  Glu Phe Glu
    1190                 1195                 1200

Ala Leu  Gly Phe Leu Asn Glu  Asp His Trp Phe Ser  Arg Glu Asn
    1205                 1210                 1215

Ser Leu  Ser Gly Val Glu Gly  Glu Gly Leu Leu Gly  Tyr Ile Leu
    1220                 1225                 1230

Arg Asp  Ile Ser Lys Ile Pro  Gly Gly Ala Met Tyr  Ala Asp Asp
    1235                 1240                 1245

Thr Ala  Gly Trp Asp Thr Arg  Ile Thr Glu Asp Asp  Leu His Asn
    1250                 1255                 1260

Glu Glu  Lys Leu Ala Lys Ala  Ile Phe Lys Leu Thr  Tyr Gln Asn
    1265                 1270                 1275

Lys Val  Val Lys Val Gln Arg  Pro Thr Pro Arg Gly  Ala Val Met
    1280                 1285                 1290

Asp Ile  Ile Ser Arg Lys Asp  Gln Arg Gly Ser Gly  Gln Val Gly
    1295                 1300                 1305
```

Thr Tyr Gly Leu Asn Thr Phe Thr Asn Met Glu Ala Gln Leu Ile
1310 1315 1320

Arg Gln Met Glu Ala Glu Gln Trp Glu Pro Ser Lys Gly Trp His
1325 1330 1335

Asp Trp Gln Gln Val Pro Phe Cys Ser His His Phe His Ile Phe
1340 1345 1350

Met Lys Asp Gly Arg Lys Leu Val Val Pro Cys Arg Asn Gln Asp
1355 1360 1365

Glu Leu Ile Gly Arg Ala Arg Ile Ser Gln Gly Ala Gly Trp Ser
1370 1375 1380

Leu Arg Glu Thr Ala Cys Leu Gly Lys Ser Tyr Ala Gln Met Trp
1385 1390 1395

Gln Leu Met Tyr Phe His Arg Arg Asp Leu Arg Leu Ala Ser Asn
1400 1405 1410

Ala Ile Cys Ser Ala Val Pro Ser His Trp Val Pro Ser Arg Thr
1415 1420 1425

Thr Trp Ser His Glu Trp Met Thr Thr Glu Asp Met Leu Ala Val
1430 1435 1440

Trp Asn Arg Val Trp His Ser Trp Glu Asp Val Pro Tyr Leu Gly
1445 1450 1455

Lys Arg Glu Asp Gln Trp Cys Gly Ser Leu Ile Gly Leu Thr Ser
1460 1465 1470

Arg Ala Thr Trp Ala Lys Asn Ile
1475 1480

<210> SEQ ID NO 24
<211> LENGTH: 78
<212> TYPE: PRT
<213> ORGANISM: Dengue virus

<400> SEQUENCE: 24

Ser Gln Ile Gly Ala Gly Val Phe Lys Glu Gly Val Phe His Thr Met
1 5 10 15

Trp His Val Thr Arg Gly Ala Val Leu Met His Gln Gly Lys Arg Ile
20 25 30

Glu Pro Ser Trp Ala Asp Val Lys Lys Asp Leu Ile Ser Tyr Gly Gly
35 40 45

Gly Trp Arg Leu Glu Gly Glu Trp Asp Glu Gly Glu Glu Val Gln Val
50 55 60

Ile Ala Val Glu Pro Gly Lys Asn Pro Lys Ala Val Gln Thr
65 70 75

<210> SEQ ID NO 25
<211> LENGTH: 24
<212> TYPE: PRT
<213> ORGANISM: Dengue virus

<400> SEQUENCE: 25

Gly Glu Ile Gly Ala Ile Ala Leu Asp Phe Lys Pro Gly Thr Ser Gly
1 5 10 15

Ser Pro Ile Val Asn Arg Glu Gly
20

<210> SEQ ID NO 26
<211> LENGTH: 22
<212> TYPE: PRT
<213> ORGANISM: Dengue virus

<400> SEQUENCE: 26

Val Gly Leu Tyr Gly Asn Gly Val Val Thr Lys Ser Gly Ala Tyr Val
1 5 10 15

Ser Ala Ile Ala Gln Thr
20

<210> SEQ ID NO 27
<211> LENGTH: 404
<212> TYPE: PRT
<213> ORGANISM: Dengue virus

<400> SEQUENCE: 27

Phe Arg Lys Arg Asn Leu Thr Ile Met Asp Leu His Pro Gly Ala Gly
1 5 10 15

Lys Thr Lys Arg Tyr Leu Pro Ala Ile Val Arg Glu Ala Ile Lys Arg
20 25 30

Arg Leu Arg Thr Leu Ile Leu Ala Pro Thr Arg Val Val Ala Ala Glu
35 40 45

Met Glu Glu Ala Leu Lys Gly Leu Pro Ile Arg Tyr Gln Thr Thr Ala
50 55 60

Ile Lys Ala Glu His Thr Gly Lys Glu Ile Val Asp Leu Met Cys His
65 70 75 80

Ala Thr Phe Thr Met Arg Leu Leu Ser Pro Val Arg Val Pro Asn Tyr
85 90 95

Asn Leu Ile Ile Met Asp Glu Ala His Phe Thr Asp Pro Ala Ser Ile
100 105 110

Ala Ala Arg Gly Tyr Ile Ser Thr Arg Val Glu Met Gly Glu Ala Ala
115 120 125

Ala Ile Phe Met Thr Ala Thr Pro Pro Gly Ser Ala Asp Ala Phe Pro
130 135 140

Gln Ser Asn Ala Pro Ile Glu Asp Glu Glu Arg Glu Ile Pro Glu Arg
145 150 155 160

Ser Trp Asn Ser Gly Phe Asp Trp Ile Thr Asp Phe Ala Gly Lys Thr
165 170 175

Val Trp Phe Val Pro Ser Ile Lys Ala Gly Asn Asp Ile Ala Asn Cys
180 185 190

Leu Arg Lys Asn Gly Lys Lys Val Ile Gln Leu Ser Arg Lys Thr Phe
195 200 205

Asp Thr Glu Tyr Pro Lys Thr Lys Leu Asn Asp Trp Asp Phe Val Val
210 215 220

Thr Thr Asp Ile Ser Glu Met Gly Ala Asn Phe Lys Ala Asp Arg Val
225 230 235 240

Ile Asp Pro Arg Arg Cys Leu Lys Pro Val Ile Leu Thr Asp Gly Pro
245 250 255

Glu Arg Val Ile Leu Ala Gly Pro Met Pro Val Thr Ala Ala Ser Ala
260 265 270

Ala Gln Arg Arg Gly Arg Ile Gly Arg Asn His Lys Lys Glu Asn Asp
275 280 285

Gln Tyr Ile Tyr Met Gly Gln Pro Leu Asn Asn Asp Glu Asp His Ala
290 295 300

His Trp Thr Glu Ala Lys Met Leu Leu Asp Asn Ile Asn Thr Pro Glu
305 310 315 320

Gly Ile Ile Pro Ala Leu Phe Glu Pro Glu Arg Glu Lys Ser Ala Ala
325 330 335

-continued

```
Ile Asp Gly Glu Tyr Arg Leu Arg Gly Glu Ala Arg Lys Thr Phe Val
            340                 345                 350

Glu Leu Met Arg Arg Gly Asp Leu Pro Val Trp Leu Ser Tyr Lys Val
        355                 360                 365

Ala Ser Ala Gly Phe Gln Tyr Lys Asp Arg Glu Trp Cys Phe Asp Gly
    370                 375                 380

Glu Arg Asn Asn Gln Ile Leu Glu Glu Asn Met Asp Val Glu Ile Trp
385                 390                 395                 400

Thr Glu Gly Glu


<210> SEQ ID NO 28
<211> LENGTH: 17
<212> TYPE: PRT
<213> ORGANISM: Dengue virus

<400> SEQUENCE: 28

Lys Lys Lys Leu Arg Pro Arg Trp Leu Asp Ala Arg Thr Tyr Ala Asp
1               5                   10                  15

Pro


<210> SEQ ID NO 29
<211> LENGTH: 20
<212> TYPE: PRT
<213> ORGANISM: Dengue virus

<400> SEQUENCE: 29

His Ala Leu Glu Glu Leu Pro Glu Thr Leu Glu Thr Leu Leu Leu Leu
1               5                   10                  15

Ala Leu Leu Gly
            20


<210> SEQ ID NO 30
<211> LENGTH: 24
<212> TYPE: PRT
<213> ORGANISM: Dengue virus

<400> SEQUENCE: 30

Phe Leu Phe Phe Leu Ser Gly Lys Gly Ile Gly Lys Met Ser Ile Gly
1               5                   10                  15

Leu Cys Cys Ile Ile Ala Ala Ser
            20


<210> SEQ ID NO 31
<211> LENGTH: 73
<212> TYPE: PRT
<213> ORGANISM: Dengue virus

<400> SEQUENCE: 31

Leu Leu Trp Met Ala Glu Ile Gln Pro His Trp Ile Ala Ala Ser Ile
1               5                   10                  15

Ile Leu Glu Phe Phe Leu Met Val Leu Leu Ile Pro Glu Pro Glu Lys
            20                  25                  30

Gln Arg Thr Pro Gln Asp Asn Gln Leu Ala Tyr Val Val Ile Gly Ile
        35                  40                  45

Leu Thr Leu Ala Ala Ala Ile Ala Ala Asn Glu Met Gly Leu Leu Glu
    50                  55                  60

Thr Thr Lys Lys Asp Leu Gly Ile Gly
65                  70
```

<210> SEQ ID NO 32
<211> LENGTH: 83
<212> TYPE: PRT
<213> ORGANISM: Dengue virus

<400> SEQUENCE: 32

```
Ala Ile Leu Asp Val Asp Leu His Pro Ala Ser Ala Trp Thr Leu Tyr
1               5                   10                  15

Ala Val Ala Thr Thr Ile Ile Thr Pro Met Leu Arg His Thr Ile Glu
            20                  25                  30

Asn Ser Thr Ala Asn Val Ser Leu Thr Ala Ile Ala Asn Gln Ala Ala
        35                  40                  45

Val Leu Met Gly Leu Asp Lys Gly Trp Pro Ile Ser Lys Met Asp Leu
    50                  55                  60

Gly Val Pro Leu Leu Ala Leu Gly Cys Tyr Ser Gln Val Asn Pro Leu
65                  70                  75                  80

Thr Leu Thr
```

<210> SEQ ID NO 33
<211> LENGTH: 61
<212> TYPE: PRT
<213> ORGANISM: Dengue virus

<400> SEQUENCE: 33

```
His Tyr Ala Ile Ile Gly Pro Gly Leu Gln Ala Lys Ala Thr Arg Glu
1               5                   10                  15

Ala Gln Lys Arg Thr Ala Ala Gly Ile Met Lys Asn Pro Thr Val Asp
            20                  25                  30

Gly Ile Met Ala Ile Asp Leu Asp Pro Ile Pro Tyr Asp Pro Lys Phe
        35                  40                  45

Glu Lys Gln Leu Gly Gln Val Met Leu Leu Ile Leu Cys
    50                  55                  60
```

<210> SEQ ID NO 34
<211> LENGTH: 64
<212> TYPE: PRT
<213> ORGANISM: Dengue virus

<400> SEQUENCE: 34

```
Ser Gln Ile Leu Leu Met Arg Thr Thr Trp Ala Leu Cys Glu Ala Leu
1               5                   10                  15

Thr Leu Ala Thr Gly Pro Ile Thr Thr Leu Trp Glu Gly Asn Pro Gly
            20                  25                  30

Lys Phe Trp Asn Thr Thr Ile Ala Val Ser Met Ala Asn Ile Phe Arg
        35                  40                  45

Gly Ser Tyr Leu Ala Gly Ala Gly Leu Ala Phe Ser Leu Ile Lys Asn
    50                  55                  60
```

<210> SEQ ID NO 35
<211> LENGTH: 18
<212> TYPE: PRT
<213> ORGANISM: Dengue virus

<400> SEQUENCE: 35

```
Gly Glu Thr Leu Gly Glu Lys Trp Lys Arg Gln Leu Asn Gln Leu Asp
1               5                   10                  15

Lys Ser
```

<210> SEQ ID NO 36

<211> LENGTH: 23
<212> TYPE: PRT
<213> ORGANISM: Dengue virus

<400> SEQUENCE: 36

Phe Glu Glu Tyr Lys Lys Ser Gly Ile Leu Glu Val Asp Arg Thr Glu
1               5                   10                  15

Ala Lys Glu Ala Ile Met Val
            20

<210> SEQ ID NO 37
<211> LENGTH: 22
<212> TYPE: PRT
<213> ORGANISM: Dengue virus

<400> SEQUENCE: 37

Val Ile Asp Leu Gly Cys Gly Arg Gly Gly Trp Ser Tyr Tyr Cys Ala
1               5                   10                  15

Gly Leu Lys Lys Val Arg
            20

<210> SEQ ID NO 38
<211> LENGTH: 33
<212> TYPE: PRT
<213> ORGANISM: Dengue virus

<400> SEQUENCE: 38

Gly Tyr Thr Lys Gly Gly Pro Gly His Glu Glu Pro Ile Pro Met Ala
1               5                   10                  15

Thr Tyr Gly Trp Asn Leu Val Lys Leu His Ser Gly Val Asp Val Phe
            20                  25                  30

Phe

<210> SEQ ID NO 39
<211> LENGTH: 37
<212> TYPE: PRT
<213> ORGANISM: Dengue virus

<400> SEQUENCE: 39

Glu Lys Cys Asp Thr Leu Leu Cys Asp Ile Gly Glu Ser Ser Pro Asn
1               5                   10                  15

Pro Thr Ile Glu Glu Gly Arg Thr Leu Arg Val Leu Lys Met Val Glu
            20                  25                  30

Pro Trp Leu Lys Gly
        35

<210> SEQ ID NO 40
<211> LENGTH: 17
<212> TYPE: PRT
<213> ORGANISM: Dengue virus

<400> SEQUENCE: 40

Asn Gln Phe Cys Ile Lys Ile Leu Asn Pro Tyr Met Pro Ser Val Ile
1               5                   10                  15

Glu

<210> SEQ ID NO 41
<211> LENGTH: 55
<212> TYPE: PRT
<213> ORGANISM: Dengue virus

<400> SEQUENCE: 41

-continued

```
Leu Glu Lys Leu Gln Arg Lys His Gly Gly Met Leu Val Arg Asn Pro
1               5                   10                  15

Leu Ser Arg Asn Ser Thr His Glu Met Tyr Trp Val Ser Asn Gly Thr
            20                  25                  30

Gly Asn Ile Val Ser Ala Val Asn Met Ile Ser Arg Met Leu Ile Asn
        35                  40                  45

Arg Phe Thr Met Ala His Lys
    50                  55


<210> SEQ ID NO 42
<211> LENGTH: 72
<212> TYPE: PRT
<213> ORGANISM: Dengue virus

<400> SEQUENCE: 42

Asp Glu Asp Asn Pro Tyr Lys Thr Trp Ala Tyr His Gly Ser Tyr Glu
1               5                   10                  15

Val Lys Ala Thr Gly Ser Ala Ser Ser Met Val Asn Gly Val Val Lys
            20                  25                  30

Leu Leu Thr Lys Pro Trp Asp Val Val Pro Met Val Thr Gln Met Ala
        35                  40                  45

Met Thr Asp Thr Thr Pro Phe Gly Gln Gln Arg Val Phe Lys Glu Lys
    50                  55                  60

Val Asp Thr Arg Thr Pro Glu Ala
65                  70


<210> SEQ ID NO 43
<211> LENGTH: 9
<212> TYPE: PRT
<213> ORGANISM: Dengue virus

<400> SEQUENCE: 43

Gln Asp Glu Asn Gly Trp Lys Ser Ala
1               5


<210> SEQ ID NO 44
<211> LENGTH: 72
<212> TYPE: PRT
<213> ORGANISM: Dengue virus

<400> SEQUENCE: 44

Leu His Leu Glu Gly Lys Cys Glu Ser Cys Val Tyr Asn Met Met Gly
1               5                   10                  15

Lys Arg Glu Lys Lys Leu Gly Glu Phe Gly Lys Ala Lys Gly Ser Arg
            20                  25                  30

Ala Ile Trp Tyr Met Trp Leu Gly Ala Arg Phe Leu Glu Phe Glu Ala
        35                  40                  45

Leu Gly Phe Leu Asn Glu Asp His Trp Phe Ser Arg Glu Asn Ser Leu
    50                  55                  60

Ser Gly Val Glu Gly Glu Gly Leu
65                  70


<210> SEQ ID NO 45
<211> LENGTH: 38
<212> TYPE: PRT
<213> ORGANISM: Dengue virus

<400> SEQUENCE: 45

Leu Gly Tyr Ile Leu Arg Asp Ile Ser Lys Ile Pro Gly Gly Ala Met
```

```
1               5                   10                  15

Tyr Ala Asp Asp Thr Ala Gly Trp Asp Thr Arg Ile Thr Glu Asp Asp
            20                  25                  30

Leu His Asn Glu Glu Lys
        35


<210> SEQ ID NO 46
<211> LENGTH: 49
<212> TYPE: PRT
<213> ORGANISM: Dengue virus

<400> SEQUENCE: 46

Leu Ala Lys Ala Ile Phe Lys Leu Thr Tyr Gln Asn Lys Val Val Lys
1               5                   10                  15

Val Gln Arg Pro Thr Pro Arg Gly Ala Val Met Asp Ile Ile Ser Arg
            20                  25                  30

Lys Asp Gln Arg Gly Ser Gly Gln Val Gly Thr Tyr Gly Leu Asn Thr
        35                  40                  45

Phe


<210> SEQ ID NO 47
<211> LENGTH: 14
<212> TYPE: PRT
<213> ORGANISM: Dengue virus

<400> SEQUENCE: 47

Thr Asn Met Glu Ala Gln Leu Ile Arg Gln Met Glu Ala Glu
1               5                   10


<210> SEQ ID NO 48
<211> LENGTH: 22
<212> TYPE: PRT
<213> ORGANISM: Dengue virus

<400> SEQUENCE: 48

Gln Trp Glu Pro Ser Lys Gly Trp His Asp Trp Gln Gln Val Pro Phe
1               5                   10                  15

Cys Ser His His Phe His
            20


<210> SEQ ID NO 49
<211> LENGTH: 74
<212> TYPE: PRT
<213> ORGANISM: Dengue virus

<400> SEQUENCE: 49

Ile Phe Met Lys Asp Gly Arg Lys Leu Val Val Pro Cys Arg Asn Gln
1               5                   10                  15

Asp Glu Leu Ile Gly Arg Ala Arg Ile Ser Gln Gly Ala Gly Trp Ser
            20                  25                  30

Leu Arg Glu Thr Ala Cys Leu Gly Lys Ser Tyr Ala Gln Met Trp Gln
        35                  40                  45

Leu Met Tyr Phe His Arg Arg Asp Leu Arg Leu Ala Ser Asn Ala Ile
    50                  55                  60

Cys Ser Ala Val Pro Ser His Trp Val Pro
65                  70


<210> SEQ ID NO 50
<211> LENGTH: 6
<212> TYPE: PRT
```

<213> ORGANISM: Dengue virus

<400> SEQUENCE: 50

Ser Arg Thr Thr Trp Ser
1               5

<210> SEQ ID NO 51
<211> LENGTH: 17
<212> TYPE: PRT
<213> ORGANISM: Dengue virus

<400> SEQUENCE: 51

His Glu Trp Met Thr Thr Glu Asp Met Leu Ala Val Trp Asn Arg Val
1               5                   10                  15

Trp

<210> SEQ ID NO 52
<211> LENGTH: 33
<212> TYPE: PRT
<213> ORGANISM: Dengue virus

<400> SEQUENCE: 52

His Ser Trp Glu Asp Val Pro Tyr Leu Gly Lys Arg Glu Asp Gln Trp
1               5                   10                  15

Cys Gly Ser Leu Ile Gly Leu Thr Ser Arg Ala Thr Trp Ala Lys Asn
            20                  25                  30

Ile

<210> SEQ ID NO 53
<211> LENGTH: 1683
<212> TYPE: PRT
<213> ORGANISM: Artificial Sequence
<220> FEATURE:
<223> OTHER INFORMATION: Fusion protein

<400> SEQUENCE: 53

Ser Gln Ile Gly Ala Gly Val Phe Lys Glu Gly Val Phe His Thr Met
1               5                   10                  15

Trp His Val Thr Arg Gly Ala Val Leu Met His Gln Gly Lys Arg Ile
            20                  25                  30

Glu Pro Ser Trp Ala Asp Val Lys Lys Asp Leu Ile Ser Tyr Gly Gly
        35                  40                  45

Gly Trp Arg Leu Glu Gly Glu Trp Asp Glu Gly Glu Glu Val Gln Val
    50                  55                  60

Ile Ala Val Glu Pro Gly Lys Asn Pro Lys Ala Val Gln Thr Lys Pro
65                  70                  75                  80

Gly Leu Phe Lys Thr Pro Glu Gly Glu Ile Gly Ala Ile Ala Leu Asp
                85                  90                  95

Phe Lys Pro Gly Thr Ser Gly Ser Pro Ile Val Asn Arg Glu Gly Lys
            100                 105                 110

Val Val Gly Leu Tyr Gly Asn Gly Val Val Thr Lys Ser Gly Ala Tyr
        115                 120                 125

Val Ser Ala Ile Ala Gln Thr Asn Ala Glu Pro Leu Pro Glu Ile Glu
    130                 135                 140

Asp Glu Val Phe Arg Lys Arg Asn Leu Thr Ile Met Asp Leu His Pro
145                 150                 155                 160

Gly Ala Gly Lys Thr Lys Arg Tyr Leu Pro Ala Ile Val Arg Glu Ala
                165                 170                 175

```
Ile Lys Arg Arg Leu Arg Thr Leu Ile Leu Ala Pro Thr Arg Val Val
            180                 185                 190

Ala Ala Glu Met Glu Glu Ala Leu Lys Gly Leu Pro Ile Arg Tyr Gln
        195                 200                 205

Thr Thr Ala Ile Lys Ala Glu His Thr Gly Lys Glu Ile Val Asp Leu
    210                 215                 220

Met Cys His Ala Thr Phe Thr Met Arg Leu Leu Ser Pro Val Arg Val
225                 230                 235                 240

Pro Asn Tyr Asn Leu Ile Ile Met Asp Glu Ala His Phe Thr Asp Pro
                245                 250                 255

Ala Ser Ile Ala Ala Arg Gly Tyr Ile Ser Thr Arg Val Glu Met Gly
            260                 265                 270

Glu Ala Ala Ala Ile Phe Met Thr Ala Thr Pro Pro Gly Ser Ala Asp
        275                 280                 285

Ala Phe Pro Gln Ser Asn Ala Pro Ile Glu Asp Glu Glu Arg Glu Ile
    290                 295                 300

Pro Glu Arg Ser Trp Asn Ser Gly Phe Asp Trp Ile Thr Asp Phe Ala
305                 310                 315                 320

Gly Lys Thr Val Trp Phe Val Pro Ser Ile Lys Ala Gly Asn Asp Ile
                325                 330                 335

Ala Asn Cys Leu Arg Lys Asn Gly Lys Lys Val Ile Gln Leu Ser Arg
            340                 345                 350

Lys Thr Phe Asp Thr Glu Tyr Pro Lys Thr Lys Leu Asn Asp Trp Asp
        355                 360                 365

Phe Val Val Thr Thr Asp Ile Ser Glu Met Gly Ala Asn Phe Lys Ala
    370                 375                 380

Asp Arg Val Ile Asp Pro Arg Arg Cys Leu Lys Pro Val Ile Leu Thr
385                 390                 395                 400

Asp Gly Pro Glu Arg Val Ile Leu Ala Gly Pro Met Pro Val Thr Ala
                405                 410                 415

Ala Ser Ala Ala Gln Arg Arg Gly Arg Ile Gly Arg Asn His Lys Lys
            420                 425                 430

Glu Asn Asp Gln Tyr Ile Tyr Met Gly Gln Pro Leu Asn Asn Asp Glu
        435                 440                 445

Asp His Ala His Trp Thr Glu Ala Lys Met Leu Leu Asp Asn Ile Asn
    450                 455                 460

Thr Pro Glu Gly Ile Ile Pro Ala Leu Phe Glu Pro Glu Arg Glu Lys
465                 470                 475                 480

Ser Ala Ala Ile Asp Gly Glu Tyr Arg Leu Arg Gly Glu Ala Arg Lys
                485                 490                 495

Thr Phe Val Glu Leu Met Arg Arg Gly Asp Leu Pro Val Trp Leu Ser
            500                 505                 510

Tyr Lys Val Ala Ser Ala Gly Phe Gln Tyr Lys Asp Arg Glu Trp Cys
        515                 520                 525

Phe Asp Gly Glu Arg Asn Asn Gln Ile Leu Glu Glu Asn Met Asp Val
    530                 535                 540

Glu Ile Trp Thr Lys Glu Gly Glu Lys Lys Lys Leu Arg Pro Arg Trp
545                 550                 555                 560

Leu Asp Ala Arg Thr Tyr Ala Asp Pro Leu Ala Leu Lys Glu Phe Lys
                565                 570                 575

Asp Phe Ala Ala Gly Arg Lys Ser Ile Ala Thr Glu Ile Gly Arg Val
            580                 585                 590

Pro Ser His Leu Ala His Arg Thr Arg Ala Tyr Gln His Ala Leu Glu
```

-continued

```
        595                 600                 605

Glu Leu Pro Glu Thr Leu Glu Thr Leu Leu Leu Leu Ala Leu Leu Gly
    610                 615                 620

Ala Phe Leu Phe Phe Leu Ser Gly Lys Gly Ile Gly Lys Met Ser Ile
625                 630                 635                 640

Gly Leu Cys Cys Ile Ile Ala Ala Ser Leu Leu Trp Met Ala Glu Ile
                645                 650                 655

Gln Pro His Trp Ile Ala Ala Ser Ile Ile Leu Glu Phe Phe Leu Met
            660                 665                 670

Val Leu Leu Ile Pro Glu Pro Glu Lys Gln Arg Thr Pro Gln Asp Asn
        675                 680                 685

Gln Leu Ala Tyr Val Val Ile Gly Ile Leu Thr Leu Ala Ala Ala Ile
    690                 695                 700

Ala Ala Asn Glu Met Gly Leu Leu Glu Thr Thr Lys Lys Asp Leu Gly
705                 710                 715                 720

Ile Gly His Val Ala Pro Thr Ala Ile Leu Asp Val Asp Leu His Pro
                725                 730                 735

Ala Ser Ala Trp Thr Leu Tyr Ala Val Ala Thr Thr Ile Ile Thr Pro
            740                 745                 750

Met Leu Arg His Thr Ile Glu Asn Ser Thr Ala Asn Val Ser Leu Thr
        755                 760                 765

Ala Ile Ala Asn Gln Ala Ala Val Leu Met Gly Leu Asp Lys Gly Trp
    770                 775                 780

Pro Ile Ser Lys Met Asp Leu Gly Val Pro Leu Leu Ala Leu Gly Cys
785                 790                 795                 800

Tyr Ser Gln Val Asn Pro Leu Thr Leu Thr Ala Ala Val Leu Leu Leu
                805                 810                 815

Ile Thr His Tyr Ala Ile Ile Gly Pro Gly Leu Gln Ala Lys Ala Thr
            820                 825                 830

Arg Glu Ala Gln Lys Arg Thr Ala Ala Gly Ile Met Lys Asn Pro Thr
        835                 840                 845

Val Asp Gly Ile Met Ala Ile Asp Leu Asp Pro Ile Pro Tyr Asp Pro
    850                 855                 860

Lys Phe Glu Lys Gln Leu Gly Gln Val Met Leu Leu Ile Leu Cys Val
865                 870                 875                 880

Ser Gln Ile Leu Leu Met Arg Thr Thr Trp Ala Leu Cys Glu Ala Leu
                885                 890                 895

Thr Leu Ala Thr Gly Pro Ile Thr Thr Leu Trp Glu Gly Asn Pro Gly
            900                 905                 910

Lys Phe Trp Asn Thr Thr Ile Ala Val Ser Met Ala Asn Ile Phe Arg
        915                 920                 925

Gly Ser Tyr Leu Ala Gly Ala Gly Leu Ala Phe Ser Leu Ile Lys Asn
    930                 935                 940

Arg Arg Gly Thr Gly Ala Gln Gly Glu Thr Leu Gly Glu Lys Trp Lys
945                 950                 955                 960

Arg Gln Leu Asn Gln Leu Asp Lys Ser Glu Phe Glu Glu Tyr Lys Lys
                965                 970                 975

Ser Gly Ile Leu Glu Val Asp Arg Thr Glu Ala Lys Glu Ala Ile Lys
            980                 985                 990

Arg Gly Glu Thr Asp His His Ala  Val Ser Arg Gly Ser  Ala Lys Leu
        995                 1000                1005

Arg Trp  Phe Val Glu Arg Asn  Met Val Ile Pro Glu  Gly Arg Val
    1010                1015                1020
```

```
Ile Asp  Leu Gly Cys Gly Arg  Gly Gly Trp Ser Tyr  Tyr Cys Ala
    1025                 1030                 1035

Gly Leu  Lys Lys Val Arg Glu  Val Arg Gly Tyr Thr  Lys Gly Gly
    1040                 1045                 1050

Pro Gly  His Glu Glu Pro Ile  Pro Met Ala Thr Tyr  Gly Trp Asn
    1055                 1060                 1065

Leu Val  Lys Leu His Ser Gly  Val Asp Val Phe Phe  Pro Glu Lys
    1070                 1075                 1080

Cys Asp  Thr Leu Leu Cys Asp  Ile Gly Glu Ser Ser  Pro Asn Pro
    1085                 1090                 1095

Thr Ile  Glu Glu Gly Arg Thr  Leu Arg Val Leu Lys  Met Val Glu
    1100                 1105                 1110

Pro Trp  Leu Lys Gly Asn Gln  Phe Cys Ile Lys Ile  Leu Asn Pro
    1115                 1120                 1125

Tyr Met  Pro Ser Val Ile Glu  Glu Leu Glu Lys Leu  Gln Arg Lys
    1130                 1135                 1140

His Gly  Gly Met Leu Val Arg  Asn Pro Leu Ser Arg  Asn Ser Thr
    1145                 1150                 1155

His Glu  Met Tyr Trp Val Ser  Asn Gly Thr Gly Asn  Ile Val Ser
    1160                 1165                 1170

Ala Val  Asn Met Ile Ser Arg  Met Leu Ile Asn Arg  Phe Thr Met
    1175                 1180                 1185

Ala His  Lys Lys Pro Thr Tyr  Glu Arg Asp Val Asp  Leu Gly Ala
    1190                 1195                 1200

Gly Ser  Thr Trp His Tyr Asp  Glu Asp Asn Pro Tyr  Lys Thr Trp
    1205                 1210                 1215

Ala Tyr  His Gly Ser Tyr Glu  Val Lys Ala Thr Gly  Ser Ala Ser
    1220                 1225                 1230

Ser Met  Val Asn Gly Val Val  Lys Leu Leu Thr Lys  Pro Trp Asp
    1235                 1240                 1245

Val Val  Pro Met Val Thr Gln  Met Ala Met Thr Asp  Thr Thr Pro
    1250                 1255                 1260

Phe Gly  Gln Gln Arg Val Phe  Lys Glu Lys Val Asp  Thr Arg Thr
    1265                 1270                 1275

Pro Glu  Ala Lys Glu Asn Ala  Ala Ile Gly Ala Val  Phe Gln Asp
    1280                 1285                 1290

Glu Asn  Gly Trp Lys Ser Ala  Arg Glu Ala Val Glu  Asp Ser Glu
    1295                 1300                 1305

Arg Ala  Leu His Leu Glu Gly  Lys Cys Glu Ser Cys  Val Tyr Asn
    1310                 1315                 1320

Met Met  Gly Lys Arg Glu Lys  Lys Leu Gly Glu Phe  Gly Lys Ala
    1325                 1330                 1335

Lys Gly  Ser Arg Ala Ile Trp  Tyr Met Trp Leu Gly  Ala Arg Phe
    1340                 1345                 1350

Leu Glu  Phe Glu Ala Leu Gly  Phe Leu Asn Glu Asp  His Trp Phe
    1355                 1360                 1365

Ser Arg  Glu Asn Ser Leu Ser  Gly Val Glu Gly Glu  Gly Leu His
    1370                 1375                 1380

Lys Leu  Gly Tyr Ile Leu Arg  Asp Ile Ser Lys Ile  Pro Gly Gly
    1385                 1390                 1395

Ala Met  Tyr Ala Asp Asp Thr  Ala Gly Trp Asp Thr  Arg Ile Thr
    1400                 1405                 1410
```

-continued

```
Glu Asp  Asp Leu His Asn Glu  Glu Lys Ile Leu Ala  Lys Ala Ile
    1415                1420                1425

Phe Lys  Leu Thr Tyr Gln Asn  Lys Val Val Lys Val  Gln Arg Pro
    1430                1435                1440

Thr Pro  Arg Gly Ala Val Met  Asp Ile Ile Ser Arg  Lys Asp Gln
    1445                1450                1455

Arg Gly  Ser Gly Gln Val Gly  Thr Tyr Gly Leu Asn  Thr Phe Thr
    1460                1465                1470

Asn Met  Glu Ala Gln Leu Ile  Arg Gln Met Glu Ala  Glu Gly Val
    1475                1480                1485

Ile Thr  Glu Cys Gly Val Asp  Arg Leu Lys Arg Met  Ala Ile Ser
    1490                1495                1500

Gly Asp  Asp Cys Val Val Lys  Pro Pro Gln Trp Glu  Pro Ser Lys
    1505                1510                1515

Gly Trp  His Asp Trp Gln Gln  Val Pro Phe Cys Ser  His His Phe
    1520                1525                1530

His Glu  Ile Phe Met Lys Asp  Gly Arg Lys Leu Val  Val Pro Cys
    1535                1540                1545

Arg Asn  Gln Asp Glu Leu Ile  Gly Arg Ala Arg Ile  Ser Gln Gly
    1550                1555                1560

Ala Gly  Trp Ser Leu Arg Glu  Thr Ala Cys Leu Gly  Lys Ser Tyr
    1565                1570                1575

Ala Gln  Met Trp Gln Leu Met  Tyr Phe His Arg Arg  Asp Leu Arg
    1580                1585                1590

Leu Ala  Ser Asn Ala Ile Cys  Ser Ala Val Pro Ser  His Trp Val
    1595                1600                1605

Pro Thr  Ser Arg Thr Thr Trp  Ser Ile His Ala His  His Glu Trp
    1610                1615                1620

Met Thr  Thr Glu Asp Met Leu  Ala Val Trp Asn Arg  Val Trp Ile
    1625                1630                1635

Glu Glu  Asn Pro Trp Met Glu  Asp Lys Thr His Ile  His Ser Trp
    1640                1645                1650

Glu Asp  Val Pro Tyr Leu Gly  Lys Arg Glu Asp Gln  Trp Cys Gly
    1655                1660                1665

Ser Leu  Ile Gly Leu Thr Ser  Arg Ala Thr Trp Ala  Lys Asn Ile
    1670                1675                1680


<210> SEQ ID NO 54
<211> LENGTH: 138
<212> TYPE: PRT
<213> ORGANISM: Dengue virus

<400> SEQUENCE: 54

Ser Gln Ile Gly Ala Gly Val Phe Lys Glu Gly Val Phe His Thr Met
1               5                   10                  15

Trp His Val Thr Arg Gly Ala Val Leu Met His Gln Gly Lys Arg Ile
            20                  25                  30

Glu Pro Ser Trp Ala Asp Val Lys Lys Asp Leu Ile Ser Tyr Gly Gly
        35                  40                  45

Gly Trp Arg Leu Glu Gly Glu Trp Asp Glu Gly Glu Glu Val Gln Val
    50                  55                  60

Ile Ala Val Glu Pro Gly Lys Asn Pro Lys Ala Val Gln Thr Lys Pro
65                  70                  75                  80

Gly Leu Phe Lys Thr Pro Glu Gly Glu Ile Gly Ala Ile Ala Leu Asp
                85                  90                  95
```

```
Phe Lys Pro Gly Thr Ser Gly Ser Pro Ile Val Asn Arg Glu Gly Lys
            100                 105                 110

Val Val Gly Leu Tyr Gly Asn Gly Val Val Thr Lys Ser Gly Ala Tyr
        115                 120                 125

Val Ser Ala Ile Ala Gln Thr Asn Ala Glu
    130                 135


<210> SEQ ID NO 55
<211> LENGTH: 414
<212> TYPE: PRT
<213> ORGANISM: Dengue virus

<400> SEQUENCE: 55

Pro Leu Pro Glu Ile Glu Asp Glu Val Phe Arg Lys Arg Asn Leu Thr
1               5                   10                  15

Ile Met Asp Leu His Pro Gly Ala Gly Lys Thr Lys Arg Tyr Leu Pro
            20                  25                  30

Ala Ile Val Arg Glu Ala Ile Lys Arg Arg Leu Arg Thr Leu Ile Leu
        35                  40                  45

Ala Pro Thr Arg Val Val Ala Ala Glu Met Glu Glu Ala Leu Lys Gly
    50                  55                  60

Leu Pro Ile Arg Tyr Gln Thr Thr Ala Ile Lys Ala Glu His Thr Gly
65                  70                  75                  80

Lys Glu Ile Val Asp Leu Met Cys His Ala Thr Phe Thr Met Arg Leu
                85                  90                  95

Leu Ser Pro Val Arg Val Pro Asn Tyr Asn Leu Ile Ile Met Asp Glu
            100                 105                 110

Ala His Phe Thr Asp Pro Ala Ser Ile Ala Ala Arg Gly Tyr Ile Ser
        115                 120                 125

Thr Arg Val Glu Met Gly Glu Ala Ala Ala Ile Phe Met Thr Ala Thr
    130                 135                 140

Pro Pro Gly Ser Ala Asp Ala Phe Pro Gln Ser Asn Ala Pro Ile Glu
145                 150                 155                 160

Asp Glu Glu Arg Glu Ile Pro Glu Arg Ser Trp Asn Ser Gly Phe Asp
                165                 170                 175

Trp Ile Thr Asp Phe Ala Gly Lys Thr Val Trp Phe Val Pro Ser Ile
            180                 185                 190

Lys Ala Gly Asn Asp Ile Ala Asn Cys Leu Arg Lys Asn Gly Lys Lys
        195                 200                 205

Val Ile Gln Leu Ser Arg Lys Thr Phe Asp Thr Glu Tyr Pro Lys Thr
    210                 215                 220

Lys Leu Asn Asp Trp Asp Phe Val Val Thr Thr Asp Ile Ser Glu Met
225                 230                 235                 240

Gly Ala Asn Phe Lys Ala Asp Arg Val Ile Asp Pro Arg Arg Cys Leu
                245                 250                 255

Lys Pro Val Ile Leu Thr Asp Gly Pro Glu Arg Val Ile Leu Ala Gly
            260                 265                 270

Pro Met Pro Val Thr Ala Ala Ser Ala Ala Gln Arg Arg Gly Arg Ile
        275                 280                 285

Gly Arg Asn His Lys Lys Glu Asn Asp Gln Tyr Ile Tyr Met Gly Gln
    290                 295                 300

Pro Leu Asn Asn Asp Glu Asp His Ala His Trp Thr Glu Ala Lys Met
305                 310                 315                 320

Leu Leu Asp Asn Ile Asn Thr Pro Glu Gly Ile Ile Pro Ala Leu Phe
```

```
                325                 330                 335

Glu Pro Glu Arg Glu Lys Ser Ala Ala Ile Asp Gly Glu Tyr Arg Leu
            340                 345                 350

Arg Gly Glu Ala Arg Lys Thr Phe Val Glu Leu Met Arg Arg Gly Asp
        355                 360                 365

Leu Pro Val Trp Leu Ser Tyr Lys Val Ala Ser Ala Gly Phe Gln Tyr
    370                 375                 380

Lys Asp Arg Glu Trp Cys Phe Asp Gly Glu Arg Asn Asn Gln Ile Leu
385                 390                 395                 400

Glu Glu Asn Met Asp Val Glu Ile Trp Thr Lys Glu Gly Glu
                405                 410


<210> SEQ ID NO 56
<211> LENGTH: 34
<212> TYPE: PRT
<213> ORGANISM: Dengue virus

<400> SEQUENCE: 56

Lys Lys Lys Leu Arg Pro Arg Trp Leu Asp Ala Arg Thr Tyr Ala Asp
1               5                   10                  15

Pro Leu Ala Leu Lys Glu Phe Lys Asp Phe Ala Ala Gly Arg Lys Ser
            20                  25                  30

Ile Ala


<210> SEQ ID NO 57
<211> LENGTH: 15
<212> TYPE: PRT
<213> ORGANISM: Dengue virus

<400> SEQUENCE: 57

Thr Glu Ile Gly Arg Val Pro Ser His Leu Ala His Arg Thr Arg
1               5                   10                  15


<210> SEQ ID NO 58
<211> LENGTH: 24
<212> TYPE: PRT
<213> ORGANISM: Dengue virus

<400> SEQUENCE: 58

Ala Tyr Gln His Ala Leu Glu Glu Leu Pro Glu Thr Leu Glu Thr Leu
1               5                   10                  15

Leu Leu Leu Ala Leu Leu Gly Ala
            20


<210> SEQ ID NO 59
<211> LENGTH: 24
<212> TYPE: PRT
<213> ORGANISM: Dengue virus

<400> SEQUENCE: 59

Phe Leu Phe Phe Leu Ser Gly Lys Gly Ile Gly Lys Met Ser Ile Gly
1               5                   10                  15

Leu Cys Cys Ile Ile Ala Ala Ser
            20


<210> SEQ ID NO 60
<211> LENGTH: 76
<212> TYPE: PRT
<213> ORGANISM: Dengue virus

<400> SEQUENCE: 60
```

```
Leu Leu Trp Met Ala Glu Ile Gln Pro His Trp Ile Ala Ala Ser Ile
1               5                   10                  15

Ile Leu Glu Phe Phe Leu Met Val Leu Leu Ile Pro Glu Pro Glu Lys
            20                  25                  30

Gln Arg Thr Pro Gln Asp Asn Gln Leu Ala Tyr Val Val Ile Gly Ile
        35                  40                  45

Leu Thr Leu Ala Ala Ala Ile Ala Ala Asn Glu Met Gly Leu Leu Glu
    50                  55                  60

Thr Thr Lys Lys Asp Leu Gly Ile Gly His Val Ala
65                  70                  75


<210> SEQ ID NO 61
<211> LENGTH: 219
<212> TYPE: PRT
<213> ORGANISM: Dengue virus

<400> SEQUENCE: 61

Pro Thr Ala Ile Leu Asp Val Asp Leu His Pro Ala Ser Ala Trp Thr
1               5                   10                  15

Leu Tyr Ala Val Ala Thr Thr Ile Ile Thr Pro Met Leu Arg His Thr
            20                  25                  30

Ile Glu Asn Ser Thr Ala Asn Val Ser Leu Thr Ala Ile Ala Asn Gln
        35                  40                  45

Ala Ala Val Leu Met Gly Leu Asp Lys Gly Trp Pro Ile Ser Lys Met
    50                  55                  60

Asp Leu Gly Val Pro Leu Leu Ala Leu Gly Cys Tyr Ser Gln Val Asn
65                  70                  75                  80

Pro Leu Thr Leu Thr Ala Ala Val Leu Leu Leu Ile Thr His Tyr Ala
                85                  90                  95

Ile Ile Gly Pro Gly Leu Gln Ala Lys Ala Thr Arg Glu Ala Gln Lys
            100                 105                 110

Arg Thr Ala Ala Gly Ile Met Lys Asn Pro Thr Val Asp Gly Ile Met
        115                 120                 125

Ala Ile Asp Leu Asp Pro Ile Pro Tyr Asp Pro Lys Phe Glu Lys Gln
    130                 135                 140

Leu Gly Gln Val Met Leu Leu Ile Leu Cys Val Ser Gln Ile Leu Leu
145                 150                 155                 160

Met Arg Thr Thr Trp Ala Leu Cys Glu Ala Leu Thr Leu Ala Thr Gly
                165                 170                 175

Pro Ile Thr Thr Leu Trp Glu Gly Asn Pro Gly Lys Phe Trp Asn Thr
            180                 185                 190

Thr Ile Ala Val Ser Met Ala Asn Ile Phe Arg Gly Ser Tyr Leu Ala
        195                 200                 205

Gly Ala Gly Leu Ala Phe Ser Leu Ile Lys Asn
    210                 215


<210> SEQ ID NO 62
<211> LENGTH: 136
<212> TYPE: PRT
<213> ORGANISM: Dengue virus

<400> SEQUENCE: 62

Arg Arg Gly Thr Gly Ala Gln Gly Glu Thr Leu Gly Glu Lys Trp Lys
1               5                   10                  15

Arg Gln Leu Asn Gln Leu Asp Lys Ser Glu Phe Glu Glu Tyr Lys Lys
            20                  25                  30
```

```
Ser Gly Ile Leu Glu Val Asp Arg Thr Glu Ala Lys Glu Ala Ile Lys
        35                  40                  45

Arg Gly Glu Thr Asp His His Ala Val Ser Arg Gly Ser Ala Lys Leu
    50                  55                  60

Arg Trp Phe Val Glu Arg Asn Met Val Ile Pro Glu Gly Arg Val Ile
65                  70                  75                  80

Asp Leu Gly Cys Gly Arg Gly Gly Trp Ser Tyr Tyr Cys Ala Gly Leu
                85                  90                  95

Lys Lys Val Arg Glu Val Arg Gly Tyr Thr Lys Gly Gly Pro Gly His
            100                 105                 110

Glu Glu Pro Ile Pro Met Ala Thr Tyr Gly Trp Asn Leu Val Lys Leu
        115                 120                 125

His Ser Gly Val Asp Val Phe Phe
    130                 135


<210> SEQ ID NO 63
<211> LENGTH: 38
<212> TYPE: PRT
<213> ORGANISM: Dengue virus

<400> SEQUENCE: 63

Pro Glu Lys Cys Asp Thr Leu Leu Cys Asp Ile Gly Glu Ser Ser Pro
1               5                   10                  15

Asn Pro Thr Ile Glu Glu Gly Arg Thr Leu Arg Val Leu Lys Met Val
            20                  25                  30

Glu Pro Trp Leu Lys Gly
        35


<210> SEQ ID NO 64
<211> LENGTH: 86
<212> TYPE: PRT
<213> ORGANISM: Dengue virus

<400> SEQUENCE: 64

Asn Gln Phe Cys Ile Lys Ile Leu Asn Pro Tyr Met Pro Ser Val Ile
1               5                   10                  15

Glu Glu Leu Glu Lys Leu Gln Arg Lys His Gly Gly Met Leu Val Arg
            20                  25                  30

Asn Pro Leu Ser Arg Asn Ser Thr His Glu Met Tyr Trp Val Ser Asn
        35                  40                  45

Gly Thr Gly Asn Ile Val Ser Ala Val Asn Met Ile Ser Arg Met Leu
    50                  55                  60

Ile Asn Arg Phe Thr Met Ala His Lys Lys Pro Thr Tyr Glu Arg Asp
65                  70                  75                  80

Val Asp Leu Gly Ala Gly
                85


<210> SEQ ID NO 65
<211> LENGTH: 79
<212> TYPE: PRT
<213> ORGANISM: Dengue virus

<400> SEQUENCE: 65

Ser Thr Trp His Tyr Asp Glu Asp Asn Pro Tyr Lys Thr Trp Ala Tyr
1               5                   10                  15

His Gly Ser Tyr Glu Val Lys Ala Thr Gly Ser Ala Ser Ser Met Val
            20                  25                  30
```

```
Asn Gly Val Val Lys Leu Leu Thr Lys Pro Trp Asp Val Val Pro Met
        35                  40                  45

Val Thr Gln Met Ala Met Thr Asp Thr Thr Pro Phe Gly Gln Gln Arg
    50                  55                  60

Val Phe Lys Glu Lys Val Asp Thr Arg Thr Pro Glu Ala Lys Glu
65                  70                  75


<210> SEQ ID NO 66
<211> LENGTH: 24
<212> TYPE: PRT
<213> ORGANISM: Dengue virus

<400> SEQUENCE: 66

Asn Ala Ala Ile Gly Ala Val Phe Gln Asp Glu Asn Gly Trp Lys Ser
1               5                   10                  15

Ala Arg Glu Ala Val Glu Asp Ser
            20


<210> SEQ ID NO 67
<211> LENGTH: 116
<212> TYPE: PRT
<213> ORGANISM: Dengue virus

<400> SEQUENCE: 67

Glu Arg Ala Leu His Leu Glu Gly Lys Cys Glu Ser Cys Val Tyr Asn
1               5                   10                  15

Met Met Gly Lys Arg Glu Lys Lys Leu Gly Glu Phe Gly Lys Ala Lys
            20                  25                  30

Gly Ser Arg Ala Ile Trp Tyr Met Trp Leu Gly Ala Arg Phe Leu Glu
        35                  40                  45

Phe Glu Ala Leu Gly Phe Leu Asn Glu Asp His Trp Phe Ser Arg Glu
    50                  55                  60

Asn Ser Leu Ser Gly Val Glu Gly Glu Gly Leu His Lys Leu Gly Tyr
65                  70                  75                  80

Ile Leu Arg Asp Ile Ser Lys Ile Pro Gly Gly Ala Met Tyr Ala Asp
                85                  90                  95

Asp Thr Ala Gly Trp Asp Thr Arg Ile Thr Glu Asp Asp Leu His Asn
            100                 105                 110

Glu Glu Lys Ile
        115


<210> SEQ ID NO 68
<211> LENGTH: 49
<212> TYPE: PRT
<213> ORGANISM: Dengue virus

<400> SEQUENCE: 68

Leu Ala Lys Ala Ile Phe Lys Leu Thr Tyr Gln Asn Lys Val Val Lys
1               5                   10                  15

Val Gln Arg Pro Thr Pro Arg Gly Ala Val Met Asp Ile Ile Ser Arg
            20                  25                  30

Lys Asp Gln Arg Gly Ser Gly Gln Val Gly Thr Tyr Gly Leu Asn Thr
        35                  40                  45

Phe


<210> SEQ ID NO 69
<211> LENGTH: 18
<212> TYPE: PRT
<213> ORGANISM: Dengue virus
```

<400> SEQUENCE: 69

Thr Asn Met Glu Ala Gln Leu Ile Arg Gln Met Glu Ala Glu Gly Val
1 5 10 15

Ile Thr

<210> SEQ ID NO 70
<211> LENGTH: 21
<212> TYPE: PRT
<213> ORGANISM: Dengue virus

<400> SEQUENCE: 70

Glu Cys Gly Val Asp Arg Leu Lys Arg Met Ala Ile Ser Gly Asp Asp
1 5 10 15

Cys Val Val Lys Pro
20

<210> SEQ ID NO 71
<211> LENGTH: 172
<212> TYPE: PRT
<213> ORGANISM: Dengue virus

<400> SEQUENCE: 71

Pro Gln Trp Glu Pro Ser Lys Gly Trp His Asp Trp Gln Gln Val Pro
1 5 10 15

Phe Cys Ser His His Phe His Glu Ile Phe Met Lys Asp Gly Arg Lys
20 25 30

Leu Val Val Pro Cys Arg Asn Gln Asp Glu Leu Ile Gly Arg Ala Arg
35 40 45

Ile Ser Gln Gly Ala Gly Trp Ser Leu Arg Glu Thr Ala Cys Leu Gly
50 55 60

Lys Ser Tyr Ala Gln Met Trp Gln Leu Met Tyr Phe His Arg Arg Asp
65 70 75 80

Leu Arg Leu Ala Ser Asn Ala Ile Cys Ser Ala Val Pro Ser His Trp
85 90 95

Val Pro Thr Ser Arg Thr Thr Trp Ser Ile His Ala His His Glu Trp
100 105 110

Met Thr Thr Glu Asp Met Leu Ala Val Trp Asn Arg Val Trp Ile Glu
115 120 125

Glu Asn Pro Trp Met Glu Asp Lys Thr His Ile His Ser Trp Glu Asp
130 135 140

Val Pro Tyr Leu Gly Lys Arg Glu Asp Gln Trp Cys Gly Ser Leu Ile
145 150 155 160

Gly Leu Thr Ser Arg Ala Thr Trp Ala Lys Asn Ile
165 170

<210> SEQ ID NO 72
<211> LENGTH: 1789
<212> TYPE: PRT
<213> ORGANISM: Artificial Sequence
<220> FEATURE:
<223> OTHER INFORMATION: Fusion protein

<400> SEQUENCE: 72

Ser Gln Ile Gly Ala Gly Val Phe Lys Glu Gly Val Phe His Thr Met
1 5 10 15

Trp His Val Thr Arg Gly Ala Val Leu Met His Gln Gly Lys Arg Ile
20 25 30

```
Glu Pro Ser Trp Ala Asp Val Lys Lys Asp Leu Ile Ser Tyr Ser Val
        35                  40                  45

Lys Lys Asp Leu Ile Ser Tyr Gly Gly Gly Trp Arg Leu Glu Gly Glu
    50                  55                  60

Trp Asp Glu Gly Glu Glu Val Gln Val Ile Ala Val Glu Pro Gly Lys
65                  70                  75                  80

Asn Pro Lys Ala Val Gln Thr Lys Pro Gly Leu Phe Lys Thr Pro Glu
                85                  90                  95

Gly Glu Ile Gly Ala Ile Ala Leu Asp Phe Lys Pro Gly Thr Ser Gly
            100                 105                 110

Ser Pro Ile Val Asn Arg Glu Gly Thr Ser Gly Ser Pro Ile Ile Asn
        115                 120                 125

Arg Glu Gly Lys Val Val Gly Leu Tyr Gly Asn Gly Val Val Thr Lys
    130                 135                 140

Ser Gly Ala Tyr Val Ser Ala Ile Ala Gln Thr Asn Ala Glu Pro Leu
145                 150                 155                 160

Pro Glu Ile Glu Asp Glu Val Phe Arg Lys Arg Asn Leu Thr Ile Met
                165                 170                 175

Asp Leu His Pro Gly Ala Gly Lys Thr Lys Arg Tyr Leu Pro Ala Ile
            180                 185                 190

Val Arg Glu Ala Ile Lys Arg Arg Leu Arg Thr Leu Ile Leu Ala Pro
        195                 200                 205

Thr Arg Val Val Ala Ala Glu Met Ala Pro Thr Arg Val Val Ala Ser
    210                 215                 220

Glu Met Glu Glu Ala Leu Lys Gly Leu Pro Ile Arg Tyr Ala Leu Arg
225                 230                 235                 240

Gly Leu Pro Ile Arg Tyr Gln Thr Thr Ala Ile Lys Ala Glu His Thr
                245                 250                 255

Gly Lys Glu Ile Val Asp Leu Met Cys His Ala Thr Phe Thr Met Arg
            260                 265                 270

Leu Leu Ser Pro Val Arg Val Pro Asn Tyr Asn Leu Ile Ile Met Asp
        275                 280                 285

Glu Ala His Phe Thr Asp Pro Ala Ser Ile Ala Ala Arg Gly Tyr Ile
    290                 295                 300

Ser Thr Arg Val Glu Met Gly Glu Ala Ala Ala Ile Phe Met Thr Ala
305                 310                 315                 320

Thr Pro Pro Gly Ser Ala Asp Ala Phe Pro Gln Ser Asn Ala Pro Ile
                325                 330                 335

Glu Asp Glu Glu Arg Glu Ile Pro Glu Arg Ser Trp Asn Ser Gly Phe
            340                 345                 350

Asp Trp Ile Thr Asp Phe Ala Gly Lys Thr Val Trp Phe Val Pro Ser
        355                 360                 365

Ile Lys Ala Gly Asn Asp Ile Ala Asn Cys Leu Arg Lys Asn Gly Lys
    370                 375                 380

Lys Val Ile Gln Leu Ser Arg Lys Thr Phe Asp Thr Glu Tyr Pro Lys
385                 390                 395                 400

Thr Lys Leu Asn Asp Trp Asp Phe Val Val Thr Thr Asp Ile Ser Glu
                405                 410                 415

Met Gly Ala Asn Phe Lys Ala Asp Arg Val Ile Asp Pro Arg Arg Cys
            420                 425                 430

Leu Lys Pro Val Ile Leu Thr Asp Gly Pro Glu Arg Val Ile Leu Ala
        435                 440                 445

Gly Pro Met Pro Val Thr Ala Ala Ser Ala Ala Gln Arg Arg Gly Arg
```

-continued

```
    450                 455                 460

Ile Gly Arg Asn His Lys Lys Glu Asn Asp Gln Tyr Ile Tyr Met Gly
465                 470                 475                 480

Gln Pro Leu Asn Asn Asp Glu Asp His Ala His Trp Thr Glu Ala Lys
                485                 490                 495

Met Leu Leu Asp Asn Ile Asn Thr Pro Glu Gly Ile Ile Pro Ala Leu
            500                 505                 510

Phe Thr Pro Glu Gly Ile Ile Pro Ser Met Phe Thr Pro Glu Gly Ile
        515                 520                 525

Ile Pro Thr Leu Phe Thr Pro Glu Gly Ile Ile Pro Ser Leu Glu Pro
    530                 535                 540

Glu Arg Glu Lys Ser Ala Ala Ile Asp Gly Glu Tyr Arg Leu Arg Gly
545                 550                 555                 560

Glu Ala Arg Lys Thr Phe Val Glu Leu Gly Glu Ala Arg Lys Thr Phe
                565                 570                 575

Val Asp Leu Gly Glu Gln Arg Lys Thr Phe Val Glu Leu Met Arg Arg
            580                 585                 590

Gly Asp Leu Pro Val Trp Leu Ser Tyr Lys Val Ala Ser Ala Gly Phe
        595                 600                 605

Gln Tyr Lys Asp Arg Glu Trp Cys Phe Asp Gly Glu Arg Asn Asn Gln
    610                 615                 620

Ile Leu Glu Glu Asn Met Asp Val Glu Ile Trp Thr Lys Glu Gly Glu
625                 630                 635                 640

Lys Lys Lys Leu Arg Pro Arg Trp Leu Asp Ala Arg Thr Tyr Ala Asp
                645                 650                 655

Pro Leu Ala Leu Lys Glu Phe Lys Asp Phe Ala Ala Gly Arg Lys Ser
            660                 665                 670

Ile Ala Thr Glu Ile Gly Arg Val Pro Ser His Leu Ala His Arg Thr
        675                 680                 685

Arg Ala Tyr Gln His Ala Leu Glu Glu Leu Pro Glu Thr Leu Glu Thr
    690                 695                 700

Leu Leu Leu Leu Ala Leu Leu Gly Ala Phe Leu Phe Phe Leu Ser Gly
705                 710                 715                 720

Lys Gly Ile Gly Lys Met Ser Ile Gly Leu Cys Cys Ile Ile Ala Ala
                725                 730                 735

Ser Leu Leu Trp Met Ala Glu Ile Gln Pro His Trp Ile Ala Ala Ser
            740                 745                 750

Ile Ile Leu Glu Phe Phe Leu Met Val Leu Leu Ile Pro Glu Pro Glu
        755                 760                 765

Lys Gln Arg Thr Pro Gln Asp Asn Gln Leu Ala Tyr Val Val Ile Gly
    770                 775                 780

Ile Leu Thr Leu Ala Ala Ala Ile Ala Ala Asn Glu Met Gly Leu Leu
785                 790                 795                 800

Glu Thr Thr Lys Lys Asp Leu Gly Ile Gly His Val Ala Pro Thr Ala
                805                 810                 815

Ile Leu Asp Val Asp Leu His Pro Ala Ser Ala Trp Thr Leu Tyr Ala
            820                 825                 830

Val Ala Thr Thr Ile Ile Thr Pro Met Leu Arg His Thr Ile Glu Asn
        835                 840                 845

Ser Thr Ala Asn Val Ser Leu Thr Ala Ile Ala Asn Gln Ala Ala Val
    850                 855                 860

Leu Met Ile Ala Asn Gln Ala Thr Val Leu Met Gly Leu Asp Lys Gly
865                 870                 875                 880
```

```
Trp Pro Ile Ser Lys Met Asp Leu Gly Val Pro Leu Leu Ala Leu Gly
                885                 890                 895

Cys Tyr Ser Gln Val Asn Pro Leu Thr Leu Thr Ala Ala Val Leu Leu
            900                 905                 910

Leu Ile Thr His Tyr Ala Ile Ile Gly Pro Gly Leu Gln Ala Lys Ala
        915                 920                 925

Thr Arg Glu Ala Gln Lys Arg Thr Ala Ala Gly Ile Met Lys Asn Pro
    930                 935                 940

Thr Val Asp Gly Ile Met Ala Ile Asp Leu Asp Pro Ile Pro Tyr Asp
945                 950                 955                 960

Pro Lys Phe Glu Lys Gln Leu Gly Gln Val Met Leu Leu Ile Leu Cys
                965                 970                 975

Val Ser Gln Ile Leu Leu Met Arg Thr Thr Trp Ala Val Leu Leu Met
            980                 985                 990

Arg Thr Thr Trp Ala Leu Cys Glu  Ala Leu Thr Leu Ala  Thr Gly Pro
        995                 1000                1005

Ile Thr  Thr Leu Trp Glu Gly  Asn Pro Gly Lys Phe  Trp Asn Thr
    1010                 1015                1020

Thr Ile  Ala Val Ser Met Ala  Asn Ile Phe Arg Gly  Ser Tyr Leu
    1025                 1030                1035

Ala Gly  Ala Gly Leu Ala Phe  Ser Leu Ile Lys Asn  Arg Arg Gly
    1040                 1045                1050

Thr Gly  Ala Gln Gly Glu Thr  Leu Gly Glu Lys Trp  Lys Arg Gln
    1055                 1060                1065

Leu Asn  Gln Leu Asp Lys Ser  Glu Phe Glu Glu Tyr  Lys Lys Ser
    1070                 1075                1080

Gly Ile  Leu Glu Val Asp Arg  Thr Glu Ala Lys Glu  Ala Ile Lys
    1085                 1090                1095

Arg Gly  Glu Thr Asp His His  Ala Val Ser Arg Gly  Ser Ala Lys
    1100                 1105                1110

Leu Arg  Trp Phe Val Glu Arg  Asn Met Val Ile Pro  Glu Gly Arg
    1115                 1120                1125

Val Ile  Asp Leu Gly Cys Gly  Arg Gly Gly Trp Ser  Tyr Tyr Cys
    1130                 1135                1140

Ala Gly  Leu Lys Lys Val Arg  Glu Val Arg Gly Tyr  Thr Lys Gly
    1145                 1150                1155

Gly Pro  Gly His Glu Glu Pro  Ile Pro Met Ala Thr  Tyr Gly Trp
    1160                 1165                1170

Asn Leu  Val Lys Leu His Ser  Gly Val Asp Val Phe  Phe Pro Glu
    1175                 1180                1185

Lys Cys  Asp Thr Leu Leu Cys  Asp Ile Gly Glu Ser  Ser Pro Asn
    1190                 1195                1200

Pro Thr  Ile Glu Glu Gly Arg  Thr Leu Arg Val Leu  Lys Met Val
    1205                 1210                1215

Glu Pro  Trp Leu Lys Gly Asn  Gln Phe Cys Ile Lys  Ile Leu Asn
    1220                 1225                1230

Pro Tyr  Met Pro Ser Val Ile  Glu Glu Leu Glu Lys  Leu Gln Arg
    1235                 1240                1245

Lys His  Gly Gly Met Leu Val  Arg Asn Pro Leu Ser  Arg Asn Ser
    1250                 1255                1260

Thr His  Glu Met Tyr Trp Val  Ser Asn Gly Thr Gly  Asn Ile Val
    1265                 1270                1275
```

```
Ser Ala  Val Asn Met Ile Ser  Arg Met Leu Ile Asn  Arg Phe Thr
    1280                 1285                 1290

Met Ala  His Lys Lys Pro Thr  Tyr Glu Arg Asp Val  Asp Leu Gly
    1295                 1300                 1305

Ala Gly  Ser Thr Trp His Tyr  Asp Glu Asp Asn Pro  Tyr Lys Thr
    1310                 1315                 1320

Trp Ala  Tyr His Gly Ser Tyr  Glu Val Lys Ala Thr  Gly Ser Ala
    1325                 1330                 1335

Ser Ser  Met Val Asn Gly Val  Val Lys Leu Leu Thr  Lys Pro Trp
    1340                 1345                 1350

Asp Val  Val Pro Met Val Thr  Gln Met Ala Met Thr  Asp Thr Thr
    1355                 1360                 1365

Pro Phe  Gly Gln Gln Arg Val  Phe Lys Glu Lys Val  Asp Thr Arg
    1370                 1375                 1380

Thr Pro  Glu Ala Lys Glu Asn  Ala Ala Ile Gly Ala  Val Phe Gln
    1385                 1390                 1395

Asp Glu  Asn Gly Trp Lys Ser  Ala Arg Glu Ala Val  Glu Asp Ser
    1400                 1405                 1410

Glu Arg  Ala Leu His Leu Glu  Gly Lys Cys Glu Ser  Cys Val Tyr
    1415                 1420                 1425

Asn Met  Met Gly Lys Arg Glu  Lys Lys Leu Gly Glu  Phe Gly Lys
    1430                 1435                 1440

Ala Lys  Gly Ser Arg Ala Ile  Trp Tyr Met Trp Leu  Gly Ala Arg
    1445                 1450                 1455

Phe Leu  Glu Phe Glu Ala Leu  Gly Phe Leu Asn Glu  Asp His Trp
    1460                 1465                 1470

Phe Ser  Arg Glu Asn Ser Leu  Ser Gly Val Glu Gly  Glu Gly Leu
    1475                 1480                 1485

His Lys  Leu Gly Tyr Ile Leu  Arg Asp Ile Ser Lys  Ile Pro Gly
    1490                 1495                 1500

Gly Ala  Met Tyr Ala Asp Asp  Thr Ala Gly Trp Asp  Thr Arg Ile
    1505                 1510                 1515

Thr Glu  Asp Asp Leu His Asn  Glu Glu Lys Ile Leu  Ala Lys Ala
    1520                 1525                 1530

Ile Phe  Lys Leu Thr Tyr Gln  Asn Lys Val Val Lys  Val Gln Arg
    1535                 1540                 1545

Pro Thr  Pro Arg Gly Ala Val  Met Asp Ile Ile Ser  Arg Lys Asp
    1550                 1555                 1560

Gln Arg  Gly Ser Gly Gln Val  Gly Thr Tyr Gly Leu  Asn Thr Phe
    1565                 1570                 1575

Thr Asn  Met Glu Ala Gln Leu  Ile Arg Gln Met Glu  Ala Glu Gly
    1580                 1585                 1590

Val Ile  Thr Glu Cys Gly Val  Asp Arg Leu Lys Arg  Met Ala Ile
    1595                 1600                 1605

Ser Gly  Asp Asp Cys Val Val  Lys Pro Pro Gln Trp  Glu Pro Ser
    1610                 1615                 1620

Lys Gly  Trp His Asp Trp Gln  Gln Val Pro Phe Cys  Ser His His
    1625                 1630                 1635

Phe His  Glu Ile Phe Met Lys  Asp Gly Arg Lys Leu  Val Val Pro
    1640                 1645                 1650

Cys Arg  Asn Gln Asp Glu Leu  Ile Gly Arg Ala Arg  Ile Ser Gln
    1655                 1660                 1665

Gly Ala  Gly Trp Ser Leu Arg  Glu Thr Ala Cys Leu  Gly Lys Ser
```

1670 1675 1680

Tyr Ala Gln Met Trp Gln Leu Met Tyr Phe His Arg Arg Asp Leu
1685 1690 1695

Arg Leu Ala Ser Asn Ala Ile Cys Ser Ala Val Pro Ser His Trp
1700 1705 1710

Val Pro Thr Ser Arg Thr Thr Trp Ser Ile His Ala His His Glu
1715 1720 1725

Trp Met Thr Thr Glu Asp Met Leu Ala Val Trp Asn Arg Val Trp
1730 1735 1740

Ile Glu Glu Asn Pro Trp Met Glu Asp Lys Thr His Ile His Ser
1745 1750 1755

Trp Glu Asp Val Pro Tyr Leu Gly Lys Arg Glu Asp Gln Trp Cys
1760 1765 1770

Gly Ser Leu Ile Gly Leu Thr Ser Arg Ala Thr Trp Ala Lys Asn
1775 1780 1785

Ile

<210> SEQ ID NO 73
<211> LENGTH: 158
<212> TYPE: PRT
<213> ORGANISM: Dengue virus

<400> SEQUENCE: 73

Ser Gln Ile Gly Ala Gly Val Phe Lys Glu Gly Val Phe His Thr Met
1 5 10 15

Trp His Val Thr Arg Gly Ala Val Leu Met His Gln Gly Lys Arg Ile
20 25 30

Glu Pro Ser Trp Ala Asp Val Lys Lys Asp Leu Ile Ser Tyr Ser Val
35 40 45

Lys Lys Asp Leu Ile Ser Tyr Gly Gly Gly Trp Arg Leu Glu Gly Glu
50 55 60

Trp Asp Glu Gly Glu Glu Val Gln Val Ile Ala Val Glu Pro Gly Lys
65 70 75 80

Asn Pro Lys Ala Val Gln Thr Lys Pro Gly Leu Phe Lys Thr Pro Glu
85 90 95

Gly Glu Ile Gly Ala Ile Ala Leu Asp Phe Lys Pro Gly Thr Ser Gly
100 105 110

Ser Pro Ile Val Asn Arg Glu Gly Thr Ser Gly Ser Pro Ile Ile Asn
115 120 125

Arg Glu Gly Lys Val Val Gly Leu Tyr Gly Asn Gly Val Val Thr Lys
130 135 140

Ser Gly Ala Tyr Val Ser Ala Ile Ala Gln Thr Asn Ala Glu
145 150 155

<210> SEQ ID NO 74
<211> LENGTH: 482
<212> TYPE: PRT
<213> ORGANISM: Dengue virus

<400> SEQUENCE: 74

Pro Leu Pro Glu Ile Glu Asp Glu Val Phe Arg Lys Arg Asn Leu Thr
1 5 10 15

Ile Met Asp Leu His Pro Gly Ala Gly Lys Thr Lys Arg Tyr Leu Pro
20 25 30

Ala Ile Val Arg Glu Ala Ile Lys Arg Arg Leu Arg Thr Leu Ile Leu
35 40 45

```
Ala Pro Thr Arg Val Val Ala Ala Glu Met Ala Pro Thr Arg Val Val
    50                  55                  60

Ala Ser Glu Met Glu Glu Ala Leu Lys Gly Leu Pro Ile Arg Tyr Ala
65                  70                  75                  80

Leu Arg Gly Leu Pro Ile Arg Tyr Gln Thr Thr Ala Ile Lys Ala Glu
                85                  90                  95

His Thr Gly Lys Glu Ile Val Asp Leu Met Cys His Ala Thr Phe Thr
            100                 105                 110

Met Arg Leu Leu Ser Pro Val Arg Val Pro Asn Tyr Asn Leu Ile Ile
        115                 120                 125

Met Asp Glu Ala His Phe Thr Asp Pro Ala Ser Ile Ala Ala Arg Gly
    130                 135                 140

Tyr Ile Ser Thr Arg Val Glu Met Gly Glu Ala Ala Ala Ile Phe Met
145                 150                 155                 160

Thr Ala Thr Pro Pro Gly Ser Ala Asp Ala Phe Pro Gln Ser Asn Ala
                165                 170                 175

Pro Ile Glu Asp Glu Glu Arg Glu Ile Pro Glu Arg Ser Trp Asn Ser
            180                 185                 190

Gly Phe Asp Trp Ile Thr Asp Phe Ala Gly Lys Thr Val Trp Phe Val
        195                 200                 205

Pro Ser Ile Lys Ala Gly Asn Asp Ile Ala Asn Cys Leu Arg Lys Asn
    210                 215                 220

Gly Lys Lys Val Ile Gln Leu Ser Arg Lys Thr Phe Asp Thr Glu Tyr
225                 230                 235                 240

Pro Lys Thr Lys Leu Asn Asp Trp Asp Phe Val Val Thr Thr Asp Ile
                245                 250                 255

Ser Glu Met Gly Ala Asn Phe Lys Ala Asp Arg Val Ile Asp Pro Arg
            260                 265                 270

Arg Cys Leu Lys Pro Val Ile Leu Thr Asp Gly Pro Glu Arg Val Ile
        275                 280                 285

Leu Ala Gly Pro Met Pro Val Thr Ala Ala Ser Ala Ala Gln Arg Arg
    290                 295                 300

Gly Arg Ile Gly Arg Asn His Lys Lys Glu Asn Asp Gln Tyr Ile Tyr
305                 310                 315                 320

Met Gly Gln Pro Leu Asn Asn Asp Glu Asp His Ala His Trp Thr Glu
                325                 330                 335

Ala Lys Met Leu Leu Asp Asn Ile Asn Thr Pro Glu Gly Ile Ile Pro
            340                 345                 350

Ala Leu Phe Thr Pro Glu Gly Ile Ile Pro Ser Met Phe Thr Pro Glu
        355                 360                 365

Gly Ile Ile Pro Thr Leu Phe Thr Pro Glu Gly Ile Ile Pro Ser Leu
    370                 375                 380

Glu Pro Glu Arg Glu Lys Ser Ala Ala Ile Asp Gly Glu Tyr Arg Leu
385                 390                 395                 400

Arg Gly Glu Ala Arg Lys Thr Phe Val Glu Leu Gly Glu Ala Arg Lys
                405                 410                 415

Thr Phe Val Asp Leu Gly Glu Gln Arg Lys Thr Phe Val Glu Leu Met
            420                 425                 430

Arg Arg Gly Asp Leu Pro Val Trp Leu Ser Tyr Lys Val Ala Ser Ala
        435                 440                 445

Gly Phe Gln Tyr Lys Asp Arg Glu Trp Cys Phe Asp Gly Glu Arg Asn
    450                 455                 460
```

```
Asn Gln Ile Leu Glu Glu Asn Met Asp Val Glu Ile Trp Thr Lys Glu
465                 470                 475                 480

Gly Glu


<210> SEQ ID NO 75
<211> LENGTH: 34
<212> TYPE: PRT
<213> ORGANISM: Dengue virus

<400> SEQUENCE: 75

Lys Lys Lys Leu Arg Pro Arg Trp Leu Asp Ala Arg Thr Tyr Ala Asp
1               5                   10                  15

Pro Leu Ala Leu Lys Glu Phe Lys Asp Phe Ala Ala Gly Arg Lys Ser
            20                  25                  30

Ile Ala


<210> SEQ ID NO 76
<211> LENGTH: 15
<212> TYPE: PRT
<213> ORGANISM: Dengue virus

<400> SEQUENCE: 76

Thr Glu Ile Gly Arg Val Pro Ser His Leu Ala His Arg Thr Arg
1               5                   10                  15


<210> SEQ ID NO 77
<211> LENGTH: 24
<212> TYPE: PRT
<213> ORGANISM: Dengue virus

<400> SEQUENCE: 77

Ala Tyr Gln His Ala Leu Glu Glu Leu Pro Glu Thr Leu Glu Thr Leu
1               5                   10                  15

Leu Leu Leu Ala Leu Leu Gly Ala
            20


<210> SEQ ID NO 78
<211> LENGTH: 24
<212> TYPE: PRT
<213> ORGANISM: Dengue virus

<400> SEQUENCE: 78

Phe Leu Phe Phe Leu Ser Gly Lys Gly Ile Gly Lys Met Ser Ile Gly
1               5                   10                  15

Leu Cys Cys Ile Ile Ala Ala Ser
            20


<210> SEQ ID NO 79
<211> LENGTH: 76
<212> TYPE: PRT
<213> ORGANISM: Dengue virus

<400> SEQUENCE: 79

Leu Leu Trp Met Ala Glu Ile Gln Pro His Trp Ile Ala Ala Ser Ile
1               5                   10                  15

Ile Leu Glu Phe Phe Leu Met Val Leu Leu Ile Pro Glu Pro Glu Lys
            20                  25                  30

Gln Arg Thr Pro Gln Asp Asn Gln Leu Ala Tyr Val Val Ile Gly Ile
        35                  40                  45

Leu Thr Leu Ala Ala Ala Ile Ala Ala Asn Glu Met Gly Leu Leu Glu
    50                  55                  60
```

```
Thr Thr Lys Lys Asp Leu Gly Ile Gly His Val Ala
65                  70                  75


<210> SEQ ID NO 80
<211> LENGTH: 237
<212> TYPE: PRT
<213> ORGANISM: Dengue virus

<400> SEQUENCE: 80

Pro Thr Ala Ile Leu Asp Val Asp Leu His Pro Ala Ser Ala Trp Thr
1               5                   10                  15

Leu Tyr Ala Val Ala Thr Thr Ile Ile Thr Pro Met Leu Arg His Thr
            20                  25                  30

Ile Glu Asn Ser Thr Ala Asn Val Ser Leu Thr Ala Ile Ala Asn Gln
        35                  40                  45

Ala Ala Val Leu Met Ile Ala Asn Gln Ala Thr Val Leu Met Gly Leu
    50                  55                  60

Asp Lys Gly Trp Pro Ile Ser Lys Met Asp Leu Gly Val Pro Leu Leu
65                  70                  75                  80

Ala Leu Gly Cys Tyr Ser Gln Val Asn Pro Leu Thr Leu Thr Ala Ala
                85                  90                  95

Val Leu Leu Leu Ile Thr His Tyr Ala Ile Ile Gly Pro Gly Leu Gln
            100                 105                 110

Ala Lys Ala Thr Arg Glu Ala Gln Lys Arg Thr Ala Ala Gly Ile Met
        115                 120                 125

Lys Asn Pro Thr Val Asp Gly Ile Met Ala Ile Asp Leu Asp Pro Ile
    130                 135                 140

Pro Tyr Asp Pro Lys Phe Glu Lys Gln Leu Gly Gln Val Met Leu Leu
145                 150                 155                 160

Ile Leu Cys Val Ser Gln Ile Leu Leu Met Arg Thr Thr Trp Ala Val
                165                 170                 175

Leu Leu Met Arg Thr Thr Trp Ala Leu Cys Glu Ala Leu Thr Leu Ala
            180                 185                 190

Thr Gly Pro Ile Thr Thr Leu Trp Glu Gly Asn Pro Gly Lys Phe Trp
        195                 200                 205

Asn Thr Thr Ile Ala Val Ser Met Ala Asn Ile Phe Arg Gly Ser Tyr
    210                 215                 220

Leu Ala Gly Ala Gly Leu Ala Phe Ser Leu Ile Lys Asn
225                 230                 235


<210> SEQ ID NO 81
<211> LENGTH: 136
<212> TYPE: PRT
<213> ORGANISM: Dengue virus

<400> SEQUENCE: 81

Arg Arg Gly Thr Gly Ala Gln Gly Glu Thr Leu Gly Glu Lys Trp Lys
1               5                   10                  15

Arg Gln Leu Asn Gln Leu Asp Lys Ser Glu Phe Glu Glu Tyr Lys Lys
            20                  25                  30

Ser Gly Ile Leu Glu Val Asp Arg Thr Glu Ala Lys Glu Ala Ile Lys
        35                  40                  45

Arg Gly Glu Thr Asp His His Ala Val Ser Arg Gly Ser Ala Lys Leu
    50                  55                  60

Arg Trp Phe Val Glu Arg Asn Met Val Ile Pro Glu Gly Arg Val Ile
65                  70                  75                  80
```

```
Asp Leu Gly Cys Gly Arg Gly Gly Trp Ser Tyr Tyr Cys Ala Gly Leu
                85                  90                  95

Lys Lys Val Arg Glu Val Arg Gly Tyr Thr Lys Gly Gly Pro Gly His
            100                 105                 110

Glu Glu Pro Ile Pro Met Ala Thr Tyr Gly Trp Asn Leu Val Lys Leu
        115                 120                 125

His Ser Gly Val Asp Val Phe Phe
    130                 135


<210> SEQ ID NO 82
<211> LENGTH: 38
<212> TYPE: PRT
<213> ORGANISM: Dengue virus

<400> SEQUENCE: 82

Pro Glu Lys Cys Asp Thr Leu Leu Cys Asp Ile Gly Glu Ser Ser Pro
1               5                   10                  15

Asn Pro Thr Ile Glu Glu Gly Arg Thr Leu Arg Val Leu Lys Met Val
            20                  25                  30

Glu Pro Trp Leu Lys Gly
        35


<210> SEQ ID NO 83
<211> LENGTH: 86
<212> TYPE: PRT
<213> ORGANISM: Dengue virus

<400> SEQUENCE: 83

Asn Gln Phe Cys Ile Lys Ile Leu Asn Pro Tyr Met Pro Ser Val Ile
1               5                   10                  15

Glu Glu Leu Glu Lys Leu Gln Arg Lys His Gly Gly Met Leu Val Arg
            20                  25                  30

Asn Pro Leu Ser Arg Asn Ser Thr His Glu Met Tyr Trp Val Ser Asn
        35                  40                  45

Gly Thr Gly Asn Ile Val Ser Ala Val Asn Met Ile Ser Arg Met Leu
    50                  55                  60

Ile Asn Arg Phe Thr Met Ala His Lys Lys Pro Thr Tyr Glu Arg Asp
65                  70                  75                  80

Val Asp Leu Gly Ala Gly
                85


<210> SEQ ID NO 84
<211> LENGTH: 79
<212> TYPE: PRT
<213> ORGANISM: Dengue virus

<400> SEQUENCE: 84

Ser Thr Trp His Tyr Asp Glu Asp Asn Pro Tyr Lys Thr Trp Ala Tyr
1               5                   10                  15

His Gly Ser Tyr Glu Val Lys Ala Thr Gly Ser Ala Ser Ser Met Val
            20                  25                  30

Asn Gly Val Val Lys Leu Leu Thr Lys Pro Trp Asp Val Val Pro Met
        35                  40                  45

Val Thr Gln Met Ala Met Thr Asp Thr Thr Pro Phe Gly Gln Gln Arg
    50                  55                  60

Val Phe Lys Glu Lys Val Asp Thr Arg Thr Pro Glu Ala Lys Glu
65                  70                  75
```

<210> SEQ ID NO 85
<211> LENGTH: 24
<212> TYPE: PRT
<213> ORGANISM: Dengue virus

<400> SEQUENCE: 85

```
Asn Ala Ala Ile Gly Ala Val Phe Gln Asp Glu Asn Gly Trp Lys Ser
1               5                   10                  15

Ala Arg Glu Ala Val Glu Asp Ser
            20
```

<210> SEQ ID NO 86
<211> LENGTH: 116
<212> TYPE: PRT
<213> ORGANISM: Dengue virus

<400> SEQUENCE: 86

```
Glu Arg Ala Leu His Leu Glu Gly Lys Cys Glu Ser Cys Val Tyr Asn
1               5                   10                  15

Met Met Gly Lys Arg Glu Lys Lys Leu Gly Glu Phe Gly Lys Ala Lys
            20                  25                  30

Gly Ser Arg Ala Ile Trp Tyr Met Trp Leu Gly Ala Arg Phe Leu Glu
        35                  40                  45

Phe Glu Ala Leu Gly Phe Leu Asn Glu Asp His Trp Phe Ser Arg Glu
    50                  55                  60

Asn Ser Leu Ser Gly Val Glu Gly Glu Gly Leu His Lys Leu Gly Tyr
65                  70                  75                  80

Ile Leu Arg Asp Ile Ser Lys Ile Pro Gly Gly Ala Met Tyr Ala Asp
                85                  90                  95

Asp Thr Ala Gly Trp Asp Thr Arg Ile Thr Glu Asp Asp Leu His Asn
            100                 105                 110

Glu Glu Lys Ile
        115
```

<210> SEQ ID NO 87
<211> LENGTH: 49
<212> TYPE: PRT
<213> ORGANISM: Dengue virus

<400> SEQUENCE: 87

```
Leu Ala Lys Ala Ile Phe Lys Leu Thr Tyr Gln Asn Lys Val Val Lys
1               5                   10                  15

Val Gln Arg Pro Thr Pro Arg Gly Ala Val Met Asp Ile Ile Ser Arg
            20                  25                  30

Lys Asp Gln Arg Gly Ser Gly Gln Val Gly Thr Tyr Gly Leu Asn Thr
        35                  40                  45

Phe
```

<210> SEQ ID NO 88
<211> LENGTH: 18
<212> TYPE: PRT
<213> ORGANISM: Dengue virus

<400> SEQUENCE: 88

```
Thr Asn Met Glu Ala Gln Leu Ile Arg Gln Met Glu Ala Glu Gly Val
1               5                   10                  15

Ile Thr
```

<210> SEQ ID NO 89
<211> LENGTH: 21
<212> TYPE: PRT
<213> ORGANISM: Dengue virus

<400> SEQUENCE: 89

```
Glu Cys Gly Val Asp Arg Leu Lys Arg Met Ala Ile Ser Gly Asp Asp
1               5                   10                  15

Cys Val Val Lys Pro
            20
```

<210> SEQ ID NO 90
<211> LENGTH: 172
<212> TYPE: PRT
<213> ORGANISM: Dengue virus

<400> SEQUENCE: 90

```
Pro Gln Trp Glu Pro Ser Lys Gly Trp His Asp Trp Gln Gln Val Pro
1               5                   10                  15

Phe Cys Ser His His Phe His Glu Ile Phe Met Lys Asp Gly Arg Lys
            20                  25                  30

Leu Val Val Pro Cys Arg Asn Gln Asp Glu Leu Ile Gly Arg Ala Arg
        35                  40                  45

Ile Ser Gln Gly Ala Gly Trp Ser Leu Arg Glu Thr Ala Cys Leu Gly
    50                  55                  60

Lys Ser Tyr Ala Gln Met Trp Gln Leu Met Tyr Phe His Arg Arg Asp
65                  70                  75                  80

Leu Arg Leu Ala Ser Asn Ala Ile Cys Ser Ala Val Pro Ser His Trp
                85                  90                  95

Val Pro Thr Ser Arg Thr Thr Trp Ser Ile His Ala His His Glu Trp
            100                 105                 110

Met Thr Thr Glu Asp Met Leu Ala Val Trp Asn Arg Val Trp Ile Glu
        115                 120                 125

Glu Asn Pro Trp Met Glu Asp Lys Thr His Ile His Ser Trp Glu Asp
    130                 135                 140

Val Pro Tyr Leu Gly Lys Arg Glu Asp Gln Trp Cys Gly Ser Leu Ile
145                 150                 155                 160

Gly Leu Thr Ser Arg Ala Thr Trp Ala Lys Asn Ile
                165                 170
```

<210> SEQ ID NO 91
<211> LENGTH: 8
<212> TYPE: PRT
<213> ORGANISM: Dengue virus

<400> SEQUENCE: 91

```
Val Lys Lys Asp Leu Ile Ser Tyr
1               5
```

<210> SEQ ID NO 92
<211> LENGTH: 9
<212> TYPE: PRT
<213> ORGANISM: Dengue virus

<400> SEQUENCE: 92

```
Ser Val Lys Lys Asp Leu Ile Ser Tyr
1               5
```

<210> SEQ ID NO 93
<211> LENGTH: 11

<212> TYPE: PRT
<213> ORGANISM: Dengue virus

<400> SEQUENCE: 93

Gly Thr Ser Gly Ser Pro Ile Val Asn Arg Glu
1 5 10

<210> SEQ ID NO 94
<211> LENGTH: 11
<212> TYPE: PRT
<213> ORGANISM: Dengue virus

<400> SEQUENCE: 94

Gly Thr Ser Gly Ser Pro Ile Ile Asn Arg Glu
1 5 10

<210> SEQ ID NO 95
<211> LENGTH: 10
<212> TYPE: PRT
<213> ORGANISM: Dengue virus

<400> SEQUENCE: 95

Ala Pro Thr Arg Val Val Ala Ala Glu Met
1 5 10

<210> SEQ ID NO 96
<211> LENGTH: 10
<212> TYPE: PRT
<213> ORGANISM: Dengue virus

<400> SEQUENCE: 96

Ala Pro Thr Arg Val Val Ala Ser Glu Met
1 5 10

<210> SEQ ID NO 97
<211> LENGTH: 9
<212> TYPE: PRT
<213> ORGANISM: Dengue virus

<400> SEQUENCE: 97

Ala Leu Lys Gly Leu Pro Ile Arg Tyr
1 5

<210> SEQ ID NO 98
<211> LENGTH: 9
<212> TYPE: PRT
<213> ORGANISM: Dengue virus

<400> SEQUENCE: 98

Ala Leu Arg Gly Leu Pro Ile Arg Tyr
1 5

<210> SEQ ID NO 99
<211> LENGTH: 10
<212> TYPE: PRT
<213> ORGANISM: Dengue virus

<400> SEQUENCE: 99

Asp Pro Ala Ser Ile Ala Ala Arg Gly Tyr
1 5 10

<210> SEQ ID NO 100
<211> LENGTH: 10
<212> TYPE: PRT
<213> ORGANISM: Dengue virus

<400> SEQUENCE: 100

Thr Pro Glu Gly Ile Ile Pro Ala Leu Phe
1 5 10

<210> SEQ ID NO 101
<211> LENGTH: 10
<212> TYPE: PRT
<213> ORGANISM: Dengue virus

<400> SEQUENCE: 101

Thr Pro Glu Gly Ile Ile Pro Ser Met Phe
1 5 10

<210> SEQ ID NO 102
<211> LENGTH: 10
<212> TYPE: PRT
<213> ORGANISM: Dengue virus

<400> SEQUENCE: 102

Thr Pro Glu Gly Ile Ile Pro Thr Leu Phe
1 5 10

<210> SEQ ID NO 103
<211> LENGTH: 9
<212> TYPE: PRT
<213> ORGANISM: Dengue virus

<400> SEQUENCE: 103

Thr Pro Glu Gly Ile Ile Pro Ser Leu
1 5

<210> SEQ ID NO 104
<211> LENGTH: 10
<212> TYPE: PRT
<213> ORGANISM: Dengue virus

<400> SEQUENCE: 104

Gly Glu Ala Arg Lys Thr Phe Val Glu Leu
1 5 10

<210> SEQ ID NO 105
<211> LENGTH: 10
<212> TYPE: PRT
<213> ORGANISM: Dengue virus

<400> SEQUENCE: 105

Gly Glu Ala Arg Lys Thr Phe Val Asp Leu
1 5 10

<210> SEQ ID NO 106
<211> LENGTH: 10
<212> TYPE: PRT
<213> ORGANISM: Dengue virus

<400> SEQUENCE: 106

Gly Glu Gln Arg Lys Thr Phe Val Glu Leu
1 5 10

<210> SEQ ID NO 107
<211> LENGTH: 9
<212> TYPE: PRT
<213> ORGANISM: Dengue virus

<400> SEQUENCE: 107

Leu Pro Val Trp Leu Ser Tyr Lys Val
1 5

<210> SEQ ID NO 108
<211> LENGTH: 10
<212> TYPE: PRT
<213> ORGANISM: Dengue virus

<400> SEQUENCE: 108

Thr Pro Met Leu Arg His Thr Ile Glu Asn
1 5 10

<210> SEQ ID NO 109
<211> LENGTH: 9
<212> TYPE: PRT
<213> ORGANISM: Dengue virus

<400> SEQUENCE: 109

Ile Ala Asn Gln Ala Ala Val Leu Met
1 5

<210> SEQ ID NO 110
<211> LENGTH: 9
<212> TYPE: PRT
<213> ORGANISM: Dengue virus

<400> SEQUENCE: 110

Ile Ala Asn Gln Ala Thr Val Leu Met
1 5

<210> SEQ ID NO 111
<211> LENGTH: 9
<212> TYPE: PRT
<213> ORGANISM: Dengue virus

<400> SEQUENCE: 111

Ile Leu Leu Met Arg Thr Thr Trp Ala
1 5

<210> SEQ ID NO 112
<211> LENGTH: 9
<212> TYPE: PRT
<213> ORGANISM: Dengue virus

<400> SEQUENCE: 112

Val Leu Leu Met Arg Thr Thr Trp Ala
1 5

<210> SEQ ID NO 113
<211> LENGTH: 9
<212> TYPE: PRT
<213> ORGANISM: Dengue virus

<400> SEQUENCE: 113

Ala Thr Gly Pro Ile Thr Thr Leu Trp
1 5

<210> SEQ ID NO 114
<211> LENGTH: 9
<212> TYPE: PRT
<213> ORGANISM: Dengue virus

<400> SEQUENCE: 114

Asp Thr Thr Pro Phe Gly Gln Gln Arg 1 5

<210> SEQ ID NO 115
<211> LENGTH: 543
<212> TYPE: DNA
<213> ORGANISM: Dengue virus

<400> SEQUENCE: 115
aaagaaaagc aggacgtgtt ctgcgacagc aagctgatga gcgccgccat caaggacaac 60
cgggccgtgc acgccgacat gggctactgg atcgagagcg ccctgaacga cacctggaag 120
atcgagaagg ccagcttcat cgaagtgaag aactgccact ggcccaagag ccacaccctg 180
tggtccaacg gcgtgctgga aagcgagatg atcatcccca agaacctggc cggacccgtg 240
tcccagcaca actacagacc cggctaccac acccagatca ccggcccctg gcacctgggc 300
aagctggaaa tggacttcga cttctgcgac ggcaccaccg tggtggtgac agaggactgc 360
ggcaacagag gccccagcct gagaaccacc accgccagcg gcaagctgat caccgagtgg 420
tgctgcagaa gctgcaccct gcccccccctg cggtacagag gcgaggatgg ctgttggtac 480
ggcatggaaa tccggcccct gaaagagaaa gaagagaacc tggtcaactc cctggtgaca 540
gcc 543

<210> SEQ ID NO 116
<211> LENGTH: 181
<212> TYPE: PRT
<213> ORGANISM: Dengue virus

<400> SEQUENCE: 116

Lys Glu Lys Gln Asp Val Phe Cys Asp Ser Lys Leu Met Ser Ala Ala
1 5 10 15

Ile Lys Asp Asn Arg Ala Val His Ala Asp Met Gly Tyr Trp Ile Glu
20 25 30

Ser Ala Leu Asn Asp Thr Trp Lys Ile Glu Lys Ala Ser Phe Ile Glu
35 40 45

Val Lys Asn Cys His Trp Pro Lys Ser His Thr Leu Trp Ser Asn Gly
50 55 60

Val Leu Glu Ser Glu Met Ile Ile Pro Lys Asn Leu Ala Gly Pro Val
65 70 75 80

Ser Gln His Asn Tyr Arg Pro Gly Tyr His Thr Gln Ile Thr Gly Pro
85 90 95

Trp His Leu Gly Lys Leu Glu Met Asp Phe Asp Phe Cys Asp Gly Thr
100 105 110

Thr Val Val Val Thr Glu Asp Cys Gly Asn Arg Gly Pro Ser Leu Arg
115 120 125

Thr Thr Thr Ala Ser Gly Lys Leu Ile Thr Glu Trp Cys Cys Arg Ser
130 135 140

Cys Thr Leu Pro Pro Leu Arg Tyr Arg Gly Glu Asp Gly Cys Trp Tyr
145 150 155 160

Gly Met Glu Ile Arg Pro Leu Lys Glu Lys Glu Glu Asn Leu Val Asn
165 170 175

Ser Leu Val Thr Ala
180

<210> SEQ ID NO 117
<211> LENGTH: 28
<212> TYPE: PRT
<213> ORGANISM: Dengue virus

<400> SEQUENCE: 117

Glu Trp Cys Cys Arg Ser Cys Thr Leu Pro Pro Leu Arg Tyr Arg Gly
1               5                   10                  15

Glu Asp Gly Cys Trp Tyr Gly Met Glu Ile Arg Pro
            20                  25

<210> SEQ ID NO 118
<211> LENGTH: 40086
<212> TYPE: DNA
<213> ORGANISM: Artificial Sequence
<220> FEATURE:
<223> OTHER INFORMATION: Vector

<400> SEQUENCE: 118
gtttaaacgc ggccgccagg cctacccact agtcaattcg ggaggatcga aacggcagat 60
cgcaaaaaac agtacataca gaaggagaca tgaacatgaa catcaaaaaa attgtaaaac 120
aagccacagt tctgactttt acgactgcac ttctggcagg aggagcgact caagccttcg 180
cgaaagaaaa taaccaaaaa gcatacaaag aaacgtacgg cgtctctcat attacacgcc 240
atgatatgct gcagatccct aaacagcagc aaaacgaaaa ataccaagtg cctcaattcg 300
atcaatcaac gattaaaaat attgagtctg caaaaggact tgatgtgtgg gacagctggc 360
cgctgcaaaa cgctgacgga acagtagctg aatacaacgg ctatcacgtt gtgtttgctc 420
ttgcgggaag cccgaaagac gctgatgaca catcaatcta catgttttat caaaaggtcg 480
gcgacaactc aatcgacagc tggaaaaacg cgggccgtgt ctttaaagac agcgataagt 540
tcgacgccaa cgatccgatc ctgaaagatc agacgcaaga atggtccggt tctgcaacct 600
ttacatctga cggaaaaatc cgtttattct acactgacta ttccggtaaa cattacggca 660
aacaaagcct gacaacagcg caggtaaatg tgtcaaaatc tgatgacaca ctcaaaatca 720
acggagtgga agatcacaaa acgatttttg acggagacgg aaaaacatat cagaacgttc 780
agcagtttat cgatgaaggc aattatacat ccggcgacaa ccatacgctg agagaccctc 840
actacgttga agacaaaggc cataaatacc ttgtattcga agccaacacg ggaacagaaa 900
acggatacca aggcgaagaa tctttattta acaaagcgta ctacggcggc ggcacgaact 960
tcttccgtaa agaaagccag aagcttcagc agagcgctaa aaaacgcgat gctgagttag 1020
cgaacggcgc cctcggtatc atagagttaa ataatgatta cacattgaaa aaagtaatga 1080
agccgctgat cacttcaaac acggtaactg atgaaatcga gcgcgcgaat gttttcaaaa 1140
tgaacggcaa atggtacttg ttcactgatt cacgcggttc aaaaatgacg atcgatggta 1200
ttaactcaaa cgatatttac atgcttggtt atgtatcaaa ctctttaacc ggcccttaca 1260
agccgctgaa caaaacaggg cttgtgctgc aaatgggtct tgatccaaac gatgtgacat 1320
tcacttactc tcacttcgca gtgccgcaag ccaaaggcaa caatgtggtt atcacaagct 1380
acatgacaaa cagaggcttc ttcgaggata aaaaggcaac atttgcgcca agcttcttaa 1440
tgaacatcaa aggcaataaa acatccgttg tcaaaaacag catcctggag caaggacagc 1500
tgacagtcaa ctaataacag caaaaagaaa atgccgatac ttcattggca ttttctttta 1560
tttctcaaca agatggtgaa ttgactagtg ggtagatcca caggacgggt gtggtcgcca 1620
tgatcgcgta gtcgatagtg gctccaagta gcgaagcgag caggactggg cggcggccaa 1680
agcggtcgga cagtgctccg agaacgggtg cgcatagaaa ttgcatcaac gcatatagcg 1740
ctagcagcac gccatagtga ctggcgatgc tgtcggaatg gacgatatcc cgcaagaggc 1800

-continued

```
ccggcagtac cggcataacc aagcctatgc ctacagcatc cagggtgacg gtgccgagga   1860
tgacgatgag cgcattgtta gatttcatac acggtgcctg actgcgttag caatttaact   1920
gtgataaact accgcattaa agcttatcga tgataagctg tcaaacatga gaattgatcc   1980
ggaaccctta atataacttc gtataatgta tgctatacga agttattagg tccctcgact   2040
atagggtcac cgtcgacagc gacacacttg catcggatgc agcccggtta acgtgccggc   2100
acggcctggg taaccaggta ttttgtccac ataaccgtgc gcaaaatgtt gtggataagc   2160
aggacacagc agcaatccac agcaggcata caaccgcaca ccgaggttac tccgttctac   2220
aggttacgac gacatgtcaa tacttgccct tgacaggcat tgatggaatc gtagtctcac   2280
gctgatagtc tgatcgacaa tacaagtggg accgtggtcc cagaccgata atcagaccga   2340
crayacgagt gggaycgtgg tcccagacta ataatcagac cgacgatacg agtgggaccg   2400
tggtcccaga ctaataatca gaccgacgat acgagtggga ccgtggtycc agwctratwa   2460
tcagaccgac gatacragtg gracmgtggk cccagasaka atawtcagrc cgagwtaygc   2520
wktckggcct gtaacaaagg acattaagta aagacagata mrmgtgrgac taaaacgtgg   2580
tcccagtctg attatcagac cgacgatacg agtgggaccg tggtcccaga ctaataatca   2640
gaccgacgat acgagtggga ccgtggtccc agactaataa tcagaccgac gatacgagtg   2700
ggaccgtggt cccagtctga ttatcagacc gacgatacaa gtggaacagt gggcccagag   2760
agaatattca ggccagttat gctttctggc ctgtaacaaa ggacattaag taaagacaga   2820
taaacgtaga ctaaaacgtg gtcgcatcag ggtgctggct tttcaagttc cttaagaatg   2880
gcctcaattt tctctataca ctcagttgga acacgagacc tgtccaggtt aagcaccatt   2940
ttatcgccct tatacaatac tgtcgctcca ggagcaaact gatgtcgtga gcttaaacta   3000
gttcttgatg cagatgacgt tttaagcaca gaagttaaaa gagtgataac ttcttcagct   3060
tcaaatatca ccccagcttt ttctgctcca tgaaggttag atgcctgctg cttaagtaat   3120
tcctctttat ctgtaaaggc tttttgaagt gcatcacctg accgggcaga tagttcaccg   3180
gggtgagaaa aaagagcaac aactgattta ggcaatttgg cggtgttgat acagcgggta   3240
ataatcttac gtgaaatatt ttccgcatca gccagcgcag aaatatttcc agcaaattca   3300
ttctgcaatc ggcttgcata acgctgacca cgttcataag cacttgttgg gcgataatcg   3360
ttacccaatc tggataatgc agccatctgc tcatcatcca gctcgccaac cagaacacga   3420
taatcacttt cggtaagtgc agcagcttta cgacggcgac tcccatcggc aatttctatg   3480
acaccagata ctcttcgacc gaacgccggt gtctgttgac cagtcagtag aaaagaaggg   3540
atgagatcat ccagtgcgtc ctcagtaagc agctcctggt cacgttcatt acctgaccat   3600
acccgagagg tcttctcaac actatcaccc cggagcactt caagagtaaa cttcacatcc   3660
cgaccacata caggcaaagt aatggcatta ccgcgagcca ttactcctac gcgcgcaatt   3720
aacgaatcca ccatcggggc agctggtgtc gataacgaag tatcttcaac cggttgagta   3780
ttgagcgtat gttttggaat aacaggcgca cgcttcatta tctaatctcc cagcgtggtt   3840
taatcagacg atcgaaaatt tcattgcaga caggttccca aatagaaaga gcatttctcc   3900
aggcaccagt tgaagagcgt tgatcaatgg cctgttcaaa aacagttctc atccggatct   3960
gacctttacc aacttcatcc gtttcacgta caacattttt tagaaccatg cttccccagg   4020
catcccgaat ttgctcctcc atccacgggg actgagagcc attactattg ctgtatttgg   4080
taagcaaaat acgtacatca ggctcgaacc ctttaagatc aacgttcttg agcagatcac   4140
gaagcatatc gaaaaactgc agtgcggagg tgtagtcaaa caactcagca ggcgtgggaa   4200
```

caatcagcac atcagcagca catacgacat taatcgtgcc gatacccagg ttaggcgcgc 4260
tgtcaataac tatgacatca tagtcatgag caacagtttc aatggccagt cggagcatca 4320
ggtgtggatc ggtgggcagt ttaccttcat caaatttgcc cattaactca gtttcaatac 4380
ggtgcagagc cagacaggaa ggaataatgt caagccccgg ccagcaagtg ggctttattg 4440
cataagtgac atcgtccttt tccccaagat agaaaggcag gagagtgtct tctgcatgaa 4500
tatgaagatc tggtacccat ccgtgataca ttgaggctgt tccctggggg tcgttacctt 4560
ccacgagcaa aacacgtagc cccttcagag ccagatcctg agcaagatga acagaaactg 4620
aggttttgta aacgccacct ttatgggcag caaccccgat caccggtgga aatacgtctt 4680
cagcacgtcg caatcgcgta ccaaacacat cacgcatatg attaatttgt tcaattgtat 4740
aaccaacacg ttgctcaacc cgtcctcgaa tttccatatc cgggtgcggt agtcgccctg 4800
ctttctcggc atctctgata gcctgagaag aaaccccaac taaatccgct gcttcaccta 4860
ttctccagcg ccgggttatt ttcctcgctt ccgggctgtc atcattaaac tgtgcaatgg 4920
cgatagcctt cgtcatttca tgaccagcgt ttatgcactg gttaagtgtt tccatgagtt 4980
tcattctgaa catcctttaa tcattgcttt gcgttttttt attaaatctt gcaatttact 5040
gcaaagcaac aacaaaatcg caaagtcatc aaaaaaccgc aaagttgttt aaaataagag 5100
caacactaca aaaggagata agaagagcac atacctcagt cacttattat cactagcgct 5160
cgccgcagcc gtgtaaccga gcatagcgag cgaactggcg aggaagcaaa gaagaactgt 5220
tctgtcagat agctcttacg ctcagcgcaa gaagaaatat ccaccgtggg aaaaactcca 5280
ggtagaggta cacacgcgga tagccaattc agagtaataa actgtgataa tcaaccctca 5340
tcaatgatga cgaactaacc cccgatatca ggtcacatga cgaagggaaa gagaaggaaa 5400
tcaactgtga caaactgccc tcaaatttgg cttccttaaa aattacagtt caaaaagtat 5460
gagaaaatcc atgcaggctg aaggaaacag caaaactgtg acaaattacc ctcagtaggt 5520
cagaacaaat gtgacgaacc accctcaaat ctgtgacaga taaccctcag actatcctgt 5580
cgtcatggaa gtgatatcgc ggaaggaaaa tacgatatga gtcgtctggc ggcctttctt 5640
tttctcaatg tatgagaggc gcattggagt tctgctgttg atctcattaa cacagacctg 5700
caggaagcgg cggcggaagt caggcatacg ctggtaactt tgaggcagct ggtaacgctc 5760
tatgatccag tcgattttca gagagacgat gcctgagcca tccggcttac gatactgaca 5820
cagggattcg tataaacgca tggcatacgg attggtgatt tcttttgttt cactaagccg 5880
aaactgcgta aaccggttct gtaacccgat aaagaaggga atgagatatg ggttgatatg 5940
tacactgtaa agccctctgg atggactgtg cgcacgtttg ataaaccaag gaaaagattc 6000
atagcctttt tcatcgccgg catcctcttc agggcgataa aaaaccactt ccttccccgc 6060
gaaactcttc aatgcctgcc gtatatcctt actggcttcc gcagaggtca atccgaatat 6120
ttcagcatat ttagcaacat ggatctcgca gataccgtca tgttcctgta gggtgccatc 6180
agattttctg atctggtcaa cgaacagata cagcatacgt tttgatcccc gggagagact 6240
atatgccgcc tcagtgaggt cgtttgactg gacgattcgc gggctatttt tacgtttctt 6300
gtgattgata accgctgttt ccgccatgac agatccatgt gaagtgtgac aagtttttag 6360
attgtcacac taaataaaaa agagtcaata agcagggata actttgtgaa aaaacagctt 6420
cttctgaggg caatttgtca cagggttaag ggcaatttgt cacagacagg actgtcattt 6480
gagggtgatt tgtcacactg aaagggcaat ttgtcacaac accttctcta gaaccagcat 6540

-continued

```
ggataaaggc ctacaaggcg ctctaaaaaa gaagatctaa aaactataaa aaaaataatt   6600
ataaaaatat ccccgtggat aagtggataa ccccaaggga agtttttttca ggcatcgtgt   6660
gtaagcagaa tatataagtg ctgttccctg gtgcttcctc gctcactcga gggcttcgcc   6720
ctgtcgctca actgcggcga gcactactgg ctgtaaaagg acagaccaca tcatggttct   6780
gtgttcatta ggttgttctg tccattgctg acataatccg ctccacttca acgtaacacc   6840
gcacgaagat ttctattgtt cctgaaggca tattcaaatc gttttcgtta ccgcttgcag   6900
gcatcatgac agaacactac ttcctataaa cgctacacag gctcctgaga ttaataatgc   6960
ggatctctac gataatggga gattttcccg actgtttcgt tcgcttctca gtggataaca   7020
gccagcttct ctgtttaaca gacaaaaaca gcatatccac tcagttccac atttccatat   7080
aaaggccaag gcatttattc tcaggataat tgtttcagca tcgcaaccgc atcagactcc   7140
ggcatcgcaa actgcacccg gtgccgggca gccacatcca gcgcaaaaac cttcgtgtag   7200
acttccgttg aactgatgga cttatgtccc atcaggcttt gcagaacttt cagcggtata   7260
ccggcataca gcatgtgcat cgcataggaa tggcggaacg tatgtggtgt gaccggaaca   7320
gagaacgtca caccgtcagc agcagcggcg gcaaccgcct ccccaatcca ggtcctgacc   7380
gttctgtccg tcacttccca gatccgcgct ttctctgtcc ttcctgtgcg acggttacgc   7440
cgctccatga gcttatcgcg aataaatacc tgtgacggaa gatcacttcg cagaataaat   7500
aaatcctggt gtccctgttg ataccgggaa gccctgggcc aacttttggc gaaaatgaga   7560
cgttgatcgg cacgtaagag gttccaactt tcaccataat gaaataagat cactaccggg   7620
cgtatttttt gagttatcga gattttcagg agctaaggaa gctaaaatgg agaaaaaaat   7680
cactggatat accaccgttg atatatccca atggcatcgt aaagaacatt ttgaggcatt   7740
tcagtcagtt gctcaatgta cctataacca gaccgttcag ctggatatta cggccttttt   7800
aaagaccgta aagaaaaata agcacaagtt ttatccggcc tttattcaca ttcttgcccg   7860
cctgatgaat gctcatccgg agttccgtat ggcaatgaaa gacggtgagc tggtgatatg   7920
ggatagtgtt cacccttgtt acaccgtttt ccatgagcaa actgaaacgt tttcatcgct   7980
ctggagtgaa taccacgacg atttccggca gtttctacac atatattcgc aagatgtggc   8040
gtgttacggt gaaaacctgg cctatttccc taaagggttt attgagaata tgtttttcgt   8100
ctcagccaat ccctgggtga gtttcaccag ttttgattta aacgtggcca atatggacaa   8160
cttcttcgcc cccgttttca ccatgggcaa atattatacg caaggcgaca aggtgctgat   8220
gccgctggcg attcaggttc atcatgccgt ttgtgatggc ttccatgtcg gcagaatgct   8280
taatgaatta caacagtact gcgatgagtg gcagggcggg gcgtaatttt tttaaggcag   8340
ttattggtgc ccttaaacgc ctggttgcta cgcctgaata agtgataata agcggatgaa   8400
tggcagaaat tcgatgataa gctgtcaaac atgagaattg gtcgacggcg cgccaaagct   8460
tgcatgcctg cagccgcgta acctggcaaa atcggttacg gttgagtaat aaatggatgc   8520
cctgcgtaag cggggcacat ttcattacct ctttctccgc acccgacata gataataact   8580
tcgtatagta tacattatac gaagttatct agtagactta atcgcgttta aacccatcat   8640
caataatata cctcaaactt tttgtgcgcg ttaatatgca aatgaggcgt ttgaatttgg   8700
gaagggagga aggtgattgg ccgagagaag ggcgaccgtt aggggcgggg cgagtgacgt   8760
tttgatgacg tgaccgcgag gaggagccag tttgcaagtt ctcgtgggaa aagtgacgtc   8820
aaacgaggtg tggtttgaac acggaaatac tcaattttcc cgcgctctct gacaggaaat   8880
gaggtgtttc taggcggatg caagtgaaaa cgggccattt tcgcgcgaaa actgaatgag   8940
```

```
gaagtgaaaa tctgagtaat ttcgcgttta tgacagggag gagtatttgc cgagggccga   9000
gtagactttg accgattacg tggggtttc gattaccgtg tttttcacct aaatttccgc   9060
gtacggtgtc aaagtccggt gtttttacgt aggtgtcagc tgatcgccag ggtatttaaa   9120
cctgcgctct ccagtcaaga ggccactctt gagtgccagc gagaagagtt ttctcctccg   9180
cgcgcgagtc agatctacac tttgaaaggc gatcgctagc gacatcgatc caaataatga   9240
ttttattttg actgatagtg acctgttcgt tgcaacaaat tgataagcaa tgctttttta   9300
taatgccaac tttgtacaaa aaagcaggct ccaccatggg aaccaattca gtcgagcctt   9360
tcactcatta gatgcatgtc gttacataac ttacggtaaa tggcccgcct ggctgaccgc   9420
ccaacgaccc ccgcccattg acgtcaataa tgacgtatgt tcccatagta acgccaatag   9480
ggactttcca ttgacgtcaa tgggtggagt atttacggta aactgcccac ttggcagtac   9540
atcaagtgta tcatatgcca agtacgcccc ctattgacgt caatgacggt aaatggcccg   9600
cctggcatta tgcccagtac atgaccttat gggactttcc tacttggcag tacatctacg   9660
tattagtcat cgctattacc atggtgatgc ggttttggca gtacatcaat gggcgtggat   9720
agcggtttga ctcacgggga tttccaagtc tccaccccat tgacgtcaat gggagtttgt   9780
tttggcacca aaatcaacgg gactttccaa aatgtcgtaa caactccgcc ccattgacgc   9840
aaatgggcgg taggcgtgta cggtgggagg tctatataag cagagctctc cctatcagtg   9900
atagagatct ccctatcagt gatagagatc gtcgacgagc tcgtttagtg aaccgtcaga   9960
tcgcctggag acgccatcca cgctgttttg acctccatag aagacaccgg gaccgatcca  10020
gcctccggtt aagctcggta ccgctagccg cgccgccacc atggatgcaa tgaagagagg  10080
gctctgctgt gtgctgctgc tgtgtggagc agtcttcgtt tcgcccagcc aggaaatcca  10140
tgcccgattc agaagaggat cgaagcttgc cctgatcctg gcccccacca gggtggtggc  10200
cagcgagatg gcccccacca gggtggtggc cgccgagatg gaggagaggg tggtggccgc  10260
cgagatggag gaggccctga agggcctgcc cagcatcgcc gccaggggct acatcagcac  10320
cagggtggag atgggcgagg ccgccgccat cctgaacgac tgggacttcg tggtgaccac  10380
cgacatcagc gagatgggcg ccaacttcaa gcccatgccc gtgaccgccg ccagcgccgc  10440
ccagaggagg ggcaggatcg gcaggaacga ccacgcccac tggaccgagg ccaagatgct  10500
gctggacaac atcaagagga ccgccgccgg catcatgaag aaccccaccg tggacggcta  10560
cgaccccaag ttcgagaagc agctgggcca ggtgatgctg ctgatgagga ccacctgggc  10620
cctgtgcgag gccctgaccc tggccaccgg cccccctgtgg gagggcaacc ccggcaagtt  10680
ctggaacacc accatcgccg tgagcatgcc cggcaagttc tggaacacca ccatcgccgt  10740
gagcatggcc aacatcttca ggggcagcta cctggccctg tgcgacatcg gcgagagcag  10800
ccccaacccc accatcgagg agtacaacat gatgggcaag agggagaaga agctgggcga  10860
gttcggcaag gccaagagca gggccatctg gtacatgtgg ctgggcgcca ggttcctgga  10920
gttcgaggcc ctgggcttca tgtacgccga cgacaccgcc ggctgggaca ccaggatcac  10980
cgaggacgac ctgttcaagc tgacctacca gaacaaggtg gtgaaggtgc agaggcccgt  11040
gatggacatc atcagcagga aggaccagag gggcagcggc caggtgggca cctacgctgg  11100
atccgggccc ggggcttcag gtaagcctat ccctaaccct ctcctcggtc tcgattctac  11160
gcggacctga tgagcggccg ctcgagcatg catctagagg gccctattct atagtgtcac  11220
ctaaatgcta gagctcgctg atcagcctcg actgtgcctt ctagttgcca gccatctgtt  11280
```

```
gtttgcccct cccccgtgcc ttccttgacc ctggaaggtg ccactcccac tgtcctttcc  11340
taataaaatg aggaaattgc atcgcattgt ctgagtaggt gtcattctat tctggggggt  11400
ggggtggggc aggacagcaa gggggaggat tgggaagaca atagcaggca tgctggggat  11460
gcggtgggct ctatggcttc tgaggcggaa agaaccagct ggggctcgag gggggatcga  11520
tcccgtcgag atatctagac ccagctttct tgtacaaagt tggcattata agaaagcatt  11580
gcttatcaat ttgttgcaac gaacaggtca ctatcagtca aaataaaatc attatttgga  11640
tcgattcgac agatcgcgat cgcagtgagt agtgttctgg ggcgggggag gacctgcatg  11700
agggccagaa tgactgaaat ctgtgctttt ctgtgtgttg cagcatcatg agcggaagcg  11760
gctcctttga gggaggggta ttcagccctt atctgacggg gcgtctcccc tcctgggcgg  11820
gagtgcgtca gaatgtgatg ggatccacgg tggacggccg gcccgtgcag cccgcgaact  11880
cttcaaccct gacctatgca accctgagct cttcgtcggt ggacgcagct gccgccgcag  11940
ctgctgcatc cgccgccagc gccgtgcgcg gaatggccat gggcgccggc tactacggca  12000
ctctggtggc caactcgagt tccaccaata atcccgccag cctgaacgag gagaagctgc  12060
tgctgctgat ggcccagctt gaggccttga cccagcgcct gggcgagctg acccagcagg  12120
tggctcagct gcaggagcag acgcgggccg cggttgccac ggtgaaatcc aaataaaaaa  12180
tgaatcaata aataaacgga gacggttgtt gattttaaca cagagtctga atctttattt  12240
gatttttcgc gcgcggtagg ccctggacca ccggtctcga tcattgagca cccggtggat  12300
cttttccagg acccggtaga ggtgggcttg gatgttgagg tacatgggca tgagcccgtc  12360
ccgggggtgg aggtagctcc attgcagggc ctcgtgctcg gggtggtgt tgtaaatcac  12420
ccagtcatag caggggcgca gggcgtggtg ttgcacaata tctttgagga ggagactgat  12480
ggccacgggc agccctttgg tgtaggtgtt tacaaatctg ttgagctggg agggatgcat  12540
gcggggggag atgaggtgca tcttggcctg gatcttgaga ttggcgatgt taccgcccag  12600
atcccgcctg ggttcatgt tgtgcaggac caccagcacg gtgtatccgg tgcacttggg  12660
gaatttatca tgcaacttgg aagggaaggc gtgaaagaat ttggcgacgc ccttgtgtcc  12720
gcccaggttt tccatgcact catccatgat gatggcaatg ggcccgtggg cggcggcctg  12780
ggcaaagacg tttcgggggt cggacacatc atagttgtgg tcctgggtga ggtcatcata  12840
ggccatttta atgaatttgg ggcggagggt gccggactgg gggacaaagg taccctcgat  12900
cccgggggcg tagttcccct cacagatctg catctcccag gctttgagct cagaggggg  12960
gatcatgtcc acctgcgggg cgataaagaa cacggtttcc ggggcgggg agatgagctg  13020
ggccgaaagc aagttccgga gcagctggga cttgccgcag ccggtggggc cgtaaatgac  13080
cccgatgacc ggctgcaggt ggtagttgag ggagagacag ctgccgtcct cccggaggag  13140
gggggccacc tcgttcatca tctcgcgcac gtgcatgttc tcgcgcacca gttccgccag  13200
gaggcgctct ccccccagag ataggagctc ctggagcgag gcgaagtttt tcagcggctt  13260
gagtccgtcg gccatgggca ttttggagag ggtctgttgc aagagttcca agcggtccca  13320
gagctcggtg atgtgctcta cggcatctcg atccagcaga cctcctcgtt tcgcgggttg  13380
ggacgactgc gggagtaggg caccagacga tgggcgtcca gcgcagccag ggtccggtcc  13440
ttccagggcc gcagcgtccg cgtcagggtg gtctccgtca cggtgaaggg gtgcgcgccg  13500
ggctgggcgc ttgcgagggt gcgcttcagg ctcatccggc tggtcgaaaa ccgctcccga  13560
tcggcgccct gcgcgtcggc caggtagcaa ttgaccatga gttcgtagtt gagcgcctcg  13620
gccgcgtggc ctttggcgcg gagcttacct ttggaagtct gcccgcaggc gggacagagg  13680
```

agggacttga gggcgtagag cttgggggcg aggaagacgg aatcgggggc gtaggcgtcc 13740
gcgccgcagt gggcgcagac ggtctcgcac tccacgagcc aggtgaggtc gggctggtcg 13800
gggtcaaaaa ccagtttccc gccgttcttt ttgatgcgtt tcttaccttt ggtctccatg 13860
agctcgtgtc cccgctgggt gacaaagagg ctgtccgtgt ccccgtagac cgactttatg 13920
ggccggtcct cgagcggtgt gccgcggtcc tcctcgtaga ggaaccccgc ccactccgag 13980
acgaaagccc gggtccaggc cagcacgaag gaggccacgt gggacgggta gcggtcgttg 14040
tccaccagcg ggtccacttt ttccagggta tgcaaacaca tgtcccccctc gtccacatcc 14100
aggaaggtga ttggcttgta agtgtaggcc acgtgaccgg gggtcccggc cgggggggta 14160
taaaaggggg cgggcccctg ctcgtcctca ctgtcttccg gatcgctgtc caggagcgcc 14220
agctgttggg gtaggtattc cctctcgaag gcgggcatga cctcggcact caggttgtca 14280
gtttctagaa acgaggagga tttgatattg acggtgccag cggagatgcc tttcaagagc 14340
ccctcgtcca tctggtcaga aaagacgatt tttttgttgt cgagcttggt ggcgaaggag 14400
ccgtagaggg cgttggaaag gagcttggcg atggagcgca tggtctggtt tttttccttg 14460
tcggcgcgct ccttggccgc gatgttgagc tgcacgtact cgcgcgccac gcacttccat 14520
tcggggaaga cggtggtcat ctcgtcgggc acgattctga cctgccaacc tcgattatgc 14580
agggtgatga ggtccacact ggtggccacc tcgccgcgca ggggctcgtt ggtccagcag 14640
aggcggccgc ccttgcgcga gcagaagggg ggcagagggt ccagcatgac ctcgtcgggg 14700
gggtcggcat cgatggtgaa gatgccgggc aggagatcgg ggtcgaagta gctgatggaa 14760
gtggccagat cgtccaggga agcttgccat tcgcgcacgg ccagcgcgcg ctcgtaggga 14820
ctgaggggcg tgccccaggg catggggtgg gtgagcgcgg aggcgtacat gccgcagatg 14880
tcgtagacgt agaggggctc ctcgaggatg ccgatgtagg tggggtagca gcgccccccg 14940
cggatgctgg cgcgcacgta gtcatacagc tcgtgcgagg gcgcgaggag ccccgggccc 15000
aggttggtgc gactgggctt ttcggcgcgg tagacgatct ggcgaaagat ggcatgcgag 15060
ttggaggaga tggtgggcct ttggaagatg ttgaagtggg cgtgggggag gccgaccgag 15120
tcgcggatga agtgggcgta ggagtcttgc agtttggcga cgagctcggc ggtgacgagg 15180
acgtccagag cgcagtagtc gagggtctcc tggatgatgt catacttgag ctggcccttt 15240
tgtttccaca gctcgcggtt gagaaggaac tcttcgcggt ccttccagta ctcttcgagg 15300
gggaacccgt cctgatctgc acggtaagag cctagcatgt agaactggtt gacggccttg 15360
taggcgcagc agcccttctc cacggggagg gcgtaggcct gggcggcctt gcgcagggag 15420
gtgtgcgtga gggcgaaggt gtccctgacc atgaccttga ggaactggtg cttgaaatcg 15480
atatcgtcgc agcccccctg ctcccagagc tggaagtccg tgcgcttctt gtaggcgggg 15540
ttgggcaaag cgaaagtaac atcgttgaaa aggatcttgc ccgcgcgggg cataaagttg 15600
cgagtgatgc ggaaaggctg gggcacctcg gcccggttgt tgatgacctg ggcggcgagc 15660
acgatctcgt cgaaaccgtt gatgttgtgg cccacgatgt agagttccac gaatcgcggg 15720
cggcccttga cgtggggcag cttcttgagc tcctcgtagg tgagctcgtc ggggtcgctg 15780
agaccgtgct gctcgagcgc ccagtcggcg agatgggggt tggcgcggag gaaggaagtc 15840
cagagatcca cggccagggc ggtttgcaga cggtcccggt actgacggaa ctgctgcccg 15900
acggccattt tttcgggggt gacgcagtag aaggtgcggg ggtccccgtg ccagcggtcc 15960
catttgagct ggagggcgag atcgagggcg agctcgacga ggcggtcgtc ccctgagagt 16020

```
ttcatgacca gcatgaaggg gacgagctgc ttgccgaagg accccatcca ggtgtaggtt  16080
tccacatcgt aggtgaggaa gagcctttcg gtgcgaggat gcgagccgat ggggaagaac  16140
tggatctcct gccaccaatt ggaggaatgg ctgttgatgt gatggaagta gaaatgccga  16200
cggcgcgccg aacactcgtg cttgtgttta tacaagcggc cacagtgctc gcaacgctgc  16260
acgggatgca cgtgctgcac gagctgtacc tgagttcctt tgacgaggaa tttcagtggg  16320
aagtggagtc gtggcgcctg catctcgtgc tgtactacgt cgtggtggtc ggcctggccc  16380
tcttctgcct cgatggtggt catgctgacg agcccgcgcg ggaggcaggt ccagacctcg  16440
gcgcgagcgg gtcggagagc gaggacgagg gcgcgcaggc cggagctgtc cagggtcctg  16500
agacgctgcg gagtcaggtc agtgggcagc ggcggcgcgc ggttgacttg caggagtttt  16560
tccagggcgc gcgggaggtc cagatggtac ttgatctcca ccgcgccgtt ggtggcgacg  16620
tcgatggctt gcagggtccc gtgcccctgg ggtgtgacca ccgtcccccg tttcttcttg  16680
ggcggctggg gcgacggggg cggtgcctct tccatggtta gaagcggcgg cgaggacgcg  16740
cgccgggcgg cagaggcggc tcggggcccg gaggcagggg cggcaggggc acgtcggcgc  16800
cgcgcgcggg taggttctgg tactgcgccc ggagaagact ggcgtgagcg acgacgcgac  16860
ggttgacgtc ctggatctga cgcctctggg tgaaggccac gggacccgtg agtttgaacc  16920
tgaaagagag ttcgacagaa tcaatctcgg tatcgttgac ggcggcctgc cgcaggatct  16980
cttgcacgtc gcccgagttg tcctggtagg cgatctcggt catgaactgc tcgatctcct  17040
cctcctgaag gtctccgcga ccggcgcgct ccacggtggc cgcgaggtcg ttggagatgc  17100
ggcccatgag ctgcgagaag gcgttcatgc ccgcctcgtt ccagacgcgg ctgtagacca  17160
cgacgccctc gggatcgcgg gcgcgcatga ccacctgggc gaggttgagc tccacgtggc  17220
gcgtgaagac cgcgtagttg cagaggcgct ggtagaggta gttgagcgtg gtggcgatgt  17280
gctcggtgac gaagaaatac atgatccagc ggcggagcgg catctcgctg acgtcgccca  17340
gcgcctccaa gcgttccatg gcctcgtaaa agtccacggc gaagttgaaa aactgggagt  17400
tgcgcgccga gacggtcaac tcctcctcca gaagacggat gagctcggcg atggtggcgc  17460
gcacctcgcg ctcgaaggcc cccgggagtt cctccacttc ctcctcttct tcctcctcca  17520
ctaacatctc ttctacttcc tcctcaggcg gtggtggtgg cgggggaggg ggcctgcgtc  17580
gccggcggcg cacgggcaga cggtcgatga agcgctcgat ggtctcgccg cgccggcgtc  17640
gcatggtctc ggtgacggcg cgcccgtcct cgcggggccg cagcgtgaag acgccgccgc  17700
gcatctccag gtggccgggg gggtccccgt tgggcaggga gagggcgctg acgatgcatc  17760
ttatcaattg ccccgtaggg actccgcgca aggacctgag cgtctcgaga tccacgggat  17820
ctgaaaaccg ttgaacgaag gcttcgagcc agtcgcagtc gcaaggtagg ctgagcacgg  17880
tttcttctgc cgggtcatgt tggggagcgg ggcgggcgat gctgctggtg atgaagttga  17940
aataggcggt tctgagacgg cggatggtgg cgaggagcac caggtctttg ggcccggctt  18000
gctggatgcg cagacggtcg gccatgcccc aggcgtggtc ctgacacctg gccaggtcct  18060
tgtagtagtc ctgcatgagc cgctccacgg gcacctcctc ctcgcccgcg cggccgtgca  18120
tgcgcgtgag cccgaagccg cgctggggct ggacgagcgc caggtcggcg acgacgcgct  18180
cggcgaggat ggcctgctgg atctgggtga gggtggtctg gaagtcgtca aagtcgacga  18240
agcggtggta ggctccggtg ttgatggtgt aggagcagtt ggccatgacg gaccagttga  18300
cggtctggtg gcccggacgc acgagctcgt ggtacttgag gcgcgagtag gcgcgcgtgt  18360
cgaagatgta gtcgttgcag gtgcgcacca ggtactggta gccgatgagg aagtgcggcg  18420
```

-continued

```
gcggctggcg gtagagcggc catcgctcgg tggcgggggc gccgggcgcg aggtcctcga  18480
gcatggtgcg gtggtagccg tagatgtacc tggacatcca ggtgatgccg gcggcggtgg  18540
tggaggcgcg cgggaactcg cggacgcggt tccagatgtt gcgcagcggc aggaagtagt  18600
tcatggtggg cacggtctgg cccgtgaggc gcgcgcagtc gtggatgctc tatacgggca  18660
aaaacgaaag cggtcagcgg ctcgactccg tggcctggag gctaagcgaa cgggttgggc  18720
tgcgcgtgta ccccggttcg aatctcgaat caggctggag ccgcagctaa cgtggtactg  18780
gcactcccgt ctcgacccaa gcctgcacca accctccagg atacggaggc gggtcgtttt  18840
gcaacttttt ttggaggccg gaaatgaaac tagtaagcgc ggaaagcggc cgaccgcgat  18900
ggctcgctgc cgtagtctgg agaagaatcg ccagggttgc gttgcggtgt gccccggttc  18960
gaggccggcc ggattccgcg gctaacgagg gcgtggctgc cccgtcgttt ccaagacccc  19020
atagccagcc gacttctcca gttacggagc gagcccctct tttgttttgt ttgtttttgc  19080
cagatgcatc ccgtactgcg gcagatgcgc ccccaccacc ctccaccgca acaacagccc  19140
cctcctccac agccggcgct tctgccccg ccccagcagc agcagcaact tccagccacg  19200
accgccgcgg ccgccgtgag cggggctgga cagacttctc agtatgatca cctggccttg  19260
gaagagggcg aggggctggc gcgcctgggg gcgtcgtcgc cggagcggca cccgcgcgtg  19320
cagatgaaaa gggacgctcg cgaggcctac gtgcccaagc agaacctgtt cagagacagg  19380
agcggcgagg agcccgagga gatgcgcgcg gcccggttcc acgcggggcg ggagctgcgg  19440
cgcggcctgg accgaaagag ggtgctgagg gacgaggatt tcgaggcgga cgagctgacg  19500
gggatcagcc ccgcgcgcgc gcacgtggcc gcggccaacc tggtcacggc gtacgagcag  19560
accgtgaagg aggagagcaa cttccaaaaa tccttcaaca accacgtgcg caccctgatc  19620
gcgcgcgagg aggtgaccct gggcctgatg cacctgtggg acctgctgga ggccatcgtg  19680
cagaacccca ccagcaagcc gctgacggcg cagctgttcc tggtggtgca gcatagtcgg  19740
gacaacgagg cgttcaggga ggcgctgctg aatatcaccg agcccgaggg ccgctggctc  19800
ctggacctgg tgaacattct gcagagcatc gtggtgcagg agcgcgggct gccgctgtcc  19860
gagaagctgg cggccatcaa cttctcggtg ctgagtctgg gcaagtacta cgctaggaag  19920
atctacaaga ccccgtacgt gcccatagac aaggaggtga agatcgacgg gttttacatg  19980
cgcatgaccc tgaaagtgct gaccctgagc gacgatctgg gggtgtaccg caacgacagg  20040
atgcaccgcg cggtgagcgc cagcaggcgg cgcgagctga gcgaccagga gctgatgcac  20100
agcctgcagc gggccctgac cggggccggg accgaggggg agagctactt tgacatgggc  20160
gcggacctgc actggcagcc cagccgccgg gccttggagg cggcaggcgg tccccccctac  20220
atagaagagg tggacgatga ggtggacgag gagggcgagt acctggaaga ctgatggcgc  20280
gaccgtattt ttgctagatg caacaacagc cacctcctga tcccgcgatg cgggcggcgc  20340
tgcagagcca gccgtccggc attaactcct cggacgattg gacccaggcc atgcaacgca  20400
tcatggcgct gacgacccgc aaccccgaag cctttagaca gcagccccag gccaaccggc  20460
tctcggccat cctggaggcc gtggtgccct cgcgctccaa ccccacgcac gagaaggtcc  20520
tggccatcgt gaacgcgctg gtggagaaca aggccatccg cggcgacgag gccggcctgg  20580
tgtacaacgc gctgctggag cgcgtggccc gctacaacag caccaacgtg cagaccaacc  20640
tggaccgcat ggtgaccgac gtgcgcgagg ccgtggccca gcgcgagcgg ttccaccgcg  20700
agtccaacct gggatccatg gtggcgctga acgccttcct cagcacccag cccgccaacg  20760
```

```
tgccccgggg ccaggaggac tacaccaact tcatcagcgc cctgcgcctg atggtgaccg  20820
aggtgcccca gagcgaggtg taccagtccg ggccggacta cttcttccag accagtcgcc  20880
agggcttgca gaccgtgaac ctgagccagg cgttcaagaa cttgcagggc ctgtggggcg  20940
tgcaggcccc ggtcggggac cgcgcgacgg tgtcgagcct gctgacgccg aactcgcgcc  21000
tgctgctgct gctggtggcc cccttcacgg acagcggcag catcaaccgc aactcgtacc  21060
tgggctacct gattaacctg taccgcgagg ccatcggcca ggcgcacgtg gacgagcaga  21120
cctaccagga gatcacccac gtgagccgcg ccctgggcca ggacgacccg ggcaatctgg  21180
aagccaccct gaactttttg ctgaccaacc ggtcgcagaa gatcccgccc cagtacacgc  21240
tcagcgccga ggaggagcgc atcctgcgat acgtgcagca gagcgtgggc ctgttcctga  21300
tgcaggaggg ggccaccccc agcgccgcgc tcgacatgac cgcgcgcaac atggagccca  21360
gcatgtacgc cagcaaccgc ccgttcatca ataaactgat ggactacttg catcgggcgg  21420
ccgccatgaa ctctgactat ttcaccaacg ccatcctgaa tccccactgg ctcccgccgc  21480
cggggttcta cacgggcgag tacgacatgc ccgaccccaa tgacgggttc ctgtgggacg  21540
atgtggacag cagcgtgttc tccccccgac cgggtgctaa cgagcgcccc ttgtggaaga  21600
aggaaggcag cgaccgacgc ccgtcctcgg cgctgtccgg ccgcgagggt gctgccgcgg  21660
cggtgcccga ggccgccagt cctttcccga gcttgccctt ctcgctgaac agtattcgca  21720
gcagcgagct gggcaggatc acgcgcccgc gcttgctggg cgaggaggag tacttgaatg  21780
actcgctgtt gagacccgag cgggagaaga acttccccaa taacgggata gagagcctgg  21840
tggacaagat gagccgctgg aagacgtatg cgcaggagca cagggacgat ccgtcgcagg  21900
gggccacgag ccggggcagc gccgcccgta aacgccggtg gcacgacagg cagcggggac  21960
tgatgtggga cgatgaggat tccgccgacg acagcagcgt gttggacttg ggtgggagtg  22020
gtaacccgtt cgctcacctg cgcccccgca tcgggcgcat gatgtaagag aaaccgaaaa  22080
taaatgatac tcaccaaggc catggcgacc agcgtgcgtt cgtttcttct ctgttgttgt  22140
atctagtatg atgaggcgtg cgtacccgga gggtcctcct ccctcgtacg agagcgtgat  22200
gcagcaggcg atggcggcgg cggcggcgat gcagcccccg ctggaggctc cttacgtgcc  22260
cccgcggtac ctggcgccta cggaggggcg gaacagcatt cgttactcgg agctggcacc  22320
cttgtacgat accacccggt tgtacctggt ggacaacaag tcggcggaca tcgcctcgct  22380
gaactaccag aacgaccaca gcaacttcct gaccaccgtg gtgcagaaca atgacttcac  22440
ccccacggag gccagcaccc agaccatcaa ctttgacgag cgctcgcggt ggggcggtca  22500
gctgaaaacc atcatgcaca ccaacatgcc caacgtgaac gagttcatgt acagcaacaa  22560
gttcaaggcg cgggtgatgg tctcccgcaa gacccccaac ggggtgacag tgacagatgg  22620
tagtcaggat atcttggagt atgaatgggt ggagtttgag ctgcccgaag gcaacttctc  22680
ggtgaccatg accatcgacc tgatgaacaa cgccatcatc gacaattact tggcggtggg  22740
gcggcagaac ggggtcctgg agagcgatat cggcgtgaag ttcgacacta ggaacttcag  22800
gctgggctgg gaccccgtga ccgagctggt catgcccggg gtgtacacca acgaggcctt  22860
ccaccccgat attgtcttgc tgcccggctg cggggtggac ttcaccgaga gccgcctcag  22920
caacctgctg ggcattcgca agaggcagcc cttccaggag ggcttccaga tcatgtacga  22980
ggatctggag gggggcaaca tccccgcgct cctggatgtc gacgcctatg agaaaagcaa  23040
ggaggagagc gccgccgcgg cgactgcagc tgtagccacc gcctctaccg aggtcagggg  23100
cgataatttt gccagccctg cagcagtggc agcggccgag gcggctgaaa ccgaaagtaa  23160
```

gatagtcatt cagccggtgg agaaggatag caaggacagg agctacaacg tgctgccgga 23220
caagataaac accgcctacc gcagctggta cctggcctac aactatggcg accccgagaa 23280
gggcgtgcgc tcctggacgc tgctcaccac ctcggacgtc acctgcggcg tggagcaagt 23340
ctactggtcg ctgcccgaca tgatgcaaga cccggtcacc ttccgctcca cgcgtcaagt 23400
tagcaactac ccggtggtgg gcgccgagct cctgcccgtc tactccaaga gcttcttcaa 23460
cgagcaggcc gtctactcgc agcagctgcg cgccttcacc tcgctcacgc acgtcttcaa 23520
ccgcttcccc gagaaccaga tcctcgtccg cccgcccgcg cccaccatta ccaccgtcag 23580
tgaaaacgtt cctgctctca cagatcacgg gaccctgccg ctgcgcagca gtatccgggg 23640
agtccagcgc gtgaccgtta ctgacgccag acgccgcacc tgcccctacg tctacaaggc 23700
cctgggcata gtcgcgccgc gcgtcctctc gagccgcacc ttctaaaaaa tgtccattct 23760
catctcgccc agtaataaca ccggttgggg cctgcgcgcg cccagcaaga tgtacggagg 23820
cgctcgccaa cgctccacgc aacaccccgt gcgcgtgcgc gggcacttcc gcgctccctg 23880
gggcgccctc aagggccgcg tgcggtcgcg caccaccgtc gacgacgtga tcgaccaggt 23940
ggtggccgac gcgcgcaact acacccccgc cgccgcgccc gtctccaccg tggacgccgt 24000
catcgacagc gtggtggccg acgcgcgccg gtacgcccgc gccaagagcc ggcggcggcg 24060
catcgcccgg cggcaccgga gcacccccgc catgcgcgcg gcgcgagcct tgctgcgcag 24120
ggccaggcgc acgggacgca gggccatgct cagggcggcc agacgcgcgg cttcaggcgc 24180
cagcgccggc aggacccgga gacgcgcggc cacggcggcg gcagcggcca tcgccagcat 24240
gtcccgcccg cggcgaggga acgtgtactg ggtgcgcgac gccgccaccg gtgtgcgcgt 24300
gcccgtgcgc acccgccccc ctcgcacttg aagatgttca cttcgcgatg ttgatgtgtc 24360
ccagcggcga ggaggatgtc caagcgcaaa ttcaaggaag agatgctcca ggtcatcgcg 24420
cctgagatct acggccccgc ggtggtgaag gaggaaagaa agccccgcaa aatcaagcgg 24480
gtcaaaaagg acaaaaagga agaagatgac gatctggtgg agtttgtgcg cgagttcgcc 24540
ccccggcggc gcgtgcagtg gcgcgggcgg aaagtgcacc cggtgctgag acccggcacc 24600
accgtggtct tcacgcccgg cgagcgctcc ggcagcgctt ccaagcgctc ctacgacgag 24660
gtgtacgggg acgaggacat cctcgagcag gcggccgagc gcctgggcga gtttgcttac 24720
ggcaagcgca gccgccccgc cctgaaggaa gaggcggtgt ccatcccgct ggaccacggc 24780
aaccccacgc cgagcctcaa gcccgtgacc ctgcagcagg tgctgccgag cgcagcgccg 24840
cgccgggggt tcaagcgcga gggcgaggat ctgtacccca ccatgcagct gatggtgccc 24900
aagcgccaga agctggaaga cgtgctggag accatgaagg tggacccgga cgtgcagccc 24960
gaggtcaagg tgcggcccat caagcaggtg gccccgggcc tgggcgtgca gaccgtggac 25020
atcaagatcc ccacggagcc catggaaacg cagaccgagc ccatgatcaa gcccagcacc 25080
agcaccatgg aggtgcagac ggatccctgg atgccatcgg ctcctagccg aagaccccgg 25140
cgcaagtacg gcgcggccag cctgctgatg cccaactacg cgctgcatcc ttccatcatc 25200
cccacgccgg gctaccgcgg cacgcgcttc taccgcggtc atacaaccag ccgccgccgc 25260
aagaccacca cccgccgccg ccgtcgccgc acagccgctg catctacccc tgccgccctg 25320
gtgcggagag tgtaccgccg cggccgcgcg cctctgaccc taccgcgcgc gcgctaccac 25380
ccgagcatcg ccatttaaac tttcgcctgc tttgcagatg gccctcacat gccgcctccg 25440
cgttcccatt acgggctacc gaggaagaaa accgcgccgt agaaggctgg cggggaacgg 25500

-continued

```
gatgcgtcgc caccaccatc ggcggcggcg cgccatcagc aagcggttgg ggggaggctt  25560
cctgcccgcg ctgatcccca tcatcgccgc ggcgatcggg gcgatccccg gcattgcttc  25620
cgtggcggtg caggcctctc agcgccactg agacacttgg aaaacatctt gtaataaacc  25680
aatggactct gacgctcctg gtcctgtgat gtgttttcgt agacagatgg aagacatcaa  25740
tttttcgtcc ctggctccgc gacacggcac gcggccgttc atgggcacct ggagcgacat  25800
cggcaccagc caactgaacg ggggcgcctt caattggagc agtctctgga gcgggcttaa  25860
gaatttcggg tccacgctta aaacctatgg cagcaaggcg tggaacagca ccacagggca  25920
ggcgctgagg gataagctga aagagcagaa cttccagcag aaggtggtcg atgggctcgc  25980
ctcgggcatc aacggggtgg tggacctggc caaccaggcc gtgcagcggc agatcaacag  26040
ccgcctggac ccggtgccgc ccgccggctc cgtggagatg ccgcaggtgg aggaggagct  26100
gcctcccctg gacaagcggg gcgagaagcg accccgcccc gacgcggagg agacgctgct  26160
gacgcacacg gacgagccgc ccccgtacga ggaggcggtg aaactgggtc tgcccaccac  26220
gcggcccatc gcgcccctgg ccaccggggt gctgaaaccc gaaagtaata agcccgcgac  26280
cctggacttg cctcctcccg cttcccgccc ctctacagtg gctaagcccc tgccgccggt  26340
ggccgtggcc cgcgcgcgac ccgggggctc cgcccgccct catgcgaact ggcagagcac  26400
tctgaacagc atcgtgggtc tgggagtgca gagtgtgaag cgccgccgct gctattaaac  26460
ctaccgtagc gcttaacttg cttgtctgtg tgtgtatgta ttatgtcgcc gctgtccgcc  26520
agaaggagga gtgaagaggc gcgtcgccga gttgcaagat ggccacccca tcgatgctgc  26580
cccagtgggc gtacatgcac atcgccggac aggacgcttc ggagtacctg agtccgggtc  26640
tggtgcagtt cgcccgcgcc acagacacct acttcagtct ggggaacaag tttaggaacc  26700
ccacggtggc gcccacgcac gatgtgacca ccgaccgcag ccagcggctg acgctgcgct  26760
tcgtgcccgt ggaccgcgag gacaacacct actcgtacaa agtgcgctac acgctggccg  26820
tgggcgacaa ccgcgtgctg gacatggcca gcacctactt tgacatccgc ggcgtgctgg  26880
atcggggccc tagcttcaaa ccctactccg gcaccgccta caacagcctg gctcccaagg  26940
gagcgcccaa ttccagccag tgggagcaaa aaaaggcagg caatggtgac actatggaaa  27000
cacacacatt tggtgtggcc ccaatgggcg gtgagaatat tacaatcgac ggattacaaa  27060
ttggaactga cgctacagct gatcaggata aaccaattta tgctgacaaa acattccagc  27120
ctgaacctca agtaggagaa gaaaattggc aagaaactga aagcttttat ggcggtaggg  27180
ctcttaaaaa agacacaagc atgaaacctt gctatggctc ctatgctaga cccaccaatg  27240
taaagggagg tcaagctaaa cttaaagttg gagctgatgg agttcctacc aaagaatttg  27300
acatagacct ggctttcttt gatactcccg gtggcacagt gaatggacaa gatgagtata  27360
aagcagacat tgtcatgtat accgaaaaca cgtatctgga aactccagac acgcatgtgg  27420
tatacaaacc aggcaaggat gatgcaagtt ctgaaattaa cctggttcag cagtccatgc  27480
ccaatagacc caactatatt gggttcagag acaactttat tgggctcatg tattacaaca  27540
gtactggcaa tatgggggtg ctggctggtc aggcctcaca gctgaatgct gtggtcgact  27600
tgcaagacag aaacaccgag ctgtcatacc agctcttgct tgactctttg ggtgacagaa  27660
cccggtattt cagtatgtgg aatcaggcgg tggacagtta tgatcctgat gtgcgcatta  27720
ttgaaaacca tggtgtggaa gacgaacttc ccaactattg cttcccccctg gatgggtctg  27780
gcactaatgc cgcttaccaa ggtgtgaaag taaaaaatgg taacgatggt gatgttgaga  27840
gcgaatggga aaatgatgat actgtcgcag ctcgaaatca attatgcaag ggcaacattt  27900
```

ttgccatgga aattaacctc caagccaacc tgtggagaag tttcctctac tcgaacgtgg 27960
ccctgtacct gcccgactct tacaagtaca cgccagccaa catcaccctg cccaccaaca 28020
ccaacactta tgattacatg aacgggagag tggtgcctcc ctcgctggtg gacgcctaca 28080
tcaacatcgg ggcgcgctgg tcgctggacc ccatggacaa cgtcaatccc ttcaaccacc 28140
accgcaacgc gggcctgcgc taccgctcca tgctcctggg caacgggcgc tacgtgccct 28200
tccacatcca ggtgccccag aaatttttcg ccatcaagag cctcctgctc ctgcccgggt 28260
cctacaccta cgagtggaac ttccgcaagg acgtcaacat gatcctgcag agctccctcg 28320
gcaacgacct gcgcacggac ggggcctcca tctccttcac cagcatcaac ctctacgcca 28380
ccttcttccc catggcgcac aacacggcct ccacgctcga ggccatgctg cgcaacgaca 28440
ccaacgacca gtccttcaac gactacctct cggcggccaa catgctctac cccatcccgg 28500
ccaacgccac caacgtgccc atctccatcc cctcgcgcaa ctgggccgcc ttccgcggct 28560
ggtccttcac gcgcctcaag accaaggaga cgccctcgct gggctccggg ttcgacccct 28620
acttcgtcta ctcgggctcc atcccctacc tcgacggcac cttctacctc aaccacacct 28680
tcaagaaggt ctccatcacc ttcgactcct ccgtcagctg gcccggcaac gaccggctcc 28740
tgacgcccaa cgagttcgaa atcaagcgca ccgtcgacgg cgagggatac aacgtggccc 28800
agtgcaacat gaccaaggac tggttcctgg tccagatgct ggcccactac aacatcggct 28860
accagggctt ctacgtgccc gagggctaca aggaccgcat gtactccttc ttccgcaact 28920
tccagcccat gagccgccag gtggtggacg aggtcaacta caaggactac caggccgtca 28980
ccctggccta ccagcacaac aactcgggct tcgtcggcta cctcgcgccc accatgcgcc 29040
agggccagcc ctaccccgcc aactacccgt acccgctcat cggcaagagc gccgtcacca 29100
gcgtcaccca gaaaaagttc ctctgcgaca gggtcatgtg gcgcatcccc ttctccagca 29160
acttcatgtc catgggcgcg ctcaccgacc tcggccagaa catgctctat gccaactccg 29220
cccacgcgct agacatgaat ttcgaagtcg accccatgga tgagtccacc cttctctatg 29280
ttgtcttcga agtcttcgac gtcgtccgag tgcaccagcc ccaccgcggc gtcatcgagg 29340
ccgtctacct gcgcaccccc ttctcggccg gtaacgccac cacctaaatt gctacttgca 29400
tgatggctga gcccacaggc tccggcgagc aggagctcag ggccatcatc cgcgacctgg 29460
gctgcgggcc ctacttcctg ggcaccttcg ataagcgctt cccgggattc atggccccgc 29520
acaagctggc ctgcgccatc gtcaacacgg ccggccgcga gaccgggggc gagcactggc 29580
tggccttcgc ctggaacccg cgctcgaaca cctgctacct cttcgacccc ttcgggttct 29640
cggacgagcg cctcaagcag atctaccagt tcgagtacga gggcctgctg cgccgtagcg 29700
ccctggccac cgaggaccgc tgcgtcaccc tggaaaagtc cacccagacc gtgcagggtc 29760
cgcgctcggc cgcctgcggg ctcttctgct gcatgttcct gcacgccttc gtgcactggc 29820
ccgaccgccc catggacaag aaccccacca tgaacttgct gacgggggtg cccaacggca 29880
tgctccagtc gccccaggtg gaacccaccc tgcgccgcaa ccaggaggcg ctctaccgct 29940
tcctcaactc ccactccgcc tactttcgct cccaccgcgc gcgcatcgag aaggccaccg 30000
ccttcgaccg catgaacaat caagacatgt aaaccgtgtg tgtatgttta aaatatcttt 30060
taataaacag cactttaatg ttacacatgc atctgagatg attttatttt agaaatcgaa 30120
agggttctgc cgggtctcgg catggcccgc gggcagggac acgttgcgga actggtactt 30180
ggccagccac ttgaactcgg ggatcagcag tttgggcagc ggggtgtcgg ggaaggagtc 30240

```
ggtccacagc ttccgcgtca gctgcagggc gcccagcagg tcgggcgcgg agatcttgaa  30300
atcgcagttg ggacccgcgt tctgcgcgcg agagttgcgg tacacggggt tgcagcactg  30360
gaacaccatc agggccgggt gcttcacgct cgccagcacc gccgcgtcgg tgatgctctc  30420
cacgtcgagg tcctcggcgt tggccatccc gaagggggtc atcttgcagg tctgccttcc  30480
catggtgggc acgcacccgg gcttgtggtt gcaatcgcag tgcaggggga tcagcatcat  30540
ctgggcctgg tcggcgttca tccccgggta catggccttc atgaaagcct ccaattgcct  30600
gaacgcctgc tgggccttgg ctccctcggt gaagaagacc ccgcaggact tgctagagaa  30660
ctggttggtg gcacagccgg catcgtgcac gcagcagcgc gcgtcgttgt tggccagctg  30720
caccacgctg cgcccccagc ggttctgggt gatcttggcc cggtcggggt tctccttcag  30780
cgcgcgctgc ccgttctcgc tcgccacatc catctcgatc atgtgctcct tctggatcat  30840
ggtggtcccg tgcaggcacc gcagtttgcc ctcggcctcg gtgcacccgt gcagccacag  30900
cgcgcacccg gtgcactccc agttcttgtg ggcgatctgg gaatgcgcgt gcacgaaccc  30960
ttgcaggaag cggcccatca tggtcgtcag ggtcttgttg ctagtgaagg tcaacgggat  31020
gccgcggtgc tcctcgttga tgtacaggtg gcagatgcgg cggtacacct cgccctgctc  31080
gggcatcagt tggaagttgg ctttcaggtc ggtctccacg cggtagcggt ccatcagcat  31140
agtcatgatt tccatgccct tctcccaggc cgagacgatg ggcaggctca tagggttctt  31200
caccatcatc ttagcactag cagccgcggc cagggggtcg ctctcatcca gggtctcaaa  31260
gctccgcttg ccgtccttct cggtgatccg caccgggggg tagctgaagc ccacggccgc  31320
cagctcctcc tcggcctgtc tttcgtcctc gctgtcctgg ctgacgtcct gcatgaccac  31380
atgcttggtc ttgcggggtt tcttcttggg cggcagtggc ggcggagatg cttgtggcga  31440
gggggagcgc gagttctcgc tcaccactac tatctcttcc tcttcttggt ccgaggccac  31500
gcggcggtag gtatgtctct tcgggggcag aggcggaggc gacgggctct cgccgccgcg  31560
acttggcgga tggctggcag agccccttcc gcgttcgggg gtgcgctccc ggcggcgctc  31620
tgactgactt cctccgcggc cggccattgt gttctcctag ggaggaacaa caagcatgga  31680
gactcagcca tcgccaacct cgccatctgc ccccaccgcc ggcgacgaga agcagcagca  31740
gcagaatgaa agcttaaccg ccccgccgcc cagccccgcc tccgacgcag ccgcggtccc  31800
agacatgcaa gagatggagg aatccatcga gattgacctg ggctatgtga cgcccgcgga  31860
gcatgaggag gagctggcag tgcgctttca atcgtcaagc caggaagata aagaacagcc  31920
agagcaggaa gcagagaacg agcagagtca ggctgggctc gagcatggcg actacctcca  31980
cctgagcggg gaggaggacg cgctcatcaa gcatctggcc cggcaggcca ccatcgtcaa  32040
ggacgcgctg ctcgaccgca ccgaggtgcc cctcagcgtg gaggagctca gccgcgccta  32100
cgagctcaac ctcttctcgc cgcgcgtgcc ccccaagcgc cagcccaacg gcacctgcga  32160
gcccaacccc cgcctcaact tctacccggt cttcgcggtg cccgaggccc tggccaccta  32220
ccacatcttt ttcaagaacc aaaagatccc cgtctcctgc cgcgccaacc gcacccgcgc  32280
cgacgccctc ttcaacctgg gtcccggcgc ccgcctacct gatatcgcct ccttggaaga  32340
ggttcccaag atcttcgagg gtctgggcag cgacgagact cgggccgcga acgctctgca  32400
aggagaagga ggaggagagc atgagcacca cagcgccctg gtcgagttgg aaggcgacaa  32460
cgcgcggctg gcggtgctca aacgcacggt cgagctgacc catttcgcct acccggctct  32520
gaacctgccc ccgaaagtca tgagcgcggt catggaccag gtgctcatca agcgcgcgtc  32580
gcccatctcc gaggacgagg gcatgcaaga ctccgaggag ggcaagcccg tggtcagcga  32640
```

```
cgagcagctg gcccggtggc tgggtcctaa tgctacccct caaagtttgg aagagcggcg  32700
caagctcatg atggccgtgg tcctggtgac cgtggagctg gagtgcctgc gccgcttctt  32760
cgccgacgcg gagaccctgc gcaaggtcga ggagaacctg cactacctct tcaggcacgg  32820
gttcgtgcgc caggcctgca agatctccaa cgtggagctg accaacctgg tctcctacat  32880
gggcatcttg cacgagaacc gcctggggca gaacgtgctg cacaccaccc tgcgcgggga  32940
ggcccgccgc gactacatcc gcgactgcgt ctacctctac ctctgccaca cctggcagac  33000
gggcatgggc gtgtggcagc agtgtctgga ggagcagaac ctgaaagagc tctgcaagct  33060
cctgcaaaag aacctcaagg gtctgtggac cgggttcgac gagcggacca ccgcctcgga  33120
cctggccgac ctcatcttcc ccgagcgcct caggctgacg ctgcgcaacg gcctgcccga  33180
ctttatgagc caaagcatgt tgcaaaactt tcgctctttc atcctcgaac gctccggaat  33240
cctgcccgcc acctgctccg cgctgccctc ggacttcgtg ccgctgacct tccgcgagtg  33300
ccccccgccg ctgtggagcc actgctacct gctgcgcctg gccaactacc tggcctacca  33360
ctcggacgtg atcgaggacg tcagcggcga gggcctgctc gagtgccact gccgctgcaa  33420
cctctgcacg ccgcaccgct ccctggcctg caaccccag ctgctgagcg agacccagat  33480
catcggcacc ttcgagttgc aagggcccag cgagggcgag ggagccaagg ggggtctgaa  33540
actcaccccg gggctgtgga cctcggccta cttgcgcaag ttcgtgcccg aggattacca  33600
tcccttcgag atcaggttct acgaggacca atcccagccg cccaaggccg agctgtcggc  33660
ctgcgtcatc acccaggggg cgatcctggc ccaattgcaa gccatccaga aatcccgcca  33720
agaattcttg ctgaaaaagg gccgcggggt ctacctcgac ccccagaccg gtgaggagct  33780
caaccccggc ttcccccagg atgccccgag gaaacaagaa gctgaaagtg gagctgccgc  33840
ccgtggagga tttggaggaa gactgggaga acagcagtca ggcagaggag atggaggaag  33900
actgggacag cactcaggca gaggaggaca gcctgcaaga cagtctggag gaagacgagg  33960
aggaggcaga ggaggaggtg gaagaagcag ccgccgccag accgtcgtcc tcggcggggg  34020
agaaagcaag cagcacggat accatctccg ctccgggtcg gggtcccgct cggccccaca  34080
gtagatggga cgagaccggg cgattcccga accccaccac ccagaccggt aagaaggagc  34140
ggcagggata caagtcctgg cgggggcaca aaaacgccat cgtctcctgc ttgcaggcct  34200
gcgggggcaa catctccttc acccggcgct acctgctctt ccaccgcggg gtgaacttcc  34260
cccgcaacat cttgcattac taccgtcacc tccacagccc ctactacttc caagaagagg  34320
cagcagcagc agaaaaagac cagaaaacca gctagaaaat ccacagcggc ggcagcggca  34380
ggtggactga ggatcgcggc gaacgagccg gcgcagaccc gggagctgag gaaccggatc  34440
tttcccaccc tctatgccat cttccagcag agtcgggggc aggagcagga actgaaagtc  34500
aagaaccgtt ctctgcgctc gctcacccgc agttgtctgt atcacaagag cgaagaccaa  34560
cttcagcgca ctctcgagga cgccgaggct ctcttcaaca agtactgcgc gctcactctt  34620
aaagagtagc ccgcgcccgc ccagtcgcag aaaaaggcgg gaattacgtc acctgtgccc  34680
ttcgccctag ccgcctccac ccagcaccgc catgagcaaa gagattccca cgccttacat  34740
gtggagctac cagccccaga tgggcctggc cgccggcgcc gcccaggact actccacccg  34800
catgaattgg ctcagcgccg ggcccgcgat gatctcacgg gtgaatgaca tccgcgccca  34860
ccgaaaccag atactcctag aacagtcagc gctcaccgcc acgccccgca atcacctcaa  34920
tccgcgtaat tggcccgccg ccctggtgta ccaggaaatt ccccagccca cgaccgtact  34980
```

```
acttccgcga gacgcccagg ccgaagtcca gctgactaac tcaggtgtcc agctggcggg  35040
cggcgccacc ctgtgtcgtc accgccccgc tcagggtata aagcggctgg tgatccgggg  35100
cagaggcaca cagctcaacg acgaggtggt gagctcttcg ctgggtctgc gacctgacgg  35160
agtcttccaa ctcgccggat cggggagatc ttccttcacg cctcgtcagg cggtcctgac  35220
tttggagagt tcgtcctcgc agccccgctc gggcggcatc ggcactctcc agttcgtgga  35280
ggagttcact ccctcggtct acttcaaccc cttctccggc tcccccggcc actacccgga  35340
cgagttcatc ccgaactttg acgccatcag cgagtcggtg gacggctacg attgattaat  35400
taatcaacta accccttacc cctttaccct ccagtaaaaa taaagattaa aaatgattga  35460
attgatcaat aaagaatcac ttacttgaaa tctgaaacca ggtctctgtc catgttttct  35520
gtcagcagca cttcactccc ctcttcccaa ctctggtact gcaggccccg gcgggctgca  35580
aacttcctcc acactctgaa ggggatgtca aattcctcct gtccctcaat cttcattttt  35640
atcttctatc agatgtccaa aaagcgcgcg cgggtggatg atggcttcga ccccgtgtac  35700
ccctacgatg cagacaacgc accgactgtg cccttcatca accctccctt cgtctcttca  35760
gatggattcc aagaaaagcc cctgggggtg ttgtccctgc gactggccga ccccgtcacc  35820
accaagaatg gggctgtcac cctcaagctg ggggaggggg tggacctcga cgactcggga  35880
aaactcatct ccaaaaatgc caccaaggcc actgcccctc tcagtatttc caacggcacc  35940
atttccctta acatggctgc cccttttac aacaacaatg gaacgttaag tctcaatgtt  36000
tctacaccat tagcagtatt tcccactttt aacactttag gtatcagtct tggaaacggt  36060
cttcaaactt ctaataagtt gctgactgta cagttaactc atcctcttac attcagctca  36120
aatagcatca cagtaaaaac agacaaagga ctctatatta attctagtgg aaacagaggg  36180
cttgaggcta acataagcct aaaaagagga ctgatttttg atggtaatgc tattgcaaca  36240
taccttggaa gtggtttaga ctatggatcc tatgatagcg atgggaaaac aagacccatc  36300
atcaccaaaa ttggagcagg tttgaatttt gatgctaata atgccatggc tgtgaagcta  36360
ggcacaggtt taagttttga ctctgccggt gccttaacag ctggaaacaa agaggatgac  36420
aagctaacac tttggactac acctgaccca agccctaatt gtcaattact ttcagacaga  36480
gatgccaaat ttaccctatg tcttacaaaa tgcggtagtc aaatactagg cactgttgca  36540
gtagctgctg ttactgtagg ttcagcacta aatccaatta atgacacagt aaaaagcgcc  36600
atagtattcc ttagatttga ctctgacggt gtgctcatgt caaactcatc aatggtaggt  36660
gattactgga actttaggga aggacagacc acccaaagtg tggcctatac aaatgctgtg  36720
ggattcatgc ccaatctagg tgcatatcct aaaacccaaa gcaaaacacc aaaaaatagt  36780
atagtaagtc aggtatattt aaatggagaa actactatgc caatgacact gacaataact  36840
ttcaatggca ctgatgaaaa agacacaaca cctgtgagca cttactccat gacttttaca  36900
tggcagtgga ctggagacta taaggacaag aatattacct ttgctaccaa ctcctttact  36960
ttctcctaca tggcccaaga ataaaccctg catgccaacc ccattgttcc caccactatg  37020
gaaaactctg aagcagaaaa aaataaagtt caagtgtttt attgattcaa cagttttctc  37080
acagaaccct agtattcaac ctgccacctc cctcccaaca cacagagtac acagtccttt  37140
ctccccggct ggccttaaaa agcatcatat catgggtaac agacatattc ttaggtgtta  37200
tattccacac ggtttcctgt cgagccaaac gctcatcagt gatattaata aactccccgg  37260
gcagctcact taagttcatg tcgctgtcca gctgctgagc cacaggctgc tgtccaactt  37320
gcggttgctt aacgggcggc gaaggagaag tccacgccta catgggggta gagtcataat  37380
```

```
cgtgcatcag gatagggcgg tggtgctgca gcagcgcgcg aataaactgc tgccgccgcc  37440
gctccgtcct gcaggaatac aacatggcag tggtctcctc agcgatgatt cgcaccgccc  37500
gcagcataag gcgccttgtc ctccgggcac agcagcgcac cctgatctca cttaaatcag  37560
cacagtaact gcagcacagc accacaatat tgttcaaaat cccacagtgc aaggcgctgt  37620
atccaaagct catggcgggg accacagaac ccacgtggcc atcataccac aagcgcaggt  37680
agattaagtg gcgacccctc ataaacacgc tggacataaa cattacctct tttggcatgt  37740
tgtaattcac cacctcccgg taccatataa acctctgatt aaacatggcg ccatccacca  37800
ccatcctaaa ccagctggcc aaaacctgcc cgccggctat acactgcagg gaaccgggac  37860
tggaacaatg acagtggaga gcccaggact cgtaaccatg gatcatcatg ctcgtcatga  37920
tatcaatgtt ggcacaacac aggcacacgt gcatacactt cctcaggatt acaagctcct  37980
cccgcgttag aaccatatcc cagggaacaa cccattcctg aatcagcgta aatcccacac  38040
tgcagggaag acctcgcacg taactcacgt tgtgcattgt caaagtgtta cattcgggca  38100
gcagcggatg atcctccagt atggtagcgc gggtttctgt ctcaaaagga ggtagacgat  38160
ccctactgta cggagtgcgc cgagacaacc gagatcgtgt tggtcgtagt gtcatgccaa  38220
atggaacgcc ggacgtagtc atatttcctg aagcaaaacc aggtgcgggc gtgacaaaca  38280
gatctgcgtc tccggtctcg ccgcttagat cgctctgtgt agtagttgta gtatatccac  38340
tctctcaaag catccaggcg ccccctggct tcgggttcta tgtaaactcc ttcatgcgcc  38400
gctgccctga taacatccac caccgcagaa taagccacac ccagccaacc tacacattcg  38460
ttctgcgagt cacacacggg aggagcggga agagctggaa gaaccatgat taactttatt  38520
ccaaacggtc tcggagcact tcaaaatgca ggtcccggag gtggcacctc tcgcccccac  38580
tgtgttggtg gaaaataaca gccaggtcaa aggtgacacg gttctcgaga tgttccacgg  38640
tggcttccag caaagcctcc acgcgcacat ccagaaacaa gaggacagcg aaagcgggag  38700
cgttttctaa ttcctcaatc atcatattac actcctgcac catccccaga taattttcat  38760
ttttccagcc ttgaatgatt cgtattagtt cctgaggtaa atccaagcca gccatgataa  38820
aaagctcgcg cagagcgccc tccaccggca ttcttaagca caccctcata attccaagag  38880
attctgctcc tggttcacct gcagcagatt aacaatggga atatcaaaat ctctgccgcg  38940
atccctaagc tcctccctca acaataactg tatgtaatct ttcatatcat ctccgaaatt  39000
tttagccata gggccgccag gaataagagc agggcaagcc acattacaga taaagcgaag  39060
tcctccccag tgwgcattgc caaatgtaag attgaaataa gcatgctggc tagaccctgt  39120
gatatcttcc agataactgg acagaaaatc aggcaagcaa tttttaagaa aatcaacaaa  39180
agaaaagtcg tccaggtgca ggtttagagc ctcaggaaca acgatggaat aagtgcaagg  39240
agtgcgttcc agcatggtta gtgttttttt ggtgatctgt agaacaaaaa ataaacatgc  39300
aatattaaac catgctagcc tggcgaacag gtgggtaaat cactctttcc agcaccaggc  39360
aggctacggg gtctccggcg cgaccctcgt agaagctgtc gccatgattg aaaagcatca  39420
ccgagagacc ttcccggtgg ccggcatgga tgattcgaga agaagcatac actccgggaa  39480
cattggcatc cgtgagtgaa aaaaagcgac ctataaagcc tcggggcact acaatgctca  39540
atctcaattc cagcaaagcc accccatgcg gatggagcac aaaattggca ggtgcgtaaa  39600
aaatgtaatt actcccctcc tgcacaggca gcaaagcccc cgctccctcc agaaacacat  39660
acaaagcctc agcgtccata gcttaccgag cacggcaggc gcaagagtca gagaaaaggc  39720
```

tgagctctaa cctgactgcc cgctcctgtg ctcaatatat agccctaacc tacactgacg 39780
taaaggccaa agtctaaaaa tacccgccaa aatgacacac acgcccagca cacgcccaga 39840
aaccggtgac acactcaaaa aaatacgtgc gcttcctcaa acgcccaaac cggcgtcatt 39900
tccgggttcc cacgctacgt caccgctcag cgactttcaa attccgtcga ccgttaaaaa 39960
cgtcactcgc cccgccccta acggtcgccc ttctctcggc caatcacctt cctcccttcc 40020
caaattcaaa cgcctcattt gcatattaac gcgcacaaaa agtttgaggt atatatttga 40080
atgatg 40086

<210> SEQ ID NO 119
<211> LENGTH: 43605
<212> TYPE: DNA
<213> ORGANISM: Artificial Sequence
<220> FEATURE:
<223> OTHER INFORMATION: Vector

<400> SEQUENCE: 119
gtttaaacgc ggccgccagg cctacccact agtcaattcg ggaggatcga aacggcagat 60
cgcaaaaaac agtacataca gaaggagaca tgaacatgaa catcaaaaaa attgtaaaac 120
aagccacagt tctgactttt acgactgcac ttctggcagg aggagcgact caagccttcg 180
cgaaagaaaa taaccaaaaa gcatacaaag aaacgtacgg cgtctctcat attacacgcc 240
atgatatgct gcagatccct aaacagcagc aaaacgaaaa ataccaagtg cctcaattcg 300
atcaatcaac gattaaaaat attgagtctg caaaaggact tgatgtgtgg gacagctggc 360
cgctgcaaaa cgctgacgga acagtagctg aatacaacgg ctatcacgtt gtgtttgctc 420
ttgcgggaag cccgaaagac gctgatgaca catcaatcta catgttttat caaaaggtcg 480
gcgacaactc aatcgacagc tggaaaaacg cgggccgtgt ctttaaagac agcgataagt 540
tcgacgccaa cgatccgatc ctgaaagatc agacgcaaga atggtccggt tctgcaacct 600
ttacatctga cggaaaaatc cgtttattct acactgacta ttccggtaaa cattacggca 660
aacaaagcct gacaacagcg caggtaaatg tgtcaaaatc tgatgacaca ctcaaaatca 720
acggagtgga agatcacaaa acgatttttg acggagacgg aaaaacatat cagaacgttc 780
agcagtttat cgatgaaggc aattatacat ccggcgacaa ccatacgctg agagaccctc 840
actacgttga agacaaaggc cataaatacc ttgtattcga agccaacacg ggaacagaaa 900
acggatacca aggcgaagaa tctttattta acaaagcgta ctacggcggc ggcacgaact 960
tcttccgtaa agaaagccag aagcttcagc agagcgctaa aaaacgcgat gctgagttag 1020
cgaacggcgc cctcggtatc atagagttaa ataatgatta cacattgaaa aaagtaatga 1080
agccgctgat cacttcaaac acggtaactg atgaaatcga gcgcgcgaat gttttcaaaa 1140
tgaacggcaa atggtacttg ttcactgatt cacgcggttc aaaaatgacg atcgatggta 1200
ttaactcaaa cgatatttac atgcttggtt atgtatcaaa ctctttaacc ggcccttaca 1260
agccgctgaa caaaacaggg cttgtgctgc aaatgggtct tgatccaaac gatgtgacat 1320
tcacttactc tcacttcgca gtgccgcaag ccaaaggcaa caatgtggtt atcacaagct 1380
acatgacaaa cagaggcttc ttcgaggata aaaaggcaac atttgcgcca agcttcttaa 1440
tgaacatcaa aggcaataaa acatccgttg tcaaaaacag catcctggag caaggacagc 1500
tgacagtcaa ctaataacag caaaaagaaa atgccgatac ttcattggca ttttctttta 1560
tttctcaaca agatggtgaa ttgactagtg ggtagatcca caggacgggt gtggtcgcca 1620
tgatcgcgta gtcgatagtg gctccaagta gcgaagcgag caggactggg cggcggccaa 1680

```
agcggtcgga cagtgctccg agaacgggtg cgcatagaaa ttgcatcaac gcatatagcg   1740
ctagcagcac gccatagtga ctggcgatgc tgtcggaatg gacgatatcc cgcaagaggc   1800
ccggcagtac cggcataacc aagcctatgc ctacagcatc cagggtgacg gtgccgagga   1860
tgacgatgag cgcattgtta gatttcatac acggtgcctg actgcgttag caatttaact   1920
gtgataaact accgcattaa agcttatcga tgataagctg tcaaacatga gaattgatcc   1980
ggaaccctta atataacttc gtataatgta tgctatacga agttattagg tccctcgact   2040
atagggtcac cgtcgacagc gacacacttg catcggatgc agcccggtta acgtgccggc   2100
acggcctggg taaccaggta ttttgtccac ataaccgtgc gcaaaatgtt gtggataagc   2160
aggacacagc agcaatccac agcaggcata caaccgcaca ccgaggttac tccgttctac   2220
aggttacgac gacatgtcaa tacttgccct tgacaggcat tgatggaatc gtagtctcac   2280
gctgatagtc tgatcgacaa tacaagtggg accgtggtcc cagaccgata atcagaccga   2340
crayacgagt gggaycgtgg tcccagacta ataatcagac cgacgatacg agtgggaccg   2400
tggtcccaga ctaataatca gaccgacgat acgagtggga ccgtggtycc agwctratwa   2460
tcagaccgac gatacragtg gracmgtggk cccagasaka atawtcagrc cgagwtaygc   2520
wktckggcct gtaacaaagg acattaagta aagacagata mrmgtgrgac taaaacgtgg   2580
tcccagtctg attatcagac cgacgatacg agtgggaccg tggtcccaga ctaataatca   2640
gaccgacgat acgagtggga ccgtggtccc agactaataa tcagaccgac gatacgagtg   2700
ggaccgtggt cccagtctga ttatcagacc gacgatacaa gtggaacagt gggcccagag   2760
agaatattca ggccagttat gctttctggc ctgtaacaaa ggacattaag taaagacaga   2820
taaacgtaga ctaaaacgtg gtcgcatcag ggtgctggct tttcaagttc cttaagaatg   2880
gcctcaattt tctctataca ctcagttgga acacgagacc tgtccaggtt aagcaccatt   2940
ttatcgccct tatacaatac tgtcgctcca ggagcaaact gatgtcgtga gcttaaacta   3000
gttcttgatg cagatgacgt tttaagcaca gaagttaaaa gagtgataac ttcttcagct   3060
tcaaatatca ccccagcttt ttctgctca tgaaggttag atgcctgctg cttaagtaat   3120
tcctctttat ctgtaaaggc tttttgaagt gcatcacctg accgggcaga tagttcaccg   3180
gggtgagaaa aaagagcaac aactgattta ggcaatttgg cggtgttgat acagcgggta   3240
ataatcttac gtgaaatatt ttccgcatca gccagcgcag aaatatttcc agcaaattca   3300
ttctgcaatc ggcttgcata acgctgacca cgttcataag cacttgttgg gcgataatcg   3360
ttacccaatc tggataatgc agccatctgc tcatcatcca gctcgccaac cagaacacga   3420
taatcacttt cggtaagtgc agcagcttta cgacggcgac tcccatcggc aatttctatg   3480
acaccagata ctcttcgacc gaacgccggt gtctgttgac cagtcagtag aaaagaaggg   3540
atgagatcat ccagtgcgtc ctcagtaagc agctcctggt cacgttcatt acctgaccat   3600
acccgagagg tcttctcaac actatcaccc cggagcactt caagagtaaa cttcacatcc   3660
cgaccacata caggcaaagt aatggcatta ccgcgagcca ttactcctac gcgcgcaatt   3720
aacgaatcca ccatcggggc agctggtgtc gataacgaag tatcttcaac cggttgagta   3780
ttgagcgtat gttttggaat aacaggcgca cgcttcatta tctaatctcc cagcgtggtt   3840
taatcagacg atcgaaaatt tcattgcaga caggttccca aatagaaaga gcatttctcc   3900
aggcaccagt tgaagagcgt tgatcaatgg cctgttcaaa aacagttctc atccggatct   3960
gacctttacc aacttcatcc gtttcacgta caacattttt tagaaccatg cttccccagg   4020
```

```
catcccgaat ttgctcctcc atccacgggg actgagagcc attactattg ctgtatttgg   4080
taagcaaaat acgtacatca ggctcgaacc ctttaagatc aacgttcttg agcagatcac   4140
gaagcatatc gaaaaactgc agtgcggagg tgtagtcaaa caactcagca ggcgtgggaa   4200
caatcagcac atcagcagca catacgacat taatcgtgcc gatacccagg ttaggcgcgc   4260
tgtcaataac tatgacatca tagtcatgag caacagtttc aatggccagt cggagcatca   4320
ggtgtggatc ggtgggcagt ttaccttcat caaatttgcc cattaactca gtttcaatac   4380
ggtgcagagc cagacaggaa ggaataatgt caagccccgg ccagcaagtg ggctttattg   4440
cataagtgac atcgtccttt tccccaagat agaaaggcag gagagtgtct tctgcatgaa   4500
tatgaagatc tggtacccat ccgtgataca ttgaggctgt tccctggggg tcgttacctt   4560
ccacgagcaa aacacgtagc cccttcagag ccagatcctg agcaagatga acagaaactg   4620
aggttttgta aacgccacct ttatgggcag caaccccgat caccggtgga aatacgtctt   4680
cagcacgtcg caatcgcgta ccaaacacat cacgcatatg attaatttgt tcaattgtat   4740
aaccaacacg ttgctcaacc cgtcctcgaa tttccatatc cgggtgcggt agtcgccctg   4800
ctttctcggc atctctgata gcctgagaag aaaccccaac taaatccgct gcttcaccta   4860
ttctccagcg ccgggttatt ttcctcgctt ccgggctgtc atcattaaac tgtgcaatgg   4920
cgatagcctt cgtcatttca tgaccagcgt ttatgcactg gttaagtgtt tccatgagtt   4980
tcattctgaa catcctttaa tcattgcttt gcgttttttt attaaatctt gcaatttact   5040
gcaaagcaac aacaaaatcg caaagtcatc aaaaaaccgc aaagttgttt aaaataagag   5100
caacactaca aaaggagata agaagagcac atacctcagt cacttattat cactagcgct   5160
cgccgcagcc gtgtaaccga gcatagcgag cgaactggcg aggaagcaaa gaagaactgt   5220
tctgtcagat agctcttacg ctcagcgcaa gaagaaatat ccaccgtggg aaaaactcca   5280
ggtagaggta cacacgcgga tagccaattc agagtaataa actgtgataa tcaaccctca   5340
tcaatgatga cgaactaacc cccgatatca ggtcacatga cgaagggaaa gagaaggaaa   5400
tcaactgtga caaactgccc tcaaatttgg cttccttaaa aattacagtt caaaaagtat   5460
gagaaaatcc atgcaggctg aaggaaacag caaaactgtg acaaattacc ctcagtaggt   5520
cagaacaaat gtgacgaacc accctcaaat ctgtgacaga taaccctcag actatcctgt   5580
cgtcatggaa gtgatatcgc ggaaggaaaa tacgatatga gtcgtctggc ggcctttctt   5640
tttctcaatg tatgagaggc gcattggagt tctgctgttg atctcattaa cacagacctg   5700
caggaagcgg cggcggaagt caggcatacg ctggtaactt tgaggcagct ggtaacgctc   5760
tatgatccag tcgattttca gagagacgat gcctgagcca tccggcttac gatactgaca   5820
cagggattcg tataaacgca tggcatacgg attggtgatt tcttttgttt cactaagccg   5880
aaactgcgta aaccggttct gtaacccgat aaagaaggga atgagatatg ggttgatatg   5940
tacactgtaa agccctctgg atggactgtg cgcacgtttg ataaaccaag gaaaagattc   6000
atagcctttt tcatcgccgg catcctcttc agggcgataa aaaaccactt ccttccccgc   6060
gaaactcttc aatgcctgcc gtatatcctt actggcttcc gcagaggtca atccgaatat   6120
ttcagcatat ttagcaacat ggatctcgca gataccgtca tgttcctgta gggtgccatc   6180
agattttctg atctggtcaa cgaacagata cagcatacgt tttgatccc gggagagact   6240
atatgccgcc tcagtgaggt cgtttgactg gacgattcgc gggctatttt tacgtttctt   6300
gtgattgata accgctgttt ccgccatgac agatccatgt gaagtgtgac aagtttttag   6360
attgtcacac taaataaaaa agagtcaata agcagggata actttgtgaa aaaacagctt   6420
```

cttctgaggg caatttgtca cagggttaag ggcaatttgt cacagacagg actgtcattt 6480
gagggtgatt tgtcacactg aaagggcaat ttgtcacaac accttctcta gaaccagcat 6540
ggataaaggc ctacaaggcg ctctaaaaaa gaagatctaa aaactataaa aaaaataatt 6600
ataaaaatat ccccgtggat aagtggataa ccccaaggga agttttttca ggcatcgtgt 6660
gtaagcagaa tatataagtg ctgttccctg gtgcttcctc gctcactcga gggcttcgcc 6720
ctgtcgctca actgcggcga gcactactgg ctgtaaaagg acagaccaca tcatggttct 6780
gtgttcatta ggttgttctg tccattgctg acataatccg ctccacttca acgtaacacc 6840
gcacgaagat ttctattgtt cctgaaggca tattcaaatc gttttcgtta ccgcttgcag 6900
gcatcatgac agaacactac ttcctataaa cgctacacag gctcctgaga ttaataatgc 6960
ggatctctac gataatggga gattttcccg actgtttcgt tcgcttctca gtggataaca 7020
gccagcttct ctgtttaaca gacaaaaaca gcatatccac tcagttccac atttccatat 7080
aaaggccaag gcatttattc tcaggataat tgtttcagca tcgcaaccgc atcagactcc 7140
ggcatcgcaa actgcacccg gtgccgggca gccacatcca gcgcaaaaac cttcgtgtag 7200
acttccgttg aactgatgga cttatgtccc atcaggcttt gcagaacttt cagcggtata 7260
ccggcataca gcatgtgcat cgcataggaa tggcggaacg tatgtggtgt gaccggaaca 7320
gagaacgtca caccgtcagc agcagcggcg gcaaccgcct ccccaatcca ggtcctgacc 7380
gttctgtccg tcacttccca gatccgcgct ttctctgtcc ttcctgtgcg acggttacgc 7440
cgctccatga gcttatcgcg aataaatacc tgtgacggaa gatcacttcg cagaataaat 7500
aaatcctggt gtccctgttg ataccgggaa gccctgggcc aacttttggc gaaaatgaga 7560
cgttgatcgg cacgtaagag gttccaactt tcaccataat gaaataagat cactaccggg 7620
cgtatttttt gagttatcga gattttcagg agctaaggaa gctaaaatgg agaaaaaaat 7680
cactggatat accaccgttg atatatccca atggcatcgt aaagaacatt ttgaggcatt 7740
tcagtcagtt gctcaatgta cctataacca gaccgttcag ctggatatta cggccttttt 7800
aaagaccgta aagaaaaata agcacaagtt ttatccggcc tttattcaca ttcttgcccg 7860
cctgatgaat gctcatccgg agttccgtat ggcaatgaaa gacggtgagc tggtgatatg 7920
ggatagtgtt cacccttgtt acaccgtttt ccatgagcaa actgaaacgt tttcatcgct 7980
ctggagtgaa taccacgacg atttccggca gtttctacac atatattcgc aagatgtggc 8040
gtgttacggt gaaaacctgg cctatttccc taaagggttt attgagaata tgtttttcgt 8100
ctcagccaat ccctgggtga gtttcaccag ttttgattta aacgtggcca atatggacaa 8160
cttcttcgcc cccgttttca ccatgggcaa atattatacg caaggcgaca aggtgctgat 8220
gccgctggcg attcaggttc atcatgccgt ttgtgatggc ttccatgtcg gcagaatgct 8280
taatgaatta caacagtact gcgatgagtg gcagggcggg gcgtaatttt tttaaggcag 8340
ttattggtgc ccttaaacgc ctggttgcta cgcctgaata agtgataata agcggatgaa 8400
tggcagaaat tcgatgataa gctgtcaaac atgagaattg gtcgacggcg cgccaaagct 8460
tgcatgcctg cagccgcgta acctggcaaa atcggttacg gttgagtaat aaatggatgc 8520
cctgcgtaag cggggcacat ttcattacct ctttctccgc acccgacata gataataact 8580
tcgtatagta tacattatac gaagttatct agtagactta atcgcgttta aacccatcat 8640
caataatata cctcaaactt tttgtgcgcg ttaatatgca aatgaggcgt ttgaatttgg 8700
gaagggagga aggtgattgg ccgagagaag ggcgaccgtt aggggcgggg cgagtgacgt 8760

```
tttgatgacg tgaccgcgag gaggagccag tttgcaagtt ctcgtgggaa aagtgacgtc   8820
aaacgaggtg tggtttgaac acggaaatac tcaattttcc cgcgctctct gacaggaaat   8880
gaggtgtttc taggcggatg caagtgaaaa cgggccattt tcgcgcgaaa actgaatgag   8940
gaagtgaaaa tctgagtaat ttcgcgttta tgacagggag gagtatttgc cgagggccga   9000
gtagactttg accgattacg tgggggtttc gattaccgtg tttttcacct aaatttccgc   9060
gtacggtgtc aaagtccggt gtttttacgt aggtgtcagc tgatcgccag ggtatttaaa   9120
cctgcgctct ccagtcaaga ggccactctt gagtgccagc gagaagagtt ttctcctccg   9180
cgcgcgagtc agatctacac tttgaaaggc gatcgctagc gacatcgatc caaataatga   9240
ttttattttg actgatagtg acctgttcgt tgcaacaaat tgataagcaa tgctttttta   9300
taatgccaac tttgtacaaa aaagcaggct ccaccatggg aaccaattca gtcgagcctt   9360
tcactcatta gatgcatgtc gttacataac ttacggtaaa tggcccgcct ggctgaccgc   9420
ccaacgaccc ccgcccattg acgtcaataa tgacgtatgt tcccatagta acgccaatag   9480
ggactttcca ttgacgtcaa tgggtggagt atttacggta aactgcccac ttggcagtac   9540
atcaagtgta tcatatgcca agtacgcccc ctattgacgt caatgacggt aaatggcccg   9600
cctggcatta tgcccagtac atgaccttat gggactttcc tacttggcag tacatctacg   9660
tattagtcat cgctattacc atggtgatgc ggttttggca gtacatcaat gggcgtggat   9720
agcggtttga ctcacgggga tttccaagtc tccaccccat tgacgtcaat gggagtttgt   9780
tttggcacca aaatcaacgg gactttccaa aatgtcgtaa caactccgcc ccattgacgc   9840
aaatgggcgg taggcgtgta cggtgggagg tctatataag cagagctctc cctatcagtg   9900
atagagatct ccctatcagt gatagagatc gtcgacgagc tcgtttagtg aaccgtcaga   9960
tcgcctggag acgccatcca cgctgttttg acctccatag aagacaccgg gaccgatcca  10020
gcctccggtt aagctcggta ccgctagccg cgccgccacc atggatgcaa tgaagagagg  10080
gctctgctgt gtgctgctgc tgtgtggagc agtcttcgtt tcgcccagcc aggaaatcca  10140
tgcccgattc agaagaggat cgaagcttgc cagccagatc ggcgccggcg tgttcaagga  10200
gggcgtgttc cacaccatgt ggcacgtgac caggggcgcc gtgctgatgc accagggcaa  10260
gaggatcgag cccagctggg ccgacgtgaa gaaggacctg atcagctacg gcggcggctg  10320
gaggctggag ggcgagtggg acgagggcga ggaggtgcag gtgatcgccg tggagcccgg  10380
caagaacccc aaggccgtgc agaccggcga gatcggcgcc atcgccctgg acttcaagcc  10440
cggcaccagc ggcagcccca tcgtgaacag ggagggcgtg ggcctgtacg gcaacggcgt  10500
ggtgaccaag agcggcgcct acgtgagcgc catcgcccag accttcagga agaggaacct  10560
gaccatcatg gacctgcacc ccggcgccgg caagaccaag aggtatctgc ccgccatcgt  10620
gagggaggcc atcaagagga ggctgaggac cctgatcctg gcccccacca gggtggtggc  10680
cgccgagatg gaggaggccc tgaagggcct gcccatcagg tatcagacca ccgccatcaa  10740
ggccgagcac accggcaagg agatcgtgga cctgatgtgc cacgccacct tcaccatgag  10800
gctgctgagc cccgtgaggg tgcccaacta caacctgatc atcatggacg aggcccactt  10860
caccgacccc gccagcatcg ccgccagggg ctacatcagc accagggtgg agatgggcga  10920
ggccgccgcc atcttcatga ccgccacccc ccccggcagc gccgacgcct tcccccagag  10980
caacgccccc atcgaggacg aggagaggga gatccccgag aggagctgga acagcggctt  11040
cgactggatc accgacttcg ccggcaagac cgtgtggttc gtgcccagca tcaaggccgg  11100
caacgacatc gccaactgcc tgaggaagaa cggcaagaag gtgatccagc tgagcaggaa  11160
```

```
gaccttcgac accgagtacc ccaagaccaa gctgaacgac tgggacttcg tggtgaccac  11220
cgacatcagc gagatgggcg ccaacttcaa ggccgacagg gtgatcgacc ccaggaggtg  11280
cctgaagccc gtgatcctga ccgacggccc cgagagggtg atcctggccg gccccatgcc  11340
cgtgaccgcc gccagcgccg cccagaggag gggcaggatc ggcaggaacc acaagaagga  11400
gaacgaccag tacatctaca tgggccagcc cctgaacaac gacgaggacc acgcccactg  11460
gaccgaggcc aagatgctgc tggacaacat caacaccccc gagggcatca tccccgccct  11520
gttcgagccc gagagggaga agagcgccgc catcgacggc gagtacaggc tgaggggcga  11580
ggccaggaag accttcgtgg agctgatgag gaggggcgac ctgcccgtgt ggctgagcta  11640
caaggtggcc agcgccggct tccagtacaa ggacagggag tggtgcttcg acggcgagag  11700
gaacaaccag atcctggagg agaacatgga cgtggagatc tggaccgagg gcgagaagaa  11760
gaagctgagg cccaggtggc tggacgccag gacctacgcc gacccccacg ccctggagga  11820
gctgcccgag accctggaga ccctgctgct gctggccctg ctgggcttcc tgttcttcct  11880
gagcggcaag ggcatcggca agatgagcat cggcctgtgc tgcatcatcg ccgccagcct  11940
gctgtggatg gccgagatcc agccccactg gatcgccgcc agcatcatcc tggagttctt  12000
cctgatggtg ctgctgatcc ccgagcccga gaagcagagg acccccccagg acaaccagct  12060
ggcctacgtg gtgatcggca tcctgaccct ggccgccgcc atcgccgcca acgagatggg  12120
cctgctggag accaccaaga aggacctggg catcggcgcc atcctggacg tggacctgca  12180
ccccgccagc gcctggaccc tgtacgccgt ggccaccacc atcatcaccc ccatgctgag  12240
gcacaccatc gagaacagca ccgccaacgt gagcctgacc gccatcgcca accaggccgc  12300
cgtgctgatg ggcctggaca agggctggcc catcagcaag atggacctgg gcgtgcccct  12360
gctggccctg ggctgctaca gccaggtgaa cccccctgacc ctgacccact acgccatcat  12420
cggccccggc ctgcaggcca aggccaccag ggaggcccag aagaggaccg ccgccggcat  12480
catgaagaac cccaccgtgg acggcatcat ggccatcgac ctggaccccca tcccctacga  12540
ccccaagttc gagaagcagc tgggccaggt gatgctgctg atcctgtgca gccagatcct  12600
gctgatgagg accacctggg ccctgtgcga ggccctgacc ctggccaccg gccccatcac  12660
caccctgtgg gagggcaacc ccggcaagtt ctggaacacc accatcgccg tgagcatggc  12720
caacatcttc aggggcagct acctggccgg cgccggcctg gccttcagcc tgatcaagaa  12780
cggcgagacc ctgggcgaga agtggaagag gcagctgaac cagctggaca agagcttcga  12840
ggagtacaag aagagcggca tcctggaggt ggacaggacc gaggccaagg aggccatcat  12900
ggtggtgatc gacctgggct gcggcagggg cggctggagc tactactgcg ccggcctgaa  12960
gaaggtgagg ggctacacca agggcggccc cggccacgag gagcccatcc ccatggccac  13020
ctacggctgg aacctggtga agctgcacag cggcgtggac gtgttcttcg agaagtgcga  13080
caccctgctg tgcgacatcg gcgagagcag ccccaacccc accatcgagg agggcaggac  13140
cctgagggtg ctgaagatgg tggagccctg gctgaagggc aaccagttct gcatcaagat  13200
cctgaacccc tacatgccca gcgtgatcga gctggagaag ctgcagagga agcacggcgg  13260
catgctggtg aggaaccccc tgagcaggaa cagcacccac gagatgtact gggtgagcaa  13320
cggcaccggc aacatcgtga gcgccgtgaa catgatcagc aggatgctga tcaacaggtt  13380
caccatggcc cacaaggacg aggacaaccc ctacaagacc tgggcctacc acggcagcta  13440
cgaggtgaag gccaccggca gcgccagcag catggtgaac ggcgtggtga agctgctgac  13500
```

```
caagccctgg gacgtggtgc ccatggtgac ccagatggcc atgaccgaca ccacccccctt  13560
cggccagcag agggtgttca aggagaaggt ggacaccagg acccccgagg cccaggacga  13620
gaacggctgg aagagcgccc tgcacctgga gggcaagtgc gagagctgcg tgtacaacat  13680
gatgggcaag agggagaaga agctgggcga gttcggcaag gccaagggca gcagggccat  13740
ctggtacatg tggctgggcg ccaggttcct ggagttcgag gccctgggct tcctgaacga  13800
ggaccactgg ttcagcaggg agaacagcct gagcggcgtg gagggcgagg gcctgctggg  13860
ctacatcctg agggacatca gcaagatccc cggcggcgcc atgtacgccg acgacaccgc  13920
cggctgggac accaggatca ccgaggacga cctgcacaac gaggagaagc tggccaaggc  13980
catcttcaag ctgacctacc agaacaaggt ggtgaaggtg cagaggccca cccccagggg  14040
cgccgtgatg gacatcatca gcaggaagga ccagaggggc agcggccagg tgggcaccta  14100
cggcctgaac accttcacca acatggaggc ccagctgatc aggcagatgg aggccgagca  14160
gtgggagccc agcaagggct ggcacgactg gcagcaggtg cccttctgca gccaccactt  14220
ccacatcttc atgaaggacg gcaggaagct ggtggtgccc tgcaggaacc aggacgagct  14280
gatcggcagg gccaggatca gccagggcgc cggctggagc ctgagggaga ccgcctgcct  14340
gggcaagagc tacgcccaga tgtggcagct gatgtacttc cacaggaggg acctgaggct  14400
ggccagcaac gccatctgca gcgccgtgcc cagccactgg gtgcccagca ggaccacctg  14460
gagccacgag tggatgacca ccgaggacat gctggccgtg tggaacaggg tgtggcacag  14520
ctgggaggac gtgccctacc tgggcaagag ggaggaccag tggtgcggca gcctgatcgg  14580
cctgaccagc agggccacct gggccaagaa catcgctgga tccgggcccg gggcttcagg  14640
taagcctatc cctaaccctc tcctcggtct cgattctacg cggacctgat gagcggccgc  14700
tcgagcatgc atctagaggg ccctattcta tagtgtcacc taaatgctag agctcgctga  14760
tcagcctcga ctgtgccttc tagttgccag ccatctgttg tttgcccctc ccccgtgcct  14820
tccttgaccc tggaaggtgc cactcccact gtcctttcct aataaaatga ggaaattgca  14880
tcgcattgtc tgagtaggtg tcattctatt ctggggggtg gggtggggca ggacagcaag  14940
ggggaggatt gggaagacaa tagcaggcat gctggggatg cggtgggctc tatggcttct  15000
gaggcggaaa gaaccagctg gggctcgagg ggggatcgat cccgtcgaga tatctagacc  15060
cagctttctt gtacaaagtt ggcattataa gaaagcattg cttatcaatt tgttgcaacg  15120
aacaggtcac tatcagtcaa aataaaatca ttatttggat cgattcgaca gatcgcgatc  15180
gcagtgagta gtgttctggg gcgggggagg acctgcatga gggccagaat gactgaaatc  15240
tgtgcttttc tgtgtgttgc agcatcatga gcggaagcgg ctcctttgag ggaggggtat  15300
tcagccctta tctgacgggg cgtctcccct cctgggcggg agtgcgtcag aatgtgatgg  15360
gatccacggt ggacggccgg cccgtgcagc ccgcgaactc ttcaaccctg acctatgcaa  15420
ccctgagctc ttcgtcggtg gacgcagctg ccgccgcagc tgctgcatcc gccgccagcg  15480
ccgtgcgcgg aatggccatg ggcgccggct actacggcac tctggtggcc aactcgagtt  15540
ccaccaataa tcccgccagc ctgaacgagg agaagctgct gctgctgatg gcccagcttg  15600
aggccttgac ccagcgcctg ggcgagctga cccagcaggt ggctcagctg caggagcaga  15660
cgcgggccgc ggttgccacg gtgaaatcca aataaaaaat gaatcaataa ataaacggag  15720
acggttgttg attttaacac agagtctgaa tctttatttg atttttcgcg cgcggtaggc  15780
cctggaccac cggtctcgat cattgagcac ccggtggatc ttttccagga cccggtagag  15840
gtgggcttgg atgttgaggt acatgggcat gagcccgtcc cgggggtgga ggtagctcca  15900
```

ttgcagggcc tcgtgctcgg gggtggtgtt gtaaatcacc cagtcatagc aggggcgcag 15960
ggcgtggtgt tgcacaatat ctttgaggag gagactgatg gccacgggca gccctttggt 16020
gtaggtgttt acaaatctgt tgagctggga gggatgcatg cggggggaga tgaggtgcat 16080
cttggcctgg atcttgagat tggcgatgtt accgcccaga tcccgcctgg ggttcatgtt 16140
gtgcaggacc accagcacgg tgtatccggt gcacttgggg aatttatcat gcaacttgga 16200
agggaaggcg tgaaagaatt tggcgacgcc cttgtgtccg cccaggtttt ccatgcactc 16260
atccatgatg atggcaatgg gcccgtgggc ggcggcctgg gcaaagacgt ttcgggggtc 16320
ggacacatca tagttgtggt cctgggtgag gtcatcatag gccattttaa tgaatttggg 16380
gcggagggtg ccggactggg ggacaaaggt accctcgatc ccgggggcgt agttcccctc 16440
acagatctgc atctcccagg ctttgagctc agaggggggg atcatgtcca cctgcggggc 16500
gataaagaac acggtttccg gggcggggga gatgagctgg gccgaaagca agttccggag 16560
cagctgggac ttgccgcagc cggtggggcc gtaaatgacc ccgatgaccg gctgcaggtg 16620
gtagttgagg gagagacagc tgccgtcctc ccggaggagg ggggccacct cgttcatcat 16680
ctcgcgcacg tgcatgttct cgcgcaccag ttccgccagg aggcgctctc cccccagaga 16740
taggagctcc tggagcgagg cgaagttttt cagcggcttg agtccgtcgg ccatgggcat 16800
tttggagagg gtctgttgca agagttccaa gcggtcccag agctcggtga tgtgctctac 16860
ggcatctcga tccagcagac ctcctcgttt cgcgggttgg gacgactgcg ggagtagggc 16920
accagacgat gggcgtccag cgcagccagg gtccggtcct tccagggccg cagcgtccgc 16980
gtcagggtgg tctccgtcac ggtgaagggg tgcgcgccgg gctgggcgct tgcgagggtg 17040
cgcttcaggc tcatccggct ggtcgaaaac cgctcccgat cggcgccctg cgcgtcggcc 17100
aggtagcaat tgaccatgag ttcgtagttg agcgcctcgg ccgcgtggcc tttggcgcgg 17160
agcttacctt tggaagtctg cccgcaggcg ggacagagga gggacttgag ggcgtagagc 17220
ttgggggcga ggaagacgga atcgggggcg taggcgtccg cgccgcagtg ggcgcagacg 17280
gtctcgcact ccacgagcca ggtgaggtcg ggctggtcgg ggtcaaaaac cagtttcccg 17340
ccgttctttt tgatgcgttt cttacctttg gtctccatga gctcgtgtcc ccgctgggtg 17400
acaaagaggc tgtccgtgtc cccgtagacc gactttatgg gccggtcctc gagcggtgtg 17460
ccgcggtcct cctcgtagag gaaccccgcc cactccgaga cgaaagcccg ggtccaggcc 17520
agcacgaagg aggccacgtg ggacgggtag cggtcgttgt ccaccagcgg gtccactttt 17580
tccagggtat gcaaacacat gtccccctcg tccacatcca ggaaggtgat tggcttgtaa 17640
gtgtaggcca cgtgaccggg ggtcccggcc gggggggtat aaaagggggc gggcccctgc 17700
tcgtcctcac tgtcttccgg atcgctgtcc aggagcgcca gctgttgggg taggtattcc 17760
ctctcgaagg cgggcatgac ctcggcactc aggttgtcag tttctagaaa cgaggaggat 17820
ttgatattga cggtgccagc ggagatgcct ttcaagagcc cctcgtccat ctggtcagaa 17880
aagacgattt ttttgttgtc gagcttggtg gcgaaggagc cgtagagggc gttggaaagg 17940
agcttggcga tggagcgcat ggtctggttt ttttccttgt cggcgcgctc cttggccgcg 18000
atgttgagct gcacgtactc gcgcgccacg cacttccatt cggggaagac ggtggtcatc 18060
tcgtcgggca cgattctgac ctgccaacct cgattatgca gggtgatgag gtccacactg 18120
gtggccacct cgccgcgcag ggctcgttg gtccagcaga ggcggccgcc cttgcgcgag 18180
cagaaggggg gcagagggtc cagcatgacc tcgtcggggg ggtcggcatc gatggtgaag 18240

-continued

```
atgccgggca ggagatcggg gtcgaagtag ctgatggaag tggccagatc gtccagggaa  18300
gcttgccatt cgcgcacggc cagcgcgcgc tcgtagggac tgaggggcgt gccccagggc  18360
atggggtggg tgagcgcgga ggcgtacatg ccgcagatgt cgtagacgta gaggggctcc  18420
tcgaggatgc cgatgtaggt ggggtagcag cgcccccgc ggatgctggc gcgcacgtag  18480
tcatacagct cgtgcgaggg cgcgaggagc cccgggccca ggttggtgcg actgggcttt  18540
tcggcgcggt agacgatctg gcgaaagatg gcatgcgagt tggaggagat ggtgggcctt  18600
tggaagatgt tgaagtgggc gtgggggagg ccgaccgagt cgcggatgaa gtgggcgtag  18660
gagtcttgca gtttggcgac gagctcggcg gtgacgagga cgtccagagc gcagtagtcg  18720
agggtctcct ggatgatgtc atacttgagc tggccctttt gtttccacag ctcgcggttg  18780
agaaggaact cttcgcggtc cttccagtac tcttcgaggg ggaacccgtc ctgatctgca  18840
cggtaagagc ctagcatgta gaactggttg acggccttgt aggcgcagca gcccttctcc  18900
acggggaggg cgtaggcctg ggcggccttg cgcagggagg tgtgcgtgag ggcgaaggtg  18960
tccctgacca tgaccttgag gaactggtgc ttgaaatcga tatcgtcgca gcccccctgc  19020
tcccagagct ggaagtccgt gcgcttcttg taggcggggt tgggcaaagc gaaagtaaca  19080
tcgttgaaaa ggatcttgcc cgcgcggggc ataaagttgc gagtgatgcg gaaaggctgg  19140
ggcacctcgg cccggttgtt gatgacctgg gcggcgagca cgatctcgtc gaaaccgttg  19200
atgttgtggc ccacgatgta gagttccacg aatcgcgggc ggcccttgac gtggggcagc  19260
ttcttgagct cctcgtaggt gagctcgtcg gggtcgctga gaccgtgctg ctcgagcgcc  19320
cagtcggcga gatgggggtt ggcgcggagg aaggaagtcc agagatccac ggccagggcg  19380
gtttgcagac ggtcccggta ctgacggaac tgctgcccga cggccatttt ttcgggggtg  19440
acgcagtaga aggtgcgggg gtccccgtgc cagcggtccc atttgagctg gagggcgaga  19500
tcgagggcga gctcgacgag gcggtcgtcc cctgagagtt tcatgaccag catgaagggg  19560
acgagctgct tgccgaagga ccccatccag gtgtaggttt ccacatcgta ggtgaggaag  19620
agcctttcgg tgcgaggatg cgagccgatg gggaagaact ggatctcctg ccaccaattg  19680
gaggaatggc tgttgatgtg atggaagtag aaatgccgac ggcgcgccga acactcgtgc  19740
ttgtgtttat acaagcggcc acagtgctcg caacgctgca cgggatgcac gtgctgcacg  19800
agctgtacct gagttccttt gacgaggaat ttcagtggga agtggagtcg tggcgcctgc  19860
atctcgtgct gtactacgtc gtggtggtcg gcctggccct cttctgcctc gatggtggtc  19920
atgctgacga gcccgcgcgg gaggcaggtc cagacctcgg cgcgagcggg tcggagagcg  19980
aggacgaggg cgcgcaggcc ggagctgtcc agggtcctga gacgctgcgg agtcaggtca  20040
gtgggcagcg gcggcgcgcg gttgacttgc aggagttttt ccagggcgcg cgggaggtcc  20100
agatggtact tgatctccac cgcgccgttg gtggcgacgt cgatggcttg cagggtcccg  20160
tgcccctggg gtgtgaccac cgtcccccgt ttcttcttgg gcggctgggg cgacgggggc  20220
ggtgcctctt ccatggttag aagcggcggc gaggacgcgc gccgggcggc agaggcggct  20280
cggggcccgg aggcaggggc ggcaggggca cgtcggcgcc gcgcgcgggt aggttctggt  20340
actgcgcccg gagaagactg gcgtgagcga cgacgcgacg gttgacgtcc tggatctgac  20400
gcctctgggt gaaggccacg ggacccgtga gtttgaacct gaaagagagt tcgacagaat  20460
caatctcggt atcgttgacg gcggcctgcc gcaggatctc ttgcacgtcg cccgagttgt  20520
cctggtaggc gatctcggtc atgaactgct cgatctcctc ctcctgaagg tctccgcgac  20580
cggcgcgctc cacggtggcc gcgaggtcgt tggagatgcg gcccatgagc tgcgagaagg  20640
```

cgttcatgcc cgcctcgttc cagacgcggc tgtagaccac gacgccctcg ggatcgcggg 20700
cgcgcatgac cacctgggcg aggttgagct ccacgtggcg cgtgaagacc gcgtagttgc 20760
agaggcgctg gtagaggtag ttgagcgtgg tggcgatgtg ctcggtgacg aagaaataca 20820
tgatccagcg gcggagcggc atctcgctga cgtcgcccag cgcctccaag cgttccatgg 20880
cctcgtaaaa gtccacggcg aagttgaaaa actgggagtt gcgcgccgag acggtcaact 20940
cctcctccag aagacggatg agctcggcga tggtggcgcg cacctcgcgc tcgaaggccc 21000
ccgggagttc ctccacttcc tcctcttctt cctcctccac taacatctct tctacttcct 21060
cctcaggcgg tggtggtggc gggggagggg gcctgcgtcg ccggcggcgc acgggcagac 21120
ggtcgatgaa gcgctcgatg gtctcgccgc gccggcgtcg catggtctcg gtgacggcgc 21180
gcccgtcctc gcggggccgc agcgtgaaga cgccgccgcg catctccagg tggccggggg 21240
ggtccccgtt gggcagggag agggcgctga cgatgcatct tatcaattgc cccgtaggga 21300
ctccgcgcaa ggacctgagc gtctcgagat ccacgggatc tgaaaaccgt tgaacgaagg 21360
cttcgagcca gtcgcagtcg caaggtaggc tgagcacggt ttcttctgcc gggtcatgtt 21420
ggggagcggg gcgggcgatg ctgctggtga tgaagttgaa ataggcggtt ctgagacggc 21480
ggatggtggc gaggagcacc aggtctttgg gcccggcttg ctggatgcgc agacggtcgg 21540
ccatgcccca ggcgtggtcc tgacacctgg ccaggtcctt gtagtagtcc tgcatgagcc 21600
gctccacggg cacctcctcc tcgcccgcgc ggccgtgcat gcgcgtgagc ccgaagccgc 21660
gctggggctg gacgagcgcc aggtcggcga cgacgcgctc ggcgaggatg gcctgctgga 21720
tctgggtgag ggtggtctgg aagtcgtcaa agtcgacgaa gcggtggtag gctccggtgt 21780
tgatggtgta ggagcagttg gccatgacgg accagttgac ggtctggtgg cccggacgca 21840
cgagctcgtg gtacttgagg cgcgagtagg cgcgcgtgtc gaagatgtag tcgttgcagg 21900
tgcgcaccag gtactggtag ccgatgagga agtgcggcgg cggctggcgg tagagcggcc 21960
atcgctcggt ggcgggggcg ccgggcgcga ggtcctcgag catggtgcgg tggtagccgt 22020
agatgtacct ggacatccag gtgatgccgg cggcggtggt ggaggcgcgc gggaactcgc 22080
ggacgcggtt ccagatgttg cgcagcggca ggaagtagtt catggtgggc acggtctggc 22140
ccgtgaggcg cgcgcagtcg tggatgctct atacgggcaa aaacgaaagc ggtcagcggc 22200
tcgactccgt ggcctggagg ctaagcgaac gggttgggct gcgcgtgtac cccggttcga 22260
atctcgaatc aggctggagc cgcagctaac gtggtactgg cactcccgtc tcgacccaag 22320
cctgcaccaa ccctccagga tacggaggcg ggtcgttttg caactttttt tggaggccgg 22380
aaatgaaact agtaagcgcg gaaagcggcc gaccgcgatg gctcgctgcc gtagtctgga 22440
gaagaatcgc cagggttgcg ttgcggtgtg ccccggttcg aggccggccg gattccgcgg 22500
ctaacgaggg cgtggctgcc ccgtcgtttc caagacccca tagccagccg acttctccag 22560
ttacggagcg agcccctctt ttgttttgtt tgtttttgcc agatgcatcc cgtactgcgg 22620
cagatgcgcc cccaccaccc tccaccgcaa caacagcccc ctcctccaca gccggcgctt 22680
ctgcccccgc cccagcagca gcagcaactt ccagccacga ccgccgcggc cgccgtgagc 22740
ggggctggac agacttctca gtatgatcac ctggccttgg aagagggcga ggggctggcg 22800
cgcctggggg cgtcgtcgcc ggagcggcac ccgcgcgtgc agatgaaaag ggacgctcgc 22860
gaggcctacg tgcccaagca gaacctgttc agagacagga gcggcgagga gcccgaggag 22920
atgcgcgcgg cccggttcca cgcggggcgg gagctgcggc gcggcctgga ccgaaagagg 22980

```
gtgctgaggg acgaggattt cgaggcggac gagctgacgg ggatcagccc cgcgcgcgcg  23040
cacgtggccg cggccaacct ggtcacggcg tacgagcaga ccgtgaagga ggagagcaac  23100
ttccaaaaat ccttcaacaa ccacgtgcgc accctgatcg cgcgcgagga ggtgaccctg  23160
ggcctgatgc acctgtggga cctgctggag gccatcgtgc agaaccccac cagcaagccg  23220
ctgacggcgc agctgttcct ggtggtgcag catagtcggg acaacgaggc gttcagggag  23280
gcgctgctga atatcaccga gcccgagggc cgctggctcc tggacctggt gaacattctg  23340
cagagcatcg tggtgcagga gcgcgggctg ccgctgtccg agaagctggc ggccatcaac  23400
ttctcggtgc tgagtctggg caagtactac gctaggaaga tctacaagac cccgtacgtg  23460
cccatagaca aggaggtgaa gatcgacggg ttttacatgc gcatgaccct gaaagtgctg  23520
accctgagcg acgatctggg ggtgtaccgc aacgacagga tgcaccgcgc ggtgagcgcc  23580
agcaggcggc gcgagctgag cgaccaggag ctgatgcaca gcctgcagcg ggccctgacc  23640
ggggccggga ccgaggggga gagctacttt gacatgggcg cggacctgca ctggcagccc  23700
agccgccggg ccttggaggc ggcaggcggt ccccccctaca tagaagaggt ggacgatgag  23760
gtggacgagg agggcgagta cctggaagac tgatggcgcg accgtatttt tgctagatgc  23820
aacaacagcc acctcctgat cccgcgatgc gggcggcgct gcagagccag ccgtccggca  23880
ttaactcctc ggacgattgg acccaggcca tgcaacgcat catggcgctg acgacccgca  23940
accccgaagc ctttagacag cagccccagg ccaaccggct ctcggccatc ctggaggccg  24000
tggtgccctc gcgctccaac cccacgcacg agaaggtcct ggccatcgtg aacgcgctgg  24060
tggagaacaa ggccatccgc ggcgacgagg ccggcctggt gtacaacgcg ctgctggagc  24120
gcgtggcccg ctacaacagc accaacgtgc agaccaacct ggaccgcatg gtgaccgacg  24180
tgcgcgaggc cgtggcccag cgcgagcggt tccaccgcga gtccaacctg ggatccatgg  24240
tggcgctgaa cgccttcctc agcacccagc ccgccaacgt gccccggggc caggaggact  24300
acaccaactt catcagcgcc ctgcgcctga tggtgaccga ggtgccccag agcgaggtgt  24360
accagtccgg gccggactac ttcttccaga ccagtcgcca gggcttgcag accgtgaacc  24420
tgagccaggc gttcaagaac ttgcagggcc tgtggggcgt gcaggccccg gtcggggacc  24480
gcgcgacggt gtcgagcctg ctgacgccga actcgcgcct gctgctgctg ctggtggccc  24540
ccttcacgga cagcggcagc atcaaccgca actcgtacct gggctacctg attaacctgt  24600
accgcgaggc catcggccag gcgcacgtgg acgagcagac ctaccaggag atcacccacg  24660
tgagccgcgc cctgggccag gacgacccgg gcaatctgga agccaccctg aactttttgc  24720
tgaccaaccg gtcgcagaag atcccgcccc agtacacgct cagcgccgag gaggagcgca  24780
tcctgcgata cgtgcagcag agcgtgggcc tgttcctgat gcaggagggg gccaccccca  24840
gcgccgcgct cgacatgacc gcgcgcaaca tggagcccag catgtacgcc agcaaccgcc  24900
cgttcatcaa taaactgatg gactacttgc atcgggcggc cgccatgaac tctgactatt  24960
tcaccaacgc catcctgaat ccccactggc tcccgccgcc ggggttctac acgggcgagt  25020
acgacatgcc cgaccccaat gacgggttcc tgtgggacga tgtggacagc agcgtgttct  25080
ccccccgacc gggtgctaac gagcgcccct tgtggaagaa ggaaggcagc gaccgacgcc  25140
cgtcctcggc gctgtccggc cgcgagggtg ctgccgcggc ggtgcccgag gccgccagtc  25200
ctttcccgag cttgcccttc tcgctgaaca gtattcgcag cagcgagctg ggcaggatca  25260
cgcgcccgcg cttgctgggc gaggaggagt acttgaatga ctcgctgttg agacccgagc  25320
gggagaagaa cttccccaat aacgggatag agagcctggt ggacaagatg agccgctgga  25380
```

agacgtatgc gcaggagcac agggacgatc cgtcgcaggg ggccacgagc cggggcagcg 25440
ccgcccgtaa acgccggtgg cacgacaggc agcggggact gatgtgggac gatgaggatt 25500
ccgccgacga cagcagcgtg ttggacttgg gtgggagtgg taacccgttc gctcacctgc 25560
gcccccgcat cgggcgcatg atgtaagaga aaccgaaaat aaatgatact caccaaggcc 25620
atggcgacca gcgtgcgttc gtttcttctc tgttgttgta tctagtatga tgaggcgtgc 25680
gtacccggag ggtcctcctc cctcgtacga gagcgtgatg cagcaggcga tggcggcggc 25740
ggcggcgatg cagcccccgc tggaggctcc ttacgtgccc ccgcggtacc tggcgcctac 25800
ggaggggcgg aacagcattc gttactcgga gctggcaccc ttgtacgata ccacccggtt 25860
gtacctggtg gacaacaagt cggcggacat cgcctcgctg aactaccaga acgaccacag 25920
caacttcctg accaccgtgg tgcagaacaa tgacttcacc cccacggagg ccagcaccca 25980
gaccatcaac tttgacgagc gctcgcggtg gggcggtcag ctgaaaacca tcatgcacac 26040
caacatgccc aacgtgaacg agttcatgta cagcaacaag ttcaaggcgc gggtgatggt 26100
ctcccgcaag acccccaacg gggtgacagt gacagatggt agtcaggata tcttggagta 26160
tgaatgggtg gagtttgagc tgcccgaagg caacttctcg gtgaccatga ccatcgacct 26220
gatgaacaac gccatcatcg acaattactt ggcggtgggg cggcagaacg gggtcctgga 26280
gagcgatatc ggcgtgaagt tcgacactag gaacttcagg ctgggctggg accccgtgac 26340
cgagctggtc atgcccgggg tgtacaccaa cgaggccttc caccccgata ttgtcttgct 26400
gcccggctgc ggggtggact tcaccgagag ccgcctcagc aacctgctgg gcattcgcaa 26460
gaggcagccc ttccaggagg gcttccagat catgtacgag gatctggagg ggggcaacat 26520
ccccgcgctc ctggatgtcg acgcctatga gaaaagcaag gaggagagcg ccgccgcggc 26580
gactgcagct gtagccaccg cctctaccga ggtcaggggc gataattttg ccagccctgc 26640
agcagtggca gcggccgagg cggctgaaac cgaaagtaag atagtcattc agccggtgga 26700
gaaggatagc aaggacagga gctacaacgt gctgccggac aagataaaca ccgcctaccg 26760
cagctggtac ctggcctaca actatggcga ccccgagaag ggcgtgcgct cctggacgct 26820
gctcaccacc tcggacgtca cctgcggcgt ggagcaagtc tactggtcgc tgcccgacat 26880
gatgcaagac ccggtcacct tccgctccac gcgtcaagtt agcaactacc cggtggtggg 26940
cgccgagctc ctgcccgtct actccaagag cttcttcaac gagcaggccg tctactcgca 27000
gcagctgcgc gccttcacct cgctcacgca cgtcttcaac cgcttccccg agaaccagat 27060
cctcgtccgc ccgcccgcgc ccaccattac caccgtcagt gaaaacgttc ctgctctcac 27120
agatcacggg accctgccgc tgcgcagcag tatccgggga gtccagcgcg tgaccgttac 27180
tgacgccaga cgccgcacct gcccctacgt ctacaaggcc ctgggcatag tcgcgccgcg 27240
cgtcctctcg agccgcacct tctaaaaaat gtccattctc atctcgccca gtaataacac 27300
cggttggggc ctgcgcgcgc ccagcaagat gtacggaggc gctcgccaac gctccacgca 27360
acaccccgtg cgcgtgcgcg ggcacttccg cgctccctgg ggcgccctca agggccgcgt 27420
gcggtcgcgc accaccgtcg acgacgtgat cgaccaggtg gtggccgacg cgcgcaacta 27480
cacccccgcc gccgcgcccg tctccaccgt ggacgccgtc atcgacagcg tggtggccga 27540
cgcgcgccgg tacgcccgcg ccaagagccg gcggcggcgc atcgcccggc ggcaccggag 27600
cacccccgcc atgcgcgcgg cgcgagcctt gctgcgcagg gccaggcgca cgggacgcag 27660
ggccatgctc agggcggcca gacgcgcggc ttcaggcgcc agcgccggca ggacccggag 27720
acgcgcggcc acggcggcgg cagcggccat cgccagcatg tcccgcccgc ggcgagggaa 27780
cgtgtactgg gtgcgcgacg ccgccaccgg tgtgcgcgtg cccgtgcgca cccgcccccc 27840
tcgcacttga agatgttcac ttcgcgatgt tgatgtgtcc cagcggcgag gaggatgtcc 27900
aagcgcaaat tcaaggaaga gatgctccag gtcatcgcgc ctgagatcta cggccccgcg 27960
gtggtgaagg aggaaagaaa gccccgcaaa atcaagcggg tcaaaaagga caaaaaggaa 28020
gaagatgacg atctggtgga gtttgtgcgc gagttcgccc cccggcggcg cgtgcagtgg 28080
cgcgggcgga aagtgcaccc ggtgctgaga cccggcacca ccgtggtctt cacgcccggc 28140
gagcgctccg gcagcgcttc caagcgctcc tacgacgagg tgtacgggga cgaggacatc 28200
ctcgagcagg cggccgagcg cctgggcgag tttgcttacg gcaagcgcag ccgccccgcc 28260
ctgaaggaag aggcggtgtc catcccgctg gaccacggca accccacgcc gagcctcaag 28320
cccgtgaccc tgcagcaggt gctgccgagc gcagcgccgc gccgggggtt caagcgcgag 28380
ggcgaggatc tgtaccccac catgcagctg atggtgccca agcgccagaa gctggaagac 28440
gtgctggaga ccatgaaggt ggacccggac gtgcagcccg aggtcaaggt gcggcccatc 28500
aagcaggtgg ccccgggcct gggcgtgcag accgtggaca tcaagatccc cacggagccc 28560
atggaaacgc agaccgagcc catgatcaag cccagcacca gcaccatgga ggtgcagacg 28620
gatccctgga tgccatcggc tcctagccga agaccccggc gcaagtacgg cgcggccagc 28680
ctgctgatgc ccaactacgc gctgcatcct tccatcatcc ccacgccggg ctaccgcggc 28740
acgcgcttct accgcggtca tacaaccagc cgccgccgca agaccaccac ccgccgccgc 28800
cgtcgccgca cagccgctgc atctacccct gccgccctgg tgcggagagt gtaccgccgc 28860
ggccgcgcgc ctctgaccct accgcgcgcg cgctaccacc cgagcatcgc catttaaact 28920
ttcgcctgct ttgcagatgg ccctcacatg ccgcctccgc gttcccatta cgggctaccg 28980
aggaagaaaa ccgcgccgta gaaggctggc ggggaacggg atgcgtcgcc accaccatcg 29040
gcggcggcgc gccatcagca agcggttggg gggaggcttc ctgcccgcgc tgatccccat 29100
catcgccgcg gcgatcgggg cgatccccgg cattgcttcc gtggcggtgc aggcctctca 29160
gcgccactga gacacttgga aaacatcttg taataaacca atggactctg acgctcctgg 29220
tcctgtgatg tgttttcgta gacagatgga agacatcaat tttcgtccc tggctccgcg 29280
acacggcacg cggccgttca tgggcacctg gagcgacatc ggcaccagcc aactgaacgg 29340
gggcgccttc aattggagca gtctctggag cgggcttaag aatttcgggt ccacgcttaa 29400
aacctatggc agcaaggcgt ggaacagcac cacagggcag gcgctgaggg ataagctgaa 29460
agagcagaac ttccagcaga aggtggtcga tgggctcgcc tcgggcatca acggggtggt 29520
ggacctggcc aaccaggccg tgcagcggca gatcaacagc cgcctggacc cggtgccgcc 29580
cgccggctcc gtggagatgc cgcaggtgga ggaggagctg cctcccctgg acaagcgggg 29640
cgagaagcga ccccgccccg acgcggagga gacgctgctg acgcacacgg acgagccgcc 29700
cccgtacgag gaggcggtga aactgggtct gcccaccacg cggcccatcg cgcccctggc 29760
caccggggtg ctgaaacccg aaagtaataa gcccgcgacc ctggacttgc ctcctcccgc 29820
ttcccgcccc tctacagtgg ctaagcccct gccgccggtg gccgtggccc gcgcgcgacc 29880
cgggggctcc gcccgccctc atgcgaactg gcagagcact ctgaacagca tcgtgggtct 29940
gggagtgcag agtgtgaagc gccgccgctg ctattaaacc taccgtagcg cttaacttgc 30000
ttgtctgtgt gtgtatgtat tatgtcgccg ctgtccgcca gaaggaggag tgaagaggcg 30060
cgtcgccgag ttgcaagatg gccaccccat cgatgctgcc ccagtgggcg tacatgcaca 30120

```
tcgccggaca ggacgcttcg gagtacctga gtccgggtct ggtgcagttc gcccgcgcca  30180
cagacaccta cttcagtctg gggaacaagt ttaggaaccc cacggtggcg cccacgcacg  30240
atgtgaccac cgaccgcagc cagcggctga cgctgcgctt cgtgcccgtg gaccgcgagg  30300
acaacaccta ctcgtacaaa gtgcgctaca cgctggccgt gggcgacaac cgcgtgctgg  30360
acatggccag cacctacttt gacatccgcg gcgtgctgga tcggggccct agcttcaaac  30420
cctactccgg caccgcctac aacagcctgg ctcccaaggg agcgcccaat tccagccagt  30480
gggagcaaaa aaaggcaggc aatggtgaca ctatggaaac acacacattt ggtgtggccc  30540
caatgggcgg tgagaatatt acaatcgacg gattacaaat tggaactgac gctacagctg  30600
atcaggataa accaatttat gctgacaaaa cattccagcc tgaacctcaa gtaggagaag  30660
aaaattggca agaaactgaa agcttttatg gcggtagggc tcttaaaaaa gacacaagca  30720
tgaaaccttg ctatggctcc tatgctagac ccaccaatgt aaagggaggt caagctaaac  30780
ttaaagttgg agctgatgga gttcctacca aagaatttga catagacctg gctttctttg  30840
atactcccgg tggcacagtg aatggacaag atgagtataa agcagacatt gtcatgtata  30900
ccgaaaacac gtatctggaa actccagaca cgcatgtggt atacaaacca ggcaaggatg  30960
atgcaagttc tgaaattaac ctggttcagc agtccatgcc caatagaccc aactatattg  31020
ggttcagaga caactttatt gggctcatgt attacaacag tactggcaat atgggggtgc  31080
tggctggtca ggcctcacag ctgaatgctg tggtcgactt gcaagacaga aacaccgagc  31140
tgtcatacca gctcttgctt gactctttgg gtgacagaac ccggtatttc agtatgtgga  31200
atcaggcggt ggacagttat gatcctgatg tgcgcattat tgaaaaccat ggtgtggaag  31260
acgaacttcc caactattgc ttcccccctgg atgggtctgg cactaatgcc gcttaccaag  31320
gtgtgaaagt aaaaaatggt aacgatggtg atgttgagag cgaatgggaa aatgatgata  31380
ctgtcgcagc tcgaaatcaa ttatgcaagg gcaacatttt tgccatggaa attaacctcc  31440
aagccaacct gtggagaagt ttcctctact cgaacgtggc cctgtacctg cccgactctt  31500
acaagtacac gccagccaac atcaccctgc ccaccaacac caacacttat gattacatga  31560
acgggagagt ggtgcctccc tcgctggtgg acgcctacat caacatcggg gcgcgctggt  31620
cgctggaccc catggacaac gtcaatccct tcaaccacca ccgcaacgcg ggcctgcgct  31680
accgctccat gctcctgggc aacgggcgct acgtgccctt ccacatccag gtgccccaga  31740
aatttttcgc catcaagagc ctcctgctcc tgcccgggtc ctacacctac gagtggaact  31800
tccgcaagga cgtcaacatg atcctgcaga gctccctcgg caacgacctg cgcacggacg  31860
gggcctccat ctccttcacc agcatcaacc tctacgccac cttcttcccc atggcgcaca  31920
acacggcctc cacgctcgag gccatgctgc gcaacgacac caacgaccag tccttcaacg  31980
actacctctc ggcggccaac atgctctacc ccatcccggc caacgccacc aacgtgccca  32040
tctccatccc ctcgcgcaac tggccgcct tccgcggctg gtccttcacg cgcctcaaga  32100
ccaaggagac gccctcgctg ggctccgggt tcgaccccta cttcgtctac tcgggctcca  32160
tcccctacct cgacggcacc ttctacctca accacacctt caagaaggtc tccatcacct  32220
tcgactcctc cgtcagctgg cccggcaacg accggctcct gacgcccaac gagttcgaaa  32280
tcaagcgcac cgtcgacggc gagggataca acgtggccca gtgcaacatg accaaggact  32340
ggttcctggt ccagatgctg gcccactaca acatcggcta ccagggcttc tacgtgcccg  32400
agggctacaa ggaccgcatg tactccttct tccgcaactt ccagcccatg agccgccagg  32460
```

```
tggtggacga ggtcaactac aaggactacc aggccgtcac cctggcctac cagcacaaca  32520
actcgggctt cgtcggctac ctcgcgccca ccatgcgcca gggccagccc taccccgcca  32580
actacccgta cccgctcatc ggcaagagcg ccgtcaccag cgtcacccag aaaaagttcc  32640
tctgcgacag ggtcatgtgg cgcatcccct tctccagcaa cttcatgtcc atgggcgcgc  32700
tcaccgacct cggccagaac atgctctatg ccaactccgc ccacgcgcta gacatgaatt  32760
tcgaagtcga ccccatggat gagtccaccc ttctctatgt tgtcttcgaa gtcttcgacg  32820
tcgtccgagt gcaccagccc caccgcggcg tcatcgaggc cgtctacctg cgcacccccct  32880
tctcggccgg taacgccacc acctaaattg ctacttgcat gatggctgag cccacaggct  32940
ccggcgagca ggagctcagg gccatcatcc gcgacctggg ctgcgggccc tacttcctgg  33000
gcaccttcga taagcgcttc ccgggattca tggccccgca caagctggcc tgcgccatcg  33060
tcaacacggc cggccgcgag accgggggcg agcactggct ggccttcgcc tggaacccgc  33120
gctcgaacac ctgctacctc ttcgacccct tcgggttctc ggacgagcgc ctcaagcaga  33180
tctaccagtt cgagtacgag ggcctgctgc gccgtagcgc cctggccacc gaggaccgct  33240
gcgtcaccct ggaaaagtcc acccagaccg tgcagggtcc gcgctcggcc gcctgcgggc  33300
tcttctgctg catgttcctg cacgccttcg tgcactggcc cgaccgcccc atggacaaga  33360
accccaccat gaacttgctg acgggggtgc ccaacggcat gctccagtcg ccccaggtgg  33420
aacccaccct gcgccgcaac caggaggcgc tctaccgctt cctcaactcc cactccgcct  33480
actttcgctc ccaccgcgcg cgcatcgaga aggccaccgc cttcgaccgc atgaacaatc  33540
aagacatgta aaccgtgtgt gtatgtttaa aatatctttt aataaacagc actttaatgt  33600
tacacatgca tctgagatga ttttatttta gaaatcgaaa gggttctgcc gggtctcggc  33660
atggcccgcg ggcagggaca cgttgcggaa ctggtacttg gccagccact tgaactcggg  33720
gatcagcagt ttgggcagcg gggtgtcggg gaaggagtcg gtccacagct tccgcgtcag  33780
ctgcagggcg cccagcaggt cgggcgcgga gatcttgaaa tcgcagttgg gacccgcgtt  33840
ctgcgcgcga gagttgcggt acacggggtt gcagcactgg aacaccatca gggccgggtg  33900
cttcacgctc gccagcaccg ccgcgtcggt gatgctctcc acgtcgaggt cctcggcgtt  33960
ggccatcccg aagggggtca tcttgcaggt ctgccttccc atggtgggca cgcacccggg  34020
cttgtggttg caatcgcagt gcagggggat cagcatcatc tgggcctggt cggcgttcat  34080
ccccgggtac atggccttca tgaaagcctc caattgcctg aacgcctgct gggccttggc  34140
tccctcggtg aagaagaccc cgcaggactt gctagagaac tggttggtgg cacagccggc  34200
atcgtgcacg cagcagcgcg cgtcgttgtt ggccagctgc accacgctgc gcccccagcg  34260
gttctgggtg atcttggccc ggtcggggtt ctccttcagc gcgcgctgcc cgttctcgct  34320
cgccacatcc atctcgatca tgtgctcctt ctggatcatg gtggtcccgt gcaggcaccg  34380
cagtttgccc tcggcctcgg tgcacccgtg cagccacagc gcgcacccgg tgcactccca  34440
gttcttgtgg gcgatctggg aatgcgcgtg cacgaaccct tgcaggaagc ggcccatcat  34500
ggtcgtcagg gtcttgttgc tagtgaaggt caacgggatg ccgcggtgct cctcgttgat  34560
gtacaggtgg cagatgcggc ggtacacctc gccctgctcg ggcatcagtt ggaagttggc  34620
tttcaggtcg gtctccacgc ggtagcggtc catcagcata gtcatgattt ccatgccctt  34680
ctcccaggcc gagacgatgg gcaggctcat agggttcttc accatcatct tagcactagc  34740
agccgcggcc agggggtcgc tctcatccag ggtctcaaag ctccgcttgc cgtccttctc  34800
ggtgatccgc accgggggt agctgaagcc cacggccgcc agctcctcct cggcctgtct  34860
```

ttcgtcctcg ctgtcctggc tgacgtcctg catgaccaca tgcttggtct tgcggggttt 34920
cttcttgggc ggcagtggcg gcggagatgc ttgtggcgag ggggagcgcg agttctcgct 34980
caccactact atctcttcct cttcttggtc cgaggccacg cggcggtagg tatgtctctt 35040
cgggggcaga ggcggaggcg acgggctctc gccgccgcga cttggcggat ggctggcaga 35100
gccccttccg cgttcggggg tgcgctcccg gcggcgctct gactgacttc ctccgcggcc 35160
ggccattgtg ttctcctagg gaggaacaac aagcatggag actcagccat cgccaacctc 35220
gccatctgcc cccaccgccg gcgacgagaa gcagcagcag cagaatgaaa gcttaaccgc 35280
cccgccgccc agccccgcct ccgacgcagc cgcggtccca gacatgcaag agatggagga 35340
atccatcgag attgacctgg gctatgtgac gcccgcggag catgaggagg agctggcagt 35400
gcgctttcaa tcgtcaagcc aggaagataa agaacagcca gagcaggaag cagagaacga 35460
gcagagtcag gctgggctcg agcatggcga ctacctccac ctgagcgggg aggaggacgc 35520
gctcatcaag catctggccc ggcaggccac catcgtcaag gacgcgctgc tcgaccgcac 35580
cgaggtgccc ctcagcgtgg aggagctcag ccgcgcctac gagctcaacc tcttctcgcc 35640
gcgcgtgccc cccaagcgcc agcccaacgg cacctgcgag cccaaccccc gcctcaactt 35700
ctacccggtc ttcgcggtgc ccgaggccct ggccacctac cacatctttt tcaagaacca 35760
aaagatcccc gtctcctgcc gcgccaaccg cacccgcgcc gacgccctct tcaacctggg 35820
tcccggcgcc cgcctacctg atatcgcctc cttggaagag gttcccaaga tcttcgaggg 35880
tctgggcagc gacgagactc gggccgcgaa cgctctgcaa ggagaaggag gaggagagca 35940
tgagcaccac agcgccctgg tcgagttgga aggcgacaac gcgcggctgg cggtgctcaa 36000
acgcacggtc gagctgaccc atttcgccta cccggctctg aacctgcccc cgaaagtcat 36060
gagcgcggtc atggaccagg tgctcatcaa gcgcgcgtcg cccatctccg aggacgaggg 36120
catgcaagac tccgaggagg gcaagcccgt ggtcagcgac gagcagctgg cccggtggct 36180
gggtcctaat gctacccctc aaagtttgga agagcggcgc aagctcatga tggccgtggt 36240
cctggtgacc gtggagctgg agtgcctgcg ccgcttcttc gccgacgcgg agaccctgcg 36300
caaggtcgag gagaacctgc actacctctt caggcacggg ttcgtgcgcc aggcctgcaa 36360
gatctccaac gtggagctga ccaacctggt ctcctacatg ggcatcttgc acgagaaccg 36420
cctggggcag aacgtgctgc acaccaccct gcgcggggag gcccgccgcg actacatccg 36480
cgactgcgtc tacctctacc tctgccacac ctggcagacg ggcatgggcg tgtggcagca 36540
gtgtctggag gagcagaacc tgaaagagct ctgcaagctc ctgcaaaaga acctcaaggg 36600
tctgtggacc gggttcgacg agcggaccac cgcctcggac ctggccgacc tcatcttccc 36660
cgagcgcctc aggctgacgc tgcgcaacgg cctgcccgac tttatgagcc aaagcatgtt 36720
gcaaaacttt cgctctttca tcctcgaacg ctccggaatc ctgcccgcca cctgctccgc 36780
gctgccctcg gacttcgtgc cgctgacctt ccgcgagtgc cccccgccgc tgtggagcca 36840
ctgctacctg ctgcgcctgg ccaactacct ggcctaccac tcggacgtga tcgaggacgt 36900
cagcggcgag ggcctgctcg agtgccactg ccgctgcaac ctctgcacgc cgcaccgctc 36960
cctggcctgc aacccccagc tgctgagcga gacccagatc atcggcacct tcgagttgca 37020
agggcccagc gagggcgagg gagccaaggg gggtctgaaa ctcaccccgg ggctgtggac 37080
ctcggcctac ttgcgcaagt tcgtgcccga ggattaccat cccttcgaga tcaggttcta 37140
cgaggaccaa tcccagccgc ccaaggccga gctgtcggcc tgcgtcatca cccagggggc 37200

-continued

```
gatcctggcc caattgcaag ccatccagaa atcccgccaa gaattcttgc tgaaaaaggg  37260
ccgcggggtc tacctcgacc cccagaccgg tgaggagctc aaccccggct tcccccagga  37320
tgccccgagg aaacaagaag ctgaaagtgg agctgccgcc cgtggaggat ttggaggaag  37380
actgggagaa cagcagtcag gcagaggaga tggaggaaga ctgggacagc actcaggcag  37440
aggaggacag cctgcaagac agtctggagg aagacgagga ggaggcagag gaggaggtgg  37500
aagaagcagc cgccgccaga ccgtcgtcct cggcgggggga gaaagcaagc agcacggata  37560
ccatctccgc tccgggtcgg ggtcccgctc ggccccacag tagatgggac gagaccgggc  37620
gattcccgaa ccccaccacc cagaccggta agaaggagcg gcagggatac aagtcctggc  37680
gggggcacaa aaacgccatc gtctcctgct tgcaggcctg cgggggcaac atctccttca  37740
cccggcgcta cctgctcttc caccgcgggg tgaacttccc ccgcaacatc ttgcattact  37800
accgtcacct ccacagcccc tactacttcc aagaagaggc agcagcagca gaaaaagacc  37860
agaaaaccag ctagaaaatc cacagcggcg gcagcggcag gtggactgag gatcgcggcg  37920
aacgagccgg cgcagacccg ggagctgagg aaccggatct ttcccaccct ctatgccatc  37980
ttccagcaga gtcgggggca ggagcaggaa ctgaaagtca agaaccgttc tctgcgctcg  38040
ctcacccgca gttgtctgta tcacaagagc gaagaccaac ttcagcgcac tctcgaggac  38100
gccgaggctc tcttcaacaa gtactgcgcg ctcactctta aagagtagcc cgcgcccgcc  38160
cagtcgcaga aaaaggcggg aattacgtca cctgtgccct tcgccctagc cgcctccacc  38220
cagcaccgcc atgagcaaag agattcccac gccttacatg tggagctacc agccccagat  38280
gggcctggcc gccggcgccg cccaggacta ctccacccgc atgaattggc tcagcgccgg  38340
gcccgcgatg atctcacggg tgaatgacat ccgcgcccac cgaaaccaga tactcctaga  38400
acagtcagcg ctcaccgcca cgccccgcaa tcacctcaat ccgcgtaatt ggcccgccgc  38460
cctggtgtac caggaaattc cccagcccac gaccgtacta cttccgcgag acgcccaggc  38520
cgaagtccag ctgactaact caggtgtcca gctggcgggc ggcgccaccc tgtgtcgtca  38580
ccgccccgct cagggtataa agcggctggt gatccggggc agaggcacac agctcaacga  38640
cgaggtggtg agctcttcgc tgggtctgcg acctgacgga gtcttccaac tcgccggatc  38700
ggggagatct tccttcacgc ctcgtcaggc ggtcctgact ttggagagtt cgtcctcgca  38760
gccccgctcg ggcggcatcg gcactctcca gttcgtggag gagttcactc cctcggtcta  38820
cttcaacccc ttctccggct cccccggcca ctacccggac gagttcatcc cgaactttga  38880
cgccatcagc gagtcggtgg acggctacga ttgattaatt aatcaactaa cccccttaccc  38940
ctttaccctc cagtaaaaat aaagattaaa aatgattgaa ttgatcaata aagaatcact  39000
tacttgaaat ctgaaaccag gtctctgtcc atgttttctg tcagcagcac ttcactcccc  39060
tcttcccaac tctggtactg caggccccgg cgggctgcaa acttcctcca cactctgaag  39120
gggatgtcaa attcctcctg tccctcaatc ttcattttta tcttctatca gatgtccaaa  39180
aagcgcgcgc gggtggatga tggcttcgac cccgtgtacc cctacgatgc agacaacgca  39240
ccgactgtgc ccttcatcaa ccctcccttc gtctcttcag atggattcca agaaaagccc  39300
ctgggggtgt tgtccctgcg actggccgac cccgtcacca ccaagaatgg ggctgtcacc  39360
ctcaagctgg gggagggggt ggacctcgac gactcgggaa aactcatctc caaaaatgcc  39420
accaaggcca ctgcccctct cagtatttcc aacggcacca tttcccttaa catggctgcc  39480
cctttttaca acaacaatgg aacgttaagt ctcaatgttt ctacaccatt agcagtattt  39540
cccactttta acactttagg tatcagtctt ggaaacggtc ttcaaacttc taataagttg  39600
```

ctgactgtac agttaactca tcctcttaca ttcagctcaa atagcatcac agtaaaaaca 39660
gacaaaggac tctatattaa ttctagtgga aacagagggc ttgaggctaa cataagccta 39720
aaaagaggac tgatttttga tggtaatgct attgcaacat accttggaag tggtttagac 39780
tatggatcct atgatagcga tgggaaaaca agacccatca tcaccaaaat tggagcaggt 39840
ttgaattttg atgctaataa tgccatggct gtgaagctag gcacaggttt aagttttgac 39900
tctgccggtg ccttaacagc tggaaacaaa gaggatgaca agctaacact ttggactaca 39960
cctgacccaa gccctaattg tcaattactt tcagacagag atgccaaatt taccctatgt 40020
cttacaaaat gcggtagtca aatactaggc actgttgcag tagctgctgt tactgtaggt 40080
tcagcactaa atccaattaa tgacacagta aaaagcgcca tagtattcct tagatttgac 40140
tctgacggtg tgctcatgtc aaactcatca atggtaggtg attactggaa ctttagggaa 40200
ggacagacca cccaaagtgt ggcctataca aatgctgtgg gattcatgcc caatctaggt 40260
gcatatccta aaacccaaag caaaacacca aaaaatagta tagtaagtca ggtatattta 40320
aatggagaaa ctactatgcc aatgacactg acaataactt tcaatggcac tgatgaaaaa 40380
gacacaacac ctgtgagcac ttactccatg acttttacat ggcagtggac tggagactat 40440
aaggacaaga atattacctt tgctaccaac tcctttactt tctcctacat ggcccaagaa 40500
taaaccctgc atgccaaccc cattgttccc accactatgg aaaactctga agcagaaaaa 40560
aataaagttc aagtgtttta ttgattcaac agttttctca cagaacccta gtattcaacc 40620
tgccacctcc ctcccaacac acagagtaca cagtcctttc tccccggctg gccttaaaaa 40680
gcatcatatc atgggtaaca gacatattct taggtgttat attccacacg gtttcctgtc 40740
gagccaaacg ctcatcagtg atattaataa actccccggg cagctcactt aagttcatgt 40800
cgctgtccag ctgctgagcc acaggctgct gtccaacttg cggttgctta acgggcggcg 40860
aaggagaagt ccacgcctac atgggggtag agtcataatc gtgcatcagg atagggcggt 40920
ggtgctgcag cagcgcgcga ataaactgct gccgccgccg ctccgtcctg caggaataca 40980
acatggcagt ggtctcctca gcgatgattc gcaccgcccg cagcataagg cgccttgtcc 41040
tccgggcaca gcagcgcacc ctgatctcac ttaaatcagc acagtaactg cagcacagca 41100
ccacaatatt gttcaaaatc ccacagtgca aggcgctgta tccaaagctc atggcgggga 41160
ccacagaacc cacgtggcca tcataccaca agcgcaggta gattaagtgg cgacccctca 41220
taaacacgct ggacataaac attacctctt ttggcatgtt gtaattcacc acctcccggt 41280
accatataaa cctctgatta aacatggcgc catccaccac catcctaaac cagctggcca 41340
aaacctgccc gccggctata cactgcaggg aaccgggact ggaacaatga cagtggagag 41400
cccaggactc gtaaccatgg atcatcatgc tcgtcatgat atcaatgttg gcacaacaca 41460
ggcacacgtg catacacttc ctcaggatta caagctcctc ccgcgttaga accatatccc 41520
agggaacaac ccattcctga atcagcgtaa atcccacact gcagggaaga cctcgcacgt 41580
aactcacgtt gtgcattgtc aaagtgttac attcgggcag cagcggatga tcctccagta 41640
tggtagcgcg ggtttctgtc tcaaaaggag gtagacgatc cctactgtac ggagtgcgcc 41700
gagacaaccg agatcgtgtt ggtcgtagtg tcatgccaaa tggaacgccg gacgtagtca 41760
tatttcctga agcaaaacca ggtgcgggcg tgacaaacag atctgcgtct ccggtctcgc 41820
cgcttagatc gctctgtgta gtagttgtag tatatccact ctctcaaagc atccaggcgc 41880
cccctggctt cgggttctat gtaaactcct tcatgcgccg ctgccctgat aacatccacc 41940

```
accgcagaat aagccacacc cagccaacct acacattcgt tctgcgagtc acacacggga  42000
ggagcgggaa gagctggaag aaccatgatt aactttattc caaacggtct cggagcactt  42060
caaaatgcag gtcccggagg tggcacctct cgccccccact gtgttggtgg aaaataacag  42120
ccaggtcaaa ggtgacacgg ttctcgagat gttccacggt ggcttccagc aaagcctcca  42180
cgcgcacatc cagaaacaag aggacagcga aagcgggagc gttttctaat tcctcaatca  42240
tcatattaca ctcctgcacc atccccagat aattttcatt tttccagcct tgaatgattc  42300
gtattagttc ctgaggtaaa tccaagccag ccatgataaa aagctcgcgc agagcgccct  42360
ccaccggcat tcttaagcac accctcataa ttccaagaga ttctgctcct ggttcacctg  42420
cagcagatta acaatgggaa tatcaaaatc tctgccgcga tccctaagct cctccctcaa  42480
caataactgt atgtaatctt tcatatcatc tccgaaattt ttagccatag ggccgccagg  42540
aataagagca gggcaagcca cattacagat aaagcgaagt cctccccagt gwgcattgcc  42600
aaatgtaaga ttgaaataag catgctggct agaccctgtg atatcttcca gataactgga  42660
cagaaaatca ggcaagcaat ttttaagaaa atcaacaaaa gaaaagtcgt ccaggtgcag  42720
gtttagagcc tcaggaacaa cgatggaata agtgcaagga gtgcgttcca gcatggttag  42780
tgttttttttg gtgatctgta gaacaaaaaa taaacatgca atattaaacc atgctagcct  42840
ggcgaacagg tgggtaaatc actctttcca gcaccaggca ggctacgggg tctccggcgc  42900
gaccctcgta gaagctgtcg ccatgattga aaagcatcac cgagagacct tcccggtggc  42960
cggcatggat gattcgagaa gaagcataca ctccgggaac attggcatcc gtgagtgaaa  43020
aaaagcgacc tataaagcct cggggcacta caatgctcaa tctcaattcc agcaaagcca  43080
ccccatgcgg atggagcaca aaattggcag gtgcgtaaaa aatgtaatta ctcccctcct  43140
gcacaggcag caaagccccc gctccctcca gaaacacata caaagcctca gcgtccatag  43200
cttaccgagc acggcaggcg caagagtcag agaaaaggct gagctctaac ctgactgccc  43260
gctcctgtgc tcaatatata gccctaacct acactgacgt aaaggccaaa gtctaaaaat  43320
acccgccaaa atgacacaca cgcccagcac acgcccagaa accggtgaca cactcaaaaa  43380
aatacgtgcg cttcctcaaa cgcccaaacc ggcgtcattt ccgggttccc acgctacgtc  43440
accgctcagc gactttcaaa ttccgtcgac cgttaaaaac gtcactcgcc ccgcccctaa  43500
cggtcgccct tctctcggcc aatcaccttc ctcccttccc aaattcaaac gcctcatttg  43560
catattaacg cgcacaaaaa gtttgaggta tatatttgaa tgatg                  43605
```

<210> SEQ ID NO 120
<211> LENGTH: 44211
<212> TYPE: DNA
<213> ORGANISM: Artificial Sequence
<220> FEATURE:
<223> OTHER INFORMATION: Vector

<400> SEQUENCE: 120

```
gtttaaacgc ggccgccagg cctacccact agtcaattcg ggaggatcga aacggcagat     60
cgcaaaaaac agtacataca gaaggagaca tgaacatgaa catcaaaaaa attgtaaaac    120
aagccacagt tctgactttt acgactgcac ttctggcagg aggagcgact caagccttcg    180
cgaaagaaaa taaccaaaaa gcatacaaag aaacgtacgg cgtctctcat attacacgcc    240
atgatatgct gcagatccct aaacagcagc aaaacgaaaa ataccaagtg cctcaattcg    300
atcaatcaac gattaaaaat attgagtctg caaaaggact tgatgtgtgg gacagctggc    360
cgctgcaaaa cgctgacgga acagtagctg aatacaacgg ctatcacgtt gtgtttgctc    420
```

ttgcgggaag cccgaaagac gctgatgaca catcaatcta catgttttat caaaaggtcg 480
gcgacaactc aatcgacagc tggaaaaacg cgggccgtgt ctttaaagac agcgataagt 540
tcgacgccaa cgatccgatc ctgaaagatc agacgcaaga atggtccggt tctgcaacct 600
ttacatctga cggaaaaatc cgtttattct acactgacta ttccggtaaa cattacggca 660
aacaaagcct gacaacagcg caggtaaatg tgtcaaaatc tgatgacaca ctcaaaatca 720
acggagtgga agatcacaaa acgatttttg acggagacgg aaaaacatat cagaacgttc 780
agcagtttat cgatgaaggc aattatacat ccggcgacaa ccatacgctg agagaccctc 840
actacgttga agacaaaggc cataaatacc ttgtattcga agccaacacg ggaacagaaa 900
acggatacca aggcgaagaa tctttattta acaaagcgta ctacggcggc ggcacgaact 960
tcttccgtaa agaaagccag aagcttcagc agagcgctaa aaaacgcgat gctgagttag 1020
cgaacggcgc cctcggtatc atagagttaa ataatgatta cacattgaaa aaagtaatga 1080
agccgctgat cacttcaaac acggtaactg atgaaatcga gcgcgcgaat gttttcaaaa 1140
tgaacggcaa atggtacttg ttcactgatt cacgcggttc aaaaatgacg atcgatggta 1200
ttaactcaaa cgatatttac atgcttggtt atgtatcaaa ctctttaacc ggcccttaca 1260
agccgctgaa caaaacaggg cttgtgctgc aaatgggtct tgatccaaac gatgtgacat 1320
tcacttactc tcacttcgca gtgccgcaag ccaaaggcaa caatgtggtt atcacaagct 1380
acatgacaaa cagaggcttc ttcgaggata aaaaggcaac atttgcgcca agcttcttaa 1440
tgaacatcaa aggcaataaa acatccgttg tcaaaaacag catcctggag caaggacagc 1500
tgacagtcaa ctaataacag caaaaagaaa atgccgatac ttcattggca ttttctttta 1560
tttctcaaca agatggtgaa ttgactagtg ggtagatcca caggacgggt gtggtcgcca 1620
tgatcgcgta gtcgatagtg gctccaagta gcgaagcgag caggactggg cggcggccaa 1680
agcggtcgga cagtgctccg agaacgggtg cgcatagaaa ttgcatcaac gcatatagcg 1740
ctagcagcac gccatagtga ctggcgatgc tgtcggaatg gacgatatcc cgcaagaggc 1800
ccggcagtac cggcataacc aagcctatgc ctacagcatc cagggtgacg gtgccgagga 1860
tgacgatgag cgcattgtta gatttcatac acggtgcctg actgcgttag caatttaact 1920
gtgataaact accgcattaa agcttatcga tgataagctg tcaaacatga gaattgatcc 1980
ggaaccctta atataacttc gtataatgta tgctatacga agttattagg tccctcgact 2040
atagggtcac cgtcgacagc gacacacttg catcggatgc agcccggtta acgtgccggc 2100
acggcctggg taaccaggta ttttgtccac ataaccgtgc gcaaaatgtt gtggataagc 2160
aggacacagc agcaatccac agcaggcata caaccgcaca ccgaggttac tccgttctac 2220
aggttacgac gacatgtcaa tacttgccct tgacaggcat tgatggaatc gtagtctcac 2280
gctgatagtc tgatcgacaa tacaagtggg accgtggtcc cagaccgata atcagaccga 2340
crayacgagt gggaycgtgg tcccagacta ataatcagac cgacgatacg agtgggaccg 2400
tggtcccaga ctaataatca gaccgacgat acgagtggga ccgtggtycc agwctratwa 2460
tcagaccgac gatacragtg gracmgtggk cccagasaka atawtcagrc cgagwtaygc 2520
wktckggcct gtaacaaagg acattaagta aagacagata mrmgtgrgac taaaacgtgg 2580
tcccagtctg attatcagac cgacgatacg agtgggaccg tggtcccaga ctaataatca 2640
gaccgacgat acgagtggga ccgtggtccc agactaataa tcagaccgac gatacgagtg 2700
ggaccgtggt cccagtctga ttatcagacc gacgatacaa gtggaacagt gggcccagag 2760

-continued

```
agaatattca ggccagttat gctttctggc ctgtaacaaa ggacattaag taaagacaga   2820
taaacgtaga ctaaaacgtg gtcgcatcag ggtgctggct tttcaagttc cttaagaatg   2880
gcctcaattt tctctataca ctcagttgga acacgagacc tgtccaggtt aagcaccatt   2940
ttatcgccct tatacaatac tgtcgctcca ggagcaaact gatgtcgtga gcttaaacta   3000
gttcttgatg cagatgacgt tttaagcaca gaagttaaaa gagtgataac ttcttcagct   3060
tcaaatatca ccccagcttt tttctgctca tgaaggttag atgcctgctg cttaagtaat   3120
tcctctttat ctgtaaaggc tttttgaagt gcatcacctg accgggcaga tagttcaccg   3180
gggtgagaaa aaagagcaac aactgattta ggcaatttgg cggtgttgat acagcgggta   3240
ataatcttac gtgaaatatt ttccgcatca gccagcgcag aaatatttcc agcaaattca   3300
ttctgcaatc ggcttgcata acgctgacca cgttcataag cacttgttgg gcgataatcg   3360
ttacccaatc tggataatgc agccatctgc tcatcatcca gctcgccaac cagaacacga   3420
taatcacttt cggtaagtgc agcagcttta cgacggcgac tcccatcggc aatttctatg   3480
acaccagata ctcttcgacc gaacgccggt gtctgttgac cagtcagtag aaaagaaggg   3540
atgagatcat ccagtgcgtc ctcagtaagc agctcctggt cacgttcatt acctgaccat   3600
acccgagagg tcttctcaac actatcaccc cggagcactt caagagtaaa cttcacatcc   3660
cgaccacata caggcaaagt aatggcatta ccgcgagcca ttactcctac gcgcgcaatt   3720
aacgaatcca ccatcggggc agctggtgtc gataacgaag tatcttcaac cggttgagta   3780
ttgagcgtat gttttggaat aacaggcgca cgcttcatta tctaatctcc cagcgtggtt   3840
taatcagacg atcgaaaatt tcattgcaga caggttccca aatagaaaga gcatttctcc   3900
aggcaccagt tgaagagcgt tgatcaatgg cctgttcaaa aacagttctc atccggatct   3960
gacctttacc aacttcatcc gtttcacgta caacattttt tagaaccatg cttccccagg   4020
catcccgaat ttgctcctcc atccacgggg actgagagcc attactattg ctgtatttgg   4080
taagcaaaat acgtacatca ggctcgaacc ctttaagatc aacgttcttg agcagatcac   4140
gaagcatatc gaaaaactgc agtgcggagg tgtagtcaaa caactcagca ggcgtgggaa   4200
caatcagcac atcagcagca catacgacat taatcgtgcc gatacccagg ttaggcgcgc   4260
tgtcaataac tatgacatca tagtcatgag caacagtttc aatggccagt cggagcatca   4320
ggtgtggatc ggtgggcagt ttaccttcat caaatttgcc cattaactca gtttcaatac   4380
ggtgcagagc cagacaggaa ggaataatgt caagccccgg ccagcaagtg ggctttattg   4440
cataagtgac atcgtccttt tccccaagat agaaaggcag gagagtgtct tctgcatgaa   4500
tatgaagatc tggtacccat ccgtgataca ttgaggctgt tccctggggg tcgttacctt   4560
ccacgagcaa aacacgtagc cccttcagag ccagatcctg agcaagatga acagaaactg   4620
aggttttgta aacgccacct ttatgggcag caaccccgat caccggtgga aatacgtctt   4680
cagcacgtcg caatcgcgta ccaaacacat cacgcatatg attaatttgt tcaattgtat   4740
aaccaacacg ttgctcaacc cgtcctcgaa tttccatatc cgggtgcggt agtcgccctg   4800
ctttctcggc atctctgata gcctgagaag aaaccccaac taaatccgct gcttcaccta   4860
ttctccagcg ccgggttatt ttcctcgctt ccgggctgtc atcattaaac tgtgcaatgg   4920
cgatagcctt cgtcatttca tgaccagcgt ttatgcactg gttaagtgtt tccatgagtt   4980
tcattctgaa catcctttaa tcattgcttt gcgttttttt attaaatctt gcaatttact   5040
gcaaagcaac aacaaaatcg caaagtcatc aaaaaaccgc aaagttgttt aaaataagag   5100
caacactaca aaaggagata agaagagcac atacctcagt cacttattat cactagcgct   5160
```

cgccgcagcc gtgtaaccga gcatagcgag cgaactggcg aggaagcaaa gaagaactgt 5220
tctgtcagat agctcttacg ctcagcgcaa gaagaaatat ccaccgtggg aaaaactcca 5280
ggtagaggta cacacgcgga tagccaattc agagtaataa actgtgataa tcaaccctca 5340
tcaatgatga cgaactaacc cccgatatca ggtcacatga cgaagggaaa gagaaggaaa 5400
tcaactgtga caaactgccc tcaaatttgg cttccttaaa aattacagtt caaaaagtat 5460
gagaaaatcc atgcaggctg aaggaaacag caaaactgtg acaaattacc ctcagtaggt 5520
cagaacaaat gtgacgaacc accctcaaat ctgtgacaga taaccctcag actatcctgt 5580
cgtcatggaa gtgatatcgc ggaaggaaaa tacgatatga gtcgtctggc ggcctttctt 5640
tttctcaatg tatgagaggc gcattggagt tctgctgttg atctcattaa cacagacctg 5700
caggaagcgg cggcggaagt caggcatacg ctggtaactt tgaggcagct ggtaacgctc 5760
tatgatccag tcgattttca gagagacgat gcctgagcca tccggcttac gatactgaca 5820
cagggattcg tataaacgca tggcatacgg attggtgatt tcttttgttt cactaagccg 5880
aaactgcgta aaccggttct gtaacccgat aaagaaggga atgagatatg ggttgatatg 5940
tacactgtaa agccctctgg atggactgtg cgcacgtttg ataaaccaag gaaaagattc 6000
atagcctttt tcatcgccgg catcctcttc agggcgataa aaaaccactt ccttccccgc 6060
gaaactcttc aatgcctgcc gtatatcctt actggcttcc gcagaggtca atccgaatat 6120
ttcagcatat ttagcaacat ggatctcgca gataccgtca tgttcctgta gggtgccatc 6180
agattttctg atctggtcaa cgaacagata cagcatacgt tttgatcccg ggagagact 6240
atatgccgcc tcagtgaggt cgtttgactg gacgattcgc gggctatttt tacgtttctt 6300
gtgattgata accgctgttt ccgccatgac agatccatgt gaagtgtgac aagtttttag 6360
attgtcacac taaataaaaa agagtcaata agcagggata actttgtgaa aaaacagctt 6420
cttctgaggg caatttgtca cagggttaag ggcaatttgt cacagacagg actgtcattt 6480
gagggtgatt tgtcacactg aaagggcaat ttgtcacaac accttctcta gaaccagcat 6540
ggataaaggc ctacaaggcg ctctaaaaaa gaagatctaa aaactataaa aaaaataatt 6600
ataaaaatat ccccgtggat aagtggataa ccccaaggga agttttttca ggcatcgtgt 6660
gtaagcagaa tatataagtg ctgttccctg gtgcttcctc gctcactcga gggcttcgcc 6720
ctgtcgctca actgcggcga gcactactgg ctgtaaaagg acagaccaca tcatggttct 6780
gtgttcatta ggttgttctg tccattgctg acataatccg ctccacttca acgtaacacc 6840
gcacgaagat ttctattgtt cctgaaggca tattcaaatc gttttcgtta ccgcttgcag 6900
gcatcatgac agaacactac ttcctataaa cgctacacag gctcctgaga ttaataatgc 6960
ggatctctac gataatggga gattttcccg actgtttcgt tcgcttctca gtggataaca 7020
gccagcttct ctgtttaaca gacaaaaaca gcatatccac tcagttccac atttccatat 7080
aaaggccaag gcatttattc tcaggataat tgtttcagca tcgcaaccgc atcagactcc 7140
ggcatcgcaa actgcacccg gtgccgggca gccacatcca gcgcaaaaac cttcgtgtag 7200
acttccgttg aactgatgga cttatgtccc atcaggcttt gcagaacttt cagcggtata 7260
ccggcataca gcatgtgcat cgcataggaa tggcggaacg tatgtggtgt gaccggaaca 7320
gagaacgtca caccgtcagc agcagcggcg gcaaccgcct ccccaatcca ggtcctgacc 7380
gttctgtccg tcacttccca gatccgcgct ttctctgtcc ttcctgtgcg acggttacgc 7440
cgctccatga gcttatcgcg aataaatacc tgtgacggaa gatcacttcg cagaataaat 7500

-continued

```
aaatcctggt gtccctgttg ataccgggaa gccctgggcc aacttttggc gaaaatgaga    7560
cgttgatcgg cacgtaagag gttccaactt tcaccataat gaaataagat cactaccggg    7620
cgtatttttt gagttatcga gattttcagg agctaaggaa gctaaaatgg agaaaaaaat    7680
cactggatat accaccgttg atatatccca atggcatcgt aaagaacatt ttgaggcatt    7740
tcagtcagtt gctcaatgta cctataacca gaccgttcag ctggatatta cggccttttt    7800
aaagaccgta aagaaaaata agcacaagtt ttatccggcc tttattcaca ttcttgcccg    7860
cctgatgaat gctcatccgg agttccgtat ggcaatgaaa gacggtgagc tggtgatatg    7920
ggatagtgtt cacccttgtt acaccgtttt ccatgagcaa actgaaacgt tttcatcgct    7980
ctggagtgaa taccacgacg atttccggca gtttctacac atatattcgc aagatgtggc    8040
gtgttacggt gaaaacctgg cctatttccc taaagggttt attgagaata tgtttttcgt    8100
ctcagccaat ccctgggtga gtttcaccag ttttgattta aacgtggcca atatggacaa    8160
cttcttcgcc cccgttttca ccatgggcaa atattatacg caaggcgaca aggtgctgat    8220
gccgctggcg attcaggttc atcatgccgt ttgtgatggc ttccatgtcg gcagaatgct    8280
taatgaatta caacagtact gcgatgagtg gcagggcggg gcgtaatttt tttaaggcag    8340
ttattggtgc ccttaaacgc ctggttgcta cgcctgaata agtgataata agcggatgaa    8400
tggcagaaat tcgatgataa gctgtcaaac atgagaattg gtcgacggcg cgccaaagct    8460
tgcatgcctg cagccgcgta acctggcaaa atcggttacg gttgagtaat aaatggatgc    8520
cctgcgtaag cggggcacat ttcattacct ctttctccgc acccgacata gataataact    8580
tcgtatagta tacattatac gaagttatct agtagactta atcgcgttta aacccatcat    8640
caataatata cctcaaactt tttgtgcgcg ttaatatgca aatgaggcgt ttgaatttgg    8700
gaagggagga aggtgattgg ccgagagaag ggcgaccgtt aggggcgggg cgagtgacgt    8760
tttgatgacg tgaccgcgag gaggagccag tttgcaagtt ctcgtgggaa aagtgacgtc    8820
aaacgaggtg tggtttgaac acggaaatac tcaattttcc cgcgctctct gacaggaaat    8880
gaggtgtttc taggcggatg caagtgaaaa cgggccattt tcgcgcgaaa actgaatgag    8940
gaagtgaaaa tctgagtaat ttcgcgttta tgacagggag gagtatttgc cgagggccga    9000
gtagactttg accgattacg tgggggtttc gattaccgtg tttttcacct aaatttccgc    9060
gtacggtgtc aaagtccggt gtttttacgt aggtgtcagc tgatcgccag ggtatttaaa    9120
cctgcgctct ccagtcaaga ggccactctt gagtgccagc gagaagagtt ttctcctccg    9180
cgcgcgagtc agatctacac tttgaaaggc gatcgctagc gacatcgatc caaataatga    9240
ttttattttg actgatagtg acctgttcgt tgcaacaaat tgataagcaa tgctttttta    9300
taatgccaac tttgtacaaa aaagcaggct ccaccatggg aaccaattca gtcgagcctt    9360
tcactcatta gatgcatgtc gttacataac ttacggtaaa tggcccgcct ggctgaccgc    9420
ccaacgaccc ccgcccattg acgtcaataa tgacgtatgt tcccatagta acgccaatag    9480
ggactttcca ttgacgtcaa tgggtggagt atttacggta aactgcccac ttggcagtac    9540
atcaagtgta tcatatgcca agtacgcccc ctattgacgt caatgacggt aaatggcccg    9600
cctggcatta tgcccagtac atgaccttat gggactttcc tacttggcag tacatctacg    9660
tattagtcat cgctattacc atggtgatgc ggttttggca gtacatcaat gggcgtggat    9720
agcggtttga ctcacgggga tttccaagtc tccaccccat tgacgtcaat gggagtttgt    9780
tttggcacca aaatcaacgg gactttccaa aatgtcgtaa caactccgcc ccattgacgc    9840
aaatgggcgg taggcgtgta cggtgggagg tctatataag cagagctctc cctatcagtg    9900
```

atagagatct ccctatcagt gatagagatc gtcgacgagc tcgtttagtg aaccgtcaga 9960
tcgcctggag acgccatcca cgctgttttg acctccatag aagacaccgg gaccgatcca 10020
gcctccggtt aagctcggta ccgctagccg cgccgccacc atggatgcaa tgaagagagg 10080
gctctgctgt gtgctgctgc tgtgtggagc agtcttcgtt tcgcccagcc aggaaatcca 10140
tgcccgattc agaagaggat cgaagcttgc cagccagatc ggcgccggcg tgttcaagga 10200
gggcgtgttc cacaccatgt ggcacgtgac caggggcgcc gtgctgatgc accagggcaa 10260
gaggatcgag cccagctggg ccgacgtgaa gaaggacctg atcagctacg gcggcggctg 10320
gaggctggag ggcgagtggg acgagggcga ggaggtgcag gtgatcgccg tggagcccgg 10380
caagaacccc aaggccgtgc agaccaagcc cggcctgttc aagacccccg agggcgagat 10440
cggcgccatc gccctggact tcaagcccgg caccagcggc agccccatcg tgaacaggga 10500
gggcaaggtg gtgggcctgt acggcaacgg cgtggtgacc aagagcggcg cctacgtgag 10560
cgccatcgcc cagaccaacg ccgagcccct gcccgagatc gaggacgagg tgttcaggaa 10620
gaggaacctg accatcatgg acctgcaccc cggcgccggc aagaccaaga ggtatctgcc 10680
cgccatcgtg agggaggcca tcaagaggag gctgaggacc ctgatcctgg cccccaccag 10740
ggtggtggcc gccgagatgg aggaggccct gaagggcctg cccatcaggt atcagaccac 10800
cgccatcaag gccgagcaca ccggcaagga gatcgtggac ctgatgtgcc acgccacctt 10860
caccatgagg ctgctgagcc ccgtgagggt gcccaactac aacctgatca tcatggacga 10920
ggcccacttc accgaccccg ccagcatcgc cgccaggggc tacatcagca ccagggtgga 10980
gatgggcgag gccgccgcca tcttcatgac cgccaccccc cccggcagcg ccgacgcctt 11040
cccccagagc aacgccccca tcgaggacga ggagagggag atccccgaga ggagctggaa 11100
cagcggcttc gactggatca ccgacttcgc cggcaagacc gtgtggttcg tgcccagcat 11160
caaggccggc aacgacatcg ccaactgcct gaggaagaac ggcaagaagg tgatccagct 11220
gagcaggaag accttcgaca ccgagtaccc caagaccaag ctgaacgact gggacttcgt 11280
ggtgaccacc gacatcagcg agatgggcgc caacttcaag gccgacaggg tgatcgaccc 11340
caggaggtgc ctgaagcccg tgatcctgac cgacggcccc gagagggtga tcctggccgg 11400
ccccatgccc gtgaccgccg ccagcgccgc ccagaggagg ggcaggatcg gcaggaacca 11460
caagaaggag aacgaccagt acatctacat gggccagccc ctgaacaacg acgaggacca 11520
cgcccactgg accgaggcca agatgctgct ggacaacatc aacacccccg agggcatcat 11580
ccccgccctg ttcgagcccg agagggagaa gagcgccgcc atcgacggcg agtacaggct 11640
gaggggcgag gccaggaaga ccttcgtgga gctgatgagg aggggcgacc tgcccgtgtg 11700
gctgagctac aaggtggcca gcgccggctt ccagtacaag gacagggagt ggtgcttcga 11760
cggcgagagg aacaaccaga tcctggagga gaacatggac gtggagatct ggaccaagga 11820
gggcgagaag aagaagctga ggcccaggtg gctggacgcc aggacctacg ccgacccccct 11880
ggccctgaag gagttcaagg acttcgccgc cggcaggaag agcatcgcca ccgagatcgg 11940
cagggtgccc agccacctgg cccacaggac cagggcctac cagcacgccc tggaggagct 12000
gcccgagacc ctggagaccc tgctgctgct ggccctgctg ggcgccttcc tgttcttcct 12060
gagcggcaag ggcatcggca agatgagcat cggcctgtgc tgcatcatcg ccgccagcct 12120
gctgtggatg gccgagatcc agccccactg gatcgccgcc agcatcatcc tggagttctt 12180
cctgatggtg ctgctgatcc ccgagcccga gaagcagagg acccccccagg acaaccagct 12240

-continued

```
ggcctacgtg gtgatcggca tcctgaccct ggccgccgcc atcgccgcca acgagatggg  12300
cctgctggag accaccaaga aggacctggg catcggccac gtggccccca ccgccatcct  12360
ggacgtggac ctgcaccccg ccagcgcctg gaccctgtac gccgtggcca ccaccatcat  12420
cacccccatg ctgaggcaca ccatcgagaa cagcaccgcc aacgtgagcc tgaccgccat  12480
cgccaaccag gccgccgtgc tgatgggcct ggacaagggc tggcccatca gcaagatgga  12540
cctgggcgtg cccctgctgg ccctgggctg ctacagccag gtgaaccccc tgaccctgac  12600
cgccgccgtg ctgctgctga tcacccacta cgccatcatc ggccccggcc tgcaggccaa  12660
ggccaccagg gaggcccaga agaggaccgc cgccggcatc atgaagaacc ccaccgtgga  12720
cggcatcatg gccatcgacc tggaccccat cccctacgac cccaagttcg agaagcagct  12780
gggccaggtg atgctgctga tcctgtgcgt gagccagatc ctgctgatga ggaccacctg  12840
ggccctgtgc gaggccctga ccctggccac cggccccatc accaccctgt gggagggcaa  12900
ccccggcaag ttctggaaca ccaccatcgc cgtgagcatg gccaacatct tcaggggcag  12960
ctacctggcc ggcgccggcc tggccttcag cctgatcaag aacaggaggg gcaccggcgc  13020
ccagggcgag accctgggcg agaagtggaa gaggcagctg aaccagctgg acaagagcga  13080
gttcgaggag tacaagaaga gcggcatcct ggaggtggac aggaccgagg ccaaggaggc  13140
catcaagagg ggcgagaccg accaccacgc cgtgagcagg ggcagcgcca agctgaggtg  13200
gttcgtggag aggaacatgg tgatccccga gggcagggtg atcgacctgg gctgcggcag  13260
gggcggctgg agctactact gcgccggcct gaagaaggtg agggaggtga ggggctacac  13320
caagggcggc cccggccacg aggagcccat ccccatggcc acctacggct ggaacctggt  13380
gaagctgcac agcggcgtgg acgtgttctt ccccgagaag tgcgacaccc tgctgtgcga  13440
catcggcgag agcagcccca accccaccat cgaggagggc aggaccctga gggtgctgaa  13500
gatggtggag ccctggctga agggcaacca gttctgcatc aagatcctga acccctacat  13560
gcccagcgtg atcgaggagc tggagaagct gcagaggaag cacggcggca tgctggtgag  13620
gaacccccctg agcaggaaca gcacccacga gatgtactgg gtgagcaacg gcaccggcaa  13680
catcgtgagc gccgtgaaca tgatcagcag gatgctgatc aacaggttca ccatggccca  13740
caagaagccc acctacgaga gggacgtgga cctgggcgcc ggcagcacct ggcactacga  13800
cgaggacaac ccctacaaga cctgggccta ccacggcagc tacgaggtga aggccaccgg  13860
cagcgccagc agcatggtga acggcgtggt gaagctgctg accaagccct gggacgtggt  13920
gcccatggtg acccagatgg ccatgaccga caccaccccc ttcggccagc agagggtgtt  13980
caaggagaag gtggacacca ggacccccga ggccaaggag aacgccgcca tcggcgccgt  14040
gttccaggac gagaacggct ggaagagcgc cagggaggcc gtggaggaca gcgagagggc  14100
cctgcacctg gagggcaagt gcgagagctg cgtgtacaac atgatgggca agagggagaa  14160
gaagctgggc gagttcggca aggccaaggg cagcagggcc atctggtaca tgtggctggg  14220
cgccaggttc ctggagttcg aggccctggg cttcctgaac gaggaccact ggttcagcag  14280
ggagaacagc ctgagcggcg tggagggcga gggcctgcac aagctgggct acatcctgag  14340
ggacatcagc aagatccccg gcggcgccat gtacgccgac gacaccgccg gctgggacac  14400
caggatcacc gaggacgacc tgcacaacga ggagaagatc ctggccaagg ccatcttcaa  14460
gctgacctac cagaacaagg tggtgaaggt gcagaggccc acccccaggg gcgccgtgat  14520
ggacatcatc agcaggaagg accagaggggg cagcggccag gtgggcacct acggcctgaa  14580
caccttcacc aacatggagg cccagctgat caggcagatg gaggccgagg gcgtgatcac  14640
```

```
cgagtgcggc gtggacaggc tgaagaggat ggccatcagc ggcgacgact gcgtggtgaa  14700
gcccccccag tgggagccca gcaagggctg gcacgactgg cagcaggtgc ccttctgcag  14760
ccaccacttc cacgagatct tcatgaagga cggcaggaag ctggtggtgc cctgcaggaa  14820
ccaggacgag ctgatcggca gggccaggat cagccagggc gccggctgga gcctgaggga  14880
gaccgcctgc ctgggcaaga gctacgccca gatgtggcag ctgatgtact tccacaggag  14940
ggacctgagg ctggccagca acgccatctg cagcgccgtg cccagccact gggtgcccac  15000
cagcaggacc acctggagca tccacgccca ccacgagtgg atgaccaccg aggacatgct  15060
ggccgtgtgg aacagggtgt ggatcgagga gaacccctgg atggaggaca agacccacat  15120
ccacagctgg gaggacgtgc cctacctggg caagagggag gaccagtggt gcggcagcct  15180
gatcggcctg accagcaggg ccacctgggc caagaacatc gctggatccg ggcccggggc  15240
ttcaggtaag cctatcccta accctctcct cggtctcgat tctacgcgga cctgatgagc  15300
ggccgctcga gcatgcatct agagggccct attctatagt gtcacctaaa tgctagagct  15360
cgctgatcag cctcgactgt gccttctagt tgccagccat ctgttgtttg cccctccccc  15420
gtgccttcct tgaccctgga aggtgccact cccactgtcc tttcctaata aaatgaggaa  15480
attgcatcgc attgtctgag taggtgtcat tctattctgg ggggtggggt ggggcaggac  15540
agcaaggggg aggattggga agacaatagc aggcatgctg gggatgcggt gggctctatg  15600
gcttctgagg cggaaagaac cagctggggc tcgagggggg atcgatcccg tcgagatatc  15660
tagacccagc tttcttgtac aaagttggca ttataagaaa gcattgctta tcaatttgtt  15720
gcaacgaaca ggtcactatc agtcaaaata aaatcattat ttggatcgat tcgacagatc  15780
gcgatcgcag tgagtagtgt tctggggcgg gggaggacct gcatgagggc cagaatgact  15840
gaaatctgtg cttttctgtg tgttgcagca tcatgagcgg aagcggctcc tttgagggag  15900
gggtattcag cccttatctg acggggcgtc tcccctcctg ggcgggagtg cgtcagaatg  15960
tgatgggatc cacggtggac ggccggcccg tgcagcccgc gaactcttca accctgacct  16020
atgcaaccct gagctcttcg tcggtggacg cagctgccgc cgcagctgct gcatccgccg  16080
ccagcgccgt gcgcggaatg gccatgggcg ccggctacta cggcactctg gtggccaact  16140
cgagttccac caataatccc gccagcctga acgaggagaa gctgctgctg ctgatggccc  16200
agcttgaggc cttgacccag cgcctgggcg agctgaccca gcaggtggct cagctgcagg  16260
agcagacgcg ggccgcggtt gccacggtga aatccaaata aaaaatgaat caataaataa  16320
acggagacgg ttgttgattt taacacagag tctgaatctt tatttgattt ttcgcgcgcg  16380
gtaggccctg gaccaccggt ctcgatcatt gagcacccgg tggatctttt ccaggacccg  16440
gtagaggtgg gcttggatgt tgaggtacat gggcatgagc ccgtcccggg ggtggaggta  16500
gctccattgc agggcctcgt gctcgggggt ggtgttgtaa atcacccagt catagcaggg  16560
gcgcagggcg tggtgttgca caatatcttt gaggaggaga ctgatggcca cgggcagccc  16620
tttggtgtag gtgtttacaa atctgttgag ctgggaggga tgcatgcggg gggagatgag  16680
gtgcatcttg gcctggatct tgagattggc gatgttaccg cccagatccc gcctggggtt  16740
catgttgtgc aggaccacca gcacggtgta tccggtgcac ttggggaatt tatcatgcaa  16800
cttggaaggg aaggcgtgaa agaatttggc gacgcccttg tgtccgccca ggttttccat  16860
gcactcatcc atgatgatgg caatgggccc gtgggcggcg gcctgggcaa agacgtttcg  16920
ggggtcggac acatcatagt tgtggtcctg ggtgaggtca tcataggcca ttttaatgaa  16980
```

```
tttggggcgg agggtgccgg actgggggac aaaggtaccc tcgatcccgg gggcgtagtt  17040
cccctcacag atctgcatct cccaggcttt gagctcagag ggggggatca tgtccacctg  17100
cggggcgata aagaacacgg tttccggggc gggggagatg agctgggccg aaagcaagtt  17160
ccggagcagc tgggacttgc cgcagccggt ggggccgtaa atgaccccga tgaccggctg  17220
caggtggtag ttgagggaga gacagctgcc gtcctcccgg aggagggggg ccacctcgtt  17280
catcatctcg cgcacgtgca tgttctcgcg caccagttcc gccaggaggc gctctccccc  17340
cagagatagg agctcctgga gcgaggcgaa gtttttcagc ggcttgagtc cgtcggccat  17400
gggcattttg gagagggtct gttgcaagag ttccaagcgg tcccagagct cggtgatgtg  17460
ctctacggca tctcgatcca gcagacctcc tcgtttcgcg ggttgggacg actgcgggag  17520
tagggcacca gacgatgggc gtccagcgca gccagggtcc ggtccttcca gggccgcagc  17580
gtccgcgtca gggtggtctc cgtcacggtg aaggggtgcg cgccgggctg ggcgcttgcg  17640
agggtgcgct tcaggctcat ccggctggtc gaaaaccgct cccgatcggc gccctgcgcg  17700
tcggccaggt agcaattgac catgagttcg tagttgagcg cctcggccgc gtggcctttg  17760
gcgcggagct tacctttgga agtctgcccg caggcgggac agaggaggga cttgagggcg  17820
tagagcttgg gggcgaggaa gacggaatcg gggggcgtagg cgtccgcgcc gcagtgggcg  17880
cagacggtct cgcactccac gagccaggtg aggtcgggct ggtcggggtc aaaaaccagt  17940
ttcccgccgt tctttttgat gcgtttctta cctttggtct ccatgagctc gtgtccccgc  18000
tgggtgacaa agaggctgtc cgtgtccccg tagaccgact ttatgggccg gtcctcgagc  18060
ggtgtgccgc ggtcctcctc gtagaggaac cccgcccact ccgagacgaa agcccgggtc  18120
caggccagca cgaaggaggc cacgtgggac gggtagcggt cgttgtccac cagcgggtcc  18180
actttttcca gggtatgcaa acacatgtcc ccctcgtcca catccaggaa ggtgattggc  18240
ttgtaagtgt aggccacgtg accgggggtc ccggccgggg gggtataaaa gggggcgggc  18300
ccctgctcgt cctcactgtc ttccggatcg ctgtccagga gcgccagctg ttggggtagg  18360
tattccctct cgaaggcggg catgacctcg gcactcaggt tgtcagtttc tagaaacgag  18420
gaggatttga tattgacggt gccagcggag atgcctttca agagcccctc gtccatctgg  18480
tcagaaaaga cgattttttt gttgtcgagc ttggtggcga aggagccgta gagggcgttg  18540
gaaaggagct tggcgatgga gcgcatggtc tggttttttt ccttgtcggc gcgctccttg  18600
gccgcgatgt tgagctgcac gtactcgcgc gccacgcact tccattcggg gaagacggtg  18660
gtcatctcgt cgggcacgat tctgacctgc caacctcgat tatgcagggt gatgaggtcc  18720
acactggtgg ccacctcgcc gcgcaggggc tcgttggtcc agcagaggcg gccgcccttg  18780
cgcgagcaga aggggggcag agggtccagc atgacctcgt cggggggggtc ggcatcgatg  18840
gtgaagatgc cgggcaggag atcggggtcg aagtagctga tggaagtggc cagatcgtcc  18900
agggaagctt gccattcgcg cacggccagc gcgcgctcgt agggactgag gggcgtgccc  18960
cagggcatgg ggtgggtgag cgcggaggcg tacatgccgc agatgtcgta gacgtagagg  19020
ggctcctcga ggatgccgat gtaggtgggg tagcagcgcc ccccgcggat gctggcgcgc  19080
acgtagtcat acagctcgtg cgagggcgcg aggagccccg ggcccaggtt ggtgcgactg  19140
ggcttttcgg cgcggtagac gatctggcga aagatggcat gcgagttgga ggagatggtg  19200
ggcctttgga agatgttgaa gtgggcgtgg gggaggccga ccgagtcgcg gatgaagtgg  19260
gcgtaggagt cttgcagttt ggcgacgagc tcggcggtga cgaggacgtc cagagcgcag  19320
tagtcgaggg tctcctggat gatgtcatac ttgagctggc ccttttgttt ccacagctcg  19380
```

cggttgagaa ggaactcttc gcggtccttc cagtactctt cgagggggaa cccgtcctga 19440
tctgcacggt aagagcctag catgtagaac tggttgacgg ccttgtaggc gcagcagccc 19500
ttctccacgg ggagggcgta ggcctgggcg gccttgcgca gggaggtgtg cgtgagggcg 19560
aaggtgtccc tgaccatgac cttgaggaac tggtgcttga aatcgatatc gtcgcagccc 19620
ccctgctccc agagctggaa gtccgtgcgc ttcttgtagg cggggttggg caaagcgaaa 19680
gtaacatcgt tgaaaaggat cttgcccgcg cggggcataa agttgcgagt gatgcggaaa 19740
ggctggggca cctcggcccg gttgttgatg acctgggcgg cgagcacgat ctcgtcgaaa 19800
ccgttgatgt tgtggcccac gatgtagagt tccacgaatc gcgggcggcc cttgacgtgg 19860
ggcagcttct tgagctcctc gtaggtgagc tcgtcggggt cgctgagacc gtgctgctcg 19920
agcgcccagt cggcgagatg gggttggcg cggaggaagg aagtccagag atccacggcc 19980
agggcggttt gcagacggtc ccggtactga cggaactgct gcccgacggc catttttcg 20040
ggggtgacgc agtagaaggt gcgggggtcc ccgtgccagc ggtcccattt gagctggagg 20100
gcgagatcga gggcgagctc gacgaggcgg tcgtcccctg agagtttcat gaccagcatg 20160
aaggggacga gctgcttgcc gaaggacccc atccaggtgt aggtttccac atcgtaggtg 20220
aggaagagcc tttcggtgcg aggatgcgag ccgatgggga agaactggat ctcctgccac 20280
caattggagg aatggctgtt gatgtgatgg aagtagaaat gccgacggcg cgccgaacac 20340
tcgtgcttgt gtttatacaa gcggccacag tgctcgcaac gctgcacggg atgcacgtgc 20400
tgcacgagct gtacctgagt tcctttgacg aggaatttca gtgggaagtg gagtcgtggc 20460
gcctgcatct cgtgctgtac tacgtcgtgg tggtcggcct ggccctcttc tgcctcgatg 20520
gtggtcatgc tgacgagccc gcgcgggagg caggtccaga cctcggcgcg agcgggtcgg 20580
agagcgagga cgagggcgcg caggccggag ctgtccaggg tcctgagacg ctgcggagtc 20640
aggtcagtgg gcagcggcgg cgcgcggttg acttgcagga gtttttccag ggcgcgcggg 20700
aggtccagat ggtacttgat ctccaccgcg ccgttggtgg cgacgtcgat ggcttgcagg 20760
gtcccgtgcc cctggggtgt gaccaccgtc ccccgtttct tcttgggcgg ctggggcgac 20820
gggggcggtg cctcttccat ggttagaagc ggcggcgagg acgcgcgccg ggcggcagag 20880
gcggctcggg gcccggaggc aggggcggca ggggcacgtc ggcgccgcgc gcgggtaggt 20940
tctggtactg cgcccggaga agactggcgt gagcgacgac gcgacggttg acgtcctgga 21000
tctgacgcct ctgggtgaag gccacgggac ccgtgagttt gaacctgaaa gagagttcga 21060
cagaatcaat ctcggtatcg ttgacggcgg cctgccgcag gatctcttgc acgtcgcccg 21120
agttgtcctg gtaggcgatc tcggtcatga actgctcgat ctcctcctcc tgaaggtctc 21180
cgcgaccggc gcgctccacg gtggccgcga ggtcgttgga gatgcggccc atgagctgcg 21240
agaaggcgtt catgcccgcc tcgttccaga cgcggctgta gaccacgacg ccctcgggat 21300
cgcgggcgcg catgaccacc tgggcgaggt tgagctccac gtggcgcgtg aagaccgcgt 21360
agttgcagag gcgctggtag aggtagttga gcgtggtggc gatgtgctcg gtgacgaaga 21420
aatacatgat ccagcggcgg agcggcatct cgctgacgtc gcccagcgcc tccaagcgtt 21480
ccatggcctc gtaaaagtcc acggcgaagt tgaaaaactg ggagttgcgc gccgagacgg 21540
tcaactcctc ctccagaaga cggatgagct cggcgatggt ggcgcgcacc tcgcgctcga 21600
aggcccccgg gagttcctcc acttcctcct cttcttcctc ctccactaac atctcttcta 21660
cttcctcctc aggcggtggt ggtggcgggg gagggggcct gcgtcgccgg cggcgcacgg 21720
gcagacggtc gatgaagcgc tcgatggtct cgccgcgccg gcgtcgcatg gtctcggtga 21780
cggcgcgccc gtcctcgcgg ggccgcagcg tgaagacgcc gccgcgcatc tccaggtggc 21840
cgggggggtc cccgttgggc agggagaggg cgctgacgat gcatcttatc aattgccccg 21900
tagggactcc gcgcaaggac ctgagcgtct cgagatccac gggatctgaa aaccgttgaa 21960
cgaaggcttc gagccagtcg cagtcgcaag gtaggctgag cacggtttct tctgccgggt 22020
catgttgggg agcggggcgg gcgatgctgc tggtgatgaa gttgaaatag gcggttctga 22080
gacggcggat ggtggcgagg agcaccaggt ctttgggccc ggcttgctgg atgcgcagac 22140
ggtcggccat gccccaggcg tggtcctgac acctggccag gtccttgtag tagtcctgca 22200
tgagccgctc cacgggcacc tcctcctcgc ccgcgcggcc gtgcatgcgc gtgagcccga 22260
agccgcgctg gggctggacg agcgccaggt cggcgacgac gcgctcggcg aggatggcct 22320
gctggatctg ggtgagggtg gtctggaagt cgtcaaagtc gacgaagcgg tggtaggctc 22380
cggtgttgat ggtgtaggag cagttggcca tgacggacca gttgacggtc tggtggcccg 22440
gacgcacgag ctcgtggtac ttgaggcgcg agtaggcgcg cgtgtcgaag atgtagtcgt 22500
tgcaggtgcg caccaggtac tggtagccga tgaggaagtg cggcggcggc tggcggtaga 22560
gcggccatcg ctcggtggcg ggggcgccgg gcgcgaggtc ctcgagcatg gtgcggtggt 22620
agccgtagat gtacctggac atccaggtga tgccggcggc ggtggtggag gcgcgcggga 22680
actcgcggac gcggttccag atgttgcgca gcggcaggaa gtagttcatg gtgggcacgg 22740
tctggcccgt gaggcgcgcg cagtcgtgga tgctctatac gggcaaaaac gaaagcggtc 22800
agcggctcga ctccgtggcc tggaggctaa gcgaacgggt tgggctgcgc gtgtaccccg 22860
gttcgaatct cgaatcaggc tggagccgca gctaacgtgg tactggcact cccgtctcga 22920
cccaagcctg caccaaccct ccaggatacg gaggcgggtc gttttgcaac tttttttgga 22980
ggccggaaat gaaactagta agcgcggaaa gcggccgacc gcgatggctc gctgccgtag 23040
tctggagaag aatcgccagg gttgcgttgc ggtgtgcccc ggttcgaggc cggccggatt 23100
ccgcggctaa cgagggcgtg gctgccccgt cgtttccaag accccatagc cagccgactt 23160
ctccagttac ggagcgagcc cctcttttgt tttgtttgtt tttgccagat gcatcccgta 23220
ctgcggcaga tgcgccccca ccaccctcca ccgcaacaac agccccctcc tccacagccg 23280
gcgcttctgc ccccgcccca gcagcagcag caacttccag ccacgaccgc cgcggccgcc 23340
gtgagcgggg ctggacagac ttctcagtat gatcacctgg ccttggaaga gggcgagggg 23400
ctggcgcgcc tgggggcgtc gtcgccggag cggcacccgc gcgtgcagat gaaaagggac 23460
gctcgcgagg cctacgtgcc caagcagaac ctgttcagag acaggagcgg cgaggagccc 23520
gaggagatgc gcgcggcccg gttccacgcg gggcgggagc tgcggcgcgg cctggaccga 23580
aagagggtgc tgagggacga ggatttcgag gcggacgagc tgacggggat cagccccgcg 23640
cgcgcgcacg tggccgcggc caacctggtc acggcgtacg agcagaccgt gaaggaggag 23700
agcaacttcc aaaaatcctt caacaaccac gtgcgcaccc tgatcgcgcg cgaggaggtg 23760
accctgggcc tgatgcacct gtgggacctg ctggaggcca tcgtgcagaa ccccaccagc 23820
aagccgctga cggcgcagct gttcctggtg gtgcagcata gtcgggacaa cgaggcgttc 23880
agggaggcgc tgctgaatat caccgagccc gagggccgct ggctcctgga cctggtgaac 23940
attctgcaga gcatcgtggt gcaggagcgc gggctgccgc tgtccgagaa gctggcggcc 24000
atcaacttct cggtgctgag tctgggcaag tactacgcta ggaagatcta caagaccccg 24060
tacgtgccca tagacaagga ggtgaagatc gacgggtttt acatgcgcat gaccctgaaa 24120

-continued gtgctgaccc tgagcgacga tctgggggtg taccgcaacg acaggatgca ccgcgcggtg 24180
agcgccagca ggcggcgcga gctgagcgac caggagctga tgcacagcct gcagcgggcc 24240
ctgaccgggg ccgggaccga gggggagagc tactttgaca tgggcgcgga cctgcactgg 24300
cagcccagcc gccgggcctt ggaggcggca ggcggtcccc cctacataga agaggtggac 24360
gatgaggtgg acgaggaggg cgagtacctg gaagactgat ggcgcgaccg tatttttgct 24420
agatgcaaca acagccacct cctgatcccg cgatgcgggc ggcgctgcag agccagccgt 24480
ccggcattaa ctcctcggac gattggaccc aggccatgca acgcatcatg gcgctgacga 24540
cccgcaaccc cgaagccttt agacagcagc cccaggccaa ccggctctcg gccatcctgg 24600
aggccgtggt gccctcgcgc tccaacccca cgcacgagaa ggtcctggcc atcgtgaacg 24660
cgctggtgga gaacaaggcc atccgcggcg acgaggccgg cctggtgtac aacgcgctgc 24720
tggagcgcgt ggcccgctac aacagcacca acgtgcagac caacctggac cgcatggtga 24780
ccgacgtgcg cgaggccgtg gcccagcgcg agcggttcca ccgcgagtcc aacctgggat 24840
ccatggtggc gctgaacgcc ttcctcagca cccagcccgc caacgtgccc cggggccagg 24900
aggactacac caacttcatc agcgccctgc gcctgatggt gaccgaggtg ccccagagcg 24960
aggtgtacca gtccgggccg gactacttct tccagaccag tcgccagggc ttgcagaccg 25020
tgaacctgag ccaggcgttc aagaacttgc agggcctgtg gggcgtgcag gccccggtcg 25080
gggaccgcgc gacggtgtcg agcctgctga cgccgaactc gcgcctgctg ctgctgctgg 25140
tggccccctt cacggacagc ggcagcatca accgcaactc gtacctgggc tacctgatta 25200
acctgtaccg cgaggccatc ggccaggcgc acgtggacga gcagacctac caggagatca 25260
cccacgtgag ccgcgccctg ggccaggacg acccgggcaa tctggaagcc accctgaact 25320
ttttgctgac caaccggtcg cagaagatcc cgccccagta cacgctcagc gccgaggagg 25380
agcgcatcct gcgatacgtg cagcagagcg tgggcctgtt cctgatgcag gagggggcca 25440
cccccagcgc cgcgctcgac atgaccgcgc gcaacatgga gcccagcatg tacgccagca 25500
accgcccgtt catcaataaa ctgatggact acttgcatcg ggcggccgcc atgaactctg 25560
actatttcac caacgccatc ctgaatcccc actggctccc gccgccgggg ttctacacgg 25620
gcgagtacga catgcccgac cccaatgacg ggttcctgtg ggacgatgtg gacagcagcg 25680
tgttctcccc ccgaccgggt gctaacgagc gccccttgtg gaagaaggaa ggcagcgacc 25740
gacgcccgtc ctcggcgctg tccggccgcg agggtgctgc cgcggcggtg cccgaggccg 25800
ccagtccttt cccgagcttg cccttctcgc tgaacagtat tcgcagcagc gagctgggca 25860
ggatcacgcg cccgcgcttg ctgggcgagg aggagtactt gaatgactcg ctgttgagac 25920
ccgagcggga gaagaacttc cccaataacg ggatagagag cctggtggac aagatgagcc 25980
gctggaagac gtatgcgcag gagcacaggg acgatccgtc gcagggggcc acgagccggg 26040
gcagcgccgc ccgtaaacgc cggtggcacg acaggcagcg gggactgatg tgggacgatg 26100
aggattccgc cgacgacagc agcgtgttgg acttgggtgg gagtggtaac ccgttcgctc 26160
acctgcgccc ccgcatcggg cgcatgatgt aagagaaacc gaaaataaat gatactcacc 26220
aaggccatgg cgaccagcgt gcgttcgttt cttctctgtt gttgtatcta gtatgatgag 26280
gcgtgcgtac ccggagggtc ctcctccctc gtacgagagc gtgatgcagc aggcgatggc 26340
ggcggcggcg gcgatgcagc ccccgctgga ggctccttac gtgcccccgc ggtacctggc 26400
gcctacggag gggcggaaca gcattcgtta ctcggagctg gcacccttgt acgataccac 26460

-continued

```
ccggttgtac ctggtggaca acaagtcggc ggacatcgcc tcgctgaact accagaacga  26520
ccacagcaac ttcctgacca ccgtggtgca gaacaatgac ttcacccccca cggaggccag  26580
cacccagacc atcaactttg acgagcgctc gcggtggggc ggtcagctga aaaccatcat  26640
gcacaccaac atgcccaacg tgaacgagtt catgtacagc aacaagttca aggcgcgggt  26700
gatggtctcc cgcaagaccc ccaacggggt gacagtgaca gatggtagtc aggatatctt  26760
ggagtatgaa tgggtggagt ttgagctgcc cgaaggcaac ttctcggtga ccatgaccat  26820
cgacctgatg aacaacgcca tcatcgacaa ttacttggcg gtggggcggc agaacggggt  26880
cctggagagc gatatcggcg tgaagttcga cactaggaac ttcaggctgg gctgggaccc  26940
cgtgaccgag ctggtcatgc ccggggtgta caccaacgag gccttccacc ccgatattgt  27000
cttgctgccc ggctgcgggg tggacttcac cgagagccgc ctcagcaacc tgctgggcat  27060
tcgcaagagg cagcccttcc aggagggctt ccagatcatg tacgaggatc tggagggggg  27120
caacatcccc gcgctcctgg atgtcgacgc ctatgagaaa agcaaggagg agagcgccgc  27180
cgcggcgact gcagctgtag ccaccgcctc taccgaggtc aggggcgata attttgccag  27240
ccctgcagca gtggcagcgg ccgaggcggc tgaaaccgaa agtaagatag tcattcagcc  27300
ggtggagaag gatagcaagg acaggagcta caacgtgctg ccggacaaga taaacaccgc  27360
ctaccgcagc tggtacctgg cctacaacta tggcgacccc gagaagggcg tgcgctcctg  27420
gacgctgctc accacctcgg acgtcacctg cggcgtggag caagtctact ggtcgctgcc  27480
cgacatgatg caagacccgg tcaccttccg ctccacgcgt caagttagca actacccggt  27540
ggtgggcgcc gagctcctgc ccgtctactc caagagcttc ttcaacgagc aggccgtcta  27600
ctcgcagcag ctgcgcgcct tcacctcgct cacgcacgtc ttcaaccgct tccccgagaa  27660
ccagatcctc gtccgcccgc ccgcgcccac cattaccacc gtcagtgaaa acgttcctgc  27720
tctcacagat cacgggaccc tgccgctgcg cagcagtatc cggggagtcc agcgcgtgac  27780
cgttactgac gccagacgcc gcacctgccc ctacgtctac aaggccctgg gcatagtcgc  27840
gccgcgcgtc ctctcgagcc gcaccttcta aaaaatgtcc attctcatct cgcccagtaa  27900
taacaccggt tggggcctgc gcgcgcccag caagatgtac ggaggcgctc gccaacgctc  27960
cacgcaacac cccgtgcgcg tgcgcgggca cttccgcgct ccctggggcg ccctcaaggg  28020
ccgcgtgcgg tcgcgcacca ccgtcgacga cgtgatcgac caggtggtgg ccgacgcgcg  28080
caactacacc cccgccgccg cgcccgtctc caccgtggac gccgtcatcg acagcgtggt  28140
ggccgacgcg cgccggtacg cccgcgccaa gagccggcgg cggcgcatcg cccggcggca  28200
ccggagcacc cccgccatgc gcgcggcgcg agccttgctg cgcagggcca ggcgcacggg  28260
acgcagggcc atgctcaggg cggccagacg cgcggcttca ggcgccagcg ccggcaggac  28320
ccggagacgc gcggccacgg cggcggcagc ggccatcgcc agcatgtccc gcccgcggcg  28380
agggaacgtg tactgggtgc gcgacgccgc caccggtgtg cgcgtgcccg tgcgcacccg  28440
ccccccctcgc acttgaagat gttcacttcg cgatgttgat gtgtcccagc ggcgaggagg  28500
atgtccaagc gcaaattcaa ggaagagatg ctccaggtca tcgcgcctga gatctacggc  28560
cccgcggtgg tgaaggagga aagaaagccc cgcaaaatca agcgggtcaa aaaggacaaa  28620
aaggaagaag atgacgatct ggtggagttt gtgcgcgagt tcgccccccg gcggcgcgtg  28680
cagtggcgcg ggcggaaagt gcacccggtg ctgagacccg gcaccaccgt ggtcttcacg  28740
cccggcgagc gctccggcag cgcttccaag cgctcctacg acgaggtgta cggggacgag  28800
gacatcctcg agcaggcggc cgagcgcctg ggcgagtttg cttacggcaa gcgcagccgc  28860
```

```
cccgccctga aggaagaggc ggtgtccatc ccgctggacc acggcaaccc cacgccgagc  28920
ctcaagcccg tgaccctgca gcaggtgctg ccgagcgcag cgccgcgccg ggggttcaag  28980
cgcgagggcg aggatctgta ccccaccatg cagctgatgg tgcccaagcg ccagaagctg  29040
gaagacgtgc tggagaccat gaaggtggac ccggacgtgc agcccgaggt caaggtgcgg  29100
cccatcaagc aggtggcccc gggcctgggc gtgcagaccg tggacatcaa gatccccacg  29160
gagcccatgg aaacgcagac cgagcccatg atcaagccca gcaccagcac catggaggtg  29220
cagacggatc cctggatgcc atcggctcct agccgaagac cccggcgcaa gtacggcgcg  29280
gccagcctgc tgatgcccaa ctacgcgctg catccttcca tcatccccac gccgggctac  29340
cgcggcacgc gcttctaccg cggtcataca accagccgcc gccgcaagac caccacccgc  29400
cgccgccgtc gccgcacagc cgctgcatct acccctgccg ccctggtgcg gagagtgtac  29460
cgccgcggcc gcgcgcctct gaccctaccg cgcgcgcgct accacccgag catcgccatt  29520
taaactttcg cctgctttgc agatggccct cacatgccgc ctccgcgttc ccattacggg  29580
ctaccgagga agaaaaccgc gccgtagaag gctggcgggg aacgggatgc gtcgccacca  29640
ccatcggcgg cggcgcgcca tcagcaagcg gttgggggga ggcttcctgc ccgcgctgat  29700
ccccatcatc gccgcggcga tcggggcgat ccccggcatt gcttccgtgg cggtgcaggc  29760
ctctcagcgc cactgagaca cttggaaaac atcttgtaat aaaccaatgg actctgacgc  29820
tcctggtcct gtgatgtgtt ttcgtagaca gatggaagac atcaattttt cgtccctggc  29880
tccgcgacac ggcacgcggc cgttcatggg cacctggagc gacatcggca ccagccaact  29940
gaacgggggc gccttcaatt ggagcagtct ctggagcggg cttaagaatt tcgggtccac  30000
gcttaaaacc tatggcagca aggcgtggaa cagcaccaca gggcaggcgc tgagggataa  30060
gctgaaagag cagaacttcc agcagaaggt ggtcgatggg ctcgcctcgg gcatcaacgg  30120
ggtggtggac ctggccaacc aggccgtgca gcggcagatc aacagccgcc tggacccggt  30180
gccgcccgcc ggctccgtgg agatgccgca ggtggaggag gagctgcctc ccctggacaa  30240
gcggggcgag aagcgacccc gccccgacgc ggaggagacg ctgctgacgc acacggacga  30300
gccgcccccg tacgaggagg cggtgaaact gggtctgccc accacgcggc ccatcgcgcc  30360
cctggccacc ggggtgctga aacccgaaag taataagccc gcgaccctgg acttgcctcc  30420
tcccgcttcc cgcccctcta cagtggctaa gcccctgccg ccggtggccg tggcccgcgc  30480
gcgacccggg ggctccgccc gccctcatgc gaactggcag agcactctga acagcatcgt  30540
gggtctggga gtgcagagtg tgaagcgccg ccgctgctat taaacctacc gtagcgctta  30600
acttgcttgt ctgtgtgtgt atgtattatg tcgccgctgt ccgccagaag gaggagtgaa  30660
gaggcgcgtc gccgagttgc aagatggcca ccccatcgat gctgccccag tgggcgtaca  30720
tgcacatcgc cggacaggac gcttcggagt acctgagtcc gggtctggtg cagttcgccc  30780
gcgccacaga cacctacttc agtctgggga acaagtttag gaaccccacg gtggcgccca  30840
cgcacgatgt gaccaccgac cgcagccagc ggctgacgct gcgcttcgtg cccgtggacc  30900
gcgaggacaa cacctactcg tacaaagtgc gctacacgct ggccgtgggc gacaaccgcg  30960
tgctggacat ggccagcacc tactttgaca tccgcggcgt gctggatcgg ggccctagct  31020
tcaaacccta ctccggcacc gcctacaaca gcctggctcc caagggagcg cccaattcca  31080
gccagtggga gcaaaaaaag gcaggcaatg gtgacactat ggaaacacac acatttggtg  31140
tggccccaat gggcggtgag aatattacaa tcgacggatt acaaattgga actgacgcta  31200
```

```
cagctgatca ggataaacca atttatgctg acaaaacatt ccagcctgaa cctcaagtag  31260
gagaagaaaa ttggcaagaa actgaaagct tttatggcgg tagggctctt aaaaaagaca  31320
caagcatgaa accttgctat ggctcctatg ctagacccac caatgtaaag ggaggtcaag  31380
ctaaacttaa agttggagct gatggagttc ctaccaaaga atttgacata gacctggctt  31440
tctttgatac tcccggtggc acagtgaatg gacaagatga gtataaagca gacattgtca  31500
tgtataccga aaacacgtat ctggaaactc cagacacgca tgtggtatac aaaccaggca  31560
aggatgatgc aagttctgaa attaacctgg ttcagcagtc catgcccaat agacccaact  31620
atattgggtt cagagacaac tttattgggc tcatgtatta caacagtact ggcaatatgg  31680
gggtgctggc tggtcaggcc tcacagctga atgctgtggt cgacttgcaa gacagaaaca  31740
ccgagctgtc ataccagctc ttgcttgact ctttgggtga cagaacccgg tatttcagta  31800
tgtggaatca ggcggtggac agttatgatc ctgatgtgcg cattattgaa aaccatggtg  31860
tggaagacga acttcccaac tattgcttcc ccctggatgg gtctggcact aatgccgctt  31920
accaaggtgt gaaagtaaaa aatggtaacg atggtgatgt tgagagcgaa tgggaaaatg  31980
atgatactgt cgcagctcga aatcaattat gcaagggcaa catttttgcc atggaaatta  32040
acctccaagc caacctgtgg agaagtttcc tctactcgaa cgtggccctg tacctgcccg  32100
actcttacaa gtacacgcca gccaacatca ccctgcccac caacaccaac acttatgatt  32160
acatgaacgg gagagtggtg cctccctcgc tggtggacgc ctacatcaac atcggggcgc  32220
gctggtcgct ggaccccatg gacaacgtca atcccttcaa ccaccaccgc aacgcgggcc  32280
tgcgctaccg ctccatgctc ctgggcaacg ggcgctacgt gcccttccac atccaggtgc  32340
cccagaaatt tttcgccatc aagagcctcc tgctcctgcc cgggtcctac acctacgagt  32400
ggaacttccg caaggacgtc aacatgatcc tgcagagctc cctcggcaac gacctgcgca  32460
cggacggggc ctccatctcc ttcaccagca tcaacctcta cgccaccttc ttccccatgg  32520
cgcacaacac ggcctccacg ctcgaggcca tgctgcgcaa cgacaccaac gaccagtcct  32580
tcaacgacta cctctcggcg gccaacatgc tctaccccat cccggccaac gccaccaacg  32640
tgcccatctc catcccctcg cgcaactggg ccgccttccg cggctggtcc ttcacgcgcc  32700
tcaagaccaa ggagacgccc tcgctgggct ccgggttcga cccctacttc gtctactcgg  32760
gctccatccc ctacctcgac ggcaccttct acctcaacca caccttcaag aaggtctcca  32820
tcaccttcga ctcctccgtc agctggcccg gcaacgaccg gctcctgacg cccaacgagt  32880
tcgaaatcaa gcgcaccgtc gacggcgagg gatacaacgt ggcccagtgc aacatgacca  32940
aggactggtt cctggtccag atgctggccc actacaacat cggctaccag ggcttctacg  33000
tgcccgaggg ctacaaggac cgcatgtact ccttcttccg caacttccag cccatgagcc  33060
gccaggtggt ggacgaggtc aactacaagg actaccaggc cgtcaccctg gcctaccagc  33120
acaacaactc gggcttcgtc ggctacctcg cgcccaccat gcgccagggc cagccctacc  33180
ccgccaacta cccgtacccg ctcatcggca agagcgccgt caccagcgtc acccagaaaa  33240
agttcctctg cgacagggtc atgtggcgca tccccttctc cagcaacttc atgtccatgg  33300
gcgcgctcac cgacctcggc cagaacatgc tctatgccaa ctccgcccac gcgctagaca  33360
tgaatttcga agtcgacccc atggatgagt ccacccttct ctatgttgtc ttcgaagtct  33420
tcgacgtcgt ccgagtgcac cagccccacc gcggcgtcat cgaggccgtc tacctgcgca  33480
ccccctctc ggccggtaac gccaccacct aaattgctac ttgcatgatg gctgagccca  33540
caggctccgg cgagcaggag ctcagggcca tcatccgcga cctgggctgc gggccctact  33600
```

tcctgggcac cttcgataag cgcttcccgg gattcatggc cccgcacaag ctggcctgcg 33660
ccatcgtcaa cacggccggc cgcgagaccg ggggcgagca ctggctggcc ttcgcctgga 33720
acccgcgctc gaacacctgc tacctcttcg acccccttcgg gttctcggac gagcgcctca 33780
agcagatcta ccagttcgag tacgagggcc tgctgcgccg tagcgccctg gccaccgagg 33840
accgctgcgt caccctggaa aagtccaccc agaccgtgca gggtccgcgc tcggccgcct 33900
gcgggctctt ctgctgcatg ttcctgcacg ccttcgtgca ctggcccgac cgccccatgg 33960
acaagaaccc caccatgaac ttgctgacgg gggtgcccaa cggcatgctc cagtcgcccc 34020
aggtggaacc caccctgcgc cgcaaccagg aggcgctcta ccgcttcctc aactcccact 34080
ccgcctactt tcgctcccac cgcgcgcgca tcgagaaggc caccgccttc gaccgcatga 34140
acaatcaaga catgtaaacc gtgtgtgtat gtttaaaata tcttttaata aacagcactt 34200
taatgttaca catgcatctg agatgatttt attttagaaa tcgaaagggt tctgccgggt 34260
ctcggcatgg cccgcgggca gggacacgtt gcggaactgg tacttggcca gccacttgaa 34320
ctcggggatc agcagtttgg gcagcggggt gtcggggaag gagtcggtcc acagcttccg 34380
cgtcagctgc agggcgccca gcaggtcggg cgcggagatc ttgaaatcgc agttgggacc 34440
cgcgttctgc gcgcgagagt tgcggtacac ggggttgcag cactggaaca ccatcagggc 34500
cgggtgcttc acgctcgcca gcaccgccgc gtcggtgatg ctctccacgt cgaggtcctc 34560
ggcgttggcc atcccgaagg gggtcatctt gcaggtctgc cttcccatgg tgggcacgca 34620
cccgggcttg tggttgcaat cgcagtgcag ggggatcagc atcatctggg cctggtcggc 34680
gttcatcccc gggtacatgg ccttcatgaa agcctccaat tgcctgaacg cctgctgggc 34740
cttggctccc tcggtgaaga agaccccgca ggacttgcta gagaactggt tggtggcaca 34800
gccggcatcg tgcacgcagc agcgcgcgtc gttgttggcc agctgcacca cgctgcgccc 34860
ccagcggttc tgggtgatct tggcccggtc ggggttctcc ttcagcgcgc gctgcccgtt 34920
ctcgctcgcc acatccatct cgatcatgtg ctccttctgg atcatggtgg tcccgtgcag 34980
gcaccgcagt ttgccctcgg cctcggtgca cccgtgcagc cacagcgcgc acccggtgca 35040
ctcccagttc ttgtgggcga tctgggaatg cgcgtgcacg aacccttgca ggaagcggcc 35100
catcatggtc gtcagggtct tgttgctagt gaaggtcaac gggatgccgc ggtgctcctc 35160
gttgatgtac aggtggcaga tgcggcggta cacctcgccc tgctcgggca tcagttggaa 35220
gttggctttc aggtcggtct ccacgcggta gcggtccatc agcatagtca tgatttccat 35280
gcccttctcc caggccgaga cgatgggcag gctcataggg ttcttcacca tcatcttagc 35340
actagcagcc gcggccaggg ggtcgctctc atccagggtc tcaaagctcc gcttgccgtc 35400
cttctcggtg atccgcaccg gggggtagct gaagcccacg gccgccagct cctcctcggc 35460
ctgtctttcg tcctcgctgt cctggctgac gtcctgcatg accacatgct tggtcttgcg 35520
gggtttcttc ttgggcggca gtggcggcgg agatgcttgt ggcgaggggg agcgcgagtt 35580
ctcgctcacc actactatct cttcctcttc ttggtccgag gccacgcggc ggtaggtatg 35640
tctcttcggg ggcagaggcg gaggcgacgg gctctcgccg ccgcgacttg gcggatggct 35700
ggcagagccc cttccgcgtt cgggggtgcg ctcccggcgg cgctctgact gacttcctcc 35760
gcggccggcc attgtgttct cctagggagg aacaacaagc atggagactc agccatcgcc 35820
aacctcgcca tctgccccca ccgccggcga cgagaagcag cagcagcaga atgaaagctt 35880
aaccgccccg ccgcccagcc ccgcctccga cgcagccgcg gtcccagaca tgcaagagat 35940

-continued

```
ggaggaatcc atcgagattg acctgggcta tgtgacgccc gcggagcatg aggaggagct  36000
ggcagtgcgc tttcaatcgt caagccagga agataaagaa cagccagagc aggaagcaga  36060
gaacgagcag agtcaggctg ggctcgagca tggcgactac ctccacctga gcggggagga  36120
ggacgcgctc atcaagcatc tggcccggca ggccaccatc gtcaaggacg cgctgctcga  36180
ccgcaccgag gtgcccctca gcgtggagga gctcagccgc gcctacgagc tcaacctctt  36240
ctcgccgcgc gtgcccccca agcgccagcc caacggcacc tgcgagccca acccccgcct  36300
caacttctac ccggtcttcg cggtgcccga ggccctggcc acctaccaca tctttttcaa  36360
gaaccaaaag atccccgtct cctgccgcgc caaccgcacc cgcgccgacg ccctcttcaa  36420
cctgggtccc ggcgcccgcc tacctgatat cgcctccttg gaagaggttc ccaagatctt  36480
cgagggtctg ggcagcgacg agactcgggc cgcgaacgct ctgcaaggag aaggaggagg  36540
agagcatgag caccacagcg ccctggtcga gttggaaggc gacaacgcgc ggctggcggt  36600
gctcaaacgc acggtcgagc tgacccattt cgcctacccg gctctgaacc tgcccccgaa  36660
agtcatgagc gcggtcatgg accaggtgct catcaagcgc gcgtcgccca tctccgagga  36720
cgagggcatg caagactccg aggagggcaa gcccgtggtc agcgacgagc agctggcccg  36780
gtggctgggt cctaatgcta cccctcaaag tttggaagag cggcgcaagc tcatgatggc  36840
cgtggtcctg gtgaccgtgg agctggagtg cctgcgccgc ttcttcgccg acgcggagac  36900
cctgcgcaag gtcgaggaga acctgcacta cctcttcagg cacgggttcg tgcgccaggc  36960
ctgcaagatc tccaacgtgg agctgaccaa cctggtctcc tacatgggca tcttgcacga  37020
gaaccgcctg ggcagaacg tgctgcacac caccctgcgc ggggaggccc gccgcgacta  37080
catccgcgac tgcgtctacc tctacctctg ccacacctgg cagacgggca tgggcgtgtg  37140
gcagcagtgt ctggaggagc agaacctgaa agagctctgc aagctcctgc aaaagaacct  37200
caagggtctg tggaccgggt tcgacgagcg gaccaccgcc tcggacctgg ccgacctcat  37260
cttccccgag cgcctcaggc tgacgctgcg caacggcctg cccgacttta tgagccaaag  37320
catgttgcaa aactttcgct ctttcatcct cgaacgctcc ggaatcctgc ccgccacctg  37380
ctccgcgctg ccctcggact tcgtgccgct gaccttccgc gagtgccccc cgccgctgtg  37440
gagccactgc tacctgctgc gcctggccaa ctacctggcc taccactcgg acgtgatcga  37500
ggacgtcagc ggcgagggcc tgctcgagtg ccactgccgc tgcaacctct gcacgccgca  37560
ccgctccctg gcctgcaacc cccagctgct gagcgagacc cagatcatcg gcaccttcga  37620
gttgcaaggg cccagcgagg gcgagggagc caagggggt ctgaaactca ccccggggct  37680
gtggacctcg gcctacttgc gcaagttcgt gcccgaggat taccatccct tcgagatcag  37740
gttctacgag gaccaatccc agccgcccaa ggccgagctg tcggcctgcg tcatcaccca  37800
gggggcgatc ctggcccaat tgcaagccat ccagaaatcc cgccaagaat tcttgctgaa  37860
aaagggccgc ggggtctacc tcgaccccca gaccggtgag gagctcaacc ccggcttccc  37920
ccaggatgcc ccgaggaaac aagaagctga aagtggagct gccgcccgtg gaggatttgg  37980
aggaagactg ggagaacagc agtcaggcag aggagatgga ggaagactgg gacagcactc  38040
aggcagagga ggacagcctg caagacagtc tggaggaaga cgaggaggag gcagaggagg  38100
aggtggaaga agcagccgcc gccagaccgt cgtcctcggc gggggagaaa gcaagcagca  38160
cggataccat ctccgctccg ggtcggggtc ccgctcggcc ccacagtaga tgggacgaga  38220
ccgggcgatt cccgaacccc accacccaga ccggtaagaa ggagcggcag ggatacaagt  38280
cctggcgggg gcacaaaaac gccatcgtct cctgcttgca ggcctgcggg ggcaacatct  38340
```

ccttcacccg gcgctacctg ctcttccacc gcggggtgaa cttcccccgc aacatcttgc 38400
attactaccg tcacctccac agcccctact acttccaaga agaggcagca gcagcagaaa 38460
aagaccagaa aaccagctag aaaatccaca gcggcggcag cggcaggtgg actgaggatc 38520
gcggcgaacg agccggcgca gacccgggag ctgaggaacc ggatctttcc caccctctat 38580
gccatcttcc agcagagtcg gggcaggag caggaactga aagtcaagaa ccgttctctg 38640
cgctcgctca cccgcagttg tctgtatcac aagagcgaag accaacttca gcgcactctc 38700
gaggacgccg aggctctctt caacaagtac tgcgcgctca ctcttaaaga gtagcccgcg 38760
cccgcccagt cgcagaaaaa ggcgggaatt acgtcacctg tgcccttcgc cctagccgcc 38820
tccacccagc accgccatga gcaaagagat tcccacgcct tacatgtgga gctaccagcc 38880
ccagatgggc ctggccgccg gcgccgccca ggactactcc acccgcatga attggctcag 38940
cgccgggccc gcgatgatct cacgggtgaa tgacatccgc gcccaccgaa accagatact 39000
cctagaacag tcagcgctca ccgccacgcc ccgcaatcac ctcaatccgc gtaattggcc 39060
cgccgccctg gtgtaccagg aaattcccca gcccacgacc gtactacttc cgcgagacgc 39120
ccaggccgaa gtccagctga ctaactcagg tgtccagctg gcgggcggcg ccaccctgtg 39180
tcgtcaccgc cccgctcagg gtataaagcg gctggtgatc cggggcagag gcacacagct 39240
caacgacgag gtggtgagct cttcgctggg tctgcgacct gacggagtct tccaactcgc 39300
cggatcgggg agatcttcct tcacgcctcg tcaggcggtc ctgactttgg agagttcgtc 39360
ctcgcagccc cgctcgggcg gcatcggcac tctccagttc gtggaggagt tcactccctc 39420
ggtctacttc aaccccttct ccggctcccc cggccactac ccggacgagt tcatcccgaa 39480
ctttgacgcc atcagcgagt cggtggacgg ctacgattga ttaattaatc aactaacccc 39540
ttaccccttt accctccagt aaaaataaag attaaaaatg attgaattga tcaataaaga 39600
atcacttact tgaaatctga aaccaggtct ctgtccatgt ttctgtcag cagcacttca 39660
ctcccctctt cccaactctg gtactgcagg ccccggcggg ctgcaaactt cctccacact 39720
ctgaagggga tgtcaaattc ctcctgtccc tcaatcttca tttttatctt ctatcagatg 39780
tccaaaaagc gcgcgcgggt ggatgatggc ttcgaccccg tgtacccta cgatgcagac 39840
aacgcaccga ctgtgccctt catcaaccct cccttcgtct cttcagatgg attccaagaa 39900
aagcccctgg gggtgttgtc cctgcgactg gccgaccccg tcaccaccaa gaatggggct 39960
gtcaccctca agctgggga gggggtggac ctcgacgact cgggaaaact catctccaaa 40020
aatgccacca aggccactgc ccctctcagt atttccaacg gcaccatttc ccttaacatg 40080
gctgcccctt tttacaacaa caatggaacg ttaagtctca atgtttctac accattagca 40140
gtatttccca cttttaacac tttaggtatc agtcttggaa acggtcttca aacttctaat 40200
aagttgctga ctgtacagtt aactcatcct cttacattca gctcaaatag catcacagta 40260
aaaacagaca aaggactcta tattaattct agtggaaaca gagggcttga ggctaacata 40320
agcctaaaaa gaggactgat ttttgatggt aatgctattg caacatacct tggaagtggt 40380
ttagactatg gatcctatga tagcgatggg aaaacaagac ccatcatcac caaaattgga 40440
gcaggtttga attttgatgc taataatgcc atggctgtga agctaggcac aggtttaagt 40500
tttgactctg ccggtgcctt aacagctgga aacaaagagg atgacaagct aacactttgg 40560
actacacctg acccaagccc taattgtcaa ttactttcag acagagatgc caaatttacc 40620
ctatgtctta caaaatgcgg tagtcaaata ctaggcactg ttgcagtagc tgctgttact 40680

```
gtaggttcag cactaaatcc aattaatgac acagtaaaaa gcgccatagt attccttaga  40740
tttgactctg acggtgtgct catgtcaaac tcatcaatgg taggtgatta ctggaacttt  40800
agggaaggac agaccaccca aagtgtggcc tatacaaatg ctgtgggatt catgcccaat  40860
ctaggtgcat atcctaaaac ccaaagcaaa acaccaaaaa atagtatagt aagtcaggta  40920
tatttaaatg gagaaactac tatgccaatg acactgacaa taactttcaa tggcactgat  40980
gaaaaagaca caacacctgt gagcacttac tccatgactt ttacatggca gtggactgga  41040
gactataagg acaagaatat tacctttgct accaactcct ttactttctc ctacatggcc  41100
caagaataaa ccctgcatgc caaccccatt gttcccacca ctatggaaaa ctctgaagca  41160
gaaaaaaata aagttcaagt gttttattga ttcaacagtt ttctcacaga accctagtat  41220
tcaacctgcc acctccctcc caacacacag agtacacagt cctttctccc cggctggcct  41280
taaaaagcat catatcatgg gtaacagaca tattcttagg tgttatattc cacacggttt  41340
cctgtcgagc caaacgctca tcagtgatat taataaactc cccgggcagc tcacttaagt  41400
tcatgtcgct gtccagctgc tgagccacag gctgctgtcc aacttgcggt tgcttaacgg  41460
gcggcgaagg agaagtccac gcctacatgg gggtagagtc ataatcgtgc atcaggatag  41520
ggcggtggtg ctgcagcagc gcgcgaataa actgctgccg ccgccgctcc gtcctgcagg  41580
aatacaacat ggcagtggtc tcctcagcga tgattcgcac cgcccgcagc ataaggcgcc  41640
ttgtcctccg ggcacagcag cgcaccctga tctcacttaa atcagcacag taactgcagc  41700
acagcaccac aatattgttc aaaatcccac agtgcaaggc gctgtatcca aagctcatgg  41760
cggggaccac agaacccacg tggccatcat accacaagcg caggtagatt aagtggcgac  41820
ccctcataaa cacgctggac ataaacatta cctcttttgg catgttgtaa ttcaccacct  41880
cccggtacca tataaacctc tgattaaaca tggcgccatc caccaccatc ctaaaccagc  41940
tggccaaaac ctgcccgccg gctatacact gcagggaacc gggactggaa caatgacagt  42000
ggagagccca ggactcgtaa ccatggatca tcatgctcgt catgatatca atgttggcac  42060
aacacaggca cacgtgcata cacttcctca ggattacaag ctcctcccgc gttagaacca  42120
tatcccaggg aacaacccat tcctgaatca gcgtaaatcc cacactgcag ggaagacctc  42180
gcacgtaact cacgttgtgc attgtcaaag tgttacattc gggcagcagc ggatgatcct  42240
ccagtatggt agcgcgggtt tctgtctcaa aaggaggtag acgatcccta ctgtacggag  42300
tgcgccgaga caaccgagat cgtgttggtc gtagtgtcat gccaaatgga acgccggacg  42360
tagtcatatt tcctgaagca aaaccaggtg cgggcgtgac aaacagatct gcgtctccgg  42420
tctcgccgct tagatcgctc tgtgtagtag ttgtagtata tccactctct caaagcatcc  42480
aggcgccccc tggcttcggg ttctatgtaa actccttcat gcgccgctgc cctgataaca  42540
tccaccaccg cagaataagc cacacccagc caacctacac attcgttctg cgagtcacac  42600
acgggaggag cgggaagagc tggaagaacc atgattaact ttattccaaa cggtctcgga  42660
gcacttcaaa atgcaggtcc cggaggtggc acctctcgcc cccactgtgt tggtggaaaa  42720
taacagccag gtcaaaggtg acacggttct cgagatgttc cacggtggct tccagcaaag  42780
cctccacgcg cacatccaga aacaagagga cagcgaaagc gggagcgttt tctaattcct  42840
caatcatcat attacactcc tgcaccatcc ccagataatt ttcatttttc cagccttgaa  42900
tgattcgtat tagttcctga ggtaaatcca agccagccat gataaaaagc tcgcgcagag  42960
cgccctccac cggcattctt aagcacaccc tcataattcc aagagattct gctcctggtt  43020
cacctgcagc agattaacaa tgggaatatc aaaatctctg ccgcgatccc taagctcctc  43080
```

```
cctcaacaat aactgtatgt aatctttcat atcatctccg aaatttttag ccatagggcc  43140
gccaggaata agagcagggc aagccacatt acagataaag cgaagtcctc cccagtgwgc  43200
attgccaaat gtaagattga aataagcatg ctggctagac cctgtgatat cttccagata  43260
actggacaga aaatcaggca agcaattttt aagaaaatca acaaaagaaa agtcgtccag  43320
gtgcaggttt agagcctcag gaacaacgat ggaataagtg caaggagtgc gttccagcat  43380
ggttagtgtt tttttggtga tctgtagaac aaaaaataaa catgcaatat taaaccatgc  43440
tagcctggcg aacaggtggg taaatcactc tttccagcac caggcaggct acggggtctc  43500
cggcgcgacc ctcgtagaag ctgtcgccat gattgaaaag catcaccgag agaccttccc  43560
ggtggccggc atggatgatt cgagaagaag catacactcc gggaacattg gcatccgtga  43620
gtgaaaaaaa gcgacctata aagcctcggg gcactacaat gctcaatctc aattccagca  43680
aagccacccc atgcggatgg agcacaaaat tggcaggtgc gtaaaaaatg taattactcc  43740
cctcctgcac aggcagcaaa gcccccgctc cctccagaaa cacatacaaa gcctcagcgt  43800
ccatagctta ccgagcacgg caggcgcaag agtcagagaa aaggctgagc tctaacctga  43860
ctgcccgctc ctgtgctcaa tatatagccc taacctacac tgacgtaaag gccaaagtct  43920
aaaaataccc gccaaaatga cacacacgcc cagcacacgc ccagaaaccg gtgacacact  43980
caaaaaaata cgtgcgcttc ctcaaacgcc caaaccggcg tcatttccgg gttcccacgc  44040
tacgtcaccg ctcagcgact ttcaaattcc gtcgaccgtt aaaaacgtca ctcgccccgc  44100
ccctaacggt cgcccttctc tcggccaatc accttcctcc cttcccaaat tcaaacgcct  44160
catttgcata ttaacgcgca caaaaagttt gaggtatata tttgaatgat g           44211
```

<210> SEQ ID NO 121
<211> LENGTH: 44529
<212> TYPE: DNA
<213> ORGANISM: Artificial Sequence
<220> FEATURE:
<223> OTHER INFORMATION: Vector

<400> SEQUENCE: 121

```
gtttaaacgc ggccgccagg cctacccact agtcaattcg ggaggatcga aacggcagat     60
cgcaaaaaac agtacataca gaaggagaca tgaacatgaa catcaaaaaa attgtaaaac    120
aagccacagt tctgactttt acgactgcac ttctggcagg aggagcgact caagccttcg    180
cgaaagaaaa taaccaaaaa gcatacaaag aaacgtacgg cgtctctcat attacacgcc    240
atgatatgct gcagatccct aaacagcagc aaaacgaaaa ataccaagtg cctcaattcg    300
atcaatcaac gattaaaaat attgagtctg caaaaggact tgatgtgtgg gacagctggc    360
cgctgcaaaa cgctgacgga acagtagctg aatacaacgg ctatcacgtt gtgtttgctc    420
ttgcgggaag cccgaaagac gctgatgaca catcaatcta catgttttat caaaaggtcg    480
gcgacaactc aatcgacagc tggaaaaacg cgggccgtgt ctttaaagac agcgataagt    540
tcgacgccaa cgatccgatc ctgaaagatc agacgcaaga atggtccggt tctgcaacct    600
ttacatctga cggaaaaatc cgtttattct acactgacta ttccggtaaa cattacggca    660
aacaaagcct gacaacagcg caggtaaatg tgtcaaaatc tgatgacaca ctcaaaatca    720
acggagtgga agatcacaaa acgatttttg acggagacgg aaaaacatat cagaacgttc    780
agcagtttat cgatgaaggc aattatacat ccggcgacaa ccatacgctg agagaccctc    840
actacgttga agacaaaggc cataaatacc ttgtattcga agccaacacg ggaacagaaa    900
```

```
acggatacca aggcgaagaa tctttattta acaaagcgta ctacggcggc ggcacgaact    960
tcttccgtaa agaaagccag aagcttcagc agagcgctaa aaaacgcgat gctgagttag   1020
cgaacggcgc cctcggtatc atagagttaa ataatgatta cacattgaaa aaagtaatga   1080
agccgctgat cacttcaaac acggtaactg atgaaatcga gcgcgcgaat gttttcaaaa   1140
tgaacggcaa atggtacttg ttcactgatt cacgcggttc aaaaatgacg atcgatggta   1200
ttaactcaaa cgatatttac atgcttggtt atgtatcaaa ctctttaacc ggcccttaca   1260
agccgctgaa caaaacaggg cttgtgctgc aaatgggtct tgatccaaac gatgtgacat   1320
tcacttactc tcacttcgca gtgccgcaag ccaaaggcaa caatgtggtt atcacaagct   1380
acatgacaaa cagaggcttc ttcgaggata aaaaggcaac atttgcgcca agcttcttaa   1440
tgaacatcaa aggcaataaa acatccgttg tcaaaaacag catcctggag caaggacagc   1500
tgacagtcaa ctaataacag caaaaagaaa atgccgatac ttcattggca ttttctttta   1560
tttctcaaca agatggtgaa ttgactagtg ggtagatcca caggacgggt gtggtcgcca   1620
tgatcgcgta gtcgatagtg gctccaagta gcgaagcgag caggactggg cggcggccaa   1680
agcggtcgga cagtgctccg agaacgggtg cgcatagaaa ttgcatcaac gcatatagcg   1740
ctagcagcac gccatagtga ctggcgatgc tgtcggaatg gacgatatcc cgcaagaggc   1800
ccggcagtac cggcataacc aagcctatgc ctacagcatc cagggtgacg gtgccgagga   1860
tgacgatgag cgcattgtta gatttcatac acggtgcctg actgcgttag caatttaact   1920
gtgataaact accgcattaa agcttatcga tgataagctg tcaaacatga gaattgatcc   1980
ggaaccctta atataacttc gtataatgta tgctatacga agttattagg tccctcgact   2040
atagggtcac cgtcgacagc gacacacttg catcggatgc agcccggtta acgtgccggc   2100
acggcctggg taaccaggta ttttgtccac ataaccgtgc gcaaaatgtt gtggataagc   2160
aggacacagc agcaatccac agcaggcata caaccgcaca ccgaggttac tccgttctac   2220
aggttacgac gacatgtcaa tacttgccct tgacaggcat tgatggaatc gtagtctcac   2280
gctgatagtc tgatcgacaa tacaagtggg accgtggtcc cagaccgata atcagaccga   2340
crayacgagt gggaycgtgg tcccagacta ataatcagac cgacgatacg agtgggaccg   2400
tggtcccaga ctaataatca gaccgacgat acgagtggga ccgtggtycc agwctratwa   2460
tcagaccgac gatacragtg gracmgtggk cccagasaka atawtcagrc cgagwtaygc   2520
wktckggcct gtaacaaagg acattaagta aagacagata mrmgtgrgac taaaacgtgg   2580
tcccagtctg attatcagac cgacgatacg agtgggaccg tggtcccaga ctaataatca   2640
gaccgacgat acgagtggga ccgtggtccc agactaataa tcagaccgac gatacgagtg   2700
ggaccgtggt cccagtctga ttatcagacc gacgatacaa gtggaacagt gggcccagag   2760
agaatattca ggccagttat gctttctggc ctgtaacaaa ggacattaag taaagacaga   2820
taaacgtaga ctaaaacgtg gtcgcatcag ggtgctggct tttcaagttc cttaagaatg   2880
gcctcaattt tctctataca ctcagttgga acacgagacc tgtccaggtt aagcaccatt   2940
ttatcgccct tatacaatac tgtcgctcca ggagcaaact gatgtcgtga gcttaaacta   3000
gttcttgatg cagatgacgt tttaagcaca gaagttaaaa gagtgataac ttcttcagct   3060
tcaaatatca ccccagcttt tttctgctca tgaaggttag atgcctgctg cttaagtaat   3120
tcctctttat ctgtaaaggc tttttgaagt gcatcacctg accgggcaga tagttcaccg   3180
gggtgagaaa aaagagcaac aactgattta ggcaatttgg cggtgttgat acagcgggta   3240
ataatcttac gtgaaatatt ttccgcatca gccagcgcag aaatatttcc agcaaattca   3300
```

-continued

```
ttctgcaatc ggcttgcata acgctgacca cgttcataag cacttgttgg gcgataatcg   3360
ttacccaatc tggataatgc agccatctgc tcatcatcca gctcgccaac cagaacacga   3420
taatcacttt cggtaagtgc agcagcttta cgacggcgac tcccatcggc aatttctatg   3480
acaccagata ctcttcgacc gaacgccggt gtctgttgac cagtcagtag aaaagaaggg   3540
atgagatcat ccagtgcgtc ctcagtaagc agctcctggt cacgttcatt acctgaccat   3600
acccgagagg tcttctcaac actatcaccc cggagcactt caagagtaaa cttcacatcc   3660
cgaccacata caggcaaagt aatggcatta ccgcgagcca ttactcctac gcgcgcaatt   3720
aacgaatcca ccatcggggc agctggtgtc gataacgaag tatcttcaac cggttgagta   3780
ttgagcgtat gttttggaat aacaggcgca cgcttcatta tctaatctcc cagcgtggtt   3840
taatcagacg atcgaaaatt tcattgcaga caggttccca aatagaaaga gcatttctcc   3900
aggcaccagt tgaagagcgt tgatcaatgg cctgttcaaa aacagttctc atccggatct   3960
gacctttacc aacttcatcc gtttcacgta caacattttt tagaaccatg cttccccagg   4020
catcccgaat ttgctcctcc atccacgggg actgagagcc attactattg ctgtatttgg   4080
taagcaaaat acgtacatca ggctcgaacc ctttaagatc aacgttcttg agcagatcac   4140
gaagcatatc gaaaaactgc agtgcggagg tgtagtcaaa caactcagca ggcgtgggaa   4200
caatcagcac atcagcagca catacgacat taatcgtgcc gatacccagg ttaggcgcgc   4260
tgtcaataac tatgacatca tagtcatgag caacagtttc aatggccagt cggagcatca   4320
ggtgtggatc ggtgggcagt ttaccttcat caaatttgcc cattaactca gtttcaatac   4380
ggtgcagagc cagacaggaa ggaataatgt caagccccgg ccagcaagtg ggctttattg   4440
cataagtgac atcgtccttt tccccaagat agaaaggcag gagagtgtct tctgcatgaa   4500
tatgaagatc tggtacccat ccgtgataca ttgaggctgt tccctggggg tcgttacctt   4560
ccacgagcaa aacacgtagc cccttcagag ccagatcctg agcaagatga acagaaactg   4620
aggttttgta aacgccacct ttatgggcag caaccccgat caccggtgga aatacgtctt   4680
cagcacgtcg caatcgcgta ccaaacacat cacgcatatg attaatttgt tcaattgtat   4740
aaccaacacg ttgctcaacc cgtcctcgaa tttccatatc cgggtgcggt agtcgccctg   4800
ctttctcggc atctctgata gcctgagaag aaaccccaac taaatccgct gcttcaccta   4860
ttctccagcg ccgggttatt ttcctcgctt ccgggctgtc atcattaaac tgtgcaatgg   4920
cgatagcctt cgtcatttca tgaccagcgt ttatgcactg gttaagtgtt tccatgagtt   4980
tcattctgaa catcctttaa tcattgcttt gcgttttttt attaaatctt gcaatttact   5040
gcaaagcaac aacaaaatcg caaagtcatc aaaaaaccgc aaagttgttt aaaataagag   5100
caacactaca aaaggagata agaagagcac atacctcagt cacttattat cactagcgct   5160
cgccgcagcc gtgtaaccga gcatagcgag cgaactggcg aggaagcaaa gaagaactgt   5220
tctgtcagat agctcttacg ctcagcgcaa gaagaaatat ccaccgtggg aaaaactcca   5280
ggtagaggta cacacgcgga tagccaattc agagtaataa actgtgataa tcaaccctca   5340
tcaatgatga cgaactaacc cccgatatca ggtcacatga cgaagggaaa gagaaggaaa   5400
tcaactgtga caaactgccc tcaaatttgg cttccttaaa aattacagtt caaaaagtat   5460
gagaaaatcc atgcaggctg aaggaaacag caaaactgtg acaaattacc ctcagtaggt   5520
cagaacaaat gtgacgaacc accctcaaat ctgtgacaga taaccctcag actatcctgt   5580
cgtcatggaa gtgatatcgc ggaaggaaaa tacgatatga gtcgtctggc ggcctttctt   5640
```

```
tttctcaatg tatgagaggc gcattggagt tctgctgttg atctcattaa cacagacctg   5700
caggaagcgg cggcggaagt caggcatacg ctggtaactt tgaggcagct ggtaacgctc   5760
tatgatccag tcgattttca gagagacgat gcctgagcca tccggcttac gatactgaca   5820
cagggattcg tataaacgca tggcatacgg attggtgatt tcttttgttt cactaagccg   5880
aaactgcgta aaccggttct gtaacccgat aaagaaggga atgagatatg ggttgatatg   5940
tacactgtaa agccctctgg atggactgtg cgcacgtttg ataaaccaag gaaaagattc   6000
atagcctttt tcatcgccgg catcctcttc agggcgataa aaaaccactt ccttccccgc   6060
gaaactcttc aatgcctgcc gtatatcctt actggcttcc gcagaggtca atccgaatat   6120
ttcagcatat ttagcaacat ggatctcgca gataccgtca tgttcctgta gggtgccatc   6180
agattttctg atctggtcaa cgaacagata cagcatacgt tttgatcccg gggagagact   6240
atatgccgcc tcagtgaggt cgtttgactg gacgattcgc gggctatttt tacgtttctt   6300
gtgattgata accgctgttt ccgccatgac agatccatgt gaagtgtgac aagtttttag   6360
attgtcacac taaataaaaa agagtcaata agcagggata actttgtgaa aaaacagctt   6420
cttctgaggg caatttgtca cagggttaag ggcaatttgt cacagacagg actgtcattt   6480
gagggtgatt tgtcacactg aaagggcaat ttgtcacaac accttctcta gaaccagcat   6540
ggataaaggc ctacaaggcg ctctaaaaaa gaagatctaa aaactataaa aaaaataatt   6600
ataaaaatat ccccgtggat aagtggataa ccccaaggga agttttttca ggcatcgtgt   6660
gtaagcagaa tatataagtg ctgttccctg gtgcttcctc gctcactcga gggcttcgcc   6720
ctgtcgctca actgcggcga gcactactgg ctgtaaaagg acagaccaca tcatggttct   6780
gtgttcatta ggttgttctg tccattgctg acataatccg ctccacttca acgtaacacc   6840
gcacgaagat ttctattgtt cctgaaggca tattcaaatc gttttcgtta ccgcttgcag   6900
gcatcatgac agaacactac ttcctataaa cgctacacag gctcctgaga ttaataatgc   6960
ggatctctac gataatggga gattttcccg actgtttcgt tcgcttctca gtggataaca   7020
gccagcttct ctgtttaaca gacaaaaaca gcatatccac tcagttccac atttccatat   7080
aaaggccaag gcatttattc tcaggataat tgtttcagca tcgcaaccgc atcagactcc   7140
ggcatcgcaa actgcacccg gtgccgggca gccacatcca gcgcaaaaac cttcgtgtag   7200
acttccgttg aactgatgga cttatgtccc atcaggcttt gcagaacttt cagcggtata   7260
ccggcataca gcatgtgcat cgcataggaa tggcggaacg tatgtggtgt gaccggaaca   7320
gagaacgtca caccgtcagc agcagcggcg gcaaccgcct ccccaatcca ggtcctgacc   7380
gttctgtccg tcacttccca gatccgcgct ttctctgtcc ttcctgtgcg acggttacgc   7440
cgctccatga gcttatcgcg aataaatacc tgtgacggaa gatcacttcg cagaataaat   7500
aaatcctggt gtccctgttg ataccgggaa gccctgggcc aacttttggc gaaaatgaga   7560
cgttgatcgg cacgtaagag gttccaactt tcaccataat gaaataagat cactaccggg   7620
cgtatttttt gagttatcga gattttcagg agctaaggaa gctaaaatgg agaaaaaaat   7680
cactggatat accaccgttg atatatccca atggcatcgt aaagaacatt ttgaggcatt   7740
tcagtcagtt gctcaatgta cctataacca gaccgttcag ctggatatta cggccttttt   7800
aaagaccgta aagaaaaata agcacaagtt ttatccggcc tttattcaca ttcttgcccg   7860
cctgatgaat gctcatccgg agttccgtat ggcaatgaaa gacggtgagc tggtgatatg   7920
ggatagtgtt cacccttgtt acaccgtttt ccatgagcaa actgaaacgt tttcatcgct   7980
ctggagtgaa taccacgacg atttccggca gtttctacac atatattcgc aagatgtggc   8040
```

```
gtgttacggt gaaaacctgg cctatttccc taaagggttt attgagaata tgtttttcgt   8100
ctcagccaat ccctgggtga gtttcaccag ttttgattta aacgtggcca atatggacaa   8160
cttcttcgcc cccgttttca ccatgggcaa atattatacg caaggcgaca aggtgctgat   8220
gccgctggcg attcaggttc atcatgccgt ttgtgatggc ttccatgtcg gcagaatgct   8280
taatgaatta caacagtact gcgatgagtg gcagggcggg gcgtaatttt tttaaggcag   8340
ttattggtgc ccttaaacgc ctggttgcta cgcctgaata agtgataata agcggatgaa   8400
tggcagaaat tcgatgataa gctgtcaaac atgagaattg gtcgacggcg cgccaaagct   8460
tgcatgcctg cagccgcgta acctggcaaa atcggttacg gttgagtaat aaatggatgc   8520
cctgcgtaag cggggcacat ttcattacct ctttctccgc acccgacata gataataact   8580
tcgtatagta tacattatac gaagttatct agtagactta atcgcgttta aacccatcat   8640
caataatata cctcaaactt tttgtgcgcg ttaatatgca aatgaggcgt ttgaatttgg   8700
gaagggagga aggtgattgg ccgagagaag ggcgaccgtt aggggcgggg cgagtgacgt   8760
tttgatgacg tgaccgcgag gaggagccag tttgcaagtt ctcgtgggaa aagtgacgtc   8820
aaacgaggtg tggtttgaac acggaaatac tcaattttcc cgcgctctct gacaggaaat   8880
gaggtgtttc taggcggatg caagtgaaaa cgggccattt tcgcgcgaaa actgaatgag   8940
gaagtgaaaa tctgagtaat ttcgcgttta tgacagggag gagtatttgc cgagggccga   9000
gtagactttg accgattacg tgggggtttc gattaccgtg tttttcacct aaatttccgc   9060
gtacggtgtc aaagtccggt gtttttacgt aggtgtcagc tgatcgccag ggtatttaaa   9120
cctgcgctct ccagtcaaga ggccactctt gagtgccagc gagaagagtt ttctcctccg   9180
cgcgcgagtc agatctacac tttgaaaggc gatcgctagc gacatcgatc caaataatga   9240
ttttattttg actgatagtg acctgttcgt tgcaacaaat tgataagcaa tgctttttta   9300
taatgccaac tttgtacaaa aaagcaggct ccaccatggg aaccaattca gtcgagcctt   9360
tcactcatta gatgcatgtc gttacataac ttacggtaaa tggcccgcct ggctgaccgc   9420
ccaacgaccc ccgcccattg acgtcaataa tgacgtatgt tcccatagta acgccaatag   9480
ggactttcca ttgacgtcaa tgggtggagt atttacggta aactgcccac ttggcagtac   9540
atcaagtgta tcatatgcca agtacgcccc ctattgacgt caatgacggt aaatggcccg   9600
cctggcatta tgcccagtac atgaccttat gggactttcc tacttggcag tacatctacg   9660
tattagtcat cgctattacc atggtgatgc ggttttggca gtacatcaat gggcgtggat   9720
agcggtttga ctcacgggga tttccaagtc tccaccccat tgacgtcaat gggagtttgt   9780
tttggcacca aaatcaacgg gactttccaa aatgtcgtaa caactccgcc ccattgacgc   9840
aaatgggcgg taggcgtgta cggtgggagg tctatataag cagagctctc cctatcagtg   9900
atagagatct ccctatcagt gatagagatc gtcgacgagc tcgtttagtg aaccgtcaga   9960
tcgcctggag acgccatcca cgctgttttg acctccatag aagacaccgg gaccgatcca  10020
gcctccggtt aagctcggta ccgctagccg cgccgccacc atggatgcaa tgaagagagg  10080
gctctgctgt gtgctgctgc tgtgtggagc agtcttcgtt tcgcccagcc aggaaatcca  10140
tgcccgattc agaagaggat cgaagcttgc cagccagatc ggcgccggcg tgttcaagga  10200
gggcgtgttc cacaccatgt ggcacgtgac caggggcgcc gtgctgatgc accagggcaa  10260
gaggatcgag cccagctggg ccgacgtgaa gaaggacctg atcagctaca gcgtgaagaa  10320
ggacctgatc agctacggcg gcggctggag gctggagggc gagtgggacg agggcgagga  10380
```

ggtgcaggtg atcgccgtgg agcccggcaa gaaccccaag gccgtgcaga ccaagcccgg 10440
cctgttcaag acccccgagg gcgagatcgg cgccatcgcc ctggacttca agcccggcac 10500
cagcggcagc cccatcgtga acagggaggg caccagcggc agccccatca tcaacaggga 10560
gggcaaggtg gtgggcctgt acggcaacgg cgtggtgacc aagagcggcg cctacgtgag 10620
cgccatcgcc cagaccaacg ccgagcccct gcccgagatc gaggacgagg tgttcaggaa 10680
gaggaacctg accatcatgg acctgcaccc cggcgccggc aagaccaaga ggtacctgcc 10740
cgccatcgtg agggaggcca tcaagaggag gctgaggacc ctgatcctgg cccccaccag 10800
ggtggtggcc gccgagatgg cccccaccag ggtggtggcc agcgagatgg aggaggccct 10860
gaagggcctg cccatcaggt acgccctgag gggcctgccc atcaggtacc agaccaccgc 10920
catcaaggcc gagcacaccg gcaaggagat cgtggacctg atgtgccacg ccaccttcac 10980
catgaggctg ctgagccccg tgagggtgcc caactacaac ctgatcatca tggacgaggc 11040
ccacttcacc gaccccgcca gcatcgccgc caggggctac atcagcacca gggtggagat 11100
gggcgaggcc gccgccatct tcatgaccgc caccccccc ggcagcgccg acgccttccc 11160
ccagagcaac gcccccatcg aggacgagga gagggagatc cccgagagga gctggaacag 11220
cggcttcgac tggatcaccg acttcgccgg caagaccgtg tggttcgtgc ccagcatcaa 11280
ggccggcaac gacatcgcca actgcctgag gaagaacggc aagaaggtga tccagctgag 11340
caggaagacc ttcgacaccg agtaccccaa gaccaagctg aacgactggg acttcgtggt 11400
gaccaccgac atcagcgaga tgggcgccaa cttcaaggcc gacagggtga tcgaccccag 11460
gaggtgcctg aagcccgtga tcctgaccga cggccccgag agggtgatcc tggccggccc 11520
catgcccgtg accgccgcca gcgccgccca gaggaggggc aggatcggca ggaaccacaa 11580
gaaggagaac gaccagtaca tctacatggg ccagcccctg aacaacgacg aggaccacgc 11640
ccactggacc gaggccaaga tgctgctgga caacatcaac acccccgagg gcatcatccc 11700
cgccctgttc acccccgagg gcatcatccc cagcatgttc acccccgagg gcatcatccc 11760
caccctgttc acccccgagg gcatcatccc cagcctggag cccgagaggg agaagagcgc 11820
cgccatcgac ggcgagtaca ggctgagggg cgaggccagg aagaccttcg tggagctggg 11880
cgaggccagg aagaccttcg tggacctggg cgagcagagg aagaccttcg tggagctgat 11940 gaggagggc gacctgcccg tgtggctgag ctacaaggtg gccagcgccg gcttccagta 12000
caaggacagg gagtggtgct tcgacggcga gaggaacaac cagatcctgg aggagaacat 12060
ggacgtggag atctggacca aggagggcga gaagaagaag ctgaggccca ggtggctgga 12120
cgccaggacc tacgccgacc ccctggccct gaaggagttc aaggacttcg ccgccggcag 12180
gaagagcatc gccaccgaga tcggcagggt gcccagccac ctggcccaca ggaccagggc 12240
ctaccagcac gccctggagg agctgcccga gaccctggag accctgctgc tgctggccct 12300
gctgggcgcc ttcctgttct tcctgagcgg caagggcatc ggcaagatga gcatcggcct 12360
gtgctgcatc atcgccgcca gcctgctgtg gatggccgag atccagcccc actggatcgc 12420
cgccagcatc atcctggagt tcttcctgat ggtgctgctg atccccgagc ccgagaagca 12480
gaggaccccc caggacaacc agctggccta cgtggtgatc ggcatcctga ccctggccgc 12540
cgccatcgcc gccaacgaga tgggcctgct ggagaccacc aagaaggacc tgggcatcgg 12600
ccacgtggcc cccaccgcca tcctggacgt ggacctgcac cccgccagcg cctggaccct 12660
gtacgccgtg gccaccacca tcatcacccc catgctgagg cacaccatcg agaacagcac 12720
cgccaacgtg agcctgaccg ccatcgccaa ccaggccgcc gtgctgatga tcgccaacca 12780

```
ggccaccgtg ctgatgggcc tggacaaggg ctggcccatc agcaagatgg acctgggcgt  12840
gcccctgctg gccctgggct gctacagcca ggtgaacccc ctgaccctga ccgccgccgt  12900
gctgctgctg atcacccact acgccatcat cggccccggc ctgcaggcca aggccaccag  12960
ggaggcccag aagaggaccg ccgccggcat catgaagaac cccaccgtgg acggcatcat  13020
ggccatcgac ctggacccca tcccctacga ccccaagttc gagaagcagc tgggccaggt  13080
gatgctgctg atcctgtgcg tgagccagat cctgctgatg aggaccacct gggccgtgct  13140
gctgatgagg accacctggg ccctgtgcga ggccctgacc ctggccaccg gccccatcac  13200
caccctgtgg gagggcaacc ccggcaagtt ctggaacacc accatcgccg tgagcatggc  13260
caacatcttc aggggcagct acctggccgg cgccggcctg gccttcagcc tgatcaagaa  13320
caggaggggc accggcgccc agggcgagac cctgggcgag aagtggaaga ggcagctgaa  13380
ccagctggac aagagcgagt tcgaggagta caagaagagc ggcatcctgg aggtggacag  13440
gaccgaggcc aaggaggcca tcaagagggg cgagaccgac caccacgccg tgagcagggg  13500
cagcgccaag ctgaggtggt tcgtggagag gaacatggtg atccccgagg gcagggtgat  13560
cgacctgggc tgcggcaggg gcggctggag ctactactgc gccggcctga agaaggtgag  13620
ggaggtgagg ggctacacca agggcggccc cggccacgag gagcccatcc ccatggccac  13680
ctacggctgg aacctggtga agctgcacag cggcgtggac gtgttcttcc ccgagaagtg  13740
cgacaccctg ctgtgcgaca tcggcgagag cagccccaac cccaccatcg aggagggcag  13800
gaccctgagg gtgctgaaga tggtggagcc ctggctgaag ggcaaccagt tctgcatcaa  13860
gatcctgaac ccctacatgc ccagcgtgat cgaggagctg gagaagctgc agaggaagca  13920
cggcggcatg ctggtgagga acccccctgag caggaacagc acccacgaga tgtactgggt  13980
gagcaacggc accggcaaca tcgtgagcgc cgtgaacatg atcagcagga tgctgatcaa  14040
caggttcacc atggcccaca agaagcccac ctacgagagg gacgtggacc tgggcgccgg  14100
cagcacctgg cactacgacg aggacaaccc ctacaagacc tgggcctacc acggcagcta  14160
cgaggtgaag gccaccggca gcgccagcag catggtgaac ggcgtggtga agctgctgac  14220
caagccctgg gacgtggtgc ccatggtgac ccagatggcc atgaccgaca ccaccccctt  14280
cggccagcag agggtgttca aggagaaggt ggacaccagg acccccgagg ccaaggagaa  14340
cgccgccatc ggcgccgtgt tccaggacga gaacggctgg aagagcgcca gggaggccgt  14400
ggaggacagc gagagggccc tgcacctgga gggcaagtgc gagagctgcg tgtacaacat  14460
gatgggcaag agggagaaga agctgggcga gttcggcaag gccaagggca gcagggccat  14520
ctggtacatg tggctgggcg ccaggttcct ggagttcgag gccctgggct tcctgaacga  14580
ggaccactgg ttcagcaggg agaacagcct gagcggcgtg gagggcgagg gcctgcacaa  14640
gctgggctac atcctgaggg acatcagcaa gatccccggc ggcgccatgt acgccgacga  14700
caccgccggc tgggacacca ggatcaccga ggacgacctg cacaacgagg agaagatcct  14760
ggccaaggcc atcttcaagc tgacctacca gaacaaggtg gtgaaggtgc agaggcccac  14820
ccccaggggc gccgtgatgg acatcatcag caggaaggac cagaggggca gcggccaggt  14880
gggcacctac ggcctgaaca ccttcaccaa catggaggcc cagctgatca ggcagatgga  14940
ggccgagggc gtgatcaccg agtgcggcgt ggacaggctg aagaggatgg ccatcagcgg  15000
cgacgactgc gtggtgaagc ccccccagtg ggagcccagc aagggctggc acgactggca  15060
gcaggtgccc ttctgcagcc accacttcca cgagatcttc atgaaggacg gcaggaagct  15120
```

```
ggtggtgccc tgcaggaacc aggacgagct gatcggcagg gccaggatca gccagggcgc  15180
cggctggagc ctgagggaga ccgcctgcct gggcaagagc tacgcccaga tgtggcagct  15240
gatgtacttc cacaggaggg acctgaggct ggccagcaac gccatctgca gcgccgtgcc  15300
cagccactgg gtgcccacca gcaggaccac ctggagcatc cacgcccacc acgagtggat  15360
gaccaccgag gacatgctgg ccgtgtggaa cagggtgtgg atcgaggaga acccctggat  15420
ggaggacaag acccacatcc acagctggga ggacgtgccc tacctgggca agagggagga  15480
ccagtggtgc ggcagcctga tcggcctgac cagcagggcc acctgggcca agaacatcgc  15540
tggatccggg cccggggctt caggtaagcc tatccctaac cctctcctcg gtctcgattc  15600
tacgcggacc tgatgagcgg ccgctcgagc atgcatctag agggccctat tctatagtgt  15660
cacctaaatg ctagagctcg ctgatcagcc tcgactgtgc cttctagttg ccagccatct  15720
gttgtttgcc cctcccccgt gccttccttg accctggaag gtgccactcc cactgtcctt  15780
tcctaataaa atgaggaaat tgcatcgcat tgtctgagta ggtgtcattc tattctgggg  15840
ggtggggtgg ggcaggacag caagggggag gattgggaag acaatagcag gcatgctggg  15900
gatgcggtgg gctctatggc ttctgaggcg gaaagaacca gctggggctc gagggggat  15960
cgatcccgtc gagatatcta gacccagctt tcttgtacaa agttggcatt ataagaaagc  16020
attgcttatc aatttgttgc aacgaacagg tcactatcag tcaaaataaa atcattattt  16080
ggatcgattc gacagatcgc gatcgcagtg agtagtgttc tggggcgggg gaggacctgc  16140
atgagggcca gaatgactga aatctgtgct tttctgtgtg ttgcagcatc atgagcggaa  16200
gcggctcctt tgagggaggg gtattcagcc cttatctgac ggggcgtctc ccctcctggg  16260
cgggagtgcg tcagaatgtg atgggatcca cggtggacgg ccggcccgtg cagcccgcga  16320
actcttcaac cctgacctat gcaaccctga gctcttcgtc ggtggacgca gctgccgccg  16380
cagctgctgc atccgccgcc agcgccgtgc gcggaatggc catgggcgcc ggctactacg  16440
gcactctggt ggccaactcg agttccacca ataatcccgc cagcctgaac gaggagaagc  16500
tgctgctgct gatggcccag cttgaggcct tgacccagcg cctgggcgag ctgacccagc  16560
aggtggctca gctgcaggag cagacgcggg ccgcggttgc cacggtgaaa tccaaataaa  16620
aaatgaatca ataaataaac ggagacggtt gttgatttta acacagagtc tgaatcttta  16680
tttgattttt cgcgcgcggt aggccctgga ccaccggtct cgatcattga gcacccggtg  16740
gatcttttcc aggacccggt agaggtgggc ttggatgttg aggtacatgg gcatgagccc  16800
gtcccggggg tggaggtagc tccattgcag ggcctcgtgc tcgggggtgg tgttgtaaat  16860
cacccagtca tagcaggggc gcagggcgtg gtgttgcaca atatctttga ggaggagact  16920
gatggccacg ggcagccctt tggtgtaggt gtttacaaat ctgttgagct gggagggatg  16980
catgcggggg gagatgaggt gcatcttggc ctggatcttg agattggcga tgttaccgcc  17040
cagatcccgc ctggggttca tgttgtgcag gaccaccagc acggtgtatc cggtgcactt  17100
ggggaattta tcatgcaact tggaagggaa ggcgtgaaag aatttggcga cgcccttgtg  17160
tccgcccagg ttttccatgc actcatccat gatgatggca atgggcccgt gggcggcggc  17220
ctgggcaaag acgtttcggg ggtcggacac atcatagttg tggtcctggg tgaggtcatc  17280
ataggccatt ttaatgaatt tggggcggag ggtgccggac tgggggacaa aggtaccctc  17340
gatcccgggg gcgtagttcc cctcacagat ctgcatctcc caggctttga gctcagaggg  17400
ggggatcatg tccacctgcg gggcgataaa gaacacggtt tccggggcgg gggagatgag  17460
ctgggccgaa agcaagttcc ggagcagctg ggacttgccg cagccggtgg ggccgtaaat  17520
```

```
gaccccgatg accggctgca ggtggtagtt gagggagaga cagctgccgt cctcccggag  17580
gaggggggcc acctcgttca tcatctcgcg cacgtgcatg ttctcgcgca ccagttccgc  17640
caggaggcgc tctcccccca gagataggag ctcctggagc gaggcgaagt ttttcagcgg  17700
cttgagtccg tcggccatgg gcattttgga gagggtctgt tgcaagagtt ccaagcggtc  17760
ccagagctcg gtgatgtgct ctacggcatc tcgatccagc agacctcctc gtttcgcggg  17820
ttgggacgac tgcgggagta gggcaccaga cgatgggcgt ccagcgcagc cagggtccgg  17880
tccttccagg gccgcagcgt ccgcgtcagg gtggtctccg tcacggtgaa ggggtgcgcg  17940
ccgggctggg cgcttgcgag ggtgcgcttc aggctcatcc ggctggtcga aaaccgctcc  18000
cgatcggcgc cctgcgcgtc ggccaggtag caattgacca tgagttcgta gttgagcgcc  18060
tcggccgcgt ggcctttggc gcggagctta cctttggaag tctgcccgca ggcgggacag  18120
aggagggact tgagggcgta gagcttgggg gcgaggaaga cggaatcggg ggcgtaggcg  18180
tccgcgccgc agtgggcgca gacggtctcg cactccacga gccaggtgag gtcgggctgg  18240
tcggggtcaa aaaccagttt cccgccgttc tttttgatgc gtttcttacc tttggtctcc  18300
atgagctcgt gtccccgctg ggtgacaaag aggctgtccg tgtccccgta gaccgacttt  18360
atgggccggt cctcgagcgg tgtgccgcgg tcctcctcgt agaggaaccc cgcccactcc  18420
gagacgaaag cccgggtcca ggccagcacg aaggaggcca cgtgggacgg gtagcggtcg  18480
ttgtccacca gcgggtccac tttttccagg gtatgcaaac acatgtcccc ctcgtccaca  18540
tccaggaagg tgattggctt gtaagtgtag gccacgtgac cggggggtccc ggccgggggg  18600
gtataaaagg gggcgggccc ctgctcgtcc tcactgtctt ccggatcgct gtccaggagc  18660
gccagctgtt ggggtaggta ttccctctcg aaggcgggca tgacctcggc actcaggttg  18720
tcagtttcta gaaacgagga ggatttgata ttgacggtgc cagcggagat gcctttcaag  18780
agcccctcgt ccatctggtc agaaaagacg atttttttgt tgtcgagctt ggtggcgaag  18840
gagccgtaga gggcgttgga aaggagcttg gcgatggagc gcatggtctg gtttttttcc  18900
ttgtcggcgc gctccttggc cgcgatgttg agctgcacgt actcgcgcgc cacgcacttc  18960
cattcgggga agacggtggt catctcgtcg ggcacgattc tgacctgcca acctcgatta  19020
tgcagggtga tgaggtccac actggtggcc acctcgccgc gcaggggctc gttggtccag  19080
cagaggcggc cgcccttgcg cgagcagaag gggggcagag ggtccagcat gacctcgtcg  19140
ggggggtcgg catcgatggt gaagatgccg ggcaggagat cggggtcgaa gtagctgatg  19200
gaagtggcca gatcgtccag ggaagcttgc cattcgcgca cggccagcgc gcgctcgtag  19260
ggactgaggg gcgtgcccca gggcatgggg tgggtgagcg cggaggcgta catgccgcag  19320
atgtcgtaga cgtagagggg ctcctcgagg atgccgatgt aggtggggta gcagcgcccc  19380
ccgcggatgc tggcgcgcac gtagtcatac agctcgtgcg agggcgcgag gagccccggg  19440
cccaggttgg tgcgactggg cttttcggcg cggtagacga tctggcgaaa gatggcatgc  19500
gagttggagg agatggtggg cctttggaag atgttgaagt gggcgtgggg gaggccgacc  19560
gagtcgcgga tgaagtgggc gtaggagtct tgcagtttgg cgacgagctc ggcggtgacg  19620
aggacgtcca gagcgcagta gtcgagggtc tcctggatga tgtcatactt gagctggccc  19680
ttttgtttcc acagctcgcg gttgagaagg aactcttcgc ggtccttcca gtactcttcg  19740
agggggaacc cgtcctgatc tgcacggtaa gagcctagca tgtagaactg gttgacggcc  19800
ttgtaggcgc agcagccctt ctccacgggg agggcgtagg cctgggcggc cttgcgcagg  19860
```

gaggtgtgcg tgagggcgaa ggtgtccctg accatgacct tgaggaactg gtgcttgaaa 19920
tcgatatcgt cgcagccccc ctgctcccag agctggaagt ccgtgcgctt cttgtaggcg 19980
gggttgggca aagcgaaagt aacatcgttg aaaaggatct tgcccgcgcg gggcataaag 20040
ttgcgagtga tgcggaaagg ctggggcacc tcggcccggt tgttgatgac ctgggcggcg 20100
agcacgatct cgtcgaaacc gttgatgttg tggcccacga tgtagagttc cacgaatcgc 20160
gggcggccct tgacgtgggg cagcttcttg agctcctcgt aggtgagctc gtcggggtcg 20220
ctgagaccgt gctgctcgag cgcccagtcg gcgagatggg ggttggcgcg gaggaaggaa 20280
gtccagagat ccacggccag ggcggtttgc agacggtccc ggtactgacg gaactgctgc 20340
ccgacggcca tttttcggg ggtgacgcag tagaaggtgc gggggtcccc gtgccagcgg 20400
tcccatttga gctggagggc gagatcgagg gcgagctcga cgaggcggtc gtcccctgag 20460
agtttcatga ccagcatgaa ggggacgagc tgcttgccga aggaccccat ccaggtgtag 20520
gtttccacat cgtaggtgag gaagagcctt tcggtgcgag gatgcgagcc gatggggaag 20580
aactggatct cctgccacca attggaggaa tggctgttga tgtgatggaa gtagaaatgc 20640
cgacggcgcg ccgaacactc gtgcttgtgt ttatacaagc ggccacagtg ctcgcaacgc 20700
tgcacgggat gcacgtgctg cacgagctgt acctgagttc ctttgacgag gaatttcagt 20760
gggaagtgga gtcgtggcgc ctgcatctcg tgctgtacta cgtcgtggtg gtcggcctgg 20820
ccctcttctg cctcgatggt ggtcatgctg acgagcccgc gcgggaggca ggtccagacc 20880
tcggcgcgag cgggtcggag agcgaggacg agggcgcgca ggccggagct gtccagggtc 20940
ctgagacgct gcggagtcag gtcagtgggc agcggcggcg cgcggttgac ttgcaggagt 21000
ttttccaggg cgcgcgggag gtccagatgg tacttgatct ccaccgcgcc gttggtggcg 21060
acgtcgatgg cttgcagggt cccgtgcccc tggggtgtga ccaccgtccc ccgtttcttc 21120
ttgggcggct ggggcgacgg gggcggtgcc tcttccatgg ttagaagcgg cggcgaggac 21180
gcgcgccggg cggcagaggc ggctcggggc ccggaggcag gggcggcagg ggcacgtcgg 21240
cgccgcgcgc gggtaggttc tggtactgcg cccggagaag actggcgtga gcgacgacgc 21300
gacggttgac gtcctggatc tgacgcctct gggtgaaggc cacgggaccc gtgagtttga 21360
acctgaaaga gagttcgaca gaatcaatct cggtatcgtt gacggcggcc tgccgcagga 21420
tctcttgcac gtcgcccgag ttgtcctggt aggcgatctc ggtcatgaac tgctcgatct 21480
cctcctcctg aaggtctccg cgaccggcgc gctccacggt ggccgcgagg tcgttggaga 21540
tgcggcccat gagctgcgag aaggcgttca tgcccgcctc gttccagacg cggctgtaga 21600
ccacgacgcc ctcgggatcg cgggcgcgca tgaccacctg ggcgaggttg agctccacgt 21660
ggcgcgtgaa gaccgcgtag ttgcagaggc gctggtagag gtagttgagc gtggtggcga 21720
tgtgctcggt gacgaagaaa tacatgatcc agcggcggag cggcatctcg ctgacgtcgc 21780
ccagcgcctc caagcgttcc atggcctcgt aaaagtccac ggcgaagttg aaaaactggg 21840
agttgcgcgc cgagacggtc aactcctcct ccagaagacg gatgagctcg gcgatggtgg 21900
cgcgcacctc gcgctcgaag gcccccggga gttcctccac ttcctcctct tcttcctcct 21960
ccactaacat ctcttctact tcctcctcag gcggtggtgg tggcgggggga gggggcctgc 22020
gtcgccggcg gcgcacgggc agacggtcga tgaagcgctc gatggtctcg ccgcgccggc 22080
gtcgcatggt ctcggtgacg gcgcgcccgt cctcgcgggg ccgcagcgtg aagacgccgc 22140
cgcgcatctc caggtggccg ggggggtccc cgttgggcag ggagagggcg ctgacgatgc 22200
atcttatcaa ttgccccgta gggactccgc gcaaggacct gagcgtctcg agatccacgg 22260

```
gatctgaaaa ccgttgaacg aaggcttcga gccagtcgca gtcgcaaggt aggctgagca  22320
cggtttcttc tgccgggtca tgttggggag cggggcgggc gatgctgctg gtgatgaagt  22380
tgaaataggc ggttctgaga cggcggatgg tggcgaggag caccaggtct ttgggcccgg  22440
cttgctggat gcgcagacgg tcggccatgc cccaggcgtg gtcctgacac ctggccaggt  22500
ccttgtagta gtcctgcatg agccgctcca cgggcacctc ctcctcgccc gcgcggccgt  22560
gcatgcgcgt gagcccgaag ccgcgctggg gctggacgag cgccaggtcg gcgacgacgc  22620
gctcggcgag gatggcctgc tggatctggg tgagggtggt ctggaagtcg tcaaagtcga  22680
cgaagcggtg gtaggctccg gtgttgatgg tgtaggagca gttggccatg acggaccagt  22740
tgacggtctg gtggcccgga cgcacgagct cgtggtactt gaggcgcgag taggcgcgcg  22800
tgtcgaagat gtagtcgttg caggtgcgca ccaggtactg gtagccgatg aggaagtgcg  22860
gcggcggctg gcggtagagc ggccatcgct cggtggcggg ggcgccgggc gcgaggtcct  22920
cgagcatggt gcggtggtag ccgtagatgt acctggacat ccaggtgatg ccggcggcgg  22980
tggtggaggc gcgcgggaac tcgcggacgc ggttccagat gttgcgcagc ggcaggaagt  23040
agttcatggt gggcacggtc tggcccgtga ggcgcgcgca gtcgtggatg ctctatacgg  23100
gcaaaaacga aagcggtcag cggctcgact ccgtggcctg gaggctaagc gaacgggttg  23160
ggctgcgcgt gtaccccggt tcgaatctcg aatcaggctg gagccgcagc taacgtggta  23220
ctggcactcc cgtctcgacc caagcctgca ccaaccctcc aggatacgga ggcgggtcgt  23280
tttgcaactt tttttggagg ccggaaatga aactagtaag cgcggaaagc ggccgaccgc  23340
gatggctcgc tgccgtagtc tggagaagaa tcgccagggt tgcgttgcgg tgtgccccgg  23400
ttcgaggccg gccggattcc gcggctaacg agggcgtggc tgccccgtcg tttccaagac  23460
cccatagcca gccgacttct ccagttacgg agcgagcccc tcttttgttt tgtttgtttt  23520
tgccagatgc atcccgtact gcggcagatg cgccccccacc accctccacc gcaacaacag  23580
ccccctcctc cacagccggc gcttctgccc ccgccccagc agcagcagca acttccagcc  23640
acgaccgccg cggccgccgt gagcggggct ggacagactt ctcagtatga tcacctggcc  23700
ttggaagagg gcgaggggct ggcgcgcctg gggggcgtcgt cgccggagcg gcacccgcgc  23760
gtgcagatga aaagggacgc tcgcgaggcc tacgtgccca agcagaacct gttcagagac  23820
aggagcggcg aggagcccga ggagatgcgc gcggcccggt tccacgcggg gcgggagctg  23880
cggcgcggcc tggaccgaaa gagggtgctg agggacgagg atttcgaggc ggacgagctg  23940
acggggatca gccccgcgcg cgcgcacgtg gccgcggcca acctggtcac ggcgtacgag  24000
cagaccgtga aggaggagag caacttccaa aaatccttca acaaccacgt gcgcaccctg  24060
atcgcgcgcg aggaggtgac cctgggcctg atgcacctgt gggacctgct ggaggccatc  24120
gtgcagaacc ccaccagcaa gccgctgacg gcgcagctgt tcctggtggt gcagcatagt  24180
cgggacaacg aggcgttcag ggaggcgctg ctgaatatca ccgagcccga gggccgctgg  24240
ctcctggacc tggtgaacat tctgcagagc atcgtggtgc aggagcgcgg gctgccgctg  24300
tccgagaagc tggcggccat caacttctcg gtgctgagtc tgggcaagta ctacgctagg  24360
aagatctaca agaccccgta cgtgcccata gacaaggagg tgaagatcga cgggttttac  24420
atgcgcatga ccctgaaagt gctgaccctg agcgacgatc tgggggtgta ccgcaacgac  24480
aggatgcacc gcgcggtgag cgccagcagg cggcgcgagc tgagcgacca ggagctgatg  24540
cacagcctgc agcgggccct gaccggggcc gggaccgagg gggagagcta ctttgacatg  24600
```

```
ggcgcggacc tgcactggca gcccagccgc cgggccttgg aggcggcagg cggtcccccc  24660
tacatagaag aggtggacga tgaggtggac gaggagggcg agtacctgga agactgatgg  24720
cgcgaccgta tttttgctag atgcaacaac agccacctcc tgatcccgcg atgcgggcgg  24780
cgctgcagag ccagccgtcc ggcattaact cctcggacga ttggacccag gccatgcaac  24840
gcatcatggc gctgacgacc cgcaaccccg aagcctttag acagcagccc caggccaacc  24900
ggctctcggc catcctggag gccgtggtgc cctcgcgctc caaccccacg cacgagaagg  24960
tcctggccat cgtgaacgcg ctggtggaga acaaggccat ccgcggcgac gaggccggcc  25020
tggtgtacaa cgcgctgctg gagcgcgtgg cccgctacaa cagcaccaac gtgcagacca  25080
acctggaccg catggtgacc gacgtgcgcg aggccgtggc ccagcgcgag cggttccacc  25140
gcgagtccaa cctgggatcc atggtggcgc tgaacgcctt cctcagcacc cagcccgcca  25200
acgtgccccg gggccaggag gactacacca acttcatcag cgccctgcgc ctgatggtga  25260
ccgaggtgcc ccagagcgag gtgtaccagt ccgggccgga ctacttcttc cagaccagtc  25320
gccagggctt gcagaccgtg aacctgagcc aggcgttcaa gaacttgcag ggcctgtggg  25380
gcgtgcaggc cccggtcggg gaccgcgcga cggtgtcgag cctgctgacg ccgaactcgc  25440
gcctgctgct gctgctggtg gccccttca cggacagcgg cagcatcaac cgcaactcgt  25500
acctgggcta cctgattaac ctgtaccgcg aggccatcgg ccaggcgcac gtggacgagc  25560
agacctacca ggagatcacc cacgtgagcc gcgccctggg ccaggacgac ccgggcaatc  25620
tggaagccac cctgaacttt ttgctgacca accggtcgca gaagatcccg ccccagtaca  25680
cgctcagcgc cgaggaggag cgcatcctgc gatacgtgca gcagagcgtg ggcctgttcc  25740
tgatgcagga gggggccacc cccagcgccg cgctcgacat gaccgcgcgc aacatggagc  25800
ccagcatgta cgccagcaac cgcccgttca tcaataaact gatggactac ttgcatcggg  25860
cggccgccat gaactctgac tatttcacca acgccatcct gaatccccac tggctcccgc  25920
cgccggggtt ctacacgggc gagtacgaca tgcccgaccc caatgacggg ttcctgtggg  25980
acgatgtgga cagcagcgtg ttctccccc gaccgggtgc taacgagcgc cccttgtgga  26040
agaaggaagg cagcgaccga cgcccgtcct cggcgctgtc cggccgcgag ggtgctgccg  26100
cggcggtgcc cgaggccgcc agtcctttcc cgagcttgcc cttctcgctg aacagtattc  26160
gcagcagcga gctgggcagg atcacgcgcc cgcgcttgct gggcgaggag gagtacttga  26220
atgactcgct gttgagaccc gagcgggaga agaacttccc caataacggg atagagagcc  26280
tggtggacaa gatgagccgc tggaagacgt atgcgcagga gcacagggac gatccgtcgc  26340
agggggccac gagccggggc agcgccgccc gtaaacgccg gtggcacgac aggcagcggg  26400
gactgatgtg ggacgatgag gattccgccg acgacagcag cgtgttggac ttgggtggga  26460
gtggtaaccc gttcgctcac ctgcgccccc gcatcgggcg catgatgtaa gagaaaccga  26520
aaataaatga tactcaccaa ggccatggcg accagcgtgc gttcgtttct tctctgttgt  26580
tgtatctagt atgatgaggc gtgcgtaccc ggagggtcct cctccctcgt acgagagcgt  26640
gatgcagcag gcgatggcgg cggcggcggc gatgcagccc ccgctggagg ctccttacgt  26700
gcccccgcgg tacctggcgc ctacggaggg gcggaacagc attcgttact cggagctggc  26760
acccttgtac gataccaccc ggttgtacct ggtggacaac aagtcggcgg acatcgcctc  26820
gctgaactac cagaacgacc acagcaactt cctgaccacc gtggtgcaga acaatgactt  26880
cacccccacg gaggccagca cccagaccat caactttgac gagcgctcgc ggtggggcgg  26940
tcagctgaaa accatcatgc acaccaacat gcccaacgtg aacgagttca tgtacagcaa  27000
```

```
caagttcaag gcgcgggtga tggtctcccg caagaccccc aacggggtga cagtgacaga  27060
tggtagtcag gatatcttgg agtatgaatg ggtggagttt gagctgcccg aaggcaactt  27120
ctcggtgacc atgaccatcg acctgatgaa caacgccatc atcgacaatt acttggcggt  27180
ggggcggcag aacggggtcc tggagagcga tatcggcgtg aagttcgaca ctaggaactt  27240
caggctgggc tgggaccccg tgaccgagct ggtcatgccc ggggtgtaca ccaacgaggc  27300
cttccacccc gatattgtct tgctgcccgg ctgcggggtg gacttcaccg agagccgcct  27360
cagcaacctg ctgggcattc gcaagaggca gcccttccag gagggcttcc agatcatgta  27420
cgaggatctg gagggggggca acatccccgc gctcctggat gtcgacgcct atgagaaaag  27480
caaggaggag agcgccgccg cggcgactgc agctgtagcc accgcctcta ccgaggtcag  27540
gggcgataat tttgccagcc ctgcagcagt ggcagcggcc gaggcggctg aaaccgaaag  27600
taagatagtc attcagccgg tggagaagga tagcaaggac aggagctaca acgtgctgcc  27660
ggacaagata aacaccgcct accgcagctg gtacctggcc tacaactatg gcgaccccga  27720
gaagggcgtg cgctcctgga cgctgctcac cacctcggac gtcacctgcg gcgtggagca  27780
agtctactgg tcgctgcccg acatgatgca agacccggtc accttccgct ccacgcgtca  27840
agttagcaac tacccggtgg tgggcgccga gctcctgccc gtctactcca agagcttctt  27900
caacgagcag gccgtctact cgcagcagct gcgcgccttc acctcgctca cgcacgtctt  27960
caaccgcttc cccgagaacc agatcctcgt ccgcccgccc gcgcccacca ttaccaccgt  28020
cagtgaaaac gttcctgctc tcacagatca cgggaccctg ccgctgcgca gcagtatccg  28080
gggagtccag cgcgtgaccg ttactgacgc cagacgccgc acctgcccct acgtctacaa  28140
ggccctgggc atagtcgcgc cgcgcgtcct ctcgagccgc accttctaaa aaatgtccat  28200
tctcatctcg cccagtaata acaccggttg gggcctgcgc gcgcccagca agatgtacgg  28260
aggcgctcgc caacgctcca cgcaacaccc cgtgcgcgtg cgcgggcact tccgcgctcc  28320
ctggggcgcc ctcaagggcc gcgtgcggtc gcgcaccacc gtcgacgacg tgatcgacca  28380
ggtggtggcc gacgcgcgca actacacccc cgccgccgcg cccgtctcca ccgtggacgc  28440
cgtcatcgac agcgtggtgg ccgacgcgcg ccggtacgcc cgcgccaaga gccggcggcg  28500
gcgcatcgcc cggcggcacc ggagcacccc cgccatgcgc gcggcgcgag ccttgctgcg  28560
cagggccagg cgcacgggac gcagggccat gctcagggcg gccagacgcg cggcttcagg  28620
cgccagcgcc ggcaggaccc ggagacgcgc ggccacggcg gcggcagcgg ccatcgccag  28680
catgtcccgc ccgcggcgag ggaacgtgta ctgggtgcgc gacgccgcca ccggtgtgcg  28740
cgtgcccgtg cgcacccgcc cccctcgcac ttgaagatgt tcacttcgcg atgttgatgt  28800
gtcccagcgg cgaggaggat gtccaagcgc aaattcaagg aagagatgct ccaggtcatc  28860
gcgcctgaga tctacggccc cgcggtggtg aaggaggaaa gaaagccccg caaaatcaag  28920
cgggtcaaaa aggacaaaaa ggaagaagat gacgatctgg tggagtttgt gcgcgagttc  28980
gccccccggc ggcgcgtgca gtggcgcggg cggaaagtgc acccggtgct gagacccggc  29040
accaccgtgg tcttcacgcc cggcgagcgc tccggcagcg cttccaagcg ctcctacgac  29100
gaggtgtacg gggacgagga catcctcgag caggcggccg agcgcctggg cgagtttgct  29160
tacggcaagc gcagccgccc cgccctgaag gaagaggcgg tgtccatccc gctggaccac  29220
ggcaacccca cgccgagcct caagcccgtg accctgcagc aggtgctgcc gagcgcagcg  29280
ccgcgccggg ggttcaagcg cgagggcgag gatctgtacc ccaccatgca gctgatggtg  29340
```

-continued

```
cccaagcgcc agaagctgga agacgtgctg gagaccatga aggtggaccc ggacgtgcag  29400
cccgaggtca aggtgcggcc catcaagcag gtggccccgg gcctgggcgt gcagaccgtg  29460
gacatcaaga tccccacgga gcccatggaa acgcagaccg agcccatgat caagcccagc  29520
accagcacca tggaggtgca gacggatccc tggatgccat cggctcctag ccgaagaccc  29580
cggcgcaagt acggcgcggc cagcctgctg atgcccaact acgcgctgca tccttccatc  29640
atccccacgc cgggctaccg cggcacgcgc ttctaccgcg gtcatacaac cagccgccgc  29700
cgcaagacca ccacccgccg ccgccgtcgc cgcacagccg ctgcatctac ccctgccgcc  29760
ctggtgcgga gagtgtaccg ccgcggccgc gcgcctctga ccctaccgcg cgcgcgctac  29820
cacccgagca tcgccattta aactttcgcc tgctttgcag atggccctca catgccgcct  29880
ccgcgttccc attacgggct accgaggaag aaaaccgcgc cgtagaaggc tggcggggaa  29940
cgggatgcgt cgccaccacc atcggcggcg gcgcgccatc agcaagcggt tgggggggagg  30000
cttcctgccc gcgctgatcc ccatcatcgc cgcggcgatc ggggcgatcc ccggcattgc  30060
ttccgtggcg gtgcaggcct ctcagcgcca ctgagacact tggaaaacat cttgtaataa  30120
accaatggac tctgacgctc ctggtcctgt gatgtgtttt cgtagacaga tggaagacat  30180
caatttttcg tccctggctc cgcgacacgg cacgcggccg ttcatgggca cctggagcga  30240
catcggcacc agccaactga acgggggcgc cttcaattgg agcagtctct ggagcgggct  30300
taagaatttc gggtccacgc ttaaaaccta tggcagcaag gcgtggaaca gcaccacagg  30360
gcaggcgctg agggataagc tgaaagagca gaacttccag cagaaggtgg tcgatgggct  30420
cgcctcgggc atcaacgggg tggtggacct ggccaaccag gccgtgcagc ggcagatcaa  30480
cagccgcctg gacccggtgc cgcccgccgg ctccgtggag atgccgcagg tggaggagga  30540
gctgcctccc ctggacaagc ggggcgagaa gcgaccccgc cccgacgcgg aggagacgct  30600
gctgacgcac acggacgagc cgccccccgta cgaggaggcg gtgaaactgg gtctgcccac  30660
cacgcggccc atcgcgcccc tggccaccgg ggtgctgaaa cccgaaagta ataagcccgc  30720
gaccctggac ttgcctcctc ccgcttcccg cccctctaca gtggctaagc ccctgccgcc  30780
ggtggccgtg gcccgcgcgc gacccggggg ctccgcccgc cctcatgcga actggcagag  30840
cactctgaac agcatcgtgg gtctgggagt gcagagtgtg aagcgccgcc gctgctatta  30900
aacctaccgt agcgcttaac ttgcttgtct gtgtgtgtat gtattatgtc gccgctgtcc  30960
gccagaagga ggagtgaaga ggcgcgtcgc cgagttgcaa gatggccacc ccatcgatgc  31020
tgccccagtg ggcgtacatg cacatcgccg gacaggacgc ttcggagtac ctgagtccgg  31080
gtctggtgca gttcgcccgc gccacagaca cctacttcag tctggggaac aagtttagga  31140
accccacggt ggcgcccacg cacgatgtga ccaccgaccg cagccagcgg ctgacgctgc  31200
gcttcgtgcc cgtggaccgc gaggacaaca cctactcgta caaagtgcgc tacacgctgg  31260
ccgtgggcga caaccgcgtg ctggacatgg ccagcaccta ctttgacatc cgcggcgtgc  31320
tggatcgggg ccctagcttc aaaccctact ccggcaccgc ctacaacagc ctggctccca  31380
agggagcgcc caattccagc cagtgggagc aaaaaaaggc aggcaatggt gacactatgg  31440
aaacacacac atttggtgtg gccccaatgg gcggtgagaa tattacaatc gacggattac  31500
aaattggaac tgacgctaca gctgatcagg ataaaccaat ttatgctgac aaaacattcc  31560
agcctgaacc tcaagtagga gaagaaaatt ggcaagaaac tgaaagcttt tatggcggta  31620
gggctcttaa aaaagacaca agcatgaaac cttgctatgg ctcctatgct agacccacca  31680
atgtaaaggg aggtcaagct aaacttaaag ttggagctga tggagttcct accaaagaat  31740
```

```
ttgacataga cctggctttc tttgatactc ccggtggcac agtgaatgga caagatgagt  31800
ataaagcaga cattgtcatg tataccgaaa acacgtatct ggaaactcca gacacgcatg  31860
tggtatacaa accaggcaag gatgatgcaa gttctgaaat taacctggtt cagcagtcca  31920
tgcccaatag acccaactat attgggttca gagacaactt tattgggctc atgtattaca  31980
acagtactgg caatatgggg gtgctggctg gtcaggcctc acagctgaat gctgtggtcg  32040
acttgcaaga cagaaacacc gagctgtcat accagctctt gcttgactct ttgggtgaca  32100
gaacccggta tttcagtatg tggaatcagg cggtggacag ttatgatcct gatgtgcgca  32160
ttattgaaaa ccatggtgtg gaagacgaac ttcccaacta ttgcttcccc ctggatgggt  32220
ctggcactaa tgccgcttac caaggtgtga aagtaaaaaa tggtaacgat ggtgatgttg  32280
agagcgaatg ggaaaatgat gatactgtcg cagctcgaaa tcaattatgc aagggcaaca  32340
tttttgccat ggaaattaac ctccaagcca acctgtggag aagtttcctc tactcgaacg  32400
tggccctgta cctgcccgac tcttacaagt acacgccagc caacatcacc ctgcccacca  32460
acaccaacac ttatgattac atgaacggga gagtggtgcc tccctcgctg gtggacgcct  32520
acatcaacat cggggcgcgc tggtcgctgg accccatgga caacgtcaat cccttcaacc  32580
accaccgcaa cgcgggcctg cgctaccgct ccatgctcct gggcaacggg cgctacgtgc  32640
ccttccacat ccaggtgccc cagaaatttt tcgccatcaa gagcctcctg ctcctgcccg  32700
ggtcctacac ctacgagtgg aacttccgca aggacgtcaa catgatcctg cagagctccc  32760
tcggcaacga cctgcgcacg gacggggcct ccatctcctt caccagcatc aacctctacg  32820
ccaccttctt ccccatggcg cacaacacgg cctccacgct cgaggccatg ctgcgcaacg  32880
acaccaacga ccagtccttc aacgactacc tctcggcggc caacatgctc taccccatcc  32940
cggccaacgc caccaacgtg cccatctcca tcccctcgcg caactgggcc gccttccgcg  33000
gctggtcctt cacgcgcctc aagaccaagg agacgccctc gctgggctcc gggttcgacc  33060
cctacttcgt ctactcgggc tccatcccct acctcgacgg caccttctac ctcaaccaca  33120
ccttcaagaa ggtctccatc accttcgact cctccgtcag ctggcccggc aacgaccggc  33180
tcctgacgcc caacgagttc gaaatcaagc gcaccgtcga cggcgaggga tacaacgtgg  33240
cccagtgcaa catgaccaag gactggttcc tggtccagat gctggcccac tacaacatcg  33300
gctaccaggg cttctacgtg cccgagggct acaaggaccg catgtactcc ttcttccgca  33360
acttccagcc catgagccgc caggtggtgg acgaggtcaa ctacaaggac taccaggccg  33420
tcaccctggc ctaccagcac aacaactcgg gcttcgtcgg ctacctcgcg cccaccatgc  33480
gccagggcca gccctacccc gccaactacc cgtacccgct catcggcaag agcgccgtca  33540
ccagcgtcac ccagaaaaag ttcctctgcg acagggtcat gtggcgcatc cccttctcca  33600
gcaacttcat gtccatgggc gcgctcaccg acctcggcca gaacatgctc tatgccaact  33660
ccgcccacgc gctagacatg aatttcgaag tcgaccccat ggatgagtcc acccttctct  33720
atgttgtctt cgaagtcttc gacgtcgtcc gagtgcacca gccccaccgc ggcgtcatcg  33780
aggccgtcta cctgcgcacc cccttctcgg ccggtaacgc caccacctaa attgctactt  33840
gcatgatggc tgagcccaca ggctccggcg agcaggagct cagggccatc atccgcgacc  33900
tgggctgcgg gccctacttc ctgggcacct tcgataagcg cttcccggga ttcatggccc  33960
cgcacaagct ggcctgcgcc atcgtcaaca cggccggccg cgagaccggg ggcgagcact  34020
ggctggcctt cgcctggaac ccgcgctcga acacctgcta cctcttcgac cccttcgggt  34080
```

```
tctcggacga gcgcctcaag cagatctacc agttcgagta cgagggcctg ctgcgccgta  34140
gcgccctggc caccgaggac cgctgcgtca ccctggaaaa gtccacccag accgtgcagg  34200
gtccgcgctc ggccgcctgc gggctcttct gctgcatgtt cctgcacgcc ttcgtgcact  34260
ggcccgaccg ccccatggac aagaacccca ccatgaactt gctgacgggg gtgcccaacg  34320
gcatgctcca gtcgccccag gtggaaccca ccctgcgccg caaccaggag gcgctctacc  34380
gcttcctcaa ctcccactcc gcctactttc gctcccaccg cgcgcgcatc gagaaggcca  34440
ccgccttcga ccgcatgaac aatcaagaca tgtaaaccgt gtgtgtatgt ttaaaatatc  34500
ttttaataaa cagcacttta atgttacaca tgcatctgag atgattttat tttagaaatc  34560
gaaagggttc tgccgggtct cggcatggcc cgcgggcagg gacacgttgc ggaactggta  34620
cttggccagc cacttgaact cggggatcag cagtttgggc agcggggtgt cggggaagga  34680
gtcggtccac agcttccgcg tcagctgcag ggcgcccagc aggtcgggcg cggagatctt  34740
gaaatcgcag ttgggacccg cgttctgcgc gcgagagttg cggtacacgg ggttgcagca  34800
ctggaacacc atcagggccg ggtgcttcac gctcgccagc accgccgcgt cggtgatgct  34860
ctccacgtcg aggtcctcgg cgttggccat cccgaagggg gtcatcttgc aggtctgcct  34920
tcccatggtg ggcacgcacc cgggcttgtg gttgcaatcg cagtgcaggg ggatcagcat  34980
catctgggcc tggtcggcgt tcatccccgg gtacatggcc ttcatgaaag cctccaattg  35040
cctgaacgcc tgctgggcct tggctccctc ggtgaagaag accccgcagg acttgctaga  35100
gaactggttg gtggcacagc cggcatcgtg cacgcagcag cgcgcgtcgt tgttggccag  35160
ctgcaccacg ctgcgccccc agcggttctg ggtgatcttg gcccggtcgg ggttctcctt  35220
cagcgcgcgc tgcccgttct cgctcgccac atccatctcg atcatgtgct ccttctggat  35280
catggtggtc ccgtgcaggc accgcagttt gccctcggcc tcggtgcacc cgtgcagcca  35340
cagcgcgcac ccggtgcact cccagttctt gtgggcgatc tgggaatgcg cgtgcacgaa  35400
cccttgcagg aagcggccca tcatggtcgt cagggtcttg ttgctagtga aggtcaacgg  35460
gatgccgcgg tgctcctcgt tgatgtacag gtggcagatg cggcggtaca cctcgccctg  35520
ctcgggcatc agttggaagt tggctttcag gtcggtctcc acgcggtagc ggtccatcag  35580
catagtcatg atttccatgc ccttctccca ggccgagacg atgggcaggc tcatagggtt  35640
cttcaccatc atcttagcac tagcagccgc ggccaggggg tcgctctcat ccagggtctc  35700
aaagctccgc ttgccgtcct tctcggtgat ccgcaccggg gggtagctga agcccacggc  35760
cgccagctcc tcctcggcct gtctttcgtc ctcgctgtcc tggctgacgt cctgcatgac  35820
cacatgcttg gtcttgcggg gtttcttctt gggcggcagt ggcggcggag atgcttgtgg  35880
cgagggggag cgcgagttct cgctcaccac tactatctct tcctcttctt ggtccgaggc  35940
cacgcggcgg taggtatgtc tcttcggggg cagaggcgga ggcgacgggc tctcgccgcc  36000
gcgacttggc ggatggctgg cagagcccct tccgcgttcg gggggtgcgct cccggcggcg  36060
ctctgactga cttcctccgc ggccggccat tgtgttctcc tagggaggaa caacaagcat  36120
ggagactcag ccatcgccaa cctcgccatc tgccccacc gccggcgacg agaagcagca  36180
gcagcagaat gaaagcttaa ccgccccgcc gcccagcccc gcctccgacg cagccgcggt  36240
cccagacatg caagagatgg aggaatccat cgagattgac ctgggctatg tgacgcccgc  36300
ggagcatgag gaggagctgg cagtgcgctt tcaatcgtca agccaggaag ataaagaaca  36360
gccagagcag gaagcagaga acgagcagag tcaggctggg ctcgagcatg gcgactacct  36420
ccacctgagc ggggaggagg acgcgctcat caagcatctg gcccggcagg ccaccatcgt  36480
```

caaggacgcg ctgctcgacc gcaccgaggt gcccctcagc gtggaggagc tcagccgcgc 36540
ctacgagctc aacctcttct cgccgcgcgt gcccccaag cgccagccca acggcacctg 36600
cgagcccaac ccccgcctca acttctaccc ggtcttcgcg gtgcccgagg ccctggccac 36660
ctaccacatc tttttcaaga accaaaagat ccccgtctcc tgccgcgcca accgcacccg 36720
cgccgacgcc ctcttcaacc tgggtcccgg cgcccgccta cctgatatcg cctccttgga 36780
agaggttccc aagatcttcg agggtctggg cagcgacgag actcgggccg cgaacgctct 36840
gcaaggagaa ggaggaggag agcatgagca ccacagcgcc ctggtcgagt tggaaggcga 36900
caacgcgcgg ctggcggtgc tcaaacgcac ggtcgagctg acccatttcg cctacccggc 36960
tctgaacctg cccccgaaag tcatgagcgc ggtcatggac caggtgctca tcaagcgcgc 37020
gtcgcccatc tccgaggacg agggcatgca agactccgag gagggcaagc ccgtggtcag 37080
cgacgagcag ctggcccggt ggctgggtcc taatgctacc cctcaaagtt tggaagagcg 37140
gcgcaagctc atgatggccg tggtcctggt gaccgtggag ctggagtgcc tgcgccgctt 37200
cttcgccgac gcggagaccc tgcgcaaggt cgaggagaac ctgcactacc tcttcaggca 37260
cgggttcgtg cgccaggcct gcaagatctc caacgtggag ctgaccaacc tggtctccta 37320
catgggcatc ttgcacgaga accgcctggg gcagaacgtg ctgcacacca ccctgcgcgg 37380
ggaggcccgc cgcgactaca tccgcgactg cgtctacctc tacctctgcc acacctggca 37440
gacgggcatg ggcgtgtggc agcagtgtct ggaggagcag aacctgaaag agctctgcaa 37500
gctcctgcaa aagaacctca agggtctgtg gaccgggttc gacgagcgga ccaccgcctc 37560
ggacctggcc gacctcatct tccccgagcg cctcaggctg acgctgcgca acggcctgcc 37620
cgactttatg agccaaagca tgttgcaaaa ctttcgctct ttcatcctcg aacgctccgg 37680
aatcctgccc gccacctgct ccgcgctgcc ctcggacttc gtgccgctga ccttccgcga 37740
gtgccccccg ccgctgtgga gccactgcta cctgctgcgc ctggccaact acctggccta 37800
ccactcggac gtgatcgagg acgtcagcgg cgagggcctg ctcgagtgcc actgccgctg 37860
caacctctgc acgccgcacc gctccctggc ctgcaacccc cagctgctga gcgagaccca 37920
gatcatcggc accttcgagt tgcaagggcc cagcgagggc gagggagcca agggggtct 37980
gaaactcacc ccggggctgt ggacctcggc ctacttgcgc aagttcgtgc ccgaggatta 38040
ccatcccttc gagatcaggt tctacgagga ccaatcccag ccgcccaagg ccgagctgtc 38100
ggcctgcgtc atcacccagg gggcgatcct ggcccaattg caagccatcc agaaatcccg 38160
ccaagaattc ttgctgaaaa agggccgcgg ggtctacctc gacccccaga ccggtgagga 38220
gctcaacccc ggcttccccc aggatgcccc gaggaaacaa gaagctgaaa gtggagctgc 38280
cgcccgtgga ggatttggag gaagactggg agaacagcag tcaggcagag gagatggagg 38340
aagactggga cagcactcag gcagaggagg acagcctgca agacagtctg gaggaagacg 38400
aggaggaggc agaggaggag gtggaagaag cagccgccgc cagaccgtcg tcctcggcgg 38460
gggagaaagc aagcagcacg gataccatct ccgctccggg tcggggtccc gctcggcccc 38520
acagtagatg ggacgagacc gggcgattcc cgaaccccac cacccagacc ggtaagaagg 38580
agcggcaggg atacaagtcc tggcgggggc acaaaaacgc catcgtctcc tgcttgcagg 38640
cctgcggggg caacatctcc ttcacccggc gctacctgct cttccaccgc ggggtgaact 38700
tcccccgcaa catcttgcat tactaccgtc acctccacag cccctactac ttccaagaag 38760
aggcagcagc agcagaaaaa gaccagaaaa ccagctagaa aatccacagc ggcggcagcg 38820
gcaggtggac tgaggatcgc ggcgaacgag ccggcgcaga cccgggagct gaggaaccgg 38880
atctttccca ccctctatgc catcttccag cagagtcggg ggcaggagca ggaactgaaa 38940
gtcaagaacc gttctctgcg ctcgctcacc cgcagttgtc tgtatcacaa gagcgaagac 39000
caacttcagc gcactctcga ggacgccgag gctctcttca acaagtactg cgcgctcact 39060
cttaaagagt agcccgcgcc cgcccagtcg cagaaaaagg cgggaattac gtcacctgtg 39120
cccttcgccc tagccgcctc cacccagcac cgccatgagc aaagagattc ccacgcctta 39180
catgtggagc taccagcccc agatgggcct ggccgccggc gccgcccagg actactccac 39240
ccgcatgaat tggctcagcg ccgggcccgc gatgatctca cgggtgaatg acatccgcgc 39300
ccaccgaaac cagatactcc tagaacagtc agcgctcacc gccacgcccc gcaatcacct 39360
caatccgcgt aattggcccg ccgccctggt gtaccaggaa attccccagc ccacgaccgt 39420
actacttccg cgagacgccc aggccgaagt ccagctgact aactcaggtg tccagctggc 39480
gggcggcgcc accctgtgtc gtcaccgccc cgctcagggt ataaagcggc tggtgatccg 39540
gggcagaggc acacagctca acgacgaggt ggtgagctct tcgctgggtc tgcgacctga 39600
cggagtcttc caactcgccg gatcggggag atcttccttc acgcctcgtc aggcggtcct 39660
gactttggag agttcgtcct cgcagccccg ctcgggcggc atcggcactc tccagttcgt 39720
ggaggagttc actccctcgg tctacttcaa ccccttctcc ggctcccccg gccactaccc 39780
ggacgagttc atcccgaact ttgacgccat cagcgagtcg gtggacggct acgattgatt 39840
aattaatcaa ctaacccctt accccttac cctccagtaa aaataaagat taaaaatgat 39900
tgaattgatc aataaagaat cacttacttg aaatctgaaa ccaggtctct gtccatgttt 39960
tctgtcagca gcacttcact cccctcttcc caactctggt actgcaggcc ccggcgggct 40020
gcaaacttcc tccacactct gaaggggatg tcaaattcct cctgtccctc aatcttcatt 40080
tttatcttct atcagatgtc caaaaagcgc gcgcgggtgg atgatggctt cgaccccgtg 40140
taccccctacg atgcagacaa cgcaccgact gtgcccttca tcaaccctcc cttcgtctct 40200
tcagatggat tccaagaaaa gcccctgggg gtgttgtccc tgcgactggc cgaccccgtc 40260
accaccaaga atggggctgt caccctcaag ctgggggagg gggtggacct cgacgactcg 40320
ggaaaactca tctccaaaaa tgccaccaag gccactgccc ctctcagtat ttccaacggc 40380
accatttccc ttaacatggc tgcccctttt tacaacaaca atggaacgtt aagtctcaat 40440
gtttctacac cattagcagt atttcccact tttaacactt taggtatcag tcttggaaac 40500
ggtcttcaaa cttctaataa gttgctgact gtacagttaa ctcatcctct tacattcagc 40560
tcaaatagca tcacagtaaa aacagacaaa ggactctata ttaattctag tggaaacaga 40620
gggcttgagg ctaacataag cctaaaaaga ggactgattt ttgatggtaa tgctattgca 40680
acataccttg gaagtggttt agactatgga tcctatgata gcgatgggaa aacaagaccc 40740
atcatcacca aaattggagc aggtttgaat tttgatgcta ataatgccat ggctgtgaag 40800
ctaggcacag gtttaagttt tgactctgcc ggtgccttaa cagctggaaa caaagaggat 40860
gacaagctaa cactttggac tacacctgac ccaagcccta attgtcaatt actttcagac 40920
agagatgcca aatttaccct atgtcttaca aaatgcggta gtcaaatact aggcactgtt 40980
gcagtagctg ctgttactgt aggttcagca ctaaatccaa ttaatgacac agtaaaaagc 41040
gccatagtat tccttagatt tgactctgac ggtgtgctca tgtcaaactc atcaatggta 41100
ggtgattact ggaactttag ggaaggacag accacccaaa gtgtggccta tacaaatgct 41160
gtgggattca tgcccaatct aggtgcatat cctaaaaccc aaagcaaaac accaaaaaat 41220
agtatagtaa gtcaggtata tttaaatgga gaaactacta tgccaatgac actgacaata 41280
actttcaatg gcactgatga aaaagacaca acacctgtga gcacttactc catgactttt 41340
acatggcagt ggactggaga ctataaggac aagaatatta cctttgctac caactccttt 41400
actttctcct acatggccca agaataaacc ctgcatgcca accccattgt tcccaccact 41460
atggaaaact ctgaagcaga aaaaaataaa gttcaagtgt tttattgatt caacagtttt 41520
ctcacagaac cctagtattc aacctgccac ctccctccca acacacagag tacacagtcc 41580
tttctccccg gctggcctta aaaagcatca tatcatgggt aacagacata ttcttaggtg 41640
ttatattcca cacggtttcc tgtcgagcca aacgctcatc agtgatatta ataaactccc 41700
cgggcagctc acttaagttc atgtcgctgt ccagctgctg agccacaggc tgctgtccaa 41760
cttgcggttg cttaacgggc ggcgaaggag aagtccacgc ctacatgggg gtagagtcat 41820
aatcgtgcat caggataggg cggtggtgct gcagcagcgc gcgaataaac tgctgccgcc 41880
gccgctccgt cctgcaggaa tacaacatgg cagtggtctc ctcagcgatg attcgcaccg 41940
cccgcagcat aaggcgcctt gtcctccggg cacagcagcg caccctgatc tcacttaaat 42000
cagcacagta actgcagcac agcaccacaa tattgttcaa aatcccacag tgcaaggcgc 42060
tgtatccaaa gctcatggcg gggaccacag aacccacgtg gccatcatac cacaagcgca 42120
ggtagattaa gtggcgaccc ctcataaaca cgctggacat aaacattacc tcttttggca 42180
tgttgtaatt caccacctcc cggtaccata taaacctctg attaaacatg gcgccatcca 42240
ccaccatcct aaaccagctg gccaaaacct gcccgccggc tatacactgc agggaaccgg 42300
gactggaaca atgacagtgg agagcccagg actcgtaacc atggatcatc atgctcgtca 42360
tgatatcaat gttggcacaa cacaggcaca cgtgcataca cttcctcagg attacaagct 42420
cctcccgcgt tagaaccata tcccagggaa caacccattc ctgaatcagc gtaaatccca 42480
cactgcaggg aagacctcgc acgtaactca cgttgtgcat tgtcaaagtg ttacattcgg 42540
gcagcagcgg atgatcctcc agtatggtag cgcgggtttc tgtctcaaaa ggaggtagac 42600
gatccctact gtacggagtg cgccgagaca accgagatcg tgttggtcgt agtgtcatgc 42660
caaatggaac gccggacgta gtcatatttc ctgaagcaaa accaggtgcg ggcgtgacaa 42720
acagatctgc gtctccggtc tcgccgctta gatcgctctg tgtagtagtt gtagtatatc 42780
cactctctca aagcatccag gcgcccccctg gcttcgggtt ctatgtaaac tccttcatgc 42840
gccgctgccc tgataacatc caccaccgca gaataagcca cacccagcca acctacacat 42900
tcgttctgcg agtcacacac gggaggagcg ggaagagctg gaagaaccat gattaacttt 42960
attccaaacg gtctcggagc acttcaaaat gcaggtcccg gaggtggcac ctctcgcccc 43020
cactgtgttg gtggaaaata acagccaggt caaaggtgac acggttctcg agatgttcca 43080
cggtggcttc cagcaaagcc tccacgcgca catccagaaa caagaggaca gcgaaagcgg 43140
gagcgttttc taattcctca atcatcatat tacactcctg caccatcccc agataatttt 43200
catttttcca gccttgaatg attcgtatta gttcctgagg taaatccaag ccagccatga 43260
taaaaagctc gcgcagagcg ccctccaccg gcattcttaa gcacaccctc ataattccaa 43320
gagattctgc tcctggttca cctgcagcag attaacaatg ggaatatcaa aatctctgcc 43380
gcgatcccta agctcctccc tcaacaataa ctgtatgtaa tctttcatat catctccgaa 43440
atttttagcc atagggccgc caggaataag agcagggcaa gccacattac agataaagcg 43500
aagtcctccc cagtgwgcat tgccaaatgt aagattgaaa taagcatgct ggctagaccc 43560

-continued

```
tgtgatatct tccagataac tggacagaaa atcaggcaag caatttttaa gaaaatcaac  43620

aaaagaaaag tcgtccaggt gcaggtttag agcctcagga acaacgatgg aataagtgca  43680

aggagtgcgt tccagcatgg ttagtgtttt tttggtgatc tgtagaacaa aaaataaaca  43740

tgcaatatta aaccatgcta gcctggcgaa caggtgggta aatcactctt tccagcacca  43800

ggcaggctac ggggtctccg gcgcgaccct cgtagaagct gtcgccatga ttgaaaagca  43860

tcaccgagag accttcccgg tggccggcat ggatgattcg agaagaagca tacactccgg  43920

gaacattggc atccgtgagt gaaaaaaagc gacctataaa gcctcggggc actacaatgc  43980

tcaatctcaa ttccagcaaa gccaccccat gcggatggag cacaaaattg gcaggtgcgt  44040

aaaaaatgta attactcccc tcctgcacag gcagcaaagc cccgctccc tccagaaaca  44100

catacaaagc ctcagcgtcc atagcttacc gagcacggca ggcgcaagag tcagagaaaa  44160

ggctgagctc taacctgact gcccgctcct gtgctcaata tatagcccta acctacactg  44220

acgtaaaggc caaagtctaa aaatacccgc caaaatgaca cacacgccca gcacacgccc  44280

agaaaccggt gacacactca aaaaaatacg tgcgcttcct caaacgccca aaccggcgtc  44340

atttccgggt tcccacgcta cgtcaccgct cagcgacttt caaattccgt cgaccgttaa  44400

aaacgtcact cgccccgccc ctaacggtcg cccttctctc ggccaatcac cttcctccct  44460

tcccaaattc aaacgcctca tttgcatatt aacgcgcaca aaaagtttga ggtatatatt  44520

tgaatgatg                                                          44529
```

<210> SEQ ID NO 122
<211> LENGTH: 6865
<212> TYPE: DNA
<213> ORGANISM: Artificial Sequence
<220> FEATURE:
<223> OTHER INFORMATION: SEQ ID NO: 122

<400> SEQUENCE: 122

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagcttgc    240

atgcatctgg aaacgggcat ctccatttaa gactagatgc cacggggttt aaaatactaa    300

tcatgacatt ttgtagagcg taattactta gtaaatccgc cgtactaggt tcatttcctc    360

ctcgtttgga tctcacatca gaaattaaaa taatcttaga aggatgcagt tgttttttga    420

tggatcgtag atattcctca tcaacgaacc gagtcactag agtcacatca cgcaatccat    480

ttaaaatagg atcatgatgg cggccgtcaa ttagcatcca tttgatgatc actcctaaat    540

tatagaaatg atctctcaaa taacgtatat gtgtaccggg agcagatcct atatacacta    600

cggtggcacc atctaatata ccgtgtcgct gtaacttact aagaaaaaat aattctccta    660

gtaatagttt taactgtcct tgatacggta gttttttgc gacctcattt gcactttctg     720

gttcgtaatc taactcatta tcaatttcct caaaatacat aaacggttta tctaacgaca    780

caacatccat ttttaagtat tatattaaaa tttaatcaat gtttattttt agttttttag    840

ataaaaaata taatattatg agtcgatgta acactttcta cacaccgatt gatacatatc    900

attacctcct attatctcta tctcggtttc ctcacccaat cgtttagaaa aggaagcctc    960

cttaaagcat ttcatacaca cagcagttag ttttaccacc atttcagata atggaataag   1020

attcaaaata ttattaaacg gtttacgttg aaatgtccca tcgagtgcgg ctactataac   1080
```

-continued

```
tatttttcct tcgtttgcca tacagatcct acgtactcga gcggccgctc atcaggtccg   1140
cgtagaatcg agaccgagga gagggttagg gataggctta cctgaagccc cgggcccgga   1200
tccagcgtag gtgcccacct ggccgctgcc cctctggtcc ttcctgctga tgatgtccat   1260
cacgggcctc tgcaccttca ccaccttgtt ctggtaggtc agcttgaaca ggtcgtcctc   1320
ggtgatcctg gtgtcccagc cggcggtgtc gtcggcgtac atgaagccca gggcctcgaa   1380
ctccaggaac ctggcgccca gccacatgta ccagatggcc ctgctcttgg ccttgccgaa   1440
ctcgcccagc ttcttctccc tcttgcccat catgttgtac tcctcgatgg tggggttggg   1500
gctgctctcg ccgatgtcgc acagggccag gtagctgccc ctgaagatgt tggccatgct   1560
cacggcgatg gtggtgttcc agaacttgcc gggcatgctc acggcgatgg tggtgttcca   1620
gaacttgccg gggttgccct cccacagggg gccggtggcc agggtcaggg cctcgcacag   1680
ggcccaggtg gtcctcatca gcagcatcac ctggcccagc tgcttctcga acttggggtc   1740
gtagccgtcc acggtggggt tcttcatgat gccggcggcg gtcctcttga tgttgtccag   1800
cagcatcttg gcctcggtcc agtgggcgtg gtcgttcctg ccgatcctgc ccctcctctg   1860
ggcggcgctg gcggcggtca cgggcatggg cttgaagttg gcgcccatct cgctgatgtc   1920
ggtggtcacc acgaagtccc agtcgttcag gatggcggcg gcctcgccca tctccaccct   1980
ggtgctgatg tagcccctgg cggcgatgct gggcaggccc ttcagggcct cctccatctc   2040
ggcggccacc accctctcct ccatctcggc ggccaccacc ctggtggggg ccatctcgct   2100
ggccaccacc ctggtggggg ccaggatcag ggcaagcttc gatcctcttc tgaatcgggc   2160
atggatttcc tggctgggcg aaacgaagac tgctccacac agcagcagca cacagcagag   2220
ccctctcttc attgcatcca tggtggcggc gcggctagcg gtaccggatc tagatgggga   2280
tccgtcactg ttctttatga ttctacttcc ttaccgtgca ataaattaga atatattttc   2340
tacttttacg agaaattaat tattgtattt attatttatg ggtgaaaaac ttactataaa   2400
aagcgggtgg gtttggaatt agtgatcagt ttatgtatat cgcaactacc gggcatatgg   2460
ctatcgacat cgagaacatt acccacatga taagagattg tatcagtttc gtagtcttga   2520
gtattggtat tactatatag tatatagatg tcgacctgca ggtcgacgaa gttcctatac   2580
tttctagaga ataggaactt cgcagccaag ctggaattca tccactttgg ataagaaatc   2640
tgcatgataa atatattgat atcctaccac ctattaaagt accattatct aatagcaata   2700
agatagataa acaaatgttt tttgatgaag ttattacgtg gataaatata tatcttcagg   2760
aaaagggtat tatgttacca gatgatataa gagaactcag agatgctatt attccttaac   2820
tagttacgtc tctttaggta cttattttga tacgttacaa gtaaaaaact atcaaatata   2880
aatggaatct gattctaata tagcgattga agaggatcca ccggtcgcca ccatggtgag   2940
caagggcgag gagctgttca ccggggtggt gcccatcctg gtcgagctgg acggcgacgt   3000
aaacggccac aagttcagcg tgtccggcga gggcgagggc gatgccacct acggcaagct   3060
gaccctgaag ttcatctgca ccaccggcaa gctgcccgtg ccctggccca ccctcgtgac   3120
caccctgacc tacggcgtgc agtgcttcag ccgctacccc gaccacatga agcagcacga   3180
cttcttcaag tccgccatgc ccgaaggcta cgtccaggag cgcaccatct tcttcaagga   3240
cgacggcaac tacaagaccc gcgccgaggt gaagttcgag ggcgacaccc tggtgaaccg   3300
catcgagctg aagggcatcg acttcaagga ggacggcaac atcctggggc acaagctgga   3360
gtacaactac aacagccaca acgtctatat catggccgac aagcagaaga acggcatcaa   3420
```

```
ggtgaacttc aagatccgcc acaacatcga ggacggcagc gtgcagctcg ccgaccacta   3480
ccagcagaac acccccatcg gcgacggccc cgtgctgctg cccgacaacc actacctgag   3540
cacccagtcc gccctgagca aagaccccaa cgagaagcgc gatcacatgg tcctgctgga   3600
gttcgtgacc gccgccggga tcactctcgg catggacgag ctgtacaagt aaagcggccg   3660
cgaagttcct atactttcta gagaatagga acttcaacaa tgtctggaaa gaactgtcct   3720
tcatcgatac ctatcacgga gaaatctgta attgattcca agacatcaca tagtttagtt   3780
gcttccaatg cttcaaaatt attcttatca tgcgtccata gtcccgttcc gtatctatta   3840
tcgttagaat attttatagt cacgcattta tattgagcta tttgataacg tctaactcgt   3900
ctaattaatt ctgtactttt acctgaaaac atggggccga ttatcaactg aatatgtccg   3960
ccgttcatga tgacaataaa gaattaatta ttgttcactt tattcgactt taatatatcc   4020
atcacgttag aaaatgcgat atcgcgacga ggatctatgt atctaacagg atctattgcg   4080
gtggtagcta gagctgattc tttttgaat cgcatcaaac taatcacaaa gtcgaacaaa   4140
tatcctttat taagtttgac ccttccatct gtaacaatag ggaccttgtt aaacagtttt   4200
ttaaaatctt gagagtctgt gaattttgtc aattgtctgt attcctctga aagagattca   4260
taacaatgac ccacggcttc taatttattt tttgattgga tcaataataa taacagaaag   4320
tctagatatt gagtgatttg caatatatca gataatgaag attcatcatc ttgactagcc   4380
aaatacttaa aaaatgaatc atcatctgcg aagaacatcg ttaagagata ctggttgtga   4440
tccatttatg agctcgcgaa agcttggcac tggccgtcgt tttacaacgt cgtgactggg   4500
aaaaccctgg cgttacccaa cttaatcgcc ttgcagcaca tccccctttc gccagctggc   4560
gtaatagcga agaggcccgc accgatcgcc cttcccaaca gttgcgcagc ctgaatggcg   4620
aatggcgcct gatgcggtat tttctcctta cgcatctgtg cggtatttca caccgcatat   4680
ggtgcactct cagtacaatc tgctctgatg ccgcatagtt aagccagccc cgacacccgc   4740
caacacccgc tgacgcgccc tgacgggctt gtctgctccc ggcatccgct tacagacaag   4800
ctgtgaccgt ctccgggagc tgcatgtgtc agaggttttc accgtcatca ccgaaacgcg   4860
cgagacgaaa gggcctcgtg atacgcctat ttttataggt taatgtcatg ataataatgg   4920
tttcttagac gtcaggtggc acttttcggg gaaatgtgcg cggaacccct atttgtttat   4980
ttttctaaat acattcaaat atgtatccgc tcatgagaca ataaccctga taaatgcttc   5040
aataatattg aaaaaggaag agtatgagta ttcaacattt ccgtgtcgcc cttattccct   5100
tttttgcggc attttgcctt cctgtttttg ctcacccaga aacgctggtg aaagtaaaag   5160
atgctgaaga tcagttgggt gcacgagtgg gttacatcga actggatctc aacagcggta   5220
agatccttga gagttttcgc cccgaagaac gttttccaat gatgagcact tttaaagttc   5280
tgctatgtgg cgcggtatta tcccgtattg acgccgggca agagcaactc ggtcgccgca   5340
tacactattc tcagaatgac ttggttgagt actcaccagt cacagaaaag catcttacgg   5400
atggcatgac agtaagagaa ttatgcagtg ctgccataac catgagtgat aacactgcgg   5460
ccaacttact tctgacaacg atcggaggac cgaaggagct aaccgctttt ttgcacaaca   5520
tgggggatca tgtaactcgc cttgatcgtt gggaaccgga gctgaatgaa gccataccaa   5580
acgacgagcg tgacaccacg atgcctgtag caatggcaac aacgttgcgc aaactattaa   5640
ctggcgaact acttactcta gcttcccggc aacaattaat agactggatg gaggcggata   5700
aagttgcagg accacttctg cgctcggccc ttccggctgg ctggtttatt gctgataaat   5760
ctggagccgg tgagcgtggg tctcgcggta tcattgcagc actggggcca gatggtaagc   5820
```

```
cctcccgtat cgtagttatc tacacgacgg ggagtcaggc aactatggat gaacgaaata   5880
gacagatcgc tgagataggt gcctcactga ttaagcattg gtaactgtca gaccaagttt   5940
actcatatat actttagatt gatttaaaac ttcattttta atttaaaagg atctaggtga   6000
agatcctttt tgataatctc atgaccaaaa tcccttaacg tgagttttcg ttccactgag   6060
cgtcagaccc cgtagaaaag atcaaaggat cttcttgaga tccttttttt ctgcgcgtaa   6120
tctgctgctt gcaaacaaaa aaaccaccgc taccagcggt ggtttgtttg ccggatcaag   6180
agctaccaac tctttttccg aaggtaactg gcttcagcag agcgcagata ccaaatactg   6240
ttcttctagt gtagccgtag ttaggccacc acttcaagaa ctctgtagca ccgcctacat   6300
acctcgctct gctaatcctg ttaccagtgg ctgctgccag tggcgataag tcgtgtctta   6360
ccgggttgga ctcaagacga tagttaccgg ataaggcgca gcggtcgggc tgaacggggg   6420
gttcgtgcac acagcccagc ttggagcgaa cgacctacac cgaactgaga tacctacagc   6480
gtgagctatg agaaagcgcc acgcttcccg aagggagaaa ggcggacagg tatccggtaa   6540
gcggcagggt cggaacagga gagcgcacga gggagcttcc agggggaaac gcctggtatc   6600
tttatagtcc tgtcgggttt cgccacctct gacttgagcg tcgatttttg tgatgctcgt   6660
caggggggcg gagcctatgg aaaaacgcca gcaacgcggc ctttttacgg ttcctggcct   6720
tttgctggcc ttttgctcac atgttctttc ctgcgttatc ccctgattct gtggataacc   6780
gtattaccgc ctttgagtga gctgataccg ctcgccgcag ccgaacgacc gagcgcagcg   6840
agtcagtgag cgaggaagcg gaaga                                         6865
```

<210> SEQ ID NO 123
<211> LENGTH: 10384
<212> TYPE: DNA
<213> ORGANISM: Artificial Sequence
<220> FEATURE:
<223> OTHER INFORMATION: Vector

<400> SEQUENCE: 123

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagcttgc    240
atgcatctgg aaacgggcat ctccatttaa gactagatgc cacggggttt aaaatactaa    300
tcatgacatt ttgtagagcg taattactta gtaaatccgc cgtactaggt tcatttcctc    360
ctcgtttgga tctcacatca gaaattaaaa taatcttaga aggatgcagt tgtttttga     420
tggatcgtag atattcctca tcaacgaacc gagtcactag agtcacatca cgcaatccat    480
ttaaaatagg atcatgatgg cggccgtcaa ttagcatcca tttgatgatc actcctaaat    540
tatagaaatg atctctcaaa taacgtatat gtgtaccggg agcagatcct atatacacta    600
cggtggcacc atctaatata ccgtgtcgct gtaacttact aagaaaaaat aattctccta    660
gtaatagttt taactgtcct tgatacggta gttttttgc gacctcattt gcactttctg     720
gttcgtaatc taactcatta tcaatttcct caaaatacat aaacggttta tctaacgaca    780
caacatccat ttttaagtat tatattaaaa tttaatcaat gtttattttt agttttttag    840
ataaaaaata taatattatg agtcgatgta acactttcta cacaccgatt gatacatatc    900
attacctcct attatctcta tctcggtttc ctcacccaat cgtttagaaa aggaagcctc    960
```

-continued

```
cttaaagcat ttcatacaca cagcagttag ttttaccacc atttcagata atggaataag   1020
attcaaaata ttattaaacg gtttacgttg aaatgtccca tcgagtgcgg ctactataac   1080
tatttttcct tcgtttgcca tacagatcct acgtactcga gcggccgctc atcaggtccg   1140
cgtagaatcg agaccgagga gagggttagg gataggctta cctgaagccc cgggcccgga   1200
tccagcgatg ttcttggccc aggtggccct gctggtcagg ccgatcaggc tgccgcacca   1260
ctggtcctcc ctcttgccca ggtagggcac gtcctcccag ctgtgccaca ccctgttcca   1320
cacggccagc atgtcctcgg tggtcatcca ctcgtggctc caggtggtcc tgctgggcac   1380
ccagtggctg ggcacggcgc tgcagatggc gttgctggcc agcctcaggt ccctcctgtg   1440
gaagtacatc agctgccaca tctgggcgta gctcttgccc aggcaggcgg tctccctcag   1500
gctccagccg gcgccctggc tgatcctggc cctgccgatc agctcgtcct ggttcctgca   1560
gggcaccacc agcttcctgc cgtccttcat gaagatgtgg aagtggtggc tgcagaaggg   1620
cacctgctgc cagtcgtgcc agcccttgct gggctcccac tgctcggcct ccatctgcct   1680
gatcagctgg gcctccatgt tggtgaaggt gttcaggccg taggtgccca cctggccgct   1740
gcccctctgg tccttcctgc tgatgatgtc catcacggcg cccctggggg tgggcctctg   1800
caccttcacc accttgttct ggtaggtcag cttgaagatg gccttggcca gcttctcctc   1860
gttgtgcagg tcgtcctcgg tgatcctggt gtcccagccg gcggtgtcgt cggcgtacat   1920
ggcgccgccg gggatcttgc tgatgtccct caggatgtag cccagcaggc cctcgccctc   1980
cacgccgctc aggctgttct ccctgctgaa ccagtggtcc tcgttcagga agcccagggc   2040
ctcgaactcc aggaacctgg cgcccagcca catgtaccag atggccctgc tgcccttggc   2100
cttgccgaac tcgcccagct tcttctccct cttgcccatc atgttgtaca cgcagctctc   2160
gcacttgccc tccaggtgca gggcgctctt ccagccgttc tcgtcctggg cctcgggggt   2220
cctggtgtcc accttctcct tgaacaccct ctgctggccg aagggggtgg tgtcggtcat   2280
ggccatctgg gtcaccatgg gcaccacgtc ccagggcttg gtcagcagct tcaccacgcc   2340
gttcaccatg ctgctggcgc tgccggtggc cttcacctcg tagctgccgt ggtaggccca   2400
ggtcttgtag ggttgtcct cgtccttgtg ggccatggtg aacctgttga tcagcatcct   2460
gctgatcatg ttcacggcgc tcacgatgtt gccggtgccg ttgctcaccc agtacatctc   2520
gtgggtgctg ttcctgctca gggggttcct caccagcatg ccgccgtgct tcctctgcag   2580
cttctccagc tcgatcacgc tgggcatgta ggggttcagg atcttgatgc agaactggtt   2640
gcccttcagc cagggctcca ccatcttcag caccctcagg gtcctgccct cctcgatggt   2700
ggggttgggg ctgctctcgc cgatgtcgca cagcagggtg tcgcacttct cgaagaacac   2760
gtccacgccg ctgtgcagct tcaccaggtt ccagccgtag gtggccatgg ggatgggctc   2820
ctcgtggccg gggccgccct tggtgtagcc cctcaccttc ttcaggccgg cgcagtagta   2880
gctccagccg cccctgccgc agcccaggtc gatcaccacc atgatggcct ccttggcctc   2940
ggtcctgtcc acctccagga tgccgctctt cttgtactcc tcgaagctct tgtccagctg   3000
gttcagctgc ctcttccact tctcgcccag ggtctcgccg ttcttgatca ggctgaaggc   3060
caggccggcg ccggccaggt agctgcccct gaagatgttg gccatgctca cggcgatggt   3120
ggtgttccag aacttgccgg ggttgccctc ccacagggtg gtgatggggc cggtggccag   3180
ggtcagggcc tcgcacaggg cccaggtggt cctcatcagc aggatctggc tgcacaggat   3240
cagcagcatc acctggccca gctgcttctc gaacttgggg tcgtaggggga tggggtccag   3300
gtcgatggcc atgatgccgt ccacggtggg gttcttcatg atgccggcgg cggtcctctt   3360
```

ctgggcctcc ctggtggcct tggcctgcag gccggggccg atgatggcgt agtgggtcag 3420
ggtcaggggg ttcacctggc tgtagcagcc cagggccagc aggggcacgc ccaggtccat 3480
cttgctgatg ggccagccct tgtccaggcc catcagcacg gcggcctggt tggcgatggc 3540
ggtcaggctc acgttggcgg tgctgttctc gatggtgtgc ctcagcatgg gggtgatgat 3600
ggtggtggcc acggcgtaca gggtccaggc gctggcgggg tgcaggtcca cgtccaggat 3660
ggcgccgatg cccaggtcct tcttggtggt ctccagcagg cccatctcgt tggcggcgat 3720
ggcggcggcc agggtcagga tgccgatcac cacgtaggcc agctggttgt cctggggggt 3780
cctctgcttc tcgggctcgg ggatcagcag caccatcagg aagaactcca ggatgatgct 3840
ggcggcgatc cagtggggct ggatctcggc catccacagc aggctggcgg cgatgatgca 3900
gcacaggccg atgctcatct tgccgatgcc cttgccgctc aggaagaaca ggaagcccag 3960
cagggccagc agcagcaggg tctccagggt ctcgggcagc tcctccaggg cgtgggggtc 4020
ggcgtaggtc ctggcgtcca gccacctggg cctcagcttc ttcttctcgc cctcggtcca 4080
gatctccacg tccatgttct cctccaggat ctggttgttc ctctcgccgt cgaagcacca 4140
ctccctgtcc ttgtactgga agccggcgct ggccaccttg tagctcagcc acacgggcag 4200
gtcgcccctc ctcatcagct ccacgaaggt cttcctggcc tcgcccctca gcctgtactc 4260
gccgtcgatg gcggcgctct tctccctctc gggctcgaac agggcgggga tgatgccctc 4320
gggggtgttg atgttgtcca gcagcatctt ggcctcggtc cagtgggcgt ggtcctcgtc 4380
gttgttcagg ggctggccca tgtagatgta ctggtcgttc tccttcttgt ggttcctgcc 4440
gatcctgccc ctcctctggg cggcgctggc ggcggtcacg ggcatggggc cggccaggat 4500
caccctctcg gggccgtcgg tcaggatcac gggcttcagg cacctcctgg ggtcgatcac 4560
cctgtcggcc ttgaagttgg cgcccatctc gctgatgtcg gtggtcacca cgaagtccca 4620
gtcgttcagc ttggtcttgg ggtactcggt gtcgaaggtc ttcctgctca gctggatcac 4680
cttcttgccg ttcttcctca ggcagttggc gatgtcgttg ccggccttga tgctgggcac 4740
gaaccacacg gtcttgccgg cgaagtcggt gatccagtcg aagccgctgt tccagctcct 4800
ctcggggatc tccctctcct cgtcctcgat gggggcgttg ctctggggga aggcgtcggc 4860
gctgccgggg ggggtggcgg tcatgaagat ggcggcggcc tcgcccatct ccaccctggt 4920
gctgatgtag cccctggcgg cgatgctggc ggggtcggtg aagtgggcct cgtccatgat 4980
gatcaggttg tagttgggca ccctcacggg gctcagcagc ctcatggtga aggtggcgtg 5040
gcacatcagg tccacgatct ccttgccggt gtgctcggcc ttgatggcgg tggtctgata 5100
cctgatgggc aggcccttca gggcctcctc catctcggcg gccaccaccc tggtgggggc 5160
caggatcagg gtcctcagcc tcctcttgat ggcctccctc acgatggcgg gcagatacct 5220
cttggtcttg ccggcgccgg ggtgcaggtc catgatggtc aggttcctct tcctgaaggt 5280
ctgggcgatg gcgctcacgt aggcgccgct cttggtcacc acgccgttgc cgtacaggcc 5340
cacgccctcc ctgttcacga tggggctgcc gctggtgccg ggcttgaagt ccagggcgat 5400
ggcgccgatc tcgccggtct gcacggcctt ggggttcttg ccgggctcca cggcgatcac 5460
ctgcacctcc tcgccctcgt cccactcgcc ctccagcctc cagccgccgc cgtagctgat 5520
caggtccttc ttcacgtcgg cccagctggg ctcgatcctc ttgccctggt gcatcagcac 5580
ggcgcccctg gtcacgtgcc acatggtgtg gaacacgccc tccttgaaca cgccggcgcc 5640
gatctggctg gcaagcttcg atcctcttct gaatcgggca tggatttcct ggctgggcga 5700

```
aacgaagact gctccacaca gcagcagcac acagcagagc cctctcttca ttgcatccat   5760
ggtggcggcg cggctagcgg taccggatct agatggggat ccgtcactgt tctttatgat   5820
tctacttcct taccgtgcaa taaattagaa tatattttct acttttacga gaaattaatt   5880
attgtattta ttatttatgg gtgaaaaact tactataaaa agcgggtggg tttggaatta   5940
gtgatcagtt tatgtatatc gcaactaccg ggcatatggc tatcgacatc gagaacatta   6000
cccacatgat aagagattgt atcagtttcg tagtcttgag tattggtatt actatatagt   6060
atatagatgt cgacctgcag gtcgacgaag ttcctatact ttctagagaa taggaacttc   6120
gcagccaagc tggaattcat ccactttgga taagaaatct gcatgataaa tatattgata   6180
tcctaccacc tattaaagta ccattatcta atagcaataa gatagataaa caaatgtttt   6240
ttgatgaagt tattacgtgg ataaatatat atcttcagga aaagggtatt atgttaccag   6300
atgatataag agaactcaga gatgctatta ttccttaact agttacgtct ctttaggtac   6360
ttattttgat acgttacaag taaaaaacta tcaaatataa atggaatctg attctaatat   6420
agcgattgaa gaggatccac cggtcgccac catggtgagc aagggcgagg agctgttcac   6480
cggggtggtg cccatcctgg tcgagctgga cggcgacgta aacggccaca agttcagcgt   6540
gtccggcgag ggcgagggcg atgccaccta cggcaagctg accctgaagt tcatctgcac   6600
caccggcaag ctgcccgtgc cctggcccac cctcgtgacc accctgacct acggcgtgca   6660
gtgcttcagc cgctaccccg accacatgaa gcagcacgac ttcttcaagt ccgccatgcc   6720
cgaaggctac gtccaggagc gcaccatctt cttcaaggac gacggcaact acaagacccg   6780
cgccgaggtg aagttcgagg gcgacaccct ggtgaaccgc atcgagctga agggcatcga   6840
cttcaaggag gacggcaaca tcctggggca caagctggag tacaactaca acagccacaa   6900
cgtctatatc atggccgaca agcagaagaa cggcatcaag gtgaacttca agatccgcca   6960
caacatcgag gacggcagcg tgcagctcgc cgaccactac cagcagaaca cccccatcgg   7020
cgacggcccc gtgctgctgc ccgacaacca ctacctgagc acccagtccg ccctgagcaa   7080
agaccccaac gagaagcgcg atcacatggt cctgctggag ttcgtgaccg ccgccgggat   7140
cactctcggc atggacgagc tgtacaagta aagcggccgc gaagttccta tactttctag   7200
agaataggaa cttcaacaat gtctggaaag aactgtcctt catcgatacc tatcacggag   7260
aaatctgtaa ttgattccaa gacatcacat agtttagttg cttccaatgc ttcaaaatta   7320
ttcttatcat gcgtccatag tcccgttccg tatctattat cgttagaata ttttatagtc   7380
acgcatttat attgagctat ttgataacgt ctaactcgtc taattaattc tgtactttta   7440
cctgaaaaca tggggccgat tatcaactga atatgtccgc cgttcatgat gacaataaag   7500
aattaattat tgttcacttt attcgacttt aatatatcca tcacgttaga aaatgcgata   7560
tcgcgacgag gatctatgta tctaacagga tctattgcgg tggtagctag agctgattct   7620
tttttgaatc gcatcaaact aatcacaaag tcgaacaaat atcctttatt aagtttgacc   7680
cttccatctg taacaatagg gaccttgtta aacagttttt taaaatcttg agagtctgtg   7740
aattttgtca attgtctgta ttcctctgaa agagattcat aacaatgacc cacggcttct   7800
aatttatttt ttgattggat caataataat aacagaaagt ctagatattg agtgatttgc   7860
aatatatcag ataatgaaga ttcatcatct tgactagcca aatacttaaa aaatgaatca   7920
tcatctgcga agaacatcgt taagagatac tggttgtgat ccatttatga gctcgcgaaa   7980
gcttggcact ggccgtcgtt ttacaacgtc gtgactggga aaaccctggc gttacccaac   8040
ttaatcgcct tgcagcacat ccccctttcg ccagctggcg taatagcgaa gaggcccgca   8100
```

```
ccgatcgccc ttcccaacag ttgcgcagcc tgaatggcga atggcgcctg atgcggtatt   8160
ttctccttac gcatctgtgc ggtatttcac accgcatatg gtgcactctc agtacaatct   8220
gctctgatgc cgcatagtta agccagcccc gacacccgcc aacacccgct gacgcgccct   8280
gacgggcttg tctgctcccg gcatccgctt acagacaagc tgtgaccgtc tccgggagct   8340
gcatgtgtca gaggttttca ccgtcatcac cgaaacgcgc gagacgaaag ggcctcgtga   8400
tacgcctatt tttataggtt aatgtcatga taataatggt ttcttagacg tcaggtggca   8460
cttttcgggg aaatgtgcgc ggaaccccta tttgtttatt tttctaaata cattcaaata   8520
tgtatccgct catgagacaa taaccctgat aaatgcttca ataatattga aaaaggaaga   8580
gtatgagtat tcaacatttc cgtgtcgccc ttattccctt ttttgcggca ttttgccttc   8640
ctgtttttgc tcacccagaa acgctggtga aagtaaaaga tgctgaagat cagttgggtg   8700
cacgagtggg ttacatcgaa ctggatctca acagcggtaa gatccttgag agttttcgcc   8760
ccgaagaacg ttttccaatg atgagcactt ttaaagttct gctatgtggc gcggtattat   8820
cccgtattga cgccgggcaa gagcaactcg gtcgccgcat acactattct cagaatgact   8880
tggttgagta ctcaccagtc acagaaaagc atcttacgga tggcatgaca gtaagagaat   8940
tatgcagtgc tgccataacc atgagtgata acactgcggc caacttactt ctgacaacga   9000
tcggaggacc gaaggagcta accgcttttt tgcacaacat gggggatcat gtaactcgcc   9060
ttgatcgttg ggaaccggag ctgaatgaag ccataccaaa cgacgagcgt gacaccacga   9120
tgcctgtagc aatggcaaca acgttgcgca aactattaac tggcgaacta cttactctag   9180
cttcccggca acaattaata gactggatgg aggcggataa agttgcagga ccacttctgc   9240
gctcggccct tccggctggc tggtttattg ctgataaatc tggagccggt gagcgtgggt   9300
ctcgcggtat cattgcagca ctggggccag atggtaagcc ctcccgtatc gtagttatct   9360
acacgacggg gagtcaggca actatggatg aacgaaatag acagatcgct gagataggtg   9420
cctcactgat taagcattgg taactgtcag accaagttta ctcatatata ctttagattg   9480
atttaaaact tcatttttaa tttaaaagga tctaggtgaa gatccttttt gataatctca   9540
tgaccaaaat cccttaacgt gagttttcgt tccactgagc gtcagacccc gtagaaaaga   9600
tcaaaggatc ttcttgagat cctttttttc tgcgcgtaat ctgctgcttg caaacaaaaa   9660
aaccaccgct accagcggtg gtttgtttgc cggatcaaga gctaccaact ctttttccga   9720
aggtaactgg cttcagcaga gcgcagatac caaatactgt tcttctagtg tagccgtagt   9780
taggccacca cttcaagaac tctgtagcac cgcctacata cctcgctctg ctaatcctgt   9840
taccagtggc tgctgccagt ggcgataagt cgtgtcttac cgggttggac tcaagacgat   9900
agttaccgga taaggcgcag cggtcgggct gaacgggggg ttcgtgcaca cagcccagct   9960
tggagcgaac gacctacacc gaactgagat acctacagcg tgagctatga gaaagcgcca  10020
cgcttcccga agggagaaag gcggacaggt atccggtaag cggcagggtc ggaacaggag  10080
agcgcacgag ggagcttcca gggggaaacg cctggtatct ttatagtcct gtcgggtttc  10140
gccacctctg acttgagcgt cgatttttgt gatgctcgtc aggggggcgg agcctatgga  10200
aaaacgccag caacgcggcc tttttacggt tcctggcctt ttgctggcct tttgctcaca  10260
tgttctttcc tgcgttatcc cctgattctg tggataaccg tattaccgcc tttgagtgag  10320
ctgataccgc tcgccgcagc cgaacgaccg agcgcagcga gtcagtgagc gaggaagcgg  10380
aaga                                                               10384
```

<210> SEQ ID NO 124
<211> LENGTH: 10990
<212> TYPE: DNA
<213> ORGANISM: Artificial Sequence
<220> FEATURE:
<223> OTHER INFORMATION: Vector

<400> SEQUENCE: 124
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240
atgcatctgg aaacgggcat ctccatttaa gactagatgc cacggggttt aaaatactaa 300
tcatgacatt ttgtagagcg taattactta gtaaatccgc cgtactaggt tcatttcctc 360
ctcgtttgga tctcacatca gaaattaaaa taatcttaga aggatgcagt tgtttttga 420 tggatcgtag atattcctca tcaacgaacc gagtcactag agtcacatca cgcaatccat 480
ttaaaatagg atcatgatgg cggccgtcaa ttagcatcca tttgatgatc actcctaaat 540
tatagaaatg atctctcaaa taacgtatat gtgtaccggg agcagatcct atatacacta 600
cggtggcacc atctaatata ccgtgtcgct gtaacttact aagaaaaaat aattctccta 660
gtaatagttt taactgtcct tgatacggta gtttttttgc gacctcattt gcactttctg 720
gttcgtaatc taactcatta tcaatttcct caaaatacat aaacggttta tctaacgaca 780
caacatccat ttttaagtat tatattaaaa tttaatcaat gtttattttt agtttttttag 840 ataaaaaata taatattatg agtcgatgta acactttcta cacaccgatt gatacatatc 900
attacctcct attatctcta tctcggtttc ctcacccaat cgtttagaaa aggaagcctc 960
cttaaagcat ttcatacaca cagcagttag ttttaccacc atttcagata atggaataag 1020
attcaaaata ttattaaacg gtttacgttg aaatgtccca tcgagtgcgg ctactataac 1080
tatttttcct tcgtttgcca tacagatcct acgtactcga gcggccgctc atcaggtccg 1140
cgtagaatcg agaccgagga gagggttagg gataggctta cctgaagccc cgggcccgga 1200
tccagcgatg ttcttggccc aggtggccct gctggtcagg ccgatcaggc tgccgcacca 1260
ctggtcctcc ctcttgccca ggtagggcac gtcctcccag ctgtggatgt gggtcttgtc 1320
ctccatccag ggttctcct cgatccacac cctgttccac acggccagca tgtcctcggt 1380
ggtcatccac tcgtggtggg cgtggatgct ccaggtggtc ctgctggtgg gcacccagtg 1440
gctgggcacg gcgctgcaga tggcgttgct ggccagcctc aggtccctcc tgtggaagta 1500
catcagctgc cacatctggg cgtagctctt gcccaggcag gcggtctccc tcaggctcca 1560
gccggcgccc tggctgatcc tggccctgcc gatcagctcg tcctggttcc tgcagggcac 1620
caccagcttc ctgccgtcct tcatgaagat ctcgtggaag tggtggctgc agaagggcac 1680
ctgctgccag tcgtgccagc ccttgctggg ctcccactgg gggggcttca ccacgcagtc 1740
gtcgccgctg atggccatcc tcttcagcct gtccacgccg cactcggtga tcacgccctc 1800
ggcctccatc tgcctgatca gctgggcctc catgttggtg aaggtgttca ggccgtaggt 1860
gcccacctgg ccgctgcccc tctggtcctt cctgctgatg atgtccatca cggcgcccct 1920
gggggtgggc ctctgcacct tcaccacctt gttctggtag gtcagcttga agatggcctt 1980
ggccaggatc ttctcctcgt tgtgcaggtc gtcctcggtg atcctggtgt cccagccggc 2040
ggtgtcgtcg gcgtacatgg cgccgccggg gatcttgctg atgtccctca ggatgtagcc 2100

-continued

```
cagcttgtgc aggccctcgc cctccacgcc gctcaggctg ttctccctgc tgaaccagtg   2160
gtcctcgttc aggaagccca gggcctcgaa ctccaggaac ctggcgccca gccacatgta   2220
ccagatggcc ctgctgccct tggccttgcc gaactcgccc agcttcttct ccctcttgcc   2280
catcatgttg tacacgcagc tctcgcactt gccctccagg tgcagggccc tctcgctgtc   2340
ctccacggcc tccctggcgc tcttccagcc gttctcgtcc tggaacacgg cgccgatggc   2400
ggcgttctcc ttggcctcgg gggtcctggt gtccaccttc tccttgaaca ccctctgctg   2460
gccgaagggg gtggtgtcgg tcatggccat ctgggtcacc atgggcacca cgtcccaggg   2520
cttggtcagc agcttcacca cgccgttcac catgctgctg gcgctgccgg tggccttcac   2580
ctcgtagctg ccgtggtagg cccaggtctt gtaggggttg tcctcgtcgt agtgccaggt   2640
gctgccggcg cccaggtcca cgtccctctc gtaggtgggc ttcttgtggg ccatggtgaa   2700
cctgttgatc agcatcctgc tgatcatgtt cacggcgctc acgatgttgc cggtgccgtt   2760
gctcacccag tacatctcgt gggtgctgtt cctgctcagg gggttcctca ccagcatgcc   2820
gccgtgcttc ctctgcagct tctccagctc ctcgatcacg ctgggcatgt aggggttcag   2880
gatcttgatg cagaactggt tgcccttcag ccagggctcc accatcttca gcaccctcag   2940
ggtcctgccc tcctcgatgg tggggttggg gctgctctcg ccgatgtcgc acagcagggt   3000
gtcgcacttc tcggggaaga acacgtccac gccgctgtgc agcttcacca ggttccagcc   3060
gtaggtggcc atggggatgg gctcctcgtg gccggggccg cccttggtgt agcccctcac   3120
ctccctcacc ttcttcaggc cggcgcagta gtagctccag ccgcccctgc cgcagcccag   3180
gtcgatcacc ctgccctcgg ggatcaccat gttcctctcc acgaaccacc tcagcttggc   3240
gctgcccctg ctcacggcgt ggtggtcggt ctcgcccctc ttgatggcct ccttggcctc   3300
ggtcctgtcc acctccagga tgccgctctt cttgtactcc tcgaactcgc tcttgtccag   3360
ctggttcagc tgcctcttcc acttctcgcc cagggtctcg ccctgggcgc cggtgcccct   3420
cctgttcttg atcaggctga aggccaggcc ggcgccggcc aggtagctgc ccctgaagat   3480
gttggccatg ctcacggcga tggtggtgtt ccagaacttg ccggggttgc cctcccacag   3540
ggtggtgatg gggccggtgg ccagggtcag ggcctcgcac agggcccagg tggtcctcat   3600
cagcaggatc tggctcacgc acaggatcag cagcatcacc tggcccagct gcttctcgaa   3660
cttggggtcg taggggatgg ggtccaggtc gatggccatg atgccgtcca cggtggggtt   3720
cttcatgatg ccggcggcgg tcctcttctg ggcctccctg gtggccttgg cctgcaggcc   3780
ggggccgatg atggcgtagt gggtgatcag cagcagcacg gcggcggtca gggtcagggg   3840
gttcacctgg ctgtagcagc ccagggccag caggggcacg cccaggtcca tcttgctgat   3900
gggccagccc ttgtccaggc ccatcagcac ggcggcctgg ttggcgatgg cggtcaggct   3960
cacgttggcg gtgctgttct cgatggtgtg cctcagcatg gggtgatga tggtggtggc   4020
cacggcgtac agggtccagg cgctggcggg gtgcaggtcc acgtccagga tggcggtggg   4080
ggccacgtgg ccgatgccca ggtccttctt ggtggtctcc agcaggccca tctcgttggc   4140
ggcgatggcg gcggccaggg tcaggatgcc gatcaccacg taggccagct ggttgtcctg   4200
gggggtcctc tgcttctcgg gctcggggat cagcagcacc atcaggaaga actccaggat   4260
gatgctggcg gcgatccagt ggggctggat ctcggccatc cacagcaggc tggcggcgat   4320
gatgcagcac aggccgatgc tcatcttgcc gatgcccttg ccgctcagga agaacaggaa   4380
ggcgcccagc agggccagca gcagcagggt ctccagggtc tcgggcagct cctccagggc   4440
```

gtgctggtag gccctggtcc tgtgggccag gtggctgggc accctgccga tctcggtggc 4500
gatgctcttc ctgccggcgg cgaagtcctt gaactccttc agggccaggg ggtcggcgta 4560
ggtcctggcg tccagccacc tgggcctcag cttcttcttc tcgccctcct tggtccagat 4620
ctccacgtcc atgttctcct ccaggatctg gttgttcctc tcgccgtcga agcaccactc 4680
cctgtccttg tactggaagc cggcgctggc caccttgtag ctcagccaca cgggcaggtc 4740
gcccctcctc atcagctcca cgaaggtctt cctggcctcg cccctcagcc tgtactcgcc 4800
gtcgatggcg gcgctcttct ccctctcggg ctcgaacagg gcggggatga tgccctcggg 4860
ggtgttgatg ttgtccagca gcatcttggc ctcggtccag tgggcgtggt cctcgtcgtt 4920
gttcaggggc tggcccatgt agatgtactg gtcgttctcc ttcttgtggt tcctgccgat 4980
cctgcccctc ctctgggcgg cgctggcggc ggtcacgggc atggggccgg ccaggatcac 5040
cctctcgggg ccgtcggtca ggatcacggg cttcaggcac ctcctggggt cgatcaccct 5100
gtcggccttg aagttggcgc ccatctcgct gatgtcggtg gtcaccacga agtcccagtc 5160
gttcagcttg gtcttggggt actcggtgtc gaaggtcttc ctgctcagct ggatcacctt 5220
cttgccgttc ttcctcaggc agttggcgat gtcgttgccg gccttgatgc tgggcacgaa 5280
ccacacggtc ttgccggcga agtcggtgat ccagtcgaag ccgctgttcc agctcctctc 5340
ggggatctcc ctctcctcgt cctcgatggg ggcgttgctc tgggggaagg cgtcggcgct 5400
gccggggggg gtggcggtca tgaagatggc ggcggcctcg cccatctcca ccctggtgct 5460
gatgtagccc ctggcggcga tgctggcggg gtcggtgaag tgggcctcgt ccatgatgat 5520
caggttgtag ttgggcaccc tcacggggct cagcagcctc atggtgaagg tggcgtggca 5580
catcaggtcc acgatctcct tgccggtgtg ctcggccttg atggcggtgg tctgatacct 5640
gatgggcagg cccttcaggg cctcctccat ctcggcggcc accaccctgg tgggggccag 5700
gatcagggtc ctcagcctcc tcttgatggc ctccctcacg atggcgggca gatacctctt 5760
ggtcttgccg gcgccggggt gcaggtccat gatggtcagg ttcctcttcc tgaacacctc 5820
gtcctcgatc tcgggcaggg gctcggcgtt ggtctgggcg atggcgctca cgtaggcgcc 5880
gctcttggtc accacgccgt tgccgtacag gcccaccacc ttgccctccc tgttcacgat 5940
ggggctgccg ctggtgccgg gcttgaagtc cagggcgatg gcgccgatct cgccctcggg 6000
ggtcttgaac aggccgggct tggtctgcac ggccttgggg ttcttgccgg gctccacggc 6060
gatcacctgc acctcctcgc cctcgtccca ctcgccctcc agcctccagc cgccgccgta 6120
gctgatcagg tccttcttca cgtcggccca gctgggctcg atcctcttgc cctggtgcat 6180
cagcacggcg cccctggtca cgtgccacat ggtgtggaac acgccctcct tgaacacgcc 6240
ggcgccgatc tggctggcaa gcttcgatcc tcttctgaat cgggcatgga tttcctggct 6300
gggcgaaacg aagactgctc cacacagcag cagcacacag cagagccctc tcttcattgc 6360
atccatggtg gcggcgcggc tagcggtacc ggatctagat ggggatccgt cactgttctt 6420
tatgattcta cttccttacc gtgcaataaa ttagaatata ttttctactt ttacgagaaa 6480
ttaattattg tatttattat ttatgggtga aaaacttact ataaaaagcg ggtgggtttg 6540
gaattagtga tcagtttatg tatatcgcaa ctaccgggca tatggctatc gacatcgaga 6600
acattaccca catgataaga gattgtatca gtttcgtagt cttgagtatt ggtattacta 6660
tatagtatat agatgtcgac ctgcaggtcg acgaagttcc tatactttct agagaatagg 6720
aacttcgcag ccaagctgga attcatccac tttggataag aaatctgcat gataaatata 6780
ttgatatcct accacctatt aaagtaccat tatctaatag caataagata gataaacaaa 6840
tgttttttga tgaagttatt acgtggataa atatatatct tcaggaaaag ggtattatgt 6900
taccagatga tataagagaa ctcagagatg ctattattcc ttaactagtt acgtctcttt 6960
aggtacttat tttgatacgt tacaagtaaa aaactatcaa atataaatgg aatctgattc 7020
taatatagcg attgaagagg atccaccggt cgccaccatg gtgagcaagg gcgaggagct 7080
gttcaccggg gtggtgccca tcctggtcga gctggacggc gacgtaaacg gccacaagtt 7140
cagcgtgtcc ggcgagggcg agggcgatgc cacctacggc aagctgaccc tgaagttcat 7200
ctgcaccacc ggcaagctgc ccgtgccctg gcccaccctc gtgaccaccc tgacctacgg 7260
cgtgcagtgc ttcagccgct accccgacca catgaagcag cacgacttct tcaagtccgc 7320
catgcccgaa ggctacgtcc aggagcgcac catcttcttc aaggacgacg gcaactacaa 7380
gacccgcgcc gaggtgaagt tcgagggcga caccctggtg aaccgcatcg agctgaaggg 7440
catcgacttc aaggaggacg gcaacatcct ggggcacaag ctggagtaca actacaacag 7500
ccacaacgtc tatatcatgg ccgacaagca gaagaacggc atcaaggtga acttcaagat 7560
ccgccacaac atcgaggacg gcagcgtgca gctcgccgac cactaccagc agaacacccc 7620
catcggcgac ggccccgtgc tgctgcccga caaccactac ctgagcaccc agtccgccct 7680
gagcaaagac cccaacgaga agcgcgatca catggtcctg ctggagttcg tgaccgccgc 7740
cgggatcact ctcggcatgg acgagctgta caagtaaagc ggccgcgaag ttcctatact 7800
ttctagagaa taggaacttc aacaatgtct ggaaagaact gtccttcatc gatacctatc 7860
acggagaaat ctgtaattga ttccaagaca tcacatagtt tagttgcttc caatgcttca 7920
aaattattct tatcatgcgt ccatagtccc gttccgtatc tattatcgtt agaatatttt 7980
atagtcacgc atttatattg agctatttga taacgtctaa ctcgtctaat taattctgta 8040
cttttacctg aaaacatggg gccgattatc aactgaatat gtccgccgtt catgatgaca 8100
ataaagaatt aattattgtt cactttattc gactttaata tatccatcac gttagaaaat 8160
gcgatatcgc gacgaggatc tatgtatcta acaggatcta ttgcggtggt agctagagct 8220
gattcttttt tgaatcgcat caaactaatc acaaagtcga acaaatatcc tttattaagt 8280
ttgacccttc catctgtaac aatagggacc ttgttaaaca gtttttttaaa atcttgagag 8340 tctgtgaatt ttgtcaattg tctgtattcc tctgaaagag attcataaca atgacccacg 8400
gcttctaatt tattttttga ttggatcaat aataataaca gaaagtctag atattgagtg 8460
atttgcaata tatcagataa tgaagattca tcatcttgac tagccaaata cttaaaaaat 8520
gaatcatcat ctgcgaagaa catcgttaag agatactggt tgtgatccat tttatgagctc 8580 gcgaaagctt ggcactggcc gtcgttttac aacgtcgtga ctgggaaaac cctggcgtta 8640
cccaacttaa tcgccttgca gcacatcccc ctttcgccag ctggcgtaat agcgaagagg 8700
cccgcaccga tcgcccttcc caacagttgc gcagcctgaa tggcgaatgg cgcctgatgc 8760
ggtattttct ccttacgcat ctgtgcggta tttcacaccg catatggtgc actctcagta 8820
caatctgctc tgatgccgca tagttaagcc agccccgaca cccgccaaca cccgctgacg 8880
cgccctgacg ggcttgtctg ctcccggcat ccgcttacag acaagctgtg accgtctccg 8940
ggagctgcat gtgtcagagg ttttcaccgt catcaccgaa acgcgcgaga cgaaagggcc 9000
tcgtgatacg cctattttta taggttaatg tcatgataat aatggtttct tagacgtcag 9060
gtggcacttt tcggggaaat gtgcgcggaa cccctatttg tttatttttc taaatacatt 9120
caaatatgta tccgctcatg agacaataac cctgataaat gcttcaataa tattgaaaaa 9180
ggaagagtat gagtattcaa catttccgtg tcgcccttat tccctttttt gcggcatttt 9240
gccttcctgt ttttgctcac ccagaaacgc tggtgaaagt aaaagatgct gaagatcagt 9300
tgggtgcacg agtgggttac atcgaactgg atctcaacag cggtaagatc cttgagagtt 9360
ttcgccccga agaacgtttt ccaatgatga gcacttttaa agttctgcta tgtggcgcgg 9420
tattatcccg tattgacgcc gggcaagagc aactcggtcg ccgcatacac tattctcaga 9480
atgacttggt tgagtactca ccagtcacag aaaagcatct tacggatggc atgacagtaa 9540
gagaattatg cagtgctgcc ataaccatga gtgataacac tgcggccaac ttacttctga 9600
caacgatcgg aggaccgaag gagctaaccg cttttttgca caacatgggg gatcatgtaa 9660
ctcgccttga tcgttgggaa ccggagctga atgaagccat accaaacgac gagcgtgaca 9720
ccacgatgcc tgtagcaatg gcaacaacgt tgcgcaaact attaactggc gaactactta 9780
ctctagcttc ccggcaacaa ttaatagact ggatggaggc ggataaagtt gcaggaccac 9840
ttctgcgctc ggcccttccg gctggctggt ttattgctga taaatctgga gccggtgagc 9900
gtgggtctcg cggtatcatt gcagcactgg ggccagatgg taagccctcc cgtatcgtag 9960
ttatctacac gacggggagt caggcaacta tggatgaacg aaatagacag atcgctgaga 10020
taggtgcctc actgattaag cattggtaac tgtcagacca agtttactca tatatacttt 10080
agattgattt aaaacttcat ttttaattta aaaggatcta ggtgaagatc ctttttgata 10140
atctcatgac caaaatccct taacgtgagt tttcgttcca ctgagcgtca gaccccgtag 10200
aaaagatcaa aggatcttct tgagatcctt tttttctgcg cgtaatctgc tgcttgcaaa 10260
caaaaaaacc accgctacca gcggtggttt gtttgccgga tcaagagcta ccaactcttt 10320
ttccgaaggt aactggcttc agcagagcgc agataccaaa tactgttctt ctagtgtagc 10380
cgtagttagg ccaccacttc aagaactctg tagcaccgcc tacatacctc gctctgctaa 10440
tcctgttacc agtggctgct gccagtggcg ataagtcgtg tcttaccggg ttggactcaa 10500
gacgatagtt accggataag gcgcagcggt cgggctgaac ggggggttcg tgcacacagc 10560
ccagcttgga gcgaacgacc tacaccgaac tgagatacct acagcgtgag ctatgagaaa 10620
gcgccacgct tcccgaaggg agaaaggcgg acaggtatcc ggtaagcggc agggtcggaa 10680
caggagagcg cacgagggag cttccagggg gaaacgcctg gtatctttat agtcctgtcg 10740
ggtttcgcca cctctgactt gagcgtcgat ttttgtgatg ctcgtcaggg gggcggagcc 10800
tatggaaaaa cgccagcaac gcggcctttt tacggttcct ggccttttgc tggccttttg 10860
ctcacatgtt ctttcctgcg ttatcccctg attctgtgga taaccgtatt accgcctttg 10920
agtgagctga taccgctcgc cgcagccgaa cgaccgagcg cagcgagtca gtgagcgagg 10980
aagcggaaga 10990

<210> SEQ ID NO 125
<211> LENGTH: 11308
<212> TYPE: DNA
<213> ORGANISM: Artificial Sequence
<220> FEATURE:
<223> OTHER INFORMATION: Vector

<400> SEQUENCE: 125
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240

-continued

```
atgcatctgg aaacgggcat ctccatttaa gactagatgc cacggggttt aaaatactaa    300
tcatgacatt ttgtagagcg taattactta gtaaatccgc cgtactaggt tcatttcctc    360
ctcgtttgga tctcacatca gaaattaaaa taatcttaga aggatgcagt tgtttttga     420
tggatcgtag atattcctca tcaacgaacc gagtcactag agtcacatca cgcaatccat    480
ttaaaatagg atcatgatgg cggccgtcaa ttagcatcca tttgatgatc actcctaaat    540
tatagaaatg atctctcaaa taacgtatat gtgtaccggg agcagatcct atatacacta    600
cggtggcacc atctaatata ccgtgtcgct gtaacttact aagaaaaaat aattctccta    660
gtaatagttt taactgtcct tgatacggta gttttttgc gacctcattt gcactttctg     720
gttcgtaatc taactcatta tcaatttcct caaaatacat aaacggttta tctaacgaca    780
caacatccat ttttaagtat tatattaaaa tttaatcaat gtttattttt agtttttag     840
ataaaaaata taatattatg agtcgatgta acactttcta cacaccgatt gatacatatc    900
attacctcct attatctcta tctcggtttc ctcacccaat cgtttagaaa aggaagcctc    960
cttaaagcat ttcatacaca cagcagttag ttttaccacc atttcagata atggaataag   1020
attcaaaata ttattaaacg gtttacgttg aaatgtccca tcgagtgcgg ctactataac   1080
tatttttcct tcgtttgcca tacagatcct acgtactcga gcggccgctc atcaggtccg   1140
cgtagaatcg agaccgagga gagggttagg gataggctta cctgaagccc cgggcccgga   1200
tccagcgatg ttcttggccc aggtggccct gctggtcagg ccgatcaggc tgccgcacca   1260
ctggtcctcc ctcttgccca ggtagggcac gtcctcccag ctgtggatgt gggtcttgtc   1320
ctccatccag gggttctcct cgatccacac cctgttccac acggccagca tgtcctcggt   1380
ggtcatccac tcgtggtggg cgtggatgct ccaggtggtc ctgctggtgg gcacccagtg   1440
gctgggcacg gcgctgcaga tggcgttgct ggccagcctc aggtccctcc tgtggaagta   1500
catcagctgc cacatctggg cgtagctctt gcccaggcag gcggtctccc tcaggctcca   1560
gccggcgccc tggctgatcc tggccctgcc gatcagctcg tcctggttcc tgcagggcac   1620
caccagcttc ctgccgtcct tcatgaagat ctcgtggaag tggtggctgc agaagggcac   1680
ctgctgccag tcgtgccagc ccttgctggg ctcccactgg gggggcttca ccacgcagtc   1740
gtcgccgctg atggccatcc tcttcagcct gtccacgccg cactcggtga tcacgccctc   1800
ggcctccatc tgcctgatca gctgggcctc catgttggtg aaggtgttca ggccgtaggt   1860
gcccacctgg ccgctgcccc tctggtcctt cctgctgatg atgtccatca cggcgcccct   1920
gggggtgggc ctctgcacct tcaccacctt gttctggtag gtcagcttga agatggcctt   1980
ggccaggatc ttctcctcgt tgtgcaggtc gtcctcggtg atcctggtgt cccagccggc   2040
ggtgtcgtcg gcgtacatgg cgccgccggg gatcttgctg atgtccctca ggatgtagcc   2100
cagcttgtgc aggccctcgc cctccacgcc gctcaggctg ttctccctgc tgaaccagtg   2160
gtcctcgttc aggaagccca gggcctcgaa ctccaggaac ctggcgccca gccacatgta   2220
ccagatggcc ctgctgccct tggccttgcc gaactcgccc agcttcttct ccctcttgcc   2280
catcatgttg tacacgcagc tctcgcactt gccctccagg tgcagggccc tctcgctgtc   2340
ctccacggcc tccctggcgc tcttccagcc gttctcgtcc tggaacacgg cgccgatggc   2400
ggcgttctcc ttggcctcgg gggtcctggt gtccaccttc tccttgaaca ccctctgctg   2460
gccgaagggg gtggtgtcgg tcatggccat ctgggtcacc atgggcacca cgtcccaggg   2520
cttggtcagc agcttcacca cgccgttcac catgctgctg gcgctgccgg tggccttcac   2580
```

-continued

```
ctcgtagctg ccgtggtagg cccaggtctt gtaggggttg tcctcgtcgt agtgccaggt   2640
gctgccggcg cccaggtcca cgtccctctc gtaggtgggc ttcttgtggg ccatggtgaa   2700
cctgttgatc agcatcctgc tgatcatgtt cacggcgctc acgatgttgc cggtgccgtt   2760
gctcacccag tacatctcgt gggtgctgtt cctgctcagg gggttcctca ccagcatgcc   2820
gccgtgcttc ctctgcagct tctccagctc ctcgatcacg ctgggcatgt aggggttcag   2880
gatcttgatg cagaactggt tgcccttcag ccagggctcc accatcttca gcaccctcag   2940
ggtcctgccc tcctcgatgg tggggttggg gctgctctcg ccgatgtcgc acagcagggt   3000
gtcgcacttc tcggggaaga acacgtccac gccgctgtgc agcttcacca ggttccagcc   3060
gtaggtggcc atggggatgg gctcctcgtg gccggggccg cccttggtgt agcccctcac   3120
ctccctcacc ttcttcaggc cggcgcagta gtagctccag ccgcccctgc cgcagcccag   3180
gtcgatcacc ctgccctcgg ggatcaccat gttcctctcc acgaaccacc tcagcttggc   3240
gctgcccctg ctcacggcgt ggtggtcggt ctcgcccctc ttgatggcct ccttggcctc   3300
ggtcctgtcc acctccagga tgccgctctt cttgtactcc tcgaactcgc tcttgtccag   3360
ctggttcagc tgcctcttcc acttctcgcc cagggtctcg ccctgggcgc cggtgcccct   3420
cctgttcttg atcaggctga aggccaggcc ggcgccggcc aggtagctgc ccctgaagat   3480
gttggccatg ctcacggcga tggtggtgtt ccagaacttg ccggggttgc cctcccacag   3540
ggtggtgatg gggccggtgg ccagggtcag ggcctcgcac agggcccagg tggtcctcat   3600
cagcagcacg gcccaggtgg tcctcatcag caggatctgg ctcacgcaca ggatcagcag   3660
catcacctgg cccagctgct tctcgaactt ggggtcgtag gggatggggt ccaggtcgat   3720
ggccatgatg ccgtccacgg tggggttctt catgatgccg gcggcggtcc tcttctgggc   3780
ctccctggtg gccttggcct gcaggccggg gccgatgatg gcgtagtggg tgatcagcag   3840
cagcacggcg gcggtcaggg tcagggggtt cacctggctg tagcagccca gggccagcag   3900
gggcacgccc aggtccatct tgctgatggg ccagcccttg tccaggccca tcagcacggt   3960
ggcctggttg gcgatcatca gcacggcggc ctggttggcg atggcggtca ggctcacgtt   4020
ggcggtgctg ttctcgatgg tgtgcctcag catgggggtg atgatggtgg tggccacggc   4080
gtacagggtc caggcgctgg cggggtgcag gtccacgtcc aggatggcgg tgggggccac   4140
gtggccgatg cccaggtcct tcttggtggt ctccagcagg cccatctcgt tggcggcgat   4200
ggcggcggcc agggtcagga tgccgatcac cacgtaggcc agctggttgt cctgggggt   4260
cctctgcttc tcgggctcgg ggatcagcag caccatcagg aagaactcca ggatgatgct   4320
ggcggcgatc cagtggggct ggatctcggc catccacagc aggctggcgg cgatgatgca   4380
gcacaggccg atgctcatct tgccgatgcc cttgccgctc aggaagaaca ggaaggcgcc   4440
cagcagggcc agcagcagca gggtctccag ggtctcgggc agctcctcca gggcgtgctg   4500
gtaggccctg gtcctgtggg ccaggtggct gggcaccctg ccgatctcgg tggcgatgct   4560
cttcctgccg gcggcgaagt ccttgaactc cttcagggcc agggggtcgg cgtaggtcct   4620
ggcgtccagc cacctgggcc tcagcttctt cttctcgccc tccttggtcc agatctccac   4680
gtccatgttc tcctccagga tctggttgtt cctctcgccg tcgaagcacc actccctgtc   4740
cttgtactgg aagccggcgc tggccacctt gtagctcagc cacacgggca ggtcgcccct   4800
cctcatcagc tccacgaagg tcttcctctg ctcgcccagg tccacgaagg tcttcctggc   4860
ctcgcccagc tccacgaagg tcttcctggc ctcgcccctc agcctgtact cgccgtcgat   4920
ggcggcgctc ttctccctct cgggctccag gctggggatg atgccctcgg gggtgaacag   4980
```

```
ggtggggatg atgccctcgg gggtgaacat gctggggatg atgccctcgg gggtgaacag   5040
ggcggggatg atgccctcgg gggtgttgat gttgtccagc agcatcttgg cctcggtcca   5100
gtgggcgtgg tcctcgtcgt tgttcagggg ctggcccatg tagatgtact ggtcgttctc   5160
cttcttgtgg ttcctgccga tcctgcccct cctctgggcg gcgctggcgg cggtcacggg   5220
catggggccg gccaggatca ccctctcggg gccgtcggtc aggatcacgg gcttcaggca   5280
cctcctgggg tcgatcaccc tgtcggcctt gaagttggcg cccatctcgc tgatgtcggt   5340
ggtcaccacg aagtcccagt cgttcagctt ggtcttgggg tactcggtgt cgaaggtctt   5400
cctgctcagc tggatcacct tcttgccgtt cttcctcagg cagttggcga tgtcgttgcc   5460
ggccttgatg ctgggcacga accacacggt cttgccggcg aagtcggtga tccagtcgaa   5520
gccgctgttc cagctcctct cggggatctc cctctcctcg tcctcgatgg gggcgttgct   5580
ctgggggaag gcgtcggcgc tgccgggggg ggtggcggtc atgaagatgg cggcggcctc   5640
gcccatctcc accctggtgc tgatgtagcc cctggcggcg atgctggcgg ggtcggtgaa   5700
gtgggcctcg tccatgatga tcaggttgta gttgggcacc ctcacggggc tcagcagcct   5760
catggtgaag gtggcgtggc acatcaggtc cacgatctcc ttgccggtgt gctcggcctt   5820
gatggcggtg gtctgatacc tgatgggcag gcccctcagg gcgtacctga tgggcaggcc   5880
cttcagggcc tcctccatct cgctggccac caccctggtg gggccatct cggcggccac    5940
caccctggtg gggccagga tcagggtcct cagcctcctc ttgatggcct ccctcacgat    6000
ggcgggcaga tacctcttgg tcttgccggc gccggggtgc aggtccatga tggtcaggtt   6060
cctcttcctg aacacctcgt cctcgatctc gggcaggggc tcggcgttgg tctgggcgat   6120
ggcgctcacg taggcgccgc tcttggtcac cacgccgttg ccgtacaggc ccaccacctt   6180
gccctccctg ttgatgatgg ggctgccgct ggtgccctcc ctgttcacga tggggctgcc   6240
gctggtgccg ggcttgaagt ccagggcgat ggcgccgatc tcgccctcgg gggtcttgaa   6300
caggccgggc ttggtctgca cggccttggg gttcttgccg ggctccacgg cgatcacctg   6360
cacctcctcg ccctcgtccc actcgccctc cagcctccag ccgccgccgt agctgatcag   6420
gtccttcttc acgctgtagc tgatcaggtc cttcttcacg tcggcccagc tgggctcgat   6480
cctcttgccc tggtgcatca gcacggcgcc cctggtcacg tgccacatgg tgtggaacac   6540
gccctccttg aacacgccgg cgccgatctg gctggcaagc ttcgatcctc ttctgaatcg   6600
ggcatggatt tcctggctgg gcgaaacgaa gactgctcca cacagcagca gcacacagca   6660
gagccctctc ttcattgcat ccatggtggc ggcgcggcta gcggtaccgg atctagatgg   6720
ggatccgtca ctgttcttta tgattctact tccttaccgt gcaataaatt agaatatatt   6780
ttctactttt acgagaaatt aattattgta tttattattt atgggtgaaa aacttactat   6840
aaaaagcggg tgggtttgga attagtgatc agtttatgta tatcgcaact accgggcata   6900
tggctatcga catcgagaac attacccaca tgataagaga ttgtatcagt ttcgtagtct   6960
tgagtattgg tattactata tagtatatag atgtcgacct gcaggtcgac gaagttccta   7020
tactttctag agaataggaa cttcgcagcc aagctggaat tcatccactt tggataagaa   7080
atctgcatga taaatatatt gatatcctac cacctattaa agtaccatta tctaatagca   7140
ataagataga taaacaaatg ttttttgatg aagttattac gtggataaat atatatcttc   7200
aggaaaaggg tattatgtta ccagatgata taagagaact cagagatgct attattcctt   7260
aactagttac gtctctttag gtacttattt tgatacgtta caagtaaaaa actatcaaat   7320
```

ataaatggaa tctgattcta atatagcgat tgaagaggat ccaccggtcg ccaccatggt 7380
gagcaagggc gaggagctgt tcaccggggt ggtgcccatc ctggtcgagc tggacggcga 7440
cgtaaacggc cacaagttca gcgtgtccgg cgagggcgag ggcgatgcca cctacggcaa 7500
gctgaccctg aagttcatct gcaccaccgg caagctgccc gtgccctggc ccaccctcgt 7560
gaccaccctg acctacggcg tgcagtgctt cagccgctac cccgaccaca tgaagcagca 7620
cgacttcttc aagtccgcca tgcccgaagg ctacgtccag gagcgcacca tcttcttcaa 7680
ggacgacggc aactacaaga cccgcgccga ggtgaagttc gagggcgaca ccctggtgaa 7740
ccgcatcgag ctgaagggca tcgacttcaa ggaggacggc aacatcctgg ggcacaagct 7800
ggagtacaac tacaacagcc acaacgtcta tatcatggcc gacaagcaga agaacggcat 7860
caaggtgaac ttcaagatcc gccacaacat cgaggacggc agcgtgcagc tcgccgacca 7920
ctaccagcag aacaccccca tcggcgacgg ccccgtgctg ctgcccgaca accactacct 7980
gagcacccag tccgccctga gcaaagaccc caacgagaag cgcgatcaca tggtcctgct 8040
ggagttcgtg accgccgccg ggatcactct cggcatggac gagctgtaca agtaaagcgg 8100
ccgcgaagtt cctatacttt ctagagaata ggaacttcaa caatgtctgg aaagaactgt 8160
ccttcatcga tacctatcac ggagaaatct gtaattgatt ccaagacatc acatagttta 8220
gttgcttcca atgcttcaaa attattctta tcatgcgtcc atagtcccgt tccgtatcta 8280
ttatcgttag aatattttat agtcacgcat ttatattgag ctatttgata acgtctaact 8340
cgtctaatta attctgtact tttacctgaa aacatggggc cgattatcaa ctgaatatgt 8400
ccgccgttca tgatgacaat aaagaattaa ttattgttca ctttattcga ctttaatata 8460
tccatcacgt tagaaaatgc gatatcgcga cgaggatcta tgtatctaac aggatctatt 8520
gcggtggtag ctagagctga ttcttttttg aatcgcatca aactaatcac aaagtcgaac 8580
aaatatcctt tattaagttt gacccttcca tctgtaacaa tagggacctt gttaaacagt 8640
tttttaaaat cttgagagtc tgtgaatttt gtcaattgtc tgtattcctc tgaaagagat 8700
tcataacaat gacccacggc ttctaattta ttttttgatt ggatcaataa taataacaga 8760
aagtctagat attgagtgat ttgcaatata tcagataatg aagattcatc atcttgacta 8820
gccaaatact taaaaaatga atcatcatct gcgaagaaca tcgttaagag atactggttg 8880
tgatccattt atgagctcgc gaaagcttgg cactggccgt cgttttacaa cgtcgtgact 8940
gggaaaaccc tggcgttacc caacttaatc gccttgcagc acatccccct ttcgccagct 9000
ggcgtaatag cgaagaggcc cgcaccgatc gcccttccca acagttgcgc agcctgaatg 9060
gcgaatggcg cctgatgcgg tattttctcc ttacgcatct gtgcggtatt tcacaccgca 9120
tatggtgcac tctcagtaca atctgctctg atgccgcata gttaagccag ccccgacacc 9180
cgccaacacc cgctgacgcg ccctgacggg cttgtctgct cccggcatcc gcttacagac 9240
aagctgtgac cgtctccggg agctgcatgt gtcagaggtt ttcaccgtca tcaccgaaac 9300
gcgcgagacg aaagggcctc gtgatacgcc tatttttata ggttaatgtc atgataataa 9360
tggtttctta gacgtcaggt ggcacttttc ggggaaatgt gcgcggaacc cctatttgtt 9420
tatttttcta aatacattca aatatgtatc cgctcatgag acaataaccc tgataaatgc 9480
ttcaataata ttgaaaaagg aagagtatga gtattcaaca tttccgtgtc gcccttattc 9540
ccttttttgc ggcattttgc cttcctgttt ttgctcaccc agaaacgctg gtgaaagtaa 9600
aagatgctga agatcagttg ggtgcacgag tgggttacat cgaactggat ctcaacagcg 9660
gtaagatcct tgagagtttt cgccccgaag aacgttttcc aatgatgagc acttttaaag 9720

```
ttctgctatg tggcgcggta ttatcccgta ttgacgccgg gcaagagcaa ctcggtcgcc   9780
gcatacacta ttctcagaat gacttggttg agtactcacc agtcacagaa aagcatctta   9840
cggatggcat gacagtaaga gaattatgca gtgctgccat aaccatgagt gataacactg   9900
cggccaactt acttctgaca acgatcggag gaccgaagga gctaaccgct tttttgcaca   9960
acatggggga tcatgtaact cgccttgatc gttgggaacc ggagctgaat gaagccatac  10020
caaacgacga gcgtgacacc acgatgcctg tagcaatggc aacaacgttg cgcaaactat  10080
taactggcga actacttact ctagcttccc ggcaacaatt aatagactgg atggaggcgg  10140
ataaagttgc aggaccactt ctgcgctcgg cccttccggc tggctggttt attgctgata  10200
aatctggagc cggtgagcgt gggtctcgcg gtatcattgc agcactgggg ccagatggta  10260
agccctcccg tatcgtagtt atctacacga cggggagtca ggcaactatg gatgaacgaa  10320
atagacagat cgctgagata ggtgcctcac tgattaagca ttggtaactg tcagaccaag  10380
tttactcata tatactttag attgatttaa aacttcattt ttaatttaaa aggatctagg  10440
tgaagatcct ttttgataat ctcatgacca aaatccctta acgtgagttt tcgttccact  10500
gagcgtcaga ccccgtagaa aagatcaaag gatcttcttg agatcctttt tttctgcgcg  10560
taatctgctg cttgcaaaca aaaaaaccac cgctaccagc ggtggtttgt ttgccggatc  10620
aagagctacc aactcttttt ccgaaggtaa ctggcttcag cagagcgcag ataccaaata  10680
ctgttcttct agtgtagccg tagttaggcc accacttcaa gaactctgta gcaccgccta  10740
catacctcgc tctgctaatc ctgttaccag tggctgctgc cagtggcgat aagtcgtgtc  10800
ttaccgggtt ggactcaaga cgatagttac cggataaggc gcagcggtcg ggctgaacgg  10860
ggggttcgtg cacacagccc agcttggagc gaacgaccta caccgaactg agatacctac  10920
agcgtgagct atgagaaagc gccacgcttc ccgaagggag aaaggcggac aggtatccgg  10980
taagcggcag ggtcggaaca ggagagcgca cgagggagct tccaggggga aacgcctggt  11040
atctttatag tcctgtcggg tttcgccacc tctgacttga gcgtcgattt ttgtgatgct  11100
cgtcaggggg gcggagccta tggaaaaacg ccagcaacgc ggccttttta cggttcctgg  11160
ccttttgctg gccttttgct cacatgttct ttcctgcgtt atcccctgat tctgtggata  11220
accgtattac cgcctttgag tgagctgata ccgctcgccg cagccgaacg accgagcgca  11280
gcgagtcagt gagcgaggaa gcggaaga                                     11308
```

<210> SEQ ID NO 126
<211> LENGTH: 20
<212> TYPE: PRT
<213> ORGANISM: Dengue virus

<400> SEQUENCE: 126

```
Ser Gln Ile Gly Ala Gly Val Phe Lys Glu Gly Val Phe His Thr Met
1               5                   10                  15

Trp His Val Thr
            20
```

<210> SEQ ID NO 127
<211> LENGTH: 20
<212> TYPE: PRT
<213> ORGANISM: Dengue virus

<400> SEQUENCE: 127

```
Gly Val Phe His Thr Met Trp His Val Thr Arg Gly Ala Val Leu Met
1               5                   10                  15
```

His Gln Gly Lys
20

<210> SEQ ID NO 128
<211> LENGTH: 20
<212> TYPE: PRT
<213> ORGANISM: Dengue virus

<400> SEQUENCE: 128

Arg Gly Ala Val Leu Met His Gln Gly Lys Arg Ile Glu Pro Ser Trp
1 5 10 15

Ala Asp Val Lys
20

<210> SEQ ID NO 129
<211> LENGTH: 20
<212> TYPE: PRT
<213> ORGANISM: Dengue virus

<400> SEQUENCE: 129

Arg Ile Glu Pro Ser Trp Ala Asp Val Lys Lys Asp Leu Ile Ser Tyr
1 5 10 15

Ser Val Lys Lys
20

<210> SEQ ID NO 130
<211> LENGTH: 20
<212> TYPE: PRT
<213> ORGANISM: Dengue virus

<400> SEQUENCE: 130

Lys Asp Leu Ile Ser Tyr Ser Val Lys Lys Asp Leu Ile Ser Tyr Gly
1 5 10 15

Gly Gly Trp Arg
20

<210> SEQ ID NO 131
<211> LENGTH: 20
<212> TYPE: PRT
<213> ORGANISM: Dengue virus

<400> SEQUENCE: 131

Asp Leu Ile Ser Tyr Gly Gly Gly Trp Arg Leu Glu Gly Glu Trp Asp
1 5 10 15

Glu Gly Glu Glu
20

<210> SEQ ID NO 132
<211> LENGTH: 20
<212> TYPE: PRT
<213> ORGANISM: Dengue virus

<400> SEQUENCE: 132

Leu Glu Gly Glu Trp Asp Glu Gly Glu Glu Val Gln Val Ile Ala Val
1 5 10 15

Glu Pro Gly Lys
20

<210> SEQ ID NO 133
<211> LENGTH: 20
<212> TYPE: PRT
<213> ORGANISM: Dengue virus

<400> SEQUENCE: 133

Val Gln Val Ile Ala Val Glu Pro Gly Lys Asn Pro Lys Ala Val Gln
1 5 10 15

Thr Lys Pro Gly
20

<210> SEQ ID NO 134
<211> LENGTH: 20
<212> TYPE: PRT
<213> ORGANISM: Dengue virus

<400> SEQUENCE: 134

Asn Pro Lys Ala Val Gln Thr Lys Pro Gly Leu Phe Lys Thr Pro Glu
1 5 10 15

Gly Glu Ile Gly
20

<210> SEQ ID NO 135
<211> LENGTH: 20
<212> TYPE: PRT
<213> ORGANISM: Dengue virus

<400> SEQUENCE: 135

Leu Phe Lys Thr Pro Glu Gly Glu Ile Gly Ala Ile Ala Leu Asp Phe
1 5 10 15

Lys Pro Gly Thr
20

<210> SEQ ID NO 136
<211> LENGTH: 20
<212> TYPE: PRT
<213> ORGANISM: Dengue virus

<400> SEQUENCE: 136

Ala Ile Ala Leu Asp Phe Lys Pro Gly Thr Ser Gly Ser Pro Ile Val
1 5 10 15

Asn Arg Glu Gly
20

<210> SEQ ID NO 137
<211> LENGTH: 20
<212> TYPE: PRT
<213> ORGANISM: Dengue virus

<400> SEQUENCE: 137

Ser Gly Ser Pro Ile Val Asn Arg Glu Gly Thr Ser Gly Ser Pro Ile
1 5 10 15

Ile Asn Arg Glu
20

<210> SEQ ID NO 138
<211> LENGTH: 20
<212> TYPE: PRT
<213> ORGANISM: Dengue virus

<400> SEQUENCE: 138

Thr Ser Gly Ser Pro Ile Ile Asn Arg Glu Gly Lys Val Val Gly Leu
1 5 10 15

Tyr Gly Asn Gly
20

<210> SEQ ID NO 139
<211> LENGTH: 20
<212> TYPE: PRT
<213> ORGANISM: Dengue virus

<400> SEQUENCE: 139

Gly Lys Val Val Gly Leu Tyr Gly Asn Gly Val Val Thr Lys Ser Gly
1 5 10 15

Ala Tyr Val Ser
20

<210> SEQ ID NO 140
<211> LENGTH: 20
<212> TYPE: PRT
<213> ORGANISM: Dengue virus

<400> SEQUENCE: 140

Val Val Thr Lys Ser Gly Ala Tyr Val Ser Ala Ile Ala Gln Thr Asn
1 5 10 15

Ala Glu Pro Leu
20

<210> SEQ ID NO 141
<211> LENGTH: 20
<212> TYPE: PRT
<213> ORGANISM: Dengue virus

<400> SEQUENCE: 141

Ala Ile Ala Gln Thr Asn Ala Glu Pro Leu Pro Glu Ile Glu Asp Glu
1 5 10 15

Val Phe Arg Lys
20

<210> SEQ ID NO 142
<211> LENGTH: 20
<212> TYPE: PRT
<213> ORGANISM: Dengue virus

<400> SEQUENCE: 142

Pro Glu Ile Glu Asp Glu Val Phe Arg Lys Arg Asn Leu Thr Ile Met
1 5 10 15

Asp Leu His Pro
20

<210> SEQ ID NO 143
<211> LENGTH: 20
<212> TYPE: PRT
<213> ORGANISM: Dengue virus

<400> SEQUENCE: 143

Arg Asn Leu Thr Ile Met Asp Leu His Pro Gly Ala Gly Lys Thr Lys
1 5 10 15

Arg Tyr Leu Pro
20

<210> SEQ ID NO 144
<211> LENGTH: 20
<212> TYPE: PRT
<213> ORGANISM: Dengue virus

<400> SEQUENCE: 144

Gly Ala Gly Lys Thr Lys Arg Tyr Leu Pro Ala Ile Val Arg Glu Ala 1 5 10 15

Ile Lys Arg Arg
20

<210> SEQ ID NO 145
<211> LENGTH: 20
<212> TYPE: PRT
<213> ORGANISM: Dengue virus

<400> SEQUENCE: 145

Ala Ile Val Arg Glu Ala Ile Lys Arg Arg Leu Arg Thr Leu Ile Leu
1 5 10 15

Ala Pro Thr Arg
20

<210> SEQ ID NO 146
<211> LENGTH: 20
<212> TYPE: PRT
<213> ORGANISM: Dengue virus

<400> SEQUENCE: 146

Leu Arg Thr Leu Ile Leu Ala Pro Thr Arg Val Val Ala Ala Glu Met
1 5 10 15

Ala Pro Thr Arg
20

<210> SEQ ID NO 147
<211> LENGTH: 20
<212> TYPE: PRT
<213> ORGANISM: Dengue virus

<400> SEQUENCE: 147

Val Val Ala Ala Glu Met Ala Pro Thr Arg Val Val Ala Ser Glu Met
1 5 10 15

Glu Glu Ala Leu
20

<210> SEQ ID NO 148
<211> LENGTH: 20
<212> TYPE: PRT
<213> ORGANISM: Dengue virus

<400> SEQUENCE: 148

Val Val Ala Ser Glu Met Glu Glu Ala Leu Lys Gly Leu Pro Ile Arg
1 5 10 15

Tyr Ala Leu Arg
20

<210> SEQ ID NO 149
<211> LENGTH: 20
<212> TYPE: PRT
<213> ORGANISM: Dengue virus

<400> SEQUENCE: 149

Lys Gly Leu Pro Ile Arg Tyr Ala Leu Arg Gly Leu Pro Ile Arg Tyr
1 5 10 15

Gln Thr Thr Ala
20

<210> SEQ ID NO 150
<211> LENGTH: 20
<212> TYPE: PRT

<213> ORGANISM: Dengue virus

<400> SEQUENCE: 150

Gly Leu Pro Ile Arg Tyr Gln Thr Thr Ala Ile Lys Ala Glu His Thr
1 5 10 15

Gly Lys Glu Ile
20

<210> SEQ ID NO 151
<211> LENGTH: 20
<212> TYPE: PRT
<213> ORGANISM: Dengue virus

<400> SEQUENCE: 151

Ile Lys Ala Glu His Thr Gly Lys Glu Ile Val Asp Leu Met Cys His
1 5 10 15

Ala Thr Phe Thr
20

<210> SEQ ID NO 152
<211> LENGTH: 20
<212> TYPE: PRT
<213> ORGANISM: Dengue virus

<400> SEQUENCE: 152

Val Asp Leu Met Cys His Ala Thr Phe Thr Met Arg Leu Leu Ser Pro
1 5 10 15

Val Arg Val Pro
20

<210> SEQ ID NO 153
<211> LENGTH: 20
<212> TYPE: PRT
<213> ORGANISM: Dengue virus

<400> SEQUENCE: 153

Met Arg Leu Leu Ser Pro Val Arg Val Pro Asn Tyr Asn Leu Ile Ile
1 5 10 15

Met Asp Glu Ala
20

<210> SEQ ID NO 154
<211> LENGTH: 20
<212> TYPE: PRT
<213> ORGANISM: Dengue virus

<400> SEQUENCE: 154

Asn Tyr Asn Leu Ile Ile Met Asp Glu Ala His Phe Thr Asp Pro Ala
1 5 10 15

Ser Ile Ala Ala
20

<210> SEQ ID NO 155
<211> LENGTH: 20
<212> TYPE: PRT
<213> ORGANISM: Dengue virus

<400> SEQUENCE: 155

His Phe Thr Asp Pro Ala Ser Ile Ala Ala Arg Gly Tyr Ile Ser Thr
1 5 10 15

Arg Val Glu Met
20

<210> SEQ ID NO 156
<211> LENGTH: 20
<212> TYPE: PRT
<213> ORGANISM: Dengue virus

<400> SEQUENCE: 156

Arg Gly Tyr Ile Ser Thr Arg Val Glu Met Gly Glu Ala Ala Ala Ile
1 5 10 15

Phe Met Thr Ala
20

<210> SEQ ID NO 157
<211> LENGTH: 20
<212> TYPE: PRT
<213> ORGANISM: Dengue virus

<400> SEQUENCE: 157

Gly Glu Ala Ala Ala Ile Phe Met Thr Ala Thr Pro Pro Gly Ser Ala
1 5 10 15

Asp Ala Phe Pro
20

<210> SEQ ID NO 158
<211> LENGTH: 20
<212> TYPE: PRT
<213> ORGANISM: Dengue virus

<400> SEQUENCE: 158

Thr Pro Pro Gly Ser Ala Asp Ala Phe Pro Gln Ser Asn Ala Pro Ile
1 5 10 15

Glu Asp Glu Glu
20

<210> SEQ ID NO 159
<211> LENGTH: 20
<212> TYPE: PRT
<213> ORGANISM: Dengue virus

<400> SEQUENCE: 159

Gln Ser Asn Ala Pro Ile Glu Asp Glu Glu Arg Glu Ile Pro Glu Arg
1 5 10 15

Ser Trp Asn Ser
20

<210> SEQ ID NO 160
<211> LENGTH: 20
<212> TYPE: PRT
<213> ORGANISM: Dengue virus

<400> SEQUENCE: 160

Arg Glu Ile Pro Glu Arg Ser Trp Asn Ser Gly Phe Asp Trp Ile Thr
1 5 10 15

Asp Phe Ala Gly
20

<210> SEQ ID NO 161
<211> LENGTH: 20
<212> TYPE: PRT
<213> ORGANISM: Dengue virus

<400> SEQUENCE: 161

Gly Phe Asp Trp Ile Thr Asp Phe Ala Gly Lys Thr Val Trp Phe Val
1 5 10 15

Pro Ser Ile Lys
20

<210> SEQ ID NO 162
<211> LENGTH: 20
<212> TYPE: PRT
<213> ORGANISM: Dengue virus

<400> SEQUENCE: 162

Lys Thr Val Trp Phe Val Pro Ser Ile Lys Ala Gly Asn Asp Ile Ala
1 5 10 15

Asn Cys Leu Arg
20

<210> SEQ ID NO 163
<211> LENGTH: 20
<212> TYPE: PRT
<213> ORGANISM: Dengue virus

<400> SEQUENCE: 163

Ala Gly Asn Asp Ile Ala Asn Cys Leu Arg Lys Asn Gly Lys Lys Val
1 5 10 15

Ile Gln Leu Ser
20

<210> SEQ ID NO 164
<211> LENGTH: 20
<212> TYPE: PRT
<213> ORGANISM: Dengue virus

<400> SEQUENCE: 164

Lys Asn Gly Lys Lys Val Ile Gln Leu Ser Arg Lys Thr Phe Asp Thr
1 5 10 15

Glu Tyr Pro Lys
20

<210> SEQ ID NO 165
<211> LENGTH: 20
<212> TYPE: PRT
<213> ORGANISM: Dengue virus

<400> SEQUENCE: 165

Arg Lys Thr Phe Asp Thr Glu Tyr Pro Lys Thr Lys Leu Asn Asp Trp
1 5 10 15

Asp Phe Val Val
20

<210> SEQ ID NO 166
<211> LENGTH: 20
<212> TYPE: PRT
<213> ORGANISM: Dengue virus

<400> SEQUENCE: 166

Thr Lys Leu Asn Asp Trp Asp Phe Val Val Thr Thr Asp Ile Ser Glu
1 5 10 15

Met Gly Ala Asn
20

<210> SEQ ID NO 167
<211> LENGTH: 20

<212> TYPE: PRT
<213> ORGANISM: Dengue virus

<400> SEQUENCE: 167

Thr Thr Asp Ile Ser Glu Met Gly Ala Asn Phe Lys Ala Asp Arg Val
1 5 10 15

Ile Asp Pro Arg
20

<210> SEQ ID NO 168
<211> LENGTH: 20
<212> TYPE: PRT
<213> ORGANISM: Dengue virus

<400> SEQUENCE: 168

Phe Lys Ala Asp Arg Val Ile Asp Pro Arg Arg Cys Leu Lys Pro Val
1 5 10 15

Ile Leu Thr Asp
20

<210> SEQ ID NO 169
<211> LENGTH: 20
<212> TYPE: PRT
<213> ORGANISM: Dengue virus

<400> SEQUENCE: 169

Arg Cys Leu Lys Pro Val Ile Leu Thr Asp Gly Pro Glu Arg Val Ile
1 5 10 15

Leu Ala Gly Pro
20

<210> SEQ ID NO 170
<211> LENGTH: 20
<212> TYPE: PRT
<213> ORGANISM: Dengue virus

<400> SEQUENCE: 170

Gly Pro Glu Arg Val Ile Leu Ala Gly Pro Met Pro Val Thr Ala Ala
1 5 10 15

Ser Ala Ala Gln
20

<210> SEQ ID NO 171
<211> LENGTH: 20
<212> TYPE: PRT
<213> ORGANISM: Dengue virus

<400> SEQUENCE: 171

Met Pro Val Thr Ala Ala Ser Ala Ala Gln Arg Arg Gly Arg Ile Gly
1 5 10 15

Arg Asn His Lys
20

<210> SEQ ID NO 172
<211> LENGTH: 20
<212> TYPE: PRT
<213> ORGANISM: Dengue virus

<400> SEQUENCE: 172

Arg Arg Gly Arg Ile Gly Arg Asn His Lys Lys Glu Asn Asp Gln Tyr
1 5 10 15

Ile Tyr Met Gly

20

<210> SEQ ID NO 173
<211> LENGTH: 20
<212> TYPE: PRT
<213> ORGANISM: Dengue virus

<400> SEQUENCE: 173

Lys Glu Asn Asp Gln Tyr Ile Tyr Met Gly Gln Pro Leu Asn Asn Asp
1 5 10 15

Glu Asp His Ala
20

<210> SEQ ID NO 174
<211> LENGTH: 20
<212> TYPE: PRT
<213> ORGANISM: Dengue virus

<400> SEQUENCE: 174

Gln Pro Leu Asn Asn Asp Glu Asp His Ala His Trp Thr Glu Ala Lys
1 5 10 15

Met Leu Leu Asp
20

<210> SEQ ID NO 175
<211> LENGTH: 20
<212> TYPE: PRT
<213> ORGANISM: Dengue virus

<400> SEQUENCE: 175

His Trp Thr Glu Ala Lys Met Leu Leu Asp Asn Ile Asn Thr Pro Glu
1 5 10 15

Gly Ile Ile Pro
20

<210> SEQ ID NO 176
<211> LENGTH: 20
<212> TYPE: PRT
<213> ORGANISM: Dengue virus

<400> SEQUENCE: 176

Asn Ile Asn Thr Pro Glu Gly Ile Ile Pro Ala Leu Phe Thr Pro Glu
1 5 10 15

Gly Ile Ile Pro
20

<210> SEQ ID NO 177
<211> LENGTH: 20
<212> TYPE: PRT
<213> ORGANISM: Dengue virus

<400> SEQUENCE: 177

Ala Leu Phe Thr Pro Glu Gly Ile Ile Pro Ser Met Phe Thr Pro Glu
1 5 10 15

Gly Ile Ile Pro
20

<210> SEQ ID NO 178
<211> LENGTH: 20
<212> TYPE: PRT
<213> ORGANISM: Dengue virus

<400> SEQUENCE: 178

Ser Met Phe Thr Pro Glu Gly Ile Ile Pro Thr Leu Phe Thr Pro Glu
1               5                   10                  15

Gly Ile Ile Pro
            20

<210> SEQ ID NO 179
<211> LENGTH: 20
<212> TYPE: PRT
<213> ORGANISM: Dengue virus

<400> SEQUENCE: 179

Thr Leu Phe Thr Pro Glu Gly Ile Ile Pro Ser Leu Glu Pro Glu Arg
1               5                   10                  15

Glu Lys Ser Ala
            20

<210> SEQ ID NO 180
<211> LENGTH: 20
<212> TYPE: PRT
<213> ORGANISM: Dengue virus

<400> SEQUENCE: 180

Ser Leu Glu Pro Glu Arg Glu Lys Ser Ala Ala Ile Asp Gly Glu Tyr
1               5                   10                  15

Arg Leu Arg Gly
            20

<210> SEQ ID NO 181
<211> LENGTH: 20
<212> TYPE: PRT
<213> ORGANISM: Dengue virus

<400> SEQUENCE: 181

Ala Ile Asp Gly Glu Tyr Arg Leu Arg Gly Glu Ala Arg Lys Thr Phe
1               5                   10                  15

Val Glu Leu Gly
            20

<210> SEQ ID NO 182
<211> LENGTH: 20
<212> TYPE: PRT
<213> ORGANISM: Dengue virus

<400> SEQUENCE: 182

Glu Ala Arg Lys Thr Phe Val Glu Leu Gly Glu Ala Arg Lys Thr Phe
1               5                   10                  15

Val Asp Leu Gly
            20

<210> SEQ ID NO 183
<211> LENGTH: 20
<212> TYPE: PRT
<213> ORGANISM: Dengue virus

<400> SEQUENCE: 183

Glu Ala Arg Lys Thr Phe Val Asp Leu Gly Glu Gln Arg Lys Thr Phe
1               5                   10                  15

Val Glu Leu Met
            20

<210> SEQ ID NO 184

<211> LENGTH: 20
<212> TYPE: PRT
<213> ORGANISM: Dengue virus

<400> SEQUENCE: 184

Glu Gln Arg Lys Thr Phe Val Glu Leu Met Arg Arg Gly Asp Leu Pro
1 5 10 15

Val Trp Leu Ser
20

<210> SEQ ID NO 185
<211> LENGTH: 20
<212> TYPE: PRT
<213> ORGANISM: Dengue virus

<400> SEQUENCE: 185

Arg Arg Gly Asp Leu Pro Val Trp Leu Ser Tyr Lys Val Ala Ser Ala
1 5 10 15

Gly Phe Gln Tyr
20

<210> SEQ ID NO 186
<211> LENGTH: 20
<212> TYPE: PRT
<213> ORGANISM: Dengue virus

<400> SEQUENCE: 186

Tyr Lys Val Ala Ser Ala Gly Phe Gln Tyr Lys Asp Arg Glu Trp Cys
1 5 10 15

Phe Asp Gly Glu
20

<210> SEQ ID NO 187
<211> LENGTH: 20
<212> TYPE: PRT
<213> ORGANISM: Dengue virus

<400> SEQUENCE: 187

Lys Asp Arg Glu Trp Cys Phe Asp Gly Glu Arg Asn Asn Gln Ile Leu
1 5 10 15

Glu Glu Asn Met
20

<210> SEQ ID NO 188
<211> LENGTH: 20
<212> TYPE: PRT
<213> ORGANISM: Dengue virus

<400> SEQUENCE: 188

Arg Asn Asn Gln Ile Leu Glu Glu Asn Met Asp Val Glu Ile Trp Thr
1 5 10 15

Lys Glu Gly Glu
20

<210> SEQ ID NO 189
<211> LENGTH: 20
<212> TYPE: PRT
<213> ORGANISM: Dengue virus

<400> SEQUENCE: 189

Asp Val Glu Ile Trp Thr Lys Glu Gly Glu Lys Lys Lys Leu Arg Pro
1 5 10 15

Arg Trp Leu Asp
20

<210> SEQ ID NO 190
<211> LENGTH: 20
<212> TYPE: PRT
<213> ORGANISM: Dengue virus

<400> SEQUENCE: 190

Lys Lys Lys Leu Arg Pro Arg Trp Leu Asp Ala Arg Thr Tyr Ala Asp
1 5 10 15

Pro Leu Ala Leu
20

<210> SEQ ID NO 191
<211> LENGTH: 20
<212> TYPE: PRT
<213> ORGANISM: Dengue virus

<400> SEQUENCE: 191

Ala Arg Thr Tyr Ala Asp Pro Leu Ala Leu Lys Glu Phe Lys Asp Phe
1 5 10 15

Ala Ala Gly Arg
20

<210> SEQ ID NO 192
<211> LENGTH: 20
<212> TYPE: PRT
<213> ORGANISM: Dengue virus

<400> SEQUENCE: 192

Lys Glu Phe Lys Asp Phe Ala Ala Gly Arg Lys Ser Ile Ala Thr Glu
1 5 10 15

Ile Gly Arg Val
20

<210> SEQ ID NO 193
<211> LENGTH: 20
<212> TYPE: PRT
<213> ORGANISM: Dengue virus

<400> SEQUENCE: 193

Lys Ser Ile Ala Thr Glu Ile Gly Arg Val Pro Ser His Leu Ala His
1 5 10 15

Arg Thr Arg Ala
20

<210> SEQ ID NO 194
<211> LENGTH: 20
<212> TYPE: PRT
<213> ORGANISM: Dengue virus

<400> SEQUENCE: 194

Pro Ser His Leu Ala His Arg Thr Arg Ala Tyr Gln His Ala Leu Glu
1 5 10 15

Glu Leu Pro Glu
20

<210> SEQ ID NO 195
<211> LENGTH: 20
<212> TYPE: PRT
<213> ORGANISM: Dengue virus

<400> SEQUENCE: 195

Tyr Gln His Ala Leu Glu Glu Leu Pro Glu Thr Leu Glu Thr Leu Leu
1 5 10 15

Leu Leu Ala Leu
20

<210> SEQ ID NO 196
<211> LENGTH: 20
<212> TYPE: PRT
<213> ORGANISM: Dengue virus

<400> SEQUENCE: 196

Thr Leu Glu Thr Leu Leu Leu Leu Ala Leu Leu Gly Ala Phe Leu Phe
1 5 10 15

Phe Leu Ser Gly
20

<210> SEQ ID NO 197
<211> LENGTH: 20
<212> TYPE: PRT
<213> ORGANISM: Dengue virus

<400> SEQUENCE: 197

Leu Gly Ala Phe Leu Phe Phe Leu Ser Gly Lys Gly Ile Gly Lys Met
1 5 10 15

Ser Ile Gly Leu
20

<210> SEQ ID NO 198
<211> LENGTH: 20
<212> TYPE: PRT
<213> ORGANISM: Dengue virus

<400> SEQUENCE: 198

Lys Gly Ile Gly Lys Met Ser Ile Gly Leu Cys Cys Ile Ile Ala Ala
1 5 10 15

Ser Leu Leu Trp
20

<210> SEQ ID NO 199
<211> LENGTH: 20
<212> TYPE: PRT
<213> ORGANISM: Dengue virus

<400> SEQUENCE: 199

Cys Cys Ile Ile Ala Ala Ser Leu Leu Trp Met Ala Glu Ile Gln Pro
1 5 10 15

His Trp Ile Ala
20

<210> SEQ ID NO 200
<211> LENGTH: 20
<212> TYPE: PRT
<213> ORGANISM: Dengue virus

<400> SEQUENCE: 200

Met Ala Glu Ile Gln Pro His Trp Ile Ala Ala Ser Ile Ile Leu Glu
1 5 10 15

Phe Phe Leu Met
20

<210> SEQ ID NO 201
<211> LENGTH: 20
<212> TYPE: PRT
<213> ORGANISM: Dengue virus

<400> SEQUENCE: 201

Ala Ser Ile Ile Leu Glu Phe Phe Leu Met Val Leu Leu Ile Pro Glu
1 5 10 15

Pro Glu Lys Gln
20

<210> SEQ ID NO 202
<211> LENGTH: 20
<212> TYPE: PRT
<213> ORGANISM: Dengue virus

<400> SEQUENCE: 202

Val Leu Leu Ile Pro Glu Pro Glu Lys Gln Arg Thr Pro Gln Asp Asn
1 5 10 15

Gln Leu Ala Tyr
20

<210> SEQ ID NO 203
<211> LENGTH: 20
<212> TYPE: PRT
<213> ORGANISM: Dengue virus

<400> SEQUENCE: 203

Arg Thr Pro Gln Asp Asn Gln Leu Ala Tyr Val Val Ile Gly Ile Leu
1 5 10 15

Thr Leu Ala Ala
20

<210> SEQ ID NO 204
<211> LENGTH: 20
<212> TYPE: PRT
<213> ORGANISM: Dengue virus

<400> SEQUENCE: 204

Val Val Ile Gly Ile Leu Thr Leu Ala Ala Ala Ile Ala Ala Asn Glu
1 5 10 15

Met Gly Leu Leu
20

<210> SEQ ID NO 205
<211> LENGTH: 20
<212> TYPE: PRT
<213> ORGANISM: Dengue virus

<400> SEQUENCE: 205

Ala Ile Ala Ala Asn Glu Met Gly Leu Leu Glu Thr Thr Lys Lys Asp
1 5 10 15

Leu Gly Ile Gly
20

<210> SEQ ID NO 206
<211> LENGTH: 20
<212> TYPE: PRT
<213> ORGANISM: Dengue virus

<400> SEQUENCE: 206

Glu Thr Thr Lys Lys Asp Leu Gly Ile Gly His Val Ala Pro Thr Ala
1 5 10 15

Ile Leu Asp Val
20

<210> SEQ ID NO 207
<211> LENGTH: 20
<212> TYPE: PRT
<213> ORGANISM: Dengue virus

<400> SEQUENCE: 207

His Val Ala Pro Thr Ala Ile Leu Asp Val Asp Leu His Pro Ala Ser
1 5 10 15

Ala Trp Thr Leu
20

<210> SEQ ID NO 208
<211> LENGTH: 20
<212> TYPE: PRT
<213> ORGANISM: Dengue virus

<400> SEQUENCE: 208

Asp Leu His Pro Ala Ser Ala Trp Thr Leu Tyr Ala Val Ala Thr Thr
1 5 10 15

Ile Ile Thr Pro
20

<210> SEQ ID NO 209
<211> LENGTH: 20
<212> TYPE: PRT
<213> ORGANISM: Dengue virus

<400> SEQUENCE: 209

Tyr Ala Val Ala Thr Thr Ile Ile Thr Pro Met Leu Arg His Thr Ile
1 5 10 15

Glu Asn Ser Thr
20

<210> SEQ ID NO 210
<211> LENGTH: 20
<212> TYPE: PRT
<213> ORGANISM: Dengue virus

<400> SEQUENCE: 210

Met Leu Arg His Thr Ile Glu Asn Ser Thr Ala Asn Val Ser Leu Thr
1 5 10 15

Ala Ile Ala Asn
20

<210> SEQ ID NO 211
<211> LENGTH: 20
<212> TYPE: PRT
<213> ORGANISM: Dengue virus

<400> SEQUENCE: 211

Ala Asn Val Ser Leu Thr Ala Ile Ala Asn Gln Ala Ala Val Leu Met
1 5 10 15

Ile Ala Asn Gln
20

<210> SEQ ID NO 212
<211> LENGTH: 20
<212> TYPE: PRT
<213> ORGANISM: Dengue virus

<400> SEQUENCE: 212

Gln Ala Ala Val Leu Met Ile Ala Asn Gln Ala Thr Val Leu Met Gly
1 5 10 15

Leu Asp Lys Gly
20

<210> SEQ ID NO 213
<211> LENGTH: 20
<212> TYPE: PRT
<213> ORGANISM: Dengue virus

<400> SEQUENCE: 213

Ala Thr Val Leu Met Gly Leu Asp Lys Gly Trp Pro Ile Ser Lys Met
1 5 10 15

Asp Leu Gly Val
20

<210> SEQ ID NO 214
<211> LENGTH: 20
<212> TYPE: PRT
<213> ORGANISM: Dengue virus

<400> SEQUENCE: 214

Trp Pro Ile Ser Lys Met Asp Leu Gly Val Pro Leu Leu Ala Leu Gly
1 5 10 15

Cys Tyr Ser Gln
20

<210> SEQ ID NO 215
<211> LENGTH: 20
<212> TYPE: PRT
<213> ORGANISM: Dengue virus

<400> SEQUENCE: 215

Pro Leu Leu Ala Leu Gly Cys Tyr Ser Gln Val Asn Pro Leu Thr Leu
1 5 10 15

Thr Ala Ala Val
20

<210> SEQ ID NO 216
<211> LENGTH: 20
<212> TYPE: PRT
<213> ORGANISM: Dengue virus

<400> SEQUENCE: 216

Val Asn Pro Leu Thr Leu Thr Ala Ala Val Leu Leu Leu Ile Thr His
1 5 10 15

Tyr Ala Ile Ile
20

<210> SEQ ID NO 217
<211> LENGTH: 20
<212> TYPE: PRT
<213> ORGANISM: Dengue virus

<400> SEQUENCE: 217

Leu Leu Leu Ile Thr His Tyr Ala Ile Ile Gly Pro Gly Leu Gln Ala
1 5 10 15

Lys Ala Thr Arg
20

<210> SEQ ID NO 218
<211> LENGTH: 20
<212> TYPE: PRT
<213> ORGANISM: Dengue virus

<400> SEQUENCE: 218

Gly Pro Gly Leu Gln Ala Lys Ala Thr Arg Glu Ala Gln Lys Arg Thr
1 5 10 15

Ala Ala Gly Ile
20

<210> SEQ ID NO 219
<211> LENGTH: 20
<212> TYPE: PRT
<213> ORGANISM: Dengue virus

<400> SEQUENCE: 219

Glu Ala Gln Lys Arg Thr Ala Ala Gly Ile Met Lys Asn Pro Thr Val
1 5 10 15

Asp Gly Ile Met
20

<210> SEQ ID NO 220
<211> LENGTH: 20
<212> TYPE: PRT
<213> ORGANISM: Dengue virus

<400> SEQUENCE: 220

Met Lys Asn Pro Thr Val Asp Gly Ile Met Ala Ile Asp Leu Asp Pro
1 5 10 15

Ile Pro Tyr Asp
20

<210> SEQ ID NO 221
<211> LENGTH: 20
<212> TYPE: PRT
<213> ORGANISM: Dengue virus

<400> SEQUENCE: 221

Ala Ile Asp Leu Asp Pro Ile Pro Tyr Asp Pro Lys Phe Glu Lys Gln
1 5 10 15

Leu Gly Gln Val
20

<210> SEQ ID NO 222
<211> LENGTH: 20
<212> TYPE: PRT
<213> ORGANISM: Dengue virus

<400> SEQUENCE: 222

Pro Lys Phe Glu Lys Gln Leu Gly Gln Val Met Leu Leu Ile Leu Cys
1 5 10 15

Val Ser Gln Ile
20

<210> SEQ ID NO 223
<211> LENGTH: 20
<212> TYPE: PRT
<213> ORGANISM: Dengue virus

<400> SEQUENCE: 223

Met Leu Leu Ile Leu Cys Val Ser Gln Ile Leu Leu Met Arg Thr Thr

```
1               5                   10                  15

Trp Ala Val Leu
            20


<210> SEQ ID NO 224
<211> LENGTH: 20
<212> TYPE: PRT
<213> ORGANISM: Dengue virus

<400> SEQUENCE: 224

Leu Leu Met Arg Thr Thr Trp Ala Val Leu Leu Met Arg Thr Thr Trp
1               5                   10                  15

Ala Leu Cys Glu
            20


<210> SEQ ID NO 225
<211> LENGTH: 20
<212> TYPE: PRT
<213> ORGANISM: Dengue virus

<400> SEQUENCE: 225

Leu Met Arg Thr Thr Trp Ala Leu Cys Glu Ala Leu Thr Leu Ala Thr
1               5                   10                  15

Gly Pro Ile Thr
            20


<210> SEQ ID NO 226
<211> LENGTH: 20
<212> TYPE: PRT
<213> ORGANISM: Dengue virus

<400> SEQUENCE: 226

Ala Leu Thr Leu Ala Thr Gly Pro Ile Thr Thr Leu Trp Glu Gly Asn
1               5                   10                  15

Pro Gly Lys Phe
            20


<210> SEQ ID NO 227
<211> LENGTH: 20
<212> TYPE: PRT
<213> ORGANISM: Dengue virus

<400> SEQUENCE: 227

Thr Leu Trp Glu Gly Asn Pro Gly Lys Phe Trp Asn Thr Thr Ile Ala
1               5                   10                  15

Val Ser Met Ala
            20


<210> SEQ ID NO 228
<211> LENGTH: 20
<212> TYPE: PRT
<213> ORGANISM: Dengue virus

<400> SEQUENCE: 228

Trp Asn Thr Thr Ile Ala Val Ser Met Ala Asn Ile Phe Arg Gly Ser
1               5                   10                  15

Tyr Leu Ala Gly
            20


<210> SEQ ID NO 229
<211> LENGTH: 20
<212> TYPE: PRT
```

<213> ORGANISM: Dengue virus

<400> SEQUENCE: 229

Asn Ile Phe Arg Gly Ser Tyr Leu Ala Gly Ala Gly Leu Ala Phe Ser
1 5 10 15

Leu Ile Lys Asn
20

<210> SEQ ID NO 230
<211> LENGTH: 20
<212> TYPE: PRT
<213> ORGANISM: Dengue virus

<400> SEQUENCE: 230

Ala Gly Leu Ala Phe Ser Leu Ile Lys Asn Arg Arg Gly Thr Gly Ala
1 5 10 15

Gln Gly Glu Thr
20

<210> SEQ ID NO 231
<211> LENGTH: 20
<212> TYPE: PRT
<213> ORGANISM: Dengue virus

<400> SEQUENCE: 231

Arg Arg Gly Thr Gly Ala Gln Gly Glu Thr Leu Gly Glu Lys Trp Lys
1 5 10 15

Arg Gln Leu Asn
20

<210> SEQ ID NO 232
<211> LENGTH: 20
<212> TYPE: PRT
<213> ORGANISM: Dengue virus

<400> SEQUENCE: 232

Leu Gly Glu Lys Trp Lys Arg Gln Leu Asn Gln Leu Asp Lys Ser Glu
1 5 10 15

Phe Glu Glu Tyr
20

<210> SEQ ID NO 233
<211> LENGTH: 20
<212> TYPE: PRT
<213> ORGANISM: Dengue virus

<400> SEQUENCE: 233

Gln Leu Asp Lys Ser Glu Phe Glu Glu Tyr Lys Lys Ser Gly Ile Leu
1 5 10 15

Glu Val Asp Arg
20

<210> SEQ ID NO 234
<211> LENGTH: 20
<212> TYPE: PRT
<213> ORGANISM: Dengue virus

<400> SEQUENCE: 234

Lys Lys Ser Gly Ile Leu Glu Val Asp Arg Thr Glu Ala Lys Glu Ala
1 5 10 15

Ile Lys Arg Gly
20

<210> SEQ ID NO 235
<211> LENGTH: 20
<212> TYPE: PRT
<213> ORGANISM: Dengue virus

<400> SEQUENCE: 235

Thr Glu Ala Lys Glu Ala Ile Lys Arg Gly Glu Thr Asp His His Ala
1               5                   10                  15

Val Ser Arg Gly
            20

<210> SEQ ID NO 236
<211> LENGTH: 20
<212> TYPE: PRT
<213> ORGANISM: Dengue virus

<400> SEQUENCE: 236

Glu Thr Asp His His Ala Val Ser Arg Gly Ser Ala Lys Leu Arg Trp
1               5                   10                  15

Phe Val Glu Arg
            20

<210> SEQ ID NO 237
<211> LENGTH: 20
<212> TYPE: PRT
<213> ORGANISM: Dengue virus

<400> SEQUENCE: 237

Ser Ala Lys Leu Arg Trp Phe Val Glu Arg Asn Met Val Ile Pro Glu
1               5                   10                  15

Gly Arg Val Ile
            20

<210> SEQ ID NO 238
<211> LENGTH: 20
<212> TYPE: PRT
<213> ORGANISM: Dengue virus

<400> SEQUENCE: 238

Asn Met Val Ile Pro Glu Gly Arg Val Ile Asp Leu Gly Cys Gly Arg
1               5                   10                  15

Gly Gly Trp Ser
            20

<210> SEQ ID NO 239
<211> LENGTH: 20
<212> TYPE: PRT
<213> ORGANISM: Dengue virus

<400> SEQUENCE: 239

Asp Leu Gly Cys Gly Arg Gly Gly Trp Ser Tyr Tyr Cys Ala Gly Leu
1               5                   10                  15

Lys Lys Val Arg
            20

<210> SEQ ID NO 240
<211> LENGTH: 20
<212> TYPE: PRT
<213> ORGANISM: Dengue virus

<400> SEQUENCE: 240

```
Tyr Tyr Cys Ala Gly Leu Lys Lys Val Arg Glu Val Arg Gly Tyr Thr
1               5                   10                  15

Lys Gly Gly Pro
            20


<210> SEQ ID NO 241
<211> LENGTH: 20
<212> TYPE: PRT
<213> ORGANISM: Dengue virus

<400> SEQUENCE: 241

Glu Val Arg Gly Tyr Thr Lys Gly Gly Pro Gly His Glu Glu Pro Ile
1               5                   10                  15

Pro Met Ala Thr
            20


<210> SEQ ID NO 242
<211> LENGTH: 20
<212> TYPE: PRT
<213> ORGANISM: Dengue virus

<400> SEQUENCE: 242

Gly His Glu Glu Pro Ile Pro Met Ala Thr Tyr Gly Trp Asn Leu Val
1               5                   10                  15

Lys Leu His Ser
            20


<210> SEQ ID NO 243
<211> LENGTH: 20
<212> TYPE: PRT
<213> ORGANISM: Dengue virus

<400> SEQUENCE: 243

Tyr Gly Trp Asn Leu Val Lys Leu His Ser Gly Val Asp Val Phe Phe
1               5                   10                  15

Pro Glu Lys Cys
            20


<210> SEQ ID NO 244
<211> LENGTH: 20
<212> TYPE: PRT
<213> ORGANISM: Dengue virus

<400> SEQUENCE: 244

Gly Val Asp Val Phe Phe Pro Glu Lys Cys Asp Thr Leu Leu Cys Asp
1               5                   10                  15

Ile Gly Glu Ser
            20


<210> SEQ ID NO 245
<211> LENGTH: 20
<212> TYPE: PRT
<213> ORGANISM: Dengue virus

<400> SEQUENCE: 245

Asp Thr Leu Leu Cys Asp Ile Gly Glu Ser Ser Pro Asn Pro Thr Ile
1               5                   10                  15

Glu Glu Gly Arg
            20


<210> SEQ ID NO 246
<211> LENGTH: 20
```

<212> TYPE: PRT
<213> ORGANISM: Dengue virus

<400> SEQUENCE: 246

Ser Pro Asn Pro Thr Ile Glu Glu Gly Arg Thr Leu Arg Val Leu Lys
1 5 10 15

Met Val Glu Pro
20

<210> SEQ ID NO 247
<211> LENGTH: 20
<212> TYPE: PRT
<213> ORGANISM: Dengue virus

<400> SEQUENCE: 247

Thr Leu Arg Val Leu Lys Met Val Glu Pro Trp Leu Lys Gly Asn Gln
1 5 10 15

Phe Cys Ile Lys
20

<210> SEQ ID NO 248
<211> LENGTH: 20
<212> TYPE: PRT
<213> ORGANISM: Dengue virus

<400> SEQUENCE: 248

Trp Leu Lys Gly Asn Gln Phe Cys Ile Lys Ile Leu Asn Pro Tyr Met
1 5 10 15

Pro Ser Val Ile
20

<210> SEQ ID NO 249
<211> LENGTH: 20
<212> TYPE: PRT
<213> ORGANISM: Dengue virus

<400> SEQUENCE: 249

Ile Leu Asn Pro Tyr Met Pro Ser Val Ile Glu Glu Leu Glu Lys Leu
1 5 10 15

Gln Arg Lys His
20

<210> SEQ ID NO 250
<211> LENGTH: 20
<212> TYPE: PRT
<213> ORGANISM: Dengue virus

<400> SEQUENCE: 250

Glu Glu Leu Glu Lys Leu Gln Arg Lys His Gly Gly Met Leu Val Arg
1 5 10 15

Asn Pro Leu Ser
20

<210> SEQ ID NO 251
<211> LENGTH: 20
<212> TYPE: PRT
<213> ORGANISM: Dengue virus

<400> SEQUENCE: 251

Gly Gly Met Leu Val Arg Asn Pro Leu Ser Arg Asn Ser Thr His Glu
1 5 10 15

Met Tyr Trp Val

20

<210> SEQ ID NO 252
<211> LENGTH: 20
<212> TYPE: PRT
<213> ORGANISM: Dengue virus

<400> SEQUENCE: 252

Arg Asn Ser Thr His Glu Met Tyr Trp Val Ser Asn Gly Thr Gly Asn
1 5 10 15

Ile Val Ser Ala
20

<210> SEQ ID NO 253
<211> LENGTH: 20
<212> TYPE: PRT
<213> ORGANISM: Dengue virus

<400> SEQUENCE: 253

Ser Asn Gly Thr Gly Asn Ile Val Ser Ala Val Asn Met Ile Ser Arg
1 5 10 15

Met Leu Ile Asn
20

<210> SEQ ID NO 254
<211> LENGTH: 20
<212> TYPE: PRT
<213> ORGANISM: Dengue virus

<400> SEQUENCE: 254

Val Asn Met Ile Ser Arg Met Leu Ile Asn Arg Phe Thr Met Ala His
1 5 10 15

Lys Lys Pro Thr
20

<210> SEQ ID NO 255
<211> LENGTH: 20
<212> TYPE: PRT
<213> ORGANISM: Dengue virus

<400> SEQUENCE: 255

Arg Phe Thr Met Ala His Lys Lys Pro Thr Tyr Glu Arg Asp Val Asp
1 5 10 15

Leu Gly Ala Gly
20

<210> SEQ ID NO 256
<211> LENGTH: 20
<212> TYPE: PRT
<213> ORGANISM: Dengue virus

<400> SEQUENCE: 256

Tyr Glu Arg Asp Val Asp Leu Gly Ala Gly Ser Thr Trp His Tyr Asp
1 5 10 15

Glu Asp Asn Pro
20

<210> SEQ ID NO 257
<211> LENGTH: 20
<212> TYPE: PRT
<213> ORGANISM: Dengue virus

<400> SEQUENCE: 257

Ser Thr Trp His Tyr Asp Glu Asp Asn Pro Tyr Lys Thr Trp Ala Tyr
1 5 10 15

His Gly Ser Tyr
20

<210> SEQ ID NO 258
<211> LENGTH: 20
<212> TYPE: PRT
<213> ORGANISM: Dengue virus

<400> SEQUENCE: 258

Tyr Lys Thr Trp Ala Tyr His Gly Ser Tyr Glu Val Lys Ala Thr Gly
1 5 10 15

Ser Ala Ser Ser
20

<210> SEQ ID NO 259
<211> LENGTH: 20
<212> TYPE: PRT
<213> ORGANISM: Dengue virus

<400> SEQUENCE: 259

Glu Val Lys Ala Thr Gly Ser Ala Ser Ser Met Val Asn Gly Val Val
1 5 10 15

Lys Leu Leu Thr
20

<210> SEQ ID NO 260
<211> LENGTH: 20
<212> TYPE: PRT
<213> ORGANISM: Dengue virus

<400> SEQUENCE: 260

Met Val Asn Gly Val Val Lys Leu Leu Thr Lys Pro Trp Asp Val Val
1 5 10 15

Pro Met Val Thr
20

<210> SEQ ID NO 261
<211> LENGTH: 20
<212> TYPE: PRT
<213> ORGANISM: Dengue virus

<400> SEQUENCE: 261

Lys Pro Trp Asp Val Val Pro Met Val Thr Gln Met Ala Met Thr Asp
1 5 10 15

Thr Thr Pro Phe
20

<210> SEQ ID NO 262
<211> LENGTH: 20
<212> TYPE: PRT
<213> ORGANISM: Dengue virus

<400> SEQUENCE: 262

Gln Met Ala Met Thr Asp Thr Thr Pro Phe Gly Gln Gln Arg Val Phe
1 5 10 15

Lys Glu Lys Val
20

<210> SEQ ID NO 263

<211> LENGTH: 20
<212> TYPE: PRT
<213> ORGANISM: Dengue virus

<400> SEQUENCE: 263

Gly Gln Gln Arg Val Phe Lys Glu Lys Val Asp Thr Arg Thr Pro Glu
1 5 10 15

Ala Lys Glu Asn
20

<210> SEQ ID NO 264
<211> LENGTH: 20
<212> TYPE: PRT
<213> ORGANISM: Dengue virus

<400> SEQUENCE: 264

Asp Thr Arg Thr Pro Glu Ala Lys Glu Asn Ala Ala Ile Gly Ala Val
1 5 10 15

Phe Gln Asp Glu
20

<210> SEQ ID NO 265
<211> LENGTH: 20
<212> TYPE: PRT
<213> ORGANISM: Dengue virus

<400> SEQUENCE: 265

Ala Ala Ile Gly Ala Val Phe Gln Asp Glu Asn Gly Trp Lys Ser Ala
1 5 10 15

Arg Glu Ala Val
20

<210> SEQ ID NO 266
<211> LENGTH: 20
<212> TYPE: PRT
<213> ORGANISM: Dengue virus

<400> SEQUENCE: 266

Asn Gly Trp Lys Ser Ala Arg Glu Ala Val Glu Asp Ser Glu Arg Ala
1 5 10 15

Leu His Leu Glu
20

<210> SEQ ID NO 267
<211> LENGTH: 20
<212> TYPE: PRT
<213> ORGANISM: Dengue virus

<400> SEQUENCE: 267

Glu Asp Ser Glu Arg Ala Leu His Leu Glu Gly Lys Cys Glu Ser Cys
1 5 10 15

Val Tyr Asn Met
20

<210> SEQ ID NO 268
<211> LENGTH: 20
<212> TYPE: PRT
<213> ORGANISM: Dengue virus

<400> SEQUENCE: 268

Gly Lys Cys Glu Ser Cys Val Tyr Asn Met Met Gly Lys Arg Glu Lys
1 5 10 15

Lys Leu Gly Glu
20

<210> SEQ ID NO 269
<211> LENGTH: 20
<212> TYPE: PRT
<213> ORGANISM: Dengue virus

<400> SEQUENCE: 269

Met Gly Lys Arg Glu Lys Lys Leu Gly Glu Phe Gly Lys Ala Lys Gly
1 5 10 15

Ser Arg Ala Ile
20

<210> SEQ ID NO 270
<211> LENGTH: 20
<212> TYPE: PRT
<213> ORGANISM: Dengue virus

<400> SEQUENCE: 270

Phe Gly Lys Ala Lys Gly Ser Arg Ala Ile Trp Tyr Met Trp Leu Gly
1 5 10 15

Ala Arg Phe Leu
20

<210> SEQ ID NO 271
<211> LENGTH: 20
<212> TYPE: PRT
<213> ORGANISM: Dengue virus

<400> SEQUENCE: 271

Trp Tyr Met Trp Leu Gly Ala Arg Phe Leu Glu Phe Glu Ala Leu Gly
1 5 10 15

Phe Leu Asn Glu
20

<210> SEQ ID NO 272
<211> LENGTH: 20
<212> TYPE: PRT
<213> ORGANISM: Dengue virus

<400> SEQUENCE: 272

Glu Phe Glu Ala Leu Gly Phe Leu Asn Glu Asp His Trp Phe Ser Arg
1 5 10 15

Glu Asn Ser Leu
20

<210> SEQ ID NO 273
<211> LENGTH: 20
<212> TYPE: PRT
<213> ORGANISM: Dengue virus

<400> SEQUENCE: 273

Asp His Trp Phe Ser Arg Glu Asn Ser Leu Ser Gly Val Glu Gly Glu
1 5 10 15

Gly Leu His Lys
20

<210> SEQ ID NO 274
<211> LENGTH: 20
<212> TYPE: PRT
<213> ORGANISM: Dengue virus

<400> SEQUENCE: 274

Ser Gly Val Glu Gly Glu Gly Leu His Lys Leu Gly Tyr Ile Leu Arg
1 5 10 15

Asp Ile Ser Lys
20

<210> SEQ ID NO 275
<211> LENGTH: 20
<212> TYPE: PRT
<213> ORGANISM: Dengue virus

<400> SEQUENCE: 275

Leu Gly Tyr Ile Leu Arg Asp Ile Ser Lys Ile Pro Gly Gly Ala Met
1 5 10 15

Tyr Ala Asp Asp
20

<210> SEQ ID NO 276
<211> LENGTH: 20
<212> TYPE: PRT
<213> ORGANISM: Dengue virus

<400> SEQUENCE: 276

Ile Pro Gly Gly Ala Met Tyr Ala Asp Asp Thr Ala Gly Trp Asp Thr
1 5 10 15

Arg Ile Thr Glu
20

<210> SEQ ID NO 277
<211> LENGTH: 20
<212> TYPE: PRT
<213> ORGANISM: Dengue virus

<400> SEQUENCE: 277

Thr Ala Gly Trp Asp Thr Arg Ile Thr Glu Asp Asp Leu His Asn Glu
1 5 10 15

Glu Lys Ile Leu
20

<210> SEQ ID NO 278
<211> LENGTH: 20
<212> TYPE: PRT
<213> ORGANISM: Dengue virus

<400> SEQUENCE: 278

Asp Asp Leu His Asn Glu Glu Lys Ile Leu Ala Lys Ala Ile Phe Lys
1 5 10 15

Leu Thr Tyr Gln
20

<210> SEQ ID NO 279
<211> LENGTH: 20
<212> TYPE: PRT
<213> ORGANISM: Dengue virus

<400> SEQUENCE: 279

Ala Lys Ala Ile Phe Lys Leu Thr Tyr Gln Asn Lys Val Val Lys Val
1 5 10 15

Gln Arg Pro Thr
20

<210> SEQ ID NO 280
<211> LENGTH: 20
<212> TYPE: PRT
<213> ORGANISM: Dengue virus

<400> SEQUENCE: 280

Asn Lys Val Val Lys Val Gln Arg Pro Thr Pro Arg Gly Ala Val Met
1               5                   10                  15

Asp Ile Ile Ser
            20

<210> SEQ ID NO 281
<211> LENGTH: 20
<212> TYPE: PRT
<213> ORGANISM: Dengue virus

<400> SEQUENCE: 281

Pro Arg Gly Ala Val Met Asp Ile Ile Ser Arg Lys Asp Gln Arg Gly
1               5                   10                  15

Ser Gly Gln Val
            20

<210> SEQ ID NO 282
<211> LENGTH: 20
<212> TYPE: PRT
<213> ORGANISM: Dengue virus

<400> SEQUENCE: 282

Arg Lys Asp Gln Arg Gly Ser Gly Gln Val Gly Thr Tyr Gly Leu Asn
1               5                   10                  15

Thr Phe Thr Asn
            20

<210> SEQ ID NO 283
<211> LENGTH: 20
<212> TYPE: PRT
<213> ORGANISM: Dengue virus

<400> SEQUENCE: 283

Gly Thr Tyr Gly Leu Asn Thr Phe Thr Asn Met Glu Ala Gln Leu Ile
1               5                   10                  15

Arg Gln Met Glu
            20

<210> SEQ ID NO 284
<211> LENGTH: 20
<212> TYPE: PRT
<213> ORGANISM: Dengue virus

<400> SEQUENCE: 284

Met Glu Ala Gln Leu Ile Arg Gln Met Glu Ala Glu Gly Val Ile Thr
1               5                   10                  15

Glu Cys Gly Val
            20

<210> SEQ ID NO 285
<211> LENGTH: 20
<212> TYPE: PRT
<213> ORGANISM: Dengue virus

<400> SEQUENCE: 285

Ala Glu Gly Val Ile Thr Glu Cys Gly Val Asp Arg Leu Lys Arg Met
1               5                   10                  15

Ala Ile Ser Gly
20

<210> SEQ ID NO 286
<211> LENGTH: 20
<212> TYPE: PRT
<213> ORGANISM: Dengue virus

<400> SEQUENCE: 286

Asp Arg Leu Lys Arg Met Ala Ile Ser Gly Asp Asp Cys Val Val Lys
1 5 10 15

Pro Pro Gln Trp
20

<210> SEQ ID NO 287
<211> LENGTH: 20
<212> TYPE: PRT
<213> ORGANISM: Dengue virus

<400> SEQUENCE: 287

Asp Asp Cys Val Val Lys Pro Pro Gln Trp Glu Pro Ser Lys Gly Trp
1 5 10 15

His Asp Trp Gln
20

<210> SEQ ID NO 288
<211> LENGTH: 20
<212> TYPE: PRT
<213> ORGANISM: Dengue virus

<400> SEQUENCE: 288

Glu Pro Ser Lys Gly Trp His Asp Trp Gln Gln Val Pro Phe Cys Ser
1 5 10 15

His His Phe His
20

<210> SEQ ID NO 289
<211> LENGTH: 20
<212> TYPE: PRT
<213> ORGANISM: Dengue virus

<400> SEQUENCE: 289

Gln Val Pro Phe Cys Ser His His Phe His Glu Ile Phe Met Lys Asp
1 5 10 15

Gly Arg Lys Leu
20

<210> SEQ ID NO 290
<211> LENGTH: 20
<212> TYPE: PRT
<213> ORGANISM: Dengue virus

<400> SEQUENCE: 290

Glu Ile Phe Met Lys Asp Gly Arg Lys Leu Val Val Pro Cys Arg Asn
1 5 10 15

Gln Asp Glu Leu
20

<210> SEQ ID NO 291
<211> LENGTH: 20
<212> TYPE: PRT
<213> ORGANISM: Dengue virus

<400> SEQUENCE: 291

Val Val Pro Cys Arg Asn Gln Asp Glu Leu Ile Gly Arg Ala Arg Ile
1 5 10 15

Ser Gln Gly Ala
20

<210> SEQ ID NO 292
<211> LENGTH: 20
<212> TYPE: PRT
<213> ORGANISM: Dengue virus

<400> SEQUENCE: 292

Ile Gly Arg Ala Arg Ile Ser Gln Gly Ala Gly Trp Ser Leu Arg Glu
1 5 10 15

Thr Ala Cys Leu
20

<210> SEQ ID NO 293
<211> LENGTH: 20
<212> TYPE: PRT
<213> ORGANISM: Dengue virus

<400> SEQUENCE: 293

Gly Trp Ser Leu Arg Glu Thr Ala Cys Leu Gly Lys Ser Tyr Ala Gln
1 5 10 15

Met Trp Gln Leu
20

<210> SEQ ID NO 294
<211> LENGTH: 20
<212> TYPE: PRT
<213> ORGANISM: Dengue virus

<400> SEQUENCE: 294

Gly Lys Ser Tyr Ala Gln Met Trp Gln Leu Met Tyr Phe His Arg Arg
1 5 10 15

Asp Leu Arg Leu
20

<210> SEQ ID NO 295
<211> LENGTH: 20
<212> TYPE: PRT
<213> ORGANISM: Dengue virus

<400> SEQUENCE: 295

Met Tyr Phe His Arg Arg Asp Leu Arg Leu Ala Ser Asn Ala Ile Cys
1 5 10 15

Ser Ala Val Pro
20

<210> SEQ ID NO 296
<211> LENGTH: 20
<212> TYPE: PRT
<213> ORGANISM: Dengue virus

<400> SEQUENCE: 296

Ala Ser Asn Ala Ile Cys Ser Ala Val Pro Ser His Trp Val Pro Thr
1 5 10 15

Ser Arg Thr Thr
20

<210> SEQ ID NO 297
<211> LENGTH: 20
<212> TYPE: PRT
<213> ORGANISM: Dengue virus

<400> SEQUENCE: 297

Ser His Trp Val Pro Thr Ser Arg Thr Thr Trp Ser Ile His Ala His
1 5 10 15

His Glu Trp Met
20

<210> SEQ ID NO 298
<211> LENGTH: 20
<212> TYPE: PRT
<213> ORGANISM: Dengue virus

<400> SEQUENCE: 298

Trp Ser Ile His Ala His His Glu Trp Met Thr Thr Glu Asp Met Leu
1 5 10 15

Ala Val Trp Asn
20

<210> SEQ ID NO 299
<211> LENGTH: 20
<212> TYPE: PRT
<213> ORGANISM: Dengue virus

<400> SEQUENCE: 299

Thr Thr Glu Asp Met Leu Ala Val Trp Asn Arg Val Trp Ile Glu Glu
1 5 10 15

Asn Pro Trp Met
20

<210> SEQ ID NO 300
<211> LENGTH: 20
<212> TYPE: PRT
<213> ORGANISM: Dengue virus

<400> SEQUENCE: 300

Arg Val Trp Ile Glu Glu Asn Pro Trp Met Glu Asp Lys Thr His Ile
1 5 10 15

His Ser Trp Glu
20

<210> SEQ ID NO 301
<211> LENGTH: 20
<212> TYPE: PRT
<213> ORGANISM: Dengue virus

<400> SEQUENCE: 301

Glu Asp Lys Thr His Ile His Ser Trp Glu Asp Val Pro Tyr Leu Gly
1 5 10 15

Lys Arg Glu Asp
20

<210> SEQ ID NO 302
<211> LENGTH: 20
<212> TYPE: PRT
<213> ORGANISM: Dengue virus

<400> SEQUENCE: 302

Asp Val Pro Tyr Leu Gly Lys Arg Glu Asp Gln Trp Cys Gly Ser Leu

```
1               5                   10                  15

Ile Gly Leu Thr
            20


<210> SEQ ID NO 303
<211> LENGTH: 19
<212> TYPE: PRT
<213> ORGANISM: Dengue virus

<400> SEQUENCE: 303

Gln Trp Cys Gly Ser Leu Ile Gly Leu Thr Ser Arg Ala Thr Trp Ala
1               5                   10                  15

Lys Asn Ile


<210> SEQ ID NO 304
<211> LENGTH: 20
<212> TYPE: PRT
<213> ORGANISM: Dengue virus

<400> SEQUENCE: 304

Asp Gln Trp Cys Gly Ser Leu Ile Gly Leu Thr Ser Arg Ala Thr Trp
1               5                   10                  15

Ala Lys Asn Ile
            20


<210> SEQ ID NO 305
<211> LENGTH: 20
<212> TYPE: PRT
<213> ORGANISM: Dengue virus

<400> SEQUENCE: 305

Lys Glu Lys Gln Asp Val Phe Cys Asp Ser Lys Leu Met Ser Ala Ala
1               5                   10                  15

Ile Lys Asp Asn
            20


<210> SEQ ID NO 306
<211> LENGTH: 20
<212> TYPE: PRT
<213> ORGANISM: Dengue virus

<400> SEQUENCE: 306

Lys Leu Met Ser Ala Ala Ile Lys Asp Asn Arg Ala Val His Ala Asp
1               5                   10                  15

Met Gly Tyr Trp
            20


<210> SEQ ID NO 307
<211> LENGTH: 20
<212> TYPE: PRT
<213> ORGANISM: Dengue virus

<400> SEQUENCE: 307

Arg Ala Val His Ala Asp Met Gly Tyr Trp Ile Glu Ser Ala Leu Asn
1               5                   10                  15

Asp Thr Trp Lys
            20


<210> SEQ ID NO 308
<211> LENGTH: 20
<212> TYPE: PRT
<213> ORGANISM: Dengue virus
```

<400> SEQUENCE: 308

Ile Glu Ser Ala Leu Asn Asp Thr Trp Lys Ile Glu Lys Ala Ser Phe
1 5 10 15

Ile Glu Val Lys
20

<210> SEQ ID NO 309
<211> LENGTH: 20
<212> TYPE: PRT
<213> ORGANISM: Dengue virus

<400> SEQUENCE: 309

Ile Glu Lys Ala Ser Phe Ile Glu Val Lys Asn Cys His Trp Pro Lys
1 5 10 15

Ser His Thr Leu
20

<210> SEQ ID NO 310
<211> LENGTH: 20
<212> TYPE: PRT
<213> ORGANISM: Dengue virus

<400> SEQUENCE: 310

Asn Cys His Trp Pro Lys Ser His Thr Leu Trp Ser Asn Gly Val Leu
1 5 10 15

Glu Ser Glu Met
20

<210> SEQ ID NO 311
<211> LENGTH: 20
<212> TYPE: PRT
<213> ORGANISM: Dengue virus

<400> SEQUENCE: 311

Trp Ser Asn Gly Val Leu Glu Ser Glu Met Ile Ile Pro Lys Asn Leu
1 5 10 15

Ala Gly Pro Val
20

<210> SEQ ID NO 312
<211> LENGTH: 20
<212> TYPE: PRT
<213> ORGANISM: Dengue virus

<400> SEQUENCE: 312

Ile Ile Pro Lys Asn Leu Ala Gly Pro Val Ser Gln His Asn Tyr Arg
1 5 10 15

Pro Gly Tyr His
20

<210> SEQ ID NO 313
<211> LENGTH: 20
<212> TYPE: PRT
<213> ORGANISM: Dengue virus

<400> SEQUENCE: 313

Ser Gln His Asn Tyr Arg Pro Gly Tyr His Thr Gln Ile Thr Gly Pro
1 5 10 15

Trp His Leu Gly
20

<210> SEQ ID NO 314
<211> LENGTH: 20
<212> TYPE: PRT
<213> ORGANISM: Dengue virus

<400> SEQUENCE: 314

Thr Gln Ile Thr Gly Pro Trp His Leu Gly Lys Leu Glu Met Asp Phe
1               5                   10                  15

Asp Phe Cys Asp
            20

<210> SEQ ID NO 315
<211> LENGTH: 20
<212> TYPE: PRT
<213> ORGANISM: Dengue virus

<400> SEQUENCE: 315

Lys Leu Glu Met Asp Phe Asp Phe Cys Asp Gly Thr Thr Val Val Val
1               5                   10                  15

Thr Glu Asp Cys
            20

<210> SEQ ID NO 316
<211> LENGTH: 20
<212> TYPE: PRT
<213> ORGANISM: Dengue virus

<400> SEQUENCE: 316

Gly Thr Thr Val Val Val Thr Glu Asp Cys Gly Asn Arg Gly Pro Ser
1               5                   10                  15

Leu Arg Thr Thr
            20

<210> SEQ ID NO 317
<211> LENGTH: 20
<212> TYPE: PRT
<213> ORGANISM: Dengue virus

<400> SEQUENCE: 317

Gly Asn Arg Gly Pro Ser Leu Arg Thr Thr Thr Ala Ser Gly Lys Leu
1               5                   10                  15

Ile Thr Glu Trp
            20

<210> SEQ ID NO 318
<211> LENGTH: 20
<212> TYPE: PRT
<213> ORGANISM: Dengue virus

<400> SEQUENCE: 318

Thr Ala Ser Gly Lys Leu Ile Thr Glu Trp Cys Cys Arg Ser Cys Thr
1               5                   10                  15

Leu Pro Pro Leu
            20

<210> SEQ ID NO 319
<211> LENGTH: 20
<212> TYPE: PRT
<213> ORGANISM: Dengue virus

<400> SEQUENCE: 319

Cys Cys Arg Ser Cys Thr Leu Pro Pro Leu Arg Tyr Arg Gly Glu Asp

-continued

```
1               5                   10                  15

Gly Cys Trp Tyr
            20


<210> SEQ ID NO 320
<211> LENGTH: 20
<212> TYPE: PRT
<213> ORGANISM: Dengue virus

<400> SEQUENCE: 320

Arg Tyr Arg Gly Glu Asp Gly Cys Trp Tyr Gly Met Glu Ile Arg Pro
1               5                   10                  15

Leu Lys Glu Lys
            20


<210> SEQ ID NO 321
<211> LENGTH: 20
<212> TYPE: PRT
<213> ORGANISM: Dengue virus

<400> SEQUENCE: 321

Gly Met Glu Ile Arg Pro Leu Lys Glu Lys Glu Glu Asn Leu Val Asn
1               5                   10                  15

Ser Leu Val Thr
            20


<210> SEQ ID NO 322
<211> LENGTH: 11
<212> TYPE: PRT
<213> ORGANISM: Dengue virus

<400> SEQUENCE: 322

Glu Glu Asn Leu Val Asn Ser Leu Val Thr Ala
1               5                   10


<210> SEQ ID NO 323
<211> LENGTH: 20
<212> TYPE: PRT
<213> ORGANISM: Dengue virus

<400> SEQUENCE: 323

Met Glu Ile Arg Pro Leu Lys Glu Lys Glu Glu Asn Leu Val Asn Ser
1               5                   10                  15

Leu Val Thr Ala
            20


<210> SEQ ID NO 324
<211> LENGTH: 181
<212> TYPE: PRT
<213> ORGANISM: Dengue virus

<400> SEQUENCE: 324

Arg Glu Ser Asn Thr Thr Glu Cys Asp Ser Lys Ile Ile Gly Thr Ala
1               5                   10                  15

Val Lys Asn Asn Leu Ala Ile His Ser Asp Leu Ser Tyr Trp Ile Glu
            20                  25                  30

Ser Arg Leu Asn Asp Thr Trp Lys Leu Glu Arg Ala Val Leu Gly Glu
        35                  40                  45

Val Lys Ser Cys Thr Trp Pro Glu Thr His Thr Leu Trp Gly Asp Gly
    50                  55                  60

Ile Leu Glu Ser Asp Leu Ile Ile Pro Val Thr Leu Ala Gly Pro Arg
```

```
65                  70                  75                  80

Ser Asn His Asn Arg Arg Pro Gly Tyr Lys Thr Gln Asn Gln Gly Pro
                85                  90                  95

Trp Asp Glu Gly Arg Val Glu Ile Asp Phe Asp Tyr Cys Pro Gly Thr
            100                 105                 110

Thr Val Thr Leu Ser Glu Ser Cys Gly His Arg Gly Pro Ala Thr Arg
        115                 120                 125

Thr Thr Thr Glu Ser Gly Lys Leu Ile Thr Asp Trp Cys Cys Arg Ser
    130                 135                 140

Cys Thr Leu Pro Pro Leu Arg Tyr Gln Thr Asp Ser Gly Cys Trp Tyr
145                 150                 155                 160

Gly Met Glu Ile Arg Pro Gln Arg His Asp Glu Lys Thr Leu Val Gln
                165                 170                 175

Ser Gln Val Asn Ala
            180


<210> SEQ ID NO 325
<211> LENGTH: 181
<212> TYPE: PRT
<213> ORGANISM: Dengue virus

<400> SEQUENCE: 325

Arg Asp Ser Tyr Thr Gln Val Cys Asp His Arg Leu Met Ser Ala Ala
1               5                   10                  15

Ile Lys Asp Ser Lys Ala Val His Ala Asp Met Gly Tyr Trp Ile Glu
            20                  25                  30

Ser Glu Lys Asn Glu Thr Trp Lys Leu Ala Arg Ala Ser Phe Ile Glu
        35                  40                  45

Val Lys Thr Cys Ile Trp Pro Lys Ser His Thr Leu Trp Ser Asn Gly
    50                  55                  60

Val Leu Glu Ser Glu Met Ile Ile Pro Lys Ile Tyr Gly Gly Pro Ile
65                  70                  75                  80

Ser Gln His Asn Tyr Arg Pro Gly Tyr Phe Thr Gln Thr Ala Gly Pro
                85                  90                  95

Trp His Leu Gly Lys Leu Glu Leu Asp Phe Asp Phe Cys Glu Gly Thr
            100                 105                 110

Thr Val Val Val Asp Glu His Cys Gly Asn Arg Gly Pro Ser Leu Arg
        115                 120                 125

Thr Thr Thr Val Thr Gly Lys Ile Ile His Glu Trp Cys Cys Arg Ser
    130                 135                 140

Cys Thr Leu Pro Pro Leu Arg Phe Lys Gly Glu Asp Gly Cys Trp Tyr
145                 150                 155                 160

Gly Met Glu Ile Arg Pro Val Lys Asp Lys Glu Glu Asn Leu Val Lys
                165                 170                 175

Ser Met Val Ser Ala
            180


<210> SEQ ID NO 326
<211> LENGTH: 181
<212> TYPE: PRT
<213> ORGANISM: Dengue virus

<400> SEQUENCE: 326

Arg Glu Lys Gln Asp Val Phe Cys Asp Ser Lys Leu Met Ser Ala Ala
1               5                   10                  15

Ile Lys Asp Asn Arg Ala Val His Ala Asp Met Gly Tyr Trp Ile Glu
```

```
            20                  25                  30

Ser Ala Leu Asn Asp Thr Trp Lys Met Glu Lys Ala Ser Phe Ile Glu
        35                  40                  45

Val Lys Ser Cys His Trp Pro Lys Ser His Thr Leu Trp Ser Asn Gly
    50                  55                  60

Val Leu Glu Ser Glu Met Ile Ile Pro Lys Ser Phe Ala Gly Pro Val
65                  70                  75                  80

Ser Gln His Asn Tyr Arg Pro Gly Tyr Tyr Thr Gln Thr Ala Gly Pro
                85                  90                  95

Trp His Leu Gly Lys Leu Glu Met Asp Phe Asp Phe Cys Glu Gly Thr
            100                 105                 110

Thr Val Val Val Thr Glu Asp Cys Gly Asn Arg Gly Pro Ser Leu Arg
        115                 120                 125

Thr Thr Thr Ala Ser Gly Lys Leu Ile Thr Glu Trp Cys Cys Arg Ser
    130                 135                 140

Cys Thr Leu Pro Pro Leu Arg Tyr Arg Gly Glu Asp Gly Cys Trp Tyr
145                 150                 155                 160

Gly Met Glu Ile Arg Pro Leu Lys Glu Lys Glu Glu Asn Leu Val Asn
                165                 170                 175

Ser Leu Val Thr Ala
            180


<210> SEQ ID NO 327
<211> LENGTH: 181
<212> TYPE: PRT
<213> ORGANISM: Dengue virus

<400> SEQUENCE: 327

Arg Glu Val Tyr Thr Gln Leu Cys Asp His Arg Leu Met Ser Ala Ala
1               5                   10                  15

Val Lys Asp Glu Arg Ala Val His Ala Asp Met Gly Tyr Trp Ile Glu
            20                  25                  30

Ser Gln Lys Asn Gly Ser Trp Lys Leu Glu Lys Ala Ser Leu Ile Glu
        35                  40                  45

Val Lys Thr Cys Thr Trp Pro Lys Ser His Thr Leu Trp Ser Asn Gly
    50                  55                  60

Val Leu Glu Ser Asp Met Ile Ile Pro Lys Ser Leu Ala Gly Pro Ile
65                  70                  75                  80

Ser Gln His Asn His Arg Pro Gly Tyr His Thr Gln Thr Ala Gly Pro
                85                  90                  95

Trp His Leu Gly Lys Leu Glu Leu Asp Phe Asn Tyr Cys Glu Gly Thr
            100                 105                 110

Thr Val Val Ile Ser Glu Asn Cys Gly Thr Arg Gly Pro Ser Leu Arg
        115                 120                 125

Thr Thr Thr Val Ser Gly Lys Leu Ile His Glu Trp Cys Cys Arg Ser
    130                 135                 140

Cys Thr Leu Pro Pro Leu Arg Tyr Met Gly Glu Asp Gly Cys Trp Tyr
145                 150                 155                 160

Gly Met Glu Ile Arg Pro Ile Asn Glu Lys Glu Glu Asn Met Val Lys
                165                 170                 175

Ser Leu Ala Ser Ala
            180


<210> SEQ ID NO 328
<211> LENGTH: 181
```

<212> TYPE: PRT
<213> ORGANISM: Dengue virus

<400> SEQUENCE: 328

Arg Glu Gly Ser Ser Glu Val Cys Asp His Arg Leu Met Ser Ala Ala
1               5                   10                  15

Ile Lys Asp Gln Lys Ala Val His Ala Asp Met Gly Tyr Trp Ile Glu
            20                  25                  30

Ser Ser Lys Asn Gln Thr Trp Gln Ile Glu Lys Ala Ser Leu Ile Glu
        35                  40                  45

Val Lys Thr Cys Leu Trp Pro Lys Thr His Thr Leu Trp Ser Asn Gly
    50                  55                  60

Val Leu Glu Ser Gln Met Leu Ile Pro Lys Ser Tyr Ala Gly Pro Phe
65                  70                  75                  80

Ser Gln His Asn Tyr Arg Gln Gly Tyr Ala Thr Gln Thr Val Gly Pro
                85                  90                  95

Trp His Leu Gly Lys Leu Glu Ile Asp Phe Gly Glu Cys Pro Gly Thr
            100                 105                 110

Thr Val Thr Ile Gln Glu Asp Cys Asp His Arg Gly Pro Ser Leu Arg
        115                 120                 125

Thr Thr Thr Ala Ser Gly Lys Leu Val Thr Gln Trp Cys Cys Arg Ser
    130                 135                 140

Cys Thr Met Pro Pro Leu Arg Phe Leu Gly Glu Asp Gly Cys Trp Tyr
145                 150                 155                 160

Gly Met Glu Ile Arg Pro Leu Ser Glu Lys Glu Glu Asn Met Val Lys
                165                 170                 175

Ser Gln Val Thr Ala
            180

<210> SEQ ID NO 329
<211> LENGTH: 181
<212> TYPE: PRT
<213> ORGANISM: Dengue virus

<400> SEQUENCE: 329

Val Phe Glu Tyr Thr Met Asp Cys Asp Gly Ser Ile Leu Gly Ala Ala
1               5                   10                  15

Val Asn Gly Lys Lys Ser Ala His Gly Ser Pro Thr Phe Trp Met Gly
            20                  25                  30

Ser His Glu Val Asn Gly Thr Trp Met Ile His Thr Leu Glu Thr Leu
        35                  40                  45

Asp Tyr Lys Glu Cys Glu Trp Pro Leu Thr His Thr Ile Gly Thr Ser
    50                  55                  60

Val Glu Glu Ser Asp Met Phe Met Pro Arg Ser Ile Gly Gly Pro Val
65                  70                  75                  80

Ser Ser His Asn His Ile Pro Gly Tyr Lys Val Gln Thr Asn Gly Pro
                85                  90                  95

Trp Met Gln Val Pro Leu Glu Val Lys Arg Glu Ala Cys Pro Gly Thr
            100                 105                 110

Ser Val Val Val Asp Gly Gly Cys Asp Gly Arg Gly Lys Ser Thr Arg
        115                 120                 125

Ser Thr Thr Asp Ser Gly Lys Ile Ile Pro Glu Trp Cys Cys Arg Ser
    130                 135                 140

Cys Thr Met Pro Pro Val Ser Phe His Gly Ser Asp Gly Cys Trp Tyr
145                 150                 155                 160

Pro Met Glu Ile Arg Pro Arg Lys Thr His Asp Asn His Leu Val Arg
165 170 175

Ser Trp Val Thr Ala
180

<210> SEQ ID NO 330
<211> LENGTH: 181
<212> TYPE: PRT
<213> ORGANISM: Dengue virus

<400> SEQUENCE: 330

Arg Glu Glu Asn Thr Asp Glu Cys Asp Gly Ala Ile Ile Gly Thr Ala
1 5 10 15

Val Lys Gly His Val Ala Leu His Ser Asp Leu Ser Tyr Trp Ile Glu
20 25 30

Ser Arg Leu Asn Asp Thr Trp Lys Leu Glu Arg Ala Val Phe Gly Glu
35 40 45

Val Lys Ser Cys Thr Trp Pro Glu Thr His Thr Leu Trp Gly Asp Gly
50 55 60

Val Glu Glu Ser Glu Leu Ile Ile Pro His Thr Ile Ala Gly Pro Arg
65 70 75 80

Ser Lys His Asn Arg Arg Glu Gly Tyr Lys Thr Gln Asn Gln Gly Pro
85 90 95

Trp Asp Glu Asn Gly Leu Val Pro Gly Leu Asp Tyr Cys Pro Gly Thr
100 105 110

Lys Val Thr Ile Thr Glu Asp Cys Gly Lys Arg Gly Pro Ser Ile Arg
115 120 125

Thr Thr Thr Asp Ser Gly Lys Leu Ile Thr Asp Trp Cys Cys Arg Ser
130 135 140

Cys Ser Leu Pro Pro Leu Arg Phe Arg Thr Glu Asn Gly Cys Trp Tyr
145 150 155 160

Gly Met Glu Ile Arg Pro Val Arg His Asp Glu Thr Thr Leu Val Arg
165 170 175

Ser Gln Val Asp Ala
180

<210> SEQ ID NO 331
<211> LENGTH: 181
<212> TYPE: PRT
<213> ORGANISM: Dengue virus

<400> SEQUENCE: 331

Arg Glu Glu Asn Thr Thr Glu Cys Asp Ser Ala Ile Ile Gly Thr Ala
1 5 10 15

Ile Lys Gly Asp Arg Ala Val His Ser Asp Leu Ser Tyr Trp Ile Glu
20 25 30

Ser Lys Lys Asn Glu Thr Trp Gln Leu Glu Arg Ala Val Met Gly Glu
35 40 45

Val Lys Ser Cys Thr Trp Pro Glu Thr His Thr Leu Trp Gly Asp Gly
50 55 60

Val Val Glu Ser Glu Met Ile Ile Pro Val Thr Leu Gly Gly Pro Lys
65 70 75 80

Ser His His Asn Lys Arg Asn Gly Tyr His Thr Gln Thr Lys Gly Pro
85 90 95

Trp Ser Glu Gly Glu Ile Thr Leu Asp Phe Asp Tyr Cys Pro Gly Thr
100 105 110

```
Thr Val Thr Val Thr Glu His Cys Gly Asn Arg Gly Ala Ser Leu Arg
        115                 120                 125

Thr Thr Thr Ala Ser Gly Lys Leu Val Thr Asp Trp Cys Cys Arg Ser
    130                 135                 140

Cys Ser Leu Pro Pro Leu Arg Tyr Thr Thr Lys Asp Gly Cys Trp Tyr
145                 150                 155                 160

Gly Met Glu Ile Arg Pro Val Lys Glu Glu Glu Ala Lys Leu Val Lys
                165                 170                 175

Ser Arg Val Thr Ala
            180


<210> SEQ ID NO 332
<211> LENGTH: 181
<212> TYPE: PRT
<213> ORGANISM: Dengue virus

<400> SEQUENCE: 332

Arg Glu Glu Asn Thr Ser Glu Cys Asp Ser Thr Ile Ile Gly Thr Ala
1               5                   10                  15

Val Lys Gly Asn His Ala Val His Ser Asp Leu Ser Tyr Trp Ile Glu
            20                  25                  30

Ser Gly Leu Asn Gly Thr Trp Lys Leu Glu Arg Ala Ile Phe Gly Glu
        35                  40                  45

Val Lys Ser Cys Thr Trp Pro Glu Thr His Thr Leu Trp Gly Asp Ala
    50                  55                  60

Val Glu Glu Thr Glu Leu Ile Ile Pro Val Thr Leu Ala Gly Pro Arg
65                  70                  75                  80

Ser Lys His Asn Arg Arg Glu Gly Tyr Lys Val Gln Val Gln Gly Pro
                85                  90                  95

Trp Asp Glu Glu Asp Ile Lys Leu Asp Phe Asp Tyr Cys Pro Gly Thr
            100                 105                 110

Thr Val Thr Val Ser Glu His Cys Gly Lys Arg Gly Pro Ser Val Arg
        115                 120                 125

Thr Thr Thr Asp Ser Gly Lys Leu Val Thr Asp Trp Cys Cys Arg Ser
    130                 135                 140

Cys Thr Leu Pro Pro Leu Arg Phe Thr Thr Ala Ser Gly Cys Trp Tyr
145                 150                 155                 160

Gly Met Glu Ile Arg Pro Met Lys His Asp Glu Ser Thr Leu Val Lys
                165                 170                 175

Ser Arg Val Gln Ala
            180


<210> SEQ ID NO 333
<211> LENGTH: 181
<212> TYPE: PRT
<213> ORGANISM: Dengue virus

<400> SEQUENCE: 333

Arg Gln Glu Pro Thr His Glu Cys Asp Thr Gly Val Met Gly Ala Ala
1               5                   10                  15

Val Lys Asn Gly Met Ala Ile His Thr Asp Gln Ser Leu Trp Met Arg
            20                  25                  30

Ser Met Lys Asn Asp Thr Gly Thr Tyr Ile Val Glu Leu Leu Val Thr
        35                  40                  45

Asp Leu Arg Asn Cys Ser Trp Pro Ala Ser His Thr Ile Asp Asn Ala
    50                  55                  60
```

-continued

```
Asp Val Val Asp Ser Glu Leu Phe Leu Pro Ala Ser Leu Ala Gly Pro
65                  70                  75                  80

Arg Ser Trp Tyr Asn Arg Ile Pro Gly Tyr Ser Glu Gln Val Lys Gly
                85                  90                  95

Pro Trp Lys Tyr Thr Pro Ile Arg Val Ile Arg Glu Glu Cys Pro Gly
            100                 105                 110

Thr Thr Val Thr Ile Asn Ala Lys Cys Asp Lys Arg Gly Ala Ser Val
        115                 120                 125

Arg Ser Thr Thr Glu Ser Gly Lys Val Ile Pro Glu Trp Cys Cys Arg
    130                 135                 140

Ala Cys Thr Met Pro Pro Val Thr Phe Arg Thr Gly Thr Asp Cys Trp
145                 150                 155                 160

Tyr Ala Met Glu Ile Arg Pro Val His Asp Gln Gly Gly Leu Val Arg
                165                 170                 175

Ser Met Val Val Ala
            180
```